US008129379B2

(12) United States Patent
Dixon et al.

(10) Patent No.: US 8,129,379 B2
(45) **Date of Patent: *Mar. 6, 2012**

(54) SUBSTITUTED 4-AMINO-PYRROLOTRIAZINE DERIVATIVES USEFUL FOR TREATING HYPER-PROLIFERATIVE DISORDERS AND DISEASES ASSOCIATED WITH ANGIOGENESIS

(75) Inventors: Julie A. Dixon, Bethany, CT (US); Barton Phillips, San Mateo, CA (US); Furahi Achebe, New Haven, CT (US); Harold C. E. Kluender, Hartland, WI (US); Jason Newcom, Northford, CT (US); Kyle Parcella, Wallingford, CT (US); Steven Magnuson, Wallingford, CT (US); Zhenqiu Hong, Milford, CT (US); Zhonghua Zhang, Derby, CT (US); Zheng Liu, Beacon Falls, CT (US); Uday Khire, Orange, CT (US); Lei Wang, Milford, CT (US); Martin Michels, Cologne (DE); Brent Chandler, Princeton, NJ (US); Stephen O'Connor, Guilford, CT (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/552,923

(22) Filed: Sep. 2, 2009

(65) Prior Publication Data

US 2010/0179125 A1 Jul. 15, 2010

Related U.S. Application Data

(63) Continuation of application No. 12/085,880, filed as application No. PCT/US2006/046081 on Dec. 1, 2006.

(60) Provisional application No. 60/741,691, filed on Dec. 2, 2005.

(51) Int. Cl.

| | |
|---|---|
| ***A61K 31/53*** | (2006.01) |
| ***A61P 35/00*** | (2006.01) |
| ***C07D 487/04*** | (2006.01) |
| ***C07D 417/02*** | (2006.01) |
| ***C07D 413/02*** | (2006.01) |

(52) U.S. Cl. .......... 514/243; 544/183; 544/60; 544/111; 514/227.8; 514/231.5

(58) Field of Classification Search ................. 544/183; 514/243

See application file for complete search history.

(56) References Cited

U.S. PATENT DOCUMENTS

| | | | | |
|---|---|---|---|---|
| 7,563,791 | B2 * | 7/2009 | Dixon et al. | 514/243 |
| 2005/0153966 | A1 | 7/2005 | Gangloff et al. | |
| 2007/0004733 | A1 | 1/2007 | Chen et al. | |
| 2009/0281079 | A1 | 11/2009 | Dixon et al. | |
| 2010/0063038 | A1 | 3/2010 | Dixon et al. | |
| 2010/0075958 | A1 | 3/2010 | Dixon et al. | |
| 2010/0273800 | A1 | 10/2010 | Magnuson et al. | |

FOREIGN PATENT DOCUMENTS

| | | | |
|---|---|---|---|
| WO | WO-00/71129 | A1 | 11/2000 |
| WO | WO-2005/121147 | A1 | 12/2005 |
| WO | WO-2007/061882 | A2 | 5/2007 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Powell et al., British Journal of Dermatology, 141: 802-810, 1999.*
Cohen et al., Current Opinion in Chemical Biology, 3,459-465, 1999.*
Golub et al., Science, 286, 531-537, 1999.*
Mass, R. D., Int. J. Radiation Oncology Bio. Phys.vol. 58(3): 932-940, 2004.*
Fabbro et al. Pharmacology & Therapeutics 93, 79-98, 2002.*
Simone, Oncology: Introduction, Cecil Textbook of Medicine, edited by Bennet, J.C., and Plum F., 20th edition, vol. 1, 1004-1010, 1996.
Freshney et al. "Culture of Animal Cells, A Manual of Basic Technique," Alan R. Liss, Inc. 1983, New York, p. 4.
Dermer et al., Bio/Technology, 12:320, 1994.
Cohen et al., Current Opinion in Chemical Biology, 3, 456-465, 1999.
Mass, R.D., International Journal of Radiation Oncology Bio Phys. vol. 58(3): 932-940, 2004.
Fabbro et al., Pharmacology & Therapeutics 93, 79-98, 2002.
West-Solid State Chemistry 1987.
Vippagunta et al., Advanced Drug Delivery Reviews 48; 3-26, 2001.
Gautschi et al., Clin. Cancer Research, 14(6), 1639-1648, 2008.
Mounlzios et al., Cancer Treatments Reviews, 34, 175-182, 2008.
Ferrara, N., Oncology, 69 suppl. 3, 11-16, 2005.
Jain et al., Nature Clinical Practice Oncology, 3(1), 24-40, 2006.
Ferrara, N. The Oncologist: 9 (Suppl. 1): 2-10, 2004.

* cited by examiner

*Primary Examiner* — Venkataraman Balasubramanian
(74) *Attorney, Agent, or Firm* — Edwards Wildman Palmer LLP; Barry Kramer; Nicholas J. DiCeglie, Jr.

(57) ABSTRACT

This invention relates to novel pyrrozolotriazine compounds, pharmaceutical compositions containing such compounds and the use of those compounds or compositions for treating hyper-proliferative and/or angiogenesis disorders, as a sole agent or in combination with other active ingredients.

2 Claims, No Drawings

SUBSTITUTED 4-AMINO-PYRROLOTRIAZINE DERIVATIVES USEFUL FOR TREATING HYPER-PROLIFERATIVE DISORDERS AND DISEASES ASSOCIATED WITH ANGIOGENESIS

FIELD OF THE INVENTION

This invention relates to novel pyrrozolotriazine compounds, pharmaceutical compositions containing such compounds and the use of those compounds or compositions for treating hyper-proliferative and/or angiogenesis disorders, as a sole agent or in combination with other active ingredients.

BACKGROUND OF THE INVENTION

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases.

Over 4.4 million people worldwide were diagnosed with breast, colon, ovarian, lung, or prostate cancer in 2002 and over 2.5 million people died of these devastating diseases (Globocan 2002 Report). In the United States alone, over 1.25 million new cases and over 500,000 deaths from cancer were predicted in 2005. The majority of these new cases were expected to be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4% (American Cancer Society, Cancer Facts and Figures 2005).

Cancer treatments are of two major types, either curative or palliative. The main curative therapies for cancer are surgery and radiation. These options are generally successful only if the cancer is found at an early localized stage (Gibbs J B, 2000). Once the disease has progressed to locally advanced cancer or metastatic cancer, these therapies are less effective and the goal of therapy aims at symptom palliation and maintaining good quality of life. The most prevalent treatment protocols in either treatment mode involve a combination of surgery, radiation therapy and/or chemotherapy.

Cytotoxic drugs (also known as cytoreductive agents) are used in the treatment of cancer, either as a curative treatment or with the aim of prolonging life or palliating symptoms. Cytotoxics may be combined with radiotherapy and/or surgery, as neo-adjuvant treatment (initial chemotherapy aimed at shrinking the tumor, thereby rendering local therapy such as surgery and radiation more effective) or as adjuvant chemotherapy (used in conjunction or after surgery and/or localized therapy). Combinations of different drugs are frequently more effective than single drugs: they may provide an advantage in certain tumors of enhanced response, reduced development of drug resistance and/or increased survival. It is for these reasons that the use of combined cytotoxic regimens in the treatment of many cancers is very common.

Cytotoxic agents in current use employ different mechanisms to block proliferation and induce cell death. They can be generally categorized into the following groups based on their mechanism of action: the microtubule modulators that interfere with the polymerization or depolymerization of microtubules (e.g. docetaxel, paclitaxel, vinblastine, vinorelbine); anti-metabolites including nucleoside analogs and other inhibitors of key cellular metabolic pathways (e.g. capecitabine, gemcitabine, methotrexate); agents that interact directly with DNA (e.g. carboplatin, cyclophosphamide); anthracycline DNA interchalators that interfere with DNA polymerase and Topoisomerase II (e.g. doxorubicin, epirubicin); and the non-anthracycline inhibitors of Topoisomerase II and I enzymatic activity (e.g. topotecan, irinotecan, and etoposide). Even though different cytotoxic drugs act via different mechanisms of action, each generally leads to at least transient shrinkage of tumors.

Cytotoxic agents continue to represent an important component in an oncologist's arsenal of weapons for use in fighting cancer. The majority of drugs currently undergoing late Phase II and Phase III clinical trials are focusing on known mechanisms of action (tubulin binding agents, anti-metabolites, DNA processing), and on incremental improvements in known drug classes (for example the taxanes or the camptothecins). A small number of cytotoxic drugs based on novel mechanisms have recently emerged. Modes of action for these cytotoxics include inhibition of enzymes involved in DNA modification [e.g. histone deacetylase (HDAC)], inhibition of proteins involved in microtubule movement and cell cycle progression (e.g. kinesins, aurora kinase), and novel inducers of the apoptotic pathway (e.g. bcl-2 inhibitors).

The link between activity in tumor cell proliferation assays in vitro and anti-tumor activity in the clinical setting has been well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother.*

Cells protect their DNA by adopting a higher-order complex termed chromatin. Chromatin condensation is evident during mitosis and cell death induced by apoptosis while chromatin decondensation is necessary for replication, repair, recombination and transcription. Histones are among some of the DNA-binding proteins that are involved in the regulation of DNA condensation; and post-translational modifications of histone tails serve a critical role in the dynamic condensation/decondensation that occurs during the cell cycle. Phoshorylation of the tails of histone H3 is involved in both transcription and cell division (Prigent et al. *J. Cell Science* 2003, 116, 3677). A number of protein kinases have been reported to phosphorylate histone H3 and these kinases function both as signal transduction and mitotic kinases.

Even though cytotoxic agents remain in the forefront of approaches to treat patients with advanced solid tumors, their limited efficacy and narrow therapeutic indices result in significant side effects. Moreover, basic research into cancer has led to the investigation of less toxic therapies based on the specific mechanisms central to tumor progression. Such studies could lead to effective therapy with improvement of the quality of life for cancer patients. Thus, a new class of therapeutic agents has emerged, referred to as cytostatics. Cytostatics direct their action on tumor stabilization and are generally associated with a more limited and less aggravating side effect profile. Their development has resulted from the identification of specific genetic changes involved in cancer progression and an understanding of the proteins activated in cancer such as tyrosine kinases and serine/threonine kinases.

In addition to direct inhibition of tumor cell targets, cytostatic drugs are being developed to block the process of tumor angiogenesis. This process supplies the tumor with existing and new blood vessels to support continued nourishment and therefore help promote tumor growth. Key tyrosine kinase receptors including Vascular Endothelial Growth Factor Receptor 2 (VEGFR2), Fibroblast Growth Factor 1 (FGFR1)

and Tie2 have been shown to regulate angiogenesis and have emerged as highly attractive drug targets.

To support progressive tumor growth beyond the size of 1-2 $mm^3$, it is recognized that tumor cells require a functional stroma, a support structure consisting of fibroblast, smooth muscle cells, endothelial cells, extracellular matrix proteins, and soluble factors (Folkman, J., *Semin Oncol,* 2002. 29 (6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. *Semin Oncol,* 2001. 28 (5 Suppl 17), 27-33; Shaheen, R. M., et al., *Cancer Res,* 2001. 61(4), 1464-8; Shaheen, R. M., et al. *Cancer Res,* 1999. 59(21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, *Adv Cancer Res,* 2001, 80, 1-38), FGF, a chemo-attractant and mitogen for fibroblasts and endothelial cells, and VEGF, a potent regulator of vascularization.

A major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. *Endocr. Rev.* 1992, 13, 18; Neufield et al. *FASEB J*=1999, 13, 9).

VEGF expression is reported to be induced by hypoxia (Shweiki et al. *Nature* 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. *J. Cell Biol.,* 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5 (Suppl. 1), 3-10; McDonald, N. Q.; Hendrickson, W. A. *Cell* 1993, 73, 421-424).

The biological activities of the VEGFs are mediated through binding to their receptors. VEGFR3 (also called Flt-4) is predominantly expressed on lymphatic endothelium in normal adult tissues. VEGFR3 function is needed for new lymphatic vessel formation, but not for maintenance of the pre-existing lymphatics. VEGFR3 is also upregulated on blood vessel endothelium in tumors. Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. *Nature Med.* 2001, 7(2), 192-198; Stacker, S. A. et al. *Nature Med.* 2001, 7(2), 186-191; Makinen, T. et al. *Nature Med.* 2001, 7(2), 199-205; Mandriota, S. J. et al. *EMBO J*=2001, 20(4), 672-82; Karpanen, T. et al. *Cancer Res.* 2001, 61(5), 1786-90; Kubo, H. et al. *Blood* 2000, 96(2), 546-53).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westeimarck, J. et al. *Cancer Res.* 2000, 60, 7156-7162; Huang, S. et al. *J. Biol. °win.* 2000, 275, 12266-12272; Simon, C. et al. *Exp. Cell Res.* 2001, 271, 344-355). Moreover, VEGF activates the extracellular signal-regulated protein kinase (ERK) in human umbilical vein endothelial cells (HUVEC) (Yu, Y.; Sato, D. *J. Cell Physiol* 1999, 178, 235-246).

The VEGF-VEGFR2 signaling pathway has been extensively characterized as an important regulator of angiogenesis. Mice lacking VEGFR2 (Flk-1) are almost completely lacking in vasculature and have very few endothelial cells (Shalaby et al., *Nature,* 1995, 376, 62-66). VEGF is a potent mitogen for endothelial cells, promotes angiogenic sprouting, and increases vascular permeability (reviewed in Yancopoulos et al. *Nature* 2000, 407, 242). Administration of soluble VEGFR2 inhibits the growth of wide variety of tumors (Shirakawa et al. *Int J Cancer,* 2002, 99, 244, Bruns et al. *Cancer,* 2000, 89, 495, Millauer et al., *Nature* 1994, 367, 576). Similarly, neutralizing antibodies to VEGF (Kim et al., *Nature,* 1993, 262, 841) or VEGFR2 (Prewett et al., *Cancer Res* 1999, 59, 5209), as well as VEGF antisense (Saleh et al. *Cancer Res* 1996, 56, 393) suppress tumor growth in vivo. Furthermore, small molecule inhibitors of VEGFR2 have been shown to inhibit tumor growth in preclinical xenograft models (reviewed in Shepherd and Sridhar, *Lung Cancer,* 2003, 41, S63) and are being tested in clinical trials. A monoclonal antibody to VEGF (Avastin™) was recently approved for use in combination with other anticancer drugs for treatment of advanced colon cancer.

The Ang-Tie2 signal transduction pathway also plays a key role in vascular formation, particularly with respect to remodeling and stabilization of vessels. The major ligands for Tie2, Angiopoietin-1 and Angiopoietin-2 (Angl and Ang2), have distinct activities. While Angl is a Tie2 agonist, promoting vessel maturation and stability, Ang2 is partial Tie2 agonist/antagonist having varied activities that are dependent on the tissue and growth factor context (Yancopoulos et al. *Nature,* 2000, 407, 242). When the local concentration of VEGF is low, Ang2 promotes vessel regression, whereas in areas where VEGF concentrations are high, Ang2 induces vessel destabilization and branching (Holash et al. *Ocogene,* 1999, 18, 5356). This latter situation is likely the case during active tumor angiogenesis. Angl has been shown to regulate endothelial cell survival (Kwak et al. *FEBS,* 1999, 448, 249, Bussolati et al. *FEBS,* 2003, 9, 1159) and migration (Witzenbichler et al. *J. Biol Chem,* 1998, 373, 18514). The role of Ang-Tie2 signaling in tumor angiogenesis is supported by numerous xenograft tumor studies involving the administration of soluble Tie2. Significant inhibition of tumor growth by soluble Tie2 was observed in the WIBC-9 and MC-5 human breast tumors (Shirakawa et al. *Int J Cancer,* 2002, 99, 344), C26 colon and TS/A breast tumors, R3230AC breast tumor (Lin et al. *J Clin Invest,* 1997, 100, 2072), A375v melanoma (Siemeister et al. *Cancer Res,* 1999, 59, 3185), as well as 4T1 murine mammary and B16F10.9 murine melanoma tumors.

The central role of the FGF-FGFR1 signal transduction pathway in angiogenesis is well established. The FGF family includes 22 members expressed from different genes and having distinct activities (Ornitz and Itoh, *Genome Biology,* 2001, 2, reviews 3005). During mammalian development, FGF1 and FGF2 regulate branching morphogenesis in tissues undergoing vascularization. Administration of FGFs can promote neovascularization in ischemic tissues (Yanagisawa-Miwa et al., *Science,* 1992, 257, 1401, Tabata et al *Cardiovasc Res,* 1997, 35, 470.). FGFR1 binds FGF1 and FGF2 with similar affinity (Dionne et al., *EMBO J,* 1990, 9, 2685). The FGF-FGFR1 pathway has also been associated with angiogenesis in a variety of tumor types. FGF2 is a key regulator of angiogenesis in prostate cancer (Doll et al. *Prostate,* 2001, 49, 293) and melanomas (Straume and Akslen *Am J Pathol,* 2002, 160, 1009). In addition, antisense targeting of FGFR1 (Wang and Becker *Nat Med,* 1997, 3, 887) or anti-FGF2 antibodies (Rofstad and Halsor *Cancer Res,* 2000, 60, 4932) inhibit tumor growth and angiogenesis in human melanomas. Similarly, expression of soluble FGFR decreases the growth of spontaneous pancreatic tumors in mice (Compagni et al. *Cancer Res,* 2000, 60, 7163), as well as xenografted pancreatic tumors (Wagner et al. *Gastroenterology,* 1998, 114, 798). Overexpression and amplification of the FGFR1 gene in human breast tumors (Jacquemier et al. *Int J Cancer,* 1994, 59, 373) and bladder cancers (Simon et al. *Cancer Res,* 2001, 61, 4514), has been reported whereas translocation of FGFR1 resulting in an activated chimeric kinase has been identified in myeloproliferative disorders with lymphoma (Gausch et al. *Mol Cell Biol* 2001, 21, 8129) and Chronic Myelogenous Leukemias (CML, Demiroglu et al., *Blood,* 2001, 98, 3778).

The activation of FGFR1 by FGF induces both the MAPK/ERK and the PI3K/Akt pathways. In contrast to Angl, which is not a mitogen, FGF stimulates cell proliferation via the MAPK/ERK pathway (Bikfalvi et al., *Endocr Rev,* 1997, 18, 26). Activation of FGFR1 leads to the recruitment of adaptor proteins FRS2 and GRB2, which recruit SOS to the plasma membrane leading to the activation of RAS (Kouhara et al., *Cell,* 1997, 89, 693). Activated RAS, which subsequently activates RAF, MEK, then ERK, leads to cell proliferation. The activation of p38 MAPK has also been reported to be involved in FGF-induced cell proliferation (Maher, *J Biol Chem,* 1999, 274, 17491). The recruitment of GRB2 to activated FGFR1 also recruits Gab1, which induces the PI3K/Akt pathway (Ong et al., *Mol Cell Biol,* 2000, 20, 979), and promotes cell survival. This effect of Akt on cell survival is mediated, in part through mTOR and $p70^{S6K}$(Gausch et al., *Mol Cell, Biol,* 2001, 21, 8129). The effects of FGF on cell migration have been shown to be mediated, in part, by ERK activation and c-Fes (reviewed in Javerzat et al., *Trends in Molecular Medicine,* 2002, 8, 483).

PDGF is another key regulator of stromal formation which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., *J Cell Sci Suppl,* 1985, 3, 65-76). The growth factor is made up of two peptide chains, referred to as A or B chains which share 60% homology in their primary amino acid sequence. The chains are disulfide cross linked to form the 30 kDa mature protein composed of either AA, BB or AB homo- or heterodimmers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., *Kidney Int,* 1997, 51(2), 438-43). PDGF binds with high affinity to the PDGF receptor, a 1106 amino acid 124 kDa transmembrane tyrosine kinase receptor (Heldin, C. H., A. Ostman, and L. Ronnstrand, *Biochim Bioplzys Acta,* 1998. 1378(1), 79-113). PDGFR is found as homo- or heterodimer chains which have 30% homology overall in their amino acid sequence and 64% homology between their kinase domains (Heldin, C. H., et al. *Embo J,* 1988, 7(5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry,* 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, *Wound Repair Regen,* 2000. 8(5), 392-8; Yu, J., A. Moon, and H. R. Kim, *Biochem Biophys Res Commun,* 2001. 282(3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix Inhibiting PDGFR activity can lower interstitial pressure and facilitate the influx of cytotoxics into tumors improving the anti-tumor efficacy of these agents (Pietras, K., et al. *Cancer Res,* 2002. 62(19), 5476-84; Pietras, K., et al. *Cancer Res,* 2001. 61(7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. *Proc Natl Acad Sci U S A.,* 1993. 90(2), 393-7; Skobe, M. and N. E. Fusenig, *Proc Natl Acad. Sci. USA,* 1998. 95(3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. *Clin Cancer Res,* 1996, 2(4), 773-82; Nakanishi, K., et al. *Mod Pathol,* 1997, 10(4), 341-7; Sundberg, C., et al. *Am J Pathol,* 1997, 151(2), 479-92; Lindmark, G., et al. *Lab Invest,* 1993, 69(6), 682-9; Vignaud, J. M., et al, *Cancer Res,* 1994, 54(20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. *Cancer Res,* 1992, 52(16), 4550-3), soft tissue sarcomas (Wang, J., M. D. Coltrera, and A. M. Gown, *Cancer Res,* 1994, 54(2), 560-4) and cancers of the ovary (Henriksen, R., et al. *Cancer Res,* 1993, 53(19), 4550-4), prostate (Fudge, K., C. Y. Wang, and M. E. Stearns, *Mod Pathol,* 1994, 7(5), 549-54), pancreas (Funa, K., et al. *Cancer Res,* 1990, 50(3), 748-53) and lung (Antoniades, H. N., et al., *Proc Natl Acad Sci USA,* 1992, 89(9), 3942-6). Ligand independent activation of the receptor is found to a lesser extent but has been reported in chronic myelomonocytic leukemia (CML) where the a chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., *Science,* 2003, 9, 9). Certain PDGFR inhibitors will interfere with tumor stromal development and are believed to inhibit tumor growth and metastasis.

Several new drugs that are directed at various molecular targets have been approved over the past several years for the treatment of cancer. Imatinib is an inhibitor of the Abl tyrosine kinase and was the first small molecule tyrosine kinase inhibitor to be approved for the treatment of chronic myeloid leukemia (CML). Based on additional activity of imatinib against the receptor tyrosine kinase activated in gastrointestinal stromal tumors (GIST), c-KIT, it was subsequently approved for the treatment of advanced GIST. Erlotinib, a small molecule inhibitor of EGFR, was approved in late 2004 for the treatment of non-small cell lung carcinoma (NSCLC). Sorafenib, an inhibitor of multiple kinases including c-Raf and VEGFR2 was approved for the treatment of advanced renal cell carcinoma (RCC) in December, 2005. Recently in January of 2006, Sunitinib, a multi-kinase inhibitor was approved for the treatment of refractory- or resistant-GIST and advanced RCC. These small molecule inhibitors demonstrate that targeted approaches are successful for the treatment of different types of cancers.

Despite advancements in the art, there remains a need for cancer treatments and anti-cancer compounds.

Compounds and compositions described herein, including salts, metabolites, solvates, solvates of salts, hydrates, prodrugs such as esters, polymorphs, and stereoisomeric forms thereof, exhibit anti-proliferative and anti-angiogenic activity and are thus useful to prevent or treat the disorders associated with hyper-proliferation and angiogenesis.

DESCRIPTION OF THE INVENTION

In embodiment one, the present invention provides a compound of formula (I)

(I)

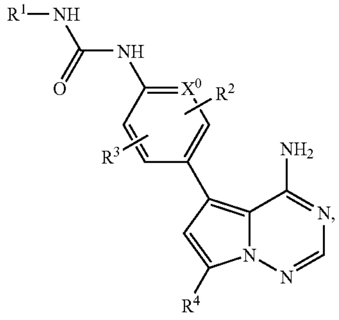

wherein $X^0$ represents C or N;

$R^1$ represents 1.1) phenyl or a bicyclic carbocycle of 9-10 ring members, in which at least one ring is aromatic, $R^1$ optionally bearing up to 4 substituents independently selected from the group consisting of 1.1.a) $(C_1\text{-}C_4)$alkyl, which may optionally bear up to 3 substituents independently selected from 1.1.a1) halogen;

1.1.a2) $OR^5$ wherein $R^5$ represents H or $(C_1\text{-}C_3)$ alkyl which may optionally bear halogen or —$(C_1\text{-}C_3)$mono- or di-alkylamino;

1.1.a3) —$NR^6R^7$ in which $R^6$ and $R^7$ are independently H or —$(C_1\text{-}C_3)$alkyl which may optionally bear halogen or $OR^{7a}$ wherein $R^{7a}$ represents H or $(C_1\text{-}C_3)$alkyl, or $R^6$ and $R^7$ may be joined and taken together with the N atom to which they are attached form a 5-6 membered ring which may optionally contain a ring member selected from O, S, and $NR^8$ wherein $R^8$ represents H or $(C_1\text{-}C_3)$alkyl; and 1.1.a4) a 5-6 membered heteroaromatic containing up to two heteroatoms selected from O, S, and N, 1.1.b) —$(C_3\text{-}C_6)$cycloalkyl which may optionally bear up to 2 substituents independently selected from 1.1.b1) halogen; and 1.1.b2) $OR^9$ wherein $R^9$ represents H or $(C_1-C_3)$alkyl which may optionally bear halogen or $(C_1-C_3)$mono- or di-alkylamino;

1.1.c) $OR^{10}$ wherein $R^{10}$ represents H; phenyl; benzyl; $(C_3-C_6)$cycloalkyl; or $(C_1-C_4)$alkyl which may optionally bear up to 3 substituents independently selected from 1.1.c1) halogen;

1.1.c2) $OR^{11}$ wherein $R^{11}$ represents H or $(C_1-C_3)$alkyl which may optionally bear $(C_1-C_3)$mono- or di-alkylamino; and 1.1.c3) $NR^{12}R^{13}$ in which $R^{12}$ and $R^{13}$ are independently H or —$(C_1-C_3)$alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or $(C_1-C_3)$alkyl;

1.1.d) —C(O)—$OR^{15}$ wherein $R^{15}$ represents H or $(C_1-C_4)$alkyl which may optionally bear up to 3 halogens;

1.1.e) —C(O)—$NR^{16}R^{17}$ wherein $R^{16}$ represents H or $(C_1-C_3)$alkyl which may optionally bear halogen; and $R^{17}$ represents H or —$(C_1-C_4)$alkyl which is optionally substituted with 1.1.e1) halogen;

1.1.e2) a 5-6 membered heteroaromatic containing up to two heteroatoms selected from O, S, and N, 1.1.e3) phenyl;

1.1.e4) —$SO_2CH_3$;

1.1.e5) —$OR^{18}$ wherein $R^{18}$ represents H or $(C_1-C_3)$alkyl which may optionally bear halogen; or 1.1.e6) —$NR^{19}R^{20}$ in which $R^{19}$ and $R^{20}$ are independently H or —$(C_1-C_3)$alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or $(C_1-C_3)$alkyl;

1.1.f) —$N(R^{22})$—C(O)—$R^{23}$ wherein $R^{22}$ represents H or $(C_1-C_3)$alkyl; and $R^{23}$ represents optionally substituted phenyl, or $(C_1-C_4)$alkyl which is optionally substituted with 1.1.f1) optionally substituted phenyl, 1.1.f2) $OR^{24}$ wherein $R^{24}$ represents H or $(C_1-C_3)$alkyl, or 1.1.f3) $NR^{25}R^{26}$ wherein $R^{25}$ and $R^{26}$ are independently H or —$(C_1-C_3)$alkyl which may optionally bear halogen, or $R^{25}$ and $R^{26}$ may be joined and taken together with the N atom to which they are attached form a 5-6 membered ring which may optionally contain a ring member selected from O, S, and $NR^{27}$ wherein $R^{27}$ represents H or $(C_1-C_3)$alkyl;

1.1.g) —$SO_2NR^{28}R^{29}$ wherein $R^{28}$ represents H or $(C_1-C_3)$alkyl which may optionally bear halogen; and $R^{29}$ represents H or —$(C_1-C_4)$alkyl which is optionally substituted with:

1.1.g1) halogen;

1.1.g2) a 5-6 membered heteroaromatic containing up to two heteroatoms selected from O, S, and N, 1.1.g3) phenyl;

1.1.g4) —$SO_2CH_3$;

1.1.g5) —$OR^{30}$ wherein $R^{30}$ represents H or $(C_1-C_3)$alkyl which may optionally bear halogen; or 1.1.g6) —$NR^{31}R^{32}$ in which $R^{31}$ and $R^{32}$ are independently H or —$(C_1-C_3)$alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or $(C_1-C_3)$alkyl;

1.1.h) —$N(R^{34})$—$SO_2$—$R^{35}$ wherein $R^{34}$ represents H or $(C_1-C_3)$alkyl, and $R^{35}$ represents optionally substituted phenyl, or $(C_1-C_4)$alkyl which is optionally substituted with 1.1.h1) halogen;

1.1.h2) optionally substituted phenyl, 1.1.h3) $OR^{36}$ wherein $R^{36}$ represents H or $(C_1-C_3)$alkyl, or 1.1.h4) $NR^{37}R^{38}$ wherein $R^{37}$ and $R^{38}$ are independently H or —$(C_1-C_3)$alkyl which may optionally bear halogen, or $R^{37}$ and $R^{38}$ may be joined and taken together with the N atom to which they are attached form a 5-6 membered ring which may optionally contain a ring member selected from O, S, and $NR^{39}$ wherein $R^{39}$ represents H or $(C_1-C_3)$alkyl;

1.1.i) —$NR^{40}R^{41}$ in which $R^{40}$ and $R^{41}$ are independently H or —$(C_1-C_3)$alkyl which may optionally bear halogen or $OR^{42}$ in which $R^{42}$ represents H or $(C_1-C_3)$alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or $(C_1-C_3)$alkyl;

1.1.j) halogen;

1.1.k) optionally substituted phenyl;

1.1.l) $NO_2$;

1.1.m) CN; and 1.1.n) a 5-6 membered heteroaromatic containing up to two heteroatoms selected from O, S, and N, 1.1.o) —C(O)—$R^{209}$ wherein $R^{209}$ represents H or $(C_1-C_4)$alkyl which may optionally bear up to 3 halogens;

or $R^1$ represents 1.2) a 5-6 membered aromatic heterocycle containing up to 3 heteroatoms independently selected from the group consisting of N, O, and S; or a bicyclic heterocycle of 8-10 ring members in which at least one ring is aromatic and contains up to 3 moieties independently selected from the group consisting of N, N→O, and S, and any non-aromatic ring of said bicyclic heterocycle optionally contains up to three moieties independently selected from the group consisting of O, S, S(O), $S(O)_2$, and $NR^{44}$ wherein $R^{44}$ represents H or —$(C_1-C_3)$alkyl; said $R^1$ heterocycle optionally bearing up to 4 substituents independently selected from the group consisting of 1.2.a) $(C_1-C_4)$alkyl, which may optionally bear up to 3 substituents independently selected from 1.2.a1) halogen;

1.2.a2) $OR^{45}$ wherein $R^{45}$ represents H or $(C_1-C_3)$ alkyl which may optionally bear halogen or $(C_1-C_3)$mono- or di-alkylamino;

1.2.a3) —$NR^{46}R^{47}$ in which $R^{46}$ and $R^{47}$ are independently H or —$(C_1-C_3)$alkyl which may optionally bear halogen or $OR^{47a}$ wherein $R^{47a}$ represents H or $(C_1-C_3)$alkyl, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1-C_3)$alkyl; and 1.2.a4) a 5-6 membered heteroaromatic containing up to two heteroatoms selected from O, S, and N, 1.2.b) —$(C_3-C_6)$cycloalkyl which may optionally bear up to 2 substituents independently selected from 1.2.b1) halogen; and 1.2.b2) $OR^{49}$ wherein $R^{49}$ represents H or $(C_1-C_3)$ alkyl which may optionally bear halogen or —$(C_1-C_3)$mono- or di-alkylamino;

1.2.c) $OR^{50}$ wherein $R^{50}$ represents H; phenyl; benzyl; —$(C_3-C_6)$cycloalkyl; or —$(C_1-C_4)$alkyl which may optionally bear up to 3 substituents independently selected from 1.2.c1) halogen;

1.2.c2) $OR^{51}$ wherein $R^{51}$ represents H or $(C_1-C_3)$ alkyl which may optionally bear —$(C_1-C_3)$ mono- or di-alkylamino; and 1.2.c3) —$NR^{52}R^{53}$ in which $R^{52}$ and $R^{53}$ are independently H or —$(C_1-C_3)$alkyl which may optionally bear halogen, or $R^{52}$ and $R^{53}$ may be joined and taken together with the N atom to which they are attached form a 5-6 membered ring which may optionally contain a ring member selected from O, S, and $NR^{54}$ wherein $R^{54}$ represents H or $(C_1-C_3)$alkyl;

1.2.d) —C(O)—$OR^{55}$ wherein $R^{55}$ represents H or —$(C_1-C_4)$alkyl which may optionally bear up to 3 halogens;

1.2.e) —C(O)—$NR^{56}R^{57}$ wherein $R^{56}$ represents H or $(C_1-C_3)$alkyl which may optionally bear halogen; and $R^{57}$ represents H or —$(C_1-C_4)$alkyl which is optionally substituted with 1.2.e1) halogen;

1.2.e2) a 5-6 membered heteroaromatic containing up to two heteroatoms selected from O, S, and N;

1.2.e3) phenyl;

1.2.e4) —$SO_2CH_3$;

1.2.e5) —$OR^{58}$ wherein $R^{58}$ represents H or $(C_1-C_3)$alkyl which may optionally bear halogen; or 1.2.e6) —$NR^{59}R^{60}$ in which $R^{59}$ and $R^{60}$ are independently H or —$(C_1-C_3)$alkyl which may optionally bear halogen, or $R^{59}$ and $R^{60}$ may be joined and taken together with the N atom to which they are attached form a 5-6 membered ring which may optionally contain a ring member selected from O, S, and $NR^{61}$ wherein $R^{61}$ represents H or $(C_1-C_3)$alkyl;

1.2.f) —$N(R^{62})$—C(O)—$R^{63}$ wherein $R^{62}$ represents H or $(C_1-C_3)$alkyl; and $R^{63}$ represents optionally substituted phenyl, or $(C_1-C_4)$alkyl which is optionally substituted with 1.2.f1) optionally substituted phenyl, 1.2.f2) $OR^{64}$ wherein $R^{64}$ represents H or $(C_1-C_3)$ alkyl, or 1.2.f3) $NR^{65}R^{66}$ wherein $R^{65}$ and $R^{66}$ are independently H or —$(C_1-C_3)$alkyl which may optionally bear halogen, or $R^{65}$ and $R^{66}$ may be joined and taken together with the N atom to which they are attached form a 5-6 membered ring which may optionally contain a ring member selected from O, S, and $NR^{67}$ wherein $R^{67}$ represents H or $(C_1-C_3)$alkyl;

1.2.g) —$SO_2NR^{68}R^{69}$ wherein $R^{68}$ represents H or $(C_1-C_3)$alkyl which may optionally bear halogen; and $R^{69}$ represents H or —$(C_1-C_4)$alkyl which is optionally substituted with 1.2.g1) halogen;

1.2.g2) a 5-6 membered heteroaromatic containing up to two heteroatoms selected from O, S, and N, 1.2.g3) phenyl;

1.2.g4) —$SO_2CH_3$;

1.2.g5) —$OR^{70}$ wherein $R^{70}$ represents H or $(C_1-C_3)$alkyl which may optionally bear halogen; or 1.2.g6 —$NR^{71}R^{72}$ in which $R^{71}$ and $R^{72}$ are independently H or —$(C_1-C_3)$alkyl which may optionally bear halogen, or $R^{71}$ and $R^{72}$ may be joined and taken together with the N atom to which they are attached form a 5-6 membered ring which may optionally contain a ring member selected from O, S, and $NR^{73}$ wherein $R^{73}$ represents H or $(C_1-C_3)$alkyl;

1.2.h) —$N(R^{74})$—$SO_2$—$R^{75}$ wherein $R^{74}$ represents H or $(C_1-C_3)$alkyl, and $R^{75}$ represents optionally substituted phenyl, or $(C_1-C_4)$alkyl which is optionally substituted with 1.2.h1) halogen;

1.2.h2) optionally substituted phenyl, 1.2.h3) $OR^{76}$ wherein $R^{76}$ represents H or $(C_1-C_3)$ alkyl, or 1.2.h4) $NR^{77}R^{78}$ wherein $R^{77}$ and $R^{78}$ are independently H or —$(C_1-C_3)$alkyl which may optionally bear halogen, or $R^{77}$ and $R^{78}$ may be joined and taken together with the N atom to which they are attached form a 5-6 membered ring which may optionally contain a ring member selected from O, S, and $NR^{79}$ wherein $R^{79}$ represents H or $(C_1-C_3)$alkyl;

1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$ alkyl;

1.2.j) halogen;

1.2.k) optionally substituted phenyl;

1.2.l) $NO_2$;

1.2.m) CN; and 1.2.n) a 5-6 membered heteroaromatic containing up to two heteroatoms selected from O, S, and N, 1.2.o) —C(O)—$R^{210}$ wherein $R^{210}$ represents H or —$(C_1-C_4)$alkyl which may optionally bear up to 3 halogens;

$R^2$ represents hydrogen; halogen; —($C_1$-$C_5$)alkyl which may optionally bear halogen; or —O($C_1$-$C_3$)alkyl which may optionally bear halogen;

$R^3$ represents hydrogen; halogen; —($C_1$-$C_5$)alkyl which may optionally bear halogen; or —O($C_1$-$C_3$)alkyl which may optionally bear halogen;

$R^4$ represents 4.1) —($C_1$-$C_5$)alkyl which is optionally substituted with 4.1.a) —($C_3$-$C_5$)cycloalkyl which may optionally bear halogen or $OR^{109}$ wherein $R^{109}$ represents H or ($C_1$-$C_3$)alkyl;

4.1.b)-halogen;

4.1.c) —$OR^{110}$ wherein $R^{110}$ represents H or —($C_1$-$C_3$)alkyl which may optionally bear up to 3 substituents independently selected from 4.1.c1) halogen;

4.1.c2) phenyl;

4.1.c3) —$S(O)_2CH_3$;

4.1.c4) $OR^{111}$ wherein $R^{111}$ represents H or ($C_1$-$C_3$)alkyl which may optionally bear halogen; and 4.1.c5) —$NR^{112}R^{113}$ in which $R^{112}$ and $R^{113}$ are independently H or —($C_1$-$C_3$)alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or ($C_1$-$C_3$)alkyl;

4.1.d) —$NR^{115}R^{116}$ wherein $R^{115}$ represents H or ($C_1$-$C_3$)alkyl which may optionally bear halogen and $R^{116}$ represents H, optionally substituted phenyl, or —($C_1$-$C_5$)alkyl which may optionally bear up to 3 substituents independently selected from 4.1.d1) halogen;

4.1.d2) —$S(O)_2CH_3$;

4.1.d3) $OR^{117}$ wherein $R^{117}$ represents H or ($C_1$-$C_3$)alkyl which may optionally bear halogen; and 4.1.d4) —$NR^{118}R^{119}$ in which $R^{118}$ and $R^{119}$ are independently H or —($C_1$-$C_3$)alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or ($C_1$-$C_3$)alkyl;

4.1.e) optionally substituted phenyl; or 4.1.f) a 5-6 membered aromatic heterocycle containing up to two heteroatoms selected from O, S, and N;

4.2)

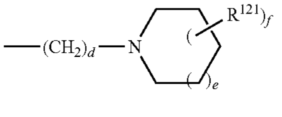

wherein $R^{121}$ represents —($C_1$-$C_3$)alkyl which may optionally bear halogen or —$OR^{122}$ in which $R^{122}$ represents H or —($C_1$-$C_3$)alkyl;

d represents 1, 2, or 3;

e represents 0 or 1;

f represents 0, 1, or 2;

4.3)

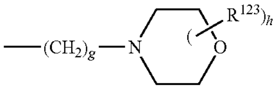

wherein $R^{123}$ represents —($C_1$-$C_3$)alkyl which may optionally bear halogen or —$OR^{124}$ in which $R^{124}$ represents H or —($C_1$-$C_3$)alkyl;

g represents 1, 2, or 3;

h represents 0, 1, or 2;

4.4)

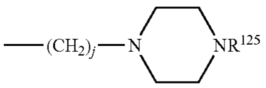

wherein $R^{125}$ represents 4.4.a) H, 4.4.b) —($C_1$-$C_3$)alkyl which may optionally bear halogen or —$OR^{126}$ in which $R^{126}$ represents H or —($C_1$-$C_3$)alkyl which in turn is optionally substituted with halogen;

4.4.c) —$SO_2R^{127}$ wherein $R^{127}$ represents optionally substituted phenyl, or —($C_1$-$C_3$)alkyl which may optionally bear halogen or $OR^{128}$ wherein $R^{128}$ represents H or ($C_1$-$C_3$)alkyl;

4.4.d) —$C(O)R^{129}$ wherein $R^{129}$ represents 4.4.d1) optionally substituted phenyl, 4.4.d2) —($C_1$-$C_3$)alkyl which may optionally bear up to 3 substituents independently selected from 4.4.d2.1) halogen;

4.4.d2.2) optionally substituted phenyl;

4.4.d2.3) —$S(O)_2$—($C_1$-$C_4$)alkyl which may optionally bear halogen;

4.4.d2.4) —$OR^{130}$ wherein $R^{130}$ represents H or —($C_1$-$C_4$)alkyl which may optionally bear halogen; and 4.4.d2.5) —$NR^{131}R^{132}$ in which $R^{131}$ and $R^{132}$ are independently H or —($C_1$-$C_3$)alkyl which may optionally bear halogen, or $R^{131}$ and $R^{132}$ may be joined and taken together with the N atom to which they are attached form a 5-6 membered ring which may optionally contain a ring member selected from O, S, and $NR^{133}$ wherein $R^{133}$ represents H or ($C_1$-$C_3$)alkyl;

4.4.d3) —$OR^{134}$ wherein $R^{134}$ represents H or ($C_1$-$C_3$)alkyl which may optionally bear halogen; or 4.4.d4) $NR^{135}R^{136}$ wherein $R^{135}$ and $R^{136}$ are independently H or —($C_1$-$C_3$)alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{137}$ represents H or $(C_1-C_3)$alkyl; and j represents 1, 2, or 3;

4.5)

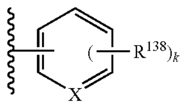

wherein

X represents C or N;

$R^{138}$ represents 4.5.a) $(C_1-C_4)$alkyl, which may optionally bear up to 3 substituents independently selected from 4.5.a1) halogen;

4.5.a2) $OR^{139}$ wherein $R^{139}$ represents H or $(C_1-C_3)$alkyl which may optionally bear halogen or —$(C_1-C_3)$mono- or di-alkylamino;

4.5.a3) —$NR^{140}R^{141}$ in which $R^{140}$ and $R^{141}$ are independently H or —$(C_1-C_3)$alkyl which may optionally bear halogen or $OR^{141a}$ wherein $R^{141a}$ represents H or $(C_1-C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1-C_3)$alkyl; and 4.5.a4) a 5-6 membered heteroaromatic containing up to two heteroatoms selected from O, S, and N, 4.5.b) —$(C_3-C_6)$cycloalkyl which may optionally bear up to 2 substituents independently selected from 4.5.b1) halogen; and 4.5.b2) $OR^{143}$ wherein $R^{143}$ represents H or $(C_1-C_3)$alkyl which may optionally bear halogen;

4.5.c) $OR^{144}$ wherein $R^{144}$ represents H; phenyl; benzyl; $(C_3-C_6)$cycloalkyl; or $(C_1-C_4)$alkyl which may optionally bear up to 3 substituents independently selected from 4.5.c1) halogen;

4.5.c2) $OR^{145}$ wherein $R^{145}$ represents H or $(C_1-C_3)$alkyl which may optionally bear $(C_1-C_3)$ mono- or di-alkylamino; and 4.5.c3) $NR^{146}R^{147}$ in which $R^{146}$ and $R^{1473}$ are independently H or —$(C_1-C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein 8148 represents H or $(C_1-C_3)$alkyl;

4.5.d) —C(O)—$OR^{149}$ wherein $R^{149}$ represents H or —$(C_1-C_4)$alkyl which may optionally bear up to 3 halogens;

4.5.e) —C(O)—$NR^{150}R^{151}$ wherein $R^{150}$ represents H or $(C_1-C_3)$alkyl which may optionally bear halogen; and $R^{151}$ represents H or —$(C_1-C_4)$alkyl which is optionally substituted with 4.5.e1) halogen;

4.5.e2) a 5-6 membered heteroaromatic containing up to two heteroatoms selected from O, S, and N;

4.5.e3) phenyl;

4.5.e4) —$SO_2CH_3$;

4.5.e5) —$OR^{152}$ wherein $R^{152}$ represents H or $(C_1-C_3)$alkyl which may optionally bear halogen; or 4.5.e6) —$NR^{153}R^{154}$ in which $R^{153}$ and $R^{154}$ are independently H or —$(C_1-C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1-C_3)$alkyl;

4.5.f) —$N(R^{156})$ —C(O)—$R^{157}$ wherein $R^{156}$ represents H or $(C_1-C_3)$alkyl; and $R^{157}$ represents H, optionally substituted phenyl, or $(C_1-C_4)$alkyl which is optionally substituted with 4.5.f1) optionally substituted phenyl, 4.5.f2) $OR^{158}$ wherein $R^{158}$ represents H or $(C_1-C_3)$alkyl, or 4.5.f3) $NR^{159}R^{160}$ wherein $R^{159}$ and $R^{160}$ are independently H or —$(C_1-C_3)$alkyl which may optionally bear halogen, or $R^{159}$ and $R^{160}$ may be joined and taken together with the N atom to which they are attached form a 5-6 membered ring which may optionally contain a ring member selected from O, S, and $NR^{161}$ wherein $R^{161}$ represents H or $(C_1-C_3)$alkyl;

4.5.g) —$SO_2NR^{162}R^{163}$ wherein $R^{162}$ represents H or $(C_1-C_3)$alkyl which may optionally bear halogen; and $R^{163}$ represents H or —$(C_1-C_4)$alkyl which is optionally substituted with 4.5.g1) halogen;

4.5.g2) a 5-6 membered heteroaromatic containing up to two heteroatoms selected from O, S, and N;

4.5.g3) phenyl;

4.5.g4) —$SO_2CH_3$;

4.5.g5) —$OR^{164}$ wherein $R^{164}$ represents H or $(C_1-C_3)$alkyl which may optionally bear halogen; or 4.5.g6) —$NR^{165}R^{166}$ in which $R^{165}$ and $R^{166}$ are independently H or —$(C_1-C_3)$alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or $(C_1-C_3)$alkyl;

4.5.h) —$N(R^{168})$ —$SO_2$—$R^{169}$ wherein $R^{168}$ represents H or $(C_1-C_3)$alkyl, and $R^{169}$ represents H, optionally substituted phenyl, or $(C_1-C_4)$alkyl which is optionally substituted with 4.5.h1) halogen, 4.5.h2) optionally substituted phenyl, 4.5.h3) $OR^{170}$ wherein $R^{170}$ represents H or $(C_1-C_3)$alkyl which may optionally bear halogen, or 4.5.h4) $NR^{171}R^{172}$ wherein $R^{171}$ and $R^{172}$ are independently H or —$(C_1-C_3)$alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or $(C_1-C_3)$alkyl;

4.5i) —$NR^{174}R^{175}$ in which $R^{174}$ and $R^{175}$ are independently H or —$(C_1-C_3)$alkyl which may optionally bear halogen or $OR^{175a}$ wherein $R^{175a}$ represents H or $(C_1-C_3)$alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or $(C_1-C_3)$alkyl;

4.5.j) halogen;

4.5.k) optionally substituted phenyl;

4.5.l) $NO_2$;

4.5.m) CN; or 4.5.n) a 5-6 membered heteroaromatic containing up to two heteroatoms selected from O, S, and N; and k represents 0, 1, or 2;

4.6)

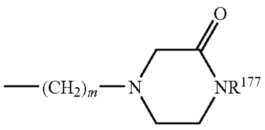

wherein $R^{177}$ represents H or —$(C_1-C_3)$alkyl; and m represents 1, 2, or 3;

4.7)

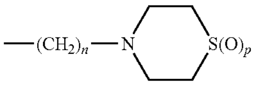

wherein n represents 1, 2, or 3; and p represents 0, 1, or 2;

4.8)

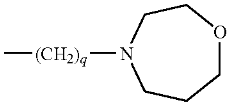

wherein q represents 1, 2, or 3;

4.9)

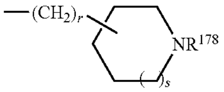

wherein $R^{178}$ represents 4.9.a) H, 4.9.b) —$(C_1-C_3)$alkyl which may optionally bear halogen or —$OR^{179}$ in which $R^{179}$ represents H or $(C_1-C_3)$alkyl optionally substituted with halogen;

4.9.c) —$(C_3-C_7)$cycloalkyl which may optionally bear halogen;

4.9.d) —$(C_2-C_5)$alkenyl which may optionally bear halogen;

4.9.e) —$SO_2R^{180}$ wherein $R^{180}$ represents optionally substituted phenyl or —$(C_1-C_3)$alkyl, which may be substituted with halogen or —$OR^{181}$ wherein $R^{181}$ represents H or $(C_1-C_3)$alkyl which may optionally bear halogen;

4.9f) —$C(O)R^{182}$ wherein $R^{182}$ represents optionally substituted phenyl or $(C_1-C_3)$alkyl which may optionally bear up to 3 substituents independently selected from 4.9.f1) halogen;

4.9.f2) optionally substituted phenyl;

4.9.f3) —$S(O)_2CH_3$;

4.9.f4) $OR^{183}$ wherein $R^{183}$ represents H or $(C_1-C_3)$ alkyl which may optionally bear halogen; and 4.9.f5) —$NR^{184}R^{185}$ in which $R^{184}$ and $R^{185}$ are independently H or —$(C_1-C_3)$alkyl which may optionally bear halogen or $OR^{185a}$ wherein $R^{185a}$ represents H or $(C_1-C_3)$alkyl, or $R^{184}$ and $R^{185}$ may be joined and taken together with the N atom to which they are attached form a 5-6 membered ring which may optionally contain a ring member selected from O, S, and $NR^{186}$ wherein $R^{186}$ represents H or $(C_1-C_3)$alkyl;

4.9g) —$C(O)OR^{187}$ wherein $R^{187}$ represents $(C_1-C_4)$ alkyl; or 4.9.h) —C(O)—$NR^{188}R^{189}$ wherein $R^{188}$ and $R^{189}$ each independently represents H or —$(C_1-C_4)$alkyl which may optionally bear halogen, or $R^{188}$ and $R^{189}$ may be joined and taken together with the N atom to which they are attached form a 5-6 membered ring which may optionally contain a ring member selected from O, S, and $NR^{190}$ wherein $R^{190}$ represents H or $(C_1-C_3)$alkyl;

r represents 0, 1, or 2; and s represents 0 or 1;

4.10)

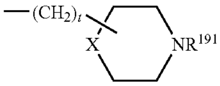

wherein $R^{191}$ represents 4.10.a) H;

4.10.b) $(C_1-C_3)$alkyl which may optionally bear halogen or —$OR^{192}$ in which $R^{192}$ represents H or $(C_1-C_3)$alkyl;

4.10c) —$SO_2R^{193}$ wherein $R^{193}$ represents phenyl or —$(C_1-C_3)$alkyl, both of which may be substituted with halogen or $(C_1-C_3)$alkyl;

4.10.d) —$C(O)R^{194}$ wherein $R^{194}$ represents $(C_1-C_3)$ alkyl which may optionally bear up to 3 substituents independently selected from 4.10.d1) halogen;

4.10.d2) phenyl;

4.10.d3) —$S(O)_2CH_3$;

4.10.d4) $OR^{195}$ wherein $R^{195}$ represents H or $(C_1-C_3)$alkyl which may optionally bear halogen; and 4.10.d5) —$NR^{196}R^{197}$ in which $R^{196}$ and $R^{197}$ are independently H or —$(C_1-C_3)$alkyl which may optionally bear halogen or $OR^{197a}$ wherein $R^{197a}$ represents H or $(C_1-C_3)$alkyl, or $R^{196}$ and $R^{197}$ may be joined and taken together with the N atom to which they are attached form a 5-6 membered ring which may optionally contain a ring member selected from O, S, and $NR^{198}$ wherein $R^{198}$ represents H or $(C_1-C_3)$alkyl;

4.10.e) —C(O)$OR^{199}$ wherein $R^{199}$ represents $(C_1-C_3)$alkyl; or 4.10.f) —C(O)—$NR^{200}R^{201}$ wherein $R^{200}$ and $R^{201}$ each independently represents H or —$(C_1-C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1-C_3)$alkyl; and X represents O, S, S(O), $S(O)_2$, or $NR^{203}$ wherein $R^{203}$ represents H or $(C_1-C_3)$alkyl; and t represents 0, 1, or 2;

4.11) —C(O)$R^{204}$ wherein $R^{204}$ represents optionally substituted phenyl or —$(C_1-C_3)$alkyl which may optionally bear up to 3 substituents independently selected from 4.11.a) halogen;

4.11.b) optionally substituted phenyl;

4.11.c) $OR^{205}$ wherein $R^{205}$ represents H or $(C_1-C_3)$ alkyl which may optionally bear halogen; and 4.11.d)

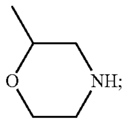

4.12) —C(O)—$NR^{206}R^{207}$ wherein $R^{206}$ and $R^{207}$ each independently represents H or $(C_1-C_3)$alkyl, or $R^{206}$ and $R^{207}$ may be joined and taken together with the N atom to which they are attached form a 5-6 membered ring which may optionally contain a ring member selected from O and S, said alkyl or ring optionally bearing up to 3 substituents independently selected from 4.12.a) halogen;

4.12.b) optionally substituted phenyl;

4.12.c) $OR^{208}$ wherein $R^{208}$ represents H or $(C_1-C_3)$ alkyl which may optionally bear halogen; and 4.12.d)

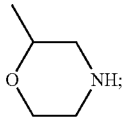

4.13) halogen; or 4.14) CN;

or a pharmaceutically acceptable salt thereof.

In a preferred embodiment, the present invention provides a compound of formula (I)

(I)

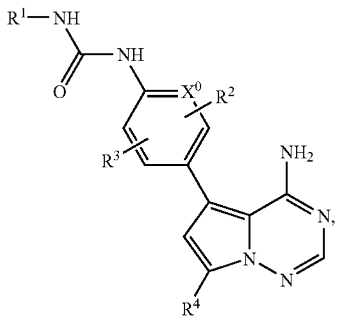

wherein:

$X^0$ represents C or N;

$R^1$ represents 1.1) phenyl which may optionally bear up to 4 substituents independently selected from the group consisting of 1.1.a) $(C_1-C_4)$alkyl, which may optionally bear up to 3 substituents independently selected from 1.1.a1) halogen;

1.1.a2) $OR^5$ wherein $R^5$ represents H or $(C_1-C_3)$ alkyl which may optionally bear halogen or —$(C_1-C_3)$mono- or di-alkylamino;

1.1.a3) —$NR^6R^7$ in which $R^6$ and $R^7$ are independently H or —$(C_1-C_3)$alkyl which may optionally bear halogen or $OR^{7a}$ wherein $R^{7a}$ represents H or $(C_1-C_3)$alkyl, or $R^6$ and $R^7$ may be joined and taken together with the N atom to which they are attached form a 5-6 membered ring which may optionally contain a ring member selected from O, S, and $NR^8$ wherein $R^8$ represents H or $(C_1-C_3)$alkyl; and 1.1.a4) a 5-6 membered heteroaromatic containing up to two heteroatoms selected from O, S, and N, 1.1.b) —$(C_3-C_6)$cycloalkyl which may optionally bear up to 2 substituents independently selected from 1.1.b1) halogen;

1.1.c) $OR^{10}$ wherein $R^{10}$ represents H; phenyl; benzyl; $(C_3-C_6)$cycloalkyl; or $(C_1-C_4)$alkyl which may optionally bear up to 3 substituents independently selected from 1.1.c1) halogen;

1.1.c2). $OR^{11}$ wherein $R^{11}$ represents H or $(C_1-C_3)$ alkyl which may optionally bear $(C_1-C_3)$mono- or di-alkylamino; and 1.1.c3) $NR^{12}R^{13}$ in which $R^{12}$ and $R^{13}$ are independently H or —$(C_1-C_3)$alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or $(C_1-C_3)$alkyl;

1.1.e) —C(O)—$NR^{16}R^{17}$ wherein $R^{16}$ represents H or $(C_1-C_3)$alkyl which may optionally bear halogen; and $R^{17}$ represents H or —$(C_1-C_4)$alkyl which is optionally substituted with 1.1.e1) halogen;
1.1.e3) phenyl;
1.1.e4) —$SO_2CH_3$;
1.1.e5) —$OR^{18}$ wherein $R^{13}$ represents H or ($C_1$-$C_3$)alkyl which may optionally bear halogen; or
1.1.e6) —$NR^{19}R^{20}$ in which $R^{19}$ and $R^{20}$ are independently H or —($C_1$-$C_3$)alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or ($C_1$-$C_3$)alkyl;
1.1.f) —$N(R^{22})$—C(O)—$R^{23}$ wherein
$R^{22}$ represents H or ($C_1$-$C_3$)alkyl; and
$R^{23}$ represents optionally substituted phenyl, or ($C_1$-$C_4$)alkyl which is optionally substituted with
1.1.f1) optionally substituted phenyl,
1.1.f2) $OR^{24}$ wherein $R^{24}$ represents H or ($C_1$-$C_3$) alkyl, or
1.1.f3) $NR^{25}R^{26}$ wherein $R^{25}$ and $R^{26}$ are independently H or —($C_1$-$C_3$)alkyl which may optionally bear halogen, or $R^{25}$ and $R^{26}$ may be joined and taken together with the N atom to which they are attached form a 5-6 membered ring which may optionally contain a ring member selected from O, S, and $NR^{27}$ wherein $R^{27}$ represents H or ($C_1$-$C_3$)alkyl;
1.1.g) —$SO_2NR^{28}R^{29}$ wherein
$R^{28}$ represents H or ($C_1$-$C_3$)alkyl which may optionally bear halogen; and
$R^{29}$ represents H or —($C_1$-$C_4$)alkyl which is optionally substituted with:
1.1.g1) halogen;
1.1.g3) phenyl;
1.1.g4) —$SO_2CH_3$;
1.1.g5) —$OR^{30}$ wherein $R^{30}$ represents H or ($C_1$-$C_3$)alkyl which may optionally bear halogen; or
1.1.g6) —$NR^{31}R^{32}$ in which $R^{31}$ and $R^{32}$ are independently H or —($C_1$-$C_3$)alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or ($C_1$-$C_3$)alkyl;
1.1.h) —$N(R^{34})$—$SO_2$—$R^{35}$ wherein
$R^{34}$ represents H or ($C_1$-$C_3$)alkyl, and
$R^{35}$ represents optionally substituted phenyl, or ($C_1$-$C_4$)alkyl which is optionally substituted with
1.1.h1) halogen;
1.1.h2) optionally substituted phenyl,
1.1.h3) $OR^{36}$ wherein $R^{36}$ represents H or ($C_1$-$C_3$) alkyl, or
1.1 h4) $NR^{37}R^{38}$ wherein $R^{37}$ and $R^{38}$ are independently H or —($C_1$-$C_3$)alkyl which may optionally bear halogen, or $R^{37}$ and $R^{38}$ may be joined and taken together with the N atom to which they are attached form a 5-6 membered ring which may optionally contain a ring member selected from O, S, and $NR^{39}$ wherein $R^{39}$ represents H or ($C_1$-$C_3$)alkyl;
1.1.i) —$NR^{40}R^{41}$ in which $R^{40}$ and $R^{41}$ are independently H or —($C_1$-$C_3$)alkyl which may optionally bear halogen or $OR^{42}$ in which $R^{42}$ represents H or ($C_1$-$C_3$)alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or ($C_1$-$C_3$) alkyl;
1.1.j) halogen;
1.1.l) $NO_2$;
1.1.m) CN; and
1.1.n) a 5-6 membered heteroaromatic containing up to two heteroatoms selected from O, S, and N;
1.1.o) —C(O)—$R^{209}$ wherein $R^{209}$ represents H or ($C_1$-$C_4$)alkyl which may optionally bear up to 3 halogens;

or $R^1$ represents
1.2) a 5-6 membered aromatic heterocycle containing up to 3 heteroatoms independently selected from the group consisting of N, O, and S; said $R^1$ heterocycle optionally bearing up to 4 substituents independently selected from the group consisting of
1.2.a) ($C_1$-$C_4$)alkyl, which may optionally bear up to 3 substituents independently selected from
1.2.a1) halogen;
1.2.a2) $OR^{45}$ wherein $R^{45}$ represents H or ($C_1$-$C_3$) alkyl which may optionally bear halogen or —($C_1$-$C_3$)mono- or di-alkylamino;
1.2.a3) —$NR^{46}R^{47}$ in which $R^{46}$ and $R^{47}$ are independently H or —($C_1$-$C_3$)alkyl which may optionally bear halogen or $OR^{47a}$ wherein $R^{47a}$ represents H or ($C_1$-$C_3$)alkyl, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or ($C_1$-$C_3$)alkyl; and
1.2.a4) a 5-6 membered heteroaromatic containing up to two heteroatoms selected from O, S, and N;
1.2.b) —($C_3$-$C_6$)cycloalkyl which may optionally bear up to 2 substituents independently selected from
1.2.b1) halogen;
1.2.c) $OR^{50}$ wherein
$R^{50}$ represents H; phenyl; benzyl; —($C_3$-$C_6$)cycloalkyl; or —($C_1$-$C_4$)alkyl which may optionally bear up to 3 substituents independently selected from
1.2.c1) halogen;
1.2.c2) $OR^{51}$ wherein $R^{51}$ represents H or ($C_1$-$C_3$) alkyl which may optionally bear —($C_1$-$C_3$) mono- or di-alkylamino; and
1.2.c3) —$NR^{52}R^{53}$ in which $R^{52}$ and $R^{53}$ are independently H or —($C_1$-$C_3$)alkyl which may optionally bear halogen, or $R^{52}$ and $R^{53}$ may be joined and taken together with the N atom to which they are attached form a 5-6 membered ring which may optionally contain a ring member selected from O, S, and $NR^{54}$ wherein $R^{54}$ represents H or ($C_1$-$C_3$)alkyl;
1.2.e) —C(O)—$NR^{56}R^{57}$ wherein
$R^{56}$ represents H or ($C_1$-$C_3$)alkyl which may optionally bear halogen; and
$R^{57}$ represents H or —($C_1$-$C_4$)alkyl which is optionally substituted with
1.2.e1) halogen;
1.2.e3) phenyl;
1.2.e4) —$SO_2CH_3$;
1.2.e5) —$OR^{58}$ wherein $R^{58}$ represents H or ($C_1$-$C_3$)alkyl which may optionally bear halogen; or 1.2.e6) —$NR^{59}R^{60}$ in which $R^{59}$ and $R^{60}$ are independently H or —$(C_1-C_3)$alkyl which may optionally bear halogen, or $R^{59}$ and $R^{60}$ may be joined and taken together with the N atom to which they are attached form a 5-6 membered ring which may optionally contain a ring member selected from O, S, and $NR^{61}$ wherein $R^{61}$ represents H or $(C_1-C_3)$alkyl;

1.2.f) —$N(R^{62})$—C(O)—$R^{63}$ wherein $R^{62}$ represents H or $(C_1-C_3)$alkyl; and $R^{63}$ represents optionally substituted phenyl, or $(C_1-C_4)$alkyl which is optionally substituted with 1.2.f1) optionally substituted phenyl, 1.2.f2) $OR^{64}$ wherein $R^{64}$ represents H or $(C_1-C_3)$ alkyl, or 1.2.f3) $NR^{65}R^{66}$ wherein $R^{65}$ and $R^{66}$ are independently H or —$(C_1-C_3)$alkyl which may optionally bear halogen, or $R^{65}$ and $R^{66}$ may be joined and taken together with the N atom to which they are attached form a 5-6 membered ring which may optionally contain a ring member selected from O, S, and $NR^{67}$ wherein $R^{67}$ represents H or $(C_1-C_3)$alkyl;

1.2.g) —$SO_2NR^{68}R^{69}$ wherein $R^{68}$ represents H or $(C_1-C_3)$alkyl which may optionally bear halogen; and $R^{69}$ represents H or —$(C_1-C_4)$alkyl which is optionally substituted with 1.2.g1) halogen;

1.2.g3) phenyl;

1.2.g4) —$SO_2CH_3$;

1.2.g5) —$OR^{70}$ wherein $R^{70}$ represents H or $(C_1-C_3)$alkyl which may optionally bear halogen; or 1.2.g6 —$NR^{71}R^{72}$ in which $R^{71}$ and $R^{72}$ are independently H or —$(C_1-C_3)$alkyl which may optionally bear halogen, or $R^{71}$ and $R^{72}$ may be joined and taken together with the N atom to which they are attached form a 5-6 membered ring which may optionally contain a ring member selected from O, S, and $NR^{73}$ wherein $R^{73}$ represents H or $(C_1-C_3)$alkyl;

1.2.h) —$N(R^{74})$—$SO_2$—$R^{75}$ wherein $R^{74}$ represents H or $(C_1-C_3)$alkyl, and $R^{75}$ represents optionally substituted phenyl, or $(C_1-C_4)$alkyl which is optionally substituted with 1.2.h1) halogen;

1.2.h2) optionally substituted phenyl, 1.2.h3) $OR^{76}$ wherein $R^{76}$ represents H or $(C_1-C_3)$ alkyl, or 1.2.h4) $NR^{77}R^{78}$ wherein $R^{77}$ and $R^{78}$ are independently H or —$(C_1-C_3)$alkyl which may optionally bear halogen, or $R^{77}$ and $R^{78}$ may be joined and taken together with the N atom to which they are attached form a 5-6 membered ring which may optionally contain a ring member selected from O, S, and $NR^{79}$ wherein $R^{79}$ represents H or $(C_1-C_3)$alkyl;

1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$ alkyl;

1.2.j) halogen;

1.2.k) optionally substituted phenyl;

1.2.l) $NO_2$;

1.2.m) CN; and 1.2.n) a 5-6 membered heteroaromatic containing up to two heteroatoms selected from O, S, and N, 1.2.o) —C(O)—$R^{210}$ wherein $R^{210}$ represents H or $(C_1-C_4)$alkyl which may optionally bear up to 3 halogens;

$R^2$ represents halogen; —$(C_1-C_5)$alkyl which may optionally bear halogen; or —$O(C_1-C_3)$alkyl which may optionally bear halogen;

$R^3$ represents hydrogen; halogen; —$(C_1-C_5)$alkyl which may optionally bear halogen; or —$O(C_1-C_3)$alkyl which may optionally bear halogen;

$R^4$ represents 4.1) —$(C_1-C_5)$alkyl which is optionally substituted with 4.1.a) —$(C_3-C_5)$cycloalkyl which may optionally bear halogen or $OR^{109}$ wherein $R^{109}$ represents H or $(C_1-C_3)$alkyl;

4.1.b)-halogen;

4.1.c) —$OR^{110}$ wherein $R^{110}$ represents H or $(C_1-C_3)$ alkyl which may optionally bear up to 3 substituents independently selected from 4.1.c1) halogen;

4.1.c2) phenyl;

4.1.c4) $OR^{111}$ wherein $R^{111}$ represents H or $(C_1-C_3)$alkyl which may optionally bear halogen; and 4.1.c5) —$NR^{112}R^{113}$ in which $R^{112}$ and $R^{113}$ are independently H or —$(C_1-C_3)$alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or $(C_1-C_3)$alkyl;

4.1.d) —$NR^{115}R^{116}$ wherein $R^{115}$ represents H or $(C_1-C_3)$alkyl which may optionally bear halogen and $R^{116}$ represents H, optionally substituted phenyl, or —$(C_1-C_5)$alkyl which may optionally bear up to 3 substituents independently selected from 4.1.d1) halogen;

4.1.d2) —$S(O)_2CH_3$;

4.1.d3) $OR^{117}$ wherein $R^{117}$ represents H or —$(C_1-C_3)$alkyl which may optionally bear halogen; and 4.1.d4) —$NR^{118}R^{119}$ in which $R^{118}$ and $R^{119}$ are independently H or —$(C_1-C_3)$alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or $(C_1-C_3)$alkyl; or 4.1.f) a 5-6 membered aromatic heterocycle containing up to two heteroatoms selected from O, S, and N;

4.2)

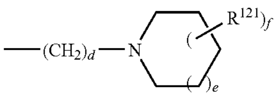

wherein $R^{121}$ represents $(C_1\text{-}C_3)$alkyl which may optionally bear halogen or —$OR^{122}$ in which $R^{122}$ represents H or —$(C_1\text{-}C_3)$alkyl;

d represents 1, 2, or 3;

e represents 0 or 1;

f represents 0, 1, or 2;

4.3)

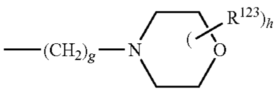

wherein $R^{123}$ represents $(C_1\text{-}C_3)$alkyl which may optionally bear halogen or —$OR^{124}$ in which $R^{124}$ represents H or —$(C_1\text{-}C_3)$alkyl;

g represents 1, 2, or 3;

h represents 0, 1, or 2;

4.4)

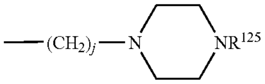

wherein $R^{125}$ represents 4.4.a) H, 4.4.b) —$(C_1\text{-}C_3)$alkyl which may optionally bear halogen or —$OR^{126}$ in which $R^{126}$ represents H or —$(C_1\text{-}C_3)$alkyl which in turn is optionally substituted with halogen;

4.4.c) —$SO_2R^{127}$ wherein $R^{127}$ represents optionally substituted phenyl, or —$(C_1\text{-}C_3)$alkyl which may optionally bear halogen or $OR^{128}$ wherein $R^{128}$ represents H or $(C_1\text{-}C_3)$alkyl;

4.4.d) —$C(O)R^{129}$ wherein $R^{129}$ represents 4.4.d1) optionally substituted phenyl, 4.4.d2) —$(C_1\text{-}C_3)$alkyl which may optionally bear up to 3 substituents independently selected from 4.4.d2.1) halogen;

4.4.d2.4) —$OR^{130}$ wherein $R^{130}$ represents H or $(C_1\text{-}C_3)$alkyl which may optionally bear halogen; and 4.4.d2.5) —$NR^{131}R^{132}$ in which $R^{131}$ and $R^{132}$ are independently H or —$(C_1\text{-}C_3)$alkyl which may optionally bear halogen, or $R^{131}$ and $R^{132}$ may be joined and taken together with the N atom to which they are attached form a 5-6 membered ring which may optionally contain a ring member selected from O, S, and $NR^{133}$ wherein $R^{133}$ represents H or $(C_1\text{-}C_3)$alkyl;

4.4.d3) —$OR^{134}$ wherein $R^{134}$ represents $(C_1\text{-}C_3)$ alkyl which may optionally bear halogen; or 4.4.d4) $NR^{135}R^{136}$ wherein $R^{135}$ and $R^{136}$ are independently H or —$(C_1\text{-}C_3)$alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{137}$ represents H or $(C_1\text{-}C_3)$alkyl; and j represents 1, 2, or 3;

4.5)

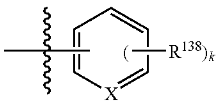

wherein

X represents C or N;

$R^{138}$ represents 4.5.a) $(C_1\text{-}C_4)$alkyl, which may optionally bear up to 3 substituents independently selected from 4.5.a1) halogen;

4.5.a2) $OR^{139}$ wherein $R^{139}$ represents H or $(C_1\text{-}C_3)$alkyl which may optionally bear halogen or —$(C_1\text{-}C_3)$mono- or di-alkylamino;

4.5.a3) —$NR^{140}R^{141}$ in which $R^{140}$ and $R^{141}$ are independently H or —$(C_1\text{-}C_3)$alkyl which may optionally bear halogen or $OR^{141a}$ wherein $R^{141a}$ represents H or $(C_1\text{-}C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1\text{-}C_3)$alkyl; and 4.5.a4) a 5-6 membered heteroaromatic containing up to two heteroatoms selected from O, S, and N, 4.5.b) —$(C_3\text{-}C_6)$cycloalkyl which may optionally bear up to 2 substituents independently selected from 4.5.b1) halogen;

4.5.c) $OR^{144}$ wherein $R^{144}$ represents H; phenyl; benzyl; $(C_3\text{-}C_6)$cycloalkyl; or $(C_1\text{-}C_4)$alkyl which may optionally bear up to 3 substituents independently selected from 4.5.c1) halogen;

4.5.c2) $OR^{145}$ wherein $R^{145}$ represents H or $(C_1\text{-}C_3)$alkyl which may optionally bear $(C_1\text{-}C_3)$ mono- or di-alkylamino; and 4.5.c3) $NR^{146}R^{147}$ in which $R^{146}$ and $R^{1473}$ are independently H or —$(C_1\text{-}C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1\text{-}C_3)$alkyl;

4.5.e) —C(O)—$NR^{150}R^{151}$ wherein $R^{150}$ represents H or $(C_1\text{-}C_3)$alkyl which may optionally bear halogen; and $R^{151}$ represents H or —$(C_1\text{-}C_4)$alkyl which is optionally substituted with 4.5.e1) halogen;

4.5.e3) phenyl;

4.5.e4) —$SO_2CH_3$;

4.5.e5) —$OR^{152}$ wherein $R^{152}$ represents H or $(C_1\text{-}C_3)$alkyl which may optionally bear halogen; or 4.5.e6) —$NR^{153}R^{154}$ in which $R^{153}$ and $R^{154}$ are independently H or —$(C_1\text{-}C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1-C_3)$alkyl;

4.5.f) —N($R^{156}$) —C(O)—$R^{157}$ wherein $R^{156}$ represents H or $(C_1-C_3)$alkyl; and $R^{157}$ represents H, optionally substituted phenyl, or $(C_1-C_4)$alkyl which is optionally substituted with 4.5.f1) optionally substituted phenyl, 4.5.f2) $OR^{158}$ wherein $R^{158}$ represents H or $(C_1-C_3)$ alkyl, or 4.5.f3) $NR^{159}R^{160}$ wherein $R^{159}$ and $R^{160}$ are independently H or —$(C_1-C_3)$alkyl which may optionally bear halogen, or $R^{159}$ and $R^{160}$ may be joined and taken together with the N atom to which they are attached form a 5-6 membered ring which may optionally contain a ring member selected from O, S, and $NR^{161}$ wherein $R^{161}$ represents H or $(C_1-C_3)$alkyl;

4.5.g) —$SO_2NR^{162}R^{163}$ wherein $R^{162}$ represents H or $(C_1-C_3)$alkyl which may optionally bear halogen; and $R^{163}$ represents H or —$(C_1-C_4)$alkyl which is optionally substituted with 4.5.g1) halogen;

4.5.g3) phenyl;

4.5.g4) —$SO_2CH_3$;

4.5.g5) —$OR^{164}$ wherein $R^{164}$ represents H or $(C_1-C_3)$alkyl which may optionally bear halogen; or 4.5.g6) —$NR^{165}R^{166}$ in which $R^{165}$ and $R^{166}$ are independently H or —$(C_1-C_3)$alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or $(C_1-C_3)$alkyl;

4.5.h) —N($R^{168}$)—$SO_2$—$R^{169}$ wherein $R^{168}$ represents H or $(C_1-C_3)$alkyl, and $R^{169}$ represents H, optionally substituted phenyl, or $(C_1-C_4)$alkyl which is optionally substituted with 4.5.h1) halogen, 4.5.h2) optionally substituted phenyl, 4.5.h3) $OR^{170}$ wherein $R^{170}$ represents H or $(C_1-C_3)$alkyl which may optionally bear halogen, or 4.5.h4) $NR^{171}R^{172}$ wherein $R^{171}$ and $R^{172}$ are independently H or —$(C_1-C_3)$alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or $(C_1-C_3)$alkyl;

4.5.i) —$NR^{174}R^{175}$ in which $R^{174}$ and $R^{175}$ are independently H or —$(C_1-C_3)$alkyl which may optionally bear halogen or $OR^{175a}$ wherein $R^{175a}$ represents H or $(C_1-C_3)$alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or $(C_1-C_3)$alkyl;

4.5.j) halogen;

4.5.l) $NO_2$;

4.5.m) CN; or 4.5.n) a 5-6 membered heteroaromatic containing up to two heteroatoms selected from O, S, and N; and k represents 0, 1, or 2;

4.6)

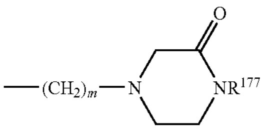

wherein $R^{177}$ represents H or —$(C_1-C_3)$alkyl; and m represents 1, 2, or 3;

4.7)

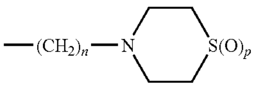

wherein n represents 1, 2, or 3; and p represents 0, 1, or 2;

4.8)

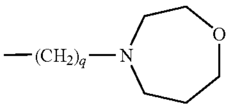

wherein q represents 1, 2, or 3;

4.9)

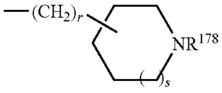

wherein $R^{178}$ represents 4.9a) H;

4.9.b) —$(C_1-C_3)$alkyl which may optionally bear halogen or —$OR^{179}$ in which $R^{179}$ represents H or $(C_1-C_3)$alkyl optionally substituted with halogen;

4.9.c) —$(C_3-C_7)$cycloalkyl which may optionally bear halogen;

4.9.d) —$(C_2-C_5)$alkenyl which may optionally bear halogen;

4.9.e) —$SO_2R^{180}$ wherein $R^{180}$ represents optionally substituted phenyl or —$(C_1-C_3)$alkyl, which may be substituted with halogen or —$OR^{181}$ wherein $R^{181}$ represents H or $(C_1-C_3)$alkyl which may optionally bear halogen;

4.9f) —C(O)$R^{182}$ wherein $R^{182}$ represents optionally substituted phenyl or $(C_1-C_3)$alkyl which may optionally bear up to 3 substituents independently selected from 4.9.f1) halogen;

4.9.f2) optionally substituted phenyl;

4.9.f3) —$S(O)_2CH_3$;

4.9.f4) $OR^{183}$ wherein $R^{183}$ represents H or $(C_1-C_3)$ alkyl which may optionally bear halogen; and 4.9.f5) —$NR^{184}R^{185}$ in which $R^{184}$ and $R^{185}$ are independently H or —$(C_1-C_3)$alkyl which may optionally bear halogen or $OR^{185a}$ wherein $R^{185a}$ represents H or $(C_1-C_3)$alkyl, or $R^{184}$ and $R^{185}$ may be joined and taken together with the N atom to which they are attached form a 5-6 membered ring which may optionally contain a ring member selected from O, S, and $NR^{186}$ wherein $R^{186}$ represents H or $(C_1-C_3)$alkyl;

4.9 g) —$C(O)OR^{187}$ wherein $R^{187}$ represents $(C_1-C_4)$ alkyl; or 4.9.h) —C(O)—$NR^{188}R^{189}$ wherein $R^{188}$ and $R^{189}$ each independently represents H or —$(C_1-C_4)$alkyl which may optionally bear halogen, or $R^{188}$ and $R^{189}$ may be joined and taken together with the N atom to which they are attached form a 5-6 membered ring which may optionally contain a ring member selected from O, S, and $NR^{190}$ wherein $R^{190}$ represents H or $(C_1-C_3)$ alkyl;

r represents 0, 1, or 2; and s represents 0 or 1;

4.10)

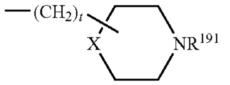

wherein $R^{191}$ represents 4.10.a) H, 4.10.b) —$(C_1-C_3)$alkyl which may optionally bear halogen or —$OR^{192}$ in which $R^{192}$ represents H or $(C_1-C_3)$alkyl;

4.10c) —$SO_2R^{193}$ wherein $R^{193}$ represents phenyl or —$(C_1-C_3)$alkyl, both of which may be substituted with halogen or $(C_1-C_3)$alkyl;

4.10.d) —$C(O)R^{194}$ wherein $R^{194}$ represents $(C_1-C_3)$ alkyl which may optionally bear up to 3 substituents independently selected from 4.10.d1) halogen;

4.10.d2) phenyl;

4.10.d4) $OR^{195}$ wherein $R^{195}$ represents H or $(C_1-C_3)$alkyl which may optionally bear halogen; and 4.10.d5) —$NR^{196}R^{197}$ in which $R^{196}$ and $R^{197}$ are independently H or —$(C_1-C_3)$alkyl which may optionally bear halogen or $OR^{197a}$ wherein $R^{197a}$ represents H or $(C_1-C_3)$alkyl, or $R^{196}$ and $R^{197}$ may be joined and taken together with the N atom to which they are attached form a 5-6 membered ring which may optionally contain a ring member selected from O, S, and $NR^{198}$ wherein $R^{198}$ represents H or $(C_1-C_3)$alkyl;

4.10.e) —$C(O)OR^{199}$ wherein $R^{199}$ represents $(C_1-C_3)$alkyl; or 4.10.f) —C(O)—$NR^{200}R^{201}$ wherein $R^{200}$ and $R^{201}$ each independently represents H or —$(C_1-C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1-C_3)$alkyl; and X represents O, S, $S(O)_2$, or $NR^{203}$ wherein $R^{203}$ represents H or $(C_1-C_3)$alkyl; and t represents 0, 1, or 2;

4.11) —$C(O)R^{204}$ wherein $R^{204}$ represents optionally substituted phenyl or —$(C_1-C_3)$alkyl which may optionally bear up to 3 substituents independently selected from 4.11.a) halogen;

4.11.b) optionally substituted phenyl;

4.11.c) $OR^{205}$ wherein $R^{205}$ represents H or $(C_1-C_3)$ alkyl which may optionally bear halogen; and 4.11.d)

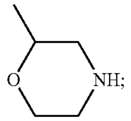

4.12) —C(O)—$NR^{206}R^{207}$ wherein $R^{206}$ and $R^{207}$ each independently represents H or $(C_1-C_3)$alkyl, or $R^{206}$ and $R^{207}$ may be joined and taken together with the N atom to which they are attached form a 5-6 membered ring which may optionally contain a ring member selected from O and S, said alkyl or ring optionally bearing up to 3 substituents independently selected from 4.12.a) halogen;

4.12.b) optionally substituted phenyl;

4.12.c) $OR^{208}$ wherein $R^{208}$ represents H or $(C_1-C_3)$ alkyl which may optionally bear halogen; and 4.12.d)

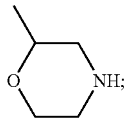

4.13) halogen; or 4.14) CN;

or a pharmaceutically acceptable salt thereof.

In yet another preferred embodiment, the present invention provides a compound of formula (I)

(I)

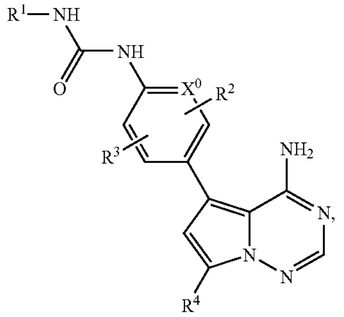

wherein:

$X^0$ represents C;

$R^1$ represents 1.1) phenyl which may optionally bear up to 4 substituents independently selected from the group consisting of 1.1.a) ($C_1$-$C_4$)alkyl, which may optionally bear up to 3 substituents independently selected from 1.1.a1) halogen;

1.1.a2) $OR^5$ wherein $R^5$ represents H or ($C_1$-$C_3$) alkyl which may optionally bear halogen;

1.1.a3) —$NR^6R^7$ in which $R^6$ and $R^7$ are independently H or —($C_1$-$C_3$)alkyl which may optionally bear halogen or $R^6$ and $R^7$ may be joined and taken together with the N atom to which they are attached form a 5-6 membered ring which may optionally contain a ring member selected from O, S, and $NR^8$ wherein $R^8$ represents H or ($C_1$-$C_3$)alkyl; and 1.1.a4) an imidazole, thiazole, oxazole, pyridine, pyrazole, pyrimidine, isoxazole, isothiazole, thiophene, or furan;

1.1.b) —($C_3$-$C_6$)cycloalkyl which may optionally bear up to 2 substituents independently selected from 1.1.b1) halogen;

1.1.c) $OR^{10}$ wherein $R^{10}$ represents H; phenyl; benzyl; ($C_3$-$C_6$)cycloalkyl; or ($C_1$-$C_4$)alkyl which may optionally bear up to 3 substituents independently selected from 1.1.c1) halogen;

1.1.c2) $OR^{11}$ wherein $R^{11}$ represents H or ($C_1$-$C_3$) alkyl; and 1.1.c3) $NR^{12}R^{13}$ in which $R^{12}$ and $R^{13}$ are independently H or —($C_1$-$C_3$)alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or ($C_1$-$C_3$)alkyl;

1.1.e) —C(O)—$NR^{16}R^{17}$ wherein $R^{16}$ represents H or ($C_1$-$C_3$)alkyl which may optionally bear halogen; and $R^{17}$ represents H or —($C_1$-$C_4$)alkyl which is optionally substituted with 1.1.e1) halogen;

1.1.e5) —$OR^{18}$ wherein $R^{18}$ represents H or ($C_1$-$C_3$)alkyl which may optionally bear halogen; or 1.1.e6) —$NR^{19}R^{20}$ in which $R^{19}$ and $R^{20}$ are independently H or —($C_1$-$C_3$)alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or ($C_1$-$C_3$)alkyl;

1.1.f) —N($R^{22}$) —C(O)—$R^{23}$ wherein $R^{22}$ represents H or ($C_1$-$C_3$)alkyl; and $R^{23}$ represents optionally substituted phenyl, or ($C_1$-$C_4$)alkyl;

1.1.g) —$SO_2NR^{28}R^{29}$ wherein $R^{28}$ represents H or ($C_1$-$C_3$)alkyl which may optionally bear halogen; and $R^{29}$ represents H or —($C_1$-$C_4$)alkyl which is optionally substituted with:

1.1.g1) halogen;

1.1.g4) —$SO_2CH_3$;

1.1.g5) —$OR^{30}$ wherein $R^{30}$ represents H or ($C_1$-$C_3$)alkyl which may optionally bear halogen; or 1.1.g6) —$NR^{31}R^{32}$ in which $R^{31}$ and $R^{32}$ are independently H or —($C_1$-$C_3$)alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or ($C_1$-$C_3$)alkyl;

1.1.h) —N($R^{34}$) —$SO_2$—$R^{35}$ wherein $R^{34}$ represents H or ($C_1$-$C_3$)alkyl, and $R^{35}$ represents optionally substituted phenyl, or ($C_1$-$C_4$)alkyl which is optionally substituted with 1.1.h1) halogen;

1.1.i) —$NR^{40}R^{44}$ in which $R^{40}$ and $R^{41}$ are independently H or —($C_1$-$C_3$)alkyl which may optionally bear halogen or $OR^{42}$ in which $R^{42}$ represents H or ($C_1$-$C_3$)alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or ($C_1$-$C_3$) alkyl;

1.1.j) halogen;

1.1.l) $NO_2$;

1.1.m) CN; and 1.1.n) an imidazole, thiazole, oxazole, pyridine, pyrazole, pyrimidine, isoxazole, isothiazole, thiophene, or furan;

1.1.o) —C(O)—$R^{209}$ wherein $R^{209}$ represents H or —($C_1$-$C_4$)alkyl which may optionally bear up to 3 halogens;

or $R^1$ represents 1.2) a 5-6 membered aromatic heterocycle selected from imidazole, thiazole, oxazole, pyridine, pyrazole, pyrimidine, isoxazole, isothiazole, thiophene, and furan; said $R^1$ heterocycle optionally bearing up to 4 substituents independently selected from the group consisting of 1.2.a) ($C_1$-$C_4$)alkyl, which may optionally bear up to 3 substituents independently selected from 1.2.a1) halogen;

1.2.a2) $OR^{45}$ wherein $R^{45}$ represents H or ($C_1$-$C_3$) alkyl which may optionally bear halogen;

1.2.a3) —$NR^{46}R^{47}$ in which $R^{46}$ and $R^{47}$ are independently H or —($C_1$-$C_3$)alkyl which may optionally bear halogen, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or ($C_1$-$C_3$)alkyl; and 1.2.a4) an imidazole, thiazole, oxazole, pyridine, pyrazole, pyrimidine, isoxazole, isothiazole, thiophene, or furan;

1.2.b)-($C_3$-$C_6$)cycloalkyl which may optionally bear up to 2 substituents independently selected from 1.2.b1) halogen;

1.2.c) $OR^{50}$ wherein $R^{50}$ represents H; phenyl; benzyl; —($C_3$-$C_6$)cycloalkyl; or —($C_1$-$C_4$)alkyl which may optionally bear up to 3 substituents independently selected from 1.2.c1) halogen;

1.2.e) —C(O)—$NR^{56}R^{57}$ wherein $R^{56}$ represents H or ($C_1$-$C_3$)alkyl which may optionally bear halogen; and $R^{57}$ represents H or —($C_1$-$C_4$)alkyl which is optionally substituted with 1.2.e1) halogen; or 1.2.e5) —$OR^{58}$ wherein $R^{58}$ represents H or ($C_1$-$C_3$)alkyl which may optionally bear halogen;

1.2f) —N($R^{62}$) —C(O)—$R^{63}$ wherein $R^{62}$ represents H or ($C_1$-$C_3$)alkyl; and $R^{63}$ represents optionally substituted phenyl, or ($C_1$-$C_4$)alkyl;

1.2.g) —$SO_2NR^{68}R^{69}$ wherein $R^{68}$ represents H or ($C_1$-$C_3$)alkyl which may optionally bear halogen; and $R^{69}$ represents H or —($C_1$-$C_4$)alkyl which is optionally substituted with 1.2.g1) halogen; or 1.2.g5) —$OR^{70}$ wherein $R^{70}$ represents H or ($C_1$-$C_3$)alkyl which may optionally bear halogen;

1.2.h) —N($R^{74}$) —$SO_2$—$R^{75}$ wherein $R^{74}$ represents H or ($C_1$-$C_3$)alkyl, and $R^{75}$ represents optionally substituted phenyl, or ($C_1$-$C_4$)alkyl which is optionally substituted with 1.2.h1) halogen;

1.2.i) —$NR^{80}R^{81}$ in which $R^{80}$ and $R^{81}$ are independently H or —($C_1$-$C_3$)alkyl which may optionally bear halogen or $OR^{81a}$ wherein $R^{81a}$ represents H or ($C_1$-$C_3$)alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or ($C_1$-$C_3$) alkyl;

1.2.j) halogen;

1.2.k) optionally substituted phenyl;

1.2.l) $NO_2$;

1.2.m) CN; and 1.2.n) an imidazole, thiazole, oxazole, pyridine, pyrazole, pyrimidine, isoxazole, isothiazole, thiophene, or furan;

1.2.o) —C(O)—$R^{210}$ wherein $R^{210}$ represents H or ($C_1$-$C_4$)alkyl which may optionally bear up to 3 halogens;

$R^2$ represents halogen; —($C_1$-$C_5$)alkyl which may optionally bear halogen; or —O($C_1$-$C_3$)alkyl which may optionally bear halogen;

$R^3$ represents hydrogen; halogen; —($C_1$-$C_5$)alkyl which may optionally bear halogen; or —O($C_1$-$C_3$)alkyl which may optionally bear halogen;

$R^4$ represents 4.1) —($C_1$-$C_5$)alkyl which is optionally substituted with 4.1.a) —($C_3$-$C_5$)cycloalkyl which may optionally bear halogen or $OR^{109}$ wherein $R^{109}$ represents H or ($C_1$-$C_3$)alkyl;

4.1.b) -halogen;

4.1.c) —$OR^{110}$ wherein $R^{110}$ represents H or ($C_1$-$C_3$) alkyl which may optionally bear up to 3 substituents independently selected from 4.1.c1) halogen;

4.1.c2) phenyl;

4.1.c4) $OR^{111}$ wherein $R^{111}$ represents H or ($C_1$-$C_3$)alkyl which may optionally bear halogen; and 4.1.c5) —$NR^{112}R^{113}$ in which $R^{112}$ and $R^{113}$ are independently H or —($C_1$-$C_3$)alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or ($C_1$-$C_3$)alkyl;

4.1.d) —$NR^{115}R^{116}$ wherein $R^{115}$ represents H or —($C_1$-$C_3$)alkyl which may optionally bear halogen and $R^{116}$ represents H, optionally substituted phenyl, or —($C_1$-$C_5$)alkyl which may optionally bear up to 3 substituents independently selected from 4.1.d1) halogen;

4.1.d2) —$S(O)_2CH_3$;

4.1.d3) $OR^{117}$ wherein $R^{117}$ represents H or ($C_1$-$C_3$)alkyl which may optionally bear halogen; and 4.1.d4) —$NR^{118}R^{119}$ in which $R^{118}$ and $R^{119}$ are independently H or —($C_1$-$C_3$)alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or ($C_1$-$C_3$)alkyl; or 4.1.f) a 5-6 membered aromatic heterocycle containing up to two heteroatoms selected from O, S, and N;

4.2)

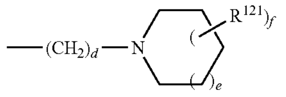

wherein $R^{121}$ represents ($C_1$-$C_3$)alkyl which may optionally bear halogen or —$OR^{122}$ in which $R^{122}$ represents H or —($C_1$-$C_3$)alkyl;

d represents 1, 2, or 3;

e represents 0 or 1;

f represents 0, 1, or 2;

4.3)

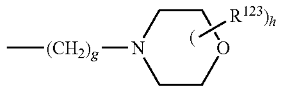

wherein $R^{123}$ represents ($C_1$-$C_3$)alkyl which may optionally bear halogen or —$OR^{124}$ in which $R^{124}$ represents H or —($C_1$-$C_3$)alkyl;

g represents 1, 2, or 3;

h represents 0, 1, or 2;

4.4)

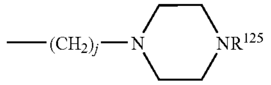

wherein $R^{125}$ represents 4.4.a) H, 4.4.b) —($C_1$-$C_3$)alkyl which may optionally bear halogen or —$OR^{126}$ in which $R^{126}$ represents H or —($C_1$-$C_3$)alkyl which in turn is optionally substituted with halogen;

4.4.c) —$SO_2R^{127}$ wherein $R^{127}$ represents optionally substituted phenyl, or —$(C_1-C_3)$alkyl which may optionally bear halogen or $OR^{128}$ wherein $R^{128}$ represents H or $(C_1-C_3)$alkyl;

4.4.d) —$C(O)R^{129}$ wherein $R^{129}$ represents 4.4.d1) optionally substituted phenyl, 4.4.d2) —$(C_1-C_3)$alkyl which may optionally bear up to 3 substituents independently selected from 4.4.d2.1) halogen;

4.4.d2.4) —$OR^{130}$ wherein $R^{130}$ represents H or $(C_1-C_3)$alkyl which may optionally bear halogen; and 4.4.d2.5) —$NR^{131}R^{132}$ in which $R^{131}$ and $R^{132}$ are independently H or —$(C_1-C_3)$alkyl which may optionally bear halogen, or $R^{131}$ and $R^{132}$ may be joined and taken together with the N atom to which they are attached form a 5-6 membered ring which may optionally contain a ring member selected from O, S, and $NR^{133}$ wherein $R^{133}$ represents H or $(C_1-C_3)$alkyl;

4.4.d3) —$OR^{134}$ wherein $R^{134}$ represents $(C_1-C_3)$ alkyl which may optionally bear halogen; or 4.4.d4) $NR^{135}R^{136}$ wherein $R^{135}$ and $R^{136}$ are independently H or —$(C_1-C_3)$alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{137}$ represents H or $(C_1-C_3)$alkyl; and j represents 1, 2, or 3;

4.5)

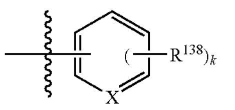

wherein

X represents C or N;

$R^{138}$ represents 4.5.a) $(C_1-C_4)$alkyl, which may optionally bear up to 3 substituents independently selected from 4.5.a1) halogen;

4.5.a2) $OR^{139}$ wherein $R^{139}$ represents H or $(C_1-C_3)$alkyl which may optionally bear halogen or —$(C_1-C_3)$mono- or di-alkylamino;

4.5.a3) —$NR^{140}R^{141}$ in which $R^{140}$ and $R^{141}$ are independently H or —$(C_1-C_3)$alkyl which may optionally bear halogen or $OR^{141a}$ wherein $R^{141a}$ represents H or $(C_1-C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1-C_3)$alkyl; and 4.5.a4) a 5-6 membered heteroaromatic containing up to two heteroatoms selected from O, S, and N, 4.5.b) —$(C_3-C_6)$cycloalkyl which may optionally bear up to 2 substituents independently selected from 4.5.b1) halogen;

4.5.c) $OR^{144}$ wherein $R^{144}$ represents H; phenyl; benzyl; $(C_3-C_6)$cycloalkyl; or $(C_1-C_4)$alkyl which may optionally bear up to 3 substituents independently selected from 4.5.c1) halogen;

4.5.c2) $OR^{145}$ wherein $R^{145}$ represents H or $(C_1-C_3)$alkyl which may optionally bear $(C_1-C_3)$ mono- or di-alkylamino; and 4.5.c3) $NR^{146}R^{147}$ in which $R^{146}$ and $R^{1473}$ are independently H or —$(C_1-C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1-C_3)$alkyl;

4.5.e) —C(O)—$NR^{150}R^{151}$ wherein $R^{150}$ represents H or $(C_1-C_3)$alkyl which may optionally bear halogen; and $R^{151}$ represents H or —$(C_1-C_4)$alkyl which is optionally substituted with 4.5.e1) halogen;

4.5.e3) phenyl;

4.5.e4) —$SO_2CH_3$;

4.5.e5) —$OR^{152}$ wherein $R^{152}$ represents H or $(C_1-C_3)$alkyl which may optionally bear halogen; or 4.5.e6) —$NR^{153}R^{154}$ in which $R^{153}$ and $R^{154}$ are independently H or —$(C_1-C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1-C_3)$alkyl;

4.5.f) —$N(R^{156})$—C(O)—$R^{157}$ wherein $R^{156}$ represents H or $(C_1-C_3)$alkyl; and $R^{157}$ represents H, optionally substituted phenyl, or $(C_1-C_4)$alkyl which is optionally substituted with 4.5.f1) optionally substituted phenyl, 4.5.f2) $OR^{158}$ wherein $R^{158}$ represents H or $(C_1-C_3)$ alkyl, or 4.5.f3) $NR^{159}R^{160}$ wherein $R^{159}$ and $R^{160}$ are independently H or —$(C_1-C_3)$alkyl which may optionally bear halogen, or $R^{159}$ and $R^{160}$ may be joined and taken together with the N atom to which they are attached form a 5-6 membered ring which may optionally contain a ring member selected from O, S, and $NR^{161}$ wherein $R^{161}$ represents H or $(C_1-C_3)$alkyl;

4.5.g) —$SO_2NR^{162}R^{163}$ wherein $R^{162}$ represents H or $(C_1-C_3)$alkyl which may optionally bear halogen; and $R^{163}$ represents H or —$(C_1-C_4)$alkyl which is optionally substituted with 4.5.g1) halogen;

4.5.g3) phenyl;

4.5.g4) —$SO_2CH_3$;

4.5.g5) —$OR^{164}$ wherein $R^{164}$ represents H or $(C_1-C_3)$alkyl which may optionally bear halogen; or 4.5.g6) —$NR^{165}R^{166}$ in which $R^{165}$ and $R^{166}$ are independently H or —$(C_1-C_3)$alkyl which may optionally bear halogen, or $R^{165}$ and $R^{166}$ may be joined and taken together with the N atom to which they are attached fowl a 5-6 membered ring which may optionally contain a ring member selected from O, S, and $NR^{167}$ wherein $R^{167}$ represents H or $(C_1\text{-}C_3)$alkyl;

4.5.h) —$N(R^{168})$—$SO_2$—$R^{169}$ wherein $R^{168}$ represents H or $(C_1\text{-}C_3)$alkyl, and $R^{169}$ represents H, optionally substituted phenyl, or $(C_1\text{-}C_4)$alkyl which is optionally substituted with 4.5.h1) halogen, 4.5.h2) optionally substituted phenyl, 4.5.h3) $OR^{170}$ wherein $R^{170}$ represents H or $(C_1\text{-}C_3)$alkyl which may optionally bear halogen, or 4.5.h4) $NR^{171}R^{172}$ wherein $R^{171}$ and $R^{172}$ are independently H or —$(C_1\text{-}C_3)$alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or $(C_1\text{-}C_3)$alkyl;

4.5i) —$NR^{174}R^{175}$ in which $R^{174}$ and $R^{175}$ are independently H or —$(C_1\text{-}C_3)$alkyl which may optionally bear halogen or $OR^{175a}$ wherein $R^{175a}$ represents H or $(C_1\text{-}C_3)$alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or $(C_1\text{-}C_3)$alkyl;

4.5.j) halogen;

4.5.l) $NO_2$;

4.5.m) CN; or 4.5.n) a 5-6 membered heteroaromatic containing up to two heteroatoms selected from O, S, and N; and k represents 0, 1, or 2;

4.6)

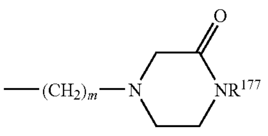

wherein $R^{177}$ represents H or —$(C_1\text{-}C_3)$alkyl; and m represents 1, 2, or 3;

4.7)

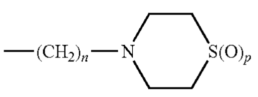

wherein n represents 1, 2, or 3; and p represents 0, 1, or 2;

4.8)

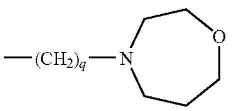

wherein q represents 1, 2, or 3;

4.9)

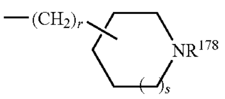

wherein $R^{178}$ represents 4.9.a) H, 4.9.b) —$(C_1\text{-}C_3)$alkyl which may optionally bear halogen or —$OR^{179}$ in which $R^{179}$ represents H or $(C_1\text{-}C_3)$alkyl optionally substituted with halogen;

4.9.c) —$(C_3\text{-}C_7)$cycloalkyl which may optionally bear halogen;

4.9.d) —$(C_2\text{-}C_5)$alkenyl which may optionally bear halogen;

4.9.e) —$SO_2R^{180}$ wherein $R^{180}$ represents optionally substituted phenyl or —$(C_1\text{-}C_3)$alkyl, which may be substituted with halogen or —$OR^{181}$ wherein $R^{181}$ represents H or $(C_1\text{-}C_3)$alkyl which may optionally hear halogen;

4.9.f) —$C(O)R^{182}$ wherein $R^{182}$ represents optionally substituted phenyl or $(C_1\text{-}C_3)$alkyl which may optionally bear up to 3 substituents independently selected from 4.9.f1) halogen;

4.9.f2) optionally substituted phenyl;

4.9.f3) —$S(O)_2CH_3$;

4.9.f4) $OR^{183}$ wherein $R^{183}$ represents H or $(C_1\text{-}C_3)$alkyl which may optionally bear halogen; and 4.9.f5) —$NR^{184}R^{185}$ in which $R^{184}$ and $R^{185}$ are independently H or —$(C_1\text{-}C_3)$alkyl which may optionally bear halogen or $OR^{185a}$ wherein $R^{185a}$ represents H or $(C_1\text{-}C_3)$alkyl, or $R^{184}$ and $R^{185}$ may be joined and taken together with the N atom to which they are attached form a 5-6 membered ring which may optionally contain a ring member selected from O, S, and $NR^{186}$ wherein $R^{186}$ represents H or $(C_1\text{-}C_3)$alkyl;

4.9g) —$C(O)OR^{187}$ wherein $R^{187}$ represents $(C_1\text{-}C_4)$alkyl; or 4.9.h) —C(O)—$NR^{188}R^{189}$ wherein $R^{188}$ and $R^{189}$ each independently represents H or —$(C_1\text{-}C_4)$alkyl which may optionally bear halogen, or $R^{188}$ and $R^{189}$ may be joined and taken together with the N atom to which they are attached form a 5-6 membered ring which may optionally contain a ring member selected from O, S, and $NR^{190}$ wherein $R^{190}$ represents H or $(C_1\text{-}C_3)$alkyl;

r represents 0, 1, or 2; and s represents 0 or 1;

4.10)

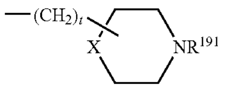

wherein $R^{191}$ represents 4.10.a) H, 4.10.b) —$(C_1$-$C_3)$alkyl which may optionally bear halogen or —$OR^{192}$ in which $R^{192}$ represents H or $(C_1$-$C_3)$alkyl;

4.10c) —$SO_2R^{193}$ wherein $R^{193}$ represents phenyl or —$(C_1$-$C_3)$alkyl, both of which may be substituted with halogen or $(C_1$-$C_3)$alkyl;

4.10.d) —$C(O)R^{194}$ wherein $R^{194}$ represents $(C_1$-$C_3)$ alkyl which may optionally bear up to 3 substituents independently selected from 4.10.d1) halogen;

4.10.d2) phenyl;

4.10.d4) $OR^{195}$ wherein $R^{195}$ represents H or $(C_1$-$C_3)$alkyl which may optionally bear halogen; and 4.10.d5) —$NR^{196}R^{197}$ in which $R^{196}$ and $R^{197}$ are independently H or —$(C_1$-$C_3)$alkyl which may optionally bear halogen or $OR^{197a}$ wherein $R^{197a}$ represents H or $(C_1$-$C_3)$alkyl, or $R^{196}$ and $R^{197}$ may be joined and taken together with the N atom to which they are attached form a 5-6 membered ring which may optionally contain a ring member selected from O, S, and $NR^{198}$ wherein $R^{198}$ represents H or $(C_1$-$C_3)$alkyl;

4.10.e) —$C(O)OR^{199}$ wherein $R^{199}$ represents $(C_1$-$C_3)$alkyl; or 4.10.f) —C(O)—$NR^{200}R^{201}$ wherein $R^{200}$ and $R^{201}$ each independently represents H or —$(C_1$-$C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1$-$C_3)$alkyl; and X represents O, S, $S(O)_2$, or $NR^{203}$ wherein $R^{203}$ represents H or $(C_1$-$C_3)$alkyl; and t represents 0, 1, or 2;

4.11) —$C(O)R^{204}$ wherein $R^{204}$ represents optionally substituted phenyl or —$(C_1$-$C_3)$alkyl which may optionally bear up to 3 substituents independently selected from 4.11.a) halogen;

4.11.b) optionally substituted phenyl;

4.11.c) $OR^{205}$ wherein $R^{205}$ represents H or $(C_1$-$C_3)$ alkyl which may optionally bear halogen; and 4.11.d)

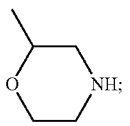

4.12) —C(O)—$NR^{206}R^{207}$ wherein $R^{206}$ and $R^{207}$ each independently represents H or $(C_1$-$C_3)$alkyl, or $R^{206}$ and $R^{207}$ may be joined and taken together with the N atom to which they are attached form a 5-6 membered ring which may optionally contain a ring member selected froth O and S, said alkyl or ring optionally bearing up to 3 substituents independently selected from 4.12.a) halogen;

4.12.b) optionally substituted phenyl;

4.12.c) $OR^{208}$ wherein $R^{208}$ represents H or $(C_1$-$C_3)$ alkyl which may optionally bear halogen; and 4.12.d)

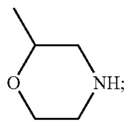

4.13) halogen; or 4.14) CN;

or a pharmaceutically acceptable salt thereof.

In still yet another preferred embodiment, the present invention provides a compound of formula (I)

(I)

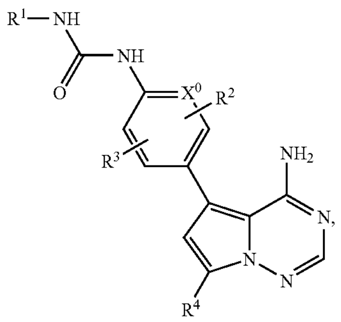

wherein:

$X^0$ represents C;

$R^1$ represents 1.1) phenyl which may optionally bear up to 4 substituents independently selected from the group consisting of 1.1.a) $(C_1$-$C_4)$alkyl, which may optionally bear up to 3 substituents independently selected from 1.1.a1) halogen;

1.1.a2) $OR^5$ wherein $R^5$ represents H or $(C_1$-$C_3)$ alkyl which may optionally bear halogen;

1.1.a3) —$NR^6R^7$ in which $R^6$ and $R^7$ are independently H or —$(C_1$-$C_3)$alkyl which may optionally bear halogen or $R^6$ and $R^7$ may be joined and taken together with the N atom to which they are attached form a 5-6 membered ring which may optionally contain a ring member selected from O, S, and $NR^8$ wherein $R^8$ represents H or $(C_1$-$C_3)$alkyl; and 1.1.a4) an imidazole, thiazole, oxazole, pyridine, pyrazole, pyrimidine, isoxazole, isothiazole, thiophene, or furan;

1.1.b) —$(C_3$-$C_6)$cycloalkyl which may optionally bear up to 2 substituents independently selected from 1.1.b1) halogen;

1.1.c) $OR^{10}$ wherein $R^{10}$ represents H; phenyl; benzyl; $(C_3$-$C_6)$cycloalkyl; or $(C_1$-$C_4)$alkyl which may optionally bear up to 3 substituents independently selected from 1.1.c1) halogen;

1.1.c2) $OR^{11}$ wherein $R^{11}$ represents H or $(C_1\text{-}C_3)$ alkyl; and 1.1.c3) $NR^{12}R^{13}$ in which $R^{12}$ and $R^{13}$ are independently H or —$(C_1\text{-}C_3)$alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or $(C_1\text{-}C_3)$alkyl;

1.1.e) —C(O)—$NR^{16}R^{17}$ wherein $R^{16}$ represents H or $(C_1\text{-}C_3)$alkyl which may optionally bear halogen; and $R^{17}$ represents H or —$(C_1\text{-}C_4)$alkyl which is optionally substituted with 1.1.e1) halogen;

1.1.e5) —$OR^{18}$ wherein $R^{18}$ represents H or $(C_1\text{-}C_3)$alkyl which may optionally bear halogen; or 1.1.e6) —$NR^{19}R^{20}$ in which $R^{19}$ and $R^{20}$ are independently H or —$(C_1\text{-}C_3)$alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or $(C_1\text{-}C_3)$alkyl;

1.1f) —$N(R^{22})$—C(O)—$R^{23}$ wherein $R^{22}$ represents H or $(C_1\text{-}C_3)$alkyl; and $R^{23}$ represents optionally substituted phenyl, or $(C_1\text{-}C_4)$alkyl;

1.1.g) —$SO_2NR^{28}R^{29}$ wherein $R^{28}$ represents H or $(C_1\text{-}C_3)$alkyl which may optionally bear halogen; and $R^{29}$ represents H or —$(C_1\text{-}C_4)$alkyl which is optionally substituted with:

1.1.g1) halogen;

1.1.g4) —$SO_2CH_3$;

1.1.g5) —$OR^{30}$ wherein $R^{30}$ represents H or $(C_1\text{-}C_3)$alkyl which may optionally bear halogen; or 1.1g6) —$NR^{31}R^{32}$ in which $R^{31}$ and $R^{32}$ are independently H or —$(C_1\text{-}C_3)$alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or $(C_1\text{-}C_3)$alkyl;

1.1.h) —$N(R^{34})$—$SO_2$—$R^{35}$ wherein $R^{34}$ represents H or $(C_1\text{-}C_3)$alkyl, and $R^{35}$ represents optionally substituted phenyl, or $(C_1\text{-}C_4)$alkyl which is optionally substituted with 1.1.h1) halogen;

1.1i) —$NR^{40}R^{41}$ in which $R^{40}$ and $R^{41}$ are independently H or —$(C_1\text{-}C_3)$alkyl which may optionally bear halogen or $OR^{42}$ in which $R^{42}$ represents H or $(C_1\text{-}C_3)$alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or $(C_1\text{-}C_3)$ alkyl;

1.1.j) halogen;

1.1.1) $NO_2$;

1.1.m) CN; and 1.1.n) an imidazole, thiazole, oxazole, pyridine, pyrazole, pyrimidine, isoxazole, isothiazole, thiophene, or furan;

1.1.o) —C(O)—$R^{209}$ wherein $R^{209}$ represents H or $(C_1\text{-}C_4)$alkyl which may optionally bear up to 3 halogens;

or $R^1$ represents 1.2) a 5-6 membered aromatic heterocycle selected from imidazole, thiazole, oxazole, pyridine, pyrazole, pyrimidine, isoxazole, isothiazole, thiophene, and furan; said $R^1$ heterocycle optionally bearing up to 4 substituents independently selected from the group consisting of 1.2.a) $(C_1\text{-}C_4)$alkyl, which may optionally bear up to 3 substituents independently selected from 1.2.a1) halogen;

1.2.a2) $OR^{45}$ wherein $R^{45}$ represents H or $(C_1\text{-}C_3)$ alkyl which may optionally bear halogen;

1.2.a3) $NR^{46}R^{47}$ in which $R^{46}$ and $R^{47}$ are independently H or —$(C_1\text{-}C_3)$alkyl which may optionally bear halogen, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or $(C_1\text{-}C_3)$alkyl; and 1.2.a4) an imidazole, thiazole, oxazole, pyridine, pyrazole, pyrimidine, isoxazole, isothiazole, thiophene, or furan;

1.2.b) —$(C_3\text{-}C_6)$cycloalkyl which may optionally bear up to 2 substituents independently selected from 1.2.b1) halogen;

1.2.c) $OR^{50}$ wherein $R^{50}$ represents H; phenyl; benzyl; —$(C_3\text{-}C_6)$cycloalkyl; or —$(C_1\text{-}C_4)$alkyl which may optionally bear up to 3 substituents independently selected from 1.2.c1) halogen;

1.2.e) —C(O)—$NR^{56}R^{57}$ wherein $R^{56}$ represents H or $(C_1\text{-}C_3)$alkyl which may optionally bear halogen; and $R^{57}$ represents H or —$(C_1\text{-}C_4)$alkyl which is optionally substituted with 1.2.e1) halogen; or 1.2.e5) —$OR^{58}$ wherein $R^{58}$ represents H or $(C_1\text{-}C_3)$alkyl which may optionally bear halogen;

1.2.f) —$N(R^{62})$—C(O)—$R^{63}$ wherein $R^{62}$ represents H or $(C_1\text{-}C_3)$alkyl; and $R^{63}$ represents optionally substituted phenyl, or $(C_1\text{-}C_4)$alkyl;

1.2.g) —$SO_2NR^{68}R^{69}$ wherein $R^{68}$ represents H or $(C_1\text{-}C_3)$alkyl which may optionally bear halogen; and $R^{69}$ represents H or —$(C_1\text{-}C_4)$alkyl which is optionally substituted with 1.2.g1) halogen; or 1.2.g5) —$OR^{70}$ wherein $R^{70}$ represents H or $(C_1\text{-}C_3)$alkyl which may optionally bear halogen;

1.2.h) —N($R^{74}$)—$SO_2$—$R^{75}$ wherein
$R^{74}$ represents H or ($C_1$-$C_3$)alkyl, and
$R^{75}$ represents optionally substituted phenyl, or ($C_1$-$C_4$)alkyl which is optionally substituted with
1.2.h1) halogen;
1.2.i) —$NR^{80}R^{81}$ in which $R^{80}$ and $R^{81}$ are independently H or —($C_1$-$C_3$)alkyl which may optionally bear halogen or $OR^{81a}$ wherein $R^{81a}$ represents H or ($C_1$-$C_3$)alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or ($C_1$-$C_3$) alkyl;
1.2.j) halogen;
1.2.k) optionally substituted phenyl;
1.2.l) $NO_2$;
1.2.m) CN; and
1.2.n) an imidazole, thiazole, oxazole, pyridine, pyrazole, pyrimidine, isoxazole, isothiazole, thiophene, or furan;
1.2.o) —C(O)—$R^{210}$ wherein $R^{210}$ represents H or ($C_1$-$C_4$)alkyl which may optionally bear up to 3 halogens;

$R^2$ represents halogen; —($C_1$-$C_5$)alkyl which may optionally bear halogen; or —O($C_1$-$C_3$)alkyl which may optionally bear halogen;

$R^3$ represents hydrogen; halogen; —($C_1$-$C_5$)alkyl which may optionally bear halogen; or —O($C_1$-$C_3$)alkyl which may optionally bear halogen;

$R^4$ represents
4.1) —($C_1$-$C_5$)alkyl which is optionally substituted with
4.1.a) —($C_3$-$C_5$)cycloalkyl which may optionally bear halogen or $OR^{109}$ wherein $R^{109}$ represents H or ($C_1$-$C_3$)alkyl;
4.1.b) -halogen;
4.1.c) —$OR^{110}$ wherein $R^{110}$ represents H or ($C_1$-$C_3$) alkyl which may optionally bear up to 3 substituents independently selected from
4.1.c1) halogen;
4.1.c2) phenyl;
4.1.c4) $OR^{111}$ wherein $R^{111}$ represents H or ($C_1$-$C_3$)alkyl which may optionally bear halogen; and
4.1.c.5) —$N^{112}R^{113}$ in which $R^{112}$ and $R^{113}$ are independently H or —($C_1$-$C_3$)alkyl which may optionally bear halogen, or $R^{112}$ and $R^{113}$ may be joined and taken together with the N atom to which they are attached form a 5-6 membered ring which may optionally contain a ring member selected from O, S, and $NR^{114}$ wherein $R^{114}$ represents H or ($C_1$-$C_3$)alkyl;
4.1.d) —$NR^{115}R^{116}$ wherein
$R^{115}$ represents H or ($C_1$-$C_3$)alkyl which may optionally bear halogen and
$R^{116}$ represents H, optionally substituted phenyl, or —($C_1$-$C_5$)alkyl which may optionally bear up to 3 substituents independently selected from
4.1.d1) halogen;
4.1.d2) —$S(O)_2CH_3$;
4.1.d3) $OR^{117}$ wherein $R^{117}$ represents H or ($C_1$-$C_3$)alkyl which may optionally bear halogen; and
4.1.d4) $NR^{118}R^{119}$ in which $R^{118}$ and $R^{119}$ are independently H or —($C_1$-$C_3$)alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or ($C_1$-$C_3$)alkyl; or
4.1.f) a 5-6 membered aromatic heterocycle containing up to two heteroatoms selected from O, S, and N;

4.2)

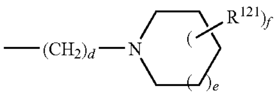

wherein $R^{121}$ represents —($C_1$-$C_3$)alkyl which may optionally bear halogen or —$OR^{122}$ in which $R^{122}$ represents H or —($C_1$-$C_3$)alkyl;
d represents 1, 2, or 3;
e represents 0 or 1;
f represents 0, 1, or 2;

4.3)

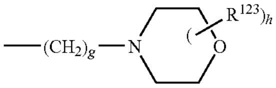

wherein $R^{123}$ represents ($C_1$-$C_3$) alkyl which may optionally bear halogen or —$OR^{124}$ in which $R^{124}$ represents H or —($C_1$-$C_3$)alkyl;
g represents 1, 2, or 3;
h represents 0, 1, or 2;

4.4)

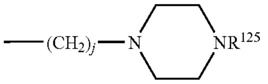

wherein
$R^{125}$ represents
4.4.a) H;
4.4.b) —($C_1$-$C_3$)alkyl which may optionally bear halogen or —$OR^{126}$ in which $R^{126}$ represents H or —($C_1$-$C_3$)alkyl which in turn is optionally substituted with halogen;
4.4.c) —$SO_2R^{127}$ wherein $R^{127}$ represents optionally substituted phenyl, or —($C_1$-$C_3$)alkyl which may optionally bear halogen or $OR^{128}$ wherein $R^{128}$ represents H or ($C_1$-$C_3$)alkyl;
4.4.d) —C(O)$R^{129}$ wherein
$R^{129}$ represents
4.4.d1) optionally substituted phenyl,
4.4.d2) —($C_1$-$C_3$)alkyl which may optionally bear up to 3 substituents independently selected from
4.4.d2.1) halogen;
4.4.d2.4) —$OR^{130}$ wherein $R^{130}$ represents H or ($C_1$-$C_3$)alkyl which may optionally bear halogen; and
4.4.d2.5) —$NR^{131}R^{132}$ in which $R^{131}$ and $R^{132}$ are independently H or —($C_1$-$C_3$)alkyl which may optionally bear halogen, or $R^{131}$ and $R^{132}$ may be joined and taken together with the N atom to which they are attached form a 5-6 membered ring which may optionally contain a ring member selected from O, S, and $NR^{133}$ wherein $R^{133}$ represents H or $(C_1-C_3)$alkyl;

4.4.d3) —$OR^{134}$ wherein $R^{134}$ represents $(C_1-C_3)$ alkyl which may optionally bear halogen; or 4.4.d4) $NR^{135}R^{136}$ wherein $R^{135}$ and $R^{136}$ are independently H or —$(C_1-C_3)$alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{437}$ represents H or $(C_1-C_3)$alkyl; and j represents 1, 2, or 3;

4.5)

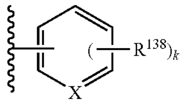

wherein

X represents C or N;

$R^{138}$ represents 4.5.a) $(C_1-C_4)$alkyl, which may optionally bear up to 3 substituents independently selected from 4.5.a1) halogen;

4.5.a2) $OR^{139}$ wherein $R^{139}$ represents H or $(C_1-C_3)$alkyl which may optionally bear halogen or —$(C_1-C_3)$mono- or di-alkylamino;

4.5.a3) —$NR^{140}R^{141}$ in which $R^{140}$ and $R^{141}$ are independently H or —$(C_1-C_3)$alkyl which may optionally bear halogen or $OR^{141a}$ wherein $R^{141a}$ represents H or $(C_1-C_3)$alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or $(C_1-C_3)$alkyl; and 4.5.a4) a 5-6 membered heteroaromatic containing up to two heteroatoms selected from O, S, and N, 4.5.b) —$(C_3-C_6)$cycloalkyl which may optionally bear up to 2 substituents independently selected from 4.5.b1) halogen;

4.5.c) $OR^{144}$ wherein $R^{144}$ represents H; phenyl; benzyl; $(C_3-C_6)$cycloalkyl; or $(C_1-C_4)$alkyl which may optionally bear up to 3 substituents independently selected from 4.5.c1) halogen;

4.5.c2) $OR^{145}$ wherein $R^{145}$ represents H or $(C_1-C_3)$alkyl which may optionally bear $(C_1-C_3)$ mono- or di-alkylamino; and 4.5.c3) $NR^{146}R^{147}$ in which $R^{146}$ and $R^{1473}$ are independently H or —$(C_1-C_3)$alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or $(C_1-C_3)$alkyl;

4.5.e) —C(O)—$NR^{150}R^{151}$ wherein $R^{150}$ represents H or $(C_1-C_3)$alkyl which may optionally bear halogen; and $R^{151}$ represents H or —$(C_1-C_4)$alkyl which is optionally substituted with 4.5.e1) halogen;

4.5.e3) phenyl;

4.5.e4) —$SO_2CH_3$;

4.5.e5) —$OR^{152}$ wherein $R^{152}$ represents H or $(C_1-C_3)$alkyl which may optionally bear halogen; or 4.5.e6) —$NR^{153}R^{154}$ in which $R^{153}$ and $R^{154}$ are independently H or —$(C_1-C_3)$alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or $(C_1-C_3)$alkyl;

4.5.f) —$N(R^{156})$ —C(O)—$R^{157}$ wherein $R^{156}$ represents H or $(C_1-C_3)$alkyl; and $R^{157}$ represents H, optionally substituted phenyl, or $(C_1-C_4)$alkyl which is optionally substituted with 4.5.f1) optionally substituted phenyl, 4.5.f2) $OR^{158}$ wherein $R^{158}$ represents H or $(C_1-C_3)$ alkyl, or 4.5.f3) $NR^{159}R^{160}$ wherein $R^{159}$ and $R^{160}$ are independently H or —$(C_1-C_3)$alkyl which may optionally bear halogen, or $R^{159}$ and $R^{160}$ may be joined and taken together with the N atom to which they are attached form a 5-6 membered ring which may optionally contain a ring member selected from O, S, and $NR^{161}$ wherein $R^{161}$ represents H or $(C_1-C_3)$alkyl;

4.5.g) —$SO_2NR^{162}R^{163}$ wherein $R^{162}$ represents H or $(C_1-C_3)$alkyl which may optionally bear halogen; and $R^{163}$ represents H or —$(C_1-C_4)$alkyl which is optionally substituted with 4.5.g1) halogen;

4.5.g3) phenyl;

4.5.g4) —$SO_2CH_3$;

4.5.g5) —$OR^{164}$ wherein $R^{164}$ represents H or $(C_1-C_3)$alkyl which may optionally bear halogen; or 4.5.g6) —$NR^{165}R^{166}$ in which $R^{165}$ and $R^{166}$ are independently H or —$(C_1-C_3)$alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or $(C_1-C_3)$alkyl;

4.5.h) —$N(R^{168})$—$SO_2$—$R^{169}$ wherein $R^{168}$ represents H or $(C_1-C_3)$alkyl, and $R^{169}$ represents H, optionally substituted phenyl, or $(C_1-C_4)$alkyl which is optionally substituted with 4.5.h1) halogen, 4.5.h2) optionally substituted phenyl, 4.5.h3) $OR^{170}$ wherein $R^{170}$ represents H or $(C_1-C_3)$alkyl which may optionally bear halogen, or 4.5.h4) $NR^{171}R^{172}$ wherein $R^{171}$ and $R^{172}$ are independently H or —$(C_1-C_3)$alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or $(C_1$-$C_3)$alkyl;

4.5.i) —$NR^{174}R^{175}$ in which $R^{174}$ and $R^{175}$ are independently H or —$(C_1$-$C_3)$alkyl which may optionally bear halogen or $OR^{175a}$ wherein $R^{175a}$ represents H or $(C_1$-$C_3)$alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or $(C_1$-$C_3)$alkyl;

4.5.j) halogen;

4.5.l) $NO_2$;

4.5.m) CN; or 4.5.n) a 5-6 membered heteroaromatic containing up to two heteroatoms selected from O, S, and N; and k represents 0, 1, or 2;

4.6)

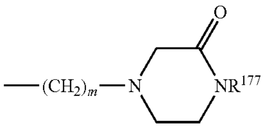

wherein $R^{177}$ represents H or —$(C_1$-$C_3)$alkyl; and m represents 1, 2, or 3;

4.7)

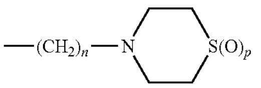

wherein n represents 1, 2, or 3; and p represents 0, 1, or 2;

4.8)

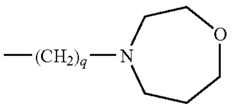

wherein q represents 1, 2, or 3;

4.9)

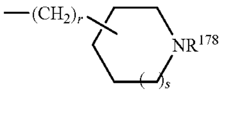

wherein $R^{178}$ represents 4.9.a) H, 4.9.b) —$(C_1$-$C_3)$alkyl which may optionally bear halogen or —$OR^{179}$ in which $R^{179}$ represents H or $(C_1$-$C_3)$alkyl optionally substituted with halogen;

4.9.c) $(C_3$-$C_7)$cycloalkyl which may optionally bear halogen;

4.9.d) $(C_2$-$C_5)$alkenyl which may optionally bear halogen;

4.9.e) —$SO_2R^{180}$ wherein $R^{180}$ represents optionally substituted phenyl or —$(C_1$-$C_3)$alkyl, which may be substituted with halogen or —$OR^{181}$ wherein $R^{181}$ represents H or $(C_1$-$C_3)$alkyl which may optionally bear halogen;

4.9.f) —$C(O)R^{182}$ wherein $R^{182}$ represents optionally substituted phenyl or $(C_1$-$C_3)$alkyl which may optionally bear up to 3 substituents independently selected from 4.9.f1) halogen;

4.9.f2) optionally substituted phenyl;

4.9.f3) —$S(O)_2CH_3$;

4.9.f4) $OR^{183}$ wherein $R^{183}$ represents H or $(C_1$-$C_3)$alkyl which may optionally bear halogen; and 4.9.f5) —$NR^{184}R^{185}$ in which $R^{184}$ and $R^{185}$ are independently H or —$(C_1$-$C_3)$alkyl which may optionally bear halogen or $OR^{185a}$ wherein $R^{185a}$ represents H or $(C_1$-$C_3)$alkyl, or $R^{184}$ and $R^{185}$ may be joined and taken together with the N atom to which they are attached form a 5-6 membered ring which may optionally contain a ring member selected from O, S, and $NR^{186}$ wherein $R^{186}$ represents H or $(C_1$-$C_3)$alkyl;

4.9 g) —$C(O)OR^{187}$ wherein $R^{187}$ represents $(C_1$-$C_4)$alkyl; or 4.9.h) —$C(O)$—$NR^{188}R^{189}$ wherein $R^{188}$ and $R^{189}$ each independently represents H or —$(C_1$-$C_4)$alkyl which may optionally bear halogen, or $R^{188}$ and $R^{189}$ may be joined and taken together with the N atom to which they are attached form a 5-6 membered ring which may optionally contain a ring member selected from O, S, and $NR^{190}$ wherein $R^{190}$ represents H or $(C_1$-$C_3)$alkyl;

r represents 0, 1, or 2; and s represents 0 or 1;

4.10)

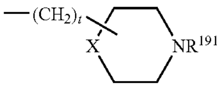

wherein $R^{191}$ represents 4.10.a) H, 4.10.b) —$(C_1$-$C_3)$alkyl which may optionally bear halogen or —$OR^{192}$ in which $R^{192}$ represents H or $(C_1$-$C_3)$alkyl;

4.10c) —$SO_2R^{193}$ wherein $R^{193}$ represents phenyl or —$(C_1$-$C_3)$alkyl, both of which may be substituted with halogen or $(C_1$-$C_3)$alkyl;

4.10.d) —$C(O)R^{194}$ wherein $R^{194}$ represents $(C_1$-$C_3)$alkyl which may optionally bear up to 3 substituents independently selected from 4.10.d1) halogen;

4.10.d2) phenyl;

4.10.d4) $OR^{195}$ wherein $R^{195}$ represents H or $(C_1$-$C_3)$alkyl which may optionally bear halogen; and 4.10.d5) —$NR^{196}R^{197}$ in which $R^{196}$ and $R^{197}$ are independently H or —$(C_1$-$C_3)$alkyl which may optionally bear halogen or $OR^{197a}$ wherein $R^{197a}$ represents H or $(C_1$-$C_3)$alkyl, or $R^{196}$ and $R^{197}$ may be joined and taken together with the N atom to which they are attached form a 5-6 membered ring which may optionally contain a ring member selected from O, S, and $NR^{198}$ wherein $R^{198}$ represents H or $(C_1-C_3)$alkyl;

4.10.e) —$C(O)OR^{199}$ wherein $R^{199}$ represents $(C_1-C_3)$alkyl; or 4.10.f) —C(O)—$NR^{200}R^{201}$ wherein $R^{200}$ and $R^{201}$ each independently represents H or —$(C_1-C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1-C_3)$alkyl; and X represents O, S, $S(O)_2$, or $NR^{203}$ wherein $R^{203}$ represents H or $(C_1-C_3)$alkyl; and t represents 0, 1, or 2;

4.11) —$C(O)R^{204}$ wherein $R^{204}$ represents optionally substituted phenyl or —$(C_1-C_3)$alkyl which may optionally bear up to 3 substituents independently selected from 4.11.a) halogen;

4.11.b) optionally substituted phenyl;

4.11.c) $OR^{205}$ wherein $R^{205}$ represents H or $(C_1-C_3)$ alkyl which may optionally bear halogen; and 4.11.d)

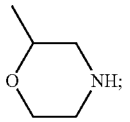

4.12) —C(O) —$NR^{206}R^{207}$ wherein $R^{206}$ and $R^{207}$ each independently represents H or $(C_1-C_3)$alkyl, or $R^{206}$ and $R^{207}$ may be joined and taken together with the N atom to which they are attached form a 5-6 membered ring which may optionally contain a ring member selected from O and S, said alkyl or ring optionally bearing up to 3 substituents independently selected from 4.12.a) halogen;

4.12.b) optionally substituted phenyl;

4.12.c) $OR^{208}$ wherein $R^{208}$ represents H or $(C_1-C_3)$ alkyl which may optionally bear halogen; and 4.12.d)

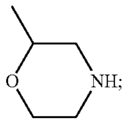

4.13) halogen; or 4.14) CN;

or a pharmaceutically acceptable salt thereof.

In another embodiment, the present invention provides a compound of formula (I)

(I)

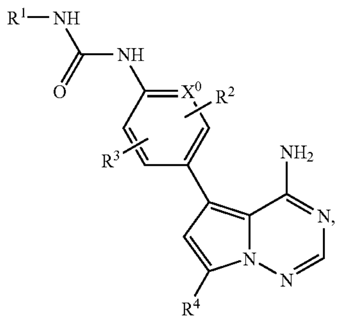

wherein:

$X^0$ represents C or N;

$R^1$ represents 1.1) phenyl which may optionally bear up to 4 substituents independently selected from the group consisting of 1.1.a) $(C_1-C_4)$alkyl, which may optionally bear up to 3 halogen substituents;

1.1.b) $OR^{10}$ wherein $R^{10}$ represents H; phenyl; benzyl; $(C_3-C_6)$cycloalkyl; or $(C_1-C_4)$alkyl which may optionally bear up to 3 halogen substituents;

1.1.c) halogen; and 1.1.d) —C(O)—$R^{209}$ wherein $R^{209}$ represents H or $(C_1-C_4)$alkyl which may optionally bear up to 3 halogens;

or $R^1$ represents 1.2) a 5-6 membered aromatic heterocycle selected from imidazole, thiazole, oxazole, pyridine, pyrazole, pyrimidine, isoxazole, isothiazole, thiophene, and furan; said $R^1$ heterocycle optionally bearing up to 4 substituents independently selected from the group consisting of 1.2.a) $(C_1-C_4)$alkyl, which may optionally bear up to 3 halogen substituents;

1.2.b) $OR^{50}$ wherein $R^{50}$ represents H; phenyl; benzyl; —$(C_3-C_6)$cycloalkyl; or —$(C_1-C_4)$alkyl which may optionally bear up to 3 halogen substituents;

1.2.c) halogen; and 1.2.d) —C(O)—$R^{210}$ wherein $R^{210}$ represents H or $(C_1-C_4)$alkyl which may optionally bear up to 3 halogens;

$R^2$ represents halogen; —$(C_1-C_5)$alkyl which may optionally bear halogen; or —$O(C_1-C_3)$alkyl which may optionally bear halogen;

$R^3$ represents hydrogen; halogen; —$(C_1-C_5)$alkyl which may optionally bear halogen; or —$O(C_1-C_3)$alkyl which may optionally bear halogen;

$R^4$ represents 4.1) —$(C_1-C_5)$alkyl which is optionally substituted with 4.1.a) -halogen;

4.1.b) —$OR^{110}$ wherein $R^{110}$ represents H or $(C_1-C_3)$ alkyl which may optionally bear up to 3 halogen substituents 4.1.c) —$NR^{115}R^{116}$ wherein $R^{115}$ represents H or $(C_1-C_3)$alkyl which may optionally bear halogen and $R^{116}$ represents H, optionally substituted phenyl, or —$(C_1$-$C_5)$alkyl which may optionally bear up to 3 substituents independently selected from 4.1.c1) halogen; and 4.1.c2) $OR^{117}$ wherein $R^{117}$ represents H or $(C_1$-$C_3)$alkyl which may optionally bear halogen;

4.2)

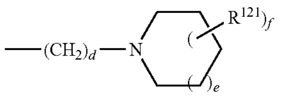

wherein $R^{121}$ represents $(C_1$-$C_3)$alkyl which may optionally bear halogen or —O—$(C_1$-$C_3)$alkyl;

d represents 1, 2, or 3;

e represents 0 or 1;

f represents 0, 1, or 2;

4.3)

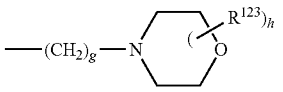

wherein $R^{123}$ represents $(C_1$-$C_3)$alkyl which may optionally bear halogen;

g represents 1, 2, or 3;

h represents 0, 1, or 2;

4.4)

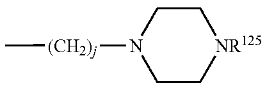

wherein $R^{125}$ represents 4.4.a) H, 4.4.b) —$(C_1$-$C_3)$alkyl which may optionally bear halogen;

4.4.c) —$SO_2R^{127}$ wherein $R^{127}$ represents optionally substituted phenyl, or —$(C_1$-$C_3)$alkyl which may optionally bear halogen;

4.4.d) —$C(O)R^{129}$ wherein $R^{129}$ represents 4.4.d1) optionally substituted phenyl, 4.4.d2) —$(C_1$-$C_3)$alkyl which may optionally bear up to 3 substituents independently selected from 4.4.d2.1) halogen; and 4.4.d2.4) —$OR^{130}$ wherein $R^{130}$ represents H or $(C_1$-$C_3)$alkyl which may optionally bear halogen;

4.4.d3) —$OR^{134}$ wherein $R^{134}$ represents $(C_1$-$C_3)$ alkyl; or 4.4.d4) $NR^{135}R^{136}$ wherein $R^{135}$ and $R^{136}$ are independently H or —$(C_1$-$C_3)$alkyl which may optionally bear halogen; and j represents 1, 2, or 3;

4.5)

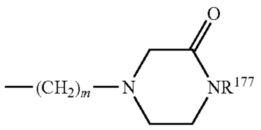

wherein $R^{177}$ represents H or —$(C_1$-$C_3)$alkyl; and m represents 1, 2, or 3;

4.6)

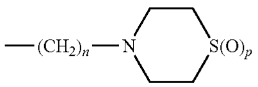

wherein n represents 1, 2, or 3; and p represents 0, 1, or 2;

4.7)

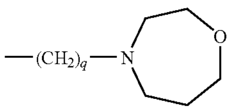

wherein q represents 1, 2, or 3;

4.8)

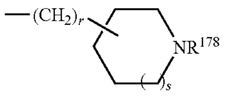

wherein $R^{178}$ represents 4.8.a) H, 4.8.b) —$(C_1$-$C_3)$alkyl which may optionally bear halogen;

4.8.c) —$SO_2R^{180}$ wherein $R^{180}$ represents optionally substituted phenyl or —$(C_1$-$C_3)$alkyl, which may be substituted with halogen;

4.8.d) —$C(O)R^{182}$ wherein $R^{182}$ represents optionally substituted phenyl or $(C_1$-$C_3)$alkyl which may optionally bear up to 3 substituents independently selected from 4.9.d1) halogen; and 4.9.d4) $OR^{183}$ wherein $R^{183}$ represents H or $(C_1$-$C_3)$alkyl which may optionally bear halogen;

4.8e) —$C(O)OR^{187}$ wherein $R^{187}$ represents $(C_1$-$C_3)$ alkyl; or 4.8f) —C(O)—$NR^{188}R^{189}$ wherein $R^{188}$ and $R^{189}$ each independently represents H or —$(C_1$-$C_3)$alkyl which may optionally bear halogen;

r represents 0, 1, or 2; and s represents 0 or 1;

4.9)

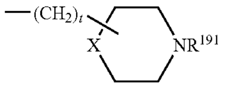

wherein $R^{191}$ represents 4.9.a) H;

4.9.b) ($C_1$-$C_3$)alkyl which may be optionally bear halogen;

4.9.c) —$SO_2R^{193}$ wherein $R^{193}$ represents phenyl or —($C_1$-$C_3$)alkyl, both of which may be substituted with halogen;

4.9.d) —C(O)$R^{194}$ wherein $R^{194}$ represents ($C_1$-$C_3$) alkyl which may optionally bear up to 3 substituents independently selected from 4.10.d1) halogen;

4.10.d2) phenyl; and 4.10.d4) $OR^{195}$ wherein $R^{195}$ represents H or ($C_1$-$C_3$)alkyl which may optionally bear halogen;

4.9.e) —C(O)$OR^{199}$ wherein $R^{199}$ represents ($C_1$-$C_3$) alkyl; or 4.9.f) —C(O)—$NR^{200}R^{201}$ wherein $R^{200}$ and $R^{201}$ each independently represents H or —($C_1$-$C_3$)alkyl which may optionally bear halogen;

X represents O, S, $S(O)_2$, or $NR^{203}$ wherein $R^{203}$ represents H or ($C_1$-$C_3$)alkyl; and t represents 0, 1, or 2;

4.10) —C(O)$R^{204}$ wherein $R^{204}$ represents optionally substituted phenyl or —($C_1$-$C_3$)alkyl which may optionally bear up to 3 substituents independently selected from 4.10.a) halogen;

4.10.b) optionally substituted phenyl;

4.10.c) $OR^{205}$ wherein $R^{205}$ represents H or —($C_1$-$C_3$)alkyl which may optionally bear halogen; and 4.10.d)

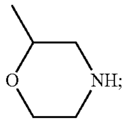

4.11) —C(O)—$NR^{206}R^{207}$ wherein $R^{206}$ and $R^{207}$ each independently represents H or ($C_1$-$C_3$)alkyl, or $R^{206}$ and $R^{207}$ may be joined and taken together with the N atom to which they are attached form a 5-6 membered ring which may optionally contain a ring member selected from O and S, said alkyl or ring optionally bearing up to 3 substituents independently selected from 4.11.a) halogen;

4.11.b) optionally substituted phenyl;

4.11.c) $OR^{208}$ wherein $R^{208}$ represents H or ($C_1$-$C_3$) alkyl which may optionally bear halogen; and 4.11.d)

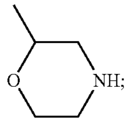

4.12) halogen; or 4.13) CN;

or a pharmaceutically acceptable salt thereof.

In still another preferred embodiment, the present invention provides a compound of formula (I)

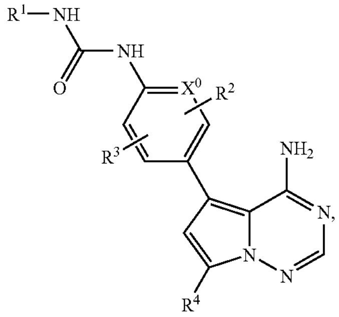

(I)

wherein:

$X^0$ represents C;

$R^1$ represents 1.1) phenyl bearing 1 or 2 substituents independently selected from the group consisting of 1.1.a) methyl;

1.1.b) trifluoromethyl; and 1.1.c) halogen;

1.1.d) —C(O)($C_1$-$C_4$)alkyl which may optionally bear up to 3 halogens;

or $R^1$ represents 1.2) a 5-6 membered aromatic heterocycle selected from imidazole, thiazole, oxazole, pyridine, pyrazole, pyrimidine, isoxazole, isothiazole, thiophene, and furan; said $R^1$ heterocycle optionally bearing up to 4 substituents independently selected from the group consisting of 1.2.a) methyl;

1.2.b) trifluoromethyl;

1.2.c) halogen; and 1.2.d) —C(O)($C_1$-$C_4$)alkyl which may optionally bear up to 3 halogens;

$R^2$ represents halogen;

$R^3$ represents hydrogen or halogen; and $R^4$ represents 4.2)

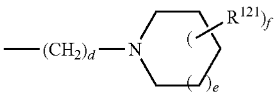

wherein $R^{121}$ represents ($C_1$-$C_3$)alkyl which may optionally bear halogen or —O—($C_1$-$C_3$)alkyl;

d represents 1, 2, or 3;

e represents 0 or 1;

f represents 0, 1, or 2;

4.3)

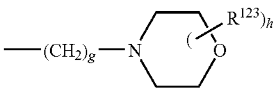

wherein $R^{123}$ represents $(C_1\text{-}C_3)$alkyl which may optionally bear halogen;

g represents 1, 2, or 3;

h represents 0, 1, or 2;

4.4)

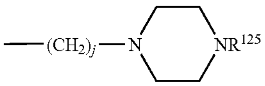

wherein $R^{125}$ represents 4.4.a) H, 4.4.b) —$(C_1\text{-}C_3)$alkyl which may optionally bear halogen;

4.4.d) —C(O)$R^{129}$ wherein $R^{129}$ represents 4.4.d1) optionally substituted phenyl, 4.4.d2) —$(C_1\text{-}C_3)$alkyl which may optionally bear up to 3 substituents independently selected from 4.4.d2.1) halogen; and 4.4.d2.4) —$OR^{130}$ wherein $R^{130}$ represents H or $(C_1\text{-}C_3)$alkyl which may optionally bear halogen;

4.4.d3) —$OR^{134}$ wherein $R^{134}$ represents $(C_1\text{-}C_3)$ alkyl; or 4.4.d4) $NR^{135}R^{136}$ wherein $R^{135}$ and $R^{136}$ are independently H or —$(C_1\text{-}C_3)$alkyl which may optionally bear halogen; and j represents 1, 2, or 3;

4.5)

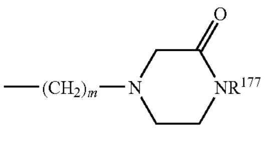

wherein $R^{177}$ represents H or —$(C_1\text{-}C_3)$alkyl; and m represents 1, 2, or 3;

4.6)

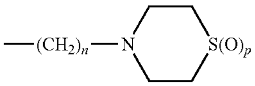

wherein n represents 1, 2, or 3; and p represents 0, 1, or 2;

4.7)

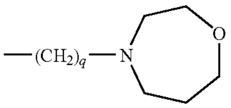

wherein q represents 1, 2, or 3;

4.8)

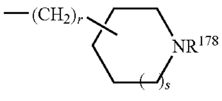

wherein $R^{178}$ represents 4.8.a) H;

4.8.b) $(C_1\text{-}C_3)$alkyl which may optionally bear halogen;

4.8.d) —C(O)$R^{182}$ wherein $R^{182}$ represents optionally substituted phenyl or $(C_1\text{-}C_3)$alkyl which may optionally bear up to 3 substituents independently selected from 4.8.d1) halogen; and 4.8.d4) $OR^{183}$ wherein $R^{183}$ represents H or $(C_1\text{-}C_3)$alkyl which may optionally bear halogen;

4.8e) —C(O)$OR^{187}$ wherein $R^{187}$ represents $(C_1\text{-}C_3)$ alkyl; or 4.8.f) —C(O)—$NR^{188}R^{189}$ wherein $R^{188}$ and $R^{189}$ each independently represents H or —$(C_1\text{-}C_3)$alkyl which may optionally bear halogen;

r represents 0, 1, or 2; and s represents 0 or 1;

or a pharmaceutically acceptable salt thereof.

In a distinct embodiment, the present invention encompasses a compound having the formula:

N-{4-[4-amino-7-(morpholin-4-ylmethyl)pyrrolo[2,1-f][1,2,4]triazin-5-yl]-2-fluorophenyl}-N'-[2-fluoro-5-(trifluoromethyl)phenyl]urea;

N-{4-[4-amino-7-(morpholin-4-ylmethyl)pyrrolo[2,1-f][1,2,4]triazin-5-yl]phenyl}-N'-(3-tert-butylisoxazol-5-yl) urea;

N-{4-[4-amino-7-(morpholin-4-ylmethyl)pyrrolo[2,1f][1,2,4]triazin-5-yl]phenyl}-N'-[4-(trifluoromethyl)pyridin-2-yl]urea;

N-{4-[4-amino-7-(morpholin-4-ylmethyl)pyrrolo[2,1-f][1,2,4]triazin-5-yl]phenyl}-N'-[2-fluoro-5-(trifluoromethyl) phenyl]urea;

N-{4-[4-amino-7-(morpholin-4-ylmethyl)pyrrolo[2,1f][1,2,4]triazin-5-yl]phenyl}-N'-[3-(trifluoromethyl)phenyl] urea;

N-{4-[4-amino-7-(morpholin-4-ylmethyl)pyrrolo[2,1-f][1,2,4]triazin-5-yl]phenyl}-N'-[4-fluoro-3-(trifluoromethyl) phenyl]urea;

N-{4-[4-amino-7-(morpholin-4-ylmethyl)pyrrolo[2,1f][1,2,4]triazin-5-yl]-2,6-difluorophenyl}-N'-[2-fluoro-5-(trifluoromethyl)phenyl]urea;

N-{4-[4-amino-7-(morpholin-4-ylmethyl)pyrrolo[2,1f][1,2,4]triazin-5-yl]-2-fluorophenyl}-N'-[4-(trifluoromethyl) pyridin-2-yl]urea;

N-{5-[4-amino-7-(morpholin-4-ylmethyl)pyrrolo[2,1-f][1,2,4]triazin-5-yl]pyridin-2-yl}[2-fluoro-5-(trifluoromethyl)phenyl]urea;

N-{4-[4-amino-7-(morpholin-4-ylmethyl)pyrrolo[2,1f][1,2,4]triazin-5-yl]-2-fluorophenyl}-N'[3-(trifluoromethyl)phenyl]urea;

N-{4-[4-amino-7-(morpholin-4-ylmethyl)pyrrolo[2,1f][1,2,4]triazin-5-yl]-3-fluorophenyl}-N'-[4-(trifluoromethyl)pyridin-2-yl]urea;

N-{5-[4-amino-7-(morpholin-4-ylmethyl)pyrrolo[2,1f][1,2,4]triazin-5-yl]pyridin-2-yl}-N'[4-(trifluoromethyl)pyridin-2-yl]urea;

N-{4-[4-amino-7-(morpholin-4-ylmethyl)pyrrolo[2,1-f][1,2,4]triazin-5-yl]-2-difluorophenyl}-N'[4-(trifluoromethyl)pyridin-2-yl]urea;

N-{4-[4-amino-7-(morpholin-4-ylmethyl)pyrrolo[2,1f][1,2,4]triazin-5-yl]-2,6-difluorophenyl}-N'-[4-(trifluoromethyl)pyridin-2-yl]urea;

N-{4-[4-amino-7-(morpholin-4-ylmethyl)pyrrolo[2,1f][1,2,4]triazin-5-yl]-2,5-difluorophenyl}-N'-[2-fluoro-5-(trifluoromethyl)phenyl]urea;

N-{4-[4-amino-7-(morpholin-4-ylmethyl)pyrrolo[2,1f][1,2,4]triazin-5-yl]-3-fluorophenyl}-N'-[2-fluoro-5-(trifluoromethyl)phenyl]urea;

N-{4-[4-amino-7-(morpholin-4-ylmethyl)pyrrolo[2,1f][1,2,4]triazin-5-yl]-3-fluorophenyl}-N'-[3-(trifluoromethyl)phenyl]urea;

N-{5-[4-amino-7-(morpholin-4-ylmethyl)pyrrolo[2,1f][1,2,4]triazin-5-yl]pyridin-2-yl}-N'-[4-fluoro-3-(trifluoromethyl)phenyl]urea;

N-{5-[4-amino-7-(morpholin-4-ylmethyl)pyrrolo[2,1f][1,2,4]triazin-5-yl]pyridin-2-yl}-N'-[4-chloro-3-(trifluoromethyl)phenyl]urea;

N-{5-[4-amino-7-(morpholin-4-ylmethyl)pyrrolo[2,1-f][1,2,4]triazin-5-yl]pyridin-2-yl}N'-[3-(trifluoromethyl)phenyl]urea;

N-{5-[4-amino-7-(morpholin-4-ylmethyl)pyrrolo[2,1f][1,2,4]triazin-5-yl]pyridin-2-yl}N'-[2-fluoro-3-(trifluoromethyl)phenyl]urea;

N-{5-[4-amino-7-(morpholin-4-ylmethyl)pyrrolo[2,1f][1,2,4]triazin-5-yl]pyridin-2-yl}N'-[3-fluoro-5-(trifluoromethyl)phenyl]urea;

N-{4-[4-amino-7-(morpholin-4-ylmethyl)pyrrolo[2,1-f][1,2,4]triazin-5-yl]-2,5-difluorophenyl}-N'-[4-fluoro-3-(trifluoromethyl)phenyl]urea;

N-{4-[4-amino-7-(morpholin-4-ylmethyl)pyrrolo[2,1-f][1,2,4]triazin-5-yl]-2,5-difluorophenyl}-N'-[3-(trifluoromethyl)phenyl]urea;

N-{4-[4-amino-7-(morpholin-4-ylmethyl)pyrrolo[2,1-f][1,2,4]triazin-5-yl]-2-methylphenyl}-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-2-methylphenyl}-N'-[4-(trifluoromethyl)pyridin-2-yl]urea;

N-{4-[4-amino-7-(morpholin-4-ylmethyl)pyrrolo[2,1-f][1,2,4]triazin-5-yl]-2-methylphenyl}-N'-[4-fluoro-3-(trifluoromethyl)phenyl]urea;

N-{4-[4-amino-7-(morpholin-4-ylmethyl)pyrrolo[2,1-f][1,2,4]triazin-5-yl]-2-methylphenyl}-N'-[3-fluoro-5-(trifluoromethyl)phenyl]urea;

N-{4-[4-amino-7-(morpholin-4-ylmethyl)pyrrolo[2,1-f][1,2,4]triazin-5-yl]-3-methylphenyl}-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-2-methoxyphenyl}-N'-(3-tert-butylisoxazol-5-yl)urea;

N-{4-[4-amino-7-(morpholin-4-ylmethyl)pyrrolo[2,1-f][1,2,4]triazin-5-yl]-2-methoxyphenyl}-N'-[4-(trifluoromethyl)pyridin-2-yl]urea;

N-{4-[4-amino-7-(morpholin-4-ylmethyl)pyrrolo[2,1-f][1,2,4]triazin-5-yl]-2-methoxyphenyl}-N'-[4-fluoro-3-(trifluoromethyl)phenyl]urea;

N-{4-[4-amino-7-(morpholin-4-ylmethyl)pyrrolo[2,1-f][1,2,4]triazin-5-yl]-2-methoxyphenyl}-N'-[3-(trifluoromethoxy)phenyl]urea;

N-{4-[4-amino-7-(morpholin-4-ylmethyl)pyrrolo[2,1-f][1,2,4]triazin-5-yl]-2-methoxyphenyl}-N'-[4-chloro-3-(trifluoromethyl)phenyl]urea;

N-{4-[4-amino-7-(morpholin-4-ylmethyl)pyrrolo[2,1-f][1,2,4]triazin-5-yl]-2-methoxyphenyl}-N'-[2-chloro-5-(trifluoromethyl)phenyl]urea;

N-{4-[4-amino-7-(morpholin-4-ylmethyl)pyrrolo[2,1-f][1,2,4]triazin-5-yl]-2-methoxyphenyl}-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-3-methoxyphenyl}-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-3-methoxyphenyl}-N'[4-(trifluoromethyl)pyridin-2-yl]urea;

N-(4-{4-amino-7-[(3-oxopiperazin-1-yl)methyl]pyrrolo[2,1-f][1,2,4]triazin-5-yl}phenyl)-N'-[2-fluoro-5-(trifluoromethyl)phenyl]urea;

N-(4-{4-amino-7-[(3-oxopiperazin-1-yl)methyl]pyrrolo[2,1-f][1,2,4]triazin-5-yl}-2-fluorophenyl)-N'-[2-fluoro-5-(trifluoromethyl)phenyl]urea;

N-(4-{4-amino-7-[(3-oxopiperazin-1-yl)methyl]pyrrolo[2,1-f][1,2,4]triazin-5-yl}phenyl)-N'-[4-(trifluoromethyl)pyridin-2-yl]urea;

N-{4-[4-amino-7-(morpholin-4-ylmethyl)pyrrolo[2,1-f][1,2,4]triazin-5-yl]-2,5-difluorophenyl}-N'-[2-fluoro-3-(trifluoromethyl)phenyl]urea;

N-{4-[4-amino-7-(morpholin-4-ylmethyl)pyrrolo[2,1-f][1,2,4]triazin-5-yl]-2-methoxyphenyl}-N'-[6-(trifluoromethyl)pyridin-2-yl]urea;

N-{4-[4-amino-7-(morpholin-4-ylmethyl)pyrrolo[2,1-f][1,2,4]triazin-5-yl]phenyl}-N'-(5-tert-butyl-2-methoxyphenyl)urea;

N-{4-[4-amino-7-(morpholin-4-ylmethyl)pyrrolo[2,1-f][1,2,4]triazin-5-yl]phenyl}-N'-(2,5-dimethylphenyl)urea;

N-{4-[4-amino-7-(morpholin-4-ylmethyl)pyrrolo[2,1-f][1,2,4]triazin-5-yl]phenyl}-N'-(2-fluoro-5-methylphenyl)urea;

N-{4-[4-amino-7-(morpholin-4-ylmethyl)pyrrolo[2,1-f][1,2,4]triazin-5-yl]phenyl}-N'-(5-methylpyridin-2-yl)urea;

N-{4-[4-amino-7-(morpholin-4-ylmethyl)pyrrolo[2,1-f][1,2,4]triazin-5-yl]phenyl}-N'-(3-methylphenyl)urea hydrochloride;

N-{4-[4-amino-7-(morpholin-4-ylmethyl)pyrrolo[2,1-f][1,2,4]triazin-5-yl]phenyl}-N'-(2-tert-butylphenyl)urea;

N-{4-[4-amino-7-(morpholin-4-ylmethyl)pyrrolo[2,1-f][1,2,4]triazin-5-yl]phenyl}-N'-(3-ethylphenyl)urea;

N-{4-[4-amino-7-(morpholin-4-ylmethyl)pyrrolo[2,1-f][1,2,4]triazin-5-yl]phenyl}-N'-[3-fluoro-5-(trifluoromethyl)phenyl]urea;

N-{4-[4-amino-7-(morpholin-4-yl-methyl)pyrrolo[2,1-f][1,2,4]triazin-5-yl]phenyl}-N'-[2-chloro-5-(trifluoromethyl)phenyl]urea;

N-{4-[4-amino-7-(morpholin-4-ylmethyl)pyrrolo[2,1f][1,2,4]triazin-5-yl]phenyl}-N'-(4-tert-butylpyridin-2-yl)urea;

N-{4-[4-amino-7-(morpholin-4-ylmethyl)pyrrolo[2,1-f][1,2,4]triazin-5-yl]phenyl}-N'-[4-chloro-3-(trifluoromethyl)phenyl]urea;

N-{4-[4-amino-7-(morpholin-4-ylmethyl)pyrrolo[2,1-f][1,2,4]triazin-5-yl]phenyl}-N'-(5-fluoropyridin-2-yl)urea;

N-{4-[4-amino-7-(morpholin-4-ylmethyl)pyrrolo[2,1-f][1,2,4]triazin-5-yl]phenyl}-N'-(5-(trifluoromethyl)pyridin-2-yl]urea;

N-{4-[4-amino-7-(morpholin-4-ylmethyl)pyrrolo[2,1-f][1,2,4]triazin-5-yl]phenyl}-N'-(6-methylpyridin-2-yl)urea;

N-{4-[4-amino-7-(morpholin-4-ylmethyl)pyrrolo[2,1f][1,2,4]triazin-5-yl]phenyl}-N'-[2-fluoro-3-(trifluoromethyl)phenyl]urea;

N-(3-acetylphenyl)-N'-{4-[4-amino-7-(morpholin-4-ylmethyl)pyrrolo[2,1-f][1,2,4]triazin-5-yl]phenyl}urea trifluoroacetate;

N-{4-[4-amino-7-(morpholin-4-ylmethyl)pyrrolo[2,1-f][1,2,4]triazin-5-yl]phenyl}-N'-(3,4-dimethylphenyl)urea trifluoroacetate;

N-{4-[4-amino-7-(morpholin-4-ylmethyl)pyrrolo[2,1-f][1,2,4]triazin-5-yl]phenyl}-N'-(3,5-dimethylphenyl)urea trifluoroacetate;

N-{4-[4-amino-7-(morpholin-4-ylmethyl)pyrrolo[2,1f][1,2,4]triazin-5-yl]phenyl}-N'-(3-chloro-4-methylphenyl)urea trifluoroacetate;

N-{4-[4-amino-7-(morpholin-4-ylmethyl)pyrrolo[2,1-f][1,2,4]triazin-5-yl]phenyl}-N'-(5-chloropyridin-2-yl)urea;

N-{4-[4-amino-7-(morpholin-4-ylmethyl)pyrrolo[2,1-f][1,2,4]triazin-5-yl]-2-fluorophenyl}-N'-(3-methylphenyl)urea;

N-{4-[4-amino-7-(morpholin-4-ylmethyl)pyrrolo[2,1f][1,2,4]triazin-5-yl]-2-fluorophenyl}-N'-[2-chloro-5-(trifluoromethyl)phenyl]urea;

N-{4-[4-amino-7-(morpholin-4-ylmethyl)pyrrolo[2,1-f][1,2,4]triazin-5-yl]-2-fluorophenyl}-N'-(3-chlorophenyl)urea;

N-{4-[4-amino-7-(morpholin-4-ylmethyl)pyrrolo[2,1-f][1,2,4]triazin-5-yl]-2-fluorophenyl}-N'-(3-bromophenyl)urea;

N-{4-[4-amino-7-(morpholin-4-ylmethyl)pyrrolo[2,1-f][1,2,4]triazin-5-yl]phenyl}-N'-[6-(trifluoromethyl)pyridin-2-yl]urea;

N-{4-[4-amino-7-(morpholin-4-ylmethyl)pyrrolo[2,1-f][1,2,4]triazin-5-yl]phenyl}-N'-(6-bromopyridin-2-yl)urea;

N-{4-[4-amino-7-(morpholin-4-ylmethyl)pyrrolo[2,1-f][1,2,4]triazin-5-yl]phenyl}-N'-(6-methoxypyridin-2-yl)urea;

N-{4-[4-amino-7-(morpholin-4-ylmethyl)pyrrolo[2,1-f][1,2,4]triazin-5-yl]phenyl}-N'-(6-ethylpyridin-2-yl)urea;

N-{4-[4-amino-7-(morpholin-4-ylmethyl)pyrrolo[2,1-f][1,2,4]triazin-5-yl]-2-fluorophenyl}-N'-(6-methoxypyridin-2-yl)urea;

N-{4-[4-amino-7-(morpholin-4-ylmethyl)pyrrolo[2,1-f][1,2,4]triazin-5-yl]-2-fluorophenyl}-N'-(6-bromopyridin-2-yl)urea;

N-{4-[4-amino-7-(morpholin-4-ylmethyl)pyrrolo[2,1-f][1,2,4]triazin-5-yl]phenyl}-N'-(3-phenoxyphenyl)urea;

N-(4-{4-amino-7-[(1,1-dioxidothiomorpholin-4-yl)methyl]pyrrolo[2,1-f][1,2,4]triazin-5-yl}-2-fluorophenyl)-N'-(3-ethylphenyl)urea;

N-(4-{4-amino-7-[(1,1-dioxidothiomorpholin-4-yl)methyl]pyrrolo[2,1-f][1,2,4]triazin-5-yl}-2-fluorophenyl)-N'-(3-methylphenyl)urea;

N-(4-{4-amino-7-[(1,1-dioxidothiomorpholin-4-yl)methyl]pyrrolo[2,1-f][1,2,4]triazin-5-yl}-2-fluorophenyl)-N'-[3-(trifluoromethyl)phenyl]urea;

N-(4-{4-amino-7-[(1,1-dioxidothiomorpholin-4-yl)methyl]pyrrolo[2,1-f][1,2,4]triazin-5-yl}-2-fluorophenyl)-N'-[4-(trifluoromethyl)pyridin-2-yl]urea;

N-(4-{4-amino-7-[(1,1-dioxidothiomorpholin-4-yl)methyl]pyrrolo[2,1-f][1,2,4]triazin-5-yl]-2-fluorophenyl)-N'-[2-fluoro-5-(trifluoromethyl)phenyl]urea;

tert-butyl 4-[(4-amino-5-{4-[([2-fluoro-5-(trifluoromethyl)phenyl]amino}carbonyl)amino]phenyl}pyrrolo[2,1-f][1,2,4]triazin-7-yl)methyl]piperazine-1-carboxylate;

N-{4-[4-amino-7-(piperazin-1-ylmethyl)pyrrolo[2,1-f][1,2,4]triazin-5-yl]phenyl}-N'-[2-fluoro-5-(trifluoromethyl)phenyl]urea;

tert-butyl 4-[(4-amino-5-{3-fluoro-4-[({[2-fluoro-5-(trifluoromethyl)phenyl]amino}carbonyl)amino]phenyl}pyrrolo[2,1-f][1,2,4]triazin-7-yl)methyl]piperazine-1-carboxylate;

N-[4-(4-amino-7-{[4-(methylsulfonyl)piperazin-1-yl]methyl}pyrrolo[2,1-f][1,2,4]triazin-5-yl)phenyl]-N'-[2-fluoro-5-(trifluoromethyl)phenyl]urea;

N-[4-(4-amino-7-[4-(ethylsulfonyl)piperazin-1-yl]methyl}pyrrolo[2,1-f][1,2,4]triazin-5-yl)phenyl]-N'-[2-fluoro-5-(trifluoromethyl)phenyl]urea;

N-[4-(4-amino-7-{[4-(isopropylsulfonyl)piperazin-1-yl]methyl}pyrrolo[2,1-f][1,2,4]triazin-5-yl)phenyl]-N'-[2-fluoro-5-(trifluoromethyl)phenyl]urea;

N-{4-[4-amino-7-({4-[(2,2,2-trifluoroethyl)sulfonyl]piperazin-1-yl]methyl)pyrrolo[2,1f][1,2,4]triazin-5-yl}phenyl}-N'-[2-fluoro-5-(trifluoromethyl)phenyl]urea;

N-(4-{7-[(4-acetylpiperazin-1-yl)methyl]-4-aminopyrrolo[2,1-f][1,2,4]triazin-5-yl}phenyl)-N'-[2-fluoro-5-(trifluoromethyl)phenyl]urea;

N-(5-{7-[(4-acetylpiperazin-1-yl)methyl]-4-aminopyrrolo[2,1-f][1,2,4]triazin-5-yl}pyridin-2-yl)-N'-[2-fluoro-5-(trifluoromethyl)phenyl]urea;

N-(4-{7-[(4-acetylpiperazin-1-yl)methyl]-4-aminopyrrolo[2,1-f][1,2,4]triazin-5-yl}-2-fluorophenyl)-N'-[2-fluoro-5-(trifluoromethyl)phenyl]urea;

tert-butyl 4-({4-amino-5-[4-({[(6-bromopyridin-2-yl)amino]carbonyl}amino)phenyl]pyrrolo[2,1-f][1,2,4]triazin-7-yl}methyl)piperazine-1-carboxylate;

N-{4-[4-amino-7-(piperazin-1-ylmethyl)pyrrolo[2,1-f][1,2,4]triazin-5-yl]phenyl}-N'-(6-bromopyridin-2-yl)urea;

N-(4-{4-amino-7-[(4-isopropylpiperazin-1-yl)methyl]pyrrolo[2,1-f][1,2,4]triazin-5-yl}phenyl)-N'-(6-bromopyridin-2-yl)urea;

N-(4-{7-[(4-acetylpiperazin-1-yl)methyl]-4-aminopyrrolo[2,1-f][1,2,4]triazin-5-yl}phenyl)-N'-(6-bromopyridin-2-yl)urea;

N-[4-(4-amino-7-{[4-(methylsulfonyl)piperazin-1-yl]methyl}pyrrolo[2,1-f][1,2,4]triazin-5-yl)phenyl]-N'-(6-bromopyridin-2-yl)urea;

N-[4-(4-amino-7-[4-(2-hydroxyethyl)piperazin-1-yl]methyl}pyrrolo[2,1-f][1,2,4]triazin-5-yl)phenyl]-N'-(6-bromopyridin-2-yl)urea;

4-amino-N-(2,2,2-trifluoroethyl)-5-{4-[([6-(trifluoromethyl)pyridin-2-yl]amino}carbonyl)amino]phenyl}pyrrolo[2,1-f][1,2,4]triazine-7-carboxamide;

4-amino-N-(tert-butyl)-5-{4-[({[6-(trifluoromethyl)pyridin-2-yl]amino}carbonyl)amino]phenyl}pyrrolo[2,1-f][1,2,4]triazine-7-carboxamide;

N-[4-(7-acetyl-4-aminopyrrolo[2,1-f][1,2,4]triazin-5-yl)phenyl]-N'46-(trifluoromethyl)pyridin-2-yl]urea;

N-[4-(7-acetyl-4-aminopyrrolo[2,1-f][1,2,4]triazin-5-yl)phenyl]-N'-(6-bromopyridin-2-yl)urea;

N-[4-(7-acetyl-4-aminopyrrolo[2,1-f][1,2,4]triazin-5-yl)phenyl]-N'-[2-fluoro-5-(trifluoromethyl)phenyl]urea;

N-{4-[4-amino-7-(1-hydroxyethyl)pyrrolo[2,1-f][1,2,4]triazin-5-yl]phenyl}-N'-[6-(trifluoromethyl)pyridin-2-yl]urea;

N-{4-[4-amino-7-(1-hydroxyethyl)pyrrolo[2,1-f][1,2,4]triazin-5-yl]phenyl}-N'-(6-bromopyridin-2-yl)urea;

N-{4-[4-amino-7-(morpholin-4-ylacetyl)pyrrolo[2,1-f][1,2,4]triazin-5-yl]phenyl}-N'-[2-fluoro-5-(trifluoromethyl)phenyl]urea;

N-{4-[4-amino-7-(1-hydroxy-1-methylethyl)pyrrolo[2,1-f][1,2,4]triazin-5-yl]phenyl}-N'-[2-fluoro-5-(trifluoromethyl)phenyl]urea;

N-{4-[4-amino-7-(hydroxymethyl)pyrrolo[2,1-f][1,2,4]triazin-5-yl]phenyl}-N'-[6-(trifluoromethyl)pyridin-2-yl]urea;

N-[4-(4-amino-7-{[(2,2,2-trifluoroethyl)amino]methyl}pyrrolo[2,1-f][1,2,4]triazin-5-yl)phenyl]-N'-[6-(trifluoromethyl)pyridin-2-yl-]urea;

N-{4-[4-amino-7-(3-morpholin-4-ylpropyl)pyrrolo[2,1-f][1,2,4]triazin-5-yl]phenyl}-N'-[4-(trifluoromethyl)pyridin-2-yl]urea;

N-{4-[4-amino-7-(3-morpholin-4-ylpropyl)pyrrolo[2,1-f][1,2,4]triazin-5-yl]phenyl}-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]-2-fluorophenyl}-N'-[2-fluoro-5-(trifluoromethyl)phenyl]urea;

tert-butyl 4-(4-amino-5-{3-fluoro-4-[({[2-fluoro-5-(trifluoromethyl)phenyl]amino}carbonyl)amino]phenyl}pyrrolo[2,1-f][1,2,4]triazin-7-yl)piperidine-1-carboxylate;

N-[4-(4-amino-7-piperidin-4-ylpyrrolo[2,1-f][1,2,4]triazin-5-yl)-2-fluorophenyl]-NT-[2-fluoro-5-(trifluoromethyl)phenyl]urea;

N-(4-{4-amino-7-[1-(trifluoroacetyl)piperidin-4-yl]pyrrolo[2,1-f][1,2,4]triazin-5-yl}-2-fluorophenyl)-N'-[2-fluoro-5-(trifluoromethyl)phenyl]urea;

N-{4-[4-amino-7-(1-methylpiperidin-4-yl)pyrrolo[2,1f][1,2,4]triazin-5-yl]-2-fluorophenyl}-N'-[2-fluoro-5-(trifluoromethyl)phenyl]urea;

N-{4-[4-amino-7-(1-glycoloylpiperidin-4-yl)pyrrolo[2,1-f][1,2,4]triazin-5-yl]-2-fluorophenyl}-N'-[2-fluoro-5-(trifluoromethyl)phenyl]urea;

N-(4-{4-amino-7-[1-(morpholin-4-ylacetyl)piperidin-4-yl]pyrrolo[2,1-f][1,2,4]triazin-5-yl}-2-fluorophenyl)-N'-[2-fluoro-5-(trifluoromethyl)phenyl]urea;

N-(4-{4-amino-7-[1-(2-hydroxyethyl)piperidin-4-yl]pyrrolo[2,1-f][1,2,4]triazin-5-yl}-2-fluorophenyl)-N'-[2-fluoro-5-(trifluoromethyl)phenyl]urea;

N-{4-[7-(1-allylpiperidin-4-yl)-4-aminopyrrolo[2,1-f][1,2,4]triazin-5-yl]-2-fluorophenyl}-N'-[2-fluoro-5-(trifluoromethyl)phenyl]urea;

ethyl[4-(4-amino-5-{3-fluoro-4-[([2-fluoro-5-(trifluoromethyl)phenyl]amino}carbonyl)amino]phenyl}pyrrolo[2,1-f][1,2,4]triazin-7-yl)piperidin-1-yl]acetate;

[4-(4-amino-5-{3-fluoro-4-[({[2-fluoro-5-(trifluoromethyl)phenyl]amino}carbonyl)amino]phenyl}pyrrolo[2,1f][1,2,4]triazin-7-yl)piperidin-1-yl]acetic acid;

2-[4-(4-amino-5-{3-fluoro-4-[({[2-fluoro-5-(trifluoromethyl)phenyl]amino}carbonyl)amino]phenyl}pyrrolo[2,1-f][1,2,4]triazin-7-yl)piperidin-1-yl]-N-methylacetamide;

N-(4-{4-amino-7-[1-(2,3-dihydroxypropyl)piperidin-4-yl]pyrrolo[2,1-f][1,2,4]triazin-5-yl}-2-fluorophenyl)-N'-[2-fluoro-5-(trifluoromethyl)phenyl]urea;

N-(4-{4-amino-7-[1-(2,2,2-trifluoro ethyl)piperidin-4-yl]pyrrolo[2,1-f][1,2,4]triazin-5-yl}-2-fluorophenyl)-N'-[2-fluoro-5-(trifluoromethyl)phenyl]urea;

4-{4-amino-5-[3-fluoro-44 [4-(trifluoromethyl)pyridin-2-yl]carbamoyl}amino)phenyl]pyrrolo[2,1f][1,2,4]triazin-7-yl}-N-ethylpiperidine-1-carboxamide;

4-{4-amino-5-[3-fluoro-4-({[4-(trifluoromethyl)pyridin-2-yl]carbamoyl}amino)phenyl]pyrrolo[2,1-f][1,2,4]triazin-7-yl}-N-tert-butylpiperidine-1-carboxamide;

4-{4-amino-5-[3-fluoro-4-({[4-(trifluoromethyl)pyridin-2-yl]carbamoyl}amino)phenyl]pyrrolo[2,1-f][1,2,4]triazin-7-yl}-N-isopropylpiperidine-1-carboxamide;

N-{4-[4-amino-7-(morpholin-4-ylmethyl)pyrrolo[2,1-f][1,2,4]triazin-5-yl]-2-chlorophenyl}-N'-[3-(trifluoromethyl)phenyl]urea;

N-{4-[4-amino-7-(morpholin-4-ylmethyl)pyrrolo[2,1-f][1,2,4]triazin-5-yl]-2-chlorophenyl}-N'-(4-tert-butylpyridin-2-yl)urea;

N-{4-[4-amino-7-(morpholin-4-ylmethyl)pyrrolo[2,1-f][1,2,4]triazin-5-yl]-2-chlorophenyl}-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-2-chlorophenyl)-N'-[4-(trifluoromethyl)pyridin-2-yl)urea;

N-{4-[4-amino-7-(morpholin-4-ylmethyl)pyrrolo[2,1f][1,2,4]triazin-5-yl]-2-chlorophenyl}-N'-(3-bromophenyl)urea;

N-{4-[4-amino-7-(morpholin-4-ylmethyl)pyrrolo[2,1f][1,2,4]triazin-5-yl]-2-chlorophenyl}-N'-(3-chlorophenyl)urea;

N-{4-[4-amino-7-(morpholin-4-ylmethyl)pyrrolo[2,1f][1,2,4]triazin-5-yl]-2-chlorophenyl}-N'-(3-methoxyphenyl)urea;

N-{4-[4-amino-7-(morpholin-4-ylmethyl)pyrrolo[2,1-f][1,2,4]triazin-5-yl]-2-chlorophenyl}-N'-(4-methylpyridin-2-yl)urea;

N-{4-[4-amino-7-(morpholin-4-ylmethyl)pyrrolo[2,1-f][1,2,4]triazin-5-yl]-2-chlorophenyl}-N'-(3-methylphenyl)urea;

N-{4-[4-amino-7-(morpholin-4-ylmethyl)pyrrolo[2,1f][1,2,4]triazin-5-yl]-2-chlorophenyl}-N'-(2-fluoro-5-methylphenyl)urea;

N-{4-[4-amino-7-(morpholin-4-ylmethyl)pyrrolo[2,1-f][1,2,4]triazin-5-yl]-2-fluoro-5-methylphenyl}-N'-[2-fluoro-5-(trifluoromethyl)phenyl]urea;

N-(4-{4-amino-7-[(1,1-dioxidothiomorpholin-4-yl)methyl]pyrrolo[2,1-f][1,2,4]triazin-5-yl}-2-fluorophenyl)-N'-(3-chlorophenyl)urea;

N-(4-{4-amino-7-[(1,1-dioxidothiomorpholin-4-yl)methyl]pyrrolo[2,1-f][1,2,4]triazin-5-yl}-2-fluorophenyl)-N'-[2-chloro-5-(trifluoromethyl)phenyl]urea;

N-(4-{4-amino-7-[(1,1-dioxidothiomorpholin-4-yl)methyl]pyrrolo[2,1-f][1,2,4]triazin-5-yl}-2-fluorophenyl)-N'-(4-tert-butylpyridin-2-yl)urea;

N-(4-{4-amino-7-[(1,1-dioxidothiomorpholin-4-yl)methyl]pyrrolo[2,1-f][1,2,4]triazin-5-yl}-2-fluorophenyl)-N'-(4-methylpyridin-2-yl)urea;

N-(4-{4-amino-7-[(1,1-dioxidothiomorpholin-4-yl)methyl]pyrrolo[2,1-f][1,2,4]triazin-5-yl}-2-fluorophenyl)-N'-(2-fluoro-5-methylphenyl)urea;

N-(4-{4-amino-7-[(1,1-dioxidothiomorpholin-4-yl)methyl]pyrrolo[2,1-f][1,2,4]triazin-5-yl}-2-fluorophenyl)-N'-(3,4-dichlorophenyl)urea;

N-{4-[4-amino-7-(morpholin-4-ylmethyl)pyrrolo[2,1-f][1,2,4]triazin-5-yl]-2,5-difluorophenyl}-N'-(3-chlorophenyl)urea;

N-{4-[4-amino-7-(morpholin-4-ylmethyl)pyrrolo[2,1-f][1,2,4]triazin-5-yl]-2,5-difluorophenyl-N'-[2-chloro-5-(trifluoromethyl)phenyl]urea;

N-{4-[4-amino-7-(morpholin-4-ylmethyl)pyrrolo[2,1-f][1,2,4]triazin-5-yl]-2,5-difluorophenyl}-N'-(2-fluoro-5-methylphenyl)urea;

N-{4-[4-amino-7-(morpholin-4-ylmethyl)pyrrolo[2,1-f][1,2,4]triazin-5-yl]-2-fluoro-5-methylphenyl}-N'-(2-fluoro-5-methylphenyl)urea;

N-{4-[4-amino-7-(morpholin-4-ylmethyl)pyrrolo[2,1-f][1,2,4]triazin-5-yl]-2-fluoro-5-methylphenyl}-N'-[2-chloro-5-(trifluoromethyl)phenyl]urea;

N-{4-[4-amino-7-(morpholin-4-ylmethyl)pyrrolo[2,1-f][1,2,4]triazin-5-yl]-2-fluoro-5-methylphenyl}-N'-(3-methylphenyl)urea;

N-{4-[4-amino-7-(morpholin-4-ylmethyl)pyrrolo[2,1-f][1,2,4]triazin-5-yl]-2-fluorophenyl}-N'-(2-fluoro-5-methylphenyl)urea;

N-{4-[4-amino-7-(morpholin-4-ylmethyl)pyrrolo[2,1-f][1,2,4]triazin-5-yl]-2-fluorophenyl}[4-chloro-3-(trifluoromethyl)phenyl]urea;

N-{4-[4-amino-7-(morpholin-4-ylmethyl)pyrrolo[2,1-f][1,2,4]triazin-5-yl]-2-fluorophenyl}-N'-(4-tert-butylpyridin-2-yl)urea;

N-{4-[4-amino-7-(morpholin-4-ylmethyl)pyrrolo[2,1-f][1,2,4]triazin-5-yl]-2,5-difluorophenyl}-N'-(3,4-dichlorophenyl)urea;

N-{4-[4-amino-7-(morpholin-4-ylmethyl)pyrrolo[2,1-f][1,2,4]triazin-5-yl]-2,5-difluorophenyl}-N'-(4-tert-butylpyridin-2-yl)urea;

N-{4-[4-amino-7-(morpholin-4-ylmethyl)pyrrolo[2,1-f][1,2,4]triazin-5-yl]-2,5-difluorophenyl}-N'-(3-tert-butylphenyl)urea;

N-{4-[4-amino-7-(morpholin-4-ylmethyl)pyrrolo[2,1f][1,2,4]triazin-5-yl]-2,5-difluorophenyl}-if-(3-ethylphenyl)urea;

N-{4-[4-amino-7-(morpholin-4-ylmethyl)pyrrolo[2,1-f][1,2,4]triazin-5-yl]-2-fluorophenyl}-N'-(3-ethylphenyl)urea;

N-{4-[4-amino-7-(morpholin-4-ylmethyl)pyrrolo[2,1-f][1,2,4]triazin-5-yl]-2,5-difluorophenyl}-N'-4-chloro-3-(trifluoromethyl)phenyl]urea;

N-{4-[4-amino-7-(morpholin-4-ylmethyl)pyrrolo[2,1f][1,2,4]triazin-5-yl]-2-fluorophenyl}-N'-(3,4-dichlorophenyl)urea;

N-{4-[4-amino-7-(morpholin-4-ylmethyl)pyrrolo[2,1f][1,2,4]triazin-5-yl]-2-fluorophenyl}-N'-(3,5-dimethylphenyl)urea;

N-{4-[4-amino-7-(morpholin-4-ylmethyl)pyrrolo[2,1-f][1,2,4]triazin-5-yl]-2-fluorophenyl}-N'-[3-fluoro-5-(trifluoromethyl)phenyl]urea;

N-(4-{4-amino-7-[(4-methylpiperazin-1-yl)carbonyl]pyrrolo[2,1-f][1,2,4]triazin-5-yl}-2-fluorophenyl)-N'-[2-fluoro-5-(trifluoromethyl)phenyl]urea;

N-(4-{4-amino-7-[(3-oxopiperazin-1-yl)methyl]pyrrolo[2,1-f][1,2,4]triazin-5-yl}-2-fluorophenyl)-N'-[3-(trifluoromethyl)phenyl]urea;

N-(4-{4-amino-7-[(3-oxopiperazin-1-yl)methyl]pyrrolo[2,1-f][1,2,4]triazin-5-yl}-2-fluorophenyl)-N'-[4-(trifluoromethyl)pyridin-2-yl]urea;

N-(4-{4-amino-7-[(3-oxopiperazin-1-yl)methyl]pyrrolo[2,1-f][1,2,4]triazin-5-yl}-2,5-difluorophenyl)-N'-[2-fluoro-5-(trifluoromethyl)phenyl]urea;

N-(4-{4-amino-7-[(3-oxopiperazin-1-yl)methyl]pyrrolo[2,1-f][1,2,4]triazin-5-yl}-2-methylphenyl)-N'-[2-fluoro-5-(trifluoromethyl)phenyl]urea;

N-(4-{4-amino-7-[(3-oxopiperazin-1-yl)methyl]pyrrolo[2,1-f][1,2,4]triazin-5-yl}-2-fluorophenyl)-N'-(2-fluoro-5-methylphenyl)urea;

N-{4-[4-amino-7-(1,4-oxazepan-4-ylmethyl)pyrrolo[2,1f][1,2,4]triazin-5-yl]phenyl}-N'-[2-fluoro-5-(trifluoromethyl)phenyl]urea;

N-{4-[4-amino-7-(1,4-oxazepan-4-ylmethyl)pyrrolo[2,1-f][1,2,4]triazin-5-yl]-2,5-difluorophenyl}-N'-[2-fluoro-5-(trifluoromethyl)phenyl]urea;

N-{4-[4-amino-7-(1,4-oxazepan-4-ylmethyl)pyrrolo[2,1-f][1,2,4]triazin-5-yl]-2-fluorophenyl}-N'-(4-tert-butylpyridin-2-yl)urea;

N-{4-[4-amino-7-(1,4-oxazepan-4-ylmethyl)pyrrolo[2,1-f][1,2,4]triazin-5-yl]-2,5-difluorophenyl}-N'-(4-tert-butylpyridin-2-yl)urea;

N-{4-[4-amino-7-(1,4-oxazepan-4-ylmethyl)pyrrolo[2,1-f][1,2,4]triazin-5-yl]-2-fluorophenyl}-N'-[2-chloro-5-(trifluoromethyl)phenyl]urea;

N-{4-[4-amino-7-(1,4-oxazepan-4-ylmethyl)pyrrolo[2,1-f][1,2,4]triazin-5-yl]-2-chlorophenyl}-N'-[3-(trifluoromethyl)phenyl]urea;

N-{4-[4-amino-7-(1-glycoloylpiperidin-4-yl)pyrrolo[2,1-f][1,2,4]triazin-5-yl]-2-chlorophenyl}-N'-[2-fluoro-5-(trifluoromethyl)phenyl]urea;

N-{4-[4-amino-7-(1,4-oxazepan-4-ylmethyl)pyrrolo[2,1-f][1,2,4]triazin-5-yl]-2-fluorophenyl}-N'-(4-fluoro-3-methylphenyl)urea;

N-{4-[4-amino-7-(1,4-oxazepan-4-ylmethyl)pyrrolo[2,1-f][1,2,4]triazin-5-yl]-2-fluorophenyl}-N'-(3-ethylphenyl)urea;

N-{4-[4-amino-7-(1,4-oxazepan-4-ylmethyl)pyrrolo[2,1-f][1,2,4]triazin-5-yl]phenyl}-N'[4-(trifluoromethyl)pyridin-2-yl]urea;

N-{4-[4-amino-7-(1,4-oxazepan-4-ylmethyl)pyrrolo[2,1-f][1,2,4]triazin-5-yl]-2-fluorophenyl}-N'-[2-fluoro-5-(trifluoromethyl)phenyl]urea;

N-{4-[4-amino-7-(1,4-oxazepan-4-ylmethyl)pyrrolo[2,1-f][1,2,4]triazin-5-yl]-2-fluorophenyl}-N'-[3-(trifluoromethyl)phenyl]urea;

N-{4-[4-amino-7-(1,4-oxazepan-4-ylmethyl)pyrrolo[2,1-f][1,2,4]triazin-5-yl]-2-fluorophenyl}-N'-[4-(trifluoromethyl)pyridin-2-yl]urea;

1-{4-[4-amino-7-(1,4-oxazepan-4-ylmethyl)pyrrolo[2,1-f][1,2,4]triazin-5-yl]-2-methylphenyl}-3-[4-(trifluoromethyl)pyridin-2-yl]urea;

N-{4-[4-amino-7-(1,4-oxazepan-4-ylmethyl)pyrrolo[2,1-f][1,2,4]triazin-5-yl]-2-methylphenyl}-N'-[2-fluoro-5-(trifluoromethyl)phenyl]urea;

1-{4-[4-amino-7-(1,4-oxazepan-4-ylmethyl)pyrrolo[2,1-f][1,2,4]triazin-5-yl]-2,5-difluorophenyl}-3-(2-fluoro-5-methylphenyl)urea;

1-{4-[4-amino-7-(1,4-oxazepan-4-ylmethyl)pyrrolo[2,1-f][1,2,4]triazin-5-yl]phenyl}-3-(2-fluoro-5-methylphenyl)urea;

N-[4-(4-amino-7-{3-[(2S)-2-(methoxymethyl)pyrrolidin-1-yl]propyl}pyrrolo[2,1-f][1,2,4]triazin-5-yl)-2-fluorophenyl]-N'-[2-fluoro-5-(trifluoromethyl)phenyl]urea;

N-[4-(4-amino-7-{3-[(2S)-2-(methoxymethyl)pyrrolidin-1-yl]propyl}pyrrolo[2,1-f][1,2,4]triazin-5-yl)-2,5-difluorophenyl]-N'-[2-fluoro-5-(trifluoromethyl)phenyl]urea;

N-{4-[4-amino-7-(3-pyrrolidin-1-yl)propyl)pyrrolo[2,1-f][1,2,4]triazin-5-yl]-2-fluorophenyl}-N'-[2-fluoro-5-(trifluoromethyl)phenyl]urea;

N-(4-{4-amino-7-[3-(4-methylpiperazin-1-yl)propyl]pyrrolo[2,1-f][1,2,4]triazin-5-yl}-2-fluorophenyl)-N'-[2-fluoro-5-(trifluoromethyl)phenyl]urea;

N-(4-{7-[3-(4-acetylpiperazin-1-yl)propyl]-4-aminopyrrolo[2,1-f][1,2,4]triazin-5-yl}-2-fluorophenyl)-N'-[2-fluoro-5-(trifluoromethyl)phenyl]urea;

N-(4-{4-amino-7-[3-(1,1-dioxidothiomorpholin-4-yl)propyl]pyrrolo[2,1-f][1,2,4]triazin-5-yl}-2-fluorophenyl)-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]-2,5-difluorophenyl}-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]-2-fluorophenyl}-N'-[4-(trifluoromethyl)pyridin-2-yl]urea;

1-{4-[4-amino-7-(3-hydroxypropyl)pyrrolo[2,1-f][1,2,4]triazin-5-yl]-2-fluorophenyl}-3-[2-fluoro-5-(trifluoromethyl)phenyl]urea;

N-(4-{4-amino-7-[3-(1,4-oxazepan-4-yl)propyl]pyrrolo[2,1-f][1,2,4]triazin-5-yl}-2-fluorophenyl)-N'-[2-fluoro-5-(trifluoromethyl)phenyl]urea;

N-(4-{4-amino-7-[3-(dimethylamino)propyl]pyrrolo[2,1-f][1,2,4]triazin-5-yl}-2-fluorophenyl)-N'-[2-fluoro-5-(trifluoromethyl)phenyl]urea;

N-(4-[4-amino-7-[3-(3-oxopiperazin-1-yl)propyl]pyrrolo[2,1f][1,2,4]triazin-5-yl]-2-fluorophenyl)-N'-[2-fluoro-5-(trifluoromethyl)phenyl]urea;

N-{4-[4-amino-7-(3-thiomorpholin-4-ylpropyl)pyrrolo[2,1-f][1,2,4]triazin-5-yl]-2-fluorophenyl}-N'-[2-fluoro-5-(trifluoromethyl)phenyl]urea;

N-[4-(4-amino-7-{3-[ethyl(2-hydroxyethyl)amino]propyl}pyrrolo[2,1-f][1,2,4]triazin-5-yl)-2-fluorophenyl]-N'-[2-fluoro-5-(trifluoromethyl)phenyl]urea;

tert-butyl 3-{4-amino-5-(3-fluoro-4-({[2-fluoro-5-(trifluoromethyl)phenyl]carbamoyl}amino)phenyl]pyrrolo[2,1-f][1,2,4]triazin-7-yl}pyrrolidine-1-carboxylate;

tert-butyl 3-{4-amino-5-[4-({[2-fluoro-5-(trifluoromethyl)phenyl]carbamoyl}amino)phenyl]pyrrolo[2,1-f][1,2,4]triazin-7-yl}pyrrolidine-1-carboxylate;

1-[4-(4-amino-7-pyrrolidin-3-ylpyrrolo[2,1-f][1,2,4]triazin-5-yl)-2-fluorophenyl]-3-[2-fluoro-5-(trifluoromethyl)phenyl]urea;

1-(4-{4-amino-7-[1-(methylsulfonyl)pyrrolidin-3-yl]pyrrolo[2,1-f][1,2,4]triazin-5-yl}-2-fluorophenyl)-3-[2-fluoro-5-(trifluoromethyl)phenyl]urea;

1-{4-[7-(1-acetylpyrrolidin-3-yl)-4-aminopyrrolo[2,1-f][1,2,4]triazin-5-yl]-2-fluorophenyl-3-[2-fluoro-5-(trifluoromethyl)phenyl]urea;

3-{4-amino-5-[3-fluoro-4-({[2-fluoro-5-(trifluoromethyl)phenyl]carbamoyl}amino)phenyl]pyrrolo[2,1-f][1,2,4]triazin-7-yl}-N,N-dimethylpyrrolidine-1-carboxamide;

1-{4-[4-amino-7-(1-glycoloylpyrrolidin-3-yl)pyrrolo[2,1f][1,2,4]triazin-5-yl]-2-fluorophenyl}-3-[2-fluoro-5-(trifluoromethyl)phenyl]urea;

1-{4-[7-(1-acetylpyrrolidin-3-yl)-4-aminopyrrolo[2,1-f][1,2,4]triazin-5-yl]-2-fluorophenyl}-3-[4-(trifluoromethyl)pyridin-2-yl]urea;

1-[4-(4-amino-7-pyrrolidin-3-ylpyrrolo[2,1-f][1,2,4]triazin-5-yl)phenyl]-3-[2-fluoro-5-(trifluoromethyl)phenyl]urea;

1-{4-[7-(1-acetylpyrrolidin-3-yl)-4-aminopyrrolo[2,1-f][1,2,4]triazin-5-yl]phenyl}-3-[2-fluoro-5-(trifluoromethyl)phenyl]urea;

tert-butyl 3-{4-amino-5-[3-fluoro-4-({[4-(trifluoromethyl)pyridin-2-yl]carbamoyl}amino)phenyl]pyrrolo[2,1-f][1,2,4]triazin-7-yl}pyrrolidine-1-carboxylate;

4-{4-amino-5-[3-fluoro-4-({[2-fluoro-5-(trifluoromethyl)phenyl]carbamoyl}amino)phenyl]pyrrolo[2,1-f][1,2,4]triazin-7-yl}-N-methylpiperidine-1-carboxamide;

4-{4-amino-5-[3-fluoro-4-({[2-fluoro-5-(trifluoromethyl)phenyl]carbamoyl}amino)phenyl]pyrrolo[2,1f][1,2,4]triazin-7-yl}-N,N-dimethylpiperidine-1-carboxamide;

N-{4-[4-amino-7-(2-morpholin-4-ylethyl)pyrrolo[2,1-f][1,2,4]triazin-5-yl]-2,5-difluorophenyl}-N'-[2-fluoro-5-(trifluoromethyl)phenyl]urea;

N-{4-[4-amino-7-(2-morpholin-4-ylethyl)pyrrolo[2,1-f][1,2,4]triazin-5-yl]-2-fluorophenyl}-N'-[2-fluoro-5-(trifluoromethyl)phenyl]urea;

N-(4-{4-amino-7-[2-(dimethylamino)ethyl]pyrrolo[2,1f][1,2,4]triazin-5-yl}-2-fluorophenyl)-N'-[2-fluoro-5-(trifluoromethyl)phenyl]urea;

N-(4-{4-amino-7-[2-(4-methylpiperazin-1-yl)ethyl]pyrrolo[2,1f][1,2,4]triazin-5-yl}-2-fluorophenyl)-N'-[2-fluoro-5-(trifluoromethyl)phenyl]urea;

N-[4-(4-amino-7-{2-[2-(methoxymethyl)pyrrolidin-1-yl]ethyl}pyrrolo[2,1-f][1,2,4]triazin-5-yl)-2-fluorophenyl]-N'-[2-fluoro-5-(trifluoromethyl)phenyl]urea;

N-{4-[4-amino-7-(2-pyrrolidin-1-ylethyl)pyrrolo[2,1-f][1,2,4]triazin-5-yl]-2-fluorophenyl}-N'-[2-fluoro-5-(trifluoromethyl)phenyl]urea;

N-{4-[4-amino-7-(3-morpholin-4-ylpropyl)pyrrolo[2,1f][1,2,4]triazin-5-yl]-2-fluorophenyl}-N'-[2-chloro-5-(trifluoromethyl)phenyl]urea;

N-{4-[4-amino-7-(3-morpholin-4-ylpropyl)pyrrolo[2,1-f][1,2,4]triazin-5-yl]-2-fluorophenyl}-N'-(2-fluoro-5-methylphenyl)urea;

N-{4-[7-(1-acetylpiperidin-4-yl)-4-aminopyrrolo[2,1-f][1,2,4]triazin-5-yl]-2-chlorophenyl}-N'-[2-fluoro-5-(trifluoromethyl)phenyl]urea;

N-{4-[4-amino-7-(2-hydroxyethyl)pyrrolo[2,1-f][1,2,4]triazin-5-yl]-2-fluorophenyl}-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]-2-methylphenyl}-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]-2-fluorophenyl}-N'-(3-methylphenyl)urea;

N-{4-[4-amino-7-(3-morpholin-4-ylpropyl)pyrrolo[2,1-f][1,2,4]triazin-5-yl]-2-fluorophenyl}-N'[3-(trifluoromethyl)phenyl]urea;

N-{4-[4-amino-7-(4-morpholin-4-ylbutyl)pyrrolo[2,1-f][1,2,4]triazin-5-yl]-2-fluorophenyl}-N'-[2-fluoro-5-(trifluoromethyl)phenyl]urea;

N-{4-[4-amino-7-(3-morpholin-4-ylpropyl)pyrrolo[2,1f][1,2,4]triazin-5-yl]-2-chlorophenyl}-N'-[2-fluoro-5-(trifluoromethyl)phenyl]urea;

N-(4-{4-amino-7-[2-(1,4-oxazepan-4-yl)ethyl]pyrrolo[2,1-f][1,2,4]triazin-5-yl}-2-fluorophenyl)-N'-[2-fluoro-5-(trifluoromethyl)phenyl]urea;

N-(4-{4-amino-7-[(3-oxopiperazin-1-yl)methyl]pyrrolo[2,1-f][1,2,4]triazin-5-yl}-2-fluorophenyl)-N'-[2-chloro-5-(trifluoromethyl)phenyl]urea;

N-{4-[4-amino-7-(2-morpholin-4-ylethyl)pyrrolo[2,1-f][1,2,4]triazin-5-yl]-2-fluorophenyl}-N'-(4-tert-butylpyridin-2-yl)urea;

N-{4-[4-amino-7-[1-lactoylpiperidin-4-yl)pyrrolo[2,1-f][1,2,4]triazin-5-yl]-2-chlorophenyl}-N'-[2-fluoro-5-(trifluoromethyl)phenyl]urea;

N-(4-{4-amino-7-[1-(cyclopropylcarbonyl)piperidin-4-yl]pyrrolo[2,1-f][1,2,4]triazin-5-yl}-2-chlorophenyl)-N'-[2-fluoro-5-(trifluoromethyl)phenyl]urea;

N-(4-{4-amino-7-[1-(morpholin-4-ylacetyl)piperidin-4-yl]pyrrolo[2,1-f][1,2,4]triazin-5-yl}-2-chlorophenyl)-N'-[2-fluoro-5-(trifluoromethyl)phenyl]urea;

N-(4-{4-amino-7-[1-(methylsulfonyl)piperidin-4-yl]pyrrolo[2,1-f][1,2,4]triazin-5-yl}-2-chlorophenyl)-N'-[2-fluoro-5-(trifluoromethyl)phenyl]urea;

N-{4-[4-amino-7-(1-glycoloylpiperidin-4-yl)pyrrolo[2,1-f][1,2,4]triazin-5-yl]-2,5-difluorophenyl)-N'-[2,fluoro-5-(trifluoromethyl)phenyl]urea;

N-[4-(4-amino-7-glycoloylpyrrolo[2,1-f][1,2,4]triazin-5-yl)-2-fluorophenyl]-N'-[2-fluoro-5-(trifluoromethyl)phenyl]urea;

N-{4-[4-amino-7-(1-cyclopropylpiperidin-4-yl)pyrrolo[2,1-f][1,2,4]triazin-5-yl]-2-fluorophenyl}-N'[4-(trifluoromethyl)pyridin-2-yl]urea;

N-{4-[4-amino-7-(1-glycoloylpiperidin-4-yl)pyrrolo[2,1-f][1,2,4]triazin-5-yl]-2-fluorophenyl}-N'[4-(trifluoromethyl)pyridin-2-yl]urea;

N-{4-[7-(1-acetylpiperidin-4-yl)-4-aminopyrrolo[2,1f][1,2,4]triazin-5-yl]-2-fluorophenyl}-N-[4-(trifluoromethyl)pyridin-2-yl]urea;

N-(4-{4-amino-7-[1-(cyclopropylcarbonyl)piperidin-4-yl]pyrrolo[2,1-f][1,2,4]triazin-5-yl}-2-fluorophenyl)-N'-[4-(trifluoromethyl)pyridin-2-yl]urea;

N-(4-{4-amino-7-[1-(methylsulfonyl)piperidin-4-yl]pyrrolo[2,1-f][1,2,4]triazin-5-yl}-2-fluorophenyl)-N'[4-(trifluoromethyl)pyridin-2-yl]urea;

N-(4-{4-amino-7-[1-(N,N-dimethylglycyl)piperidin-4-yl]pyrrolo[2,1-f][1,2,4]triazin-5-yl}-2-chlorophenyl)-N'-[2-fluoro-5-(trifluoromethyl)phenyl]urea;

N-(4-{4-amino-7-[1-(2-methoxyethyl)piperidin-4-yl]pyrrolo[2,1-f][1,2,4]triazin-5-yl}-2-chlorophenyl)-N'-[2-fluoro-5-(trifluoromethyl)phenyl]urea;

N-[4-(4-amino-7-piperidin-4-ylpyrrolo[2,1f][1,2,4]triazin-5-yl)phenyl]-N'-[2-fluoro-5-(trifluoromethyl)phenyl]urea;

N-(4-{4-amino-7-[1-(2-ethoxyethyl)piperidin-4-yl]pyrrolo[2,1-f][1,2,4]triazin-5-yl}-2-chlorophenyl)-N'-[2-fluoro-5-(trifluoromethyl)phenyl]urea;

N-(4-{4-amino-7-[1-(2-ethoxyethyl)piperidin-4-yl]pyrrolo[2,1-f][1,2,4]triazin-5-yl}phenyl)-N'-[2-fluoro-5-(trifluoromethyl)phenyl]urea;

N-(4-{4-amino-7-[1-(2,2-difluoroethyl)piperidin-4-yl]pyrrolo[2,1f][1,2,4]triazin-5-yl}phenyl)-N'-[2-fluoro-5-(trifluoromethyl)phenyl]urea;

N-{4-[4-amino-7-(1-glycoloylpiperidin-4-yl)pyrrolo[2,1-f][1,2,4]triazin-5-yl]phenyl}-N'-[2-fluoro-5-(trifluoromethyl)phenyl]urea;

4-(4-amino-5-{4-[({[2-fluoro-5-(trifluoromethyl)phenyl]amino}carbonyl)amino]phenyl}pyrrolo[2,1-f][1,2,4]triazin-7-yl)-N,N-dimethylpiperidine-1-carboxamide;

N-{4-[4-amino-7-(1-cyclopropylpiperidin-4-yl)pyrrolo[2,1-f][1,2,4]triazin-5-yl]phenyl}-N'-[2-fluoro-5-(trifluoromethyl)phenyl]urea;

1-{4-[4-amino-7-(2-morpholin-4-ylethyl)pyrrolo[2,1-f][1,2,4]triazin-5-yl]phenyl}-3-[2-fluoro-5-(trifluoromethyl)phenyl]urea;

1-{4-[4-amino-7-(2-morpholin-4-ylethyl)pyrrolo[2,1f][1,2,4]triazin-5-yl]-2-fluorophenyl-3-[4-(trifluoromethyl)pyridin-2-yl]urea;

N-{4-[4-amino-7-(1-hydroxyprop-2-en-1-yl)pyrrolo[2,1-f][1,2,4]triazin-5-yl]-2-fluorophenyl}-N'-[2-fluoro-5-(trifluoromethyl)phenyl]urea;

N-{4-[4-amino-7-(1-hydroxyethyl)pyrrolo[2,1-f][1,2,4]triazin-5-yl]-2-fluorophenyl}-N'-[2-fluoro-5-(trifluoromethyl)phenyl]urea;

N-{4-(7-acetyl-4-aminopyrrolo[2,1-f][1,2,4]triazin-5-yl)-2-fluorophenyl-N'-[2-fluoro-5-(trifluoromethyl)phenyl]urea;

N-{4-[4-amino-7-(1,2-dihydroxyethyl)pyrrolo[2,1-f][1,2,4]triazin-5-yl]-2-fluorophenyl}-N'-[2-fluoro-5-(trifluoromethyl)phenyl]urea;

N-{4-[4-amino-7-(1,2,3-trihydroxypropyl)pyrrolo[2,1f][1,2,4]triazin-5-yl]-2-fluorophenyl}-N'-[2-fluoro-5-(trifluoromethyl)phenyl]urea;

2-(4-amino-5-{3-fluoro-4-[({[2-fluoro-5-(trifluoromethyl)phenyl]amino}carbonyl)amino]phenyl}pyrrolo[2,1f][1,2,4]triazin-7-yl)-2-oxoethyl acetate;

N-{4-[4-amino-7-(bromoacetyl)pyrrolo[2,1-f][1,2,4]triazin-5-yl]-2-fluorophenyl}-N'-[2-fluoro-5-(trifluoromethyl)phenyl]urea;

N-(4-{4-amino-7-[(3-morpholin-4-ylpropoxy)acetyl]pyrrolo[2,1f][1,2,4]triazin-5-yl]-2-fluorophenyl)-N'-[2-fluoro-5-(trifluoromethyl)phenyl]urea;

N-[4-(7-acetyl-4-aminopyrrolo[2,1-f][1,2,4]triazin-5-yl)-2-fluorophenyl]-N'-[4-(trifluoromethyl)pyridin-2-yl]urea;

N-(4-{4-amino-7-[(2-morpholin-4-ylethoxy)acetyl]pyrrolo[2,1f][1,2,4]triazin-5-yl}-2-fluorophenyl)-N'-[2-fluoro-5-(trifluoromethyl)phenyl]urea;

N-(4-{4-amino-7-[1-(2,2-difluoroethyl)piperidin-4-yl]pyrrolo[2,1f][1,2,4]triazin-5-yl-2,5-difluorophenyl)-N'-[2-fluoro-5-(trifluoromethyl)phenyl]urea;

N-{4-[4-amino-7-(1-cyclopropylpiperidin-4-yl)pyrrolo[2,1-f][1,2,4]triazin-5-yl]-2,5-difluorophenyl}-N'-[2-fluoro-5-(trifluoromethyl)phenyl]urea;

N-(4-{4-amino-7-[1-(2,2-difluoroethyl)piperidin-4-yl]pyrrolo[2,1-f][1,2,4]triazin-5-yl-2-chlorophenyl)-N'-[2-fluoro-5-(trifluoromethyl)phenyl]urea;

N-{4-[4-amino-7-(1-cyclopropylpiperidin-4-yl)pyrrolo[2,1-f][1,2,4]triazin-5-yl]-2-chlorophenyl}-N'-[2-fluoro-5-(trifluoromethyl)phenyl]urea;

tert-butyl-4-(4-amino-5-{3-chloro-4-[([2-fluoro-5-(trifluoromethyl)phenyl]amino}carbonyl)amino]phenyl pyrrolo[2,1-f][1,2,4]triazin-7-yl)piperidine-1-carboxylate;

N-[4-(4-amino-7-piperidin-4-ylpyrrolo[2,1-f][1,2,4]triazin-5-yl)-2-chlorophenyl]-N'-[2-fluoro-5-(trifluoromethyl)phenyl]urea;

N-[4-(4-amino-7-formylpyrrolo[2,1-f][1,2,4]triazin-5-yl)-2-fluorophenyl]-N'-[4-(trifluoromethyl)pyridin-2-yl]urea;

N-{4-[4-amino-7-(morpholin-4-ylmethyl)pyrrolo[2,1-f][1,2,4]triazin-5-yl]-2-(trifluoromethyl)phenyl]-N'[3-(trifluoromethyl)phenyl]urea;

tert-butyl-4-(4-amino-5-{3-fluoro-4-[({[4-(trifluoromethyl)pyridin-2-yl]amino}carbonyl)amino]phenyl}pyrrolo[2,1-f][1,2,4]triazin-7-yl)piperidine-1-carboxylate;

N-[4-(4-amino-7-piperidin-4-ylpyrrolo[2,1f][1,2,4]triazin-5-yl)-2-fluorophenyl]-N'-[4-(trifluoromethyl)pyridin-2-yl]urea;

tert-butyl-4-(4-amino-5-{4-[([2-fluoro-5-(trifluoromethyl)phenyl]amino}carbonyl)amino]phenyl pyrrolo[2,1-f][1,2,4]triazin-7-yl)piperidine-1-carboxylate;

N-{4-[4-amino-7-(1,3-oxazol-5-yl)pyrrolo[2,1-f][1,2,4]triazin-5-yl]-2-fluorophenyl}-N'-[4-(trifluoromethyl)pyridin-2-yl]urea;

tert-butyl-4-(4-amino-5-{2,5-difluoro-4-[({[2-fluoro-5-(trifluoromethyl)phenyl]amino}carbonyl)amino]phenyl}pyrrolo[2,1-f][1,2,4]triazin-7-yl)piperidine-1-carboxylate;

N-[4-(4-amino-7-piperidin-4-ylpyrrolo[2,1-f][1,2,4]triazin-5-yl)-2,5-difluorophenyl]-N'-[2-fluoro-5-(trifluoromethyl)phenyl]urea;

N-{4-[4-amino-7-(morpholin-2-ylmethyl)pyrrolo[2,1-f][1,2,4]triazin-5-yl]-2-fluorophenyl}-N'-[2-fluoro-5-(trifluoromethyl)phenyl]urea;

N-[4-[4-amino-7-(morpholin-4-ylmethyl)pyrrolo[2,1-f][1,2,4]triazin-5-yl]-2-(trifluoromethoxy)phenyl]-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-2-methyl-phenyl}-N'-(4-tert-butylpyridin-2-yl)urea;

N-{4-[4-amino-7-(morpholin-4-ylmethyl)pyrrolo[2,1-f][1,2,4]triazin-5-yl]-2-methylphenyl}-N'-(2-fluoro-5-methylphenyl)urea;

N-{4-[4-amino-7-(morpholin-4-ylmethyl)pyrrolo[2,1f][1,2,4]triazin-5-yl]-2-methylphenyl}-N'-[2-chloro-5-(trifluoromethyl)phenyl]urea;

N-{4-[4-amino-7-(morpholin-4-ylmethyl)pyrrolo[2,1-f][1,2,4]triazin-5-yl]-2-methylphenyl}-N'-[3-(trifluoromethyl)phenyl]urea;

tert-butyl-2-({[(4-amino-5-{3-fluoro-4-[({[2-fluoro-5-(trifluoromethyl)phenyl]amino}carbonyl)amino]phenyl}pyrrolo[2,1f][1,2,4]triazin-7-yl)carbonyl]amino}methyl)morpholine-4-carboxylate;

4-amino-5-{3-fluoro-4-[([2-fluoro-5-(trifluoromethyl)phenyl]amino}carbonyl)amino]phenyl}-N-(morpholin-2-ylmethyl)pyrrolo[2,1-f][1,2,4]triazine-7-carboxamide;

N-[4-(4-amino-7-{[2-(methoxymethyl)pyrrolidin-1-yl]carbonyl}pyrrolo[2,1-f][1,2,4]triazin-5-yl)-2-fluorophenyl]-N'-[2-fluoro-5-(trifluoromethyl)phenyl]urea;

N-[4-(4-amino-7-[2-(methoxymethyl)pyrrolidin-1-yl]carbonyl}pyrrolo[2,1-f][1,2,4]triazin-5-yl)-2-methylphenyl]-N'-[2-fluoro-5-(trifluoromethyl)phenyl]urea;

N-[4-(4-amino-7-[2-(methoxymethyl)pyrrolidin-1-yl]carbonyl}pyrrolo[2,1-f][1,2,4]triazin-5-yl)-2-fluorophenyl]-N'-[3-(trifluoromethyl)phenyl]urea;

N-[4-[4-amino-7-(morpholin-4-ylmethyl)pyrrolo[2,1-f][1,2,4]triazin-5-yl]-2-fluorophenyl]-N'-[1-oxido-4-(trifluoromethyl)pyridin-2-yl]urea;

N-{4-[4-amino-7-(morpholin-4-ylmethyl)pyrrolo[2,1-f][1,2,4]triazin-5-yl]-phenyl}-N'-[1-oxido-4-(trifluoromethyl)pyridin-2-yl]urea;

N-{4-[4-amino-7-(morpholin-2-ylcarbonyl)pyrrolo[2,1-f][1,2,4]triazin-5-yl]-2-fluorophenyl}-N'-[2-fluoro-5-(trifluoromethyl)phenyl]urea;

N-(4-{4-amino-7-[(4-methylpiperazin-1-yl)carbonyl]pyrrolo[2,1-f][1,2,4}triazin-5-yl]phenyl)-N'-[2-fluoro-5-(trifluoromethyl)phenyl]urea;

N-(4-{4-amino-7-[(4-methylpiperazin-1-yl)carbonyl]pyrrolo[2,1f][1,2,4]triazin-5-yl}-2-fluorophenyl)-N'-[3-(trifluoromethyl)phenyl]urea;

4-amino-5-{4-[({[2-fluoro-5-(trifluoromethyl)phenyl]amino}carbonyl)amino]phenyl}-N-(morpholin-2-ylmethyl)pyrrolo[2,1-f][1,2,4]triazine-7-carboxamide;

4-amino-5-{3-fluoro-4-[({[3-(trifluoromethyl)phenyl]amino}carbonyl)amino]phenyl}-N-(morpholin-2-ylmethyl)pyrrolo[2,1-f][1,2,4]triazine-7-carboxamide;

4-amino-5-{4-[([2-chloro-5-(trifluoromethyl)phenyl]amino}carbonyl)amino]phenyl}-N-(morpholin-2-ylmethyl)pyrrolo[2,1-f][1,2,4]triazine-7-carboxamide;

4-amino-5-{2,5-difluoro-4-[({[2-fluoro-5-(trifluoromethyl)phenyl]amino}carbonyl)amino]phenyl}-N-(morpholin-2-ylmethyl)pyrrolo[2,1-f][1,2,4]triazine-7-carboxamide;

1-{4-[4-amino-7-(1,4-oxazepan-4-ylmethyl)pyrrolo[2,1f][1,2,4]triazin-5-yl]-2-fluorophenyl}-3-[1-oxido-4-(trifluoromethyl)pyridin-2-yl]urea;

N-(4-{4-amino-7-[(4-methylpiperazin-1-yl)carbonyl]pyrrolo[2,1-f][1,2,4]triazin-5-yl-2-fluorophenyl)-N'-[4-(trifluoromethyl)pyridin-2-yl]urea;

1-{4-[4-amino-7-(1,4-oxazepan-4-ylmethyl)pyrrolo[2,1-f][1,2,4]triazin-5-yl]phenyl}-3-[1-oxido-4-(trifluoromethyl)pyridin-2-yl]urea;

N-{4-[4-amino-7-(morpholin-4-ylmethyl)pyrrolo[2,1-f][1,2,4]triazin-5-yl]-2-methylphenyl}-N'-[1-oxido-4-(trifluoromethyl)pyridin-2-yl]urea;

N-{4-[4-amino-7-(morpholin-2-ylcarbonyl)pyrrolo[2,1-f][1,2,4]triazin-5-yl]-2-fluorophenyl}-N'-[3-(trifluoromethyl)phenyl]urea;

N-{4-[4-amino-7-(morpholin-2-ylmethyl)pyrrolo[2,1-f][1,2,4]triazin-5-yl]-2-fluorophenyl}-N'-[3-(trifluoromethyl)phenyl]urea;

or a pharmaceutically acceptable salt thereof.

In another preferred embodiment, the present invention provides a compound having the formula:

N-{4-[4-amino-7-(morpholin-4-ylmethyl)pyrrolo[2,1-f][1,2,4]triazin-5-yl]-2-fluorophenyl-N'-[2-fluoro-5-(trifluoromethyl)phenyl]urea;

N-{4-[4-amino-7-(morpholin-4-ylmethyl)pyrrolo[2,1-f][1,2,4]triazin-5-yl]phenyl}(trifluoromethyl)pyridin-2-yl]urea;

N-{4-[4-amino-7-(morpholin-4-ylmethyl)pyrrolo[2,1-f][1,2,4]triazin-5-yl]phenyl}-N'-[2-fluoro-5-(trifluoromethyl)phenyl]urea;

N-{4-[4-amino-7-(morpholin-4-ylmethyl)pyrrolo[2,1f][1,2,4]triazin-5-yl]-2-fluorophenyl}-N'-[4-(trifluoromethyl)pyridin-2-yl]urea;

N-{4-amino-7-(morpholin-4-ylmethyl)pyrrolo[2,1f][1,2,4]triazin-5-yl]pyridin-2-yl}-N'-[2-fluoro-5-(trifluoromethyl)phenyl]urea;

N-{4-[4-amino-7-(morpholin-4-ylmethyl)pyrrolo[2,1f][1,2,4]triazin-5-yl]-2-fluorophenyl}-N'-[3-(trifluoromethyl)phenyl]urea;

N-{4-[4-amino-7-(morpholin-4-ylmethyl)pyrrolo[2,1-f][1,2,4]triazin-5-yl]-2,5-difluorophenyl}-N'-[2-fluoro-5-(trifluoromethyl)phenyl]urea;

N-{4-[4-amino-7-(morpholin-4-ylmethyl)pyrrolo[2,1f][1,2,4]triazin-5-yl]-2-methylphenyl}-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-2-methylphenyl}-N'[4-(trifluoromethyl)pyridin-2-yl]urea;

N-(4-{4-amino-7-[(3-oxopiperazin-1-yl)methyl]pyrrolo[2,1-f][1,2,4]triazin-5-yl]-2-fluorophenyl)-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-2-fluorophenyl}-N'-[2-chloro-5-(trifluoromethyl)phenyl]urea;

N-(4-{4-amino-7-[(1,1-dioxidothiomorpholin-4-yl)methyl]pyrrolo[2,1f][1,2,4]triazin-5-yl}-2-fluorophenyl)-N'-[4-(trifluoromethyl)pyridin-2-yl]urea;

N-(4-{4-amino-7-[(1,1-dioxidothiomorpholin-4-yl)methyl]pyrrolo[2,1f][1,2,4]triazin-5-yl}-2-fluorophenyl)-N'-[2-fluoro-5-(trifluoromethyl)phenyl]urea;

N-(4-{7-[(4-acetylpiperazin-1-yl)methyl]-4-aminopyrrolo[2,1f][1,2,4]triazin-5-yl}-2-fluorophenyl)-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]phenyl}-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]-2-fluorophenyl}-N'-[2-fluoro-5-(trifluoromethyl)phenyl]urea;

N-{4-[4-amino-7-(1-glycoloylpiperidin-4-yl)pyrrolo[2,1-f][1,2,4]triazin-5-yl]-2-fluorophenyl}-N'-[2-fluoro-5-(trifluoromethyl)phenyl]urea;

[4-(4-amino-5-{3-fluoro-4-[({[2-fluoro-5-(trifluoromethyl)phenyl]amino}carbonyl)amino]phenyl}pyrrolo[2,1-f][1,2,4]triazin-7-yl)piperidin-1-yl]acetic acid;

2-[4-(4-amino-5-{3-fluoro-4-[({[2-fluoro-5-(trifluoromethyl)phenyl]amino}carbonyl)amino]phenyl}pyrrolo[2,1-f][1,2,4]triazin-7-yl)piperidin-1-yl-]-N-methylacetamide;

N-{4-[4-amino-7-(morpholin-4-ylmethyl)pyrrolo[2,1-f][1,2,4]triazin-5-yl]-2-chlorophenyl}-N'-[3-(trifluoromethyl)phenyl]urea;

N-{4-[4-amino-7-(morpholin-4-ylmethyl)pyrrolo[2,1f][1,2,4]triazin-5-yl]-2-chlorophenyl}-N'-[2-fluoro-5-(trifluoromethyl)phenyl]urea;

N-{4-[4-amino-7-(morpholin-4-ylmethyl)pyrrolo[2,1-f][1,2,4]triazin-5-yl]-2-chlorophenyl}-N'-[4-(trifluoromethyl)pyridin-2-yl]urea;

N-(4-{4-amino-7-[(1,1-dioxidothiomorpholin-4-yl)methyl]pyrrolo[2,1-f][1,2,4]triazin-5-yl}-2-fluorophenyl)-N'-(2-fluoro-5-methylphenyl)urea;

N-{4-[4-amino-7-(morpholin-4-ylmethyl)pyrrolo[2,1-f][1,2,4]triazin-5-yl]-2,5-difluorophenyl}-N'-(2-fluoro-5-methylphenyl)urea;

N-{4-[4-amino-7-(morpholin-4-ylmethyl)pyrrolo[2,1-f][1,2,4]triazin-5-yl]-2-fluorophenyl}-N'-(2-fluoro-5-methylphenyl)urea;

N-(4-{4-amino-7-[(3-oxopiperazin-1-yl)methyl]pyrrolo[2,1-f][1,2,4]triazin-5-yl}-2-fluorophenyl)-N'[4-(trifluoromethyl)pyridin-2-yl]urea;

N-(4-{4-amino-7-[(3-oxopiperazin-1-yl)methyl]pyrrolo[2,1-f][1,2,4]triazin-5-yl}-2,5-difluorophenyl)-N'-[2-fluoro-5-(trifluoromethyl)phenyl]urea;

N-{4-[4-amino-7-(1,4-oxazepan-4-ylmethyl)pyrrolo[2,1f][1,2,4]triazin-5-yl]phenyl}-N'-[2-fluoro-5-(trifluoromethyl)phenyl]urea;

N-{4-[4-amino-7-(1,4-oxazepan-4-ylmethyl)pyrrolo[2,1-f][1,2,4]triazin-5-yl]-2,5-difluorophenyl}-N'-[2-fluoro-5-(trifluoromethyl)phenyl]urea;

N-{4-[4-amino-7-(1-glycoloylpiperidin-4-yl)pyrrolo[2,1-f][1,2,4]triazin-5-yl]-2-chlorophenyl}-N'-[2-fluoro-5-(trifluoromethyl)phenyl]urea;

N-{4-[4-amino-7-(1,4-oxazepan-4-ylmethyl)pyrrolo[2,1-f][1,2,4]triazin-5-yl]-2-fluorophenyl}-N'-(4-fluoro-3-methylphenyl)urea;

N-{4-[4-amino-7-(1,4-oxazepan-4-ylmethyl)pyrrolo[2,1-f][1,2,4]triazin-5-yl]-2-fluorophenyl}-N'-[2-fluoro-5-(trifluoromethyl)phenyl]urea;

N-{4-[4-amino-7-(1,4-oxazepan-4-ylmethyl)pyrrolo[2,1-f][1,2,4]triazin-5-yl]-2-fluorophenyl}-N'-[4-(trifluoromethyl)pyridin-2-yl]urea;

N-[4-(4-amino-7-{3-[(2S)-2-(methoxymethyl)pyrrolidin-1-yl]propyl}pyrrolo[2,1-f][1,2,4]triazin-5-yl)-2-fluorophenyl]-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]-2,5-difluorophenyl}-N'-[2-fluoro-5-(trifluoromethyl)phenyl]urea;

N-{4-[4-amino-7-(3-morpholin-4-ylpropyl)pyrrolo[2,1-f][1,2,4]triazin-5-yl]-2-fluorophenyl}-N'[4-(trifluoromethyl)pyridin-2-yl]urea;

1-{4-[4-amino-7-(1-glycoloylpyrrolidin-3-yl)pyrrolo[2,1-f][1,2,4]triazin-5-yl]-2-fluorophenyl}-3-[2-fluoro-5-(trifluoromethyl)phenyl]urea;

1-{4-[7-(1-acetylpyrrolidin-3-yl)-4-aminopyrrolo[2,1-f][1,2,4]triazin-5-yl]-2-fluorophenyl}-3-[4-(trifluoromethyl)pyridin-2-yl]urea;

4-[4-amino-5-[3-fluoro-4-({[2-fluoro-5-(trifluoromethyl)phenyl]carbamoyl}amino)phenyl]pyrrolo[2,1-f][1,2,4]triazin-7-yl}-N-methylpiperidine-1-carboxamide;

N-{4-[4-amino-7-(2-morpholin-4-ylethyl)pyrrolo[2,1-f][1,2,4]triazin-5-yl]-2-fluorophenyl}-N'-[2-fluoro-5-(trifluoromethyl)phenyl]urea;

N-{4-[4-amino-7-(1-glycoloylpiperidin-4-yl)pyrrolo[2,1-f][1,2,4]triazin-5-yl]-2,5-difluorophenyl}-N'-[2-fluoro-5-(trifluoromethyl)phenyl]urea;

N-{4-[4-amino-7-(1-glycoloylpiperidin-4-yl)pyrrolo[2,1-f][1,2,4]triazin-5-yl]-2-fluorophenyl}-N'-[4-(trifluoromethyl)pyridin-2-yl]urea;

N-{4-[7-(1-acetylpiperidin-4-yl)-4-aminopyrrolo[2,1-f][1,2,4]triazin-5-yl]-2-fluorophenyl}-N'-[4-(trifluoromethyl)pyridin-2-yl]urea;

N-{4-[4-amino-7-(morpholin-4-ylmethyl)pyrrolo[2,1-f][1,2,4]triazin-5-yl]-2-fluorophenyl}-N'-[1-oxido-4-(trifluoromethyl)pyridin-2-yl]urea;

or a pharmaceutically acceptable salt thereof.

DEFINITIONS

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centers, depending upon the location and nature of the various substituents desired. Asymmetric carbon atoms may be present in the (R) or (S) configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivitization, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of this invention can likewise be obtained by chiral syntheses utilizing optically active starting materials.

The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

The term "solvates" for the purposes of the invention are those forms of the compounds that coordinate with solvent molecules to form a complex in the solid or liquid state. Hydrates are a specific form of solvates, wherein the solvent is water.

The term "alkyl" refers to a straight-chain or branched saturated hydrocarbon radical having generally 1 to 6, 1 to 4 or 1 to 3 carbon atoms, illustratively representing methyl, ethyl, 71-propyl, isopropyl, tert-butyl, n-pentyl and n-hexyl.

The term "cycloalkyl" refers to saturated carbocyclic groups. Preferred cycloalkyl groups include $C_3$-$C_6$ rings, illustratively representing cyclopropyl, cyclopentyl, and cyclohexyl.

The term "alkoxy" refers to a straight-chain or branched hydrocarbon radical having 1 to 6, 1 to 4 or 1 to 3 carbon atoms and bound via an oxygen atom, illustratively representing methoxy, ethoxy, propoxy, isopropoxy, butoxy, isobutoxy, pentoxy, isopentoxy, hexoxy, isohexoxy. The terms "alkoxy" and "alkyloxy" are often used synonymously.

The term "alkylamino" refers to an amino radical having one or two (independently selected) alkyl substituents, illustratively representing methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

The term "alkylaminocarbonyl" refers to an alkylaminocarbonyl radical having one or two (independently selected) alkyl substituents, illustratively representing methylaminocarbonyl, ethylaminocarbonyl, n-propylaminocarbonyl, isopropylaminocarbonyl, tert-butylamino-carbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentylamino-carbonyl and N-n-hexyl-N-methylaminocarbonyl.

The term "alkylaminosulfonyl" refers to an aminosulfonyl radical having one or two (independently selected) alkyl substitutents on the amino moiety, illustratively representing methylaminosulfonyl, ethylaminosulfonyl, n-propylaminosulfonyl, isopropylaminosulfonyl, tert-butylaminosulfonyl, n-pentylaminosulfonyl, n-hexyl-aminosulfonyl, N,N-dimethylaminosulfonyl, N,N-diethylaminosulfonyl, N-ethyl-N-methylaminosulfonyl, N-methyl-N-n-propylamino sulfonyl, N-isopropyl-N-n-propylaminosulfonyl, N-t-butyl-N-methylaminosulfonyl, N-ethyl-N-n-pentylaminosulfonyl and N-n-hexyl-N-methylaminosulfonyl.

The term "alkylsulfonylamino" refers to a sulfonylamino radical having an alkyl substitutent on the sulfonylamino moiety, illustratively representing methylsulfonylamino, ethylsulfonylamino, n-propylsulfonylamino, isopropylsulfonylamino, tert-butyl-sulfonylamino, n-pentylsulfonylamino and n-hexylsulfonylamino.

The term "alkoxycarbonyl" refers to a carbonyl radical being substituted with an alkoxy radical, illustratively representing methoxycarbonyl, ethoxycarbonyl, n-propoxycarbonyl, isopropoxycarbonyl, tert-butoxycarbonyl, n-pentoxycarbonyl and n-hexoxycarbonyl.

The term "alkoxycarbonylamino" refers to a carbonylamino radical being substituted with an alkoxy radical on the carbonyl moiety, illustratively representing methoxycarbonylamino, ethoxycarbonylamino, n-propoxycarbonylamino, isopropoxycarbonylamino, tert-butoxy-carbonylamino, n-pentoxycarbonylamino and n-hexoxycarbonylamino.

The term "heteroaryl" refers to a mono- or bicyclic radical having 5 to 10 or 5 or 6 ring atoms and up to 4 hetero atoms selected from the group consisting of nitrogen, oxygen and sulfur, which is aromatic at least in one ring. It can be attached via a ring carbon atom or a ring nitrogen atom. If it represents a bicycle, wherein one ring is aromatic and the other one is not, it can be attached at either ring. Illustrative examples of such groups are the thiophene, furan, pyrrole, thiazole, oxazole, imidazole, pyridine, pyrimidine, pyridazine, indole, indazole, benzofuran, benzothiophene, quinoline and isoquinoline groups.

Language reciting a 5-6 membered aromatic heterocycle containing up to 3 heteroatoms independently selected from the group consisting of N, O, and S is meant to refer to aromatic heterocycles such as furan, thiophene, pyrrole, pyrazole, triazole, isoxazole, oxazole, thiazole, isothiazole, imidaxole, an oxadiazole, 1,3,2-dioxazole, 1,2,5-oxathiazole, 1,2-pyrone, 1,4-pyrone, pyridine, pyridazine, pyrimidine, pyrazine, a triazine, o- and p-isoxazines, 1,2,5-oxathiazine, 1,2,4-oxadiazine, and the like.

Language reciting a bicyclic heterocycle of 8-10 ring members in which at least one ring is aromatic and contains up to 3 moieties independently selected from the group consisting of N, N→O, O, and S, and any non-aromatic ring of said bicyclic heterocycle optionally contains up to three moieties independently selected from the group consisting of O, S, S(O), S(O)$_2$, and NR, is meant to refer to bicyclic heterocycles in which at least one ring is a 5-6-membered aromatic heterocycle as discussed above, which is fused to a second ring which may be aromatic or nonaromatic. Where this second ring is aromatic, it may also optionally contain up to 3 moieties independently selected from the group consisting of N, N→O, O, and S, and where this second ring is nonaromatic, it may optionally contain up to three moieties independently selected from O, S, S(O), $S(O)_2$, and NR.

The term "heterocyclyl" refers to a saturated or partially unsaturated mono- or bicyclic heterocyclic ring which contains 3 to 8 or 5 to 6 ring atoms and 1 to 3 heteroatoms or hetero groups selected independently from the group consisting of nitrogen, oxygen and sulfur, CO, SO and $SO_2$, such as tetrahydrofuran-2-yl, pyrrolidin-2-yl, pyrrolidin-3-yl, pyrrolinyl, piperidinyl, morpholinyl, or perhydroazepinyl. It can be attached via a ring carbon atom or a ring nitrogen atom.

The terms "halo" and "halogen" refer to fluorine, chlorine, bromine or iodine.

A bicyclic carbocycle of 9-10 ring members in which at least one ring is aromatic is a compound such as indene, isoindene, and tetrahydronaphthalene.

Language stating that an alkyl or alkoxy group may optionally bear halogen or may be substituted with halogen means that the group may bear one or more halogens, up to perhalo.

Language reciting that in a group —NRR, the two R groups may be joined and taken together with the N atom to which they are attached form a 5-6 membered ring which may optionally contain a ring member selected from O, S, and $NR^x$ wherein $R^x$ represents H or $(C_1\text{-}C_3)$alkyl, is meant to indicate formation of groups such as pyrrolidine, imidazolidine, piperidine piperazine, morpholine, thiomorpholine, and the like.

Language indicating that two substituent groups of a tertiary amino moiety may be joined and taken together with the N to which they are attached form an aromatic or nonaromatic 5-6 membered ring which may optionally contain a ring member selected from O, S, and NR is meant to indicate the possibility of forming 5-6-membered N-containing heterocycles such as pyrrole, pyrazole, piperazine, morpholine, piperidine, imidazole, pyrrolidine, imidazolidene, and the like.

When NR is indicated as being part of a heterocycle, this means that the N atom is the ring member and R is a substituent.

Language reciting a 5-6 membered heteroaromatic containing up to two heteroatoms selected from O, S, and N is meant to refer to groups such as furan, thiophene, pyrrole, pyrazole, oxazole, isoxazole, thiazole, isothiazole, imidazole, pyridine, pyridazine, pyrimidine, pyrazine, isoxazine, and the like.

The term "aryl" refers to a mono- to tricyclic carbocyclic radical, which is aromatic at least in one ring, having generally 6 to 14 carbon atoms, illustratively representing phenyl, naphthyl and phenanthrenyl.

The term "substituted phenyl" refers to an phenyl radical having one or more (but typically not more than three) groups independently selected from halogen; alkyl such as $(C_1\text{-}C_3)$ alkyl; alkoxy such as $O(C_1\text{-}C_3)$alkyl; CN; cycloalkyl; heteroaryl; heterocyclyl; amino; alkylamino such as mono- or di-$(C_1\text{-}C_3)$alkylamino; acylamino wherein for example the acyl group is —$C(O)(C_1\text{-}C_3)$alkyl or —C(O)phenyl alkoxycarbonyl; CN; $NO_2$; alkynyl; alkenyl; $C(O)NH_2$; C(O)NH $(C_1\text{-}C_3)$alkyl; $C(O)N((C_1\text{-}C_3)alkyl)_2$; C(O)NH-phenyl; —$NHC(O)NH_2$ alkylaminosulfonyl; alkylsulfonylamino; and alkoxycarbonylamino, and in these groups, alkyl and phenyl groups may be further substituted with halogen.

Language stating that phenyl may be optionally substituted with halogen means that the phenyl group optionally may bear one or more substituents independently selected from fluorine, chlorine, bromine and iodine, up to a maximum of perhalo, but typically not more than three such groups.

Language stating that a cycloalkyl group may optionally bear halogen or alkoxy is meant to indicate that the cycloalkyl group may be bear one or more halogen substituents, up to perhalo, and/or it may bear one or more alkoxy groups, generally up to a maximum of three.

The skilled in the art understand that when two hetero atoms are attached to a single aliphatic carbon atom, the resulting material is usually not stable. Accordingly, in this invention, when an aliphatic group bears two heteroatom-containing substituents (such as amino and alkoxy, for example) in which the heteroatoms are joined to the aliphatic group, such heteroatom-containing substituents will generally need to be located on different carbon atoms of the aliphatic material.

A wavy line across the end of a line which indicates a chemical bond extending from a chemical substructure or functional group means that the substructure or group is attached to the remainder of the molecule via that bond.

A carbonyl group is indicated as C═O in a chemical structure or substructure, or by C(O) in a typed formula.

In naming a multiunit functional group by listing the constituent units, the terminal unit is recited first, then the adjacent unit is recited, etc. An example of this style of nomenclature would be "alkylphenyl", which connotes an alkyl group located on a phenyl group, which is in turn connected to the remainder of the molecule. Conversely, the term "phenylalkyl" would connote a phenyl group located on an alkyl group which is in turn connected to the remainder of the molecule. Another example would be "cycloalkylalkyl", which connotes a cycloalkyl group connected to an alkyl group which is in turn connected to the remainder of the molecule.

In this document, for the sake of simplicity, the names of substituent groups are generally (but not always) given as names of the parent compounds rather than using nomenclature which indicates their status as substituents. Thus, for example, if a substituent in a compound of the invention were a pyridine ring, it would generally be termed a "pyridine" substituent rather than a being referred to as a "pyridyl" group. Where the nomenclature indicating status as a substituent is not employed, and a substituent is named in terms of its parent, its status as a substituent will be clear from the context.

Salts of the compounds identified herein can be obtained by isolating the compounds as hydrochloride salts, prepared by treatment of the free base with anhydrous HCl in a suitable solvent such as THF. Generally, a desired salt of a compound of this invention can be prepared in situ during the final isolation and purification of a compound by means well known in the art. Or, a desired salt can be prepared by separately reacting the purified compound in its free base form with a suitable organic or inorganic acid and isolating the salt thus formed. These methods are conventional and would be readily apparent to one skilled in the art.

If used as active compounds, the compounds according to the invention are preferably isolated in more or less pure form, that is more or less free from residues from the synthetic procedure. The degree of purity can be determined by methods known to the chemist or pharmacist (see especially Remington's Pharmaceutical Sciences, $18^{th}$ ed. 1990, Mack Publishing Group, Enolo). Preferably the compounds are greater than 99% pure (w/w), while purities of greater than 95%, 90% or 85% can be employed if necessary.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of claim 1" is meant to include the simultaneous treatment of more than one disease as well as the administration of more than one compound of claim 1.

The compounds according to the invention exhibit an unforeseeable, useful pharmacological and pharmacokinetic activity spectrum. They are therefore suitable for use as medicaments for the treatment and/or prophylaxis of disorders in humans and animals.

Pharmaceutical Compositions of the Compounds of the Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art. It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 mono stearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant kinase activity (such as tyrosine kinase activity), including, FGFR1, FGFR2, FGFR3, FGFR4, VEGFR1, VEGFR2, VEGFR3, Tie2, PDGFR, Aurora A, Aurora B, EphB4, EphA2, p70S6K, RSK, TrkA, Trk B, RET, Src, c-Yes and Fyn.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of FGFR1, FGFR2, FGFR3, FGFR4, VEGFR1, VEGFR2, VEGFR3, Tie2, PDGFR, Aurora A, Aurora B, EphB4, EphA2, p70S6K, RSK, TrkA, Trk B, RET, Src, c-Yes and Fyn comprising administering an effective amount of a compound of the present invention, including salts, polymorphs, metabolites, hyrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. *Invest. Opththalmol. Vis. Sci.* 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. For example, the compounds of this invention can be combined with known anti-hyper-proliferative or other indication agents, and the like, as well as with admixtures and combinations thereof.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gamrnagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofuran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 1 Edition of the *Merck index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemo-therapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

EXPERIMENTAL

Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

ABBREVIATIONS AND ACRONYMS $^{1}$H-NMR proton nuclear magnetic resonance spectroscopy
$^{31}$P-NMR phosphorus-31 nuclear magnetic resonance spectroscopy
AcOH acetic acid
$(Ac)_2O$ acetic anhydride
abs absolute
aq aqueous
ap approximate
atm atmosphere
br broad
BOP benzotriazole-1-yloxy-tris(dimethylamino)phosphonium hexafluorophosphate
Bu butyl
ACN acetonitrile
$Ac_2O$ acetic anhydride
AcOH acetic acid
Celite® brand of diatomaceous earth from Celite Corp.
$CD_3CN$ acetonitrile-$d_3$
$CD_3OD$ methanol-$d_4$
d doublet
DCE dichloroethane
DCM dichloromethane
dd double doublet
DIBAL diisobutylaluminum hydride
DMF N,N-dimethylformamide DMSO dimethylsulfoxide
$DMSO-d_6$ dimethyldsulfoxide-$d_6$
equiv equivalent(s)
ES-MS electrospray mass spectrometry
$Et_3N$ triethylamine
$Et_2O$ diethyl ether
EtOAc ethyl acetate
EtOH ethanol
FBS fetal bovine serum
g gram(s)
h hour(s)
Hex Hexanes
HPLC high performance liquid chromatography
Hz hertz
J NMR coupling constant
KOAc Potassium Acetate
L liter(s)
LCMS liquid chromatography-mass spectrometry
LHMDS lithium hexamethyldisilazide
M molar
mCPBA meta-Chloroperoxybenzoic acid
Me methyl
MeOH methanol
mg milligram(s)
MHz megahertz
min minute(s)
mL milliliter
mmol millimole
MPLC medium pressure liquid chromatography
MS mass spectrometry
Ms methanesulfonyl
N normal
nM nanomolar
Pr propyl
py-BOP benzotriazol-1-yl-oxytripyrrolidineophosphonium hexafluorophosphate
q quartet
Ra—Ni Raney-Nickel
$R_f$ TLC retention factor
Rochelle's potassium sodium tartrate
salt
RPMI Roswell Park Memorial Institute
RT retention time
rt room temperature
s singlet
satd. saturated
t triplet
TEA triethylamine
TFA trifluoroacetic acid
THF tetrahydrofuran
TLC thin layer chromatography
TosMIC Tosylmethyl isocyanide
TPP triphenylphosphine
Ts p-toluenesulfonyl
v/v volume-to-volume proportion
v/v/v volume-to-volume-to-volume proportion
μL microliter
μm micrometer The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at approximately 15 mm of Hg. All temperatures are reported uncorrected in degrees Celsius (° C.). Thin layer chromatography (TLC) was performed on pre-coated glass-backed silica gel 60 A F-254 250 μm plates.

The structures of compounds of this invention were confirmed using one or more of the following procedures.

NMR

NMR spectra were acquired for each compound and were consistent with the structures shown.

Routine one-dimensional NMR spectroscopy was performed on either 300 or 400 MHz Varian® Mercury-plus spectrometers. The samples were dissolved in deuterated solvents. Chemical shifts were recorded on the ppm scale and were referenced to the appropriate solvent signals, such as 2.49 ppm for DMSO-d6, 1.93 ppm for CD3CN, 3.30 ppm for CD3OD, 5.32 ppm for CD2Cl2 and 7.26 ppm for CDCl3 for 1H spectra.

GC/MS

Electron impact mass spectra (EI-MS) were obtained with a Hewlett Packard 5973 mass spectrometer equipped Hewlett Packard 6890 Gas. Chromatograph with a J & W HP-5 column (0.25 uM coating; 30 m×0.32 mm). The ion source was maintained at 250° C. and spectra were scanned from 50-550 amu at 0.34 sec per scan.

LC/MS

Unless otherwise noted, all retention times are obtained from the LC/MS and correspond to the molecular ion. High pressure liquid chromatography-electrospray mass spectra (LC/MS) were obtained using one of the following:

Method A (LCQ)

Hewlett-Packard 1100 HPLC equipped with a quaternary pump, a variable wavelength detector set at 254 nm, a Waters Sunfire C18 column (2.1×30 mm, 3.50m), a Gilson autosampler and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonitrile with 0.018% TFA. Gradient elution from 10% B to 95% B over 3.5 minutes at a flow rate of 1.0 mL/min was used with an initial hold of 0.5 minutes and a final hold at 95% B of 0.5 minutes. Total run time was 6.5 minutes.

Method B (LCQ5)

Agilent 1100 HPLC system. The Agilent 1100 HPLC system was equipped with an Agilent 1100 autosampler, quaternary pump, a variable wavelength detector set at 254 nm. The HPLC column used was a Waters Sunfire C-18 column (2.1×30 mm, 3.5 μm). The HPLC eluent was directly coupled without splitting to a Finnigan LCQ DECA ion trap mass spectrometer with electrospray ionization. Spectra were scanned from 140-1200 amu using a variable ion time according to the number of ions in the source using positive ion mode. The eluents were A: 2% acetonitrile in water with 0.02% TFA, and B: 2% water in acetonitrile with 0.02% TFA. Gradient elution from 10% B to 90% B over 3.0 minutes at a flow rate of 1.0 mL/min was used with an initial hold of 1.0 minutes and a final hold at 95% B of 1.0 minutes. Total run time was 7.0 minutes.

Method C (LTQ)

Agilent 1100 HPLC system. The Agilent 1100 HPLC system was equipped with an Agilent 1100 autosampler, quaternary pump, and a diode array. The HPLC column used was a Waters Sunfire C18 column (2.1×30 mm, 3.5 μm). The HPLC eluent was directly coupled with a 1:4 split to a Finnigan LTQ ion trap mass spectrometer with electrospray ionization. Spectra were scanned from 50-800 amu using a variable ion time according to the number of ions in the source using positive or negative ion mode. The eluents were A: water with 0.1 formic acid, and B: acetonitrile with 0.1% formic acid. Gradient elution from 10% B to 90% B over 3.0 minutes at a flowrate of 1.0 mL/min was used with an initial hold of 2.0 minutes and a final hold at 95% B of 1.0 minutes. Total run time was 8.0 minutes.

Method D

Gilson HPLC system equipped with a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluants were A: 2% acetonitrile in water with 0.02% TFA and B: 2% water in acetonitrile with 0.018% TFA. Gradient elution from 10% B to 95% over 3.5 minutes at a flow rate of 1.0 mL/min was used with an initial hold of 0.5 minutes and a final hold at 95% B of 0.5 minutes. Total run time was 6.5 minutes.

Method E

Agilent 1100 HPLC system. The Agilent 1100 HPLC system was equipped with an Agilent 1100 autosampler, quaternary pump, and a diode array. The HPLC column used was a Waters Sunfire (2.1×30 mm, 3.5 μm). The HPLC eluent was directly coupled with a 1:4 split to a Finnigan LTQ ion trap mass spectrometer with electrospray ionization. Spectra were scanned from 50-1000 amu using a variable ion time according to the number of ions in the source in either positive or negative ion mode. The eluents were A: water with 0.1 formic acid, and B: acetonitrile with 0.1% formic acid. Gradient elution from 10% B to 90% B over 3.0 minutes at a flow rate of 1.0 mL/min was used with an initial hold of 2.0 minutes and a final hold at 95% B of 1.0 minutes. Total run time was 8.0 minutes.

Preparative HPLC:

Preparative HPLC was carried out in reversed phase mode, typically using a Gilson HPLC system equipped with two Gilson 322 pumps, a Gilson 215 Autosampler, a Gilson diode array detector, and a C-18 column (e.g. YMC Pro 20×150 mm, 120 A). Gradient elution was used with solvent A as water with 0.1% TFA, and solvent B as acetonitrile with 0.1% TFA. Following injection onto the column as a solution, the compound was typically eluted with a mixed solvent gradient, such as 10-90% Solvent B in Solvent A over 15 minutes with flow rate of 25 mL/min. The fraction(s) containing the desired product were collected by UV monitoring at 254 or 220 nm.

Preparative MPLC:

Preparative medium pressure liquid chromatography (MPLC) was carried out by standard silica gel "flash chromatography" techniques (e.g., Still, W. C. et al. *J. Org. Chem.* 1978, 43, 2923-5), or by using silica gel cartridges and devices such as the Biotage Flash systems. A variety of eluting solvents were used, as described in the experimental protocols.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Synthetic transformations that may be employed in the synthesis of compounds of this invention and in the synthesis of intermediates involved in the synthesis of compounds of this invention are known by or accessible to one skilled in the art. Collections of synthetic transformations may be found in compilations, such as:

J. March. *Advanced Organic Chemistry,* 4th ed.; John Wiley: New York (1992)

R. C. Larock. *Comprehensive Organic Transformations,* 2nd ed.; Wiley-VCH: New York (1999)

F. A. Carey; R. J. Sundberg. *Advanced Organic Chemistry,* 2nd ed.; Plenum Press: New York (1984)

T. W. Greene; P. G. M. Wuts. *Protective Groups in Organic Synthesis,* 3rd ed.; John Wiley: New York (1999)

L. S. Hegedus. *Transition Metals in the Synthesis of Complex Organic Molecules,* 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; Organic Syntheses; John Wiley: New York; *Reagents for Organic Synthesis*: John Wiley: New York; *The Total Synthesis of Natural Products*; John Wiley New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

Methods for preparing pyrrolotriazines are also disclosed in published U.S. application Ser. No. 10/289,010 (Publication No. US 2003-0186982 A1), U.S. Pat. No. 6,670,357 (U.S. application Ser. No. 10/036,293), as well as WO 2003/042172, WO 2004/009542, WO2004/009601, WO 2004/009784, WO 2004/013145 and WO 2005/121147 all of which are hereby incorporated by reference in their entirety.

General Methods of Preparation of Invention Compounds

It is also to be understood that starting materials are commercially available or readily prepared by standard methods well known in the art. Such methods include, but are not limited to the transformations listed herein.

If not mentioned otherwise, the reactions are usually carried out in inert organic solvents which do not change under the reaction conditions. These include ethers, such as diethyl ether, 1,4-dioxane or tetrahydrofuran, halogenated hydrocarbons, such as dichloromethane, trichloromethane, carbon tetrachloride, 1,2-dichloroethane, trichloroethane or tetrachloroethane, hydrocarbons, such as benzene, toluene, xylene, hexane, cyclohexane or mineral oil fractions, alcohols, such as methanol, ethanol or iso-propanol, nitromethane, dimethylformamide or acetonitrile. It is also possible to use mixtures of the solvents.

The reactions are generally carried out in a temperature range of from 0° C. to 150° C., preferably from 0° C. to 70° C. The reactions can be carried out under atmospheric, elevated or under reduced pressure (for example from 0.5 to 5 bar). In general, they are carried out under atmospheric pressure of air or inert gas, typically nitrogen.

I

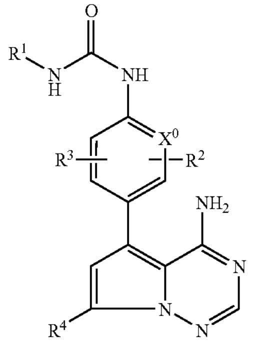

Compounds of the present invention of formula I can be prepared by straightforward means as described in the reaction schemes below or by means well known to those skilled in the art. In these reaction schemes, unless otherwise specifically defined, the meanings of $R^1$, $R^2$, $R^3$, $R^4$ and $X^0$ are identical to those described above.

Reaction Scheme 1 illustrates a general method of preparing compounds of formula I from the corresponding bromo compounds of formula 1-3 by methods of cross coupling (Suzuki) that are well known in the art. Thus, coupling bromide of formula 1-1 with the appropriately substituted boronate ($G^1$=C(O)NHR$^1$) of formula 1-2 to furnish compounds of formula I directly. Alternatively, coupling bromide of formula 1-1 with the appropriately substituted boronate ($G^1$=H, PG; where PG is an optional protecting group known in the art) lead to anilines of formulas 1-3 and 1-4. If necessary, the protecting group (PG) can be removed first by methods well known in the art (e.g. acid catalyzed removal of BOC carbamates). The reaction of anilines of formula 1-4 with either an isocyanate of formula 1-5 or carbamate of formula 1-6, generally in an inert solvent, provides compounds of formula I directly.

Reaction Scheme 1

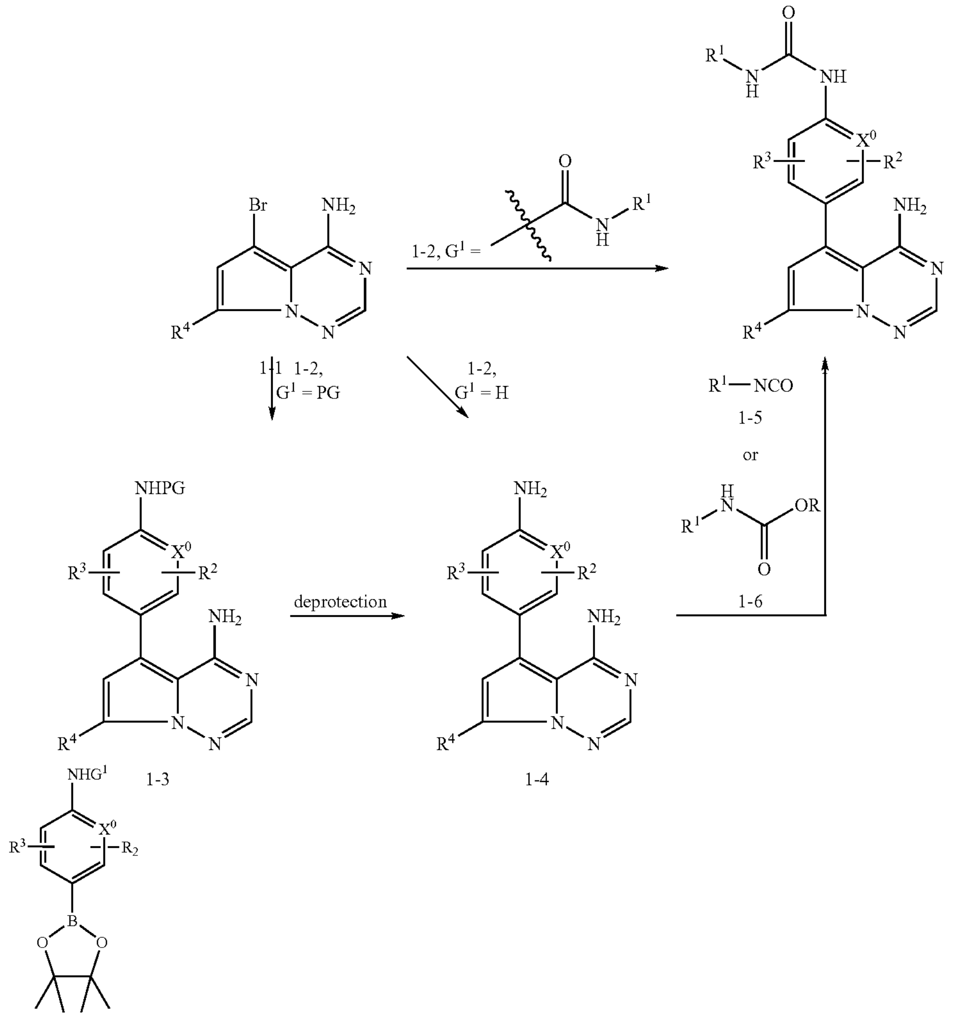

Reaction Scheme 2 outlines a method for preparing substituted boronates of formula 1-2, starting from bromides of formula 2-1. Thus, reactions of 2-1 with bis(pincolato) diboron under coupling conditions well known in the art (Step A) will provide boronates of formula 1-2 ($G^1$=H) directly. Alternatively, treatment of anilines of formula 2-1 isocyanates or carbamates under conditions described in Scheme 1 will provide bromides of formula 2-2 ($G^1$=C(O)NHR$^1$). Additionally anilines of formula 2-1 can be protected with an appropriate group ($G^1$=PG), which can be synthesized under conditions well know in the art. Boronates of formula 1-2 ($G^1$=PG, C(O)NHR$^1$) can be generated from the corresponding bromides of formula 2-2 under the conditions given in Step A. If necessary boronates of formula 1-2 ($G^1$=H) can be further transformed into boronates of formula 1-2 ($G^1$=PG, C(O) NHR$^1$) by the conditions outlined in step B.

Reaction Scheme 2

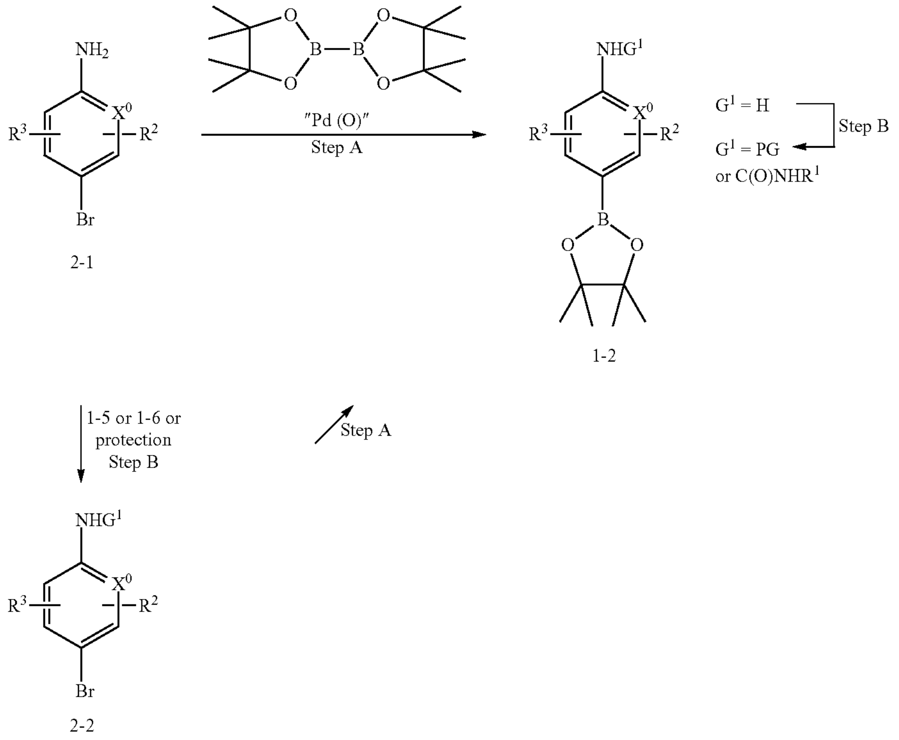

Reaction Scheme 3 describes the preparation of common intermediates 3-5, 3-6, and 3-7 from a common precursor 3-4. Common intermediates 3-5, 3-6 and 3-7 are useful precursors to ones skilled in the art toward generation of diversity at $R^4$. Treatment of commercially available 2,5-dialkoxy tetrahydrofuran (3-1) with a protected hydrazine under acidic conditions provides the n-substituted amino pyrrole 3-2. Cyanation at the 2-position is easily effected by treatment with reagents such chlorosulphonyl isocyanate. The protecting group (PG) can then be removed by methods well know in the art (e.g. HCl in an aprotic solvent for the removal of a BOC carbamate) to provide intermediate 3-3. Cyclization of 3-3 can be affected by treatment with a formamiding derivative such as formamidine acetate or the like in a solvent such as EtOH to provide the pyrrolotriazine intermediate of formula 3-4. Differentiation can be effected by the regioselective electrophilic addition of various functional groups at the 7-position of formula 3-4. Treatment of compounds of 3-4 under Mannich conditions, such as by treatment with an amine, such as a primary or secondary (cyclic or acyclic) amine, and formaldehyde and the like in a solvent such as acetic acid or the like provide compounds of formula 3-5. Compounds of formula 3-6 can be prepared directly from compounds of formula 3-4 using a lewis acid such as $AlCl_3$ and the like and an acid chloride such as acetyl chloride and the like. Bromination of 3-4 with reagents such as 1,3-dibromo-5,5-dimethylhydantoin or other brominating agent in an appropriate solvent, such as DMF or the like, provides 3-7

Reaction Scheme 3

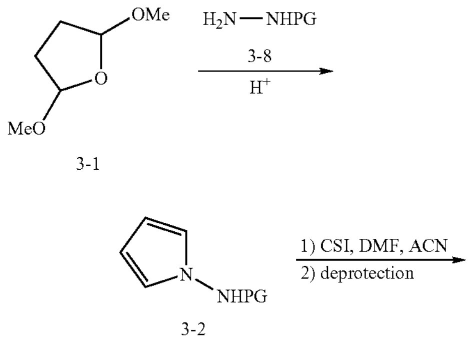

-continued

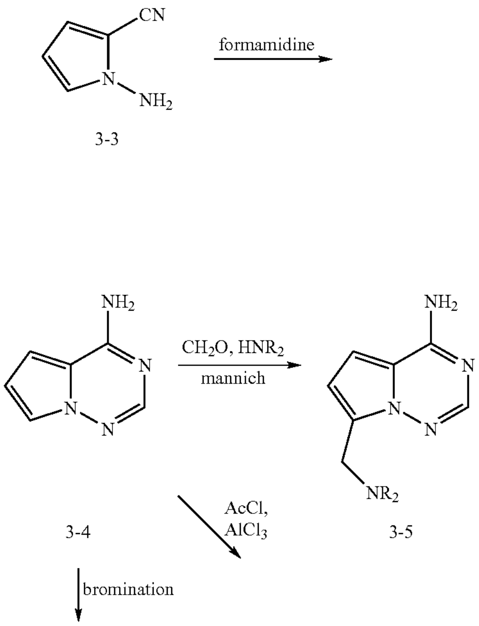

3-3

3-4

3-5

-continued

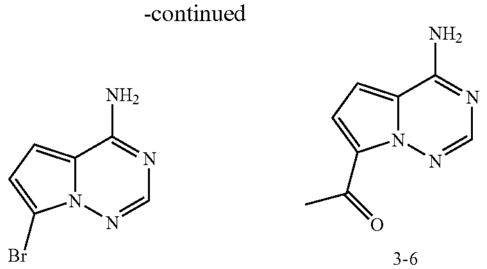

3-6

3-7

Reaction Scheme 4 outlines some of the ways in which common intermediate 3-7 can be utilized to provide functionality at the $R^4$ position. Halogen metal exchange on common intermediate 3-7 with an appropriate organometallic reagent, such as n-butyl lithium and the like, in an inert solvent (eg. THF) provides the transient species 4-1, which can be quenched with a variety of electrophiles that are well known in the art. Treatment of 4-1 with reagents such as DMF and the like provides aldehyde intermediate 4-2. Treatment of 4-1 with $CO_2$ provides acid intermediate 4-3. Treatment of 4-1 with reagents such as ethylene oxide and the like provides alcohol intermediate 4-3. Treatment of 4-1 with reagents such as Weinreb amides such as compounds of formula 4-6 provides substituted ketones of formula 4-5.

Reaction Scheme 4

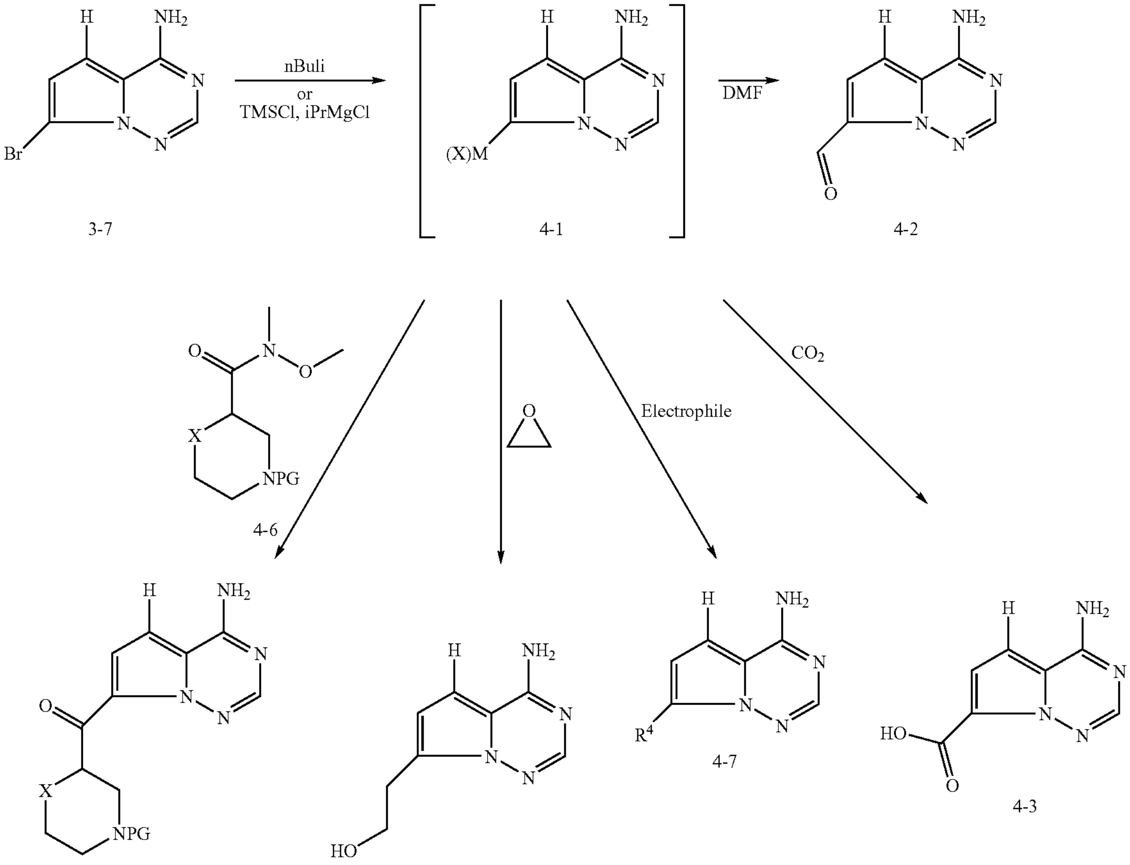

3-7

4-1

4-2

4-6

4-5

4-4

4-7

4-3

Reaction Scheme 5 outlines some additional of the ways in which functionality at the $R^4$ position can be introduced and modified through common intermediate 3-7. Metal insertion into 3-7 with an appropriate metal (e.g. palladium, nickel, zinc and the like), provides the transient species 5-1, which can be coupled with a variety of reagents familiar to those skilled in the art. Treatment of 5-1 with vinyl boronates or boronic acids such as 5-2 or 5-5 under conditions that are well known in the art and provides the appropriately protected intermediates 5-3 and 5-7 respectively. Alternatively, 5-1 can be treated with alkynes of formula 5-4 in presence of a Pd(II) catalyst, a Cu(I) co-catalyst and an amine base such as pyrrolidine or triethylamine or the like, in a solvent such as DMF or the like to provide compounds of formula 5-6. Intermediate 5-1 can also be treated with alcohols under a carbon monoxide atmosphere to provide intermediates of formula 5-8.

Reaction Scheme 6 describes the preparation of compounds of formula 6-3, where $G^2$ is defined as a subset of $R^4$ including intermediates describe in Schemes 3, 4, and 5. Thus, treatment of compounds of formula 6-1 with a brominating reagent such as 1,3-dibromo-5,5-dimethylhydantoin or the like in an appropriate solvent, such as THF or the like, provides compounds of formula 6-2. A metal mediated cross coupling such as Suzuki or the like under conditions well known in the art provide compounds of the formula 6-3. Compounds of formula 6-3 can be formula I. Alternatively, in compounds of formula 6-3 $G^2$ can be further elaborated as described in Schemes 7-12 to provide $R^4$.

Reaction Scheme 5

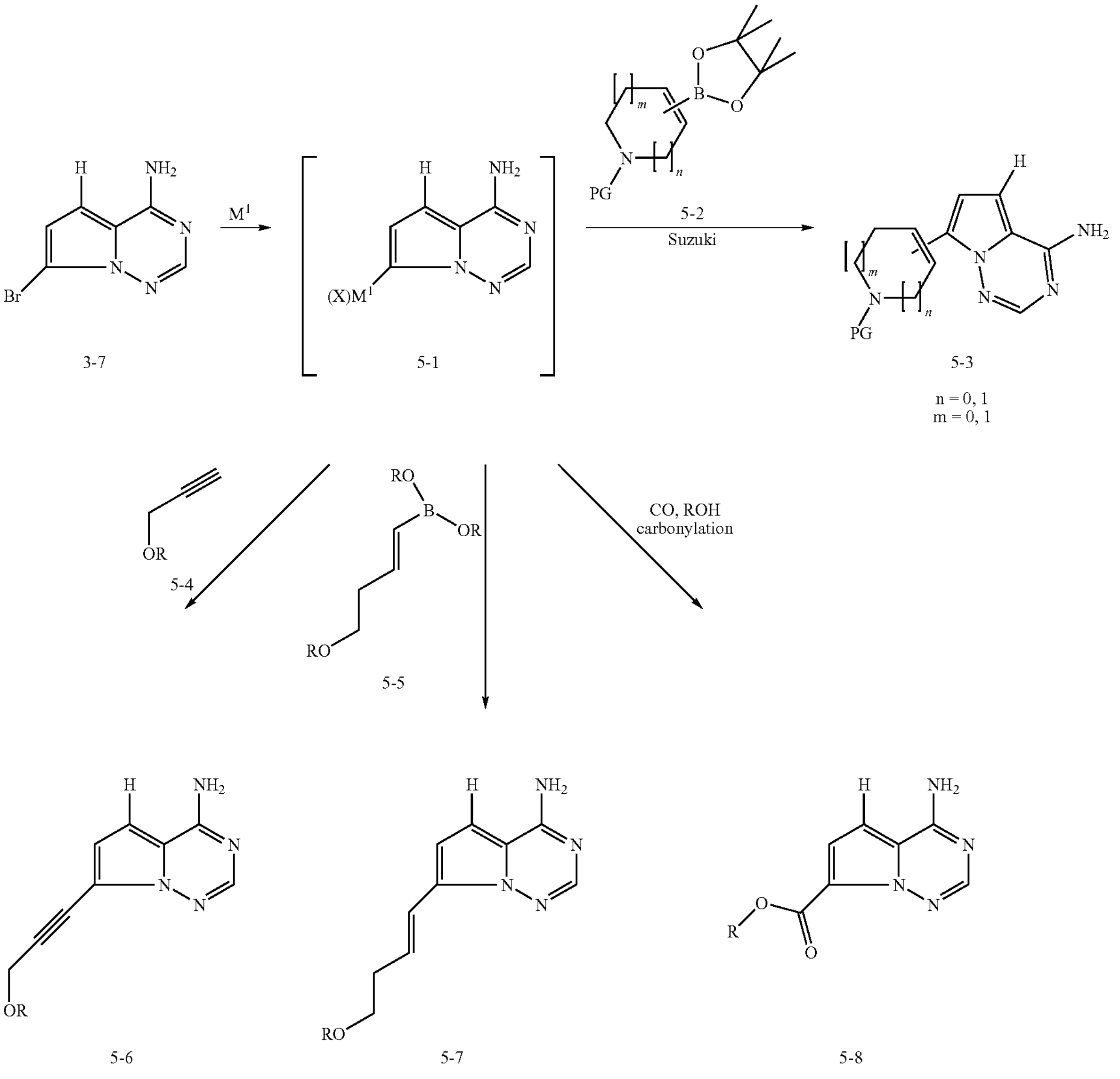

Reaction Scheme 6

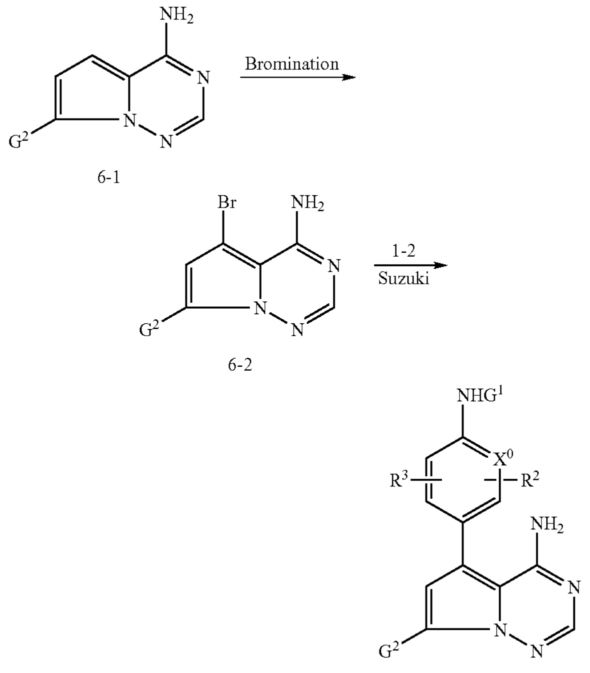

6-1

6-2

6-3

Reaction Scheme 7 describes some of the ways the aldehyde functional group in compounds of formula 7-1 can be manipulated, where $G^3$ is defined in Scheme 7 and $G^1$ is defined in Scheme 1. Thus, compounds of formula 7-2 can be prepared by ones skilled in the art by treatment with an amine, such as a primary or secondary (cyclic or acyclic) amine, in the presence of a suitable reducing agent, such as sodium triacetoxyborohydride or the like in a suitable solvent such as dichloroethane or the like. Alternatively, compounds of formula 7-1 can be treated with a Grignard reagent or the like, in an appropriate solvent such as THF or the like provides alcohols of formula 7-3. Cyclized compounds of formula 7-4 can also be synthesized by treatment of 7-1 with isocyanide reagents (eg. TosMIC and the like). Thus, treatment of compounds of formula 7-1 with a reducing agent, preferably DIBAL-H, in a solvent such as THF or the like will provide primary alcohols of formula 7-5. Halogenation of 7-5 with a reagent such as thionyl chloride or the like in a suitable solvent such as $CH_2Cl_2$ provides α-halo compounds of formula 7-6 (X═Cl, Br or I). Treatment of 7-6 with alcohols in a suitable solvent such as DMF or the like, in the presence of a base such as Hunigs base or the like and optionally with a catalyst such as potassium iodide or the like provides ethers of formula 7-7. Alternatively, treatment of 7-6 with an amine, such as a primary or secondary (cyclic or acyclic) amine, in the presence of a suitable base, such as Hunigs base or the like provides compounds of structure 7-2.

Reaction Scheme 7

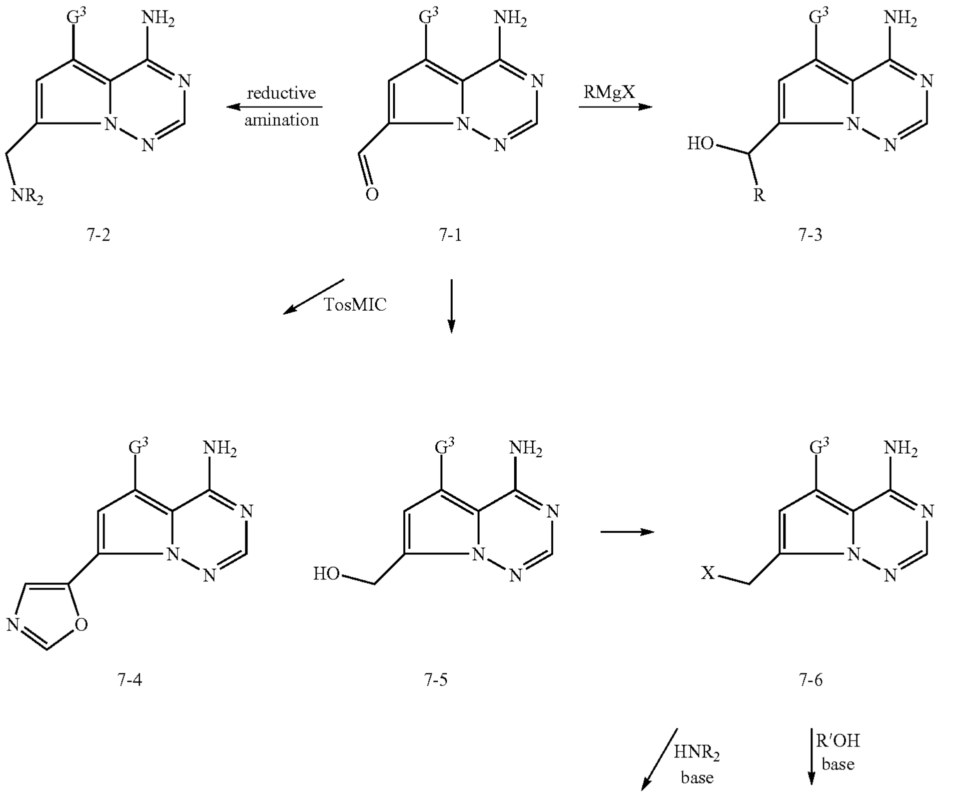

7-2

7-1

7-3

7-4

7-5

7-6

-continued

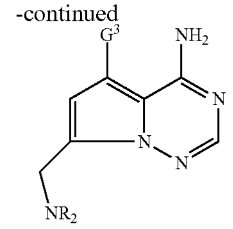

7-2

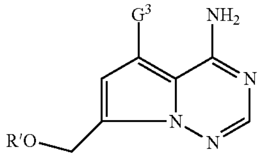

7-7

G3 = H, Halogen or 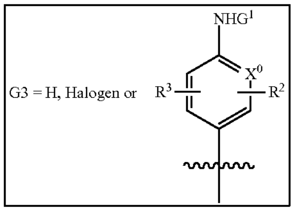

Reaction Scheme 8 describes some of the ways the ketone functional group in compounds of formula 8-1 can be manipulated, where $G^3$ is defined in Scheme 7. Thus, compounds of formula 8-1 can be treated with a reducing agent, such as DIBAL-H and the like in an appropriate solvent such as THF and others, to provide secondary alcohols of the formula 8-3. Tertiary alcohols of formula 8-3 may also be generated by treatment of 8-1 with Grignard reagents or the like in aprotic solvents such as THF and the like. Additionally, compounds of formula 8-1 can be treated with a silyl-triflate secondary (cyclic or acyclic) amine, or as an alcohol or carboxylic acid, in a suitable solvent such as DMF or the like and optionally in the presence of a catalyst such as potassium iodide and/or a base such as potassium carbonate or the like. Optionally substituted heterocycles of the formula 8-6 (Y can be independently N, O or S) can also be generated by treatment of 8-4 with a variety of nucleophiles, which are well known to those in the art (e.g. thioamides, or formamides for the formation of thiazoles and imidazoles respectively).

Reaction Scheme 8

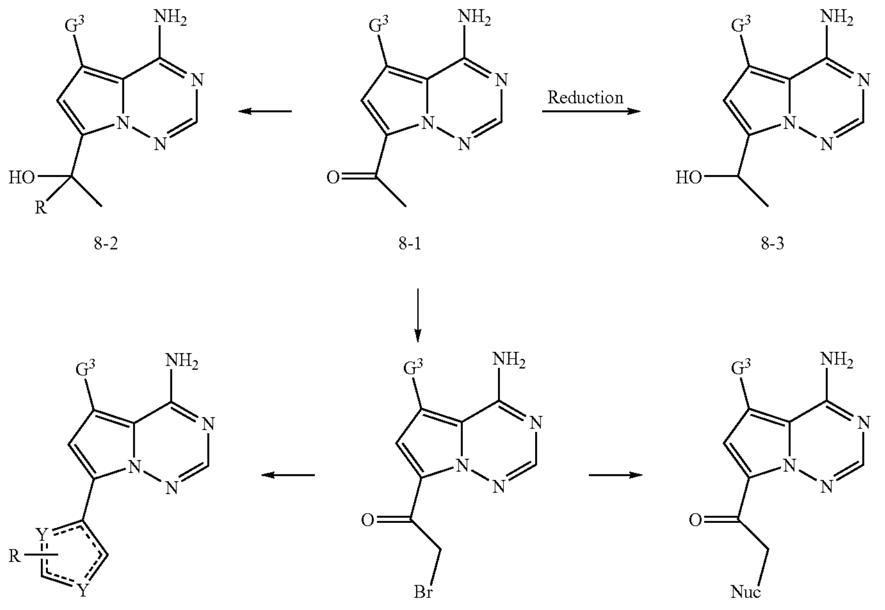

8-2 8-1 8-3

8-6 8-4 8-5 in the presence of a tertiary amine in solvents such as THF to provide a silyl-enol ether. The compounds can be transformed into compounds of formula 8-4 by treatment with a brominating agent such as 1,3-dibromo-5,5-dimethylhydantoin or the like. The compounds of formula 8-4 can be converted to compounds of formula 8-5 by treatment with a nucleophile Nuc, wherein Nuc is defined as an amine, such as a primary or Reaction Scheme 9 describes some of the ways amides of formula 9-2 can be synthesized, where $G^3$ is defined in Scheme 7. Intermediate 9-1 can be synthesized by those experienced in the art by Scheme 4 or 5 and/or Scheme 6. The carboxylic acid moiety can be synthesized directly from intermediate 4-3 or from esters derived from intermediate 5-8, which can be hydrolyzed under basic conditions (e.g. aqueous NaOH and the like) in an appropriate solvent. Coupling of compounds of formula 9-1 (carboxylic acids) with primary and secondary (cyclic or acyclic) amines under peptide coupling conditions well known to those skilled in the art provides amides of formula 9-2.

Reaction Scheme 9

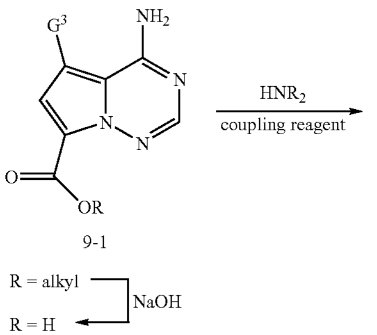

9-1 9-2

Reaction Scheme 10 describes the preparation of 10-4, which constitutes a subset of $R^4$ wherein a primary or secondary (cyclic or acyclic) amine is connected by a 2, 3 or 4 carbon tether and $G^3$ as defined in Scheme 7. Compounds of formula 10-1 contain either a alkene or alkyne moiety and can exist as either the free alcohol or protected by a protecting group (PG) which is well known in the art. Hydrogenation of the alkene or alkyne of 10-1 in the presence of a catalyst such as $PtO_2$ or the like provides compounds of the formula 10-2 (n 2, 3). Alternatively, compounds of formula 10-2 (n=1) can be derived directly from intermediate 4-4. If necessary the PG could be removed at this time by process well know in the art. Halogentaton of the resulting alcohol could be effected with reagents well know in the art (e.g. carbon tetrabromide and triphenylphosphine, or $SOCl_2$) in an aprotic solvent to afford compounds of the formula 10-3. Nucleophilic addition of a primary or secondary (cyclic or acyclic) amine in a suitable solvent such as DMF or the like and optionally in the presence of a catalyst such as potassium iodide and/or a base such as potassium carbonate or the like provides compounds of the formula 10-4.

Reaction Scheme 10

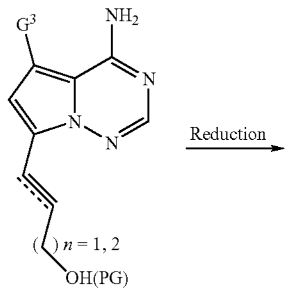

10-1

-continued

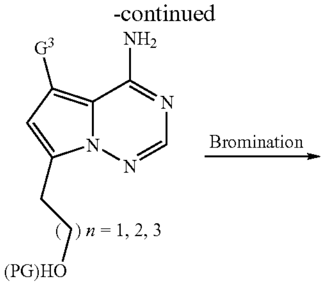

10-2

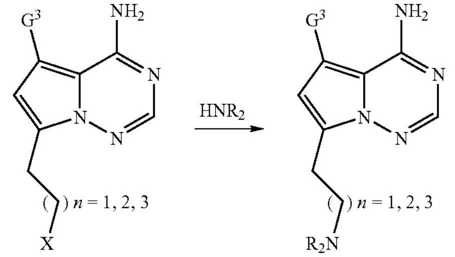

10-3 10-4

Reaction Scheme 11 describes the preparation of compounds of formula 11-3 ($R^4$=unsubstituted piperidine or pyrollidine) or 11-4 ($R^5$=optionally substituted piperidine or pyrollidine) wherein $G^3$ is defined as above in Scheme 7. Reduction of the double bond of 11-1 with hydrogen in the presence of a catalyst such as $PtO_2$ or the like in a solvent such as acetic acid or the like provides cyclic amines of formula 11-2. Deprotection of 11-2 using procedures well known in the art (acid catalyzed deprotection of BOC carbamate, e.g.) provides compounds of formula 11-3. Reaction of compounds of formula 11-3 with an appropriate alkylating agent such as ethylene carbonate in the presence of a suitable base such as sodium hydroxide provides compounds of the formula 11-6. Compounds of formula 11-4 are also prepared by treatment of compounds of the formula 11-3 with an aldehyde such as formaldehyde and the like and a reducing agent such as sodium triacetoxyborohydride or the like in a solvent such as 1,2-dichloroethane or the like. Compounds of formula 11-4 can also be prepared by the reaction of the amines of formula 11-3 with an acylating or sulfonating reagent, such as an acyl anhydride, acyl chloride, sulfonyl chloride or the like, in the presence of a suitable base such as pyridine, potassium carbonate, a tertiary amine or the like, in appropriate solvents such as THF, dichloromethane, or others. Additionally amines of formula 11-3 can be treated with isocyanates or carbamates in appropriate solvents such as THF and the like to provide ureas of the formula 11-4.

Reaction Scheme 11

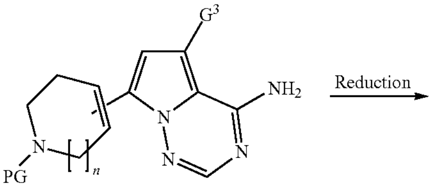

11-1

-continued

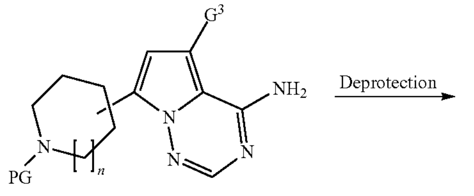

11-2

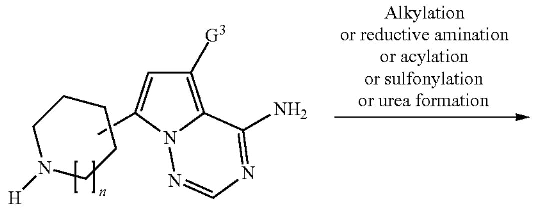

11-3

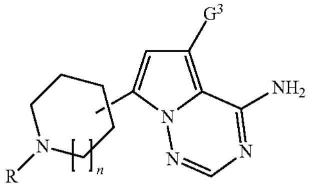

11-4 n = 0, 1

Reaction Scheme 12 outlines the preparation of compounds of 12-2 wherein $R^4$ is described as 2-substituted morpholine attached by a methylene linker and $G^3$ is defined as above in Scheme 7. Ketone 12-1 (PG is either H or an optional protecting group well known to those, in the art) can reduced directly under lewis acid mediated conditions (e.g. $BF_3$—$OEt_2$ and the like) in the presence of a hydride source (e.g. triethylsilane and the like). At this point the protecting group can be removed under conditions well known in the art (e.g. acid catalyzed removal of BOC carbamates).

Reaction Scheme 12

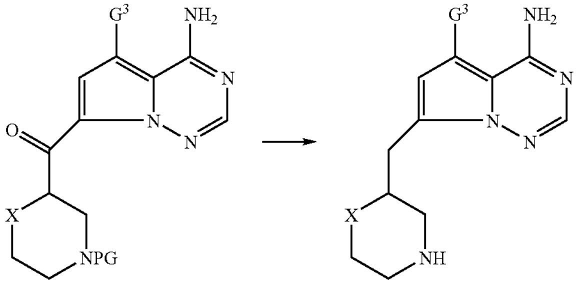

12-1 12-2

Additionally, sensitive or reactive groups on the compound of this invention may need to be protected and deprotected during any of the above methods. Protecting groups in general may be added and removed by conventional methods well known in the art (see, for example, T. W. Greene and P. G. M. Wuts, *Protective Groups in Organic Synthesis*; Wiley: New York, (1999).

In order that this invention may be better understood, the following examples are set forth. These examples are for the purpose of illustration only, and are not to be construed as limiting the scope of the invention in any manner. All publications mentioned herein are incorporated by reference in their

Preparation of Intermediates

Intermediate A: Preparation of Pyrrolo[2,1-f][1,2,4]triazin-4-ylamine

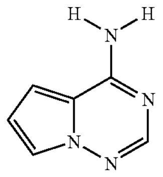

Step 1: Preparation of Pyrrol-1-yl-carbamic acid tert-butyl ester

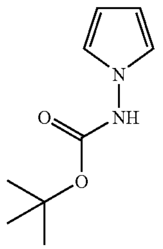

A flask (fitted with a Dean-Stark trap) containing a stirred solution of tert-butylcarbazate (100, 0.757 mol), 2,5-dimethoxytetrahydrofuran (108 g, 0.832 mol) and 2N HCl (10 mL) in 1,4-dioxane (700 mL) was heated under nitrogen at 90° C. As the reaction progressed over several hours, the solution changed from pale yellow to orange and began to reflux. The reaction was monitored by the amount of distillate collected in the D/S trap (primarily $CH_3OH$, 2 moles/1 mole reagent). As methanol collection approached the theoretical amount (50 mL) a sample was analyzed by TLC (silica gel, GHLF, 1:3 EtOAc/hexane, ninhydrin stain) to confirm reaction completion. Heating was shut off and the reaction was allowed to cool somewhat before adding saturated sodium bicarbonate solution (~25 mL) to neutralize the hydrochloric acid. The quenched mixture was filtered through a sintered-glass funnel and concentrated in vacuo to leave an orange, semi-solid residue. The residue was suspended in diethyl ether (minimum volume) and the nearly colorless solids were collected by suction filtration, washed with hexane and air-dried to afford 60.2 g (40%) of product. A second crop (yellow-tan solids) from the mother liquors was isolated: 29.0 g, (19%). Additional material which was present in the mother liquors could be recovered by silica gel chromatography to increase the yield.

$^1$H-NMR ($CD_3OD$): δ 10.23 (br s, 1H), 6.66 (t, 2H, J=2.2 Hz), 5.94 (t, 2H, J=2.2), 1.42 (s, 9H); MS: GC/MS (+esi): m/z=182.9 $[MH]^+$ Step 2: Preparation of (2-Cyano-pyrrol-1-yl)-carbamic acid, tert-butyl ester

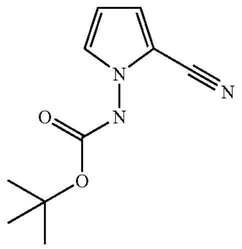

A 2 L, 3-neck RB was fitted w/stir bar, N2 inlet, rubber septum low-temp. thermometer and ice/acetone cooling bath. Pyrrol-1-yl-carbamic acid tert-butyl ester (99.0 g, 0.543 mol) was added to the reactor, dissolved w/anhydrous acetonitrile (700 mL) and the stirred solution was cooled to 0° C. Chlorosulfonyl isocyanate (49.7 mL, 0.57 mol) was added dropwise via syringe (maintaining an internal temp. below 5° C.); after ~20 minutes a suspension was observed. After 45 minutes N,N-dimethylformamide (anhydrous, 100 mL) was added dropwise via addition funnel (keeping internal temp. below 5° C.) and the reaction mixture became a solution. Stirring @ 0° C. was continued for 45 minutes, then the reaction was allowed to warm to RT; monitoring by TLC (silica gel, 1:3 ethyl acetate/hexane, UV, ninydrin stain) of a quenched sample indicated that the reaction had progressed to completion. The mixture was poured onto ice (~2 L) and stirred with addition of EtOAc (2 L). The layers were separated and the organic layer was dried over magnesium sulfate. The dried solution was filtered through a pad of 30/40 Magnesol and the filtrate was concentrated to dryness in vacuo, then the residue was dissolved in a minimum volume of dichloromethane and chromatographed on a plug of silica gel, eluting with ethyl acetate/hexane, 0-50% ethyl acetate. The clean, product-containing fractions were combined and concentrated to dryness in vacuo, to afford the desired product as a white solid, 69.8 g (62%). A somewhat impure fraction provided additional material, 16.8 g (15%), bringing the total recovery to 86.6 g, (77%). $^1$H-NMR ($CD_3OD$): 0.01 (dd, 1H, J=3.0, 1.6 Hz), 6.82 (dd, 1H, J=4.4, 1.7 Hz), 6.19 (dd, 1H, J=4.2, 2.9 Hz), 4.88 (s, 1H, $H_2O$+NH—), 1.50 (br s, 9H, HN—BOC); MS: LC/MS (+esi), m/z=207.9 [M+H]

Step 3: Preparation of 1-Amino-1H-pyrrole-2-carbonitrile hydrochloride

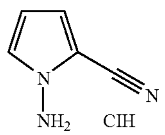

A 3 L, 3-neck RB flask was fitted with a mechanical stirrer, nitrogen inlet, thermocouple/JKEM thermocontroller, addition funnel and ice water cooling bath. (2-Cyano-pyrrol-1-yl)-carbamic acid, tert-butyl ester (85 g, 0.41 mol) was added and dissolved with 1,4-dioxane (400 mL), then the stirred orange solution was cooled to 0° C. and HCl/dioxane (4N, 820 mL, 8 eq.) was slowly added from the addition funnel, maintaining an internal temperature below 5° C. After ~30 minutes the solution became cloudy and stirring @ room temperature was continued for 5 hours; the reaction was monitored for completion by TLC (silica gel, GHLF, 1:3 EtOAc/hexane, UV; Note: the free base may be observed as a high-Rf spot and can be misinterpreted as incomplete reaction). The reaction mixture was diluted with diethyl ether (2 L) and the precipitated solids were collected by suction filtration and washed with ether (1 L). Drying (vacuum oven @ 50° C.) afforded the desired product as 50.5 g (85%) of a tan solid. $^1$H-NMR ($CD_3OD$): δ7.05 (dd, 1H, J=2.8, 1.9 Hz), 6.75 (dd, 1H, J=1.8, 4.2 Hz), 6.13 (dd, 1H, J=2.8, 4.4 Hz), 5.08 (s, 3H, $NH_3^+$); MS: GC/MS, m/z=108.2 [M+H].

Step 4: Preparation of the Title Compound

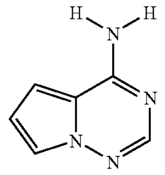

To a stirred suspension of 1-Amino-1H-pyrrole-2-carbonitrile hydrochloride (50 g, 0.35 mol) in absolute ethanol (800 mL) was added formamidine acetate (181.3 g, 1.74 mol) and potassium phosphate (370 g, 1.74 mol). The suspension was heated for 18 hours @ 78° C. (under $N_2$), then cooled, filtered and concentrated to dryness in vacuo. The residue was mixed with ice water (2 L) and the dark grayish-brown solids were collected by suction filtration. The filter cake was washed with water, sucked dry and the solids were dissolved (on the funnel) with hot ethyl acetate and filtered into a collection vessel. The dark solution was filtered through a long plug of 30/40 Magnesol and the pale yellow filtrate was concentrated to dryness in vacuo to afford a yellow-tinged solid (20.6 g, 44.1% yield). The plug was washed with ethyl acetate/ethanol and the washings were concentrated in vacuo to afford additional material, 10.7 g (23%). Extraction of the aqueous work-up filtrate with ethyl acetate followed by drying, Magnesol filtration and concentration gave another 6.3 g (14%) of clean product, bringing the total recovery to 37.6 g (81%). $^1$H-NMR ($CD_3OD$): δ 7.72 (s, 1H), 7.52 (dd, 1H, J=2.5, 1.6 Hz), 6.85 (dd, 1H, J=4.5, 1.6 Hz), 6.64 (dd, 1H, J=4.5, 2.7 Hz) LC/MS (+esi): [M+H].

Intermediate B: Preparation of 7-Bromo-pyrrolo[2,1-f][1,2,4]triazin-4-ylamine

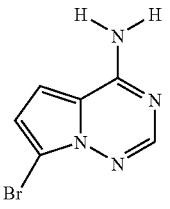

A stirred solution containing pyrrolo[2,1-f][1,2,4]triazin-4-ylamine (21.0 g, 0.157 mol) in anhydrous DMF (200 mL) was cooled to −20° C. and 1,3-dibromo-5,5-dimethylhydantoin (22.4 g, 0.078 mol) was added portionwise over ~45 minutes. The reaction was stirred for another 45 minutes and monitored for completion by TLC (silica gel, GHLF, 5% $CH_3OH/CH_2Cl_2$). Saturated $Na_2SO_3$ solution (300 mL) was added, the resulting suspension was stirred and the solids were collected by suction filtration. The filter cake was washed with water, dried by suction and then partitioned between ethyl acetate (1 L) and 5% sodium carbonate solution (1 L). The layers were separated, the organic layer was washed with fresh sodium carbonate solution and dried over magnesium sulfate. The filtrate from the work-up was also extracted and combined with the main batch then filtered through a pad of Magnesol and concentrated in vacuo to afford crude mono-bromide, KRAM 206-3-1, 29.9 g, 90% yield. Trituration of a 21.5 g quantity of the crude mono-/di-bromo product in hot ethyl acetate (300 mL, 70° C.) provided colorless solids (12.3 g) containing only ~2% of the di-brominated side-product. $^1$H-NMR ($CD_3OD$): δ 7.84 (s, 1H), 6.95 (d, 1H, J=4.7 Hz), 6.71 (d, 1H, J=4.7 Hz), 4.89 (s, 3H, —$NH_2$+$H_2O$); MS: LC/MS (+esi), m/z=213.1 [M+H].

Intermediate C: 5-Bromo-7-(morpholin-4-ylmethyl) pyrrolo[2,1f][1,2,4]triazin-4-amine

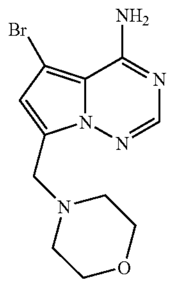

Step 1: 7-(morpholin-4-ylmethyl)pyrrolo[2,1-f][1,2,4]triazin-4-amine

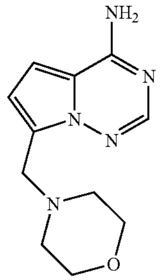

A solution of formaldehyde (7.9 ml, 10.9 g, 134 mmol) and morpholine (8.0 ml, 11.7 g, 134 mmol) in AcOH (90 mL) was allowed to stir for 20 minutes (slightly exothermic). A solution of the intermediate A (15.00 g, 112 mmol) in AcOH (500 mL) was then added and the resulting mixture was heated to 60° C. over night (Note-solution gets darker in color over time). The reaction was concentrated in vacuo and the residue was dissolved in EtOAc (~300 mL) and washed with 1N NaOH (pH is ~10) (~300 mL). The aqueous phase was back-extracted with EtOAc (3×100 mL). Because the product is somewhat water soluble and the aqueous extracts still indicated heavy UV, the aqueous layer was diluted with brine (1:1) and extracted 3×100 mL EtOAc (note—pH of aqueous phase was checked after each extraction and re-adjusted with 1N NaOH to remain in the 9-10 range). The combined organic layer was washed with brine (~200 mL), dried ($Na_2SO_4$), filtered and concentrated in vacuo to afford a yellow solid. The crude material was recrystallized from 10% THF in EtOAc to afford 19.5 g (75% yield) of a light yellow free flowing solid. Product $R_f$=0.20 in 9:1 DCM:EtOH $^1$H-NMR (DMSO-$d_6$) δ 7.82 (s, 1H), 7.73 to 7.56 (br s, 2H), 6.84 (d, J=4.5 Hz, 1H), 6.54 (d, J=4.4 Hz, 1H), 3.76 (s, 2H), 3.52 (t, J=4.5 Hz, 4H), 2.38 (t, J=4.4 Hz, 4H); MS: LC/MS (+esi) RT=1.01 min m/z=234 [M+H]

Step 2. Preparation of Title Compound

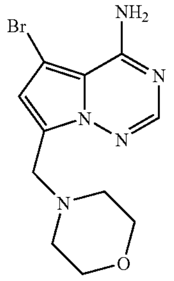

In a 3-neck round bottom flask flushed with nitrogen was dissolved the morpholino pyrrolotriazine (8.91 g, 38.2 mmol) in THF (275 ml). This resulting solution was cooled to −78° C. (acetone/dry ice). To this was added the 1,3-Dibromo-5,5-dimethylhydantoin in 4 (approximately equal) portions (total amount used=5.242 g, 18.33 mmol, 0.48 equiv) 30 minutes apart. The reaction was allowed to stir for an additional 30 min at −78° C. and was then warmed to −45° C. with a dry ice/MeCN bath and stirred for 30 min. Lastly, the reaction was allowed to warm to −10° C. in an ice/acetone bath and allow to stir for an additional 30 min. TLC (9:1 DCM:EtOH,) indicates major component is desired product ($R_f$ 0.52) also note small amount of SM ($R_f$=0.20) and/or dibromide ($R_f$=0.58)-obtained through retro-mannich followed by bromination at C-7). The reaction was quenched at −10° C. with Sat'd $Na_2SO_3$ (30 mL) and stirred for 30 minutes, allowing reaction to warm to RT. The mixture was diluted with EtOAc (300 mL) and water (100 ml) and separated. The aqueous phase was back-extracted with EtOAc (6×100 mL) (note-desired product was highly water soluble). The combined organic layer was washed with brine (200 mL), dried ($Na_2SO_4$), filtered and concentrated in vacuo to afford a light yellow solid. The crude material was recrystallized from THF to afford 5.24 grams of slightly pink free flowing solid. The mother liquor was concentrated to provide a yellow residue and was recrystallized from THF to afford a second batch (1.73 grams, combined yield of 58.5%) of slightly pink material. Product $R_f$=0.52 in 9:1 DCM:EtOH. $^1$H-NMR (DMSO- $d_6$) δ 7.86 (s, 1H), 6.72 (s, 1H), 3.75 (s, 2H), 3.53 (t, J=4.5 Hz, 4H), 2.38 (t, J=4.3 Hz, 4H); MS: LC/MS (+esi), RT=0.25 min m/z=311.9 [M+H].

Intermediate D: 4-[(4-amino-5-bromopyrrolo[2,1-f][1,2,4]triazin-7-yl)methyl]-piperazin-2-one

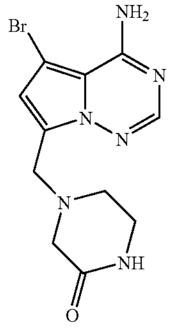

Step 1: Preparation of 4-[(4-aminopyrrolo[2,1f][1,2,4]triazin-7-yl)methyl]piperazin-2-one

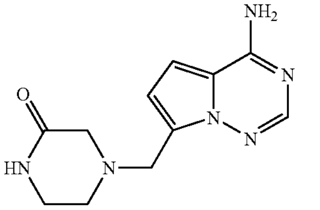

A solution of paraformaldehyde (726 mg, 8.95 mmol) and 2-oxopiperazine (1.49 g, 14.9 mmol) in acetic acid (35 ml) was stirred under nitrogen for 10 minutes and then Intermediate A (1.00 g, 7.46 mmol) was added. The resultant mixture was heated at 60° C. for 2 hr and then evaporated in vacuo to give dark oily residue. This raw product was diluted with about 200 ml of EtOAc and then filtered twice to remove a very dark solid which was rinsed with additional EtOAc and give an orange filtrate which was mixed with saturated aqueous NaHCO3 to precipitate a cream colored solid precipitate. This material was collected by filtration, washed with water and EtOAc and then dried in vacuo to give pure 4-[(4-aminopyrrolo[2,1-f][1,2,4]triazin-7-yl)methyl]piperazin-2-one (948 mg, 52%). $^1$H-NMR (DMSO-$d_6$) δ7.82 (s, 1H), 7.6-7.7 (bs, 3H), 6.86 (d, 1H, J=4.8), 6.56 (d, 1H, J=4.8), 3.85 (s, 2H), 3.09 (m, 2H), 2.91 (s, 2H), and 2.55 (m, 2H); MS LC-MS $[M+H]^+$=247.3 and $[M+Na]^+$=275.9, RT=1.03 min.

Step 2: Preparation of the Title Compound

A suspension of 4-[(4-aminopyrrolo[2,1-f][1,2,4]triazin-7-yl)methyl]piperazin-2-one (900 mg, 3.65 mmol) was stirred under nitrogen in DMF (24 ml) as trifluoroacetic acid (0.40 ml, 5.2 mmol) was added via syringe resulting in a solution. This solution was stirred under nitrogen with −20 to −30° C. bath cooling as 1,3-dibromo-5,5-dimethylhydantoin (470 mg, 01.65 mmol) was added in 6 portions every 5-20 minutes. A small aliquot was removed, diluted with MeOH and assayed by HPLC to show that 87 area % product had formed along with about 2% later side product thought to be dibromide. The reaction mixture was diluted with EtOAc and washed with ca. 20 ml saturated $NaHCO_3$. The aqueous was back extracted three times with 10% isopropanol in dichloromethane. The combined extract was dried ($Na_2SO_4$) and evaporated in vacuo. The residue was chromatographed on 40 g silica gel using a gradient from 0-10% MeOH in $CH_2Cl_2$. The best fractions were combined, evaporated and the residue was triturated with a mixture of hot THF, MeOH and $CH_2Cl_2$ and then cooled in a refrigerator before collecting the solid which was dried in vacuo to give pure 4-[(4-aminopyrrolo[2,1-f][1,2,4]triazin-7-yl)methyl]piperazin-2-one (724 mg, 61%). $^1$H-NMR (DMSO-$d_6$) δ7.86 (s, 1H), 7.71 (bs, 1H), 6.76 (s, 1H), 3.84 (s, 2H), 3.09 (m, 2H), 2.93 (s, 2H), and 2.56 (t, 2H, J=5.4); MS LC-MS $[M+H]^+$=325/327 (weak), RT=1.08 min.

Intermediate E: Preparation of 5-(4-aminophenyl)-7-(morpholin-4-ylmethyl)pyrrolo-[2,1-f][1,2,4]triazin-4-amine

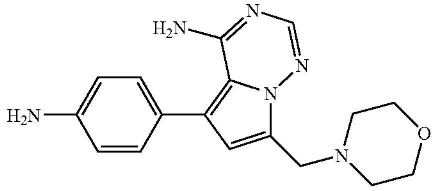

Step 1: Preparation of 4-aminopyrrolo[2,1f][1,2,4]triazine-7-carbaldehyde

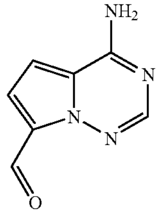

To a solution of Intermediate B (50 mg, 0.23 mmol) in THF (2 ml) at −78° C. under $N_2$ was added n-butyllithium (0.38 ml, 0.93 mmol) slowly. After stirred for 15 min, DMF (0.10 ml, 1.4 mmol) was added and the dry-ice bath was removed and the reaction was allowed to warm up to rt. The reaction mixture was diluted with ethyl acetate and was quenched with $H_2O$. The organic was collected, dried over $Na_2SO_4$ and concentrated to yield 34 mg of a mixture of the title compound and a byproduct pyrrolo[2,1f][1,2,4]triazin-4-amine. The mixture was not separable via column chromatography and was subject to next step reaction without further purification. $^1H$-NMR (DMSO-$d_6$) δ 10.3 (—CHO). MS $[M+H]^+$=163.2; LCMS RT=1.11 min.

Step 2: Preparation of 7-(morpholin-4-ylmethyl) pyrrolo[2,1-f][1,2,4]triazin-4-amine

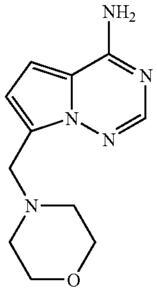

To 4-aminopyrrolo[2,1-f][1,2,4]triazine-7-carbaldehyde (235 mg, 1.45 mmol) in 1,2-dichloroethane (5 ml) was added morpholine (0.25 ml, 2.9 mmol) and sodium triacetoxyborohydride (611 mg, 2.9 mmol). The reaction mixture was stirred at rt under $N_2$ for 16 h. The reaction was quenched with saturated aq. sodium bicarbonate and followed by extraction with $CH_2Cl_2$. The organic was dried over $Na_2SO_4$, concentrated and purified via column chromatography (5:95 v/v $CH_3OH$—$CH_2Cl_2$) to afford 66 mg of the title compound (yield 20%). $^1H$-NMR (DMSO-$d_6$) δ 7.80 (s, 1H), 7.62 (br, 2H), 6.83 (d, J=4 Hz, 1H), 6.52 (d, J=4 Hz, 1H), 3.75 (s, 2H), 3.51 (t, J=4 Hz, 4H), 2.37 (t, J=4 Hz, 4H); MS $[M+H]^+$=234; LCMS RT=1.00 min.

Step 3: Preparation of 5-bromo-7-(morpholin-4-ylmethyl)pyrrolo[2,1f][1,2,4]triazin-4-amine

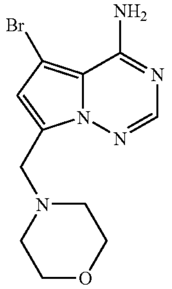

To a solution of 7-(morpholin-4-ylmethyl)pyrrolo[2,1-f][1,2,4]triazin-4-amine (562 mg, 2.40 mmol) in THF (19 ml) at −20 C was added 1,3-dibromo-5,5-dimethylimidazolidine-2,4-dione (344 mg, 1.2 mmol) in three portions. The reaction was stirred at −20 C for 3 h. Upon the completion, the reaction was quenched with aqueous saturated $Na_2SO_3$ and allowed to warm up to rt. The crude was extracted with ethyl acetate. The organic was washed with brine, dried over $Na_2SO_4$ and concentrated. The resulting crude was purified via column chromatography (95:5 v/v $CH_2Cl_2$—$CH_3OH$) to afford 600 mg of the title compound as yellow solid (yield 79%). $^1H$-NMR (DMSO-$d_6$) δ 7.84 (s, 1H), 6.71 (s, 1H), 3.74 (s, 2H), 3.51 (t, J=4 Hz, 4H), 2.37 (t, J=4 Hz, 4H); MS $[M+H]^+$=312; LCMS RT=1.04 min.

Step 4. Preparation of Title Compound

A mixture of Intermediate C (100 mg, 0.32 mmol), 4-(4,4,5,5-tetramethyl-1,3,2-dioxaborolan-2-yl)aniline (210 mg, 0.96 mmol), 2M $Na_2CO_3$ (0.48 ml, 0.96 mmol) and tetrakis (triphenylphosphine)palladium (37 mg, 0.03 mmol) in 1,2-dimethoxyethane (2 ml) was degassed and filled with $N_2$ and was s heated at 80 C under $N_2$ for 16 h. After cooled to rt, the reaction mixture was partitioned between $CH_2Cl_2$ and water. The aqueous phase was extracted with $CH_2Cl_2$ two times. The combined organic was washed with brine and dried over $Na_2SO_4$. The crude was concentrated to give the raw product as yellow oil. The resulting crude oil was purified via column chromatography (95:5 v/v $CH_2Cl_2$-$CH_3OH$) to afford 52 mg of the title compound (yield 50%). $^1H$-NMR (DMSO-$d_6$) δ 7.83 (s, 1H), 7.10 (d, J=9 Hz, 2H), 6.63 (d, J=9 Hz, 2H), 6.49 (s, 1H), 5.24 (s, 2H), 3.78 (s, 2H), 3.51 (t, J=4 Hz, 4H), 2.41 (t, J=4 Hz, 4H); MS $[M+H]^+$=324.9; LCMS RT=1.00 min.

Intermediate F: 5-(4-amino-3-fluorophenyl)-7-(morpholin-4-ylmethyl)pyrrolo[2,14]-[1,2,4]triazin-4-amine

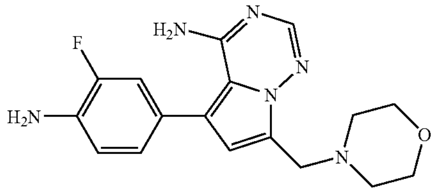

Step 1: Preparation of tert-butyl {4-[4-amino-7-(morpholin-4-ylmethyl)pyrrolo[2,1-f][1,2,4]triazin-5-yl]-2-fluorophenyl}carbamate

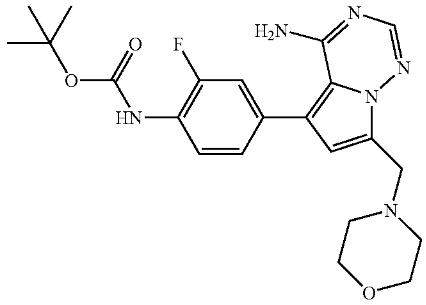

To a solution of Intermediate C (500 mg, 1.6 mmol) in dioxane (30 mL) and 2N Na2CO3 (30 mL) was added Intermediate P (576 mg, 1.68 mmol). The solution was degassed and back filled with $N_2$. Palladium tetrakis triphenylphosphine (185 mg, 0.16 mmol) was added and the reaction mixture was heated to 80° C. over night. The reaction was cooled to room temperature and diluted with EtOAc (100 mL). The organic layer was washed with brine, dried over $Na_2SO_4$ and concentrated in vacuo. The product was purified by flash column chromatography (Eluent gradient 1-10% MeOH/$CH_2Cl_2$) to provide the t-butyl {4-[4-amino-7-(morpholin-4-ylmethyl)pyrrolo[2,1-f][1,2,4]triazin-5-yl]-2-fluoro-phenyl} carbamate (1.9 g, 4.29 mmol) as a white powder in 92% yield.

$^1$H-NMR (DMSO-$d_6$) δ9.08 (s, 1H), 7.90 (s, 1H), 7.70 (t, J=8.4 Hz, 1H), 7.27 (dd, J=12, 2 Hz, 1H), 7.20 (dd, J=8.4, 2 Hz, 1H), 6.65 (s, 1H), 3.80 (s, 2H), 3.54 (m, 4H), 2.43 (m, 4H), 1.46 (s, 9H); MS [M+H]$^+$=442.8; LCMS RT=2.18.

Step 2. Preparation of Title Compound

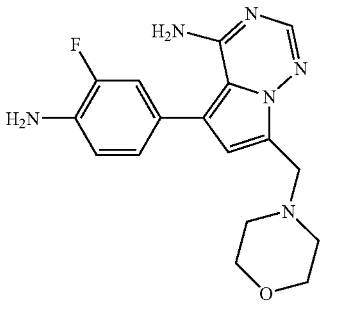

To a slurry of the t-butyl carbamate (510 mg, 1.15 mmol) in $CH_2Cl_2$ (10 mL) was added TFA (5 mL). The reaction mixture became homogenous instantly and was allowed to stir for 1 h. The reaction mixture was poured into 1N aqueous NaOH (100 mL) and extracted with EtOAc (100 mL). The organic layer was dried over $Na_2SO_4$ and concentrated in vacuo to provide the title compound (392 mg, 1.14 mmol) in 99% yield. The product was used immediately without further purification. $^1$H-NMR (DMSO-$d_6$) δ7.86 (s, 1H), 7.07 (dd, J=12, 2 Hz, 1H), 6.95 (dd, J=8, 2 Hz, 1H), 6.82 (dd, J=9.4, 8 Hz, 1H), 6.55 (s, 1H), 5.29 (s, 2H), 3.79 (s, 2H), 3.54 (m, 4H), 2.43 (m, 4H).

Intermediate G: 5-(4-amino-3-fluorophenyl)-7-[(1,1-dioxidothiomorpholin-4-yl)methyl]-pyrrolo[2,1f][1,2,4]triazin-4-amine

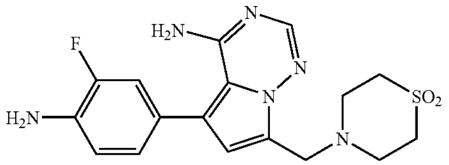

The procedure used for the preparation of Intermediate F was used to prepare the title compound by substituting thiomorpholine 1,1-dioxide for morpholine.

Intermediate H: Preparation of phenyl[4-(trifluoromethyl)pyridin-2-yl]carbamate

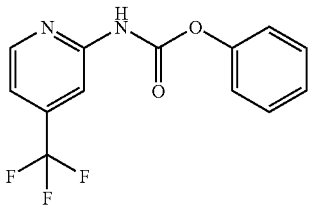

A solution of the commerically available 2-amino-4-trifluoromethylpyridine (20.86 g, 128.7 mmol) in 250 mL $CH_2Cl_2$ was treated with phenylchloroformate (17.81 mL, 141.5 mmol) and pyridine (22.85 mL, 283 mmol). During addition of the pyridine a yellow precipitate formed and a considerable exotherm was observed. After 0.5 h the homogeneous reaction was diluted with 1 L $Et_2O$ and washed with 1N bisulfate buffer (pH 2) and sat. $NaHCO_3$. The organic layer was dried with $Na_2SO_4$ and evaporated to yield a gray solid. Trituration with $Et_2O$:hexanes (1:5) gave the title compound as cottony white crystals (33.5 g, 92% Yield). $^1$H-NMR (DMSO-$d_6$) δ11.28 (s, 1H), 8.60 (d, J=5.1 Hz, 1H), 8.12 (bs, 1H), 7.40 to 7.48 (m, 3H), 7.22 to 7.31 (m, 3H); MS [M+H]$^+$=283.1; LCMS RT=3.51.

Intermediate I: Preparation of tert-butyl 4-{[4-amino-5-(4-aminophenyl)pyrrolo[2,1-f][1,2,4]triazin-7-yl]methyl}piperazine-1-carboxylate

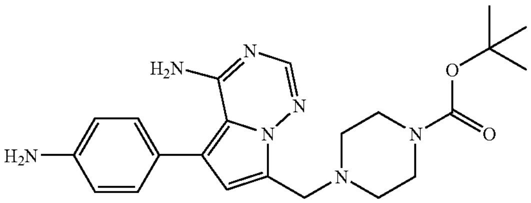

Step 1: Preparation of tert-butyl 4-[(4-aminopyrrolo[2,1f][1,2,4]triazin-7-yl)methyl]piperazine-1-carboxylate

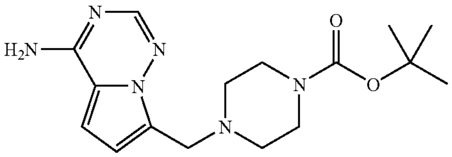

The procedure used for the preparation of Intermediate C, Step 1 was used to prepare the t-butyl 4-[(4-aminopyrrolo[2,1-f][1,2,4]triazin-7-yl)methyl]piperazine-1-carboxylate by substituting tert-butyl piperazine-1-carboxylate for morpholine. $^1$H-NMR (DMSO-$d_6$) δ 7.81 (s, 1H), 7.63 (br, 2H), 6.83 (d, J=4 Hz, 1H), 6.53 (d, J=5 Hz, 1H), 5.74 (s, 1H), 3.99 (s, 2H), 3.39 to 3.34 (m, 4H), 2.35 to 2.30 (m, 4H), 1.97 (s, 3H); MS [M+H]$^+$=333.0; LCMS RT=1.16 min Step 2: 4-(4-amino-5bromo-pyrrolo[2,1-f][1,2,4] triazin-7-ylmethyl)-piperazine-1-carboxylic acid tert-butyl ester

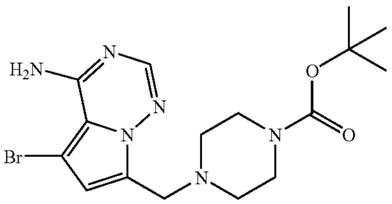

To a solution of 4-(4-amino-pyrrolo[2,1-f][1,2,4]triazin-7-ylmethyl)-piperazine-1-carboxylic acid tert-butyl ester (252 mg, 0.758 mmol) in THF (8 mL) at −20° C. (IPA and dry ice) was added 1,3-dibromo-5,5-dimethyl-imidazolidine-2,4-dione (108 mg, 0.379 mmol). The reaction was stirred at −20° C. for 4 h. After removal of solvent, the residue was purified by silica gel column using 4% methanol in dichloromethane to obtain 209 mg (67%) of desired product. $^1$H-NMR ($CD_2Cl_2$) δ 7.81 (s, 1H), 7.23 (s, 1H), 6.61 (s, 1H), 3.86 (s, 1H), 3.41 (t, J=2.4, 4H), 2.48 (s, 4H), 1.43 (s, 9H) MS $[M+H]^+$=410.9; LCMS RT=1.87 min Step 3: Preparation of Title Compound The procedure used for the preparation of Intermediate E, step 4 was used to prepare the t-butyl 4-{[4-amino-5-(4-aminophenyl)pyrrolo[2,1-f][1,2,4]triazin-7-yl]methyl}-piperazine-1-carboxylate by substituting 4-(4-amino-5-bromo-pyrrolo[2,1-f][1,2,4]triazin-7-ylmethyl)-piperazine-1-carboxylic acid tert-butyl ester for Intermediate C.

Intermediate J: Preparation of 7-[(4-acetylpiperazin-1-yl)methyl]-5-(4-amino-3-fluorophenyl)pyrrolo[2,1-f][1,2,4]triazin-4-amine

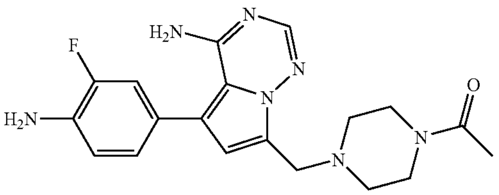

Step 1: Preparation of 7-[(4-acetylpiperazin-1-yl) methyl]pyrrolo[2,1-f][1,2,4]triazin-4-amine

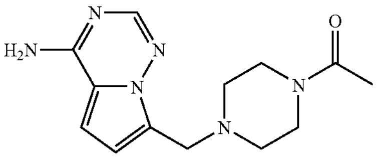

The procedure used for the preparation of Intermediate C, Step 1 was used to prepare 7-[(4-acetylpiperazin-1-yl)methyl]pyrrolo[2,1-f][1,2,4]triazin-4-amine by substituting N-acetyl piperizine for morpholine. $^1$H-NMR (DMSO-$d_6$) δ 7.81 (s, 1H), 7.63 (br, 2H), 6.83 (d, J=4 Hz 1H), 6.53 (d, J=5 Hz, 1H), 5.74 (s, 1H), 3.99 (s, 2H), 3.39 to 3.34 (m, 4H), 2.35 to 2.30 (m, 4H), 1.97 (s, 3H); MS $[M+H]^+$=275.1; LCMS RT=1.02 min.

Step 2 Preparation of 7-[(4-acetylpiperazin-1-yl) methyl]-5-bromopyrrolo[2,1-f][1,2,4]triazin-4-amine

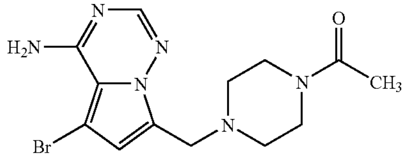

The procedure used for the preparation of Intermediate C, step 2 was used to prepare 7-[(4-acetylpiperazin-1-yl)methyl]-5-bromopyrrolo[2,1-f][1,2,4]triazin-4-amine by substituting 7[(4-acetylpiperazin-1-yl)methyl]pyrrolo[2,1f][1,2,4]triazin-4-amine for 7-(morpholin-4-ylmethyl)pyrrolo[2,1-f][1,2,4]triazin-4-amine. $^1$H-NMR (DMSO-$d_6$) δ 7.82 (s, 1H), 6.72 (s, 1H), 3.81 (s, 2H), 3.42 to 3.38 (m, 4H), 2.45 to 2.40 (m, 4H), 1.95 (s, 3H); MS $[M+H]^+$=354.9; LCMS RT=1.10 min.

Step 3: Preparation of tert-butyl (4-{7-[(4-acetylpiperazin-1-yl)methyl]-4-amino-pyrrolo[2,1-f][1,2,4]triazin-5-yl}-2-fluorophenyl)carbamate

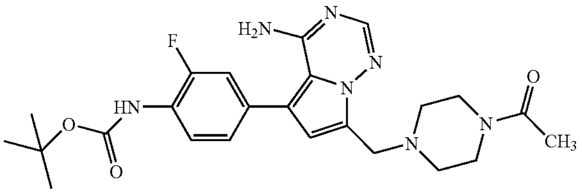

The procedure used for the preparation of Intermediate F, step 1 was used to prepare the t-butyl (4-{7-[(4-acetylpiperazin-1-yl)methyl]-4-amino-pyrrolo[2,1-f][1,2,4]triazin-5-yl}-2-fluorophenyl)carbamate by substituting 7-[(4-acetylpiperazin-1-yl)methyl]-5-bromopyrrolo[2,1-f][1,2,4]triazin-4-amine for Intermediate C. MS $[M+H]^+$=483.9; LCMS RT=2.15 min.

Step 4: Preparation of Title Compound

To a solution of t-butyl (4-{7-[(4-acetylpiperazin-1-yl)methyl]-4-aminopyrrolo[2,1-f][1,2,4]triazin-5-yl}-2-fluorophenyl)carbamate (320 mg, 0.62 mmol) in $CH_2Cl_2$ (8 ml) was added TFA (3 ml) and was stirred at rt for 3 h. The reaction mixture was partially evaporated and was added 10 ml ethyl acetate and washed with saturated aq. $NaHCO_3$. The organic was dried over $Na_2SO_4$, concentrated and purified via column chromatography (95:5, v/v, $CH_2Cl_2$-$CH_3OH$) to afford 74 mg of the title compound (yield 30%). $^1$H-NMR ($CH_3OH$-$d_4$) δ 7.85 (s, 1H), 7.10 to 7.00 (m, 3H), 6.66 (s, 1H), 4.00 (s, 2H), 3.60 to 3.50 (m, 4H), 2.63 to 2.55 (m, 4H), 20.6 (s, 3H); MS $[M+H]^+$=383.9; LCMS RT=1.10 min.

Intermediate K: Preparation of 5-(4-amino-3-methoxyphenyl)-7-(morpholin-4-ylmethyl)pyrrolo[2,1-f][1,2,4]triazin-4-amine

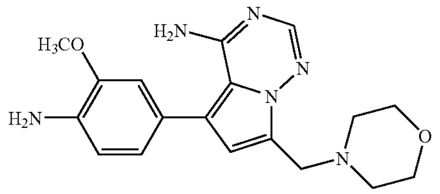

Step 1: Preparation of tert-butyl {4-[4-amino-7-(morpholin-4-ylmethyl)pyrrolo[2,1-f][1,2,4]triazin-5-yl]-2-methoxyphenyl}carbamate

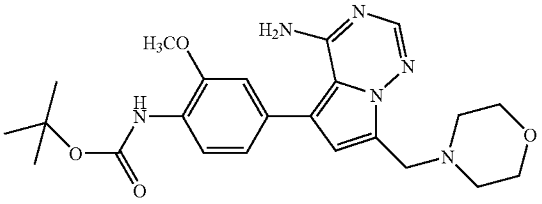

The procedure used for the preparation of Intermediate F, step 1 was used to prepare the t-butyl {4-[4-amino-7-(morpholin-4-ylmethyl)pyrrolo[2,1-f][1,2,4]triazin-5-yl]-2-methoxyphenyl}carbamate by substituting Intermediate BV for Intermediate X (t-butyl [2-fluoro-4-(4,4,5,5-tetramethyl-1,3,2-dioxaboraolan-2-yl)phenyl]carbamate) and substituting 1,4-dioxane for 1,2-dimethoxyethane. $^1$H-NMR (DMSO-$d_6$) δ 7.98 (s, 1H), 7.89 (s, 1H), 7.78 (d, J=8 Hz, 1H), 7.05 (d, J=2 Hz, 1H), 6.96 (dd, J=8, 2 Hz, 1H), 6.65 (s, 1H), 3.83 (s, 3H), 3.80 (s, 2H), 3.53 (t, J=4 Hz, 4H), 2.42 (t, J=4 Hz, 4H), 1.41 (s, 9H); MS $[M+H]^+$=455.0; LCMS RT=2.44 min.

Step 2: Preparation of Title Compound

To a solution of t-butyl {4-[4-amino-7-(morpholin-4-ylmethyl)pyrrolo[2,1-f][1,2,4]triazin-5-yl]-2-methoxyphenyl}carbamate (100 mg, 0.22 mmol) in $CH_2Cl_2$ (4 ml) was added trifluoroacetic acid (1.5 ml) and was stirred at rt for 3 h. The reaction mixture was partially evaporated and was added 10 ml ethyl acetate and washed with saturated aq. $NaHCO_3$. The organic was dried over $Na_2SO_4$ and concentrated to afford 80 mg of the title compound. $^1$H-NMR (DMSO-$d_6$) δ 7.84 (s, 1H), 6.84 (d, J=2 Hz, 1H), 6.84 to 6.68 (m, 2H), 6.55 (s, 1H), 4.87 (s, 2H), 4.01 to 3.99 (m, 5H), 3.53 (t, J=4 Hz, 4H), 2.42 (t, J=4 Hz, 4H).

Intermediate L Preparation of 5-(4-amino-2-methylphenyl)-7-(morpholin-4-ylmethyl)pyrrolo[2,1f][1,2,4]triazin-4-amine

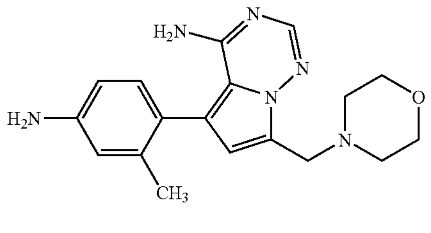

The procedure used for the preparation of Intermediate E, Step 4 was used to prepare the title compound by substituting Intermediate BU for 4-(4,4,5,5-tetramethyl-1,3,2-dioxaborolan-2-yl)aniline and toluene for 1,2-dimethoxyethane. $^1$H-NMR (DMSO-$d_6$) δ 7.82 (s, 1H), 6.86 (d, J=8 Hz, 2H), 6.50 (d, J=2 Hz, 1H), 6.42 (d, J=8 Hz, 2H), 5.16 (s, 2H), 3.78 (s, 2H), 3.53 (t, J=4 Hz, 4H), 2.41 (t, J=4 Hz, 4H), 1.97 (s, 3H); MS $[M+H]^+$=338.9; LCMS RT=1.01 min.

Intermediate M: Preparation of N-[2-fluoro-5-(trifluoro-methyl)phenyl]-N'-[4-(4,4,5,5-tetramethyl-1,3,2-dioxaborolan-2-yl)phenyl]urea

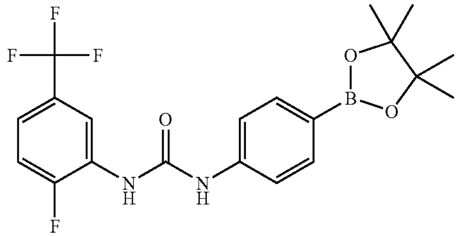

To a solution of 1,2 dichloroethane (80 mL) was added 4-(4,4,5,5,-tetramethyl-1,3,2-dioxaborolan-2-yl)aniline (5.00 g, 22.82 mmol) and allowed to stir until completely dissolved. To this solution was added 2-fluoro-5-trifluoromethyl phenylisocyante (4.92 g, 23.96 mmol) in one portion. The solution was allowed to stir overnight at rt, and then filter off the solids obtained. Rinse with 1,2 dichloroethane. A second crop of product is obtained by concentrating the mother liquor, stirring in 20 ml of 1,2 dichloroethane, filtering, and rinsing with 1,2 dichloroethane. Total amount of white crystals obtained was 9.56 g (22.54 mmol, 98.8% yield). $^1$H-NMR (DMSO-$d_6$) δ9.30 (s, 1H), 8.92 (s, 1H), 8.60 (d, J=5.0 Hz 1H), 7.60 (d, J=6.8 Hz, 2H), 7.51 to 7.46 (m, 3H), 7.4 to 7.36 (br m, 1H), 1.26 (s, 12H); MS $[M+H]^+$=425 LCMS RT=4.11 min.

Intermediate N: Preparation of N-[2-chloro-5-(trifluoro-methyl)phenyl]-N'-[4-(4,4,5,5-tetramethyl-1,3,2-dioxaborolan-2-yl)phenyl]urea

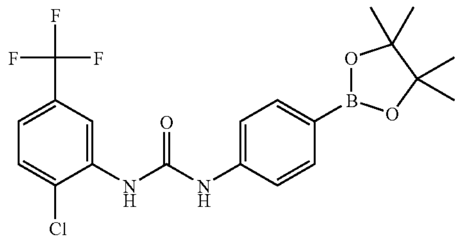

The procedure used for the preparation of Intermediate M was used to prepare the title compound by substituting 2-chloro-5-trifluoromethyl phenylisocyante for 2-fluoro-5-trifluoromethyl phenylisocyante. $^{1}$H-NMR (DMSO-d$_6$) δ9.71 (s, 1H), 8.63 (m, 2H), 7.71 (d, J=8.2 Hz, 1H), 7.61 (d, J=6.8 Hz, 2H), 7.49 (d, J=6.9 Hz, 2H), 7.37 (d, J=8.0 Hz 1H), 1.26 (s, 12H); MS [M+H]$^+$=441 LCMS RT=4.38 min Intermediate O: Preparation of N-[2-fluoro-4-(4,4,5,5-tetramethyl-1,3,2-dioxa-borolan-2-yl)phenyl]-N'-[2-fluoro-5-(trifluoromethyl)phenyl]urea

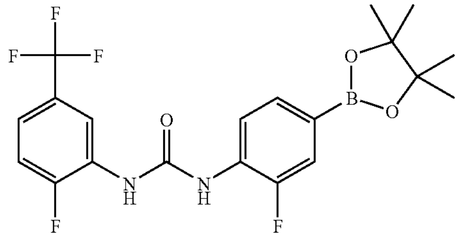

Step 1. Preparation of N-(4-bromo-2-fluorophenyl)-N'-[2-fluoro-5-(trifluoromethyl)phenyl]urea

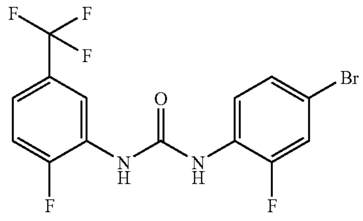

To a solution of 1,2 dichloroethane (100 mL) was added 4-Bromo-2-fluoroaniline (5.00 g, 26.31 mmol) and allowed to stir until completely dissolved. To this solution was added 2-fluoro-5-trifluoromethyl phenylisocyante (5.67 g, 27.63 mmol) in one portion. The solution was allowed to stir overnight at rt, and then filter off the solids obtained. Rinse several times with 1,2 dichloroethane (15 ml total). A second crop of product was obtained by concentrating the mother liquor, stirring in 20 ml of 1,2 dichloroethane, heat to reflux with stirring, cool to rt, filter, and rinse with 1,2 dichloroethane. Total amount of white solids obtained was 10.13 g (25.64 mmol, 97.4% yield). $^{1}$H-NMR (DMSO-d$_6$) δ9.37 (s, 1H), 9.23 (s, 1H), 8.60 (d, J=7.2 Hz 1H), 8.15 (t, J=8.8 Hz, 1H), 7.58 to 7.50 (dd, J=8.9, 2.2 1H), 7.48 (m, 1H), 7.40 to 7.32 (m, 2H); LCMS RT=4.22 min.

Step 2: Preparation of Title Compound

To a solution of 1,4-dioxane (60 mL) was added the N-(4-bromo-2-fluorophenyl)-N'-[2-fluoro-5-(trifluoromethyl)phenyl]urea (10.00 g, 25.31 mmol, intermediate B) and allowed to stir under nitrogen. DMF is added dropwise until solution was homogeneous. Reaction was degassed 3×. To this solution was added Bis(pinacolato)diboron (7.71 g, 30.37 mmol) in one portion. Reaction was degassed 5×. Potassium acetate (7.45 g, 75.92 mmol) was then added in one portion. Reaction was then degassed 3× more. To this heterogeneous reaction was added 1,1'-Bis(diphenylphosphino)ferrocenepalladium dichloride (925 mg, 1.26 mmol). Reaction was degassed 5× and then heated to 80° C. and allowed to stir at temperature overnight. Reaction is filtered through a thin pad of silica to remove solids and then purified via flash column using a gradient of 15:1 to 5:1 Hex:EtOAc to obtain 12.24 g as a white solid. (109% yield, 27.68 mmol used as is). $^{1}$H-NMR (DMSO-d$_6$) δ9.46 (s, 1H), 9.33 (s, 1H), 8.63 (d, J=7.4 Hz, 1H), 8.28 (t, J=8.2 Hz, 1H), 7.52 to 7.35 (br m, 4H), 1.27 (s, 12H); MS [M+H]$^+$=443; LCMS RT=4.31 min.

Intermediate P: Preparation of tert-butyl [2-fluoro-4-(4,4,5,5-tetramethyl-1,3,2-dioxaborolan-2-yl)phenyl] carbamate

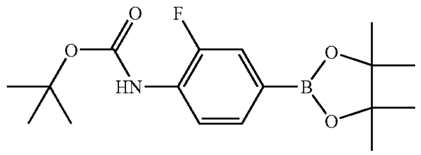

Step 1: Preparation of tert-butyl (4-bromo-2-fluorophenyl)carbamate

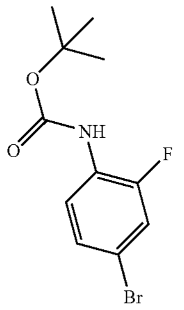

To a solution of THF (400 ml) in a water bath was added 4-bromo-2-fluoroaniline (50 g, 263.13 mmol). To this solution is added a 1M solution of sodium bis(Trimethylsilyl) amide in THF (526 ml) dropwise over 1 hour. Di-tert-butyl dicarbonate is dissolved in 100 ml of THF and added dropwise to the reaction flask. Stir at RT for 2 hours. Reaction solution is now poured into 1.2 L of saturated sodium bicartbonate and stirred. Add 1.2 L of diethyl ether and extract. Extract 2× more with diethyl ether (500 ml each) and combine organics. Wash organics 2× water, 1× brine, separate, dry organics over sodium sulfate, filter and strip of solvent to obtain 65.6 g (85.9%, 226.10 mmol) orange waxy solids that are used as is. $^1$H-NMR (DMSO-$d_6$) δ 9.08 (s, 1H), 7.58 (t, J=8.5 Hz 1H), 7.49 (dd, J=10.4, 2.4 Hz 2H), 7.32 to 7.29 (m, 1H), 1.45 (s, 12H); LC RT=3.77 min Step 2: Preparation of Title Compound The procedure used for the preparation of Intermediate O, step 2 was used to prepare the title compound by substituting tert-butyl (4-bromo-2-fluorophenyl)carbamate (41 g, 141.31 mmol) for N-(4-bromo-2-fluorophenyl)-N'-[2-fluoro-5-(trifluoromethyl)phenyl]urea. $^1$H-NMR (DMSO-$d_6$) δ 9.16 (s, 1H), 7.76 (t, J=8.0 Hz 1H), 7.41 (d, J=8.1 Hz 1H), 7.31 (d, J=11.3 Hz 1H), 1.45 (s, 9H), 1.27 (s, 12H); LC RT=4.25 min Intermediate Q: Preparation of N-[2-fluoro-4-(4,4,5,5-tetramethyl-1,3,2-dioxa-borolan-2-yl)phenyl]-N'-[3-(trifluoromethyl)phenyl]urea

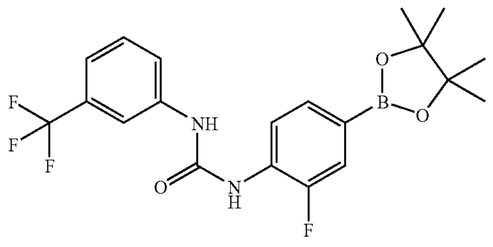

Step 1: Preparation of N-(4-bromo-2-fluorophenyl)-N'-[3-(trifluoromethyl)-phenyl]-urea

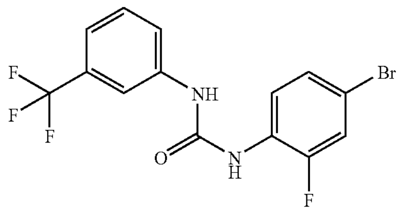

To a solution of 4-bromo-2-fluoroaniline (3.0 g, 15.8 mmol) in THF (15 mL) was added 1-isocyanato-3-(trifluoromethyl)benzene (3.55 g, 18.9 mmol). The reaction was stirred at room temperature overnight. Solid product was present in the reaction vessel. Product was further precipitated by the addition of 1:2 ether/hexanes. The solids were collected by filtration, dried under hi vacuum and found to be clean title compound in 60% yield. $^1$H-NMR (DMSO-$d_6$) δ 9.44 (s, 1H), 8.76 (d, J=1.2 Hz, 1H), 8.12 (t, J=8.7, 1H), 8.05 (s, 1H), 7.64-7.37 (m, 5H); MS $[M+H]^+$=378.9, LCMS RT=3.92 min.

Step 2: Preparation of Title Compound

Potassium acetate (1.56 g, 15.9 mmol.) and the bis(pinacolato)diboron (1.35 g, 5.3 mmol) were added as solids to a flask then placed under N2. N-(4-bromo-2-fluorophenyl)-N'-[3-(trifluoromethyl)phenyl]urea (2.0 g, 5.3 mmol) in DMSO (30 mL) was then added to the flask.

The reaction was taken through three purge-fill cycles using high vacuum then nitrogen. $Pd(dppf)_2Cl_2CH_2Cl_2$ (0.129 g, 0.159 mmol) was added. The reaction was again placed under vacuum then blanketed with nitrogen. The reaction was heated at 80° C. until TLC showed the complete consumption of starting bromide (approximately 90 minutes). The reaction was cooled to room temperature. ETOAc was added, the reaction was then partitioned between EtOAc and saturated aqueous bicarbonate. The organic layer was washed with brine seven times to remove DMSO. The material was then dried with $Na_2SO_4$ and concentrated under vacuum. The residue was chromatographed with eluent 0-30% v/v ETOAc/Hexanes. Pure product was thus obtained in 73% yield. $^1$H-NMR (DMSO-$d_6$) δ 9.52 (s, 1H), 8.85 (s, 1H) 8.27 (t, J=8.1 Hz, 1H), 8.07 (s, 1H), 7.56-7.37 (m, 5H), 1.31 (s, 12H); MS $[M+H]^+$=425.3, LCMS RT=4.24 min.

Intermediate R: Preparation of N-[2,6-difluoro-4-(4,4,5,5-tetramethyl-1,3,2-dioxaborolan-2-yl)phenyl]-N'-[2-fluoro-5-(trifluoromethyl)phenyl]urea

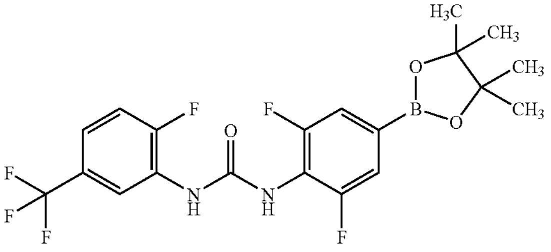

Step 1: Preparation of 2,6-difluoro-4-(4,4,5,5-tetramethyl-1,3,2-dioxaborolan-2-yl)aniline

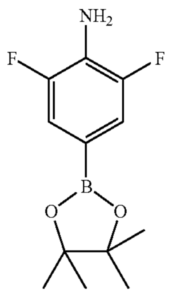

Potassium acetate (3.54 g, 36.1 mmol) and the boronate (3.36 g, 13.2 mmol) were added as solids to a flask then placed under N2. 4-bromo-2,6-difluoroaniline (2.50 g, 12.0 mmol) in DMSO (30 mL) was then added to the flask. The reaction was taken through three purge-fill cycles using high vacuum then nitrogen. $Pd(dppf)CH_2Cl_2$ (0.129 g, 0.159 mmol) was added. The reaction was again placed under vacuum then blanketed with nitrogen. The reaction was heated at 80° C. until TLC showed the complete consumption of starting bromide (approximately 90 minutes). The reaction was cooled to room temperature. ETOAc was added, the reaction was then partitioned between EtOAc and saturated aqueous bicarbonate. The organic layer was washed with brine seven times to remove DMSO. The material was then dried with $Na_2SO_4$ and concentrated under vacuum. The residue was chromatographed with eluent 0-100% v/v $CH_2Cl_2$/Hexanes. Pure product was obtained in 62% yield. $^1$H-NMR (DMSO-$d_6$) δ 7.03 (dd, J=6.6 Hz, 1.8 Hz, 2H), 5.76 (s, 2H) 1.26 (s, 12H); MS $[M+H]^+$=256.3, LCMS RT=3.30 min; $R_1$=0.37 in 40% $CH_2Cl_2$/Hexanes.

Step 2: Preparation of the Title Compound

To a solution of 2,6-difluoro-4-(4,4,5,5-tetramethyl-1,3,2-dioxaborolan-2-yl)aniline (0.300 g, 1.18 mmol) in THF (2 mL) was added 1-fluoro-2-isocyanato-4-(trifluoromethyl) benzene (0.314 g, 1.53 mmol). The reaction was stirred at 45 C overnight. Solid product was present in the reaction vessel. Product was further precipitated by the addition of 1:3 ether/hexanes. The solids were collected by filtration, dried under hi vacuum and found to be clean title compound in 71% yield. $^1$H-NMR (DMSO-$d_6$) δ 7.03 (dd, J=6.6, 1.8 Hz, 2H), 5.76 (s, 2H), 1.26 (s, 12H); MS $[M+H]^+$=461.2, LCMS RT=4.11 min Intermediate S: Preparation of N-[2,6-difluoro-4-(4,4,5,5-tetramethyl-1,3,2-dioxaborolan-2-yl)phenyl]-N'-[4-(trifluoromethyl)pyridin-2-yl]urea

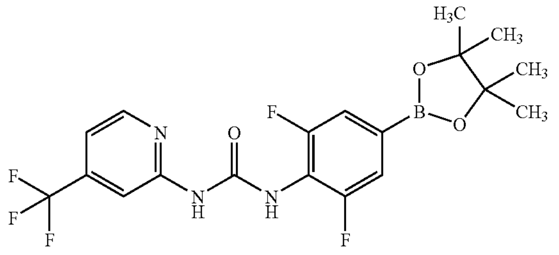

Step 1: Preparation of N-(4-bromo-2,6-difluorophenyl)-N'-[4-(trifluoromethyl)-pyridin-2-yl]urea

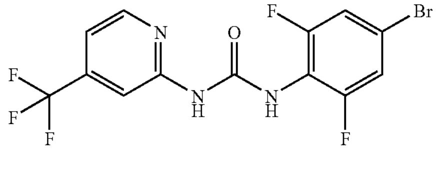

4-bromo-2,6-difluoroaniline (0.300 g, 1.44 mmol) was weighed into a vial, THF (3 mL) was added. Intermediate H (407 mg, 1.44 mmol) was added as a solid, followed by TEA (0.437 g, 4.37 mmol). The vial was capped and the reaction was heated at 60° C. overnight. Product was precipitated by the addition of hexanes. The solids were rinsed with 2:1 hexanes/ether to yield clean product (66%). $^1$H-NMR (DMSO-$d_6$) δ 10.0 (s, 1H), 9.27 (s, 1H), 8.51 (d, J=5.4 Hz, 1H), 7.91 (s, 1H), 7.55 (m, 2H) 7.37 (m, 1H), MS $[M+H]^+$=396.0, LCMS RT=3.62 min.

Step 2: Preparation of the Title Compound

The title compound was prepared using step 2 of the procedure to make Intermediate Q by substituting N-(4-bromo-2,6-difluorophenyl)-N'-[4-(trifluoromethyl)pyridin-2-yl] urea for the bromide. Material was used crude thus no isolated yield was recorded. $^1$H-NMR (DMSO-$d_6$) δ 9.99 ((s, 1H), 9.39 (s, 1H), 8.54 (m, 1H), 7.94 (s, 1H), 7.44-7.11 (m, 3H), 1.29 (s, 12H); MS $[M+H]^+$=444.1, LCMS RT=4.01 min.

Intermediate T: Preparation of N-[2,5-difluoro-4-(4,4,5,5-tetramethyl-1,3,2-dioxaborolan-2-yl)phenyl]-N'-[4-(trifluoromethyl)pyridin-2-yl]urea

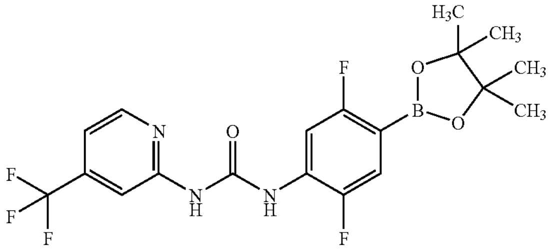

Step 1: Preparation of 2,5-difluoro-4-(4,4,5,5-tetramethyl-1,3,2-dioxaborolan-2-yl)aniline

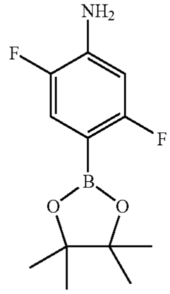

2,5-difluoro-4-(4,4,5,5-tetramethyl-1,3,2-dioxaborolan-2-yl)aniline was prepared following step 1 of the procedure to make Intermediate S by substituting 4-Bromo 2, 5 difluoroaniline for the bromide. $^1$H-NMR (DMSO-$d_6$) δ 7.03 (dd, J=11.7 Hz, 5.4 Hz, 1H), 6.38 (dd, 10.8 Hz, 3.9 Hz, 1H), 5.91 (s 2H) 1.22 (s, 12H); MS $[M+H]^+$=256.3, LCMS RT=3.13 min.

Step 2: Preparation of the Title Compound

N-[2,5-difluoro-4-(4,4,5,5-tetramethyl-1,3,2-dioxaborolan-2-yl)phenyl]-N'-[4-(trifluoro-methyl)pyridin-2-yl]urea was prepared using step 1 of the procedure to make Intermediate S by replacing the aniline with 2,5-difluoro-4-(4,4,5,5-tetramethyl-1,3,2-dioxaborolan-2-yl)aniline. $^1$H-NMR (DMSO-$d_6$) δ; 10.25 (s, 1H), 8.55 (m, 1H), 8.15-7.97 (m, 2H) 7.47-7.23 (m, 3H), 1.27 (s, 12H); MS $[M+H]^+$=444.1, LCMS RT=4.01 min.

Intermediate U: Preparation of N-[3-fluoro-4-(4,4,5,5-tetramethyl-1,3,2-dioxaborolan-2-yl)phenyl]-N'-[4-(trifluoromethyl)pyridin-2-yl]urea

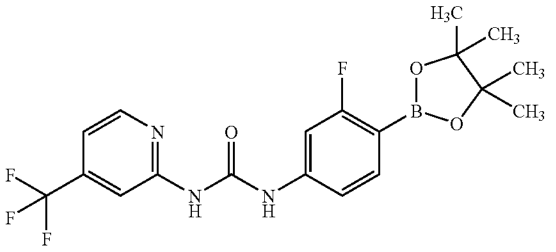

Step 1: Preparation of 3-fluoro-4-(4,4,5,5-tetramethyl-1,3,2-dioxaborolan-2-yl)aniline

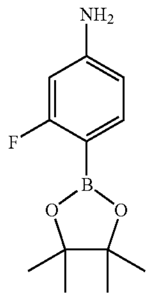

3-fluoro-4-(4,4,5,5-tetramethyl-1,3,2-dioxaborolan-2-yl) aniline was prepared following step 1 of the procedure to make Intermediate R by substituting 4-Bromo 3 fluoroaniline for the bromide. $^1$H-NMR (DMSO-$d_6$) δ 7.24 (t, J=4.8 1H), 6.31 (dd, J=8.1, 2.1 Hz, 1H), 6.16 (dd, J=12.3 Hz, 2.4 Hz, 1H) 5.81 (s, 2H), 1.22 (s, 12H); MS $[M+H]^+$=238.4, LCMS RT=3.07 min.

Step 2: Preparation of Title Compound

N-[3-fluoro-4-(4,4,5,5-tetramethyl-1,3,2-dioxaborolan-2-yl)phenyl]-N'-[4-(trifluoro-methyl)pyridin-2-yl]urea was prepared using step 1 of the procedure to make Intermediate S by replacing the aniline with 3-fluoro-4-(4,4,5,5-tetramethyl-1,3,2-dioxaborolan-2-yl)aniline $^1$H-NMR (DMSO-$d_6$) δ; 10.0 (s, 1H) 9.80 (s, 1H), 8.54 (d, J=5.4 Hz, 1H), 8.02 (s, 1H), 7.56-7.18 (m, 4H), 1.27 (s, 12H); MS $[M+H]^+$=426.1, LCMS RT=4.04 min.

Intermediate V: Preparation of 5-bromo-7-(3-morpholin-4-ylpropyl)pyrrolo[2,1-f][1,2,4]triazin-4-amine

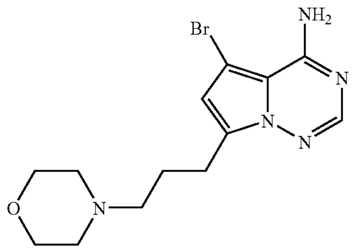

Step 1: Preparation of 3-(4-Aminopyrrolo[2,1f][1,2,4]trazin-7-yl)-prop-2-yn-1-ol

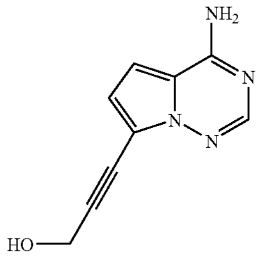

To a degassed solution of 7-bromopyrrolo[2,1-f][1,2,4]triazin-4-ylamine (10.0 g, 46.9 mmol) in anhydrous DMF (78 mL) and triethylamine (47 mL) was added tetrakis(triphenylphosphine)palladium(0) (2.17 g, 1.88 mmol, 0.04 eq) and copper (I) bromide dimethylsulfide complex (0.77 g, 3.75 mmol, 0.08 eq). After degassing with $N_2$ for 5 min., propargyl alcohol (8.2 mL, 140.8 mmol, 3.0 eq) was added, and the reaction mixture was stirred at 90° C. for 6 h. The reaction was quenched with 5% aq. $NH_3$ in saturated aq. $NH_4Cl$. The aqeuous layer was washed with EtOAc (1×) followed by 25% iPrOH in DCM (3×). The combined organic layers were dried over $MgSO_4$, filtered through a pad of celite, and concentrated at reduced pressure. The crude product was purified by MPLC eluted with 5% EtOH/DCM. Trituration from EtOAc afforded 4.75 g (53.8%) of the desired product as a yellow solid. $^1$H-NMR (DMSO-$d_6$) δ7.89 (s, 1H), 7.88 (broad s, 2H), 6.85 (dd, 2H), 5.39 (t, 1H), 4.36 (d, 2H); MS LC-MS $[M+H]^+$=189, RT=1.08 min.

Step 2: Preparation of 3-(4-Aminopyrrolo[2,1-f][1,2,4]triazin-7-yl)-propan-1-ol

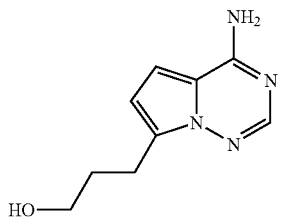

Palladium on carbon (474 mg, 10% by wt.) was placed under an inert atmosphere and suspended in EtOH (15 mL). A solution of 3-(4-aminopyrrolo[2,1f][1,2,4]trazin-7-yl)-prop-2-yn-1-ol (4.74 g, 25.2 mmol) dissolved in 2:1 v/v EtOH/THF was added. The reaction mixture was placed under $H_2$ atmosphere (1 Atm pressure) and stirred overnight. The resulting mixture was filtered through a pad of Celite® and the solvent was concentrated under reduced pressure. Trituration from EtOAc/hexane afforded 4.64 g (95.8%) of the desired product as an off-white solid. $^1$H-NMR (DMSO-$d_6$) δ7.77 (s, 1H), 7.54 (broad s, 2H), 6.78 (d, 1H), 6.39 (d, 1H), 4.50 (t, 1H), 3.43 (q, 2H), 2.84 (t, 2H), 1.74 to 1.82 (m, 2H); MS LC-MS $[M+H]^+$=193, RT=1.06 min.

Step 3: Preparation of 3-(4-Amino-5-bromopyrrolo[2,1-f][1,2,4]triazin-7-yl)-propan-1-ol

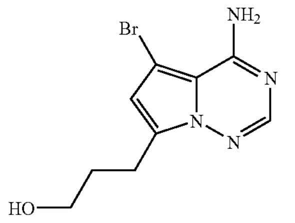

To a solution of 3-(4-aminopyrrolo[2,1f][1,2,4]triazin-7-yl)-propan-1-ol (5.40 g, 28.09 mmol) in anhydrous DMF (56 mL) was added 1,3-dibromo-5,5-dimethylhydantoin (3.96 g, 13.9 mmol, 0.50 eq) proportionwise at −50° C. The reaction mixture was warmed to 0° C. and stirred at 0° C. for 2 h. The reaction mixture was quenched with water and poured into EtOAc. The organic layer was washed with water and brine, dried over $Na_2SO_4$, filtered, and concentrated at reduced pressure. Crystallization from DCM afforded 6.54 g (85.9%) of the desired product as a beige solid. $^1$H-NMR (DMSO-$d_6$) δ7.83 (s, 1H), 6.61 (s, 1H), 4.52 (broad s, 1H), 3.41 (t, 2H), 2.83 (t, 2H), 1.75 to 1.77 (m, 2H); MS LC-MS $[M+H]^+$271/273, RT=1.40 min.

Step 4: Preparation of 5-bromo-7-(3-bromopropyl)pyrrolo[2,1-f][1,2,4]triazin-4-amine

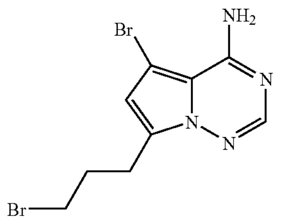

To a solution of 3-(4-Amino-5-bromopyrrolo[2,1-f][1,2,4]triazin-7-yl)-propan-1-ol (1.20 g, 4.43 mmol) in anhydrous THF (22 mL) at 0° C. was added carbon tetrabromide (1.62 g, 4.87 mmol, 1.1 eq) and triphenylphosphine (1.16 g, 4.43 mmol, 1.0 eq). After 5 minutes the ice bath was removed and the reaction mixture was stirred at RT for 1 hour. Then another 0.1 equivalents of both carbon tetrabromide (0.15 g, 0.44 mmol) and triphenylphosphine (0.12 g, 0.44 mmol) were added. The reaction was stirred another hour at ambient temperature before it was filtered to remove some solid which was rinsed with some THF. The combined filtrate and rinse were concentrated at reduced pressure to give a crude product which was purified by MPLC on 120 g of silica gel eluted with a gradient from 0-100% EtOAc in hexane to give 950 mg (64.2%) of desired product as a white solid after evaporation of best fractions which eluted from 55-65% EtOAc. $^1$H-NMR (DMSO-$d_6$) 7.84 (s, 1H), 6.65 (s, 1H), 3.54 (t, 2H, J=6.4), 2.94 (t, 2H, J=6.4), and 2.16 (q, 2H, J=6.4); MS LC-MS $[M+H]^+$=333.3/335.1/337.1, RT=2.77 min. Evidence showed in the NMR and the LC-MS for about 16% contamination with 5,6-dibromo-7-(3-bromopropyl)pyrrolo[2,1-f][1,2,4]triazin-4-amine which came from an analogous contaminant (3-(4-Amino-5,6-dibromopyrrolo[2,1-f][1,2,4]triazin-7-yl)-propan-1-ol) in the starting material. Products that came from this contaminant were removed by chromatography of the product of step 5 below.

Step 5: Preparation of the Title Compound

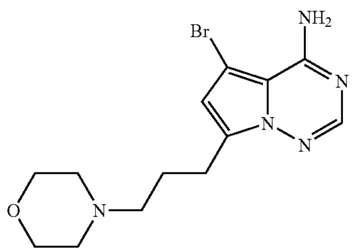

A solution of 5-bromo-7-(3-bromopropyl)pyrrolo[2,1-f][1,2,4]triazin-4-amine (931 mg, 2.78 mmol), morpholine (1.214 g, 13.94 mmol, 5.0 eq), triethylamine (1.16 ml, 8.36 mmol, 3.0 eq), and sodium iodide (63 mg, 0.42 mmol, 0.15 eq) in anhydrous DMF (20 mL) was stirred at 55° C. for 17 h. The reaction mixture was diluted with EtOAc and washed with saturated aqueous $NaHCO_3$ followed by saturated brine.

It was dried over $Na_2SO_4$, filtered, concentrated at reduced pressure to first remove EtOAc followed by some DMF with pumping. The crude was dissolved in THF and then preloaded by evaporation onto about 5 ml silica gel and then chromatographed on 40 g silica gel using a gradient from 0-10% MeOH in $CH_2Cl_2$ to provide 457 mg (47.9%) of the desired product as a white solid along with another 435 mg (46%) of mixed fractions contaminated with the dibromide which came from the tribromide contaminant in the starting material as noted above in step 4. $^1$H-NMR (DMSO-$d_6$) δ7.86 (s, 1H), 6.65 (s, 1H), 3.56 (t, 4H, J=4.6), 2.84 (t, 2H), 2.25-2.35 (m, 6H), and 1.80 (pent, 2H, J=7.4); MS LC-MS=340.2/342.2, RT=1.09 min.

Intermediate W: Preparation of 1-(4-amino-5-bromopyrrolo[2,1-f][1,2,4]triazin-7-yl)ethanone

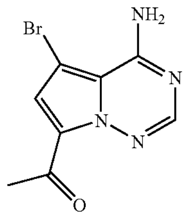

Step 1: Preparation of 1-(4-aminopyrrolo[2,1-f][1,2,4]triazin-7-yl)ethanone

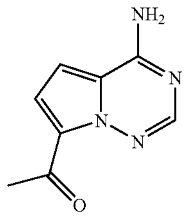

To a suspension of pyrrolo[2,1-f][1,2,4]triazin-4-amine (1.00 g, 7.46 mmol) in nitrobenzene (40 mL) was added $AlCl_3$ (2.98 g, 22.36 mmol), followed by acetyl chloride (2.34 g, 29.82 mmol). The resulting solution was heated (60° C.) for 5 h and cooled to rt. The reaction mixture was poured onto ice-water and solid sodium bicarbonate was added with stirring until the solution was basic. This mixture was extracted with ethyl acetate (3×100 mL) and then the combined organic layers were concentrated under reduced pressure. The residue was stirred with MeOH (100 mL) and potassium carbonate (5 g) overnight. The solid was removed by filtration and the filtrate was concentrated under reduced pressure. The residue was purified by HPLC using a gradient of 5-30% MeCN in water to afforded 448.0 mg (34%) of the title compound. $^1$H-NMR (DMSO-$d_6$) δ 9.63 (bs, 1H), 8.47 (bs, 1H), 8.03 (s, 1H), 7.76 (d, J=3.2 Hz, 1H), 7.40 (d, J=2.9 Hz, 1H), 2.57 (s, 3H); MS $[M+H]^+$=177.1; LCMS RT=1.37 min.

Step 2: Preparation of Title Compound

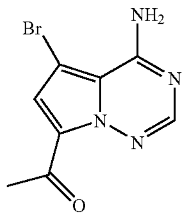

To a cooled (0° C.) solution of 1-(4-aminopyrrolo[2,1f][1,2,4]triazin-7-yl)ethanone (262.0 mg, 1.49 mmol) in DMF (21 mL) was added 1,3-dibromo-5,5-dimethylhydantoin (212.6 mg, 0.74 mmol). The mixture was stirred for 80 min and then quenched by addition of saturated aqueous sodium sulphite (10 mL) and water (60 mL). The mixture was allowed to warm to rt and the precipitate was collected by filtration. The solid was air-dried to yield 360.0 mg (95%) of the title compound. $^1$H-NMR (DMSO-$d_6$) δ 9.49 (bs, 1H), 8.49 (bs, 1H), 8.12 (s, 1H), 7.64 (s, 1H), 2.56 (s, 3H); MS $[M+H]^+$=255.3; LCMS RT=1.96 min.

Intermediate X: Preparation of 5-(4-aminophenyl)-7-(3-morpholin-4-ylpropyl)-pyrrolo[2,1-f][1,2,4]triazin-4-amine

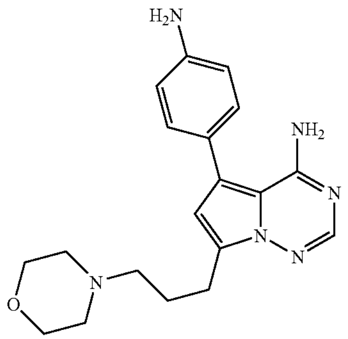

The procedure used for the preparation of Intermediate E, step 4 was used to prepare the title compound by substituting Intermediate V (5-bromo-7-(3-morpholin-4-ylpropyl)pyrrolo[2,1-f][1,2,4]triazin-4-amine) for Intermediate C. $^1$H-NMR (MeOH-$d_4$) δ 7.74 (d, J=1 Hz, 1H), 7.17 (dd, J=6, 2 Hz, 2H), 6.81 (dd, J=6, 2 Hz, 2H), 3.67 (t, J=5 Hz, 4H), 2.98 to 2.91 (m, 2H), 2.48 to 2.39 (m, 6H), 1.98 to 1.91 (m, 2H); MS $[M+H]^+$=353.1; LCMS RT=1.03 min.

Intermediate Y: 5-(4-amino-3-chlorophenyl)-7-(morpholin-4-ylmethyl)pyrrolo[2,1-t][1,2,4]triazin-4-amine

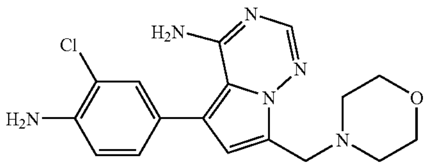

The procedure used for the preparation of Intermediate F was used to prepare the title compound by substituting tert-butyl [2-chloro-4-(4,4,5,5-tetramethyl-1,3,2-dioxaborolan-2-yl)phenyl]carbamate for Intermediate P. MS $[M+H]^+=359$; LCMS RT=1.30.

Intermediate Z: 5-bromo-7-(1,4-oxazepan-4-ylmethyl)pyrrolo[2,1f][1,2,4]triazin-4-amine

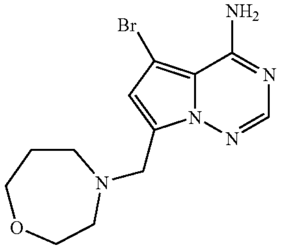

Step 1: Preparation of 7-(1,4-oxazepan-4-ylmethyl) pyrrolo[2,1f][1,2,4]triazin-4-amine

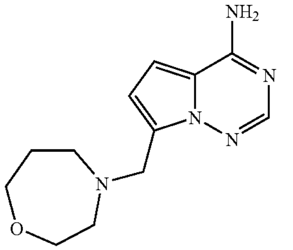

Pyrrolo[2,1-f][1,2,4]triazin-4-amine (4000 mg, 29.8 mmol) was dissolved in acetic acid (160 mL). 37% wt formaldehyde in water is added (2.90 mL, 35.8 mmol) followed by 1,4-oxazepane hydrochloride (4.92 g, 35.8 mmol) and potassium acetate (5.27 g, 53.7 mmol). The reaction was heated at 60° C. under a nitrogen atmosphere overnight then cooled to room temperature. The reaction was concentrated under vacuum. The residue was partitioned between EtOAc (300 mL) and saturated aqueous bicarbonate (150 mL). The aqueous layer is extracted with EtOAc (5×100 mL). The combined organics were washed with brine (100 mL) then dried with Na2SO4 to yield 6.78 g (92%) of desired product. $^1$H-NMR (DMSO-$d_6$) δ7.80 (s, 1H), 7.63 (bs, 2H), 6.84 (d, J=4.5 Hz, 1H), 6.54 (d, J=4.5, 1H), 3.64 (t, J=6 Hz, 2H), 3.55 (m, 2H), 2.63 (m, 4H), 1.76 (m, 2H); MS $[M+H]^+=248.1$; LCMS RT=1.02.

Step 2: Preparation of the Title Compound

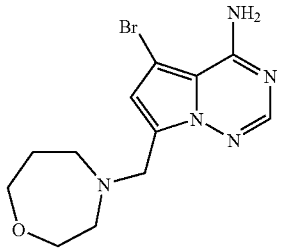

7-(1,4-oxazepan-4-ylmethyl)pyrrolo[2,1-f][1,2,4]triazin-4-amine (1.90 g, 7.68 mmol) was suspended in chloroform (76 mL). The solution was cooled to −20 to −30° C. 1,3-dibromo-5,5-dimethylimidazolidine-2,4-dione (989 g, 3.46 mmol) was added. The reaction was maintained at −20° C. for 20 minutes then warmed to room temperature. An LC taken at that time showed the reaction to be essentially complete. The reaction was then quenched by the addition of saturated aqueous sodium sulfite. The resultant slurry was partitioned between ethyl acetate (300 mL) and saturated bicarbonate (100 mL). The organic layer was washed (3×100 mL) with bicarb then dried with $Na_2SO_4$ and concentrated under vacuum.

The residue was triturated with ether to yield 2.09 g (83%) desired product. $^1$H-NMR (DMSO-$d_6$) δ7.85 (s, 1H), 7.60 (bs, 2H), 6.72 (s, 1H), 3.91 (s, 2H), 3.64 (m, 2H), 2.63 (m, 4H), 1.78 (m, 2H); MS $[M+H]^+=325.8$; LCMS RT=1.07

Intermediate AA: 1-[2-fluoro-5-methyl-4-(4,4,5,5-tetramethyl-1,3,2-dioxaborolan-2-yl)phenyl]-3-[2-fluoro-5-(trifluoromethyl)phenyl]urea

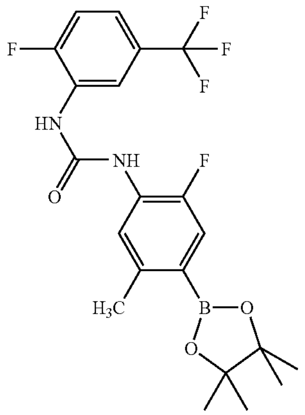

Step 1: 4-bromo-2-fluoro-5-methylaniline

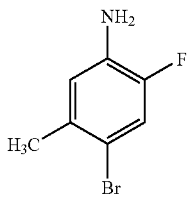

To a slurry of 2-fluoro-5-methylaniline (6.75 g, 54 mmol) and $CaCO_3$ (10 g, 100 mmol) in $CH_2Cl_2$ (1 L) and MeOH (400 mL) was added a solution of Benzyltrimethylammonium tribromide (22.3 g, 57 mmol) in $CH_2Cl_2$ (180 mL) and MeOH (70 mL). The solution was added dropwise and the mixture was stirred over night. The solution was a light orange/tan color. The mixture was filtered and the solvent was removed under reduced pressure. The resulting slurry was diluted with $H_2O$ (100 mL) and extracted with $Et_2O$ (3×200 mL). The mixture was purified by flash column chromatography (Hex:$Et_2O$ 2:1 to $Et_2O$) to provide (9 g, 69.5% yield) the product as a white solid. $^1H$-NMR (DMSO-$d_6$) δ 7.23 (d, J=10.8 Hz, 1H), 6.74 (d, J=10.8 Hz, 1H), 5.27 (s, 2H), 2.20 (s, 3H).

Step 2: 1-(4-bromo-2-fluoro-5-methylphenyl)-3-[2-fluoro-5-(trifluoromethyl)phenyl]urea

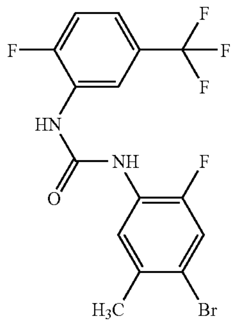

To a solution of 4-bromo-2-fluoro-5-methylaniline (500 mg, 2.45 mmol.) in THF (3 mL) was added the 2-fluoro-5-(trifluoromethyl)phenyl isocyanate (625 mg, 3.0 mmol). The reaction generated a white solid within 10 min. An additional portion of THF (3 mL) was added and the mixture dissolved. TLC analysis (1:1 $Et_2O$:Hex) indicated that the reaction was complete. The product was purified by flash column chromatography (Hex:$Et_2O$ 2:1 to $Et_2O$). $^1H$-NMR (DMSO-$d_6$) δ 9.37 (d, J=2.8 Hz, 1H), 9.17 (d, J=2.4 Hz, 1H), 8.61 (dd, J=7.2, 2 Hz, 1H), 8.19 (d, J=8.0 Hz, 1H), 7.55 (d, J=10.8 Hz, 1H), 7.49 (dd, J=10.8, 8.8 Hz, 2H), 7.39 (m, 1H), 2.29 (s, 3H); MS $[M+H]^+$=409.3, LCMS RT=3.91 min.

Step 3: Preparation of the Title Compound

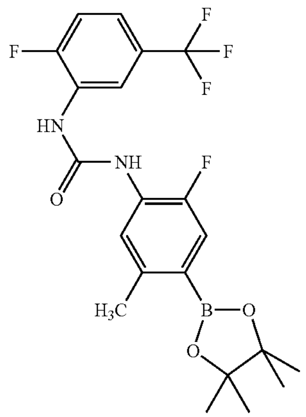

To a solution of 1-(4-bromo-2-fluoro-5-methylphenyl)-3-[2-fluoro-5-(trifluoromethyl)phenyl]urea (300 mg, 0.73 mmol), bis(pinacolato) diboron (225 mg, 0.88 mmol) and KOAc (216 mg, 2.2 mmol) in Dioxane (10 mL) was added Pd(dppf)$Cl_2$ (27 mg, 0.04 mmol). The reaction was capped and the heated to 85° C. and allowed to stir for 12 h. TLC analysis (3:1 Hex:EtOAc) indicated consumption of starting material. The compound was purified by flash column chromatography to provide a white solid. $^1H$-NMR (DMSO-$d_6$) δ 9.41 (d, J=2.8 Hz, 1H), 9.23 (d, J=2.8 Hz, 1H), 8.63 (dd, J=7.6, 2 Hz, 1H), 8.08 (d, J=7.6 Hz, 1H), 7.46 (dd, J=10, 8 Hz, 1H), 7.37 (m, 3H), 7.30 (d, J=12 Hz, 1H), 2.42 (s, 3H), 1.27 (s, 12H); MS $[M+H]^+$-457.2, LCMS RT=4.09 min.

Intermediate AB: Preparation of tert-butyl 3-(4-amino-5-bromopyrrolo[2,1-f][1,2,4]triazin-7-yl)pyrrolidine-1-carboxylate

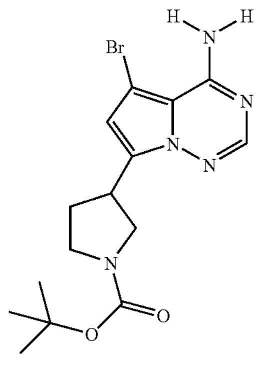

Step 1: Preparation of tert-butyl 3-(4-aminopyrrolo[2,14f][1,2,4]triazin-7-yl)-2,5-dihydro-1H-pyrrole-1-carboxylate

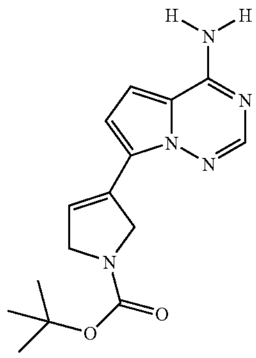

A 2 L, 3-neck RB flask was fitted with a mechanical stirrer, a nitrogen inlet, thermocouple and thermocontroller, and a water cooling bath. In the flask, 7-bromopyrrolo[2,1-f][1,2,4]triazin-4-amine (18.4 g, 86.3 mmol) was suspended in tetrahydrofuran (250 mL) and treated with chlorotrimethylsilane (18.8 g, 172 mmol). The mixture was allowed to stir 16 h at rt. A solution of isopropylmagnesium chloride in THF (2M, 173 mL, 345 mmol) was added slowly over 20 min taking care that the internal temperature never rose above 40° C. After 1.5 h, a sample was quenched in MeOH and analyzed by RP-HPLC indicated that the metallation was 95% complete. The water bath was replaced with an ice-acetone bath and stirring was continued until the internal temperature fell to −10° C. test-Butyl 3-oxopyrrolidine-1-carboxylate (20 g, 108 mmol) was added as a solid, and the reaction was allowed to warm to rt over 30 min. The reaction was again cooled to −10° C. and cautiously treated with trifluoroacetic anhydride (45.4 g, 216 mmol), diisopropylethylamine (33.5 g, 259 mmol) and dimethylaminopyridine (527 mg, 4.3 mmol). The reaction was warmed to rt and allowed to stir for 30 min, then treated with a 25% solution of NaOMe in MeOH (46 g, 215 mmol) and stirred for an additional 15 min. The reaction was partitioned between EtOAc and 1N aq citric acid. After 15 min stirring the organic layer was separated, washed with brine and dried with sodium sulfate. After filtering the solution through a plug of silica, the filtrate was concentrated in vacuo and the residue triturated with ethyl ether to provide the desired product as a bright yellow solid (16.8 g, 65%). $^1$H-NMR (DMSO): δ 7.72 (dd, 1H), 7.61 (dd, 1H), 7.23 to 7.36 (m, 3H), 7.15 to 7.20 (m, 2H), 6.96 (dd, 1H), 5.60 (s, 2H), 2.58 (s, 1H); MS: LC/MS (+esi): m/z=275.1 [MH]$^+$; LC/MS rt=3.51 min.

Step 2: Preparation of tert-butyl 3-(4-aminopyrrolo[2,1f][1,2,4]triazin-7-yl)pyrrolidine-1-carboxylate

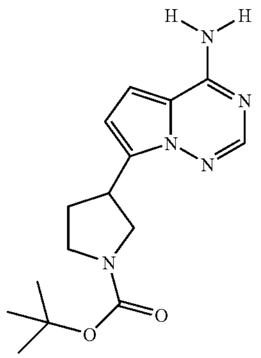

A suspension of platinum(IV) oxide (2.1 g, 9.5 mmol) and tert-butyl 3-(4-aminopyrrolo[2,1-f][1,2,4]triazin-7-yl)-2,5-dihydro-1H-pyrrole-1-carboxylate (11.4 g, 37.8 mmol) in AcOH (150 mL) was stirred for 16 h under a $H_2$ atmosphere. The reaction was purged with $N_2$ and filtered through Celite®, washing with AcOH. After removal of solvent in vacuo, the residue was dissolved in THF:EtOAc and washed with saturated, aqueous sodium carbonate solution. The organic layer was dried and concentrated in vacuo to provide the desired product as a dark solid (10.7 g, 93%). MS: LC/MS (+esi): m/z=304.1 [MH]$^+$; LC/MS rt=2.74 min.

Step 3: Preparation of the Title Compound

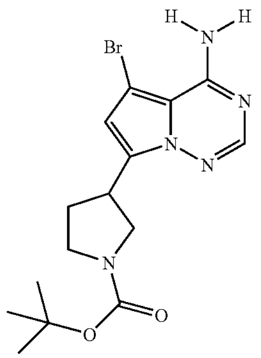

A solution of test-butyl 3-(4-aminopyrrolo[2,1-f][1,2,4]triazin-7-yl)pyrrolidine-1-carboxylate (1.2 g, 3.96 mmol) in DMF (20 mL) was cooled to −40° C. and treated with 1,3-dibromo-5,5-dimethylhydantoin (508 mg, 1.78 mmol). The reaction was allowed to warm slowly to rt over a 2 h period and was then partitioned between EtOAc and bicarbonate solution. After concentration, the residue was triturated with EtOAc to yield the desired product (1.28 g, 85%). $^1$H-NMR (DMSO): δ 7.86 (s, 1H), 6.69 (s, 1H), 3.68 to 3.80 (m, 2H), 3.36 to 3.46 (m, 1H), 3.20 to 3.30 (m, 2H), 2.16 to 2.30 (m, 1H), 1.98 to 2.08 (m, 1H), 1.37 (s, 9H); MS: LC/MS (+esi), m/z=382.1 [M+H]; LC/MS rt=3.08 min.

Intermediate AC: Preparation of tert-butyl 4-(4-amino-5-bromopyrrolo[2,1-f][1,2,4]triazin-7-yl)piperidine-1-carboxylate

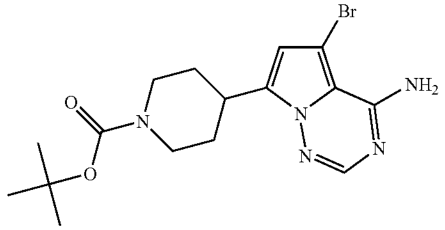

Step 1: Preparation of tert-butyl 4-(4-aminopyrrolo [2,1f][1,2,4]triazin-7-yl)-3,6-dihydropyridine-1(2H)-carboxylate

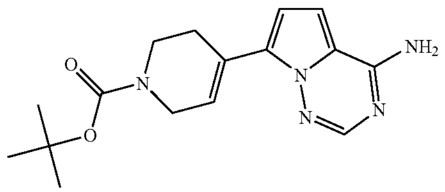

To a stirred suspension of Intermediate B (523 mg, 2.46 mmol), tert-butyl 4-(4,4,5,5-tetramethyl-1,3,2-dioxaborolan-2-yl)-3,6-dihydropyridine-1(2H)-carboxylate (Eastwood, P. R. *Tetrahedron Lett.* 2000, 41, 3705) (950 mg, 3.07 mmol), and 1,1'-bis(diphenylphosphino)-ferrocene]dichloro palladium(II)-complex with dichloromethane (180 mg, 0.25 mmol) in degassed DME (18 mL) was added aqueous $Na_2CO_3$ solution (2 M, 3.7 mL). The reaction was heated (80° C.) for 17 h and then cooled to rt. The mixture was partitioned between ethyl acetate (50 mL) and $H_2O$ (50 mL). The layers were separated and the organic layer was washed with brine (25 mL), dried ($Na_2SO_4$), and concentrated to dryness. The crude residue was purified by ISCO® chromatography using a gradient of 50 to 75% ethyl acetate in hexanes to afford 584 mg (75%) of the desired product as an off-white solid, which contained trace impurities. $^1$H NMR (300 MHz, DMSO-$d_6$) δ 7.85 (s, 1H), 7.68 (br s, 2H), 6.97 (br s, 1H), 6.87 (d, 1H), 6.66 (d, 1H), 4.07-4.00 (m, 2H), 3.53 (t, 2H), 2.56-2.50 (m, 2H), 1.42 (s, 9H); ES-MS m/z 316.1 $[M+H]^+$, HPLC RT (min) 2.31.

Step 2: Preparation of tert-butyl 4-(4-aminopyrrolo [2,1-f][1,2,4]triazin-7-yl)piperidine-1-carboxylate

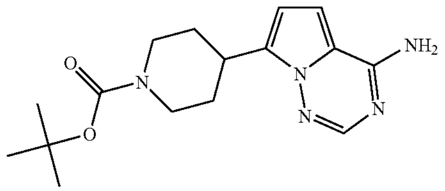

To a dry flask purged with $N_2$ was added platinum(IV) oxide (127 mg, 0.56 mmol) followed by tert-butyl 4-(4-aminopyrrolo[2,1-f][1,2,4]triazin-7-yl)-3,6-dihydropyridine-1 (2H)-carboxylate (587 mg, 1.86 mmol) as a solution in acetic acid (19 mL). The mixture was stirred under an $H_2$ atmosphere for 16 h. The mixture was filtered through a pad of Celite® rinsing with acetic acid and ethanol. The solvent was evaporated under reduced pressure and the residue was dissolved in ethyl acetate (100 mL). The organic was washed with saturated aqueous $NaHCO_3$ (2×75 mL) and the aqueous mixture was back extracted with ethyl acetate (3×50 mL). The combined organics were washed with brine, dried ($Na_2SO_4$) and concentrated to dryness to afford 610 mg (100%) of the desired product as a gray solid. $^1$H NMR (300 MHz, DMSO-$d_6$) δ 7.78 (s, 1H), 7.57 (br s, 2H), 6.78 (d, 1H), 6.42 (d, 1H), 4.08-3.97 (m, 2H), 3.28-3.18 (m, 1H), 1.94 (d, 2H), 1.55-1.42 (m, 2H), 1.41 (s, 9H); ES-MS m/z 318.1 $[M+H]^+$, HPLC RT (min) 2.21.

Step 3: Preparation of the Title Compound

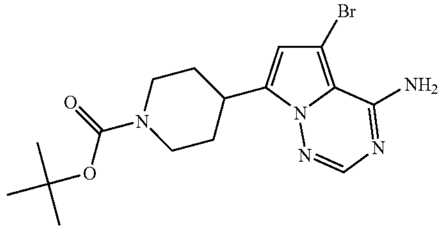

To a cooled (−20° C.) solution of tert-butyl 4-(4-aminopyrrolo[2,1-f][1,2,4]triazin-7-yl)piperidine-1-carboxylate (660 mg, 2.08 mmol) in tetrahydrofuran (10 mL) was added 1,3-dibromo-5,5-dimethylhydantoin (297 mg, 1.04 mmol) in 3 portions over 10 min. The mixture was allowed to stir (−20° C.) for 1 h. The reaction was quenched with the addition saturated aqueous $Na_2SO_3$ (10 mL) and was allowed to warm to rt. The mixture was extracted with ethyl acetate (3×20 mL). The combined organics were washed with brine (25 mL), dried ($Na_2SO_4$) and evaporated. The crude material was purified by ISCO® chromatography using a gradient of 75 to 100% ethyl acetate in hexanes to afford 494 mg (60%) of the desired product. $^1$H NMR (300 MHz, DMSO-$d_6$) δ 7.83 (s, 1H), 6.64 (s, 1H), 4.10-3.96 (m, 2H), 3.29-3.19 (m, 1H), 1.90 (d, 2H), 1.55-1.42 (m, 2H), 1.41 (s, 9H); ES-MS m/z 396.1 $[M+H]^+$, HPLC RT (min) 2.79.

The following boronates can be prepared in the same manner as Intermediate O by substituting the appropriate bromide for N-(4-bromo-2-fluorophenyl)-N'-[2-fluoro-5-(trifluoromethyl)phenyl]urea. Alternatively, they can be prepared in the same manner as Intermediate M, by substituting the appropriate aniline for 4-(4,4,5,5,-tetramethyl-1,3,2-dioxaborolan-2-yl)aniline and the appropriate isocyanate for 2-fluoro-5-trifluoromethyl phenylisocyante. Alternatively, they can be prepared in the same manner as Intermediate T, by substituting the appropriate aniline for 2,5-difluoro-4-(4,4,5,5,-tetramethyl-1,3,2-dioxaborolan-2-yl)aniline and the appropriate carbamate for phenyl [4-(trifluoromethyl)pyridin-2-yl] carbamate.

| Int | Structure | IUPAC Name | LC-MS m/z [M + H], RT, Method |
|---|---|---|---|
| O | 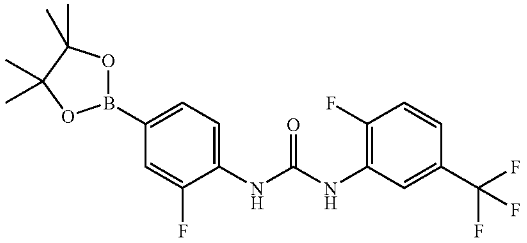 | 1-[2-fluoro-4-(4,4,5,5-tetramethyl-1,3,2-dioxaborolan-2-yl)phenyl]-3-[2-fluoro-5-(trifluoromethyl)phenyl]urea | 443.3, 3.91 min, A |
| AD | 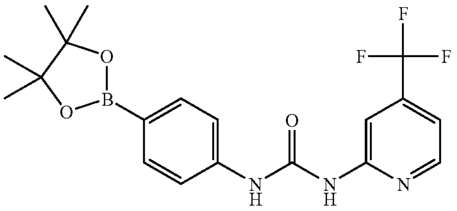 | 1-[4-(4,4,5,5-tetramethyl-1,3,2-dioxaborolan-2-yl)phenyl]-3-[4-(trifluoromethyl)pyridin-2-yl]urea | 407.9, 3.93 min, A |
| AE | 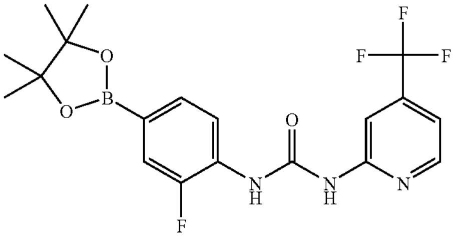 | 1-[2-fluoro-4-(4,4,5,5-tetramethyl-1,3,2-dioxaborolan-2-yl)phenyl]-3-[4-(trifluoromethyl)pyridin-2-yl]urea | 425.9, 4.17 min, A |
| AF | 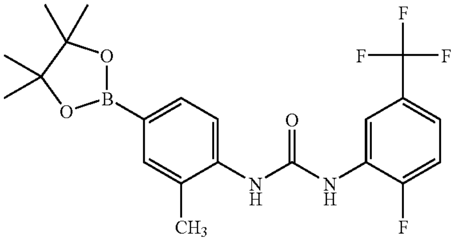 | 1-[2-fluoro-5-(trifluoromethyl)phenyl]-3-[2-methyl-4-(4,4,5,5-tetramethyl-1,3,2-dioxaborolan-2-yl)phenyl]urea | 439.2, 3.81 min, A |
| AG | 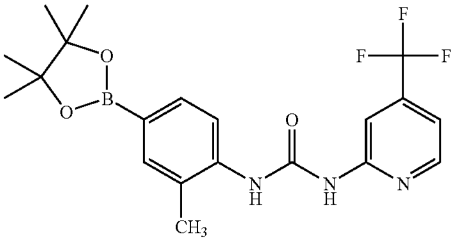 | 1-[2-methyl-4-(4,4,5,5-tetramethyl-1,3,2-dioxaborolan-2-yl)phenyl]-3-[4-(trifluoromethyl)pyridin-2-yl]urea | 422.2, 3.77 min, A |

-continued

| Int | Structure | IUPAC Name | LC-MS m/z [M + H], RT, Method |
|---|---|---|---|
| AH | 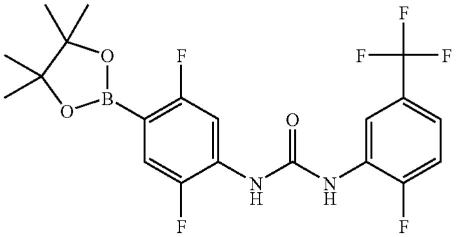 | 1-[2,5-difluoro-4-(4,4,5,5-tetramethyl-1,3,2-dioxaborolan-2-yl)phenyl]-3-[2-fluoro-5-(trifluoromethyl)phenyl]urea | 461.2, 4.38 min, A |
| AI | 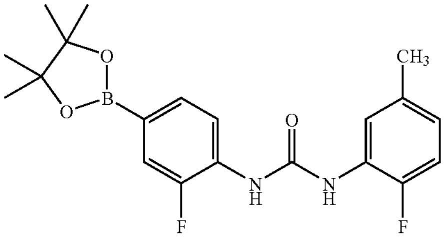 | 1-(2-fluoro-5-methylphenyl)-3-[2-fluoro-4-(4,4,5,5-tetramethyl-1,3,2-dioxaborolan-2-yl)phenyl]urea | 389.3, 3.83 min, A |
| AJ | 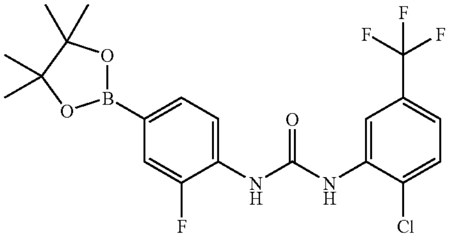 | 1-[2-chloro-5-(trifluoromethyl)phenyl]-3-[2-fluoro-4-(4,4,5,5-tetramethyl-1,3,2-dioxaborolan-2-yl)phenyl]urea | 459.1, 4.53 min, A |
| N | 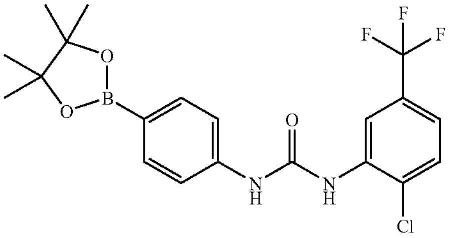 | 1-[2-chloro-5-(trifluoromethyl)phenyl]-3-[4-(4,4,5,5-tetramethyl-1,3,2-dioxaborolan-2-yl)phenyl]urea | 441, 4.38 min, A |
| AK | 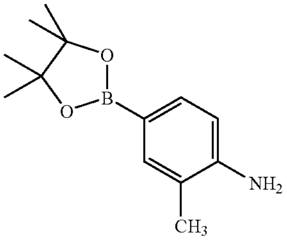 | 2-methyl-4-(4,4,5,5-tetramethyl-1,3,2-dioxaborolan-2-yl)aniline | 234.2, 3.06 min, A |
| P | 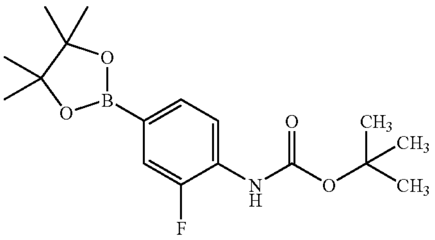 | tert-butyl [2-fluoro-4-(4,4,5,5-tetramethyl-1,3,2-dioxaborolan-2-yl)phenyl]carbamate | 238.4 (M-Boc), 4.25 min, A |

-continued

| Int | Structure | IUPAC Name | LC-MS m/z [M + H], RT, Method |
|---|---|---|---|
| T STEP 1 | 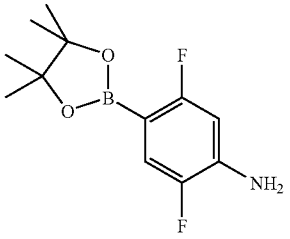 | 2,5-difluoro-4-(4,4,5,5-tetramethyl-1,3,2-dioxaborolan-2-yl)aniline | 256.3, 3.33 min, A |
| M | 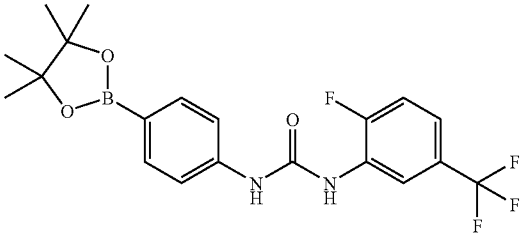 | 1-[2-fluoro-5-(trifluoromethyl)phenyl]-3-[4-(4,4,5,5-tetramethyl-1,3,2-dioxaborolan-2-yl)phenyl]urea | 425, 4.11 min, A |
| AL | 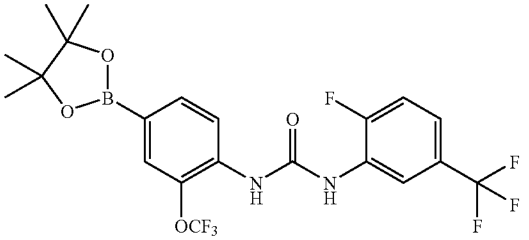 | 1-[2-fluoro-5-(trifluoromethyl)phenyl]-3-[4-(4,4,5,5-tetramethyl-1,3,2-dioxaborolan-2-yl)-2-(trifluoromethoxy)phenyl] urea | 509.3, 4.08 min, A |
| AM | 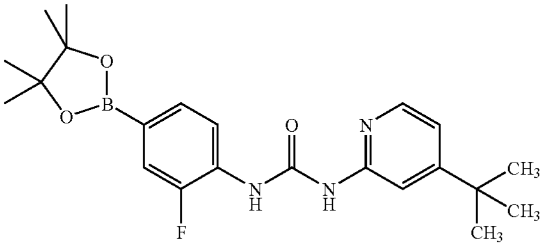 | 1-(4-tert-butylpyridin-2-yl)-3-[2-fluoro-4-(4,4,5,5-tetramethyl-1,3,2-dioxaborolan-2-yl)phenyl]urea | 414.3, 3.83 min, A |
| Q | 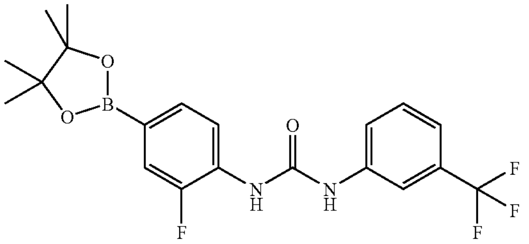 | 1-[2-fluoro-4-(4,4,5,5-tetramethyl-1,3,2-dioxaborolan-2-yl)phenyl]-3-[3-(trifluoromethyl)phenyl]urea | 425.2, 4.24 min, A |
| AN | 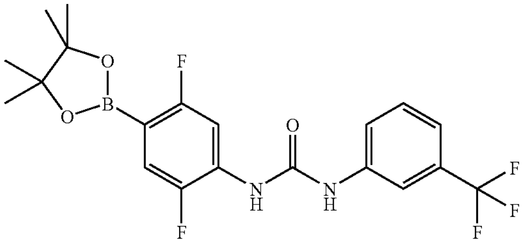 | 1-[2,5-difluoro-4-(4,4,5,5-tetramethyl-1,3,2-dioxaborolan-2-yl)phenyl]-3-[3-(trifluoromethyl)phenyl]urea | 443.2, 4.26 min, A |

-continued

| Int | Structure | IUPAC Name | LC-MS m/z [M + H], RT, Method |
|---|---|---|---|
| AO | 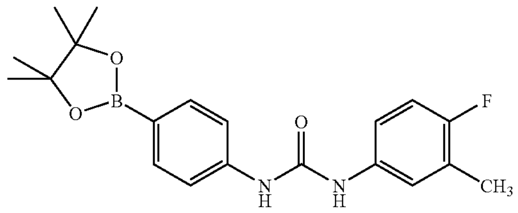 | 1-(4-fluoro-3-methylphenyl)-3-[4-(4,4,5,5-tetramethyl-1,3,2-dioxaborolan-2-yl)phenyl]urea | 389.1, 4.06 min, A |
| AP | 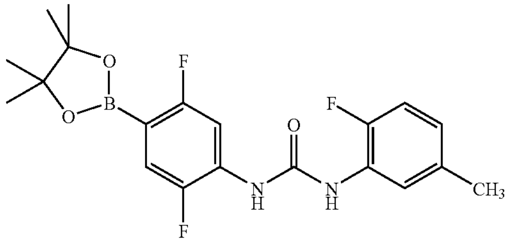 | 1-[2,5-difluoro-4-(4,4,5,5-tetramethyl-1,3,2-dioxaborolan-2-yl)phenyl]-3-(2-fluoro-5-methylphenyl)urea | 406.9, 4.15 min, A |
| AQ | 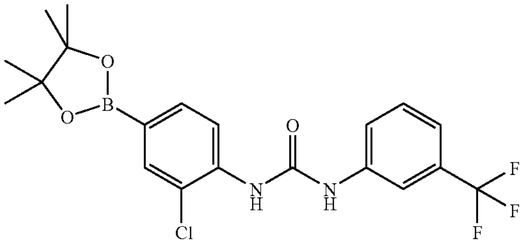 | 1-[2-chloro-4-(4,4,5,5-tetramethyl-1,3,2-dioxaborolan-2-yl)phenyl]-3-[3-(trifluoromethyl)phenyl]urea | 441.2, 4.48 min, A |
| AR | 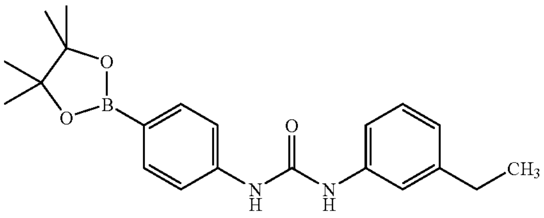 | 1-(3-ethylphenyl)-3-[4-(4,4,5,5-tetramethyl-1,3,2-dioxaborolan-2-yl)phenyl]urea | |
| AS | 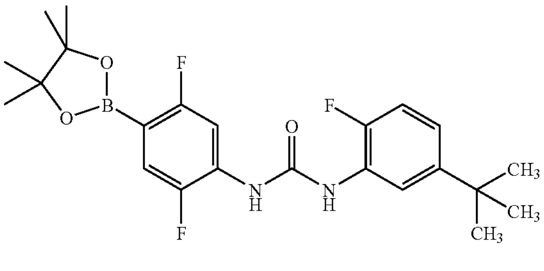 | 1-(5-tert-butyl-2-fluorophenyl)-3-[2,5-difluoro-4-(4,4,5,5-tetramethyl-1,3,2-dioxaborolan-2-yl)phenyl]urea | |
| AT | 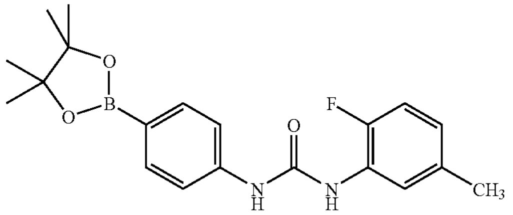 | 1-(2-fluoro-5-methylphenyl)-3-[4-(4,4,5,5-tetramethyl-1,3,2-dioxaborolan-2-yl)phenyl]urea | 370.9, 3.91 min, A |

-continued

| Int | Structure | IUPAC Name | LC-MS m/z [M + H], RT, Method |
| --- | --- | --- | --- |
| AU | 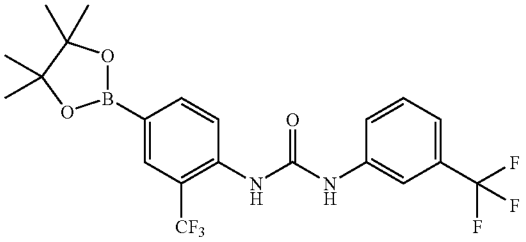 | 1-[4-(4,4,5,5-tetramethyl-1,3,2-dioxaborolan-2-yl)-2-(trifluoromethyl)phenyl]-3-[3-(trifluoromethyl)phenyl]urea | 475.0, 4.38 min, A |
| AV | 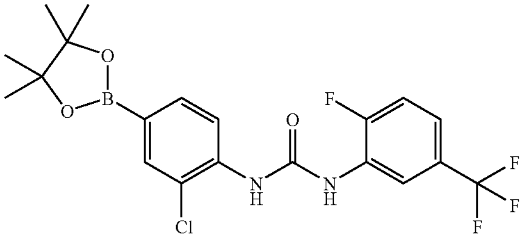 | 1-[2-chloro-4-(4,4,5,5-tetramethyl-1,3,2-dioxaborolan-2-yl)phenyl]-3-[2-fluoro-5-(trifluoromethyl)phenyl]urea | 459.2, 4.43 min, A |
| AW | 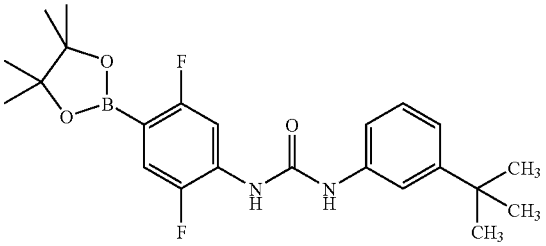 | 1-(3-tert-butylphenyl)-3-[2,5-difluoro-4-(4,4,5,5-tetramethyl-1,3,2-dioxaborolan-2-yl)phenyl]urea | 431.2, 4.57 min, A |
| AX | 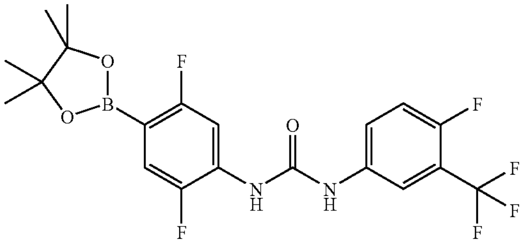 | 1-[2,5-difluoro-4-(4,4,5,5-tetramethyl-1,3,2-dioxaborolan-2-yl)phenyl]-3-[4-fluoro-3-(trifluoromethyl)phenyl]urea | 461.1, 4.28 min, A |
| AY | 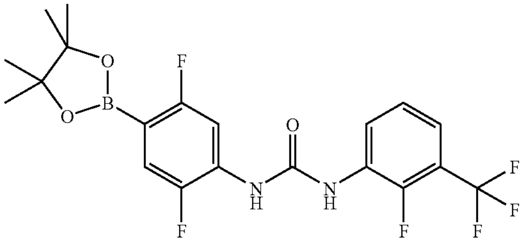 | 1-[2,5-difluoro-4-(4,4,5,5-tetramethyl-1,3,2-dioxaborolan-2-yl)phenyl]-3-[2-fluoro-3-(trifluoromethyl)phenyl]urea | 461.1, 4.28 min, A |
| AZ | 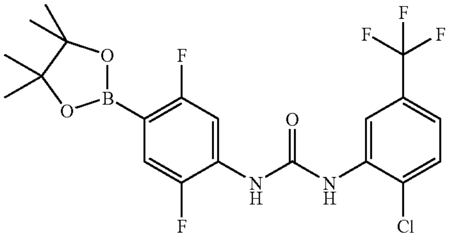 | 1-[2-chloro-5-(trifluoromethyl)phenyl]-3-[2,5-difluoro-4-(4,4,5,5-tetramethyl-1,3,2-dioxaborolan-2-yl)phenyl]urea | |

-continued

| Int | Structure | IUPAC Name | LC-MS m/z [M + H], RT, Method |
|---|---|---|---|
| BA | 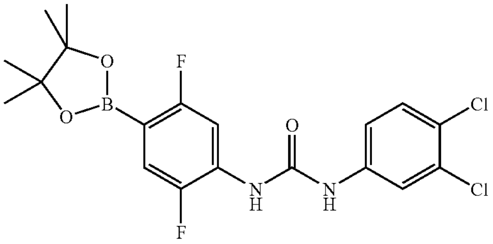 | 1-(3,4-dichlorophenyl)-3-[2,5-difluoro-4-(4,4,5,5-tetramethyl-1,3,2-dioxaborolan-2-yl)phenyl]urea | |
| BB | 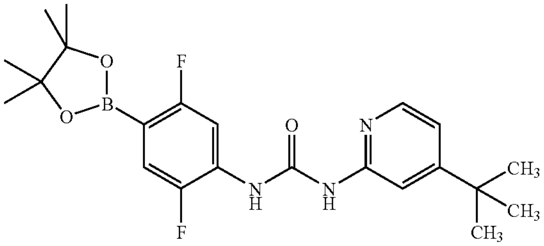 | 1-(4-tert-butylpyridin-2-yl)-3-[2,5-difluoro-4-(4,4,5,5-tetramethyl-1,3,2-dioxaborolan-2-yl)phenyl]urea | 432.2, 4.04 min, A |
| T | 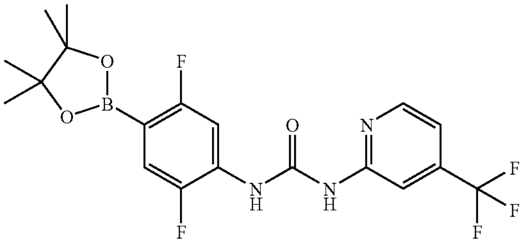 | 1-[2,5-difluoro-4-(4,4,5,5-tetramethyl-1,3,2-dioxaborolan-2-yl)phenyl]-3-[4-(trifluoromethyl)pyridin-2-yl]urea | 444.2, 4.24 min, A |
| BC | 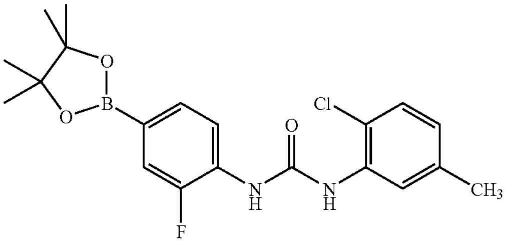 | 1-(2-chloro-5-methylphenyl)-3-[2-fluoro-4-(4,4,5,5-tetramethyl-1,3,2-dioxaborolan-2-yl)phenyl]urea | 4-5.4, 3.87 min, A |
| BD | 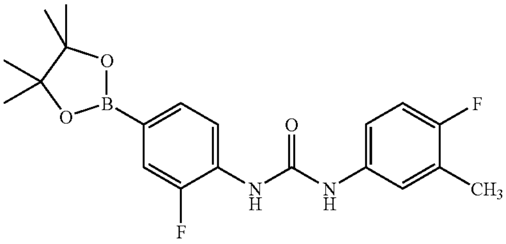 | 1-(4-fluoro-3-methylphenyl)-3-[2-fluoro-4-(4,4,5,5-tetramethyl-1,3,2-dioxaborolan-2-yl)phenyl]urea | 389.1, 4.06 min, A |
| BE | 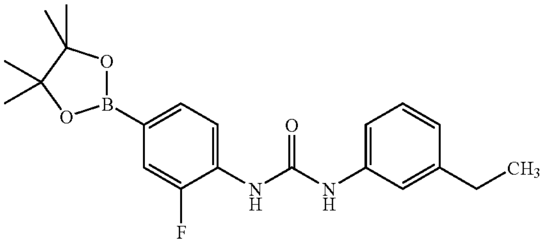 | 1-(3-ethylphenyl)-3-[2-fluoro-4-(4,4,5,5-tetramethyl-1,3,2-dioxaborolan-2-yl)phenyl]urea | 385.1, 4.17 min, A |

-continued

| Int | Structure | IUPAC Name | LC-MS m/z [M + H], RT, Method |
|---|---|---|---|
| BF | 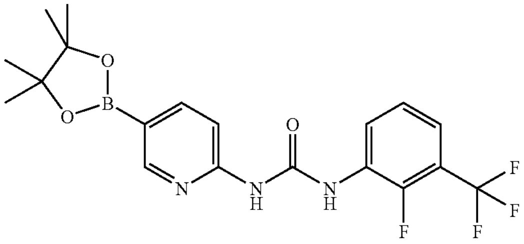 | 1-[2-fluoro-3-(trifluoromethyl)phenyl]-3-[5-(4,4,5,5-tetramethyl-1,3,2-dioxaborolan-2-yl)pyridin-2-yl]urea | 426.3, 3.86 min, A |
| BG | 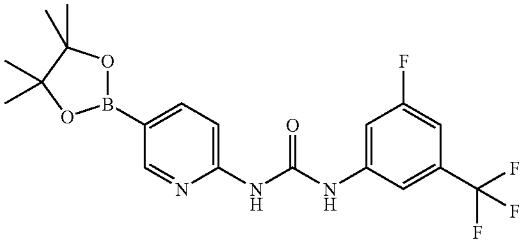 | 1-[3-fluoro-5-(trifluoromethyl)phenyl]-3-[5-(4,4,5,5-tetramethyl-1,3,2-dioxaborolan-2-yl)pyridin-2-yl]urea | 426.4, 3.88 min, A |
| BH | 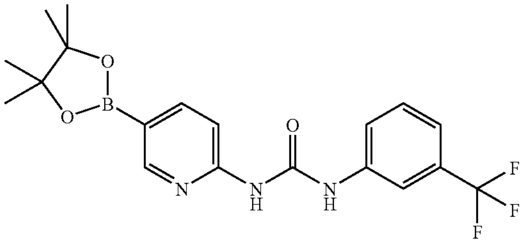 | 1-[5-(4,4,5,5-tetramethyl-1,3,2-dioxaborolan-2-yl)pyridin-2-yl]-3-[3-(trifluoromethyl)phenyl]urea | 326.1 ($-C_6H_{10}$), 2.65 min, A |
| BI | 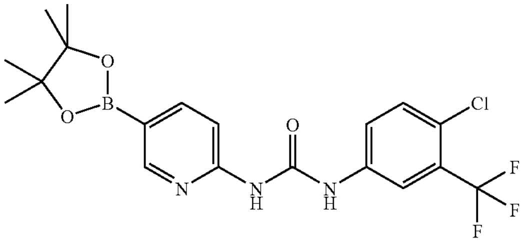 | 1-[4-chloro-3-(trifluoromethyl)phenyl]-3-[5-(4,4,5,5-tetramethyl-1,3,2-dioxaborolan-2-yl)pyridin-2-yl]urea | 442.2, 4.19 min, A |
| BJ | 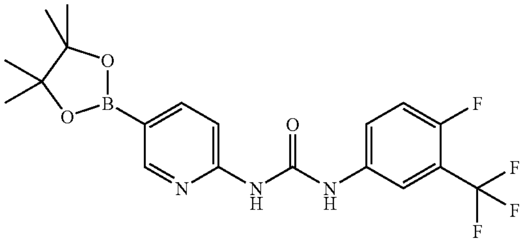 | 1-[4-fluoro-3-(trifluoromethyl)phenyl]-3-[5-(4,4,5,5-tetramethyl-1,3,2-dioxaborolan-2-yl)pyridin-2-yl]urea | 426.1, 3.97 min, A |
| BK | 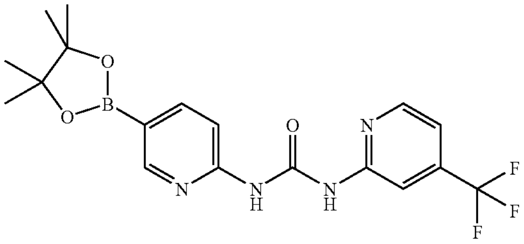 | 1-[5-(4,4,5,5-tetramethyl-1,3,2-dioxaborolan-2-yl)pyridin-2-yl]-3-[4-(trifluoromethyl)pyridin-2-yl]urea | 409.1, 3.68 min, A |

-continued

| Int | Structure | IUPAC Name | LC-MS m/z [M + H], RT, Method |
|---|---|---|---|
| BL | 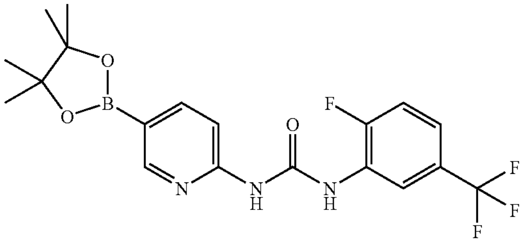 | 1-[2-fluoro-5-(trifluoromethyl)phenyl]-3-[5-(4,4,5,5-tetramethyl-1,3,2-dioxaborolan-2-yl)pyridin-2-yl]urea | 426.3, 4.17 min, A |
| BM | 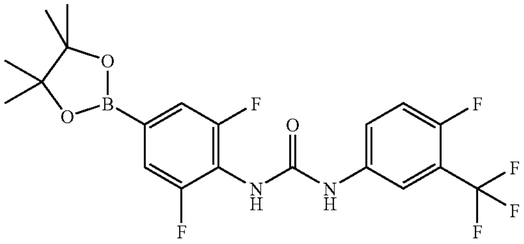 | 1-[2,6-difluoro-4-(4,4,5,5-tetramethyl-1,3,2-dioxaborolan-2-yl)phenyl]-3-[4-fluoro-3-(trifluoromethyl)phenyl]urea | 461.3, 3.92 min, A |
| R | 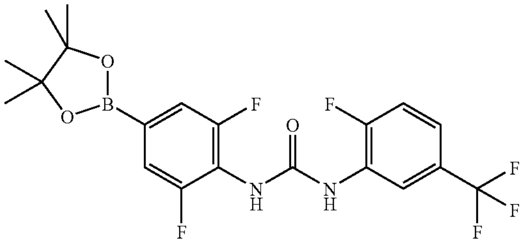 | 1-[2,6-difluoro-4-(4,4,5,5-tetramethyl-1,3,2-dioxaborolan-2-yl)phenyl]-3-[2-fluoro-5-(trifluoromethyl)phenyl]urea | 461.2, 3.92 min, A |
| S | 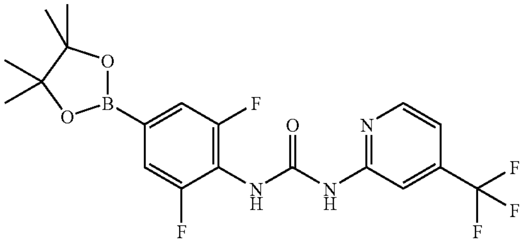 | 1-[2,6-difluoro-4-(4,4,5,5-tetramethyl-1,3,2-dioxaborolan-2-yl)phenyl]-3-[4-(trifluoromethyl)pyridin-2-yl]urea | 444.1, 4.00 min, A |
| BN | 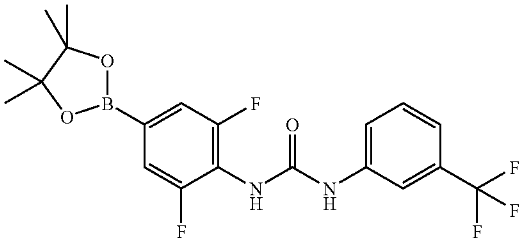 | 1-[2,6-difluoro-4-(4,4,5,5-tetramethyl-1,3,2-dioxaborolan-2-yl)phenyl]-3-[3-(trifluoromethyl)phenyl]urea | 443.3, 4.03 min, A |
| BO | 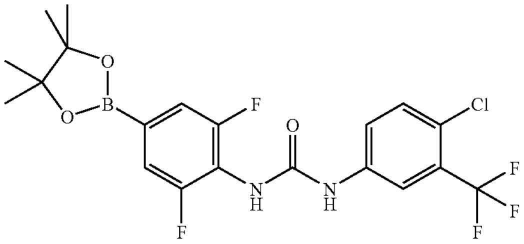 | 1-[4-chloro-3-(trifluoromethyl)phenyl]-3-[2,6-difluoro-4-(4,4,5,5-tetramethyl-1,3,2-dioxaborolan-2-yl)phenyl]urea | 477.2, 4.23 mni, A |

-continued

| Int | Structure | IUPAC Name | LC-MS m/z [M + H], RT, Method |
|---|---|---|---|
| BP | 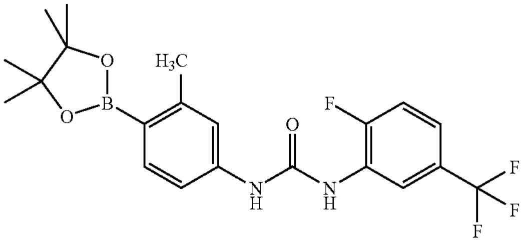 | 1-[2-fluoro-5-(trifluoromethyl)phenyl]-3-[3-methyl-4-(4,4,5,5-tetramethyl-1,3,2-dioxaborolan-2-yl)phenyl]urea | 439.2, 4.10 min, A |
| BQ | 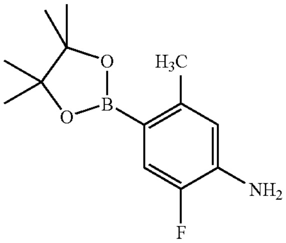 | 2-fluoro-5-methyl-4-(4,4,5,5-tetramethyl-1,3,2-dioxaborolan-2-yl)aniline | 252.4 3.64 min, A |
| BR | 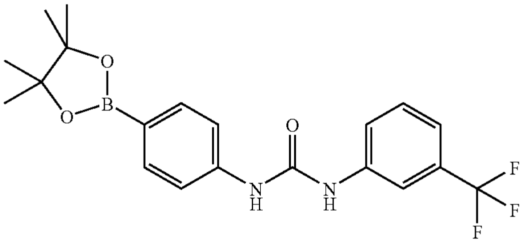 | 1-[4-(4,4,5,5-tetramethyl-1,3,2-dioxaborolan-2-yl)phenyl]-3-[3-(trifluoromethyl)phenyl]urea | 406.8, 4.02 min, A |
| U | 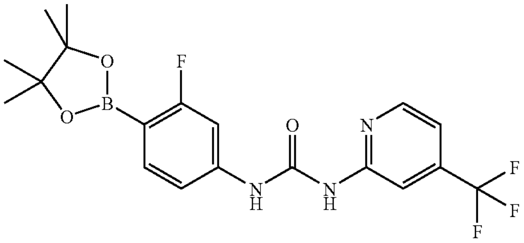 | 1-[3-fluoro-4-(4,4,5,5-tetramethyl-1,3,2-dioxaborolan-2-yl)phenyl]-3-[4-(trifluoromethyl)pyridin-2-yl]urea | 426.1, 4.04 min, A |
| BS | 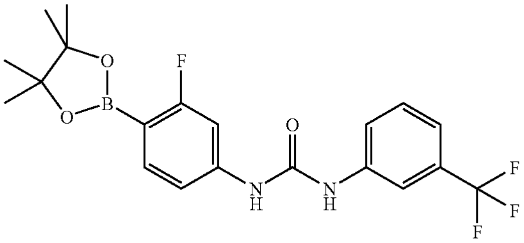 | 1-[3-fluoro-4-(4,4,5,5-tetramethyl-1,3,2-dioxaborolan-2-yl)phenyl]-3-[3-(trifluoromethyl)phenyl]urea | 425.2, 4.09 min, A |
| BT | 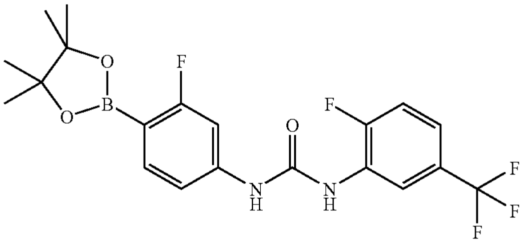 | 1-[3-fluoro-4-(4,4,5,5-tetramethyl-1,3,2-dioxaborolan-2-yl)phenyl]-3-[2-fluoro-5-(trifluoromethyl)phenyl]urea | 443.1, 4.21 min, A |

-continued

| Int | Structure | IUPAC Name | LC-MS m/z [M + H], RT, Method |
|---|---|---|---|
| BU | 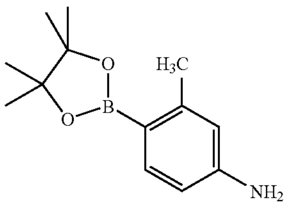 | 3-methyl-4-(4,4,5,5-tetramethyl-1,3,2-dioxaborolan-2-yl)aniline | 234.3, 2.93 min, A |
| R STEP 1 | 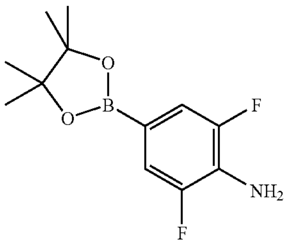 | 2,6-difluoro-4-(4,4,5,5-tetramethyl-1,3,2-dioxaborolan-2-yl)aniline | 256.3, 3.30 min, A |
| BV | 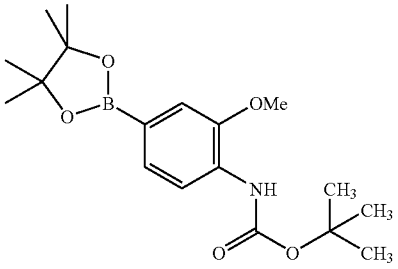 | tert-butyl [2-methoxy-4-(4,4,5,5-tetramethyl-1,3,2-dioxaborolan-2-yl)phenyl]carbamate | 290.7, 4.37 min, A |
| U STEP 1 | 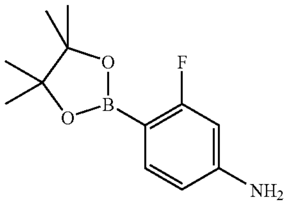 | 3-fluoro-4-(4,4,5,5-tetramethyl-1,3,2-dioxaborolan-2-yl)aniline | 238.4, 3.07 min, A |
| BW | 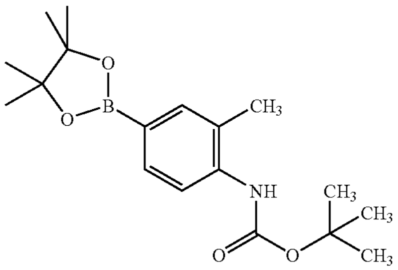 | tert-butyl [2-methyl-4-(4,4,5,5-tetramethyl-1,3,2-dioxaborolan-2-yl)phenyl]carbamate | 234.1 (-Boc), 4.14 min, A |
| BX | 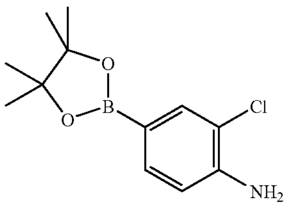 | 2-chloro-4-(4,4,5,5-tetramethyl-1,3,2-dioxaborolan-2-yl)aniline | 294.6 (M + K), 3.51 min, A |

-continued

| Int | Structure | IUPAC Name | LC-MS m/z [M + H], RT, Method |
|---|---|---|---|
| BY | 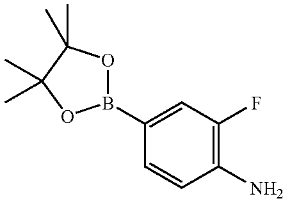 | 2-fluoro-4-(4,4,5,5-tetramethyl-1,3,2-dioxaborolan-2-yl)aniline | 278.1 (M + K), 3.35 min, A |
| BZ | 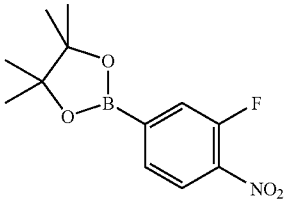 | 2-(3-fluoro-4-nitrophenyl)-4,4,5,5-tetramethyl-1,3,2-dioxaborolane | KXG-220 No Ion! |
| CA | 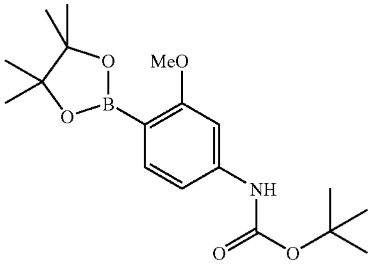 | tert-butyl [3-methoxy-4-(4,4,5,5-tetramethyl-1,3,2-dioxaborolan-2-yl)phenyl]carbamate | ABF-1891 H-NMR |

Example 1

Preparation of N-{4-[4-amino-7-(morpholin-4-ylmethyl)pyrrolo[2,1-f][1,2,4]triazin-5-yl]-2-fluorophenyl}-N'-[2-fluoro-5-(trifluoro-methyl)phenyl]urea

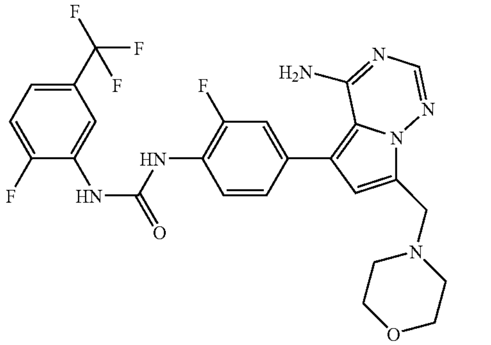

To a solution of 1,4-dioxane (35 mL) was added Intermediate C (0.783 g, 2.51 mmol) and Intermediate O (1.264 g, 2.88 mmol). The reaction mixture was allowed to stir under nitrogen to dissolve and the reaction was degassed 5×. Sodium carbonate (1M, 7.5 mL) was added and the reaction was degassed 5×. Finally tetrakis(triphenylphosphine)palladium(0) (0.290 g, 0.25 mmol) is added and the reaction degassed 5× and then heated to 80° C. overnight. After cooling to rt, the reaction mixture was diluted with EtOAc (300 ml) and washed 2× with saturated sodium bicarbonate, 1× brine, dried over sodium sulfate, filtered and concentrated to dryness. The residue was dissolved in THF (~50 ml) and silicon thiol (2 g, silicycle, 1.2 mmol/g loading) was added and stir vigorously for 90 minutes. The silica gel derivative was removed by filtration and the filtrate was purified via flash column (9:1 DCM:EtOH). The purified desired product was tritrated with DCM to obtain a white free flowing solid (650 mg, 47.3% yield). $^1$H-NMR (DMSO-$d_6$) 9.41 (s, 1H), 9.26 (s, 1H), 8.65 (d, J=7.4 Hz 1H), 8.27 (t, J=8.6 Hz 1H), 7.91 (s, 1H), 7.51 (t, J=9.7 Hz 1H), 7.42 to 7.38 (br m, 1H), 7.35 (d, J=12.4 Hz 1H), 7.24 (d, J=8.4 Hz 1H), 6.67 (s, 1H), 3.81 (s, 2H), 3.55 (t, J=4.5 Hz 4H), 2.44 (m, 4H); MS $[M+H]^+$=548; LCMS RT=2.52 min

Example 2

Preparation of N-{4-[4-amino-7-(morpholin-4-ylmethyl)pyrrolo[2,1-f][1,2,4]triazin-5-yl]phenyl}-N-(3-tert-butylisoxazol-5-yl)urea

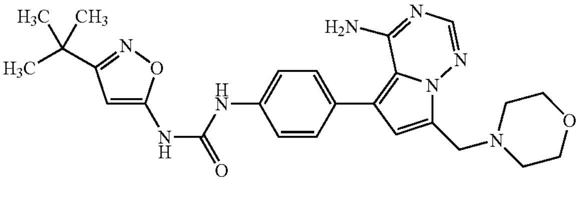

A mixture of Intermediate E (35 mg, 0.10 mmol), phenyl (3-tert-butylisoxazol-5-yl)carbamate (28 mg, 0.10 mmol) and triethylamine (0.015 ml, 0.10 mmol) in THF (2 ml) was heated at 60° C. under $N_2$ for 16 h. Upon completion, the reaction was cooled to rt and the solvent was evaporated. The resulting crude was purified via column chromatography (95:5 v/v $CH_2Cl_2$-$CH_3OH$) to afford 21 mg of the title compound (yield 39%). $^1$H-NMR (DMSO-$d_6$) δ 9.86 (s, 1H), 8.69 (s, 1H), 7.63 (s, 1H), 7.30 (d, J=8 Hz, 2H), 7.13 (d, J=8 Hz, 2H), 6.36 (s, 1H), 5.80 (s, 1H), 3.55 (s, 2H), 3.29 to 3.12 (m, 4H), 2.19 to 2.16 (m, 4H), 1.05 (s, 9H); MS $[M+H]^+$=491.0; LCMS RT=2.24 min.

Example 3

Preparation of N-{4-[4-amino-7-(morpholin-4-ylmethyl)pyrrolo[2,1-f][1,2,4]triazin-5-yl]phenyl}-N'-[4-(trifluoromethyl)pyridin-2-yl]urea

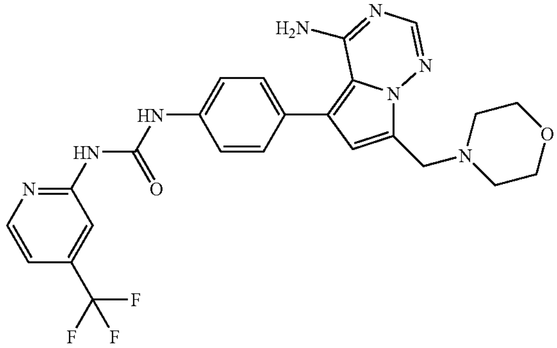

The procedure used for the preparation of Example 2 was used to prepare the title compound by substituting Intermediate H (phenyl [4-(trifluoromethyl)pyridin-2-yl]carbamate) for phenyl (3-tert-butylisoxazol-5-yl)carbamate. $^1$H-NMR (DMSO-$d_6$) δ 9.86 (s, 1H), 9.73 (s, 1H), 8.54 (d, J=5 Hz, 1H), 8.05 (s, 1H), 7.63 (d, J=6 Hz, 2H), 7.40 (d, J=6 Hz, 2H) 7.34 (t, J=6 Hz, 1H), 6.62 (s, 1H), 3.81 (s, 2H), 3.55 (t, J–4 Hz, 4H), 2.43 (t, J=4 Hz, 4H); MS $[M+H]^+$=513.0; LCMS RT=2.40 min.

Example 4

Preparation of N-{4-[4-amino-7-(morpholin-4-ylmethyl)-pyrrolo[2,1-f][1,2,4]triazin-5-yl]phenyl}-N'-[2-fluoro-5-(trifluoromethyl)phenyl]urea

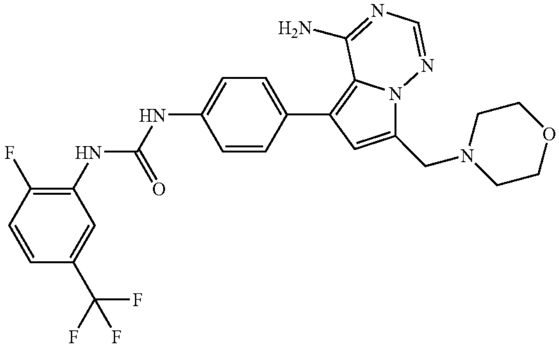

To a solution of Intermediate E (37 mg, 0.11 mmol) in $CH_2Cl_2$ (3 ml) was added 2-fluoro-5-(trifluoromethyl)phenyl isocynate (48 mg, 0.22 mmol) and stirred at rt under $N_2$ for 16 h. Analytical HPLC showed all starting materials consumed. To the reaction mixture was added DMF (3 ml) and 2N HCl (0.07 ml, 0.14 mmol) and was heated at 80° C. for 3 h. Cooled to rt, the reaction solvent was evaporated partially. Diluted with ethyl acetate (20 ml), the mixture was washed with aq. saturated $NaHCO_3$ and $H_2O$. After dried over $Na_2SO_4$, the crude product was concentrated and triturated with $CH_2Cl_2$ (3×), hexane and ethyl ether (3×) to afford 27 mg of the title compound as a white solid (yield 45%). $^1$H-NMR (DMSO-$d_6$) δ 9.26 (s, 1H), 8.90 (s, 1H), 8.59 (dd, J=7, 3 Hz, 1H), 7.86 (s, 1H), 7.54 (d, J=8 Hz, 2H), 7.47 to 7.35 (m, 3H) 6.59 (s, 1H), 3.78 (s, 2H), 3.51 (t, J=4 Hz, 4H), 2.43 (t, J=4 Hz, 4H); MS $[M+H]^+$=530.0; LCMS RT=2.45 min.

Example 5

Preparation of N-{4-[4-amino-7-(morpholin-4-ylmethyl)-pyrrolo[2,1-f][1,2,4]triazin-5-yl}phenyl]-N'-[3-(trifluoromethyl)phenyl]urea

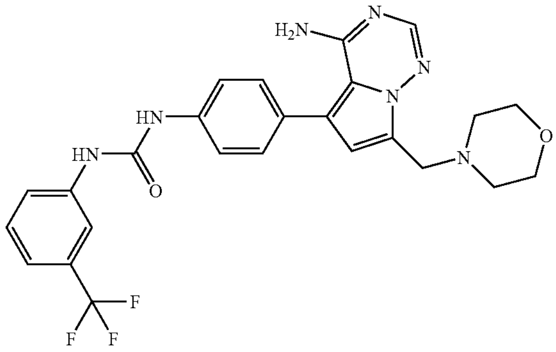

The procedure used for the preparation Example 4 was used to prepare the title compound by substituting 3-trifluoromethyl-phenylisocyanate for 2-fluoro-5-(trifluoromethyl)-phenyl isocyanate. $^1$H-NMR($CH_3OH$-$d_4$) δ 7.92 (s, 1H), 7.63 to 7.60 (m, 3H), 7.47 to 7.43 (m, 3H), 7.31 to 7.28 (m, 1H), 6.70 (s, 1H), 3.95 (s, 2H), 3.69 (t, J=4 Hz, 4H), 2.59 (t, J=4 Hz, 1H); MS $[M+H]^+$=511.9; LCMS RT=2.38 min.

Example 6

Preparation of N-{4-[4-amino-7-(morpholin-4-ylmethyl)-pyrrolo[2,1-f][1,2,4]triazin-5-yl]phenyl}-N'-[4-fluoro-3-(trifluoromethyl)phenyl]urea

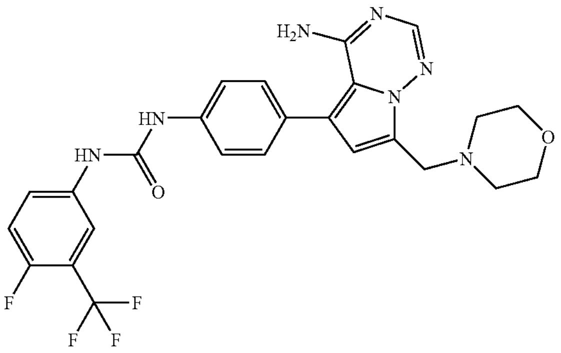

The procedure used for the preparation of Example 4 was used to prepare the title compound by substituting 4-fluoro-3-(trifluoromethyl)phenyl isocyanate for 2-fluoro-5-(trifluoromethyl)-phenyl isocyanate. $^1$H-NMR (DMSO-$d_6$) δ 9.06 (s, 1H), 8.93 (s, 1H), 8.02 to 7.99 (dd, J=7, 3 Hz, 1H), 7.65 to 7.61 (m, 1H), 7.57 to 7.54 (dd, J=7 Hz, 2H), 7.43 to 7.40 (m, 1H), 7.40 to 7.36 (dd, J=7, 2 Hz, 2H), 6.61 (s, 1H), 3.80 (s, 2H), 3.53 (t, J=4 Hz, 4H), 2.42 (t, J=4 Hz, 4H); MS $[M+H]^+$=529.9; LCMS RT=2.48 min.

Example 7

Preparation of N-{4-[4-amino-7-(morpholin-4-ylmethyl)-pyrrolo[2,1-f][1,2,4]triazin-5-yl]-2,6-difluorophenyl}-N'-[2-fluoro-5-(trifluoro-methyl)phenyl] urea

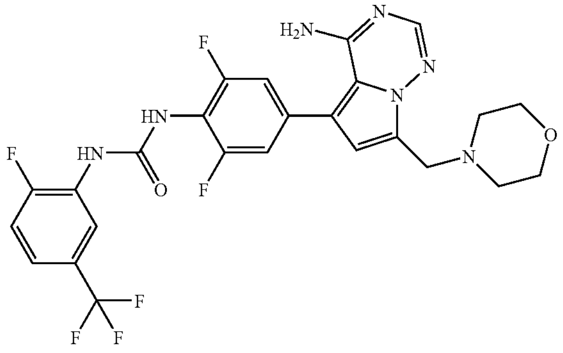

Intermediate C (0.100 g, 0.32 mmol) and Intermediate R (0.176 g, 0.38 mmol) were added as solids to a flask. Dioxane (17 mL) was then added to the flask followed by 2N aqueous sodium carbonate (0.64 mmol, 0.32 uL). The reaction was degassed and tetrakis(triphenylphosphine) palladium (0) (0.037 g, 0.032 mmol) was added and the reaction was again placed under vacuum then blanketed with nitrogen. The reaction was heated at 80° C. until TLC showed the complete consumption of starting bromide (~20 h). The reaction was cooled to rt and EtOAc was added and washed with water. The combined organic layer was washed with brine, dried with $Na_2SO_4$ and concentrated under vacuum. The residue was purified using silica gel column chromotography (0-6% v/v $MeOH/CH_2Cl_2$) to afford the desired product in 29% yield. $^1$H-NMR (DMSO-$d_6$) δ 9.14 (d, J=3.3 Hz, 1H), 8.66 (s, 1H), 8.54 (d, J=7.2 Hz, 1H), 7.93 (s, 1H), 7.54-7.40 (m, 2H), 7.25 (d, J=5.7 Hz, 2H), 6.75 (s, 1H), 3.81 (s, 2H), 3.55 (t, J=4.5 Hz, 4H), 2.44 (t, J=4.5 Hz, 4H); MS $[M+H]^+$=566.1, LCMS RT=2.94 min.

Example 8

Preparation of N-{4-[4-amino-7-(morpholin-4-ylmethyl)pyrrolo[2,1-f]f][1,2,4]triazin-5-yl]-2-fluorophenyl}-N'-[4-(trifluoromethyl)pyridin-2-yl]urea

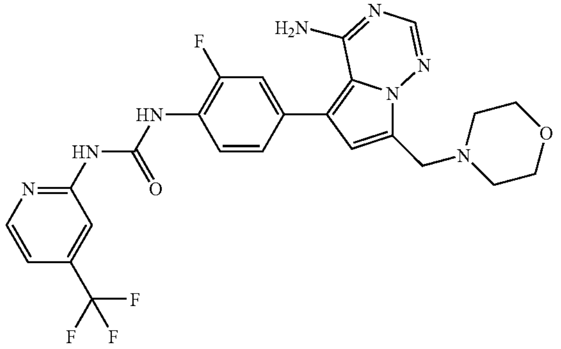

The procedure used for the preparation of Example 7 was used to prepare the title compound by substituting Intermediate AE for Intermediate R. The requisite boronate, was made using the procedure used to prepare Intermediate S, step 1, followed by step 2 of the procedure used to make Intermediate Q. $^1$H-NMR (MeOD-$d_4$) δ 8.48 (d, J=5.4 Hz, 1H), 8.30 (t, J=8.1 Hz, 1H), 7.85 (s, 1H), 7.79 (s, 1H), 7.33-7.25 (m, 3H), 6.71 (s, 1H), 3.97 (s, 1H), 3.70 (t, J=4.2, 4H), 2.60 (t, J=4.5 Hz, 4H); MS $[M+H]^+$=530.9, LCMS RT=2.33 min.

Example 9

Preparation of N-{5-[4-amino-7-(morpholin-4-ylmethyl)pyrrolo[2,1-f][1,2,4]triazin-5-yl]pyridin-2-yl}-N'-[2-fluoro-5-(trifluoromethyl)phenyl]urea

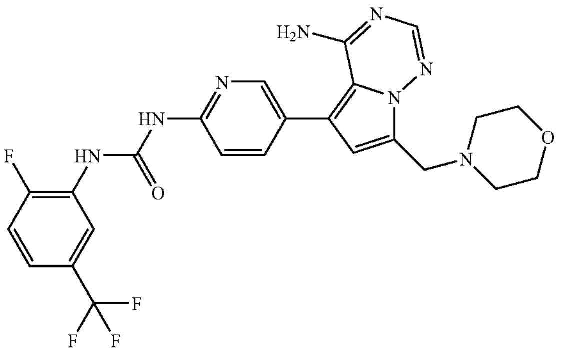

The title compound was prepared using the procedure to Example 7 by substituting Intermediate BL for Intermediate R. $^1$H-NMR (DMSO-$d_6$) δ 10.07 (s, 1H), 8.68 (dd, J=6.9, 2.1, 1H), 8.32 (m, 1H), 7.86-7.43 (m, 3H), 7.91 (s, 1H), 3.81 (s, 2H), 3.55 (m, 4H), 2.44 (m, 4H); MS $[M+H]^+$=531.0, LCMS RT=2.50 min.

Example 10

Preparation of N-{4-[4-amino-7-(morpholin-4-ylmethyl)pyrrolo[2,1-f][1,2,4]triazin-5-yl]-2-fluorophenyl}-N'-[3-(trifluoromethyl)phenyl]urea

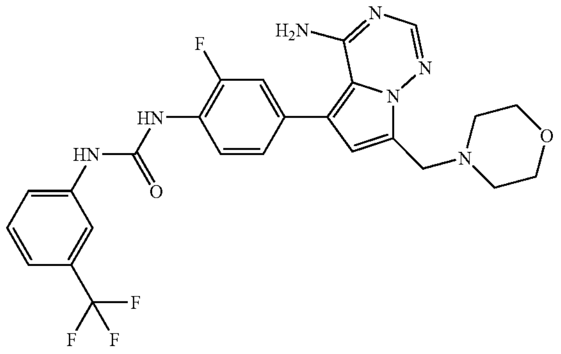

The title compound was prepared by substituting Intermediate Q for Intermediate O in the procedure to make Example 1. $^1$H-NMR (DMSO-$d_6$) δ 9.43 (s, 1H), 8.73 (s, 1H), 8.21 (t, J=8.4, 1H), 8.05 (s, 1H), 7.91 (s, 1H), 6.66 (s, 1H) 3.81 (s, 2H), 3.54 (t, J=4.2 Hz, 4H), 2.44 (t, J=4.2 Hz, 4H); MS $[M+H]^+$=529.9, LCMS RT=2.47 min.

Example 11

Preparation of N-{4-[4-amino-7-(morpholin-4-ylmethyl)pyrrolo[2,1-f]1][1,2,4]triazin-5-yl]-3-fluorophenyl}-N'-[4-(trifluoromethyl)pyridin-2-yl]urea

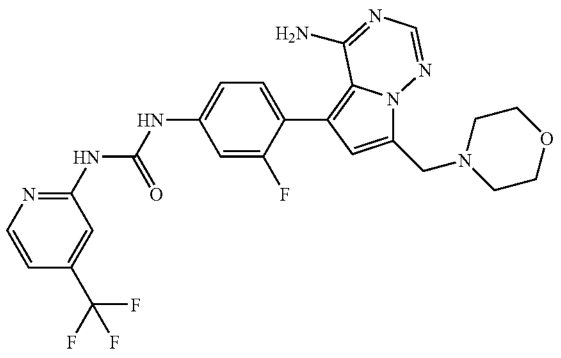

The title compound was prepared using the procedure to make Example 7 by substituting Intermediate U for Intermediate R. $^1$H-NMR (DMSO-$d_6$) δ 10.04 (s, 1H), 9.80 (s, 1H), 8.55 (m, 1H), 8.04 (s, 1H), 7.90 (s, 1H), 7.66 (dd, J=12.6 Hz, 2.1 Hz, 1H), 7.39-7.29 (m, 3H), 6.61 (s, 1H), 3.81 (s, 2H), 3.54 (t, J=4.5, 4H), 2.43 (t, J=4.2 Hz, 4H); MS $[M+H]^+$=531.0, LCMS RT=2.85 min Example 12

Preparation of N-{5-[4-amino-7-(morpholin-4-ylmethyl)pyrrolo[2,1-f][1,2,4]triazin-5-yl]pyridin-2-yl}-N'-[4-(trifluoromethyl)pyridin-2-yl]urea

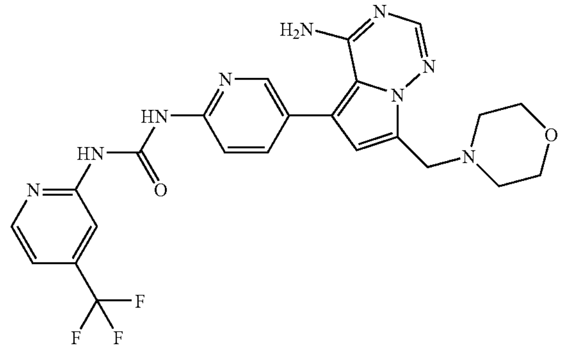

The title compound was prepared using the procedure to prepare Example 7 by substituting Intermediate BK for Intermediate R. $^1$H-NMR (DMSO-$d_6$) δ 10.26 (s, 1H), 8.56 (d, J=5.1, 1H), 8.35 (s, 1H), 8.22 (s, 1H), 7.92 (s, 1H), 7.87-7.35 (m, 2H), 7.42 (dd, J=1.8, 0.6, 1H), 6.76 (s, 1H), 3.81 (s, 2H), 3.54 (t, J=3.9 HZ, 4H), 2.44 (t, J=4.2, 4H); MS $[M+H]^+$=513.9, LCMS RT=2.31 min.

Example 13

Preparation of N-{4-[4-amino-7-(morpholin-4-ylmethyl)pyrrolo[2,1-f][1,2,4]triazin-5-yl]-2,5-difluorophenyl}-N'-[4-(trifluoromethyl)pyridin-2-yl]urea

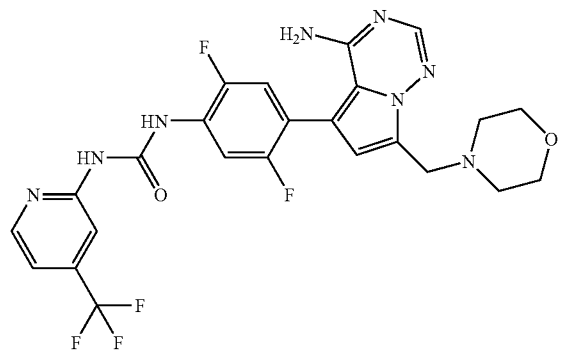

The title compound was prepared using the procedure to make Example 7 by substituting intermediate R with Intermediate T. NMR (DMSO-$d_6$) δ 10.19 (m, 2H) 8.53 (d, J=5.1 Hz, 1H), 8.10 (dd, J=11.7, 5.1 1H), 8.00 (s, 1H), 7.90 (s, 1H), 7.37-7.30 (m, 2H), 6.63 (s, 1H), 3.81 (s, 2H), 3.54 (t, J=3.6 Hz, 4H), 2.44 (t, J=4.5 Hz, 4H); MS $[M+H]^+=549.0$, LCMS RT=2.48 min Example 14

Preparation of N-{4-[4-amino-7-(morpholin-4-ylmethyl)pyrrolo[2,1-f][1,2,4]triazin-5-yl]-2,6-difluorophenyl}-N'-[4-(trifluoromethyl)pyridin-2-yl]urea

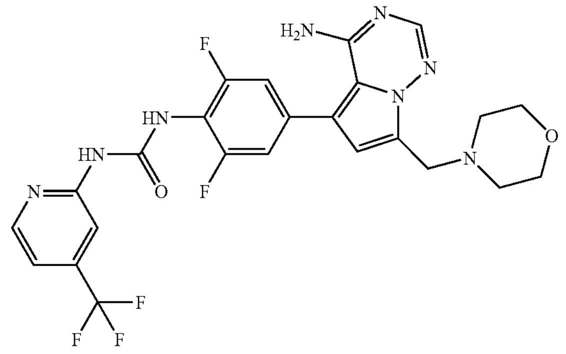

The title compound was prepared using the procedure to make Example 7 by substituting Intermediate S for Intermediate R. $^1$H-NMR (DMSO-$d_6$) δ 9.95 (s, 1H), 9.30 (s, 1H), 8.50 (d, J=5.4, 1H) 7.97 (s, 1H), 7.92 (s, 1H), 7.32-7.20 (m, 3H), 6.72 (s, 1H), 3.82 (s, 2H), 3.56 (m, 4H), 2.46 (m, 4H) MS $[M+H]^+=549.0$, LCMS RT=2.82 min.

Example 15

Preparation of N-{4-[4-amino-7-(morpholin-4-ylmethyl)pyrrolo[2,1-f][1,2,4]triazin-5-yl]-2,5-difluorophenyl}-N'-[2-fluoro-5-(trifluoromethyl)phenyl] urea

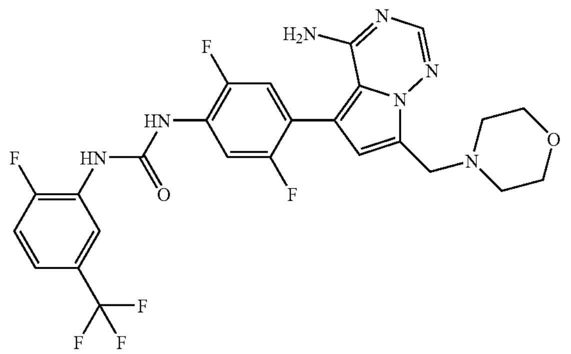

The title compound was prepared using the procedure to make Example 7 by substituting Intermediate AH for Intermediate R. $^1$H-NMR (DMSO-$d_6$) δ 9.47 (d, J=2.7, 1H), 9.43 (s, 1H), 8.63 (d, J=3.9 Hz, 1H), 8.15 (dd, 12.3, Hz, 7.2 Hz, 1H), 7.91 (s, 1H) 7.55-7.42 (m, 2H), 7.32 (dd, J=11.7 Hz, 6.9 Hz, 1H), 6.63 (s, 1H), 3.81 (s, 2H), 3.54 (t, J=4.5, 4H), 2.43 (t, J=4.5, 4H); MS $[M+H]^+=565.9$, LCMS RT=2.75 min.

Example 16

Preparation of N-{4-[4-amino-7-(morpholin-4-ylmethyl)pyrrolo[2,1-f][1,2,4]triazin-5-yl}-3-fluorophenyl]-N'-[2-fluoro-5-(trifluoromethyl)phenyl]urea

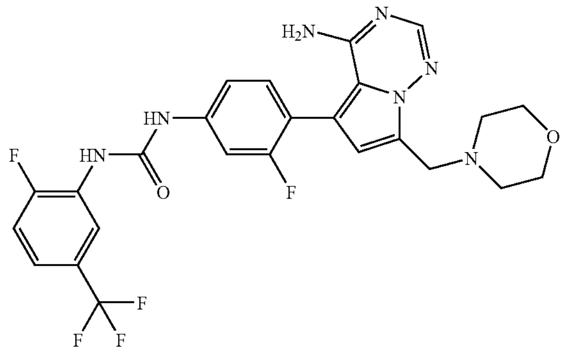

The title compound was prepared using the procedure to make Example 7 by substituting Intermediate BT for Intermediate R. $^1$H-NMR (MeOD-$d_4$) δ 8.59 (m, 1H), 7.90 (s, 1H), 7.62 (d, J=10.2 Hz, 1H), 7.52-7.30 (m, 3H), 7.20 (d, 1H), 6.60 (s, 1H), 3.53 (m, 4H), 2.35 (m, 4H); MS $[M+H]^+=547.9$, LCMS RT=2.67 min.

Example 17

Preparation of N-{4-[4-amino-7-(morpholin-4-ylmethyl)pyrrolo[2,1-f][1,2,4]triazin-5-yl]-3-fluorophenyl}-N'-[3-(trifluoromethyl)phenyl]urea

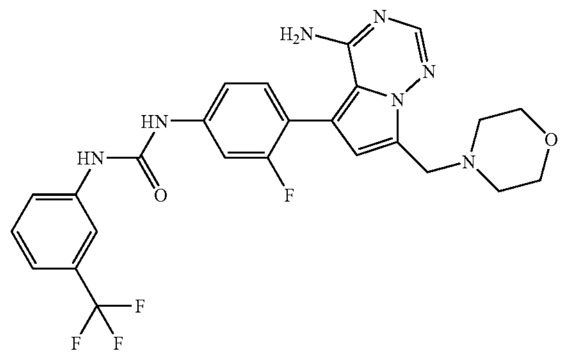

The title compound was prepared using the procedure to make Example 7 by substituting Intermediate BS for Intermediate R. $^1$H-NMR (DMSO-d6) δ 9.15 (s, 1H), 9.13 (s, 1H) 8.01 (s, 1H), 7.90 (s, 1h), 7.63-7.52 (m, 3h), 7.35-7.23 (m, 3H) 6.60 (s, 1H) 3.81 (s, 2H), 3.57 (m, 4H), 2.45, (m, 4h); MS [M+H]+=530.1, LCMS RT=2.56 min.

Example 18

Preparation of N-{5-[4-amino-7-(morpholin-4-ylmethyl)pyrrolo[2,1-f][1,2,4]triazin-5-yl]pyridin-2-yl}-N'-[4-fluoro-3-(trifluoromethyl)phenyl]urea

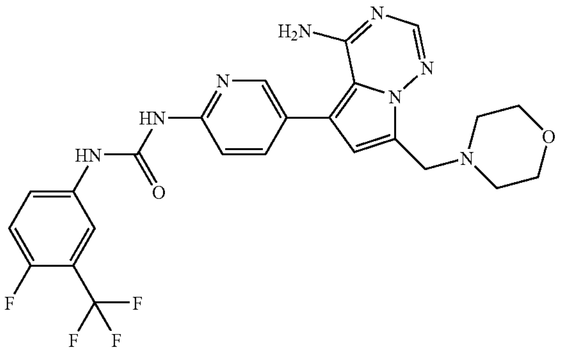

The title compound was prepared using the procedure to make Example 7 by substituting Intermediate BJ for Intermediate R. $^1$H-NMR (MeOD-$d_4$) δ 8.41 (d, J=2.4 Hz, 1H), 7.94-7.73 (m, 4H), 7.32 (d, J=8.4 Hz, 1H), 7.22 (t, J=9.6, 1H), 6.86-6.66 (m, 2H), 3.99 (s, 2H), 3.68 (m, 4H), 2.57 (m, 4H) MS [M+H]+=531.0, LCMS RT=2.56 min.

Example 19

Preparation of N-{5-[4-amino-7-(morpholin-4-ylmethyl)pyrrolo[2,1-f][1,2,4]triazin-5-yl]pyridin-2-yl}-N'-[4-chloro-3-(trifluoromethyl)phenyl]urea

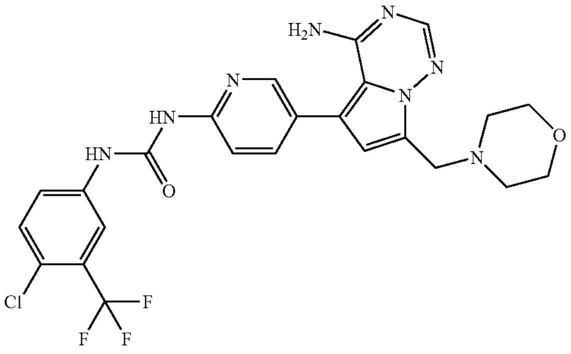

The title compound was prepared using the procedure to make Example 7 by substituting Intermediate BI for Intermediate R. $^1$H-NMR (DMSO-$d_6$) δ10.95 (s, 1H), 9.71 (s, 1H) 8.67 (d, J=2.4, 1H),8.19 (d, J=2.7, 1H), 7.92 (s, 1H), 7.82 (dd, J=8.7 Hz, J=2.4 Hz, 1H), 7.75 (dd, J=8.7 Hz, J=2.4 Hz, 1H), 7.65 (d, J=9.3 Hz, 1H), 7.55 (d, J=8.4 Hz, 1H) 6.68 (s, 1H), 3.82 (s, 2H), 3.54 (m, 4H), 2.40 (m, 4H); MS [M+H]+=547.0, LCMS RT=2.68 min.

Example 20

Preparation of N-{5-[4-amino-7-(morpholin-4-ylmethyl)pyrrolo[2,1-f][1,2,4]triazin-5-yl]pyridin-2-yl}-N' [3-(trifluoromethyl)phenyl]urea

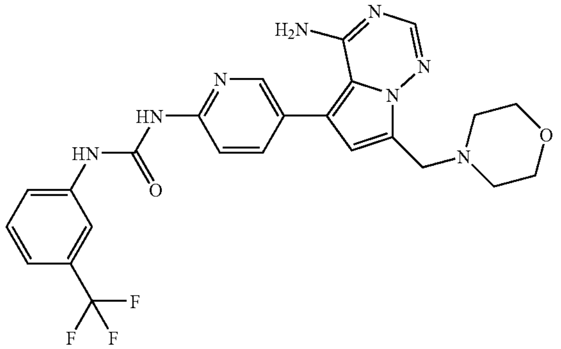

The title compound was prepared using the procedure to make Example 7 by substituting Intermediate BH for Intermediate R. $^1$H-NMR (MeOD-$d_4$) δ 8.41 (m, 1H) 7.96 (m, 1H), 7.88 (s, 1H), 7.84 (s, 1H), 7.33 (d, J=8.7 Hz, 1H), 7.23 (t, J=9.2 Hz, 1H), 6.86-6.64 (m, 2H) 5.39 (s, 2H), 3.95 (s, 1H), 3.69 (m, 4H), 2.59, (m, 4H) MS [M+H]-1-=513.0, LCMS RT=2.52 min.

Example 21

Preparation of N-{5-[4-amino-7-(morpholin-4-ylmethyl)pyrrolo[2,1-f][1,2,4]triazin-5-yl]pyridin-2-yl}-N'-[2-fluoro-3-(trifluoromethyl)phenyl]urea

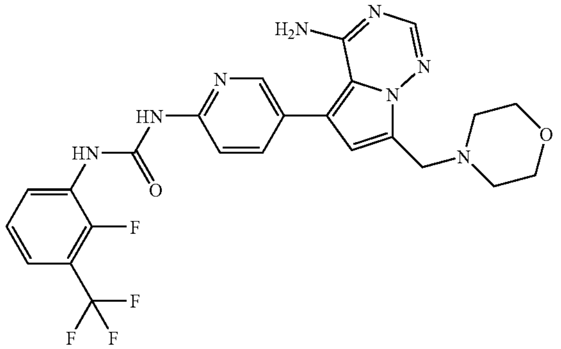

The title compound was prepared using the procedure to make Example 7 by substituting Intermediate BF for Intermediate R. $^1$H-NMR (DMSO-$d_6$) δ 10.05 (s, 1H), 8.56 (m, 1H), 7.92 (s, 1H), 7.84 (dd, J=8.7 Hz, 2.4 Hz, 11-1) 7.41-7.38

(m, 3H), 6.70 (s, 1H), 3.82 (s, 2H), 3.58-3.53 (m, 4H), 2.49-2.44 (m, 4H);MS [M+H]-1-=530.9, LCMS RT=2.42 min.

Example 22

Preparation of N-{5-[4-amino-7-(morpholin-4-ylmethyl)pyrrolo[2,1-f][1,2,4]triazin-5-yl]pyridin-2-yl}-N'-[3-fluoro-5-(trifluoromethyl)phenyl]urea

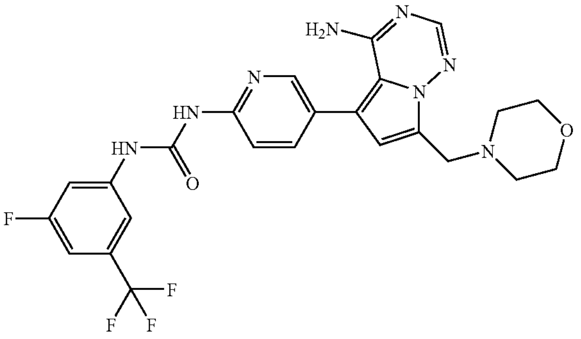

The title compound was prepared using the procedure to make Example 7 by substituting Intermediate BG for Intermediate R. $^1$H-NMR (DMSO-$d_6$) δ 11.18 (s, 1H), 9.46 (s, 1H), 9.80 (s, 1H), 8.39 (d, J=1.8 Hz, 1H), 7.91 (s, 1H), 7.85-7.75 (m, 2H), 7.52 (d, J=9.6 Hz, 1H), 7.29 (d, J=3.6 Hz, 1H), 6.68 (s, 1H), 3.82 (s, 2H) 3.57 (m, 4H), 2.41 (m, 4H);MS [M+H]+=531.1 LCMS RT=2.81 min.

Example 23

Preparation of N-{4-[4-amino-7-(morpholin-4-ylmethyl)pyrrolo[2,1-f][1,2,4]triazin-5-yl]-2,5-difluorophenyl}-N'-[4-fluoro-3-(trifluoromethyl)phenyl]urea

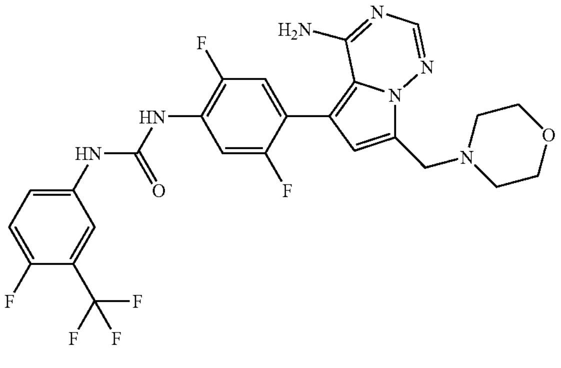

The title compound was prepared using the procedure to make Example 7 by substituting Intermediate AX for Intermediate R. $^1$H-NMR (DMSO-$d_6$) δ 9.46 (s, 1H), 8.91 (s, 1H), 8.49 (dd, J=11.7 Hz, J=6.9,Hz, 1H), 8.01 (m, 1H), 7.91 (s, 1H), 7.61 (m, 1H), 7.46 (t, J=9.9 Hz, 1H) 7.31 (dd, 11.7 Hz, J=6.9 Hz, 1H) 6.63 (s, 1H), 3.80 (s, 2H), 3.54 (t, J=4.5 Hz, 4H) 2.43 (t, J=4.5 Hz, 4H);MS [M+H]+=566.0 LCMS RT=2.75 min.

Example 24

Preparation of N-{4-[4-amino-7-(morpholin-4-ylmethyl)pyrrolo[2,1-f][1,2,4]triazin-5-yl]-2,5-difluorophenyl}-N'-[3-(trifluoromethyl)phenyl]urea

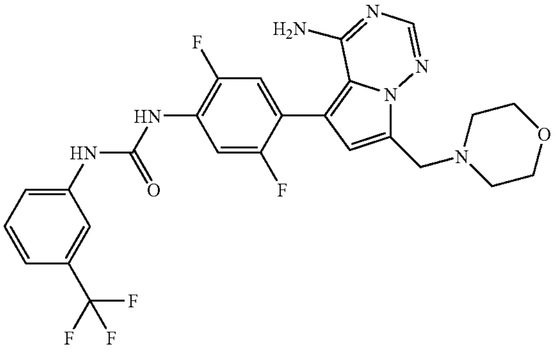

The title compound was prepared using the procedure to make Example 7 by substituting Intermediate AN for Intermediate R. $^1$H-NMR (DMSO-$d_6$) δ 9.48 (s, 1H), 8.93 (s, 1H), 8.12 (q, J=6.9 Hz, 1H), 8.04 (s, 1H), 7.91 (s, 1H), 7.54 (d, J=5.1 Hz, 2H), 7.36-7.28 (m, 3H), 6.63 (s, 1H), 3.81 (s, 2H), 3.54 (t, J=4.5 Hz, 4H), 2.44 (t, J=4.5 Hz, 4H); MS [M+H]+=548.0 LCMS RT=2.72 min.

Example 25

Preparation of N-{4-[4-amino-7-(morpholin-4-ylmethyl)pyrrolo[2,1-f][1,2,4]triazin-5-yl]-2-methylphenyl}-N'-[2-fluoro-5-(trifluoromethyl)phenyl]urea

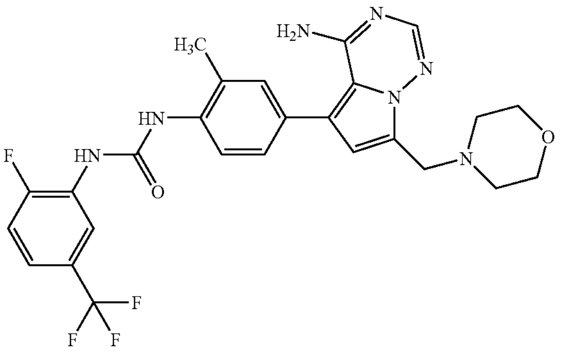

The title compound was prepared using the procedure to make Example 7 by substituting boronate, N-[2-fluoro-5-(trifluoromethyl)phenyl]-N'-[2-methyl-4-(4,4,5,5-tetramethyl-1,3-dioxolan-2-yl)phenyl]urea for Intermediate R. The boronate, was made using the procedure used to make Intermediate R. $^1$H-NMR (DMSO-$d_6$) δ 9.38 (s, 1H), 8.66 (dd, J=4.2 Hz, J=1.8 Hz, 1H) 8.57 (s, 1H) 7.99 (d, J=8.4, 1H) 7.89

(s, 1H), 7.50 (m, 1H), 7.38 (m, 1H), 7.27 (m, 1H), 6.611 (s, 1H) 3.81 (s, 2H) 3.65 (m, 4H) 2.40 (m, 4H)); MS [M+H]+=544.1 LCMS RT=2.64 min Example 26

Preparation of N-{4-[4-amino-7-(morpholin-4-ylmethyl)pyrrolo[2,1-f][1,2,4]triazin-5-yl]-2-methylphenyl}-N'-[4-(trifluoromethyl)pyridin-2-yl]urea

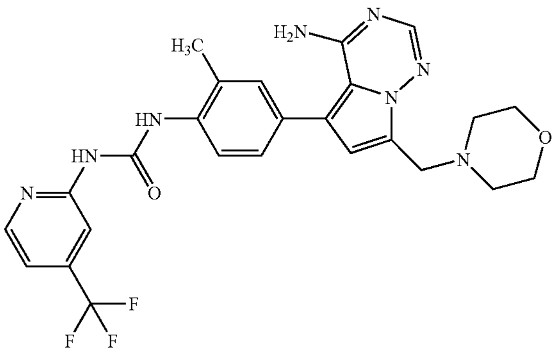

The title compound was prepared using the procedure to make Example 7 by substituting Intermediate AG for Intermediate R. $^1$H-NMR (DMSO-$d_6$) δ 10.16 (s, 1H), 9.9 (s, 1H), 8.55 (d, J=5.1 Hz, 1H), 8.09 (d. J=8.4, 1H) 7.89 (s, 1H), 7.87 (s, 1H), 7.35 (m, 2H), 7.27 (dd, J=7.8 Hz, J=1.5 Hz, 1H) 6.62 (s, 1H), 3.81 (s, 2H), 3.47 (m, 4H), 2.46 (m, 4H), 2.35 (s, 3H); MS $[M+H]^+$=527.1 LCMS RT=2.53 min Example 27

Preparation of N-{4-[4-amino-7-(morpholin-4-ylmethyl)pyrrolo[2,1-f][1,2,4]triazin-5-yl]-2-methylphenyl}-N'-[4-fluoro-3-(trifluoromethyl)phenyl]urea

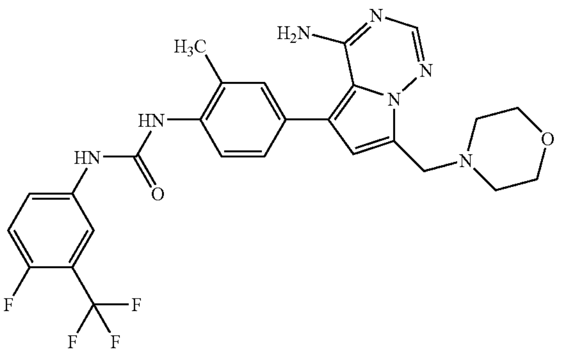

The title compound was prepared using the procedure to make Example 7 by substituting boronate, N-[4-fluoro-3-(trifluoromethyl)phenyl]-N'-[2-methyl-4-(4,4,5,5-tetramethyl-1,3,2-dioxaborolan-2-yl)phenyl]urea for Intermediate R. The boronate, was made using the procedure used to make Intermediate R. $^1$H-NMR (DMSO-$d_6$) δ 9.56 (s, 1H), 8.21 (s, 1H), 7.89-7.85 (m, 2H), 7.68 (s, 1H), 7.60 (d, J=11.4, 2H), 7.30 (s, 1H), 7.27-7.23 (m, 2H), 6.61 (s, 1H), 3.81 (s, 2H), 3.54 (m, 4H), 2.43 (m, 4H), 2.29 (s, 3H) MS [M+H]+=544.1 LCMS RT=2.64 min Example 28

Preparation of N-{4-[4-amino-7-(morpholin-4-ylmethyl)pyrrolo[2,1-f][1,2,4]triazin-5-yl]-2-methylphenyl}-N'-[3-fluoro-5-(trifluoromethyl)phenyl]-urea

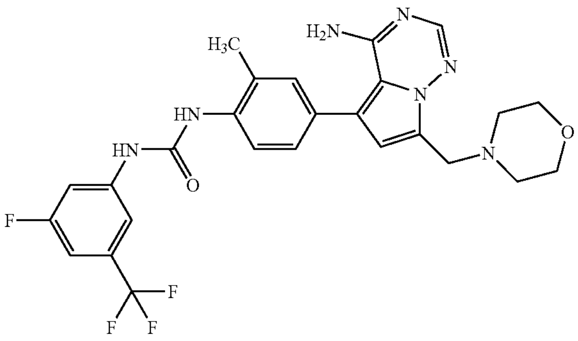

The title compound was prepared using the procedure to make Example 7 by substituting boronate, N-[3-fluoro-5-(trifluoromethyl)phenyl]-N'-[2-methyl-4-(4,4,5,5-tetramethyl-1,3,2-dioxaborolan-2-yl)phenyl]urea for Intermediate R. The boronate, was made using the procedure used to make Intermediate R. $^1$H-NMR (DMSO-$d_6$) δ 9.57 (s, 1H), 8.22 (s, 1H), 7.87 (m, 2H), 7.60 (m, 2H), 7.26 (m, 2H), 6.61 (s, 1H), 3.81 (s, 2H), 3.64 (m, 4H), 2.33 (m, 4H), 2.25 (s, 3H); MS [M+H]+=544.1 LCMS RT=2.70 min Example 29

Preparation of N-{4-[4-amino-7-(morpholin-4-ylmethyl)pyrrolo[2,1-f][1,2,4]triazin-5-yl]-3-methylphenyl}-N'-[2-fluoro-5-(trifluoromethyl)phenyl]urea

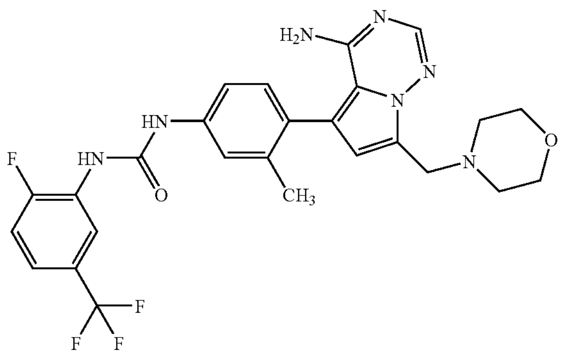

The procedure used for the preparation of Example 4 was used to prepare the title compound by substituting Intermediate L for Intermediate E. $^1$H-NMR (DMSO-$d_6$) δ 9.26 (s, 1H), 8.92 (d, J=3 Hz, 1H), 8.61 (dd, J=8, 3 Hz, 1H), 7.89 (s, 1H), 7.56 to 7.32 (m, 4H), 7.20 (dd, J=8, 3 Hz, 1H), 6.52 (s, 1H), 3.82 (s, 2H), 3.46 (t, J=4 Hz, 4H), 2.44 (t, J=4 Hz, 4H), 2.14 (s, 3H); MS $[M+H]^+$=544.9; LCMS RT=2.49 min.

Example 30

Preparation of N-{4-[4-amino-7-(morpholin-4-ylmethyl)pyrrolo[2,1-f][1,2,4]triazin-5-yl]-2-methoxyphenyl}-N'-(3-tert-butylisoxazol-5-yl)urea

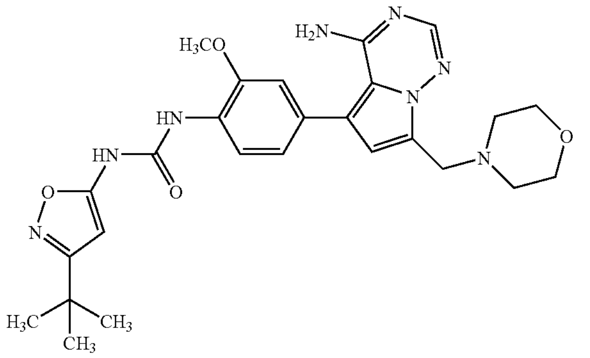

The procedure used for the preparation of Example 2 was used to prepare the title compound by substituting Intermediate K for Intermediate E. $^1$H-NMR($CH_3OH-d_4$) δ 8.20 (d, J=8 Hz, 1H), 7.83 (s, 1H), 7.10 to 7.02 (m, 2H), 6.72 (s, 1H), 6.12 (s, 1H), 3.90 (s, 5H), 3.68 (t, J=5 Hz, 4H), 2.56 (t, J=5 Hz, 4H), 1.30 (s, 9H); MS $[M+H]^+$=520.8; LCMS RT=2.74 min.

Example 31

Preparation of N-{4-[4-amino-7-(morpholin-4-ylmethyl)pyrrolo[2,1-f][1,2,4]triazin-5-yl]-2-methoxyphenyl}-N'-[4-(trifluoromethyl)pyridin-2-yl]urea

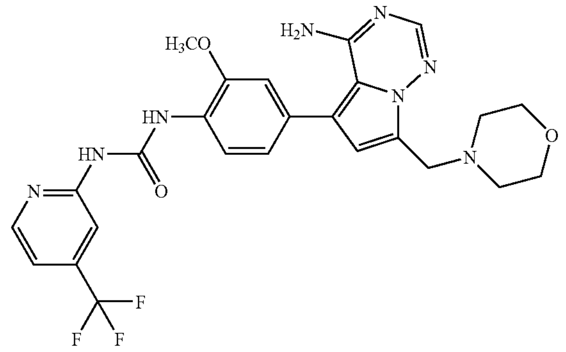

The procedure used for the preparation of Example 2 was used to prepare the title compound by substituting Intermediate K for Intermediate E and substituting phenyl [4-(trifluoromethyl)pyridin-2-yl]carbamate for phenyl(3-tert-butylisoxazol-5-yl)carbamate. NMR (DMSO-$d_6$) δ 10.25 (s, 2H), 8.55 (d, J=5 Hz, 1H), 8.25 (d, J=9 Hz, 1H), 7.88 (d, J=3 Hz, 2H), 7.35 (d, J=3 Hz, 1H), 7.10 (d, J=2 Hz, 1H), 7.00 (dd, J=8, 2 Hz, 1H), 6.67 (s, 1H), 3.94 (s, 3H), 3.81 (s, 2H), 3.54 (m, 4H), 2.42 (m, 4H); MS=543.1; LCMS RT=2.53 min.

Example 32

Preparation of N-{4-[4-amino-7-(morpholin-4-ylmethyl)pyrrolo[2,1-f][1,2,4]triazin-5-yl]-2-methoxyphenyl}-N'-[4-fluoro-3-(trifluoromethyl)phenyl]urea

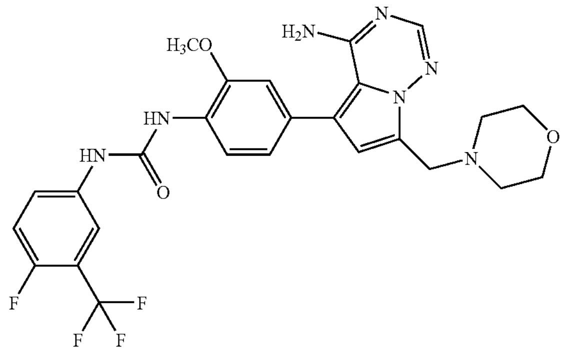

The procedure used for the preparation of Example 2 was used to prepare the title compound by substituting Intermediate K for Intermediate E and by substituting phenyl [4-fluoro-3-(trifluoromethyl)phenyl]carbamate for phenyl (3-tert-butylisoxazol-5-yl)carbamate. $^1$H-NMR (DMSO-$d_6$) δ 9.69 (s, 1H), 8.35 (s, 1H), 8.19 (d, J=8 Hz, 1H), 8.01 (dd, J=8, 2 Hz, 1H), 7.89 (s, 1H), 7.57 to 7.54 (m, 1H), 7.43 (t, J=9 Hz, 1H), 7.08 (d, J=2 Hz, 1H), 7.00 to 6.97 (dd, J=8, 2 Hz, 1H), 6.54 (s, 1H), 3.92 (s, 3H), 3.81 (s, 2H), 3.54 (t, J=4 Hz, 4H), 2.43 (t, J=4 Hz, 4H); MS $[M+H]^+$=560.2; LCMS RT=2.71 min.

Example 33

Preparation of N-{4-[4-amino-7-(morpholin-4-ylmethyl)pyrrolo[2,1-f][1,2,4]triazin-5-yl]-2-methoxyphenyl}-N'-[3-(trifluoromethoxy)phenyl]urea

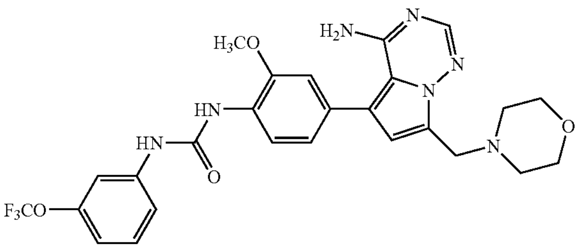

The procedure used for the preparation of Example 2 was used to prepare the title compound by substituting Intermediate K for Intermediate E and by substituting phenyl [4-fluoro-3-(trifluoromethoxy)phenyl]carbamate for phenyl (3-tert-butylisoxazol-5-yl)carbamate. $^1$H-NMR (MeOH-$d_4$) δ 8.18 (d, J=4 Hz, 1H), 7.83 (s, 1H), 7.79 (s, 1H), 7.65 to 7.63 (m, 1H), 7.38 to 7.30 (m, 2H), 7.29 to 7.26 (m, 2H), 7.09 to 7.02 (m, 2H), 6.91 to 6.64 (m, 4H), 3.94 (s, 3H), 3.87 (s, 2H), 3.31 (m, 4H), 2.58 (m, 4H); MS $[M+H]^+$=558.1; LCMS RT=2.77 min.

Example 34

Preparation of N-{4-[4-amino-7-(morpholin-4-ylmethyl)pyrrolo[2,1-f][1,2,4]triazin-5-yl]-2-methoxyphenyl}-N'-[4-chloro-3-(trifluoromethyl)phenyl] urea

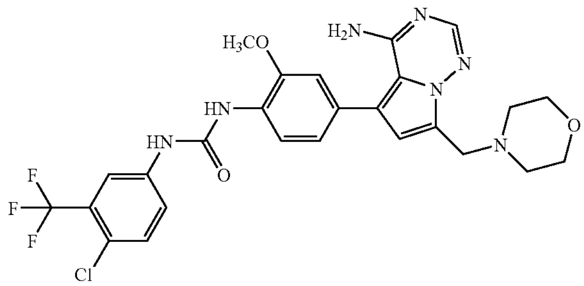

The procedure used for the preparation of Example 2 was used to prepare the title compound by substituting Intermediate K for Intermediate E and by substituting phenyl [4-chloro-3-(trifluoromethyl)phenyl]carbamate for phenyl (3-tert-butylisoxazol-5-yl)carbamate. $^1$H-NMR (MeOH-$d_4$) δ 8.18 (d, J=8 Hz, 1H), 8.02 (d, J=3 Hz, 1H), 7.83 (s, 1H), 7.63 to 7.59 (m, 1H), 7.48 (d, J=8 Hz, 1H), 7.10 (d, J=2 Hz, 1H), 7.02 (dd, J=8, 2 Hz, H), 6.72 (s, 1H), 3.97 (s, 3H), 3.96 (s, 2H), 3.68 (t, J=5 Hz, 4H), 2.58 (t, J=5 Hz, 4H); MS $[M+H]^+$=576.1; LCMS RT=2.81 min.

Example 35

Preparation of N-{4-[4-amino-7-(morpholin-4-ylmethyl)pyrrolo[2,1-f][1,2,4]triazin-5-yl]-2-methoxyphenyl}-N'-[2-chloro-5-(trifluoromethyl)phenyl] urea

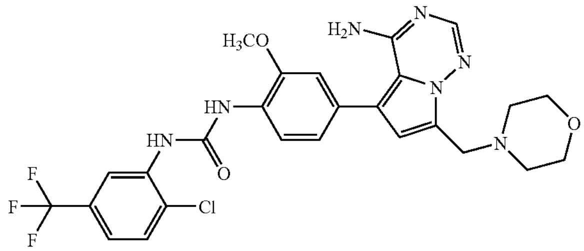

The procedure used for the preparation of Example 4 was used to prepare the title compound by substituting Intermediate K for Intermediate E and by substituting 1-chloro-2-isocyanato-4-(trifluoromethyl)benzene for 2-fluoro-5-(trifluoromethyl)phenyl isocynate. $^1$H-NMR (DMSO-$d_6$) δ 9.28 (d, J=3 Hz, 2H), 8.59 (d, J=3 Hz, 1H), 8.17 (d, J=8 Hz, 1H), 7.89 (s, 1H), 7.70 (dd, J=8, 3 Hz, 1H), 7.37 (dd, J=8, 3 Hz, 1H), 7.10 (d, J=3 Hz, 1H), 7.03 (dd, J=8, 2 Hz, 1H), 6.67 (s, 1H), 3.92 (s, 3H), 3.81 (s, 2H), 3.54 (t, J=4 Hz, 4H), 2.43 (t, J=4 Hz, 4H); MS $[M+H]^+$=576.0; LCMS RT=2.98 min.

Example 36

Preparation of N-{4-[4-amino-7-(morpholin-4-ylmethyl)pyrrolo[2,1-f][1,2,4]triazin-5-yl]-2-methoxyphenyl}-N'-[2-fluoro-5-(trifluoromethyl)phenyl] urea

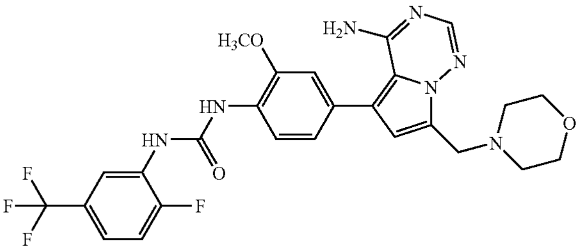

The procedure used for the preparation of Example 4 was used to prepare the title compound by substituting Intermediate K for Intermediate E. $^1$H-NMR (DMSO-$d_6$) δ 9.61 (d, J=3 Hz, 1H), 9.00 (s, 1H), 8.17 (dd, J=8, 2 Hz, 1H), 8.22 (d, J=8 Hz, 1H), 7.89 (s, 1H), 7.51 to 7.45 (m, 1H), 7.39 to 7.34 (m, 1H), 7.09 (d, J=5 Hz, 1H), 7.00 (dd, J=8, 2 Hz, 1H), 6.67 (s, 1H), 3.92 (s, 3H), 3.81 (s, 2H), 3.54 (t, J=4 Hz, 4H), 2.43 (t, J=4 Hz, 4H); MS $[M+H]^+$=559.9; LCMS RT=2.56 min.

Example 37

Preparation of N-{4-[4-amino-7-(morpholin-4-ylmethyl)pyrrolo[2,1-f][1,2,4]triazin-5-yl]-3-methoxyphenyl}-N'-[2-fluoro-5-(trifluoromethyl)phenyl] urea

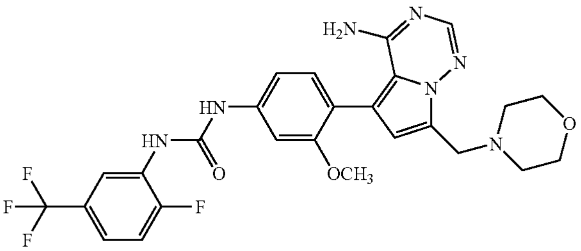

The title compound was prepared using the procedure to make Example 7 by substituting boronate, N-[2-fluoro-5-(trifluoromethyl)phenyl]-N'-[3-methoxy-4-(4,4,5,5-tetramethyl-1,3,2-dioxaborolan-2-yl)phenyl]urea for Intermediate R. The boronate, was made using the procedure used to make Intermediate R. $^1$H-NMR (DMSO-$d_6$) δ 9.35 (s, 1H), 8.93 (m, 1H), 8.62 (dd, J=7.2 Hz, J=1.8 Hz, 1H), 7.54 (s, 1H), 7.49 (m, 1H), 7.40 (s, 1H), 7.18 (d, J=7.8 Hz, 1H), 7.04 (d, J=7.8 Hz, 1H), 7.01 (m, 1H), 6.50 (s, 1H), 3.78 (s, 2H), 3.62 (s, 3H), 3.54 (m, 4H), 2.43 (m, 4H); MS $[M+H]^+$=559.8, 560.9 LCMS RT=2.44 min Example 38

Preparation of N-{4-[4-amino-7-(morpholin-4-ylmethyl)pyrrolo[2,1-f][1,2,4]triazin-5-yl]-3-methoxyphenyl}-N'-[4-(trifluoromethyl)pyridin-2-yl]urea

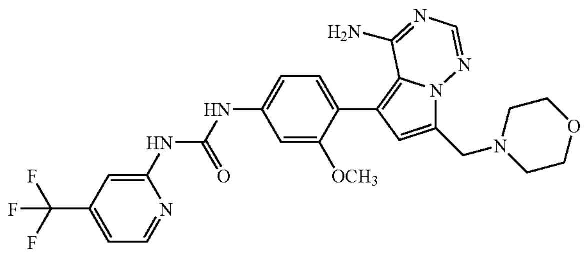

The title compound was prepared using the procedure to make example 7 by substituting boronate, N-[3-methoxy-4-(4,4,5,5-tetramethyl-1,3,2-dioxaborolan-2-yl)phenyl]-N'44-(trifluoromethyl)pyridin-2-yl]urea for Intermediate R. The boronate, was made using the procedure used to make Intermediate R. $^1$H-NMR (DMSO-$d_6$) δ 9.85 (s, 1H), 9.71 (s, 1H), 8.54 (d, J=5.4, 1H), 8.06 (s, 1H), 7.84 (s, 1H), 7.42 (s, 1H), 7.36 (d, J=5.4 Hz, 1H), 7.18 (d, J=5.4 Hz, 1H) 7.09 (m, 1H), 6.50 (s, 1H), 3.79 (s, 2H), 3.72 (s, 3H), 3.50 (m, 4H), 2.41 (m, 4H); MS [M+H]+=543.5 LCMS RT=2.49 min Example 39

Preparation of N-(4-{4-amino-7-[(3-oxopiperazin-1-yl)methyl]pyrrolo[2,1f][1,2,4]triazin-5-yl}phenyl)-N'-[2-fluoro-5-(trifluoromethyl)phenyl]urea

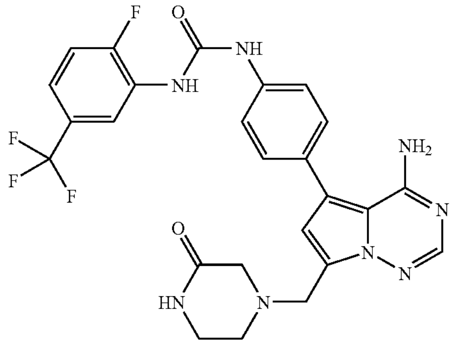

A solution of Intermediate D (70 mg, 0.215 mmol) and Intermediate M (100 mg, 0.237 mmol) in 1,4-dioxane (2.0 ml) was degassed 3 times by pulling a vacuum and then releasing to a nitrogen stream. Aqueous $Na_2CO_3$ (0.646 ml, 1 M, 0.646 mmol) was added and the mixture was degassed again. Tetrakis(triphenylphosphine)palladium (0) (25 mg, 0.022 mmol) was added and the mixture was again degassed followed by addition of another 1 ml of 1,4-dioxane to rinse down solids from the sidewalls of the reaction vial. This vial was sealed under nitrogen with a septa cap and heated with stirring at 80° C. for 13.5 hours. The resultant mixture was diluted with EtOAc, washed with saturated aqueous NaHCO3 and with brine, dried (Na2SO4) and evaporated in vacuo. The residue was chromatographed on 12 g of silica gel using a gradient from 0-10% MeOH in $CH_2Cl_2$ to give pure title Example 40

Preparation of N-(4-{4-amino-7-[(3-oxopiperazin-1-yl)methyl]pyrrolo[2,1f][1,2,4]triazin-5-yl}-2-fluorophenyl)-N'-[2-fluoro-5-(trifluoromethyl)phenyl]urea

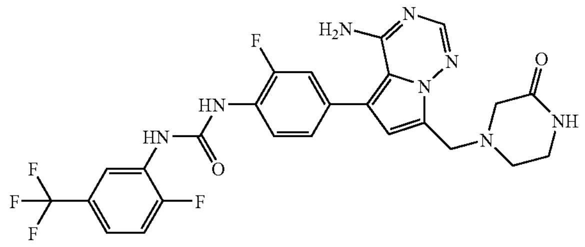

The procedure used for the preparation of Example 39 was used to prepare the title compound by substituting Intermediate O for Intermediate M. $^1$H-NMR (DMSO-$d_6$) δ 9.40 (d, J=3 Hz, 1H), 9.24 (d, J=3 Hz, 1H), 8.64 (dd, J=7, 3 Hz, 1H), 8.25 (t, J=7 Hz, 1H), 7.91 (s, 1H), 7.52 (t, J=7 Hz, 1H), 7.46 to 7.32 (m, 2H), 7.25 (dd, J=8, 3 Hz, 1H), 6.70 (s, 1H), 3.90 (s, 2H), 3.11 (m, 4H), 2.98 (s, 2H), J=5 Hz, 2H); MS $[M+H]^+$=560.8; LCMS RT=2.51 min.

Example 41

Preparation of N-(4-{4-amino-7-[(3-oxopiperazin-1-yl)methyl]pyrrolo[2,1-f][1,2,4]triazin-5-yl}phenyl)-N'-[4-(trifluoromethyl)pyridin-2-yl]urea

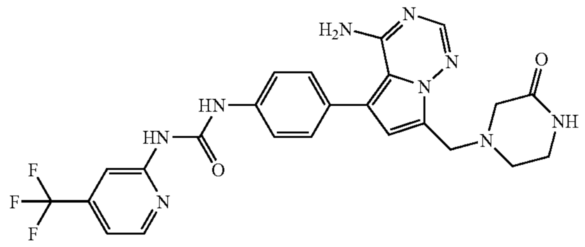

The title compound was prepared using the procedure to make Example 39 by substituting boronate, Intermediate AD for Intermediate M. $^1$H-NMR (DMSO-$d_6$) δ 9.89 (s, 1H), 9.76 (s, 1H), 8.53 (d, J=5.1 Hz, 1H), 8.06 (S, 1H), 7.90 (s, 1H), 7.71 (bs, 1H), 7.61 (d, J=6.9 Hz, 2H), 7.42 (d, J=6.9 Hz, 2H), 7.36

(m, 1H), 6.67 (s, 1H), 3.91 (s, 2H), 3.27 (m, 2H), 3.11 (s, 2H), 2.62 (m, 2H); MS [M+H]+=526.0 LCMS RT=2.37 min Example 42

Preparation of N-{4-[4-amino-7-(morpholin-4-ylmethyl)pyrrolo[2,1-f][1,2,4]triazin-5-yl]-2,5-difluorophenyl}-N'-[2-fluoro-3-(trifluoromethyl)phenyl]urea

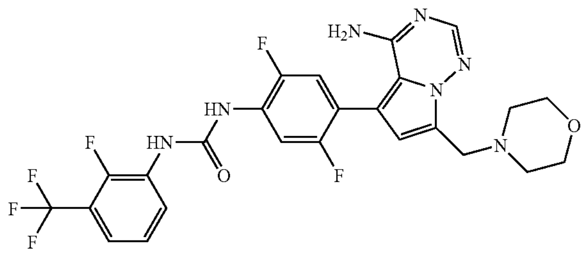

The title compound was prepared using the procedure to make Example 7 by substituting Intermediate AX for Intermediate R. $^1$H-NMR (DMSO-$d_6$) δ 9.39 (m, 1H), 8.26 (m, 1H), 8.10 (m, 1H), 7.90 (s, 1H), 7.37 (m, 2H), 7.07 (m, 1H), 6.62 (m, 2H); MS [M+H]+=566.8 LCMS RT=2.63 min.

Example 43

Preparation of N-{4-[4-amino-7-(morpholin-4-ylmethyl)-pyrrolo[2,1-f][1,2,4]triazin-5-yl]-2-methoxyphenyl}-N'-[6-(trifluoromethyl)pyridin-2-yl]urea

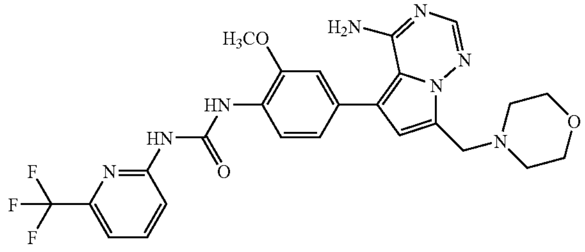

The procedure used for the preparation of Example 2 was used to prepare the title compound by substituting Intermediate K for Intermediate E and substituting phenyl [6-(trifluoromethyl)pyridin-2-yl]carbamate for phenyl (3-tert-butylisoxazol-5-yl)carbamate. $^1$H-NMR (DMSO-$d_6$) δ 10.33 (s, 1H), 10.09 (br, 1H), 8.25 (d, J=8 Hz, 1H), 8.03 (m, 1H), 7.89 (s, 1H), 7.73 (d, J=8 Hz, 1H), 7.48 (d, J=7 Hz, 1H), 7.10 (d, J=2 Hz, 1H), 7.00 (dd, J=8, 2 Hz, 1H), 6.67 (s, 1H), 3.90 (s, 3H), 3.81 (s, 2H), 3.54 (m, 4H), 2.42 (m, 4H); MS $[M+H]^+$=543.0; LCMS RT=2.53 min.

Example 44

Preparation of N-{4-[4-amino-7-(morpholin-4-ylmethyl)pyrrolo[2,1-f][1,2,4]triazin-5-yl]phenyl}-N'-(5-tert-butyl-2-methoxyphenyl)urea

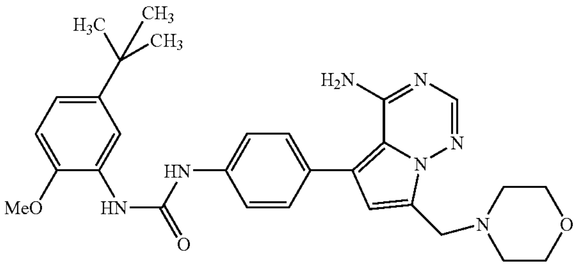

The procedure used for the preparation of Example 4 was used to prepare the title compound by substituting 5-tert-butyl-2-methoxyphenyl isocyanate for 2-fluoro-5-trifluoromethylphenyl isocyanate. $^1$H-NMR (DMSO-$d_6$) δ 9.40 (s, 1H), 8.29 (s, 1H), 8.20 (s, 1H), 7.86 (s, 1H), 7.59 (d, J=8.8 Hz, 2H), 7.38 (d, J=8.8 Hz, 2H), 6.82-6.95 (m, 2H), 6.60 (s, 1H), 3.85 (s, 3H), 3.82 (s, 2H), 3.48-3.60 (m, 4H), 2.38-2.2.5 (m, 4H), 1.28 (s, 9H); MS $[M+H]^+$=530; LCMS RT=2.57.

Example 45

Preparation of N-{4-[4-amino-7-(morpholin-4-ylmethyl)pyrrolo[2,1-f][1,2,4]triazin-5-yl]phenyl}-N'-(2,5-dimethylphenyl)urea

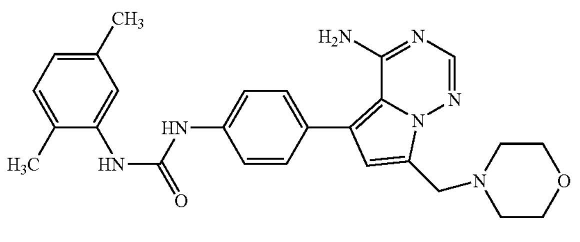

The procedure used for the preparation of Example 4 was used to prepare the title compound by substituting 2,5-dimethylphenyl isocyanate for 2-fluoro-5-trifluoromethylphenyl isocyanate. $^1$H-NMR (DMSO-$d_6$) δ 9.17 (s, 1H), 7.92 (s, 1H), 7.88 (s, 1H), 7.66 (s, 1H), 7.55 (d, J=8.8 Hz, 2H), 7.35 (d, J=8.8 Hz, 2H), 7.03 (d, J=8.0 Hz, 1H), 6.75 (d, J=8.0 Hz, 1H), 6.61 (s, 1H), 3.82 (s, 2H), 3.56-3.54 (m, 4H), 2.49-2.44 (m, 4H), 2.25 (s, 3H), 2.20 (s, 3H); MS $[M+H]^+$=472.2; LCMS RT=2.29.

Example 46

Preparation of N-{4-[4-amino-7-(morpholin-4-ylmethyl)pyrrolo[2,1-f][1,2,4]triazin-5-yl]phenyl}-N'-(2-fluoro-5-methylphenyl)urea

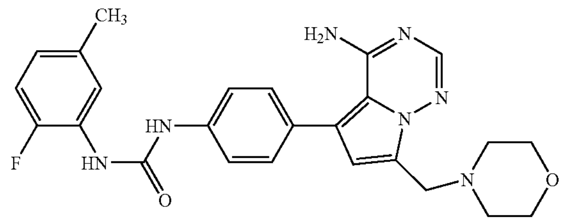

The procedure used for the preparation of Example 4 was used to prepare the title compound by substituting 2-fluoro-5-methylphenyl isocyanate for 2-fluoro-5-trifluoromethylphenyl isocyanate. $^1$H-NMR (DMSO-$d_6$) δ 9.17 (s, 1H), 8.50 (d, J=2.4, 1H), 7.97 (dd, J=8.4, 2.8 Hz, 1H), 7.88 (s, 1H), 7.54 (d, J=8.8 Hz, 2H), 7.37 (d, J=8.8 Hz, 2H), 7.09 (dd, J=11.6, 8.0 Hz, 1H), 6.82-6.75 (m, 1H), 6.61 (s, 1H), 3.82 (s, 2H), 3.55 (t, J=4.4 Hz, 4H), 2.48 (t, J=4.4 Hz, 4H), 2.72 (s, 3H); MS $[M+H]^+$=476; LCMS RT=2.22.

Example 47

Preparation of N-{4-[4-amino-7-(morpholin-4-ylmethyl)pyrrolo[2,1-f][1,2,4]triazin-5-yl]phenyl}-N'-(5-methylpyridin-2-yl)urea

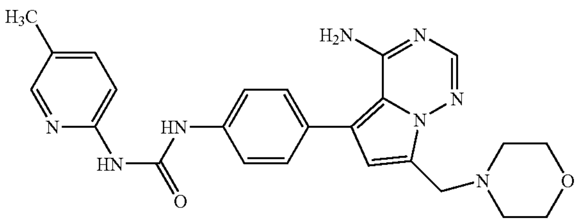

The procedure used for the preparation of Example 4 was used to prepare the title compound by substituting phenyl (5-methylpyridin-2-yl)carbamate for 2-fluoro-5-trifluoromethylphenyl isocyanate. $^1$H-NMR (DMSO-$d_6$) δ 10.60 (s, 1H), 9.38 (s, 1H), 8.10 (s, 1H), 7.88 (s, 1H), 7.62-7.55 (m, 3H), 7.40-7.37 (m, 3H), 6.62 (s, 1H), 3.82 (s, 2H), 3.55 (t, J=4.4 Hz, 4H), 2.45 (t, J=4.4 Hz, 4H), 2.23 (s, 3H); MS $[M+H]^+$=459; LCMS RT=1.77.

Example 48

Preparation of N-{4-[4-amino-7-(morpholin-4-ylmethyl)pyrrolo[2,1-f][1,2,4]triazin-5-yl]phenyl}-Ns-(3-methylphenyl)urea hydrochloride

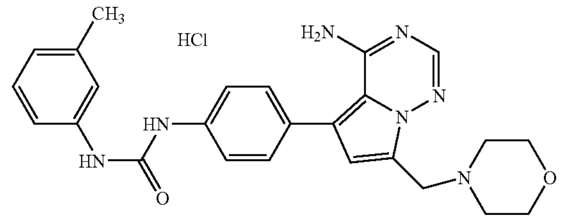

The procedure used for the preparation of Example 4 was used to prepare the title compound by substituting 3-methylphenyl isocyanate for 2-fluoro-5-trifluoromethylphenyl isocyanate. $^1$H-NMR (DMSO-$d_6$) δ 8.78 (s, 1H), 8.63 (s, 1H), 7.89 (s, 1H), 7.55 (d, J=8.8 Hz, 2H), 7.36 (d, J=8.8 Hz, 2H), 7.3 (s, 1H), 7.23 (d, J=7.6 Hz, 1H), 7.15 (t, J=7.6 Hz, 1H), 6.78 (t, J=6.8 Hz, 1H) 6.61 (s, 1H), 3.82 (s, 2H), 3.55 (t, J=4.4 Hz, 4H), 2.45 (t, J=4.4 Hz, 4H), 2.27 (s, 3H); MS $[M+H]^+$=458; LCMS RT=1.70.

Example 49

Preparation of N-{4-[4-amino-7-(morpholin-4-ylmethyl)pyrrolo[2,1-f][1,2,4]triazin-5-yl]phenyl}-N'-(2-tert-butylphenyl)urea

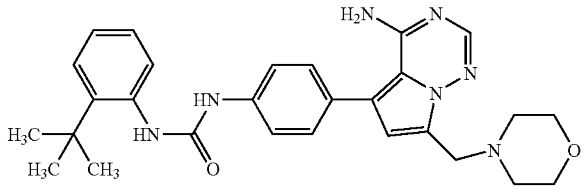

The procedure used for the preparation of Example 4 was used to prepare the title compound by substituting 2-tert-butylphenyl isocyanate for 2-fluoro-5-trifluoromethylphenyl isocyanate. $^1$H-NMR (DMSO-$d_6$) δ 9.32 (s, 1H), 7.89 (s, 1H), 7.78 (s, 1H), 7.57 (d, J=6.8 Hz, 2H), 7.38-7.34 (m, 3H), 7.27 (dd, J=7.6, 1.6 Hz, 1H), 7.22-7.14 (m, 2H), 6.61 (s, 1H), 3.82

(s, 2H), 3.55 (t, J=4.4 Hz, 4H), 2.45 (t, J=4.4 Hz, 4H), 1.38 (s, 9H); MS $[M+H]^+$=500.3; LCMS RT=2.34.

Example 50

Preparation of N-{4-[4-amino-7-(morpholin-4-ylmethyl)pyrrolo[2,1-f][1,2,4]triazin-5-yl]phenyl}-N'-(3-ethylphenyl)urea

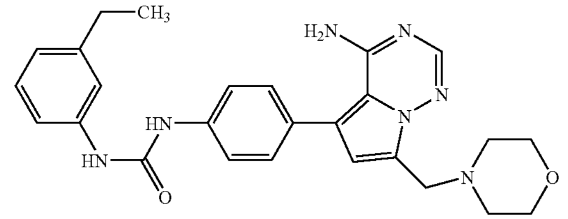

The procedure used for the preparation of Example 4 was used to prepare the title compound by substituting 3-ethylphenyl isocyanate for 2-fluoro-5-trifluoromethylphenyl isocyanate. $^1$H-NMR (DMSO-$d_6$) δ 8.88 (s, 1H), 8.74 (s, 1H), 7.90 (s, 1H), 7.56 (d, J=7.6 Hz, 2H), 7.37 (d, J=7.6 Hz, 2H), 7.33 (s, 1H), 7.26 (d, J=8.0 Hz, 1H), 7.18 (t, J=7.6 Hz, 1H), 6.82 (d, J=7.6 Hz, 1H), 6.62 (s, 1H) 3.82 (s, 2H), 3.55 (t, J=4.4 Hz, 4H), 2.56 (q, J=7.6 Hz, 2H), 2.45 (t, J=4.4 Hz, 4H), 1.17 (t, J=7.6 Hz, 3H); MS $[M+H]^+$=472.2; LCMS RT=2.33.

Example 51

Preparation of N-{4-[4-amino-7-(morpholin-4-ylmethyl)pyrrolo[2,1-f][1,2,4]triazin-5-yl]phenyl}-N'-[3-fluoro-5-(trifluoromethyl)phenyl]urea

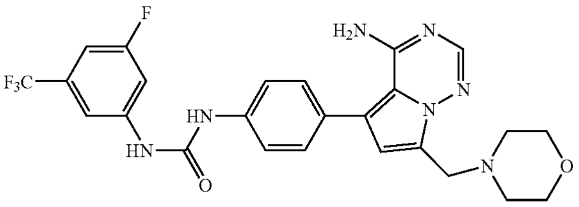

The procedure used for the preparation of Example 4 was used to prepare the title compound by substituting 3-fluoro-5-(trifluoromethyl)phenyl isocyanate for 2-fluoro-5-trifluoromethylphenyl isocyanate. $^1$H-NMR (DMSO-$d_6$) δ 9.39 (s, 1H), 9.22 (s, 1H), 7.90 (s, 1H), 7.72 (s, 1H), 7.63 (d, J=10.4 Hz, 1H), 7.58 (d, J=8.4 Hz, 2H), 7.40 (d, J=8.4 Hz, 2H), 7.23 (d, J=10.4 Hz, 1H), 6.63 (s, 1H), 3.82 (s, 2H), 3.55 (t, J=4.4 Hz, 4H), 2.45 (t, J=4.4 Hz, 4H); MS $[M+H]^+$=529.9; LCMS RT=2.64.

Example 52

Preparation of N-{4-[4-amino-7-(morpholin-4-ylmethyl)pyrrolo[2,1-f][1,2,4]triazin-5-yl]phenyl}-N'-[2-chloro-5-(trifluoromethyl)phenyl]urea

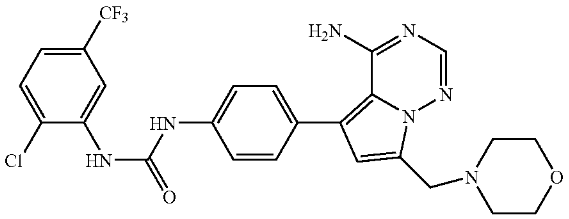

The procedure used for the preparation of Example 4 was used to prepare the title compound by substituting 2-chloro-5-(trifluoromethyl)phenyl isocyanate for 2-fluoro-5-trifluoromethylphenyl isocyanate. $^1$H-NMR (DMSO-$d_6$) δ 9.74 (s, 1H), 8.69 (s, 1H), 8.65 (s, 1H), 7.90 (s, 1H), 7.73 (d, J=8.0 Hz, 1H), 7.59 (d, J=8.4 Hz, 2H), 7.41 (d, J=8.4 Hz, 2H), 7.38 (s, 1H), 6.63 (s, 1H), 3.82 (s, 2H), 3.55 (t, J=4.4 Hz, 4H), 2.45 (t, J=4.4 Hz, 4H); MS $[M+H]^+$=546; LCMS RT=2.98.

Example 53

Preparation of N-{4-[4-amino-7-(morpholin-4-ylmethyl)pyrrolo[2,1-f][1,2,4]triazin-5-yl]phenyl}-N'-(4-tert-butylpyridin-2-yl)urea

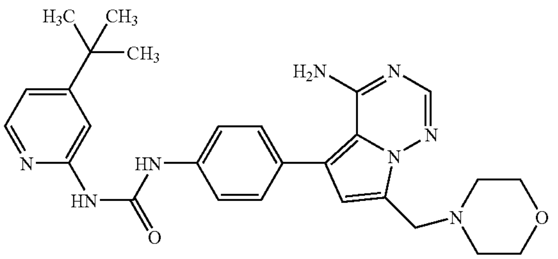

The procedure used for the preparation of Example 4 was used to prepare the title compound by substituting phenyl 4-tert-butylpyridin-2-yl carbamate for 2-fluoro-5-trifluoromethylphenyl isocyanate. $^1$H-NMR (DMSO-$d_6$) δ 10.89 (s, 1H), 9.45 (s, 1H), 8.20 (d, J=5.2 Hz, 1H), 7.90 (s, 1H), 7.64 (d, J=8.8 Hz, 2H), 7.49 (s, 1H), 7.40 (d, J=8.8 Hz, 2H), 7.07 (d, J=5.6 Hz, 1H) 6.63 (s, 1H), 3.82 (s, 2H), 3.55 (t, J=4.4 Hz, 4H), 2.45 (t, J=4.4 Hz, 4H), 1.26 (s, 9H); MS $[M+H]^+$=501.1; LCMS RT=2.65.

Example 54

Preparation of N-{4-[4-amino-7-(morpholin-4-ylmethyl)pyrrolo[2,1-f][1,2,4]triazin-5-yl]phenyl}-N'-[4-chloro-3-(trifluoromethyl)phenyl]urea

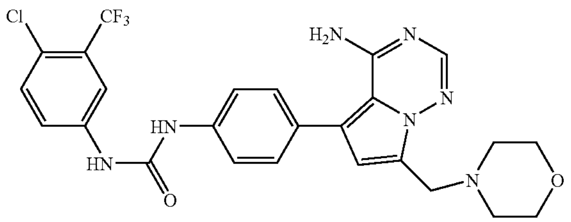

The procedure used for the preparation of Example 4 was used to prepare the title compound by substituting 4-chloro-3-(trifluoromethyl)phenyl isocyanate for 2-fluoro-5-trifluoromethylphenyl isocyanate. $^1$H-NMR (DMSO-$d_6$) δ 9.25 (s, 1H), 9.02 (s, 1H), 8.12 (d, J=2.0 Hz, 1H), 7.90 (s, 1H), 7.64-7.58 (m, 2H), 7.57 (d, J=7.6 Hz, 2H), 7.39 (d, J=7.6 Hz, 2H), 6.63 (s, 1H), 3.82 (s, 2H), 3.55 (t, J=4.4 Hz, 4H), 2.45 (t, J=4.4 Hz, 4H); MS $[M+H]^+$=546.1; LCMS RT=3.00.

Example 55

Preparation of N-{4-[4-amino-7-(morpholin-4-ylmethyl)pyrrolo[2,1-f][1,2,4]-triazin-5-yl]phenyl}-N'-(5-fluoropyridin-2-yl)urea

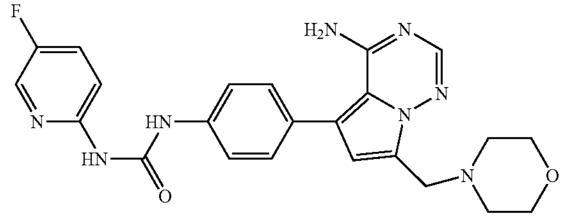

The procedure used for the preparation of Example 4 was used to prepare the title compound by substituting phenyl 5-fluoropyridin-2-yl carbamate for 2-fluoro-5-trifluoromethylphenyl isocyanate. $^1$H-NMR (DMSO-$d_6$) δ 9.95 (s, 1H), 9.44 (s, 1H), 8.38 (s, 1H), 7.90 (s, 1H), 7.75-7.70 (m, 2H), 7.60 (d, J=8.4 Hz, 2H), 7.40 (d, J=8.4 Hz, 2H), 6.63 (s, 1H), 3.82 (s, 2H), 3.55 (t, J=4.4 Hz, 4H), 2.45 (t, J=4.4 Hz, 4H); MS $[M+H]^+$=463; LCMS RT=2.17.

Example 56

Preparation of N-{4-[4-amino-7-(morpholin-4-ylmethyl)pyrrolo[2,1-f][1,2,4]-triazin-5-yl]phenyl}-N'-[5-(trifluoromethyl)pyridin-2-yl]urea

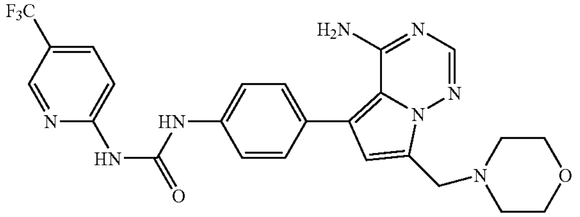

The procedure used for the preparation of Example 4 was used to prepare the title compound by substituting phenyl 5-(trifluoromethyl)pyridin-2-yl carbamate for 2-fluoro-5-trifluoromethylphenyl isocyanate. $^1$H-NMR (DMSO-$d_6$) δ 10.14 (s, 1H), 9.87 (s, 1H), 8.67 (s, 1H), 8.14 (dd, J=8.8, 3.2 Hz, 1H), 7.90 (s, 1H), 7.83 (d, J=9.2 Hz, 1H), 7.63 (d, J=8.8 Hz, 2H), 7.42 (d, J=8.8 Hz, 2H), 6.63 (s, 1H), 3.82 (s, 2H), 3.55 (t, J=4.4 Hz, 4H), 2.45 (t, J=4.4 Hz, 4H);MS $[M+H]^+$=513; LCMS RT=2.46.

Example 57

Preparation of N-{4-[4-amino-7-(morpholin-4-ylmethyl)pyrrolo[2,1-f][1,2,4]-triazin-5-yl]phenyl}-N'-(6-methylpyridin-2-yl)urea

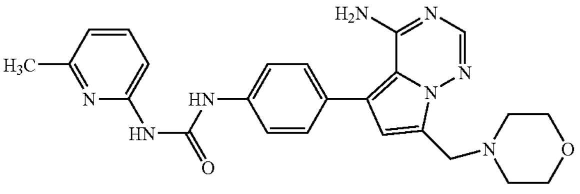

The procedure used for the preparation of Example 4 was used to prepare the title compound by substituting phenyl 6-methylpyridin-2-yl carbamate for 2-fluoro-5-trifluoromethylphenyl isocyanate. $^1$H-NMR (DMSO-$d_6$) δ 9.55 (s, 1H), 7.91 (s, 1H), 7.66-7.62 (m, 3H), 7.63 (d, J=8.4 Hz, 2H), 7.20 (d, J=8.0 Hz, 1H), 6.88 (d, J=8.0 Hz, 2H),), 6.63 (s, 1H), 3.82

(s, 2H), 3.55 (t, J=4.4 Hz, 4H), 2.46 (s, 3H), 2.45 (t, J=4.4 Hz, 41-1); MS $[M+H]^+$=459; LCMS RT=0.72.

Example 58

Preparation of N-{4-[4-amino-7-(morpholin-4-ylmethyl)pyrrolo[2,1-f][1,2,4]-triazin-5-yl]phenyl}-N'-[2-fluoro-3-(trifluoromethyl)phenyl]urea

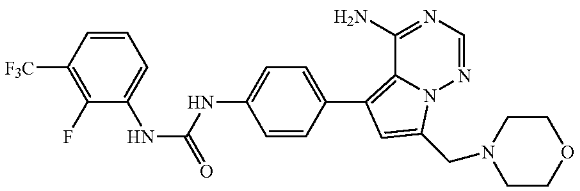

The procedure used for the preparation of Example 4 was used to prepare the title compound by substituting 2-fluoro-3-(trifluoromethyl)phenyl isocyanate for 2-fluoro-5-trifluoromethylphenyl isocyanate. $^1$H-NMR (DMSO-$d_6$) δ 11.70 (s, 1H), 9.55 (s, 1H), 9.07 (s, 1H), 8.51-8.42 (m, 1H), 7.89 (s, 1H), 7.58 (d, J=8.8 Hz, 2H), 7.40-7.35 (m, 3H), 6.62 (s, 1H), 3.82 (s, 2H), 3.55 (t, J=4.4 Hz, 4H), 2.45 (t, J=4.4 Hz, 4H); MS $[M+H]^+$=529.9; LCMS RT=2.97.

Example 59

Preparation of N-(3-acetylphenyl)-N'-{4-[4-amino-7-(morpholin-4-ylmethyl)pyrrolo[2,1-f][1,2,4]triazin-5-yl]phenyl}urea

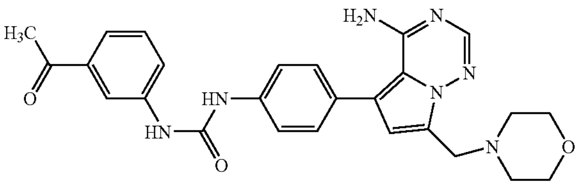

The procedure used for the preparation of Example 4 was used to prepare the title compound by substituting 3-acetylphenyl isocyanate for 2-fluoro-5-trifluoromethylphenyl isocyanate. $^1$H-NMR (DMSO-$d_6$) δ 9.13 (s, 1H), 9.06 (s, 1H), 8.11 (t, J=2.0 Hz, 1H), 8.06 (s, 1H), 7.66-7.58 (m, 4H), 7.44 (d, J=7.6 Hz, 2H), 7.42 to 7.38 (m, 1H), 6.92 (s, 1H), 4.72 (s, 2H), 4.02-3.94 (m, 2H), 3.68-3.59 (m, 2H), 3.42-3.35 (m, 2H), 3.38-3.15 (m, 2H), 2.56 (s, 3H); MS $[M+H]^+$=486; LCMS RT=0.63.

Example 60

Preparation of N-{4-[4-amino-7-(morpholin-4-ylmethyl)pyrrolo[2,1-f][1,2,4]-triazin-5-yl]phenyl}-N'-(3,4-dimethylphenyl)urea

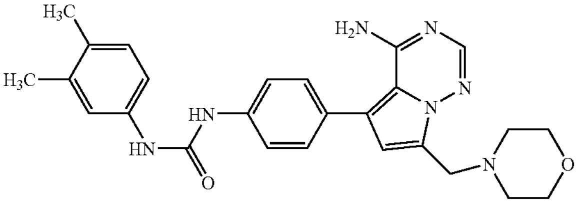

The procedure used for the preparation of Example 4 was used to prepare the title compound by substituting 3,4-dimethylphenyl isocyanate for 2-fluoro-5-trifluoromethylphenyl isocyanate. $^1$H-NMR (DMSO-$d_6$) δ 8.84 (s, 1H), 8.60 (s, 1H), 8.05 (s, 1H), 7.58 (d, J=6.8 Hz, 2H), 7.37 (d, J=6.8 Hz, 2H), 7.23 (s, 1H), 7.17 (d, J=8.4 Hz, 1H), 7.02 (d, J=8.4 Hz, 1H), 6.91 (s, 1H), 4.71 (s, 2H), 4.02-3.94 (m, 2H), 3.68-3.59 (m, 2H), 3.42-3.35 (m, 2H), 3.38-3.15 (m, 2H), 2.18 (s, 3H), 2.14 (s, 3H); MS $[M+H]^+$=472.1; LCMS RT=2.53.

Example 61

Preparation of N-{4-[4-amino-7-(morpholin-4-ylmethyl)pyrrolo[2,1-f][1,2,4]-triazin-5-yl]phenyl}-N'-(3,5-dimethylphenyl)urea

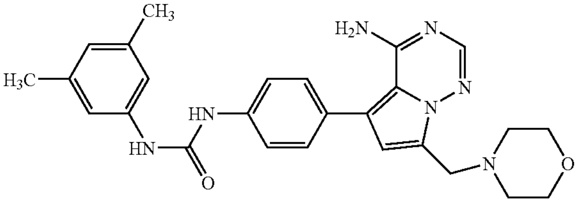

The procedure used for the preparation of Example 4 was used to prepare the title compound by substituting 3,5-dimethylphenyl isocyanate for 2-fluoro-5-trifluoromethylphenyl isocyanate. $^1$H-NMR (DMSO-$d_6$) δ 9.01 (s, 1H), 8.76 (s, 1H), 8.06 (s, 1H), 7.59 (d, J=9.2 Hz, 2H), 7.37 (d, J=9.2 Hz, 2H), 7.08 (s, 2H), 6.92 (s, 1H), 6.61 (s, 1H), 4.72 (s, 2H), 4.08-3.15 (m, 8H), 2.22 (s, 6H); MS $[M+H]^+$=472.1; LCMS RT=2.64.

Example 62

Preparation of N-{4-[4-amino-7-(morpholin-4-ylmethyl)pyrrolo[2,1-f][1,2,4]-triazin-5-yl]phenyl}-N'-(3-chloro-4-methylphenyl)urea

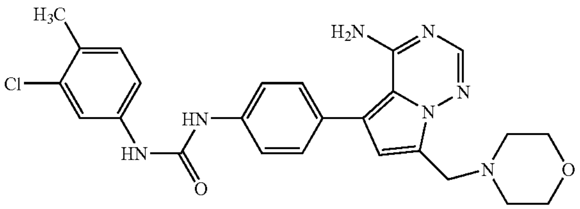

The procedure used for the preparation of Example 4 was used to prepare the title compound by substituting 3-chloro-4-methylphenyl isocyanate for 2-fluoro-5-trifluoromethylphenyl isocyanate. $^{1}$H-NMR (DMSO-$d_6$) δ 8.99 (s, 1H), 8.94 (s, 1H), 8.05 (s, 1H), 7.71 (d, J=2.4 Hz, 1H), 7.59 (d, J=8.4 Hz, 2H), 7.38 (d, J=8.4 Hz, 2H), 7.24 (d, J=8.8 Hz, 1H), 7.19 (dd, J=8.4, 2.4 Hz, 1H), 6.92 (s, 1H), 4.71 (s, 2H), 4.08-3.15 (m, 8H), 2.25 (s, 3H); MS $[M+H]^+$=492.1; LCMS RT=2.85.

Example 63

Preparation of N-{4-[4-amino-7-(morpholin-4-ylmethyl)pyrrolo[2,1-f][1,2,4]triazin-5-yl]phenyl}-N'-(5-chloropyridin-2-yl)urea

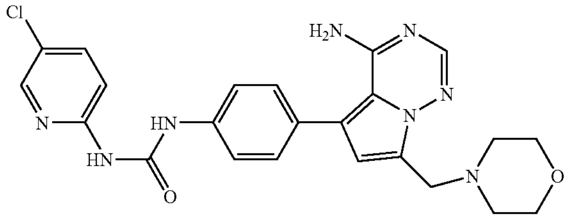

The procedure used for the preparation of Example 4 was used to prepare the title compound by substituting phenyl 5-chloropyridin-2-yl carbamate for 2-fluoro-5-trifluoromethylphenyl isocyanate. $^{1}$H-NMR (DMSO-$d_6$) δ 9.93 (s, 1H), 9.51 (s, 1H), 8.31 (d, J=2.8 Hz, 1H), 7.88 (s, 1H), 7.60 (dd, J=9.2, 2.8 Hz, 1H), 7.69 (d, J=8.8 Hz, 1H), 7.59 (d, J=8.4 Hz, 2H), 7.39 (d, J=8.4 Hz, 2H), 6.62 (s, 1H), 3.82 (s, 2H), 3.55 (t, J=4.4 Hz, 4H), 2.45 (t, J=4.4 Hz, 4H); MS $[M+H]^+$=478.9; LCMS RT=2.27.

Example 64

N-4-[4-amino-7-(morpholin-4-ylmethyl)pyrrolo[2,1-f][1,2,4]triazin-5-yl]-2-fluorophenyl-M-(3-methylphenyl)urea

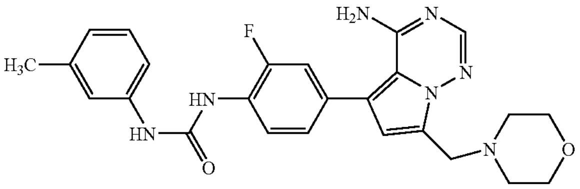

The procedure used for the preparation of Example 4 was used to prepare the title compound by substituting Intermediate E for Intermediate F and by substituting 3-methylphenyl isocyanate for 2-fluoro-5-trifluoromethylphenyl isocyanate. $^{1}$H-NMR (DMSO-$d_6$) δ 9.09 (s, 1H), 8.72 (d, J=2.8 Hz, 1H), 8.32 (t, J=8.4 Hz, 1H), 8.09 (s, 1H), 7.35 (dd, J=11.6, 2 Hz, 1H); 7.32 (d, J=2.8 Hz, 1H), 7.26 (m, 2H) 7.19 (t, J=8.4 Hz, 1H), 6.97 (s, 1H), 6.83 (m 1H), 4.73 (s, 2H), 3.97 (m, 2H), 3.64 (m, 2H), 3.38 (m, 2H), 3.22 (m, 2H), 2.30 (s, 3H); MS $[M+H]^+$=476.1; LCMS RT=2.35.

Example 65

N-4-[4-amino-7-(morpholin-4-ylmethyl)pyrrolo[2,1-f][1,2,4]triazin-5-yl]-2-fluorophenyl-N'-[2-chloro-5-(trifluoromethyl)phenyl]urea

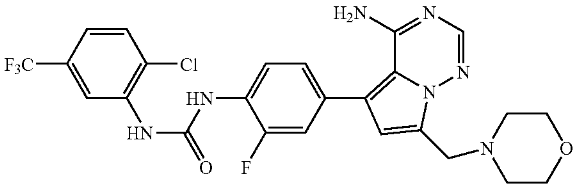

The procedure used for the preparation of Example 4 was used to prepare the title compound by substituting Intermediate E for Intermediate F and by substituting 2-chloro-5-(trifluoromethyl)phenyl isocyanate for 2-fluoro-5-trifluoromethylphenyl isocyanate. $^{1}$H-NMR (DMSO-$d_6$) δ 9.64 (d, J=2.4 Hz, 1H), 9.15 (s, 1H), 8.66 (d, J=2 Hz, 1H), 8.28 (t, J=8.8 Hz, 1H), 7.93 (s, 1H), 7.74 (d, J=8 Hz, 1H), 7.40 (dd, J=8.4, 2.0 Hz, 1H), 7.37 (dd, J=12.4, 2.0 Hz, 1H), 7.26 (dd, J=8.4, 1H), 3.83 (s, 2H), 3.56 (m, 4H), 2.46 (m, 4H); MS $[M+H]^+$=564.0; LCMS RT=2.70.

Example 66

N-4-[4-amino-7-(morpholin-4-ylmethyl)pyrrolo[2,1-f][1,2,4]triazin-5-yl]-2-fluorophenyl-N'-(3-chlorophenyl)urea

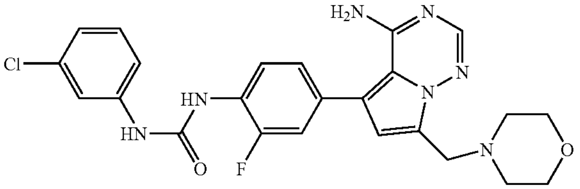

The procedure used for the preparation of Example 4 was used to prepare the title compound by substituting Intermediate E for Intermediate F and by substituting 3-chloro-phenyl isocyanate for 2-fluoro-5-trifluoromethylphenyl isocyanate. $^{1}$H-NMR (DMSO-$d_6$) δ 9.45 (s, 1H), 8.85 (s, 1H), 8.23 (t, J=8.4 Hz, 1H), 7.96 (s, 1H), 7.78 (t, J=2 Hz, 1H), 7.38-7.25 (m, 3H), 7.07 (m, 1H), 3.90 (s, 2H), 3.45 (m, 4H), 2.45 (m, 4H); MS $[M+H]^+$=495.9; LCMS RT=2.39.

Example 67

N-4-4-amino-7-(morpholin-4-ylmethyl)pyrrolo[2,1-f][1,2,4]triazin-5-yl]-2-fluorophenyl-N'-(3-bromophenyl)urea

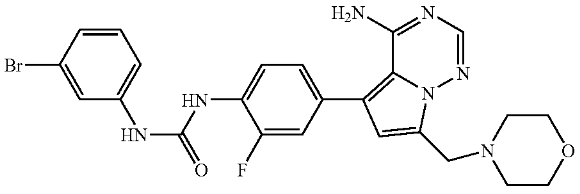

The procedure used for the preparation of Example 4 was used to prepare the title compound by substituting Intermediate E for Intermediate F and by substituting 3-bromo-phenyl isocyanate for 2-fluoro-5-trifluoromethylphenyl isocyanate. $^{1}$H-NMR (DMSO-$d_6$) δ 9.40 (s, 1H), 8.85 (d, J=2.4 Hz, 1H), 8.27 (t, J=8.8 Hz, 1H), 8.10 (s, 1H), 7.92 (m, 1H), 7.36 (dd, J=12.0, 2.0 Hz, 1H), 7.32-7.25 (m, 3H), 7.19 (dt, J=7.2, 2.0 Hz, 1H), 6.98 (s, 1H), 4.73 (s, 2H), 3.95 (m, 2H), 3.67 (m, 2H), 3.38 (m, 2H), 3.22 (m, 2H); MS $[M+H]^+$=453.2; LCMS RT=2.50.

Example 68

Preparation of N-{4-[4-amino-7-(morpholin-4-ylmethyl)pyrrolo[2,1-f][1,2,4]triazin-5-yl]phenyl}-N'-[6-(trifluoromethyl)pyridin-2-yl]urea

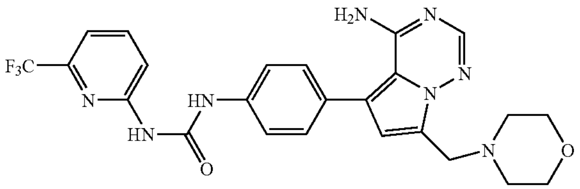

The procedure used for the preparation of Example 4 was used to prepare the title compound by substituting phenyl (6-trifluoromethyl)pyridin-2-yl carbamate for 2-fluoro-5-trifluoromethylphenyl isocyanate. $^{1}$H-NMR (DMSO-$d_6$) δ 9.92 (s, 1H), 9.78 (s, 1H), 8.05-7.99 (m, 3H), 7.60 (d, J=8.8 Hz, 2H), 7.51 (d, J=7.6 Hz, 1H), 7.43 (d, J=8.8 Hz, 2H), 6.62 (s, 1H), 3.80 (s, 2H), 3.58-3.50 (m, 4H), 2.46-2.38 (m, 4H); MS $[M+H]^+$=513; LCMS RT=2.41.

Example 69

Preparation of N-4-[4-amino-7-(morpholin-4-ylmethyl)pyrrolo[2,1-f][1,2,4]triazin-5-yl]phenyl-N'-(6-bromopyridin-2-yl)urea

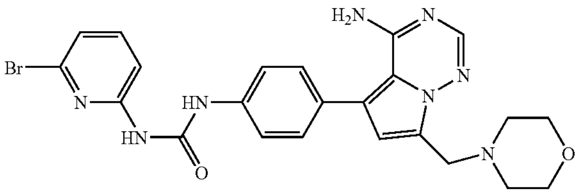

The procedure used for the preparation of Example 4 was used to prepare the title compound by substituting (6-bromo-pyridin-2-yl)-carbamic acid phenyl ester for 2-fluoro-5-trifluoromethylphenyl isocyanate. $^{1}$H-NMR (DMSO-$d_6$) δ 9.95 (s, 1H), 9.83 (s, 1H), 7.89 (s, 1H), 7.79 (d, J=8.4, 1H), 7.65 (t, J=8.4, 1H), 7.59 (d, J=8.8, 2H), 7.39 (d, J=8.8, 2H), 7.21 (d, J=8.4, 1H), 6.62 (s, 1H), 3.81 (s, 2H), 3.58 (t, J=2.4, 4H), 2.44 (s, 4H); MS $[M+H]^+$=523; LCMS RT=2.30.

Example 70

Preparation of N-4-[4-amino-7-(morpholin-4-ylmethyl)pyrrolo[2,1-f][1,2,4]triazin-5-yl]phenyl-N'-(6-methoxypyridin-2-yl)urea

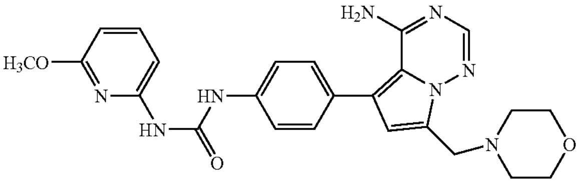

The procedure used for the preparation of Example 4 was used to prepare the title compound by substituting (6-methoxy-pyridin-2-yl)-carbamic acid phenyl ester for 2-fluoro-5-trifluoromethylphenyl isocyanate. $^{1}$H-NMR (DMSO-$d_6$) δ 9.95 (s, 1H), 9.28 (s, 1H), 7.90 (s, 1H), 7.63 (t, J=8.4, 1H), 7.60 (d, J=8.4, 2H), 7.40 (d, J=8.4, 2H), 7.19 (d, J=8.8, 1H), 6.61 (s, 1H) 6.43 (d, J=8.8, 1H), 3.90 (s, 3H), 3.83 (s, 2H), 3.58 (t, J=2.4, 4H), 2.43-2.40 (br, 4H); MS $[M+H]^+$=475; LCMS RT=2.11.

Example 71

Preparation of N-4-[4-amino-7-(morpholin-4-ylmethyl)pyrrolo[2,1-f][1,2,4]triazin-5-yl]phenyl-N'-(6-ethylpyridin-2-yl)urea

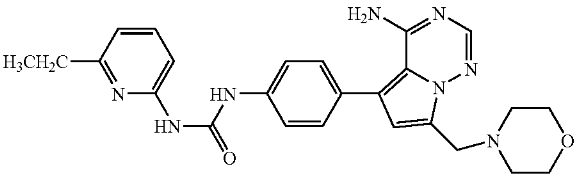

The procedure used for the preparation of Example 4 was used to prepare the title compound by substituting (6-ethyl-pyridin-2-yl)-carbamic acid phenyl ester for 2-fluoro-5-trifluoromethylphenyl isocyanate. $^{1}$H-NMR (DMSO-$d_6$) δ 11.11 (s, 1H), 9.58 (s, 1H), 7.89 (s, 1H), 7.69-7.60 (m, 3H), 7.40 (d, J=8.4, 2H), 7.19 (d, J=8.4, 1H), 6.85 (d, J=8.4, 1H), 6.61 (s, 1H), 3.82 (s, 2H), 3.55 (t, J=2.4, 4H), 2.78 (q, J=2.8, 2H), 2.42 (s, 4H), 1.25 (t, J=2.8, 3H); MS $[M+H]^+$=473; LCMS RT=2.00.

Example 72

Preparation of N-4-[4-amino-7-(morpholin-4-ylm-ethyl)pyrrolo[2,1-f][1,2,4]triazin-5-yl]-2-fluorophenyl-N'-(6-methoxypyridin-2-yl)urea

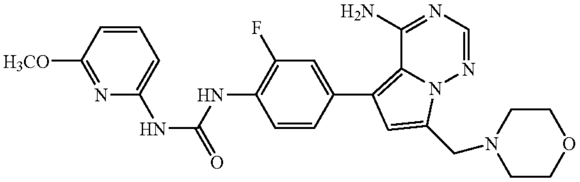

The procedure used for the preparation of Example 4 was used to prepare the title compound by substituting Intermediate E for Intermediate F and by substituting (6-methoxy-pyridin-2-yl)-carbamic acid phenyl ester for 2-fluoro-5-trifluoromethylphenyl isocyanate. $^1$H-NMR (DMSO-$d_6$) δ 10.10 (s, 1H), 9.92 (s, 1H), 8.25 (t, J=8.8, 1H), 7.91 (s, 1H), 7.72 (t, J=8.8, 1H), 7.63 (d, J=8.8, 1H), 7.35 (d, J=8.8, 1H), 7.32-7.28 (m, 2H), 6.66 (s, 1H), 3.81 (s, 2H), 3.57 (s, 4H), 3.40 (s, 3H), 2.41 (s, 4H); MS [M+H]$^+$=493; LCMS RT=2.25.

Example 73

Preparation of N-4-[4-amino-7-(morpholin-4-ylm-ethyl)pyrrolo[2,1-f][1,2,4]-triazin-5-yl]-2-fluorophenyl-N'-(6-bromopyridin-2-yl)urea

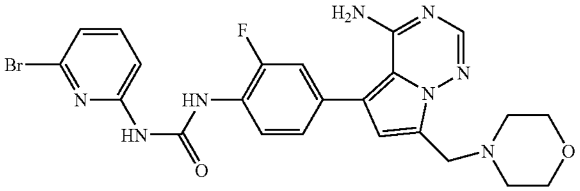

The procedure used for the preparation of Example 4 was used to prepare the title compound by substituting Intermediate E for Intermediate F and by substituting (6-methoxy-pyridin-2-yl)-carbamic acid phenyl ester for 2-fluoro-5-trifluoromethylphenyl isocyanate. $^1$H-NMR (DMSO-$d_6$) δ 9.95 (s, 1H), 9.73 (s, 1H), 8.26 (t, J=8.8, 1H), 7.92 (s, 1H), 7.65 (t, J=8.8, 1H), 7.38 (d, J=8.8, 1H), 7.25 (d, J=8.8, 1H), 7.20 (d, J=8.8, 1H), 6.67 (s, 1H), 6.42 (d, J=8.8, 1H), 3.83 (s, 2H), 3.59 (t, J=2.8, 4H), 2.43 (s, 4H); MS [M+H]$^+$=541; LCMS RT=2.45.

Example 74

Preparation of N-4-[4-amino-7-(morpholin-4-ylm-ethyl)pyrrolo[2,1-f][1,2,4]triazin-5-yl]phenyl-N'-(3-phenoxyphenyl)urea

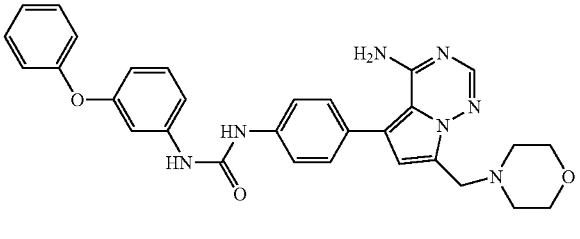

The procedure used for the preparation of Example 4 was used to prepare the title compound by substituting (6-phenoxy-pyridin-2-yl)-carbamic acid phenyl ester for 2-fluoro-5-trifluoromethylphenyl isocyanate. $^1$H-NMR (DMSO-$d_6$) δ 9.58 (s, 1H), 9.50 (s, 1H), 7.88 (s, 1H), 7.58 (d, J=8.8, 2H), 7.41-7.30 (m, 4H), 7.26 (t, J=8.8, 1H), 7.19-7.10 (m, 2H), 7.02 (d, J=8.8, 2H), 6.62-6.58 (m, 2H), 3.82 (s, 2H), 3.55 (t, J=2.8, 4H), 2.42 (s, 4H); MS [M+H]$^+$=537; LCMS RT=2.53.

Example 75

Preparation of N-(4-{4-amino-7-[(1,1-dioxidothio-morpholin-4-yl)methyl]pyrrolo[2,1f][1,2,4]triazin-5-yl}-2-fluorophenyl)-N'-(3-ethylphenyl)urea

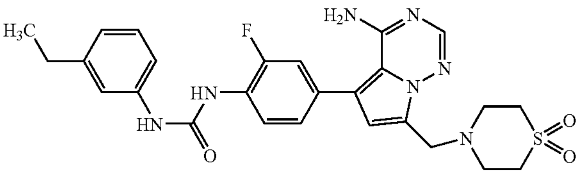

The procedure used for the preparation of Example 4 was used to prepare the title compound by substituting Intermediate E for Intermediate G and by substituting 3-ethylphenyl isocyanate for 2-fluoro-5-trifluoromethylphenyl isocyanate. $^1$H-NMR (DMSO-$d_6$) δ 9.04 (s, 1H), 8.62 (d, J=2.8, 1H), 8.25 (t, J=8.4, 1H), 7.91 (s, 1H); 7.33 to 7.30 (m, 2H), 7.25 to 7.16 (m, 3H), 6.83 (d, J=7.2, 1H), 6.73 (s, 1H), 4.02 (s, 2H), 3.10 (d, J=5.2, 4H), 2.95 (d, J=2.8, 4H), 2.56 (q, J=7.6, 2H), 1.16 (t, J=7.2, 3H); MS [M+H]$^+$=539.0; LCMS RT=3.34.

Example 76

Preparation of N-(4-{4-amino-7-[(1,1-dioxidothio-morpholin-4-yl)methyl]pyrrolo[2,1f][1,2,4]triazin-5-yl}-2-fluorophenyl)-N'-(3-methylphenyl)urea

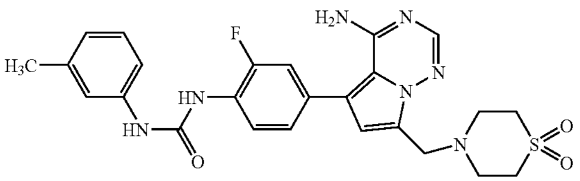

The procedure used for the preparation of Example 4 was used to prepare the title compound by substituting Intermediate E for Intermediate G and by substituting 3-methylphenyl isocyanate for 2-fluoro-5-trifluoromethylphenyl isocyanate. $^1$H-NMR (DMSO-$d_6$) δ 9.02 (s, 1H), 8.63 (d, J=2.0, 1H), 8.25 (t, J=8.8, 1H), 7.91 (s, 1H); 7.34 to 7.30 (m, 2H), 7.23 to 7.14 (m, 3H), 6.82 (d, J=7.2, 1H), 6.73 (s, 1H), 4.02 (s, 2H), 3.11 (d, J=5.2, 4H), 2.94 (d, J=2.7, 4H), 2.27 (s, 3H); MS [M+H]$^+$=524.0; LCMS RT=3.19.

Example 77

Preparation of N-(4-{4-amino-7-[(1,1-dioxidothiomorpholin-4-yl)methyl]pyrrolo[2,1-f][1,2,4]triazin-5-yl}-2-fluorophenyl)-N'-[3-(trifluoromethyl)phenyl]urea

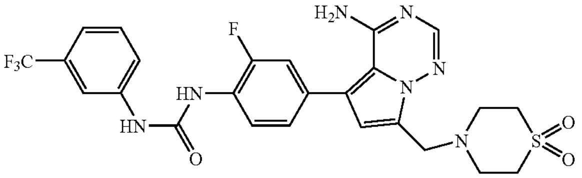

The procedure used for the preparation of Example 4 was used to prepare the title compound by substituting Intermediate E for Intermediate G and by substituting 3-trifluoromethylphenyl isocyanate for 2-fluoro-5-trifluoromethylphenyl isocyanate. $^1$H-NMR (DMSO-$d_6$) δ 9.45 (s, 1H), 8.76 (s, 1H), 8.22 (t, J=8.4, 1H); 8.05 (s, 1H), 7.92 (s, 1H), 7.53 (dd, J=4.8, 1.2, 2H), 7.36 to 7.32 (m, 2H), 7.24 (dd, J=8.4, 1.2, 1H), 6.74 (s, 1H), 4.03 (s, 2H), 3.12 to 3.10 (m, 4H), 2.95 to 2.94 (m, 4H); MS $[M+H]^+$=577.9; LCMS RT=2.75.

Example 78

Preparation of N-(4-[4-amino-7-[(1,1-dioxidothiomorpholin-4-yl)methyl]pyrrolo[2,1f][1,2,4]triazin-5-yl]-2-fluorophenyl)-N'-[4-(trifluoromethyl)pyridin-2-yl]urea

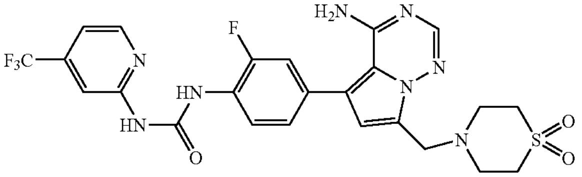

The procedure used for the preparation of Example 4 was used to prepare the title compound by substituting Intermediate E for Intermediate G and by substituting Intermediate H for 2-fluoro-5-trifluoromethylphenyl isocyanate $^1$H-NMR (DMSO-$d_6$) δ 10.16 (s, 1H), 10.11 to 10.09 (m, 1H), 8.57 (d, J=5.2, 1H); 8.30 (t, J=8.4, 1H), 8.03 (s, 1H), 7.95 (s, 1H), 7.41 to 7.38 (m, 2H), 7.29 (d, J=8.8, 1H), 6.77 (s, 1H), 4.06 (s, 2H), 3.16 to 3.12 (m, 4H), 3.00 to 2.96 (m, 4H); MS $[M+H]^+$=580.9; LCMS RT=2.67.

Example 79

Preparation of N-(4-{4-amino-7-[(1,1-dioxidothiomorpholin-4-yl)methyl]pyrrolo[2,1f][1,2,4]triazin-5-yl}-2-fluorophenyl)-N'-[2-fluoro-5-(trifluoromethyl)phenyl]urea

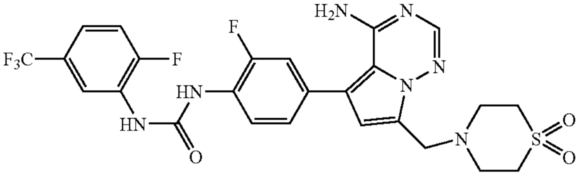

The procedure used for the preparation of Example 4 was used to prepare the title compound by substituting Intermediate E for Intermediate G. $^1$H-NMR (DMSO-$d_6$) δ 9.42 to 9.40 (m, 1H), 9.27 to 9.25 (m, 1H), 8.65 (dd, J=7.2, 2.0, 1H); 8.27 (t, J=8.8, 1H), 7.92 (s, 1H), 7.51 (t, J=8.8, 1H), 7.42 to 7.38 (m, 1H), 7.35 (dd, J=12.0, 1.6, 1H), 7.25 (dd, J=7.6, 2.0, 1H), 6.74 (s, 1H), 4.03 (s, 2H), 3.13 to 3.09 (m, 4H), 2.96 to 2.93 (m, 4H); MS $[M+H]^+$=595.9; LCMS RT=2.80.

Example 80

Preparation of tert-butyl 4-[(4-amino-5-{4-[({[2-fluoro-5-(trifluoromethyl)phenyl]amino}carbonyl)amino]phenyl}pyrrolo[2,1-f][1,2]triazin-7-yl)methyl]piperazine-1-carboxylate

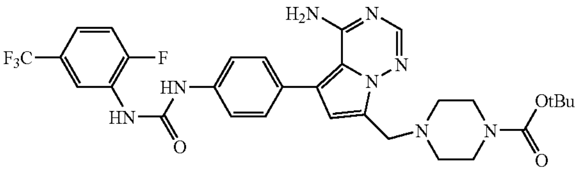

The procedure used for the preparation of Example 4 was used to prepare the title compound by substituting Intermediate I for Intermediate E. $^1$H-NMR (DMSO-$d_6$) δ 9.29 (s, 1H), 8.93 (d, 3=3 Hz, 1H), 8.62 (dd, J=5, 2 Hz, 1H), 7.89 (s, 1H), 7.57 (dd, J=5, 2 Hz, 1H), 7.53 to 7.46 (m, 4H), 6.62 (s, 1H), 3.83 (s, 2H), 3.29 (m, 4H), 2.39 (t, J=5 Hz, 4H), 1.35 (s, 9H); MS $[M+H]^+$=629.0; LCMS RT=2.82 min.

Example 81

Preparation of N-4-[4-amino-7-(piperazin-1-ylmethyl)pyrrolo[2,1-f][1,2,4]triazin-5-yl]phenyl-N'-[2-fluoro-5-(trifluoromethyl)phenyl]urea

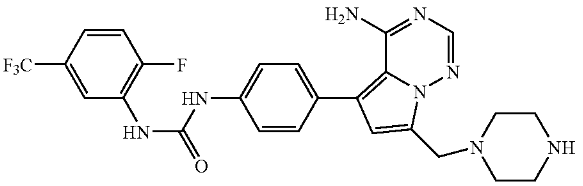

To a solution of Example 80 (100 mg, 0.13 mmol) in $CH_2Cl_2$ (5 ml) was added TFA (1.6 ml) and 2N HCl (1 ml) and stirred at rt for 48 h. The reaction mixture was partially evaporated and ethyl acetate (10 ml) was added and washed with saturated aq. $NaHCO_3$. The organic was dried over $Na_2SO_4$ and concentrated to afford 60 mg of the title compound (yield 85%). $^1$H-NMR (MeOH-$d_4$) δ 8.60 (dd, J=7, 1 Hz, 1H), 7.97 (s, 1H), 7.83 (s, 1H), 7.60 (m, 2H), 7.45 to 7.42 (m, 2H), 7.35 to 7.32 (m, 2H), 6.69 (s, 2H), 3.96 (s, 2H), 3.66 (t, J=4 Hz, 1H), 2.87 to 2.84 (t, J=4 Hz, 4H), 2.53 (t, J=4 Hz, 4H); MS $[M+H]^+$=529.0; LCMS RT=2.29 min.

Example 82

Preparation of tert-butyl 4-[(4-amino-5-{3-fluoro-4-[({[2-fluoro-5-(trifluoromethyl)phenyl]amino}carbonyl)amino]phenyl}pyrrolo[2,1-f][1,2,4]triazin-7-yl)methyl]piperazine-1-carboxylate

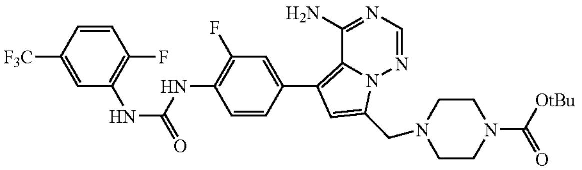

The procedure used for the preparation of Example 1 was used to prepare the title compound by substituting the product of step 2 in the preparation of Intermediate I for Intermediate C. $^1$H-NMR($CH_2Cl_2$-$d_2$) δ 8.63 (dd, J=4, 2 Hz, 1H), 8.35 to 8.28 (m, 3H), 7.91 (s, 1H), 7.31 to 7.16 (m, 3H), 6.70 (s, 1H), 5.67 to 5.63 (broad, 2H), 4.10 (s, 2H), 3.47 (t, J=3 Hz, 4H), 2.53 (t, J=3 Hz, 4H), 1.41 (s, 9H); MS $[M+H]^+$=529.0; LCMS RT=2.29 min.

Example 83

Preparation of N-[4-(4-amino-7{[4(methylsulfonyl)-piperazin-1-yl]methyl}pyrrolo[2,1-f][1,2,4]triazin-5-yl)phenyl]-N'-[2-fluoro-5-(trifluoromethyl)phenyl]urea

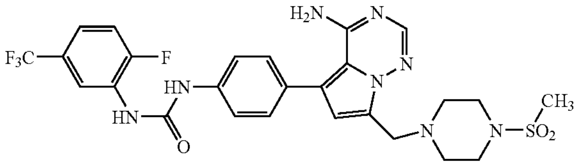

To a solution of Example 81 (60 mg, 0.10 mmol) in $CH_2Cl_2$/THF (3/1, 2 ml) was added triethylamine (0.01 ml, 0.10 mmol) and methanesulfonyl chloride (0.01 mml, 0.10 mmol). The reaction was stirred at rt for 2 h and the reaction was concentrated. The resulting crude product was purified via column chromatography (5:95, v/v, $CH_2Cl_2$—$CH_3OH$) to afford 21 mg of the title compound (yield 50%). $^1$H-NMR (DMSO-$d_6$) δ 9.29 (s, 1H), 8.93 (d, J=3 Hz, 1H), 8.62 (dd, J=7, 2 Hz, 1H), 7.89 (s, 1H), 7.57 (dd, J=7, 2 Hz, 2H), 7.53 to 7.46 (m, 4H), 6.63 (s, 1H), 3.83 (s, 2H), 3.08 (m, 4H), 2.83 (s, 3H), 2.55 (m, 4H); MS $[M+H]^+$=607.1; LCMS RT=2.56 min.

Example 84

Preparation of N-[4-(4-amino-7-{[4-(ethylsulfonyl)piperazin-1-yl]methyl}pyrrolo[2,1-f][1,2,4]triazin-5-yl)phenyl]-N'-[2-fluoro-5-(trifluoromethyl)phenyl]urea

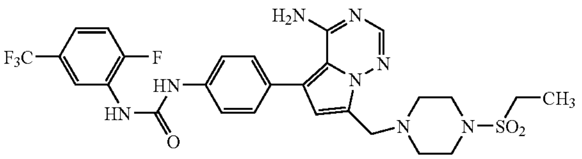

The procedure used for the preparation of Example 83 was used to prepare the title compound by substituting ethanesulfonyl chloride for methanesulfonyl chloride. $^1$H-NMR (DMSO-$d_6$) δ 9.29 (s, 1H), 8.93 (d, J=3 Hz, 1H), 8.62 (dd, J=7, 2 Hz, 1H), 7.89 (s, 1H), 7.57 (dd, J=7, 2 Hz, 2H), 7.53 to 7.46 (m, 4H), 6.63 (s, 1H), 3.87 (s, 2H), 3.15 (t, J=5 Hz, 4H), 3.01 (q, J=7 Hz, 2H), 2.52 (t, J=5 Hz, 4H), 1.17 (t, J=7 Hz, 3H); MS $[M+H]^+$=621.0; LCMS RT=2.61 min.

Example 85

Preparation of N-[4-(4-amino-7-{[4(isopropylsulfonyl)piperazin-1-yl]methyl}pyrrolo[2,14f][1,2,4]triazin-5-yl)phenyl]-N'-[2-fluoro-5-(trifluoromethyl)phenyl]urea

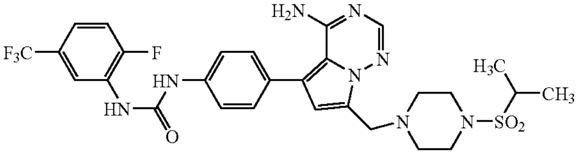

The procedure used for the preparation of Example 83 was used to prepare the title compound by substituting isopropylsulfonyl chloride for methanesulfonyl chloride. $^1$H-NMR ($CH_3OH$-$d_4$) δ 8.60 (d, J=7 Hz, 1H), 7.85 (d, J=3 Hz, 1H), 7.61 to 7.58 (m, 2H), 7.47 to 7.42 (m, 2H), 7.35 to 7.32 (m, 2H), 4.10 (s, 2H), 3.35 (t, J=5 Hz, 4H), 2.15 (q, J=2 Hz), 2.63 (t, J=5 Hz, 4H), 1.29 (d, J=5 Hz, 6H); MS $[M+H]^+$=635.0; LCMS RT=2.69 min.

Example 86

Preparation of N-{4-[4-amino-7-({4-[(2,2,2-trifluoroethyl)sulfonyl]piperazin-1-yl}methyl)pyrrolo[2,1-f][1,2,4]triazin-5-yl]phenyl}-N'-[2-fluoro-5-(trifluoromethyl)phenyl]urea

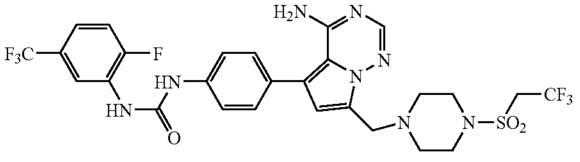

The procedure used for the preparation of Example 83 was used to prepare the title compound by substituting 2,2,2-trifluoroethanesulfonyl chloride for methanesulfonyl chloride. $^1$H-NMR (DMSO-$d_6$) δ 9.29 (s, 1H), 8.93 (d, J=3 Hz, 1H), 8.62 (dd, J=7, 2 Hz, 1H), 7.89 (s, 1H), 7.57 (dd, J=7, 2 Hz, 2H), 7.50 to 7.38 (m, 4H), 6.63 (s, 1H), 4.57 (q, J=8 Hz), 3.15 (br, 4H), 2.52 (br, 4H); MS $[M+H]^+$=675.2; LCMS RT=2.83 min Example 87

Preparation of N-(4-{7-[(4-acetylpiperazin-1-yl) methyl]-4-aminopyrrolo[2,1f][1,2,4]triazin-5-yl}phenyl)-N'-[2-fluoro-5-(trifluoromethyl)phenyl] urea

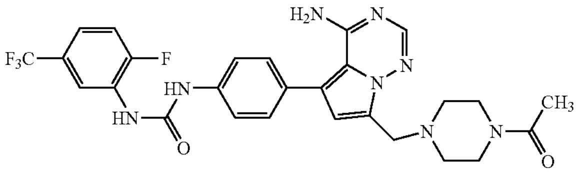

To a solution of Example 81 (40 mg, 0.08 mmol) in 2-propanol anhydrous (2 ml) was added acetyl chloride (0.02 ml, 0.22 mmol) and sodium carbonate (10 mg). The reaction was stirred at rt for 2 h and the solvent was stripped by rotary evaporation and the resulting crude was added $CH_2Cl_2$ (3 ml) and washed with saturated aq. sodium carbonate and dried (Na2SO4). After concentrated, the resulting brown solid was triturated with $CH_2Cl_2$ to afford 20 mg of the title compound (yield 46%). $^1$H-NMR (DMSO-$d_6$) δ 9.29 (br, 2H), 8.62 (dd, J=7, 2 Hz, 1H), 7.89 (s, 1H), 7.58 (d, J=3 Hz, 2H), 7.56 to 7.34 (m, 4H), 6.63 (s, 1H), 3.87 (s, 2H), 3.40 (t, J=3 Hz, 4H), 2.25 (t, J=3 Hz, 4H), 1.95 (s, 3H); MS $[M+H]^+$=571.0; LCMS RT=2.91 min.

Example 88

Preparation of N-(5-{7-[(4-acetylpiperazin-1-yl) methyl]-4-aminopyrrolo[2,1-f][1,2,4]triazin-5-yl}pyridin-2-yl)-N'-[2-fluoro-5(trifluoromethyl)phenyl]urea

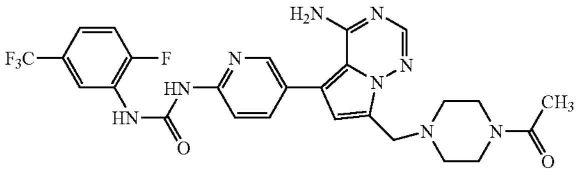

The procedure used for the preparation of Example 1 was used to prepare the title compound by substituting the product of step 2 in the preparation of Intermediate J for Intermediate C and the appropriate boranate ureas. $^1$H-NMR (DMSO-$d_6$) δ 10.01 (s, 1H), 8.68 (m, 1H), 8.32 (d, J=3 Hz, 1H), 7.98 (s, 1H), 7.91 to 7.82 (m, 2H), 7.56 to 7.43 (m, 3H), 6.7 (s, 1H), 3.87 (s, 2H), 3.42 to 3.38 (m, 4H), 2.45 to 2.40 (m, 4H), 1.95 (s, 3H); MS 572.0; LCMS RT=2.87 min.

Example 89

Preparation of N-(4-{7-[(4-acetylpiperazin-1-yl) methyl]-4-aminopyrrolo[2,1-f][1,2,4]triazin-5-yl}-2-fluorophenyl)-N'-[2-fluoro-5-(trifluoromethyl)phenyl]urea

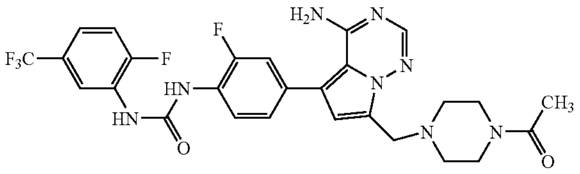

The procedure used for the preparation of Example 4 was used to prepare the title compound by substituting Intermediate J for Intermediate E. $^1$H-NMR (DMSO-$d_6$) δ 9.4 (d, J=3 Hz, 1H), 9.24 (d, J=3 Hz, 1H), 8.64 (dd, J=5, 2 Hz, 1H), 8.26 (t, J=8 Hz, 1H), 7.90 (s, 1H), 7.53 to 7.22 (m, 4H), 6.70 (s, 1H), 3.85 (s, 2H), 3.41 to 3.39 (m, 4H), 2.45 to 2.40 (m, 4H), 1.94 (s, 3H); MS $[M+H]^+$=589.0; LCMS RT=2.48 min.

Example 90

Preparation of tert-butyl 4-(4-amino-5-[4-([(6-bromopyridin-2-yl)amino]carbonylamino)phenyl]pyrrolo[2,1-f][1,2,4]triazin-7-ylmethyl)piperazine-1-carboxylate

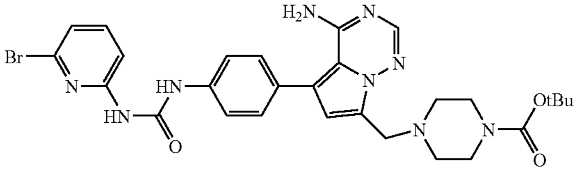

To a solution of Intermediate I (600 mg, 1.42 mmol), triethylamine (215 mg, 2.12 mmol) in DMF (18 mL) was added (6-bromo-pyridin-2-yl)-carbamic acid phenyl ester (498 mg, 1.70 mmol). The reaction was stirred overnight, concentrated and purified by silica gel column using 4% methanol in dichloromethane to obtain 700 mg (79%) of desired product as yellow solid. $^1$H-NMR (DMSO-$d_6$) δ 11.33 (s, 1H), 7.90 (s, 1H), 7.75 (d, J=8.4, 2H), 7.58 (t, J=8.4, 1H), 7.48 (d, J=8.4, 2H), 7.20 (d, J=8.4, 1H), 6.89 (d, J=8.4, 1H), 6.65 (s, 1H), 3.98 (s, 2H), 3.42 (s, 4H), 2.58 (s, 4H), 1.45 (s, 9H); MS $[M+H]^+$=622; LCMS RT=2.67.

Example 91

Preparation of N-4-[4-amino-7-(piperazin-1-ylmethyl)pyrrolo[2,1-f][1,2,4]-triazin-5-yl]phenyl-N'-(6-bromopyridin-2-yl)urea

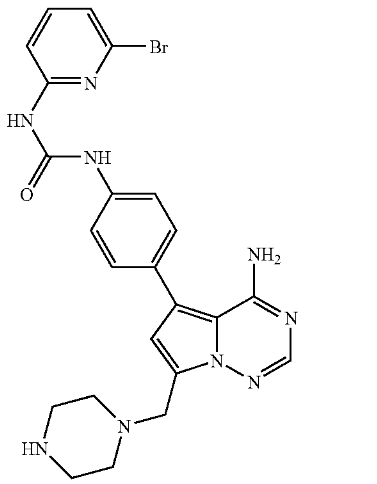

To a solution of Example 90 (150 mg, 0.24 mmol) in dichloromethane (2 mL) was added TFA (1 mL). The reaction was stirred 4 h and concentrated. The residue was dissolved in dichloromethane and washed with saturated $Na_2CO_3$ solution (3×). The organic layer was dried over $Na_2SO_4$ and concentrated to afford 100 mg (78%) of desired product as brown oil.

$^1$H-NMR (DMSO-$d_6$) δ 9.62 (s, 1H), 7.90 (s, 1H), 7.80 (d, J=8.4, 1H), 7.68 (t, J=8.4, 1H), 7.59 (d, J=8.4, 2H), 7.40 (d, 3=8.4, 2H) 7.21 (d, J=8.4, 1H), 6.61 (s, 1H), 3.80 (s, 2H), 2.68 (t, J=2.4, 4H), 2.40 (s, 4H); MS $[M+H]^+$=522; LCMS RT=1.65.

Example 92

Preparation of N-(4-4-amino-7-[(4-isopropylpiperazin-1-yl)methyl]pyrrolo[2,1f][1,2,4]triazin-5-ylphenyl)-N'-(6-bromopyridin-2-yl)urea

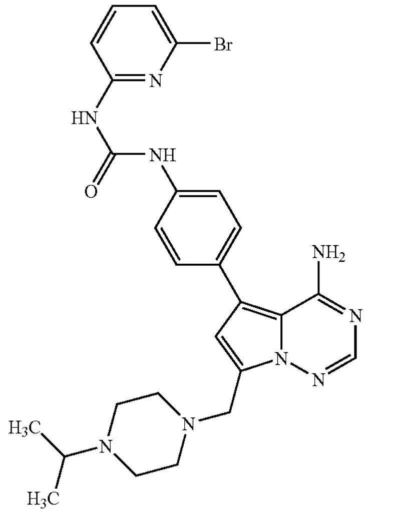

To a solution of Example 91 (40 mg, 0.077 mmol), $Cs_2CO_3$ (32 mg, 0.1 mmol) in MeCN (1 mL) was added 2-iodopropane (15 mg, 0.084 mmol). The reaction mixture was stirred at 50° C. overnight. The crude product was purified by HPLC to afford 13 mg (30%) of desired product. $^1$H-NMR (DMSO-$d_6$) δ 11.40 (s, 1H), 11.32 (s, 1H), 7.90-7.85 (M, 2H), 7.68 (d, J=8.4, 2H), 7.62 (t, J=8.8, 1H), 7.36 (d, J=8.4, 2H), 7.15 (d, J=8.8, 1H), 6.59 (s, 1H), 3.80 (s, 2H), 2.50-2.35 (br, 9H), 0.95 (d, J=8.4, 6H); MS $[M+H]^+$=564; LCMS RT=2.18.

Example 93

Preparation of N-(4-7-[(4-acetylpiperazin-1-yl)methyl]-4-aminopyrrolo[2,1-f][1,2,4]triazin-5-ylphenyl)-N'-(6-bromopyridin-2-yl)urea

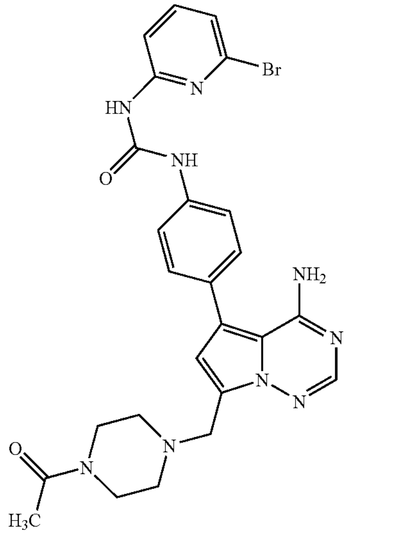

To a solution of Example 91 (40 mg, 0.077 mmol), $Na_2CO_3$ (11 mg, 0.1 mmol) in DMF (1 mL) was added acetyl chloride (6 mg, 0.084 mmol). The reaction mixture was stirred at rt overnight. After removal of solvent, the crude product was purified by silica gel column using 4% methanol in dichloromethane to obtain 28 mg (65%) of desired product. $^1$H-NMR (DMSO-$d_6$) δ 9.75 (s, 1H), 9.62 (s, 1H), 7.91 (s, 1H), 7.78 (d, J=8.8, 1H), 7.68 (t, J=8.8, 1H), 7.59 (d, J=8.8, 2H), 7.42 (d, J=8.8, 2H), 7.25 (d, J=8.8, 1H), 6.62 (s, 1H), 3.85 (s, 2H), 2.42-2.38 (m, 8H), 1.95 (s, 3H); MS $[M+H]^+$=564; LCMS RT=2.20.

Example 94

Preparation of N-[4-(4-amino-7-[4-(methylsulfonyl)piperazin-1-yl]methyl}pyrrolo[2,1f][1,2,4]triazin-5-yl)phenyl]-N'-(6-bromopyridin-2-yl)urea

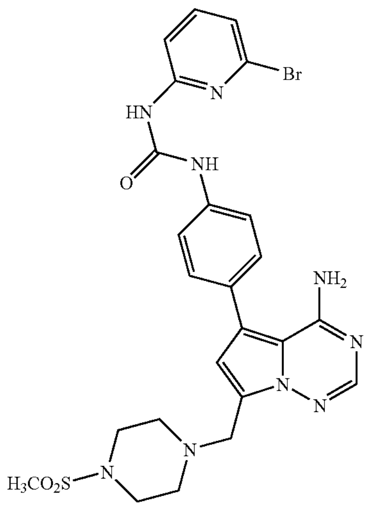

To a solution of Example 91 (40 mg, 0.077 mmol), $Na_2CO_3$ (11 mg, 0.1 mmol) in DMF (1 mL) was added methanesulfonyl chloride (9.6 mg, 0.084 mmol). The reaction mixture was stirred at rt overnight. After removal of solvent, the crude product was purified by silica gel column using 4% methanol in dichloromethane to obtain 23 mg (50%) of desired product. $^1$H-NMR (DMSO-$d_6$) δ 9.75 (s, 1H), 9.60 (s, 1H), 7.90 (s, 1H), 7.78 (d, J=8.4, 1H), 7.70 (t, J=8.4, 1H), 7.59 (d, J=8.4, 2H), 7.42 (d, J=8.4, 2H), 7.25 (d, J=8.4, 1H), 6.63 (s, 1H), 3.87 (s, 2H), 3.10 (s, 4H), 2.83 (s, 3H), 2.43 (s, 4H); MS $[M+H]^+$=601; LCMS RT=2.50.

Example 95

Preparation of N-[4-(4-amino-7-[4-(2-hydroxyethyl)piperazin-1-yl]methylpyrrolo[2,1-f][1,2,4]triazin-5-yl)phenyl]-N'-(6-bromopyridin-2-yl)urea

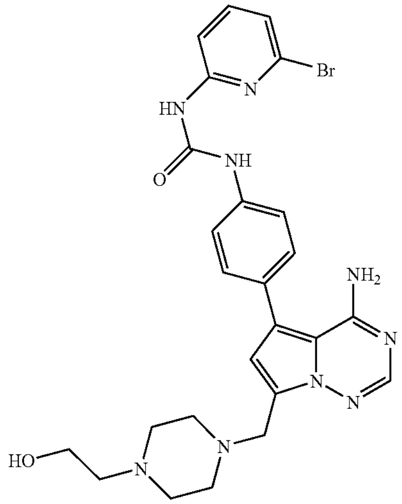

To a solution of Example 91 (50 mg, 0.096 mmol), $Cs_2CO_3$ (40 mg, 0.124 mmol) in DMF (1 mL) was added (2-bromoethoxy)-t-butyldimethylsilane (25 mg, 0.105 mmol). The reaction mixture was stirred at rt overnight. After removal of solvent, the crude product was dissolved in methanol (1 mL) followed by adding 10% TFA in water (1 mL). The solution was stirred for 3 hr at 50° C. Cooled and concentrated, the crude product was purified by silica gel column using 4% methanol in dichloromethane to obtain 3 mg (5%) of desired product. $^1$H-NMR (DMSO-$d_6$) δ 10.30 (s, 2H), 7.90 (s, 1H), 7.83 (d, J=8.4, 1H), 7.66 (t, J=8.4, 1H), 7.61 (d, J=8.4, 2H), 7.40 (d, J=8.4, 2H), 7.21 (d, J=8.4, 1H), 6.61 (s, 1H), 3.81 (s, 1H), 3.30 (t, J=8.8, 2H), 3.15 (s, 4H), 2.43 (s, 4H), 2.31 (t, J=8.8, 2H); MS $[M+H]^+$=567; LCMS RT=2.29.

Example 96

Preparation of 4-amino-N-(2,2,2-trifluoroethyl)-5-{4-[({[6-(trifluoromethyl)pyridin-2-yl]amino}carbonyl)amino]phenyl}pyrrolo[2,1-f][1,2,4]triazine-7-carboxamide

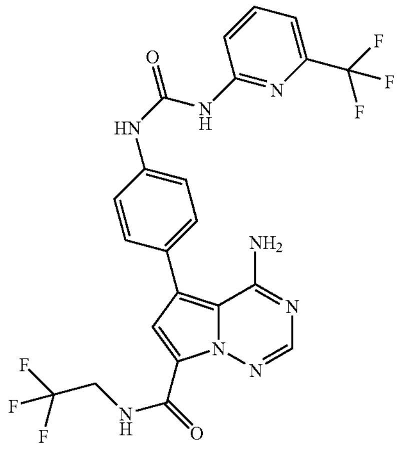

Step 1: Preparation of butyl 4-aminopyrrolo[2,1-f][1,2,4]triazine-7-carboxylate

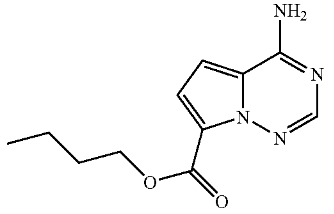

A mixture of 7-bromopyrrolo[2,1f][1,2,4]triazin-4-amine (670.0 mg, 3.15 mmol), palladium acetate (70.6 mg, 0.31 mmol), 1,3-bis(diphenylphosphino)propane (142.7 mg, 0.35 mmol), potassium carbonate (652.0 mg, 4.72 mmol), and 1-butanol (4 mL) in DMF (4 mL) was stirred under carbon monoxide at 80° C. for 4 h. The solid was filtered away and the filtrate was purified by HPLC using a gradient of 25-50% of MeCN in water to yield 107.3 mg (15%) of the title compound as a white solid. $^1$H-NMR (DMSO-$d_6$) δ 8.28 (bs, 1H), 8.17, (bs, 1H), 8.05 (s, 1H), 7.25 (d, J=4.7 Hz, 1H), 7.00 (d, J=4.6 Hz, 1H), 4.24 (t, J=.=6.6 Hz, 2H), 1.69-1.62 (m, 2H), 1.45-1.36 (m, 2H), 0.92 (t, J=7.3, 3H); MS $[M+H]^+$=235.2; LCMS RT=2.73 min.

Step 2: Preparation of butyl 4-amino-5-bromopyrrolo[2,1-f][1,2,4]triazine-7-carboxylate

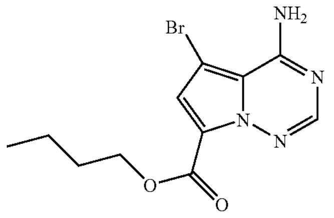

To a solution of butyl 4-aminopyrrolo[2,1-f][1,2,4]triazine-7-carboxylate (225.0 mg, 0.96 mmol) in DMF (7.5 mL) was added 1,3-dibromo-5,5-dimethylhydantoin (137.3 mg, 0.48 mmol) in two portions. The solution was stirred for 4 days and then quenched by addition of saturated aqueous sodium sulfate solution (20 mL) and water (20 mL). The solid was filtered, washed with water and air-dried. The crude material was purified by HPLC using a gradient of 30-80% of MeCN in water to afford 232.0 mg (77%) of the title compound as an off-white solid. $^1$H-NMR (DMSO-$d_6$) δ 8.42 (bs, 1H), 8.03 (s, 1H), 7.35 (s, 1H), 7.03 (bs, 1H), 4.23 (t, J=6.4 Hz, 2H), 1.69-1.62 (m, 2H), 1.46-1.36 (m, 2H), 0.92 (t, J=7.3, 3H); MS $[M+H]^+$=313.0; LCMS RT=2.83 min.

Step 3: Preparation of butyl 4-amino-5-{4-[(tert-butoxycarbonyl)amino]phenyl}-pyrrolo[2,1-f][1,2,4]triazine-7-carboxylate

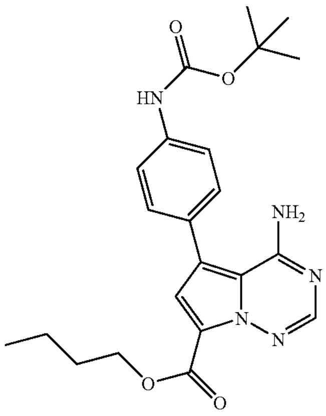

A mixture of butyl 4-amino-5-bromopyrrolo[2,1-f][1,2,4]triazine-7-carboxylate (456.0 mg, 1.46 mmol), {4-[(tert-butoxycarbonyl)amino]phenyl}boronic acid (517.8 mg, 2.18 mmol), 2 M aqueous sodium carbonate solution (2.2 mL, 4.40 mmol), and tetrakis(triphenylphosphine)palladium(0) (168.3 mg, 0.15 mmol) in 1,2-dimethoxyethane (11 mL) was heated (80° C.) overnight. The reaction mixture was diluted with DMF and purified by HPLC using a gradient of 30-95% of MeCN in water to give 163.2 mg (26%) of the title compound as a white solid. $^1$H-NMR (DMSO-$d_6$) δ 9.52 (s, 1H), 8.08 (bs, 1H), 8.06 (s, 1H), 7.56 (d, J=8.6 Hz, 2H), 7.35 (d, J=8.6 Hz, 2H), 7.18 (s, 1H), 5.67 (bs, 1H), 4.25 (t, J=6.5 Hz, 2H), 1.71-1.64 (m, 2H), 1.47-1.37 (m, 2H), 0.93 (t, J=7.4, 3H); MS [M+H]$^+$=426.2; LCMS RT=3.43 min Step 4: Preparation of butyl 4-amino-5-(4-aminophenyl)pyrrolo[2,1-f][1,2,4]triazine-7-carboxylate

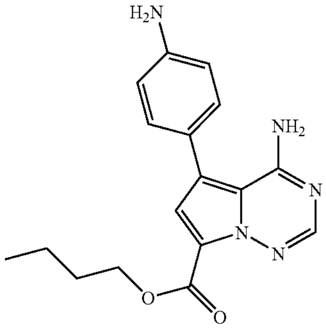

To a suspension of butyl 4-amino-5-{4-[(tert-butoxycarbonyl)amino]phenyl}pyrrolo[2,1-f][1,2,4]triazine-7-carboxylate (174.5 mg, 0.41 mmol) in dichloromethane (4 mL) was added TFA (2 mL). The solution was stirred at rt for 6.5 h and then the volatiles were evaporated under reduced pressure. The residue was dissolved in ethyl acetate (150 mL) and then this solution was washed with saturated aqueous sodium bicarbonate solution and water, dried over sodium sulfate, and concentrated to dryness under reduced pressure to afford 132.7 mg (99%) of the title compound. $^1$H-NMR (DMSO-$d_6$) δ 8.10 (bs, 1H), 8.02 (s, 1H), 7.10 (d, J=8.3 Hz, 2H), 7.08 (s, 1H), 6.64 (d, J=8.4 Hz, 2H), 5.55 (bs, 1H), 5.34 (s, 2H), 4.24 (t, J=6.5 Hz, 2H), 1.70-1.63 (m, 2H), 1.46-1.37 (m, 2H), 0.93 (t, J=7.4, 3H); MS [M+H]$^+$=326.3; LCMS RT=2.07 min.

Step 5: Preparation of butyl 4-amino-5-{4-[({[6-(trifluoromethyl)pyridin-2-yl]amino}carbonyl)amino]phenyl}pyrrolo[2,1-f][1,2,4]triazine-7-carboxylate

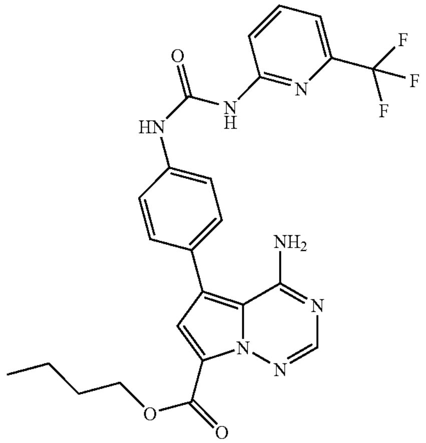

To a solution of butyl 4-amino-5-(4-aminophenyl)pyrrolo[2,1f][1,2,4]triazine-7-carboxylate (118.0 mg, 0.36 mmol) in DMF (3.5 mL) was added phenyl [6-(trifluoromethyl)pyridin-2-yl]carbamate (153.5 mg, 0.54 mmol,), followed by triethylamine (0.10 mL, 0.73 mmol). The solution was stirred at rt overnight and then purified directly by HPLC using a gradient of 50-80% MeCN in water to yield 107.7 mg (58%) of the title compound as a white solid. $^1$H-NMR (DMSO-$d_6$) δ 9.88 (s, 1H), 9.73 (s, 1H), 8.08 (s, 1H), 8.04 to 7.97 (m, 2H), 7.58 (d, J=8.6 Hz, 2H), 7.51 to 7.49 (m, 1H), 7.44 (d, J=8.5 Hz, 2H), 7.22 (s, 1H), 4.26 (t, J=6.6 Hz, 2H), 1.71-1.64 (m, 2H), 1.47-1.38 (m, 2H), 0.93 (t, J=7.3, 3H); MS [M+H]$^+$=514.2; LCMS RT=3.49 min.

Step 6: Preparation of 4-amino-5-{4-[({[6-(trifluoromethyl)pyridin-2-yl]amino}carbonyl)amino]phenyl}pyrrolo[2,1f][1,2,4]triazine-7-carboxylic acid

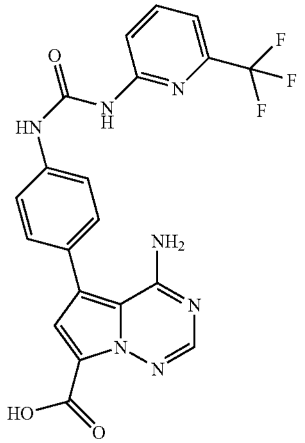

A mixture of butyl 4-amino-5-{4-[({[6-(trifluoromethyl)pyridin-2-yl]amino}carbonyl)amino]phenyl}pyrrolo[2,1-f][1,2,4]triazine-7-carboxylate (96.0 mg, 0.19 mmol) and 1 N aqueous sodium hydroxide solution (0.94 mL, 0.94 mmol) in THF (4 mL) and MeOH (5 mL) was stirred at rt for 4 h and acidified to pH 3 using 2N hydrochloric acid. The organic solvents were evaporated under reduced pressure and the residue was suspended in water (5 mL). The solid was filtered, washed with water and air-dried to give 63.0 mg (74%) of the title compound. $^1$H-NMR (DMSO-$d_6$) δ 12.76 (s, 1H), 9.87 (s, 1H), 9.71 (s, 1H), 8.08 (s, 1H), 8.04-7.97 (m, 2H), 7.57 (d, J=8.6 Hz, 2H), 7.50-7.49 (m, 1H), 7.43 (d, J=8.5 Hz, 2H), 7.20 (s, 1H); MS $[M+H]^+$=458.0; LCMS RT=2.90 min.

Step 7: Preparation of Title Compound

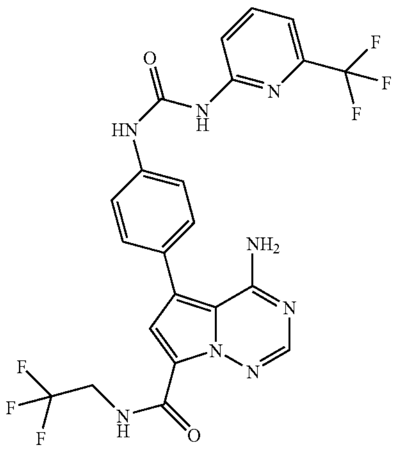

A mixture of 4-amino-5-{4-[({[6-(trifluoromethyl)pyridin-2-yl]amino}carbonyl)amino]phenyl}pyrrolo[2,1-f][1,2,4]triazine-7-carboxylic acid (30.0 mg, 0.066 mmol), 2,2,2-trifluoroethylamine (32.5 mg, 0.33 mmol), benzotriazol-1-yloxytris(dimethylamino)phosphonium hexafluorophosphate (58.0 mg, 0.13 mmol), and 4-methylmorpholine (13.3 mg, 0.13 mmol) in DMF (2 mL) was stirred at rt overnight. The crude reaction mixture was purified directly by HPLC using a gradient of 30-90% MeCN in water to afford 16.4 mg (36%) of the title compound as a white solid. $^1$H-NMR (DMSO-$d_6$) δ 9.88 (s, 1H), 9.73 (s, 1H), 9.40 (t, J=6.6 Hz, 1H), 8.34 (bs, 1H), 8.18 (s, 1H), 8.05 to 7.98 (m, 2H), 7.58 (d, J=8.6 Hz, 2H), 7.51-7.49 (m, 1H), 7.44 (d, J=8.7 Hz, 2H), 7.24 (s, 1H), 5.94 (bs, 1H), 4.33-4.24 (m, 2H); MS $[M+H]^+$=539.0; LCMS RT=3.24 min.

Example 97

Preparation of 4-amino-N-(tert-butyl)-5-{4-[({[6-(trifluoromethyl)pyridin-2-yl]amino}carbonyl)amino]phenyl}pyrrolo[2,1-f][1,2,4]triazine-7-carboxamide

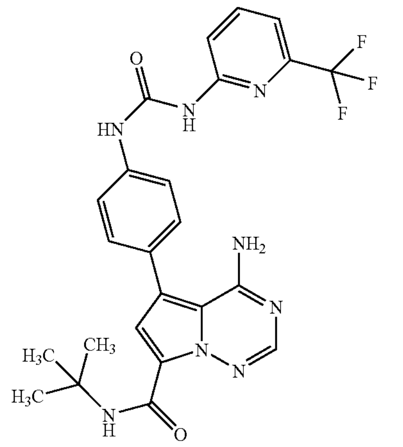

The procedure used for the preparation of Example 96 was used to prepare the title compound by substituting tert-butylamine for 2,2,2-trifluoroethylamine in step 7. $^1$H-NMR (DMSO-$d_6$) δ 9.87 (s, 1H), 9.72 (s, 1H), 8.97 (s, 1H), 8.21 (bs, 1H), 8.12 (s, 1H), 8.05-7.97 (m, 2H), 7.57 (d, J=8.8 Hz, 2H), 7.51-7.49 (m, 1H), 7.42 (d, J=8.6 Hz, 2H), 7.13 (s, 1H), 5.86 (bs, 1H), 1.44 (s, 9H); MS $[M+H]^+$=513.2; LCMS RT=3.37 min.

Example 98

Preparation of N-[4-(7-acetyl-4-aminopyrrolo[2,1-f][1,2,4]triazin-5-yl)phenyl]-N'-[6-(trifluoromethyl)pyridin-2-yl]urea

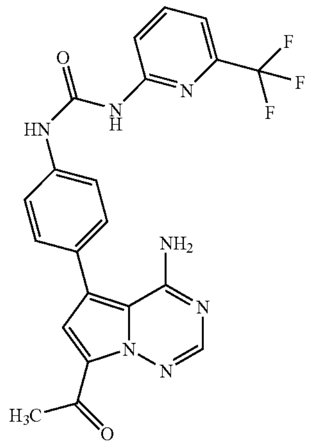

Step 1: Preparation of 1-[4-amino-5-(4-aminophenyl)pyrrolo[2,1-f][1,2,4]triazin-7-yl]ethanone

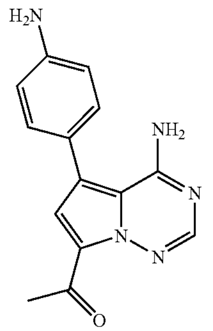

A mixture of Intermediate W (360.0 mg, 1.41 mmol), 4-(4,4,5,5-tetramethyl-1,3,2-dioxaborolan-2-yl)aniline (618.4 mg, 2.82 mmol), tetrakis(triphenylphosphine)palladium(0) (163.1 mg, 0.14 mmol), and 2 M aqueous potassium carbonate solution (2.82 mL, 5.64 mmol) in 1,2-dimethoxyethane (7 mL) was heated (80° C.) overnight. After cooling the reaction mixture was purified directly by silica gel chromatography using a 1:1 mixture of ethyl acetate and hexanes to give 300.0 mg (80%) of the title compound. $^1$H-NMR (DMSO-$d_6$) δ 9.56 (d, J=3.2 Hz, 1H), 8.21 (d, J=3.0, 1H), 8.04 (s, 1H), 7.71 (d, J=8.5 Hz, 2H), 7.54 (s, 1H), 6.64 (d, J=8.7 Hz, 2H), 5.38 (bs, 2H), 2.61 (s, 3H); MS $[M+H]^+$=268.2; LCMS RT=1.79 min.

Step 2: Preparation of Title Compound

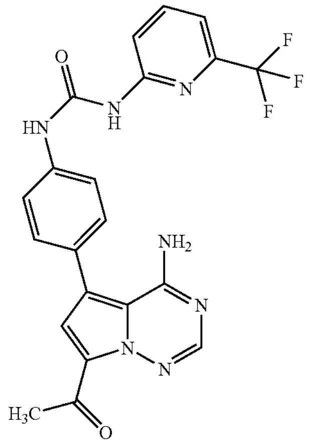

A mixture of 1-[4-amino-5-(4-aminophenyl)pyrrolo[2,1-f][1,2,4]triazin-7-yl]ethanone (50.0 mg, 0.19 mmol), phenyl [6-(trifluoromethyl)pyridin-2-yl]carbamate (105.6 mg, 0.37 mmol,), and triethylamine (0.10 mL, 0.75 mmol) in DMF (2 mL) was stirred overnight resulting in formation of a precipitate. The mixture was diluted with DMSO (1 mL) and then the solid was collected by filtration, washed with MeOH, and air-dried to give 53.0 mg (62%) of the title compound. $^1$H-NMR (DMSO-$d_6$) δ 9.87 (s, 1H), 9.71 (s, 1H), 9.60 (d, J=3.2 Hz, 1H), 8.34 (d, J=3.3, 1H), 8.10 (s, 1H), 8.04-8.02 (m, 4H), 7.76 (s, 1H), 7.59 (d, J=8.7 Hz, 2H), 7.52-7.50 (m, 1H), 2.64 (s, 3H); MS $[M+H]^+$=456.1; LCMS RT=3.25 min.

Example 99

Preparation of N-[4-(7-acetyl-4-aminopyrrolo[2,1-f][1,2,4]triazin-5-yl)phenyl]-N'-(6-bromopyridin-2-yl)urea

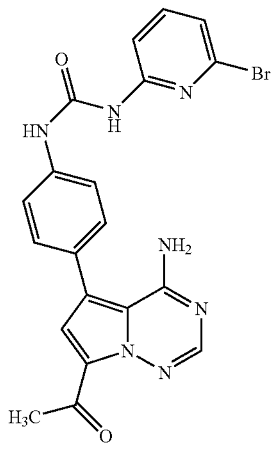

The procedure used for the preparation of Example 98 was used to prepare the title compound by substituting phenyl (6-bromopyridin-2-yl)carbamate for phenyl [6-(trifluoromethyl)pyridin-2-yl]carbamate in step 4. $^1$H-NMR (DMSO-$d_6$) δ 9.63 (s, 1H), 9.60 (d, J=2.5 Hz, 1H), 9.46 (s, 1H), 8.34 (d, J=3.2, 1H), 8.10 (s, 1H), 8.01 (d, J=8.7 Hz, 2H), 7.80 (d, J=8.2 Hz, 1H), 7.74 (s, 1H), 7.71-7.67 (m, 1H), 7.57 (d, J=8.6 Hz, 2H), 7.24 (d, J=7.6 Hz, 1H), 2.63 (s, 3H); MS $[M+H]^+$=466.1; LCMS RT=3.36 min.

Example 100

Preparation of N-[4-(7-acetyl-4-aminopyrrolo[2,1-f][1,2,4]triazin-5-yl)phenyl]-N'-[2-fluoro-5-(trifluoromethyl)phenyl]urea

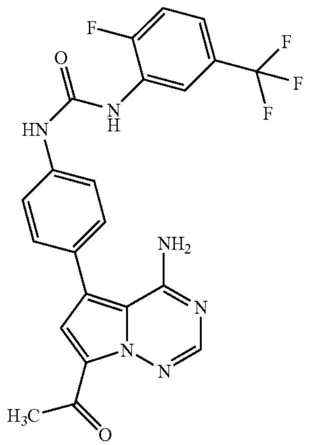

A suspension of 1-[4-amino-5-(4-aminophenyl)pyrrolo[2,1-f][1,2,4]triazin-7-yl]ethanone (50.0 mg, 0.19 mmol) and 2-fluoro-5-trifluoromethyl isocyanate (76.7 mg, 0.37 mmol) in 1,2-dichloroethane (2 mL) was heated (80° C.) overnight. After cooling, DMF (2 mL) and 2 N hydrochloric acid (0.1 mL) were added and the resulting solution was heated (80° C.) overnight. 1,2-Dichloroethane was evaporated under reduced pressure and the residue was suspended in MeOH (10 mL). The product was filtered and air-dried to give 65.2 mg (74%) of the title compound. $^1$H-NMR (DMSO-$d_6$) δ 9.60 (d, J=3.5 Hz, 1H), 9.37 (s, 1H), 8.95 (d, J=2.9, 1H), 8.64-8.62 (m, 1H), 8.34 (d, J=3.42 Hz, 1H), 8.10 (s, 1H), 8.02 (d, J=8.8 Hz, 2H), 7.75 (s, 1H), 7.59 (d, J=8.7 Hz, 2H), 7.53-7.48 (m, 1H), 7.41-7.38 (m, 1H), 2.64 (s, 3H); MS $[M+H]^+$=473.2; LCMS RT=3.35 min.

Example 101

Preparation of N-{4-[4-amino-7-(1-hydroxyethyl)pyrrolo[2,1-f][1,2,4]triazin-5-yl]phenyl}-N'-[6-trifluoromethyl)pyridin-2-yl]urea

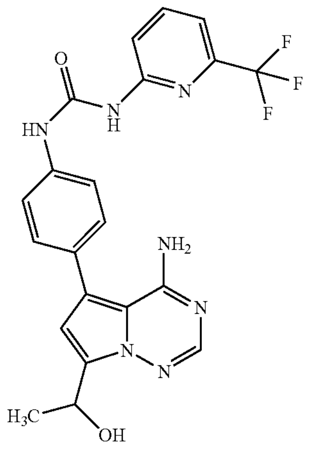

To a suspension of Example 98 (74.8 mg, 1.98 mmol) in MeOH (6 mL) was added $NaBH_4$ (24.9 mg, 0.66 mmol). The mixture was stirred at rt for 2 d. and then diluted with DMF (3 mL). This solution was purified directly by HPLC using a gradient of 15-90% MeCN in water to afford 14.4 mg (48%) of the title compound. $^1H$-NMR (DMSO-$d_6$) δ 9.87 (bs, 1H), 9.71 (bs, 1H), 8.04-7.98 (m, 5H), 7.56 (d, J=9.1 Hz, 2H), 7.52-7.50 (m, 1H), 7.03 (s, 1H), 6.68 (bs, 2H), 5.11 (q, J=6.4 Hz, 1H), 1.74 (s, 1H), 1.47 (d, J=6.7 Hz, 3H); MS $[M+H]^+$=458.1; LCMS RT=2.76 min.

Example 102

Preparation of N-{4-[4-amino-7-(1-hydroxyethyl) pyrrolo[2,1-f][1,2,4]triazin-5-yl]phenyl}-N'-(6-bromopyridin-2-yl)urea

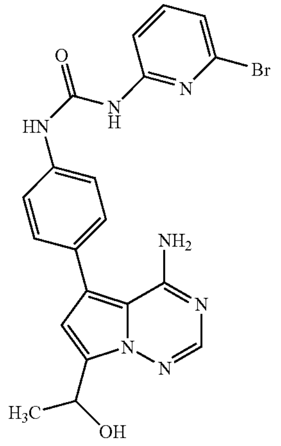

The procedure used for the preparation of Example 101 was used to prepare the title compound by substituting Example 99 for Example 98. $^1H$-NMR (DMSO-$d_6$) δ 9.63 (bs, 1H), 9.47 (bs, 1H), 8.02 (s, 1H), 7.98 (d, J=8.8 Hz, 2H), 7.79 (d, J=8.1 Hz, 1H), 7.71-7.68 (m, 1H), 7.56 (d, J=8.8 Hz, 2H), 7.24 (d, J=7.4 Hz, 1H), 7.02 (s, 1H), 6.68 (bs, 2H), 5.11 (q, J=6.0 Hz, 1H), 1.74 (s, 1H), 1.47 (d, J=6.7 Hz, 3H); MS $[M+H]^+$=468.0; LCMS RT=2.72 min.

Example 103

Preparation of N-{4-[4-amino-7-(morpholin-4-ylacetyl)pyrrolo[2,1-f][1,2,4]triazin-5-yl]phenyl}-N'-[2-fluoro-5-(trifluoromethyl)-phenyl]urea

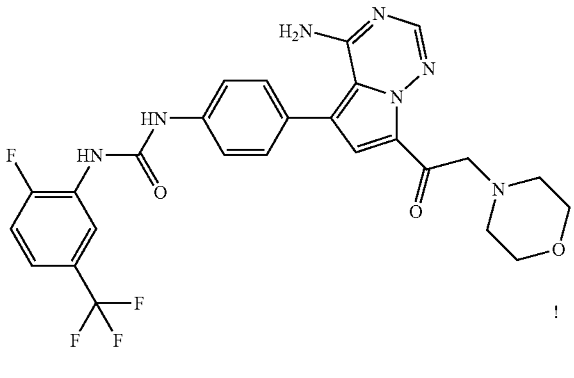

Step 1: Preparation of N-[4-(7-acetyl-4-aminopyrrolo[2,1-f][1,2,4]triazin-5-yl)-phenyl]-N'-[2-fluoro-5-(trifluoromethyl)phenyl]urea

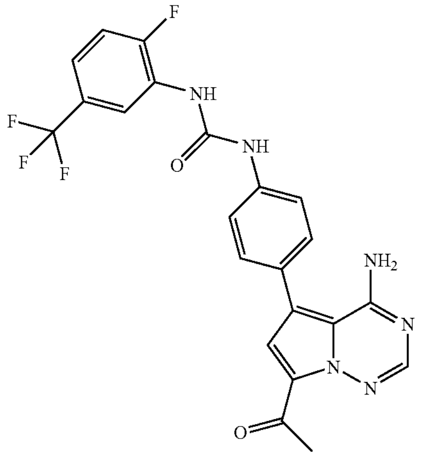

Step 1: Preparation of N-[4-(7-bromoacetyl-4-aminopyrrolo[2,1-f][1,2,4]triazin-5-yl)phenyl]-N'-[2-fluoro-5-(trifluoromethyl)phenyl]urea

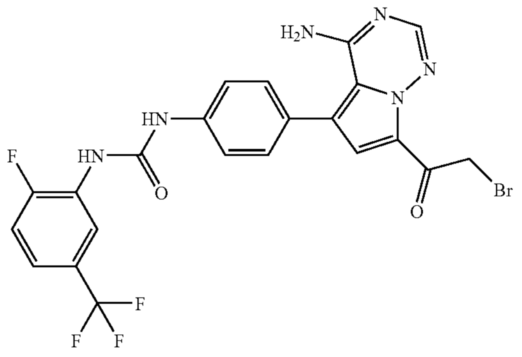

A suspension of Example 100 in THF (5 mL) was cooled to −78° C. and treated with diisopropylethyl amine (0.424 mL, 2.57 mmol) followed by trimethylsilyltriflate (0.421 mL, 2.177 mmol). The reaction was allowed to warm to rt over 30 min, then cooled again to −78° C. and treated with 1,3-dibromo-5,5-dimethylhydantoin (62 mg, 0.218 mmol). The reaction was allowed to stir for 1 h at −78 C, then warmed to rt and quenched with methanol (200 uL) and diluted with ethyl acetate and 1N sodium sulfite solution. The organic layer was separated, washed with 1 N bisulfate buffer (pH 2), dried with sodium sulfate and passed thru a silica plug. Evaporation of the solvent gave a yellow solid which was triturated with $Et_2O$:hexanes (1:1) to provide the title compound as a yellow solid (154 mg, 70% Yield). $^1H$-NMR (DMSO-$d_6$) δ 9.18 (s, 1H), 8.45 to 8.48 (m, 1H), 8.02 (s, 1H), 7.43 (d, J=8.4 Hz, 2H), 7.27 (d, J=8.4 Hz, 2H), 7.27 (s, 1H), 7.20 to 7.37 (m, 4H), 4.77 (s, 2H). MS $[M+H]^+$=551.2; LCMS RT=3.63.

Step 2; Preparation of Title Compound

A solution of N-[4-(7-bromoacetyl-4-aminopyrrolo[2,1-f][1,2,4]triazin-5-yl)phenyl]-N'-[2-fluoro-5-(trifluoromethyl)

phenyl]urea (65 mg, 0.12 mmol) in 2 mL THF was treated with morpholine (53 uL, 0.59 mmol) and allowed to stir for 15 min. The reaction was then diluted with 50 mL EtOAc and 5 mL toluene & washed with sodium carbonate solution (1×). The organic layer dried with sodium sulfate and concentrated to give a yellow oil. Trituration with $Et_2O$:hexanes (1:1) gave the title compound as a fainly yellow powder (52.4 mg, 79% Yield). $^1$H-NMR (DMSO-$d_6$) δ9.28 (s, 1H), 8.84 (s, 1H), 8.43 to 8.47 (m, 1H). 7.95 (s, 1H), 7.42 (d, J=8.7 Hz, 2H), 7.19 to 7.31 (m, 3H) 7.25 (d, J=8.7 Hz, 2H), 7.17 (s, 1H), 3.76 (s, 2H), 3.38 to 3.43 (m, 4H), 2.35 to 2.41 (m, 4H); MS $[M+H]^+$=557.9; LCMS RT=2.57.

Example 104

Preparation of N-{4-[4-amino-7-(1-hydroxy-1-methylethyl)pyrrolo[2,1-f][1,2,4]triazin-5-yl]phenyl}-N'-[2-fluoro-5-(trifluoromethyl)phenyl]urea

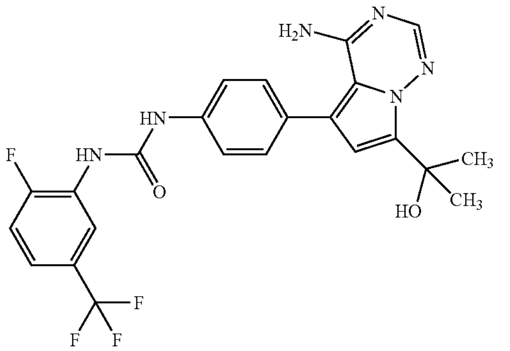

A suspension of the product of step 1 of Example 103 (48 mg, 0.10 mmol) in 2 mL THF was treated with methylmagnesium bromide (3N solution in $Et_2O$, 339 uL, 1 mmol) at rt. After stirring for 15 min at rt the reaction appeared complete by TLC (EtOAc). The reaction was quenched with 200 uL MeOH and diluted with 100 mL EtOAc and 100 mL 1N $NaH_2PO_4$ solution. The organic layer was dried ($Na_2SO_4$) and filtered through a silica plug before concentrating to a white solid (42.2 mg, 85% Yield). $^1$H-NMR (DMSO-$d_6$) 9.51 (s, 1H), 9.04 (bs, 1H), 8.62 (dd, J=7.2, 2 Hz, 1H), 7.88 (s, 1H), 7.57 (d, J=8.7 Hz, 2H), 7.44 to 7.53 (m, 1H), 7.39 (m, 1H), 7.37 (d, J=8.7 Hz, 2H), 7.13 (bs, 1H), 6.57 (s, 1H), 5.31 (s, 1H), 1.60 (s, 6H); MS $[M+H]^+$=489.2; LCMS RT=3.01.

Example 105

Preparation of N-{4-[4-amino-7-(hydroxymethyl)pyrrolo[2,1-f][1,2,4]triazin-5-yl]phenyl}-N'-[6-(trifluoromethyl)pyridin-2-yl]urea

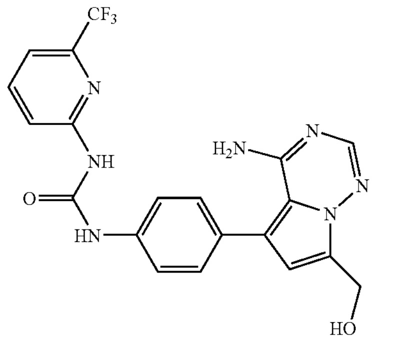

Step 1: Preparation of [4-amino-5-(4-aminophenyl)pyrrolo[2,1-f][1,2,4]triazin-7-yl]methanol

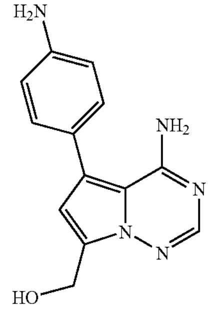

To a cooled (0° C.) solution of the product of step 4 of Example 96 (220.0 mg, 0.68 mmol) in THF (23 mL) was added diisobutylaluminum hydride (1 M in THF, 7.4 mL, 7.4 mmol). The mixture was allowed to warm to rt and stirred for 30 min. The reaction was cooled (0° C.) and quenched with methanol (1 mL). The mixture was poured into a vigorously stirred 1.2 M aqueous Rochelle's salt solution (50 mL). The resultant mixture was stirred for 30 min and then extracted with ethyl acetate (3×50 mL). The combined organic extracts were dried over sodium sulfate and concentrated to dryness under reduced pressure. The crude material was purified by HPLC using a gradient of 50-90% MeCN in water to yield 170.0 mg (99%) of the desired product containing trace impurities. $^1$H-NMR (DMSO-$d_6$) δ 8.14 (s, 1H), 7.38 (d, J=8.0 Hz, 2H), 7.07 (d, J=8.0 Hz, 2H), 6.76 (s, 1H), 4.75 (s, 2H); MS $[M+H]^+$=256.2; LCMS RT=1.05 min.

Step 2: Preparation of Title Compound

A solution of [4-amino-5-(4-aminophenyl)pyrrolo[2,1-f][1,2,4]triazin-7-yl]methanol (170.0 mg, 0.67 mmol), phenyl [6-(trifluoromethyl)pyridin-2-yl]carbamate (281.9 mg, 1.00 mmol), and triethylamine (0.46 mL, 1.33 mmol) in DMF (5 mL) was stirred at rt for 3 d. The crude reaction mixture was purified directly by HPLC using a gradient of 20-90% MeCN in water to yield 21.1 mg (7%) of the title compound. $^1$H-NMR (DMSO-$d_6$) δ9.89 (bs, 1H), 9.72 (bs, 1H), 8.05-7.98 (m, 2H), 7.89 (s, 1H), 7.57 (d, J=8.6 Hz, 2H), 7.51-7.49 (m, 1H), 7.40 (d, J=8.6 Hz, 1H), 6.64 (s, 1H), 5.19 (t, J=5.7 Hz, 1H), 4.74 (d, J=5.6 Hz, 3H); MS $[M+H]^+$=444.1; LCMS RT=2.63 min.

Example 106

Preparation of N-[4-(4-amino-7-{[(2,2,2-trifluoroethyl)amino]methyl}pyrrolo[2,1f][1,2,4]triazin-5-yl)phenyl]-M-[6-(trifluoromethyl)pyridin-2-yl]urea

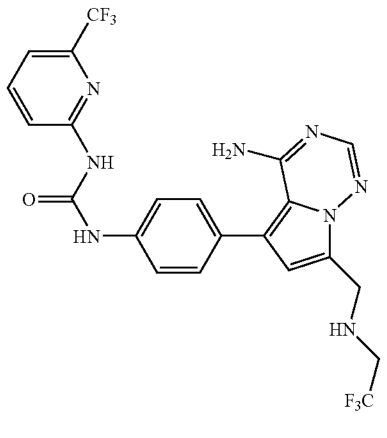

Step 1: Preparation of N-[4-(4-amino-7-formylpyrrolo[2,1-f][1,2,4]triazin-5-yl)phenyl]-N'-[6-(trifluoromethyl)pyridin-2-yl]urea

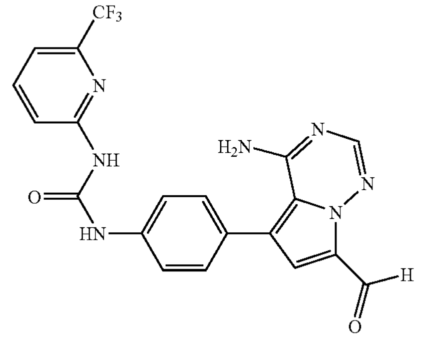

To a suspension of Example 105 (14.7 mg, 0.033 mmol) in THF (3 mL) was added 3,3,3-triacetoxy-3-iodophthalide (42.2 mg, 0.10 mmol). The mixture was stirred at rt under nitrogen for 4 d. The solvent was evaporated under reduced pressure. The residue was dissolved in DMF and purified by HPLC using a gradient of 20-90% MeCN in water to yield 6.0 mg (41%) of the title compound. $^1$H-NMR (DMSO-$d_6$) δ10.34 (s, 1H), 9.90 (bs, 1H), 9.75 (bs, 1H), 8.15 (s, 1H), 8.06-7.99 (m, 2H), 7.59 (d, J=8.6, 2H), 7.51 (dd, J=7.0, 1.1, Hz, 1H), 7.46 (d, J=8.5 Hz, 2H), 7.25 (s, 1H); MS $[M+H]^+$=442.1; LCMS RT=3.29 min.

Step 2: Preparation of Title Compound

To a suspension of N-[4-(4-amino-7-formylpyrrolo[2,1-f][1,2,4]triazin-5-yl)phenyl]-N'-[6-(trifluoromethyl)pyridin-2-yl]urea (5.0 mg, 0.011 mmol) in 1,2-dichloroethane (2 mL) was added 2,2,2-trifluoroethylamine (11.2 mg, 0.11 mmol), followed by sodium triacetoxyborohydride (24.0 mg, 0.11 mg). The mixture was stirred at rt under nitrogen for 4 d. The solvent was evaporated under reduced pressure. The residue was dissolved in DMF and purified by HPLC using a gradient of 20-90% MeCN in water to yield 2.1 mg (35%) of the title compound. $^1$H-NMR (DMSO-$d_6$) δ9.95 (bs, 1H), 9.79 (bs, 1H), 8.05-7.99 (m, 2H), 7.90 (s, 1H), 7.57 (d, J=8.6, 2H), 7.50 (dd, J=6.4, 1.7, Hz, 1H), 7.40 (d, J=8.6 Hz, 2H), 6.66 (s, 1H), 4.07 (d, J=6.8 Hz, 2H), 3.30-3.23 (m, 2H), 2.92-2.85 (m, 1H); MS $[M+H]^+$=525.1; LCMS RT=2.91 min.

Example 107

Preparation of N-{4-[4-amino-7-(3-morpholin-4-ylpropyl)pyrrolo[2,1-f][1,2,4]triazin-5-yl]phenyl}-N'-[4-(trifluoromethyl)pyridin-2-yl]urea

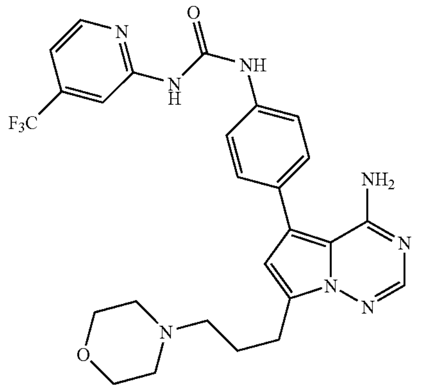

The procedure used for the preparation of Example 2 was used to prepare the title compound by substituting Intermediate X for Intermediate E and substituting Intermediate H for phenyl(3-tert-butylisoxazol-5-yl)carbamate. $^1$H-NMR (DMSO-$d_6$) δ 9.84 (s, 1H), 9.72 (s, 1H), 8.52 (d, J=6 Hz, 1H), 8.05 (s, 1H), 7.86 (s, 1H), 7.61 to 7.59 (m, 2H), 7.40 to 7.34 (m, 3H), 6.52 (s, 1H), 3.57 to 3.52 (m, 4H), 2.87 (t, J=7 Hz, 2H), 2.35 to 2.24 (m, 6H), 1.83 (t, J=7 Hz, 2H); MS $[M+H]^+$=541.2; LCMS RT=2.44 min Example 108

Preparation of N-{4-[4-amino-7-(3-morpholin-4-ylpropyl)pyrrolo[2,1-f][1,2,4]triazin-5-yl]phenyl}-N'-[2-fluoro-5-(trifluoromethyl)phenyl]urea

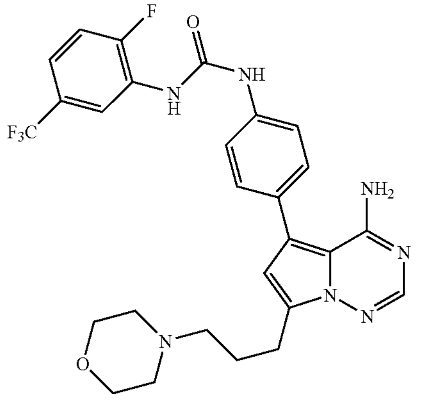

A mixture of Intermediate V (70 mg, 0.20 mmol), Intermediate M (130 mg, 0.30 mmol), $Na_2CO_3$ (44 mg, 0.40 mmol), tetrakis-(triphenylphosphine)palladium (24 mg, 0.02 mmol), toluene (3.5 ml) and $H_2O$ (0.45 ml) was degassed and filled with $N_2$ and was heated at 80 C under $N_2$ for 16 h. After cooled to rt, the reaction mixture was added ethyl acetate and washed with aq. saturated $NaHCO_3$ and dried over $Na_2SO_4$. The crude was concentrated and purified via column chromatography (95:5 v/v $CH_2Cl_2$-$CH_3OH$) to afford 17 mg of the title compound (yield 15%). $^1$H-NMR (DMSO-$d_6$) δ 9.28 (s, 1H), 8.93 (d, J=3 Hz, 1H), 8.62 (dd, J=8, 3 Hz, 1H), 7.86 (s, 1H), 7.57 to 7.35 (m, 6H), 6.52 (s, 1H), 3.53 (t, J=4 Hz, 4H), 2.87 (t, J=7 Hz, 2H), 2.35 to 2.24 (m, 6H), 1.85 to 1.80 (m, 2H); MS $[M+H]^+$=558.2; LCMS RT=2.62 min Example 109

Preparation of N-{4-[4-amino-7-(3-morpholin-4-ylpropyl)pyrrolo[2,1-f][1,2,4]triazin-5-yl]-2-fluorophenyl}-N'-[2-fluoro-5-(trifluoromethyl)phenyl]urea

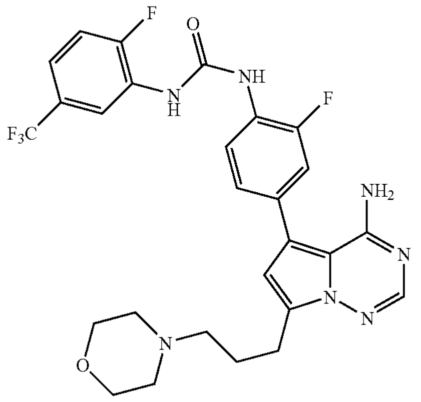

The procedure used for the preparation of Example 108 was used to prepare the title compound by substituting Intermediate O for Intermediate M. $^1$H-NMR (DMSO-$d_6$) δ 9.39 (d, J=3 Hz, 1H), 9.24 (d, J=3 Hz, 1H), 8.65 (dd, J=7, 3 Hz, 1H), 8.24 (t, J=7 Hz, 1H), 7.87 (s, 1H), 7.53 (t, J=8 Hz, 1H), 7.41 to 7.38 (m, 1H), 7.32 to 7.19 (m, 2H), 6.56 (s, 1H), 3.53 (t, J=4 Hz, 4H), 2.87 (t, J=4 Hz, 2H), 2.35 to 2.24 (m, 6H), 1.85 to 1.80 (m, 2H); MS $[M+H]^+$=576.2; LCMS RT=2.92 min.

Example 110

Preparation of tert-butyl 4-(4-amino-5-3-fluoro-4-[([2-fluoro-5-(trifluoromethyl)phenyl]aminocarbonyl)amino]phenylpyrrolo[2,1f][1,2,4]triazin-7-yl)piperidine-1-carboxylate

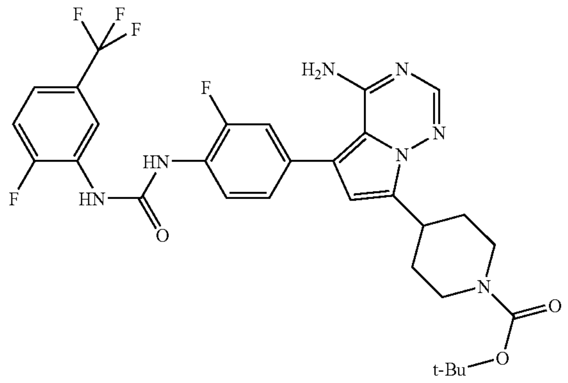

To a flask charged with $N_2$ was added Intermediate AC (1.29 g, 3.26 mmol) and Intermediate O (1.44 g, 3.26 mmol) followed by 1,4-dioxane (31 mL). $N_2$ was bubbled through the solution for 15 min and then dichlorobis(triphenylphosphine)palladium(II) (229 mg, 0.326 mmol) was added followed by aq 1M $Na_2CO_3$ (6.51 mL, 6.51 mmol). $N_2$ was bubbled through the solution for an additional 15 min and, then the reaction was heated to 80° C. for 17 h. The reaction material was allowed to cool to rt and was diluted with EtOAc and water. The solution was separated and the aqueous layer was back extracted with EtOAc. The organic fractions were combined, dried ($MgSO_4$), filtered, condensed, and purified by flash column chromatography (9:1 $CH_2Cl_2$/MeOH). The material was further purified by flash chromatography (50:47:3 $CH_2Cl_2$/EtOAc/MeOH). The purified fractions were collected, evaporated, and left under vacuum overnight to yield 942 mg (46%) of the desired product. $^1$H-NMR (DMSO-$d_6$) δ 9.43 (s, 1H), 9.27 (s, 1H), 8.67 (d, J=7.5 Hz, 1H), 8.28 (t, J=8.5 Hz, 1H), 7.92 (s, 1H), 7.53 (t, J=9.9 Hz, 1H), 7.45-7.40 (m, 1H), 7.34 (d, J=10.5 Hz, 1H), 7.24 (d, J=9.5 Hz, 1H), 6.62 (s, 1H), 4.08 (d, J=11.2 Hz, 2H), 3.343.29 (m, 1H), 2.97-2.82 (br s, 2H), 2.00 (d, T=7.4 Hz, 2H), 1.60-1.51 (m, 2H), 1.42 (s, 9H); MS $[M+H]^+$=632; LCMS RT=3.42.

Example 111

Preparation of N-[4-(4-amino-7-piperidin-4-ylpyrrolo[2,1-f][1,2,4]-triazin-5-yl)-2-fluorophenyl]-N'-[2-fluoro-5-(trifluoromethyl)phenyl]urea

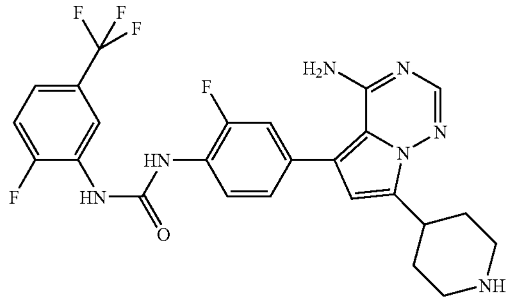

To a solution of Example 110 (40 mg, 0.063 mmol) in $CH_2Cl_2$ (1.5 mL) was added trifluoroacetic acid (0.15 mL). The solution was stirred at rt for 2 h and was then treated with aq $NaHCO_3$, EtOAc, and separated washing with water. The product was purified by prep HPLC (1:9 ACN/$H_2O$ ramping to 9:1 ACN/$H_2O$ with 0.1% TFA). The resulting fractions were combined and treated with aq $NaHCO_3$, EtOAc, and separated. The organic was washed with water, collected, dried ($Na_2SO_4$), filtered, and evaporated to dryness yielding 29 mg (86%) of the desired product as a white solid. $^1$H-NMR (DMSO-$d_6$) δ 9.41 (s, 1H), 9.25 (s, 1H), 8.65 (d, J=7.6 Hz, 1H), 8.25 (t, J=8.6 Hz, 1H), 7.88 (s, 1H), 7.51 (t, J=9.6 Hz, 1H), 7.41-7.38 (m, 1H), 7.32 (d, J=12.3 Hz, 1H), 7.23 (d, J=8.3 Hz, 1H), 6.53 (s, 1H), 3.23-3.15 (m, 1H), 3.02 (d, J=12.1 Hz, 2H), 2.63 (t, J=12.0 Hz, 2H), 1.92 (d, J=13.7 Hz, 2H), 1.54 (d, J=12.2 Hz, 2H); MS $[M+H]^+$=532; LCMS RT=2.38.

Example 112

Preparation of N-(4-4-amino-7,1-(trifluoroacetyl)piperidin-4-yl]pyrrolo[2,1f][1,2,4]triazin-5-yl-2-fluorophenyl)-N'-[2-fluoro-5-(trifluoromethyl)-phenyl]urea

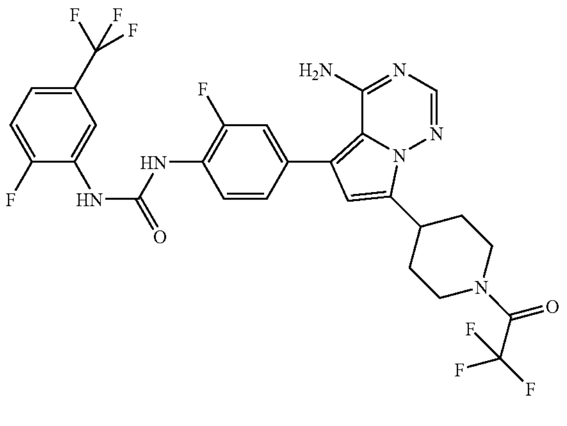

To a solution of Example 111 (90 mg, 0.17 mmol) in THF (1.7 mL) was added trifluoroacetic anhydride (48 μL, 0.34 mmol). The solution was heated to 60° C. for 2 h. The cooled reaction material was diluted with EtOAc, aq 1N NaOH, and separated. The organic layer was washed with water and the organic was collected, dried ($Na_2SO_4$), filtered, and evaporated. The material was purified by flash chromatography (9:1 $CH_2Cl_2$/MeOH) producing 66 mg (62%) of the title compound. $^1$H-NMR (DMSO-$d_6$) δ 9.41 (s, 1H), 9.26 (s, 1H), 8.65 (d, J=8.9 Hz, 1H), 8.26 (t, J=8.7 Hz, 1H), 7.91 (s, 1H), 7.51 (t, J=9.8 Hz, 1H), 7.43-7.39 (m, 1H), 7.32 (d, J=14.1 Hz, 1H), 7.23 (d, J=8.9 Hz, 1H), 6.63 (s, 1H), 4.40 (d, J=11.4 Hz, 1H), 3.96 (d, J=14.9 Hz, 1H), 3.55-3.44 (m, 2H), 3.12-3.05 (m, 1H), 2.17-2.10 (m, 2H), 1.70-1.64 (m, 2H); MS $[M+H]^+$=628; LCMS RT=3.39.

Example 113

Preparation of N-4-[4-amino-7-(1-methylpiperidin-4-yl)pyrrolo[2,1-f][1,2,4]triazin-5-yl]-2-fluorophenyl-N'-[2-fluoro-5-(trifluoromethyl)phenyl]urea

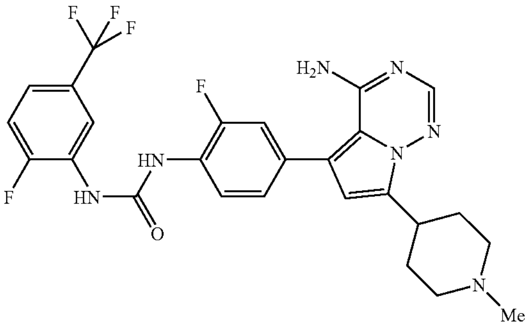

To a solution of Example 111 (40 mg, 0.075 mmol) in THF (1.0 mL) was added 37% formaldehyde in water (6 μL, 0.075 mmol) followed by AcOH (6 μL, 0.11 mmol). The solution was stirred at it for 1 h and then sodium triacetoxyborohydride (32 mg, 0.15 mmol) was added. The reaction was allowed to stir for an additional 1 h. The reaction mixture was diluted with aq $NaHCO_3$ and EtOAc and was transferred to a separatory funnel, separated, washed with water, dried, ($Na_2SO_4$), filtered and evaporated under reduced pressure. The material was purified by flash chromatography (85:15 $CH_2Cl_2$/MeOH with 1% ammonium hydroxide). The resulting purified fractions were combined and evaporated, diluted with aq $NaHCO_3$ and EtOAc, transferred to a separatory funnel, separated, washed with water, dried, ($Na_2SO_4$), filtered and evaporated to yield 26 mg (63%) of the title compound as a white solid. $^1$H-NMR (DMSO-$d_6$) δ 9.41 (s, 1H), 9.24 (s, 1H), 8.65 (d, J=9.0 Hz, 1H), 8.25 (t, J=8.5 Hz, 1H), 7.88 (s, 1H), 7.51 (t, J=8.7 Hz, 1H), 7.42-7.38 (m, 1H), 7.32 (d, J=12.1 Hz, 1H), 7.23 (d, J=8.3 Hz, 1H), 6.55 (s, 1H), 3.06-3.00 (m, 1H), 2.85 (d, J=11.0 Hz, 2H), 2.18 (s, 3H), 2.02-1.93 (m, 2H), 1.72-1.63 (m, 2H); MS $[M-F1-1]^+$=546; LCMS RT=2.39.

Example 114

Preparation of N-4-[4-amino-7-(1-glycoloylpiperidin-4-yl)pyrrolo[2,1-f][1,2,4]triazin-5-yl]-2-fluorophenyl-N'-[2-fluoro-5-(trifluoromethyl)phenyl]urea

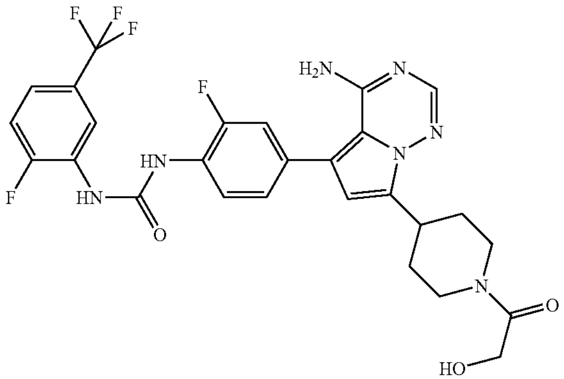

To a solution of Example 111 (50 mg, 0.094 mmol) in DMF (1.0 mL) was added glycolic acid (7 mg, 0.094 mmol), and benzotriazolyloxytris(dimethylamino)phosphonium $PF_6$ (42 mg, 0.094 mmol) followed by 4-methylmorpholine (10 μL, 0.094 mmol). The solution was stirred at rt for 17 h, then evaporated under reduced pressure, and purified by flash chromatography (9:1 $CH_2Cl_2$/MeOH). The purified fractions were combined and triturated with $CH_2Cl_2/Et_2O$ yielding 55 mg (99%) of desired compound. $^1$H-NMR (DMSO-$d_6$) δ 9.42 (s, 1H), 9.25 (s, 1H), 8.65 (d, J=7.6 Hz, 1H), 8.26 (t, J=8.6 Hz, 1H), 7.91 (s, 1H), 7.51 (t, J=10.1 Hz, 1H), 7.42-7.38 (m, 1H), 7.31 (d, J=12.1 Hz, 1H), 7.22 (d, J=9.8 Hz, 1H), 6.57 (s, 1H), 4.53-4.45 (m, 2H), 4.12-4.09 (m, 2H), 3.78 (d, J=11.4 Hz, 1H), 3.14 (t, J=11.5 Hz, 1H), 2.78 (t, J=12.3 Hz, 1H), 2.02 (d, J=12.3 Hz, 2H), 1.68-1.49 (m, 2H); MS $[M+H]^+$=590; LCMS RT=2.88.

Example 115

Preparation of N-(4-4-amino-7-[1-(morpholin-4-ylacetyl)piperidin-4-yl]pyrrolo[2,1-f][1,2,4]triazin-5-yl-2-fluorophenyl)-N'-[2-fluoro-5-(trifluoromethyl)-phenyl]urea

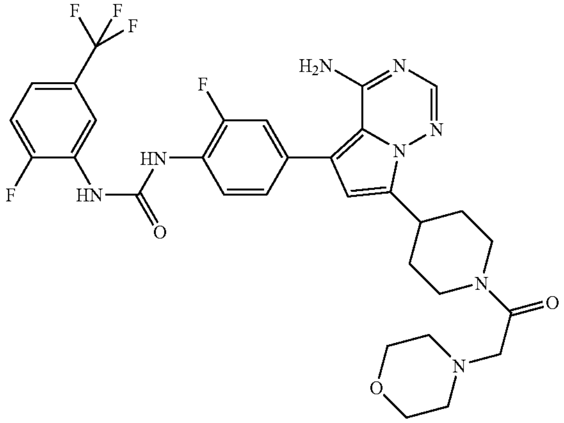

To a solution of Example 114 (20 mg, 0.034 mmol) in THF (2 mL) was added 2M $SOCl_2$ in $CH_2Cl_2$ (0.17 mL, 0.34 mmol). The solution was allowed to stir at rt for 15 min and was then evaporated under reduced pressure chasing with $CH_2Cl_2$. THF (4 mL) was added to the crude reaction mixture followed by morpholine (30 μL, 0.34 mmol) and the reaction was heated to 60° C. for 6 h. The reaction mixture was allowed to cool, was evaporated, and then purified by flash chromatography (5:4:1 $CH_2Cl_2$/EtOAc/MeOH). The resulting fractions, upon evaporation, yielded 19 mg (85%) of the desired compound as a yellow solid. $^1$H-NMR (DMSO-$d_6$) δ 9.41 (s, 1H), 9.25 (s, 1H), 8.65 (d, J=6.7 Hz, 1H), 8.25 (t, J=8.6 Hz, 1H), 7.89 (s, 1H), 7.51 (t, J=9.7 Hz, 1H), 7.42-7.38 (m, 1H), 7.32 (d, J=12.1 Hz, 1H), 7.22 (d, J=8.0 Hz, 1H), 6.56 (s, 1H), 4.46 (d, J=13.2 Hz, 1H), 4.16 (d, J=13.1 Hz, 1H), 3.58-3.53 (m, 4H), 3.42-3.35 (m, 1H), 3.26 (d, J=14.7 Hz, 1H), 3.18-3.12 (m, 1H), 3.05 (d, J=13.1 Hz, 1H), 2.73-2.67 (m, 1H), 2.42-2.38 (m, 4H), 2.06-1.98 (m, 2H), 1.73-1.63 (m, 1H), 1.52-1.45 (m, 1H); MS $[M+H]^+$=659; LCMS RT=2.57.

Example 116

Preparation of N-(4-4-amino-7-[1-(2-hydroxyethyl) piperidin-4-yl]pyrrolo[2,1f][1,2,4]triazin-5-yl-2-fluorophenyl)-N'-[2-fluoro-5-(trifluoromethyl)phenyl]urea

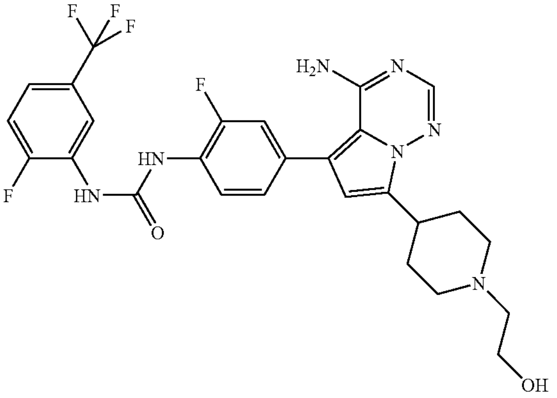

A suspension of Example 114 (27 mg, 0.046 mmol) in THF (2.5 mL) was sonicated for 10 min and then treated with 1 M diisobutylaluminum hydride in THF (0.92 mL, 0.92 mmol). The solution was stirred at rt for 1 h. The rxn mixture was treated with EtOAc followed by aq Rochelle's salt. This heterogeneous mixture was then heated at 60° C. for 30 min. The solution was transferred to a separatory funnel, separated and washed with water. The aq layer was back extracted with EtOAc. The organic solution was dried ($Na_2SO_4$), filtered, evaporated, and purified by prep HPLC (1:9 ACN/$H_2O$ ramping to 9:1 ACN/$H_2O$ with 0.1% TFA). The purified fractions were diluted in EtOAc washed with 1N NaOH, aq saturated $NaHCO_3$, and water, and then dried ($Na_2SO_4$), filtered and evaporated under reduced pressure yielding 19 mg (72%) of desired product as a white solid. $^1$H-NMR (DMSO-$d_5$) δ 9.42 (s, 1H), 9.26 (s, 1H), 8.66 (d, J=7.1 Hz, 1H), 8.26 (t, J=8.7 Hz, 1H), 7.89 (s, 1H), 7.54-7.49 (m, 1H), 7.42-7.39 (m, 1H), 7.32 (d, J=11.8 Hz, 1H), 7.23 (d, J=7.9 Hz, 1H), 6.56 (s, 1H), 4.38 (t, J=5.1 Hz, 1H), 3.52-3.48 (m, 2H), 3.10-3.02 (m, 1H), 2.98-2.95 (m, 2H), 2.40 (t, J=6.4 Hz, 2H), 2.11-2.05 (m, 2H), 1.98-1.92 (m, 2H), 1.73-1.63 (m, 2H); MS $[M+H]^+$=576; LCMS RT=2.38.

Example 117

Preparation of N-4-[7-(1-allylpiperidin-4-yl)-4-aminopyrrolo[2,1-f][1,2,4]triazin-5-yl]-2-fluorophenyl-N'-[2-fluoro-5-(trifluoromethyl)phenyl]urea

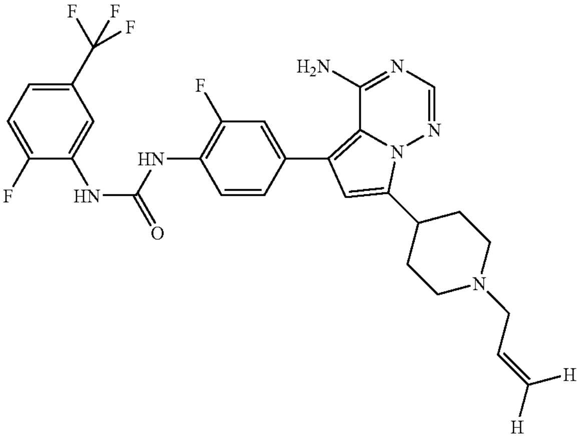

A suspension of Example 111 (100 mg, 0.19 mmol) in THF (4 mL) was sonicated for 5 min and then treated with $K_2CO_3$ (36 mg, 0.26 mmol) followed by allyl bromide (23 μL, 0.26 mmol). The solution was heated at 60° C. for 5 h. The reaction material was diluted with EtOAc and washed with water, dried ($Na_2SO_4$), filtered, evaporated yielding 99 mg (92%) of the desired product as a white solid. $^1$H-NMR ($CD_3OD$) δ 8.64 (d, J=7.9 Hz, 1H), 8.25 (t, J=8.6 Hz, 1H), 7.82 (s, 1H), 7.36-7.33 (m, 2H), 7.30-7.25 (m, 2H), 6.58 (s, 1H), 6.01-5.91 (m, 1H), 5.43-5.36 (m, 2H), 3.37 (d, J=7.0 Hz, 2H), 3.34-3.29 (m, 2H), 2.58 (t, J=11.6 Hz, 2H), 2.25 (d, J=13.5 Hz, 2H), 1.97-1.88 (m, 3H); MS $[M+H]^+$=572; LCMS RT=2.48.

Example 118

Preparation of ethyl [4-(4-amino-5-3-fluoro-4-[([2-fluoro-5-(trifluoromethyl)phenyl]aminocarbonyl) amino]phenylpyrrolo[2,1f][1,2,4]triazin-7-yl)piperidin-1-yl]acetate

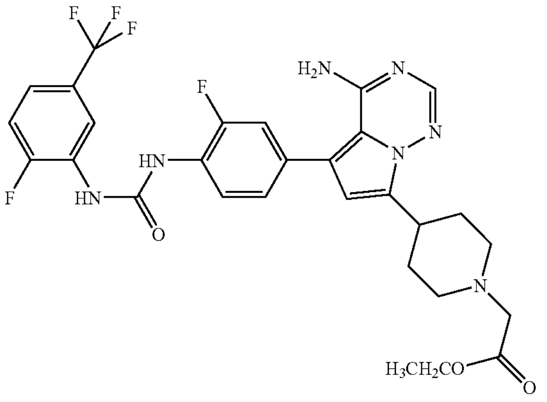

A suspension of Example 111 (100 mg, 0.19 mmol) in THF (2 mL) was sonicated for 5 min and then treated with $K_2CO_3$ (29 mg, 0.21 mmol) followed by ethyl chloroacetate (22 μL, 0.21 mmol). The solution was heated at 60° C. for 23 h. The reaction material was diluted with EtOAc and washed with water. The aqueous layer was back extracted with EtOAc twice, and the combined organic fractions were dried ($Na_2SO_4$), filtered, and evaporated. The crude material was purified first by flash chromatography (50:45:5 $CH_2Cl_2$/EtOAc/MeOH) and finally by prep HPLC (1:9 ACN/$H_2O$ ramping to 9:1 ACN/$H_2O$ with 0.1% TFA. The resulting purified fractions were taken into EtOAc, washed with aq 1N NaOH, aq saturated $NaHCO_3$, and water, and then dried ($Na_2SO_4$), filtered and reduced yielding 95 mg (82%) of the title compound as a white solid. $^1$H-NMR (DMSO-$d_6$) 9.41 (s, 1H), 9.25 (s, 1H), 8.65 (d, J=6.8 Hz, 1H), 8.26 (t, J=8.6 Hz, 1H), 7.88 (s, 1H), 7.53-7.48 (m, 1H), 7.42-7.38 (m, 1H), 7.32 (d, J=12.2 Hz, 1H), 7.23 (d, J=8.4 Hz, 1H), 6.58 (s, 1H), 4.08 (q, J=7.1 Hz, 2H), 3.23 (s, 2H), 3.10-3.02 (m, 1H), 2.93 (d, J=10.0 Hz, 2H), 2.34-2.29 (m, 2H), 1.96 (d, J=12.1 Hz, 2H), 1.75-1.65 (m, 2H), 1.19 (t, J=7.0 Hz, 3H); MS [M+H]$^+$=618; LCMS RT=2.59.

Example 119

Preparation of [4-(4-amino-5-3-fluoro-4-[({[2-fluoro-5-(trifluoromethyl)-phenyl]aminocarbonyl) amino}phenylpyrrolo[2,1f][1,2,4]triazin-7-yl)piperidin-1-yl]acetic acid

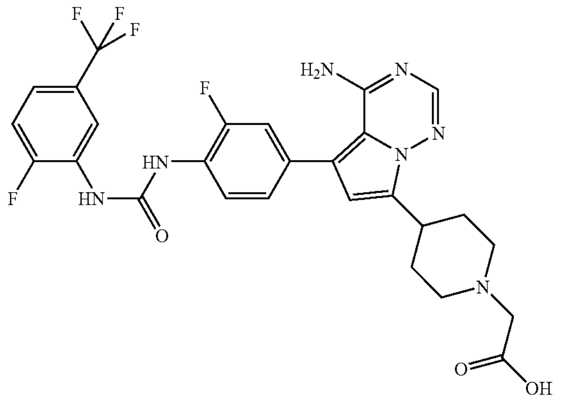

To a solution of THF (5 mL) was added MeOH (2.5 mL) followed by Example 118 (57 mg, 0.093 mmol) and aq 1N NaOH (0.93 mL, 0.93 mmol). The solution was stirred at 60° C. for 1 h and then aq 1N HCl (0.93 mL, 0.93 mmol) was added. The solution was slowly reduced by rotary evaporation as a white precipitate formed which was filtered and washed with water. The solid was collected and dried under vacuum yielding 49 mg (90%) of the desired compound. $^1$H-NMR (DMSO-$d_6$) δ 9.43 (s, 1H), 9.28 (s, 1H), 8.65 (d, J=7.2 Hz, 1H), 8.27 (t, J=8.6 Hz, 1H), 7.91 (s, 1H), 7.54-7.49 (m, 1H), 7.43-7.39 (m, 1H), 7.33 (d, J=12.4 Hz, 1H), 7.24 (d, J=7.8 Hz, 1H), 6.60 (s, 1H), 3.59 (s, 2H), 3.39-3.35 (m, 2H), 3.30-3.24 (m, 2H), 2.92-2.86 (m, 2H), 2.15-2.10 (m, 2H), 1.96-1.88 (m, 2H); MS [M+H]$^+$=590; LCMS RT=2.49.

Example 120

Preparation of 2-[4-(4-amino-5-3-fluoro-4-[([2-fluoro-5-(trifluoromethyl)phenyl]aminocarbonyl) amino]phenylpyrrolo[2,1-f][1,2,4]triazin-7-yl)piperidin-1-yl]-N-methylacetamide

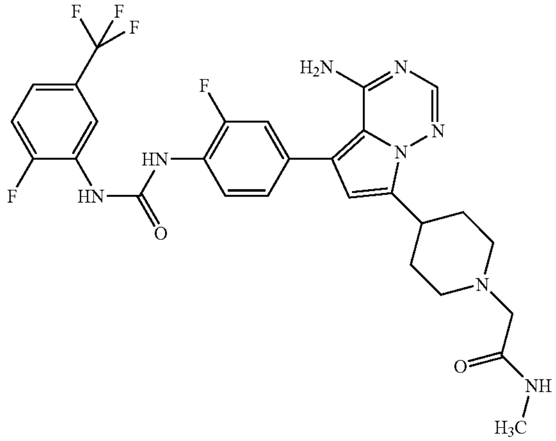

The procedure used for the preparation of Example 114 was used to prepare the title compound by substituting methyl amine for Example 111 and Example 119 for glycolic acid. $^1$H-NMR (DMSO-$d_6$) δ 9.43 (s, 1H), 9.27 (s, 1H), 8.66 (d, J=7.4 Hz, 1H), 8.26 (t, J=8.6 Hz, 1H), 7.89 (s, 1H), 7.71-7.67 (m, 1H), 7.54-7.49 (m, 1H), 7.43-7.39 (m, 1H), 7.32 (d, J=12.2 Hz, 1H), 7.23 (d, J=8.5 Hz, 1H), 6.55 (s, 1H), 3.10-3.04 (m, 1H), 2.91 (s, 2H), 2.87 (d, J=6.4 Hz, 2H), 2.61 (d, J=4.7 Hz, 3H), 2.22-2.17 (m, 2H), 1.97 (d, J=11.6 Hz, 2H), 1.82-1.76 (m, 2H); MS [M+H]$^+$=603; LCMS RT=2.47.

Example 121

Preparation of N-(4-4-amino-7-[1-(2,3-dihydroxypropyl)piperidin-4-yl]pyrrolo[2,1-f][1,2,4]triazin-5-yl-2-fluorophenyl)-N %[2-fluoro-5-(trifluoromethyl)-phenyl]urea

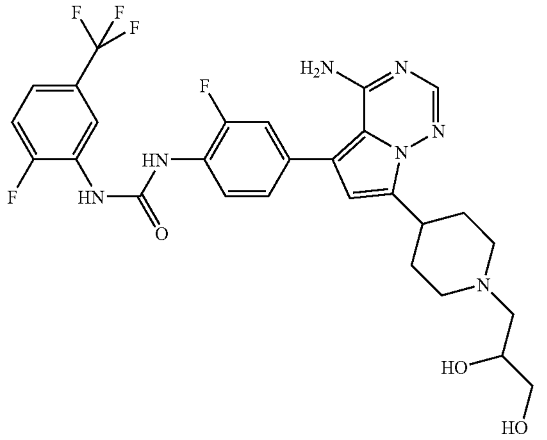

To a solution of Example 117 (80 mg, 0.14 mmol) in THF (2 mL) was added water (1 mL) 2.5% osmium tetroxide in isopropanol (0.14 mL, 0.014 mmol), and N-methylmorpholine N-oxide (25 mg, 0.21 mmol). The solution was stirred at rt for 17 h and then treated with aq saturated $Na_2SO_3$ in aq saturated $NaHCO_3$ (1:1) and EtOAc. The reaction mixture was allowed to stir for 1 h and then was separated washing with aq saturated $Na_2CO_3$ and water. The water layer was back extracted with EtOAc (3×). The combined organic fractions were dried $Na_2SO_4$, filtered, evaporated, and triturated in MeOH. The solid was collected and washed with ether. The mother liquor was evaporated and purified by prep HPLC (1:9 ACN/$H_2O$ ramping to 9:1 ACN/$H_2O$ with 0.1% TFA). The resulting purified fractions were taken into EtOAc, washed with aq $Na_2CO_3$, and water, dried ($Na_2SO_4$), filtered, evaporated, and dried under vacuum yielding a combined 58 mg (68%) of the title compound. $^1$H-NMR (DMSO-$d_6$) δ 9.41 (s, 1H), 9.25 (s, 1H), 8.65 (d, J=7.3 Hz, 1H), 8.25 (t, J=8.6 Hz, 1H), 7.83 (s, 1H), 7.53-7.48 (m, 1H), 7.42-7.38 (m, 1H), 7.32 (d, J=12.2 Hz, 1H), 7.23 (d, J=8.9 Hz, 1H), 6.56 (s, 1H), 4.61-4.52 (br s, 1H), 4.39 (s, 1H), 3.64-3.58 (m, 1H), 3.10-2.94 (m, 3H), 2.42-2.36 (m, 1H), 2.32-2.24 (m, 1H), 2.14-2.06 (m, 2H), 1.98-1.93 (m, 2H), 1.72-1.63 (m, 2H); MS $[M+H]^+$=606; LCMS RT=2.36.

Example 122

Preparation of N-(4-4-amino-7-[1-(2,2,2-trifluoroethyl)piperidin-4-yl]pyrrolo[2,1-f][1,2,4]triazin-5-yl-2-fluorophenyl)-N'-[2-fluoro-5-(trifluoromethyl)phenyl]urea

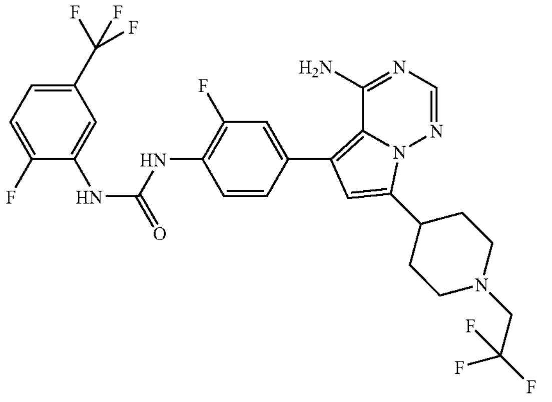

The procedure used for the preparation of Example 116 was used to prepare the title compound by substituting Example 112 for Example 114. $^1$H-NMR ($CD_2Cl_2$) δ 8.58 (d, J=7.3 Hz, 1H), 8.24 (t, J=8.4 Hz, 1H), 7.90 (s, 1H), 7.59 (s, 1H), 7.50 (s, 1H), 7.32-7.19 (m, 4H), 6.49 (s, 1H), 5.52 (s, 2H), 3.24-3.17 (m, 1H), 3.09-2.99 (m, 2H), 2.54 (t, J=11.6 Hz, 2H), 2.08 (d, J=11.6 Hz, 2H), 1.85-1.76 (m, 21-1); MS $[M+H]^+$=614; LCMS RT=3.15.

Example 123

Preparation of 4-4-amino-5-[3-fluoro-4-([4-(trifluoromethyl)pyridin-2-yl]carbamoylamino)phenyl]pyrrolo[2,1-f][1,2,4]triazin-7-yl-N-ethylpiperidine-1-carboxamide

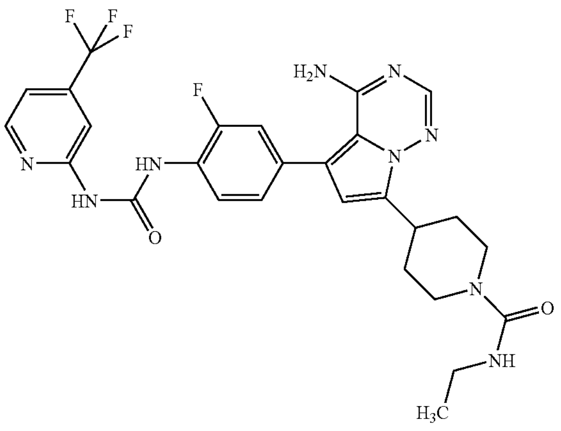

To a solution of DCE (1.5 mL) was added Example 271 (40 mg, 0.078 mmol) and ethyl isocyanate (6 μL, 0.078 mmol). The solution was stirred at rt for 17 h. A solid precipitate formed which was filtered and washed with $CH_2Cl_2$ yielding 37 mg (81%) of the desired compound. $^1$H-NMR (DMSO-$d_6$) δ 10.13 (s, 1H), 10.06-10.04 (br s, 1H), 8.54 (d, J=5.3 Hz, 1H), 8.25 (t, J=8.5 Hz, 1H), 8.00 (s, 1H), 7.89 (s, 1H), 7.38 (d, J=5.4 Hz, 1H), 7.34 (d, J=12.2 Hz, 1H), 7.24 (d, J=8.3 Hz, 1H), 6.58 (s, 1H), 6.47 (t, J=5.4 Hz, 1H), 4.06 (d, J=12.3 Hz, 2H), 3.29-3.23 (m, 1H), 3.07-3.00 (m, 2H), 2.78 (t, J=12.2 Hz, 2H), 1.94 (d, J=13.2 Hz, 2H), 1.57-1.47 (m, 2H), 0.99 (t, J=7.2 Hz, 3H); MS $[M+H]^+$=586; LCMS RT=2.85.

Example 124

Preparation of 4-4-amino-5-[3-fluoro-4-([4-(trifluoromethyl)pyridin-2-yl]carbamoylamino)phenyl]pyrrolo[2,1-f][1,2,4]triazin-7-yl-N-tert-butylpiperidine-1-carboxamide

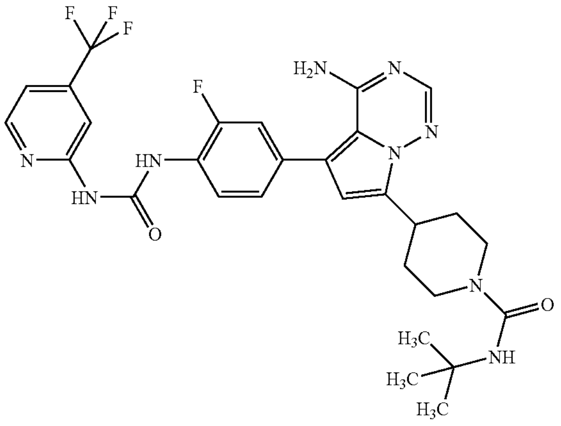

The procedure used for the preparation of Example 123 was used to prepare the title compound by substituting tert-butyl isocyanate for ethyl isocyanate. $^1$H-NMR (DMSO-$d_6$) δ 10.12 (s, 1H), 10.07-10.03 (br s, 1H), 8.54 (d, J=5.2 Hz, 1H), 8.26 (t, J=8.6 Hz, 1H), 8.00 (s, 1H), 7.89 (s, 1H), 7.38 (d, J=5.4 Hz, 1H), 7.35 (d, J=11.8 Hz, 1H), 7.24 (d, J=8.1 Hz, 1H), 6.57 (s, 1H), 5.77 (s, 1H), 4.06 (d, J=12.8 Hz, 2H), 3.25-3.22 (m, 1H), 2.73 (t, J=11.8 Hz, 2H), 1.94 (d, J=13.3 Hz, 2H), 1.58-1.49 (m, 2H), 1.24 (s, 9H); MS $[M+H]^+$=614; LCMS RT=3.09.

Example 125

Preparation of 4-4-amino-5-[3-fluoro-4-([4-(trifluoromethyl)pyridin-2-yl]carbamoylamino)phenyl]pyrrolo[2,1-f][1,2,4]triazin-7-yl-N-isopropylpiperidine-1-carboxamide

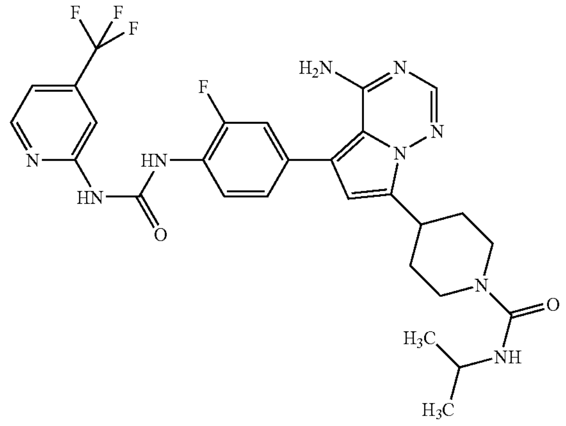

The procedure used for the preparation of Example 123 was used to prepare the title compound by substituting isopropyl isocyanate for ethyl isocyanate. $^1$H-NMR (DMSO-$d_6$) δ 10.13 (s, 1H), 10.08-10.02 (br s, 1H), 8.54 (d, J=4.7 Hz, 1H), 8.26 (t, J=8.4 Hz, 1H), 8.00 (s, 1H), 7.90 (s, 1H), 7.38 (d, J=5.6 Hz, 1H), 7.34 (d, J=12.1 Hz, 1H), 7.24 (d, J=8.1 Hz, 1H), 6.58 (s, 1H), 6.16 (d, J=7.7 Hz, 1H), 4.08 (d, J=14.6 Hz, 2H), 3.77-3.72 (m, 1H), 3.28-3.22 (m, 1H), 2.76 (t, J=11.9 Hz, 2H), 1.94 (d, J=9.7 Hz, 2H), 1.57-1.47 (m, 2H), 1.04 (d, J=6.7 Hz, 6H); MS $[M+H]^+$=600; LCMS RT=2.84.

Example 126

Preparation of N-4-[4-amino-7-(morpholin-4-ylmethyl)pyrrolo[2,1-f][1,2,4]triazin-5-yl]-2-chlorophenyl-N'-[3-(trifluoromethyl)phenyl]urea

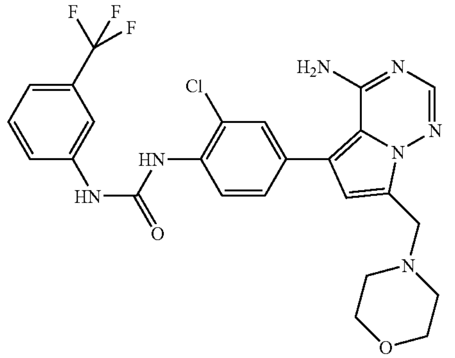

The procedure used for the preparation of Example 4 was used to prepare the title compound by substituting Intermediate Y for Intermediate E and 1-isocyanato-3-(trifluoromethyl)benzene for 2-fluoro-5-trifluoromethylphenyl isocyanate. $^1$H-NMR (DMSO-$d_6$) δ 9.84 (s, 1H), 8.52 (s, 1H), 8.30 (d, J=8.7 Hz, 1H), 8.10 (s, 1H), 7.96 (s, 1H), 7.61-7.57 (m, 3H), 7.46-7.38 (m, 2H), 6.73 (s, 1H), 3.86 (s, 2H), 3.61-3.58 (m, 4H), 2.50-2.48 (m, 4H); MS $[M+H]^+$=546; LCMS RT=2.68.

Example 127

Preparation of N-4-[4-amino-7-(morpholin-4-ylmethyl)pyrrolo[2,1-f][1,2,4]triazin-5-yl]-2-chlorophenyl-N'-(4-tert-butylpyridin-2-yl)urea

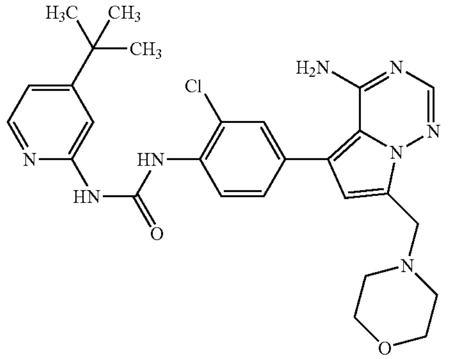

The procedure used for the preparation of Example 2 was used to prepare the title compound by substituting Intermediate Y for Intermediate E and phenyl [4-(trifluoromethyl)pyridin-2-yl]carbamate for phenyl(3-tert-butylisoxazol-5-yl)-carbamate. $^1$H-NMR (DMSO-$d_6$) δ 12.20-12.06 (br s, 1H), 9.93 (s, 1H), 8.43 (d, J=8.6 Hz, 1H), 8.21 (d, J=5.9 Hz, 1H), 7.91 (s, 1H), 7.55 (s, 1H), 7.38 d, J=8.6 Hz, 1H), 7.22 (s, 1H), 7.09 d, J=5.8 Hz, 1H), 6.68 (s, 1H), 3.81 (s, 2H), 3.57-3.52 (m, 4H), 2.46-2.41 (m, 4H), 1.25 (s, 9H); MS $[M+H]^+$=547; LCMS RT=2.47.

Example 128

Preparation of N-4-[4-amino-7-(morpholin-4-ylmethyl)pyrrolo[2,1-f][1,2,4]triazin-5-yl]-2-chlorophenyl-N'-[2-fluoro-5-(trifluoromethyl)phenyl]urea

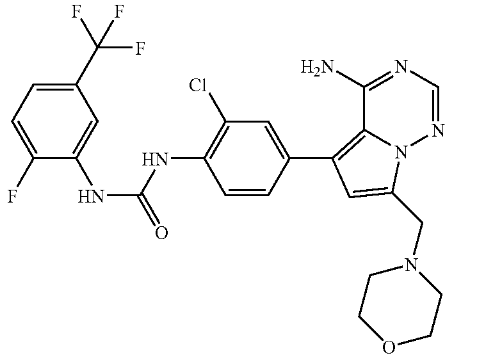

The procedure used for the preparation of Example 4 was used to prepare the title compound by substituting Intermediate Y for Intermediate E. $^1$H-NMR (DMSO-$d_6$) δ 9.73 (s, 1H), 9.01 (s, 1H), 8.65 (d, J=7.1 Hz, 1H), 8.24 (d, J=8.5 Hz, 1H), 7.91 (s, 1H), 7.54-7.49 (m, 2H), 7.43-7.38 (m, 2H), 6.68

(s, 1H), 3.81 (s, 2H), 3.55-3.53 (m, 4H), 2.45-2.43 (m, 4H); MS $[M+H]^+$=564; LCMS RT=2.73.

Example 129

Preparation of N-4-[4-amino-7-(morpholin-4-ylmethyl)pyrrolo[2,1-f][1,2,4]triazin-5-yl]-2-chlorophenyl-N'-[4-(trifluoromethyl)pyridin-2-yl]urea

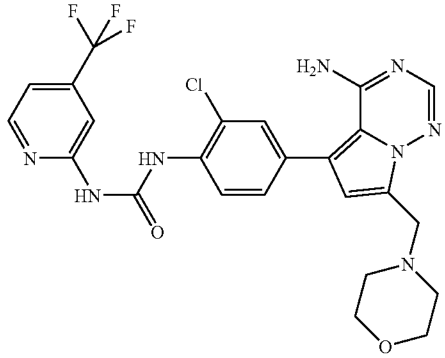

The procedure used for the preparation of Example 1 was used to prepare the title compound by substituting 1-[2-chloro-4-(4,4,5,5-tetramethyl-1,3,2-dioxaborolan-2-yl)phenyl]-3-[4-(trifluoromethyl)pyridin-2-yl]urea for Intermediate O. $^1$H-NMR (DMSO-$d_6$) δ 10.89-10.70 (br s, 1H), 10.42 (s, 1H), 8.58 (d, J=5.2 Hz, 1H), 8.36 (d, J=8.7 Hz, 1H), 7.91 (s, 1H), 7.78 (s, 1H), 7.57 (s, 1H), 7.42-7.37 (m, 2H), 6.69 (s, 1H), 3.81 (s, 2H), 3.56-3.53 (m, 4H), 2.45-2.43 (m, 4H); MS $[M+H]^+$=547; LCMS RT=2.47.

Example 130

Preparation of N-4-[4-amino-7-(morpholin-4-ylmethyl)pyrrolo[2,1-f][1,2,4]triazin-5-yl]-2-chlorophenyl-N'-(3-bromophenyl)urea

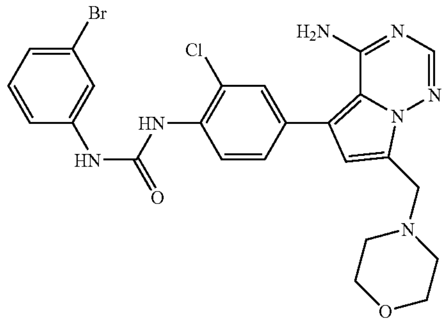

The procedure used for the preparation of Example 4 was used to prepare the title compound by substituting Intermediate Y for Intermediate E and 1-bromo-3-isocyanatobenzene for 2-fluoro-5-trifluoromethylphenyl isocyanate. $^1$H-NMR (DMSO-$d_6$) δ 9.61 (s, 1H), 8.43 (s, 1H), 8.23 (d, J=8.6 Hz, 1H), 7.91 (s, 1H), 7.90-7.89 (m, 1H), 7.53 (s, 1H), 7.38 (d, J=8.6 Hz, 1H), 7.29-7.23 (m, 2H), 7.18-7.16 (m, 1H), 6.67 (s, 1H), 3.81 (s, 2H), 3.55-3.53 (m, 4H), 2.45-2.43 (m, 4H); MS $[M+H]^+$=556; LCMS RT=2.63.

Example 131

Preparation of N-4-[4-amino-7-(morpholin-4-ylmethyl)pyrrolo[2,1-f][1,2,4]triazin-5-yl]-2-chlorophenyl-N'-(3-chlorophenyl)urea

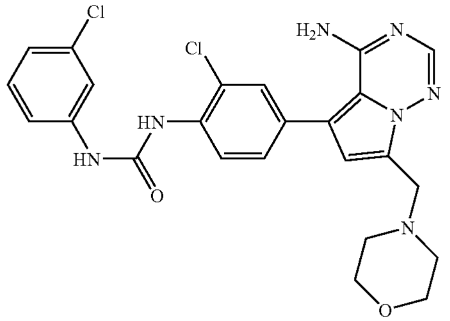

The procedure used for the preparation of Example 4 was used to prepare the title compound by substituting Intermediate Y for Intermediate E and 1-chloro-3-isocyanatobenzene for 2-fluoro-5-trifluoromethylphenyl isocyanate. $^1$H-NMR (DMSO-$d_6$) δ 9.73 (s, 1H), 8.54 (s, 1H), 8.32 (d, J=7.8 Hz, 1H), 8.00 (s, 1H), 7.85 (s, 1H), 7.63 (s, 1H), 7.47 (d, J=8.2 Hz, 1H), 7.42 (t, J=8.2 Hz, 1H), 7.33 (d, J=8.2 Hz, 1H), 7.14 (d, J=8.3 Hz, 1H), 6.77 (s, 1H), 3.90 (s, 2H), 3.65-3.62 (m, 4H), 2.55-2.51 (m, 4H); MS $[M+H]^+$=512; LCMS RT=2.44.

Example 132

Preparation of N-4-[4-amino-7-(morpholin-4-ylmethyl)pyrrolo[2,1-f][1,2,4]triazin-5-yl]-2-chlorophenyl-N'-(3-methoxyphenyl)urea

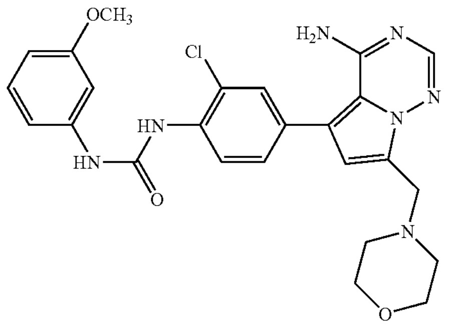

The procedure used for the preparation of Example 4 was used to prepare the title compound by substituting Intermediate Y for Intermediate E and 1-isocyanato-3-methoxybenzene for 2-fluoro-5-trifluoromethylphenyl isocyanate. $^1$H-NMR (DMSO-$d_6$) δ 9.50 (s, 1H), 8.43 (s, 1H), 8.30 (d, J=8.4 Hz, 1H), 7.95 (s, 1H), 7.57 (s, 1H), 7.42 (d, J=8.3 Hz, 1H), 7.26-7.22 (m, 2H), 6.99 (d, J=8.6 Hz, 1H), 6.72 (s, 1H), 6.62 (d, J=7.8 Hz, 1H), 3.85 (s, 2H), 3.77 (s, 3H), 3.60-3.58 (m, 4H), 2.50-2.48 (m, 4H); MS $[M+H]^+$=508; LCMS RT=2.25.

Example 133

Preparation of N-4-[4-amino-7-(morpholin-4-ylmethyl)pyrrolo[2,1-f][1,2,4]triazin-5-yl]-2-chlorophenyl-N'-(4-methylpyridin-2-yl)urea

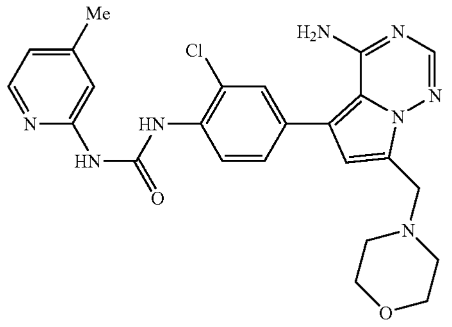

The procedure used for the preparation of Example 2 was used to prepare the title compound by substituting Intermediate Y for Intermediate E and phenyl (4-methylpyridin-2-yl) carbamate for phenyl(3-tert-butylisoxazol-5-yl)carbamate. $^1$H-NMR (DMSO-$d_6$) δ 10.05 (s, 1H), 8.50 (d, J=9.5 Hz, 1H), 8.24 (d, J=5.0 Hz, 1H), 7.98 (s, 1H), 7.63 (s, 1H), 7.46 (d, J=8.2 Hz, 1H), 7.07 (s, 1H), 6.96-6.94 (m, 1H), 6.75 (s, 1H), 3.88 (s, 2H), 3.63-3.60 (m, 4H), 2.63-2.59 (m, 4H), 2.35 (s, 31-1); MS $[M+H]^+$=493; LCMS RT=2.03.

Example 134

Preparation of N-4-[4-amino-7-(morpholin-4-ylmethyl)pyrrolo[2,1-f][1,2,4]triazin-5-yl]-2-chlorophenyl-N'-(3-methylphenyl)urea

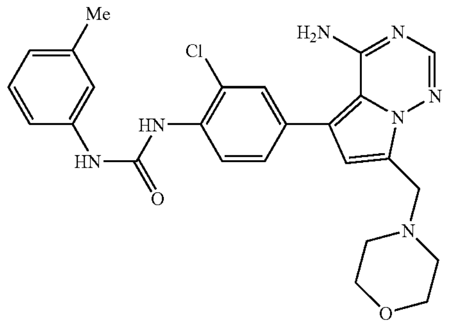

The procedure used for the preparation of Example 4 was used to prepare the title compound by substituting Intermediate Y for Intermediate E and 1-isocyanato-3-methylbenzene for 2-fluoro-5-trifluoromethylphenyl isocyanate. $^1$H-NMR (DMSO-$d_6$) δ 9.38 (s, 1H), 8.37 (s, 1H), 8.26 (d, J=8.6 Hz, 1H), 7.91 (s, 1H), 7.52 (s, 1H), 7.37 (d, J=8.6 Hz, 1H), 7.32 (s, 1H), 7.24 (d, J=7.4 Hz, 1H), 7.17 (t, J=7.8 Hz, 1H), 6.8.1 (d, J=7.4 Hz, 1H), 6.67 (s, 1H), 3.81 (s, 2H), 3.57-3.52 (m, 4H), 2.45-2.42 (m, 4H), 2.28 (s, 3H); MS $[M+H]^+$=492; LCMS RT=2.52.

Example 135

Preparation of N-4-[4-amino-7-(morpholin-4-ylmethyl)pyrrolo[2,1-f][1,2,4]triazin-5-yl]-2-chlorophenyl-N'-(2-fluoro-5-methylphenyl)urea

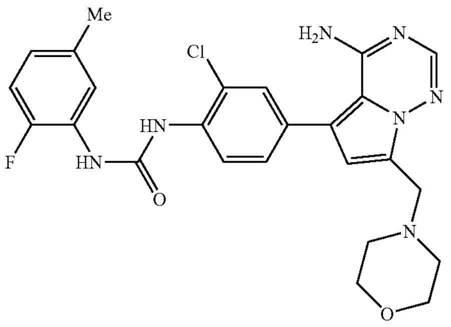

The procedure used for the preparation of Example 4 was used to prepare the title compound by substituting Intermediate Y for Intermediate E and 1-fluoro-2-isocyanato-4-methylbenzene for 2-fluoro-5-trifluoromethylphenyl isocyanate. $^1$H-NMR (DMSO-$d_6$) δ 9.34 (s, 1H), 8.87 (s, 1H), 8.24 (d, J=8.7 Hz, 1H), 8.01 (d, J=8.3 Hz, 1H), 7.91 (s, 1H), 7.53 (s, 1H), 7.38 (d, J=8.5 Hz, 1H), 7.14-7.09 (m, 1H), 6.84-6.80 (m, 1H), 6.68 (s, 1H), 3.81 (s, 2H), 3.56-3.54 (m, 4H), 2.46-2.43 (m, 4H), 2.27 (s, 3H); MS $[M+H]^+$=510; LCMS RT=2.56.

Example 136

Preparation of N-{4-[4-amino-7-(morpholin-4-ylmethyl)pyrrolo[2,1-f][1,2,4]triazin-5-yl}-2-fluoro-5-methylphenyl]-N'-[2-fluoro-5 (trifluoromethyl)-phenyl]urea

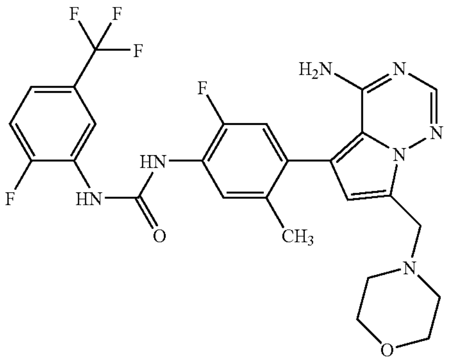

A solution of Intermediate C and Intermediate AA in DMF (2 mL) was degassed. To that was added Tetrakis(triphenylphosphine)palladium(0). The reaction vial was sealed and heated to 80° C. for 12 h. The reaction mixture was filtered through a 0.5 micron frit and purified by HPLC. The isolated fractions were concentrated in vacuo and the resulting solids were diluted with EtOAc (50 mL) and washed with saturated $NaHCO_3$. The organic layer was dried over $Na_2SO_4$ and concentrated in vacuo. MS $[M+H]^+$=562.0; LCMS RT=2.56.

Example 137

Preparation of N-(4-{4-amino-7-[(1,1-dioxidothiomorpholin-4-yl)methyl]pyrrolo[2,1-f][1,2,4]triazin-5-yl}-2-fluorophenyl)-N'-(3-chlorophenyl)urea

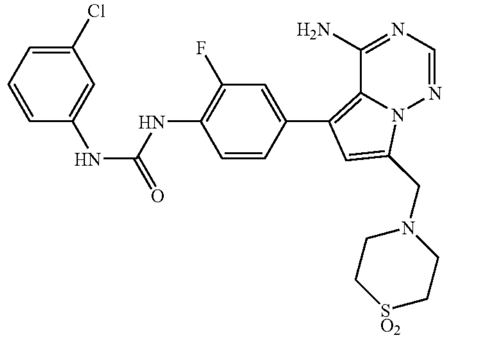

To a solution of Intermediate G (80 mg, 0.205 mmol) and 1-chloro-3-isocyanatobenzene (47 mg, 0.307 mmol) in THF (4 mL) was added triethylamine (86 µL, 0.615 mmol). The solution was heated and stirred over 12 h. The reaction mixture was concentrated in vacuo to provide a thick oil. The residue was dissolved in DMF (3 ml) and 2N HCl (2 mL) was added. The mixture was heated at 88° C. for 1 h. The reaction mixture was cooled to rt and the solvent was concentrated in vacuo. The compound was loaded onto silica gel and flashed beginning at 2% THF in DCM and ending at 90% THF in DCM. The pure fractions were combined and concentrated in vacuo. The white solid that formed on the flask was washed with ether and ethyl acetate to remove traces of BHT and any slight impurities. The white solid was filtered and dried under vacuum with heat (40° C.) to provide the title product (6 mg, 5% yield). $^1$H-NMR (DMSO-$d_6$) δ 9.28 (s, 1H), 8.71 (d, J=2.8, 1H), 8.22 (t, J=8.8, 1H), 7.92 (s, 1H), 7.74 (t, J=2.0, 1H), 7.35 to 7.31 (m, 2H), 7.24 (dd, J=8.4, 0.8, 2H), 7.05 to 7.03 (m, 1H), 6.73 (s, 1H), 4.02 (s, 2H), 3.11 to 3.09 (m, 4H), 2.96 to 2.93 (m, 4H); MS $[M+H]^+$=544.2; LCMS RT=2.76.

Example 138

Preparation of N-(4-{4-amino-7-[(1,1-dioxidothiomorpholin-4-yl)methyl]pyrrolo[2,1-f][1,2,4]triazin-5-yl}-2-fluorophenyl)-N'-[2-chloro-5-(trifluoromethyl)phenyl]urea

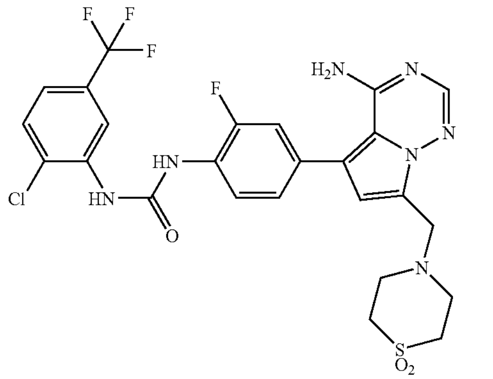

The title compound was prepared in a manner similar to the procedure described for the preparation of Example 137, using 1-chloro-2-isocyanato-4-(trifluoromethyl)benzene in place of 1-chloro-3-isocyanatobenzene. 10 mg (8%) of the desired product was isolated. $^1$H-NMR (DMSO-$d_6$) δ 9.63 (s, 1H), 9.13 (s, 1H), 8.63 (d, J=2.4, 1H), 8.28 (t, J=8.4, 1H), 7.92 (s, 1H), 7.74 (d, J=8.4, 1H), 7.39 (dd, J=8.8, 2.4, 1H), 7.35 (dd, J=12.0, 1.6, 1H), 7.25 (dd, J=8.4, 2.0, 1H), 6.74 (s, 1H), 4.02 (s, 2H), 3.11 to 3.09 (m, 4H), 2.96 to 2.93 (m, 4H); MS $[M+H]^+$=612.2; LCMS RT=3.01.

Example 139

Preparation of N-(4-{4-amino-7-[(1,1-dioxidothiomorpholin-4-yl)methyl]pyrrolo[2,1f][1,2,4]triazin-5-yl}-2-fluorophenyl)-N'-(4-tert-butylpyridin-2-yl)urea

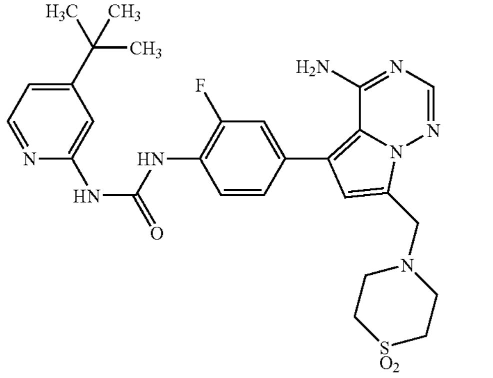

To a solution of Intermediate G (80 mg, 0.205 mmol) and phenyl {4-(trifluoromethyl)pyridin-2-yl}carbamate (61 mg, 0.225 mmol) in THF (4 mL) was added triethylamine (29 µL, 0.205 mmol). The solution was heated to 60° C. and stirred over 12 h. The reaction mixture was concentrated in vacuo to provide a thick oil. Upon cooling the reaction mixture to rt, the product crashed out of solution. The white solid was filtered and washed with ether and ethyl acetate to remove traces of BHT and any slight impurities. The white solid was dried under vacuum with heat (40° C.) to provide the title product (18 mg, 16% yield). $^1$H-NMR (DMSO-$d_6$) δ 9.79 (s, 1H), 8.35 (t, J=8.8, 1H), 8.17 (d, J=5.2, 1H), 7.92 (s, 1H), 7.40 to 7.36 (m, 1H), 7.35 (dd, J=12.0, 2.0, 1H), 7.24 (dd, J=8.8, 1.6, 1H), 7.08 (dd, J=5.6, 1.6, 1H), 6.74 (s, 1H), 4.03 (s, 2H), 3.12 to 3.09 (m, 4H), 2.96 to 2.93 (m, 4H), 1.25 (s, 9H); MS $[M+H]^+$=567.2; LCMS RT=2.67.

Example 140

Preparation of N-(4-{4-amino-7-[(1,1-dioxidothiomorpholin-4-yl)methyl]pyrrolo[2,1f][1,2,4]triazin-5-yl}-2-fluorophenyl)-N'-(4-methylpyridin-2-yl)urea

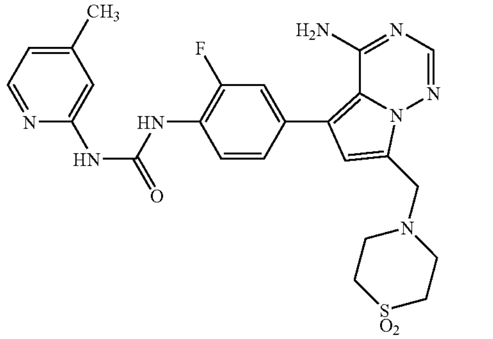

The title compound was prepared in a manner similar to the procedure described for the preparation of Example 137, using phenyl (4-methylpyridin-2-yl)carbamate in place of phenyl [4-(trifluoromethyl)pyridin-2-yl]carbamate. 16 mg (17%) of the desired product was isolated. $^1$H-NMR (DMSO-$d_6$) δ 9.85 (s, 1H), 8.31 (t, J=8.4, 1H), 8.12 (d, J=5.2, 1H), 7.91 (s, 1H), 7.35 (dd, J=12.4, 2.0, 1H), 7.25 (dd, J=8.8, 2.0, 1H), 7.19 to 7.15 (m, 1H), 6.87 (dd, J=5.2, 1.6, 1H), 6.74 (s, 1H), 4.02 (s, 2H), 3.12 to 3.09 (m, 4H), 2.96 to 2.93 (m, 4H), 2.28 (s, 3H); MS $[M+H]^+$=525.1; LCMS RT=2.28.

Example 141

Preparation of N-(4-{4-amino-7-[(1,1-dioxidothiomorpholin-4-yl)methyl]pyrrolo[2,1-f][1,2,4]triazin-5-yl}-2-fluorophenyl)-N'-(2-fluoro-5-methylphenyl) urea

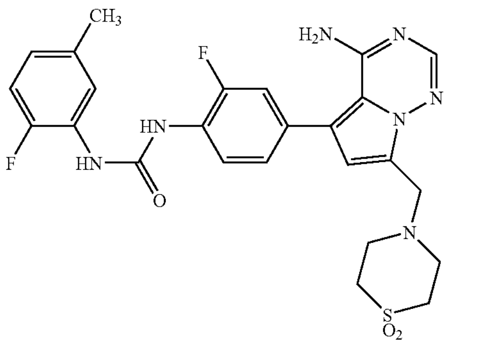

The title compound was prepared in a manner similar to the procedure described for the preparation of Example 137, using 1-fluoro-2-isocyanato-4-methylbenzene in place of 1-chloro-3-isocyanatobenzene. 10 mg (9%) of the desired product was isolated. $^1$H-NMR (DMSO-$d_6$) δ 9.12 (d, J=2.8, 1H), 9.01 (d, J=2.8, 1H), 8.27 (t, J=8.8, 1H), 8.02 (dd, J=7.2, 1.6, 1H), 7.91 (s, 1H), 7.32 (dd, J=12.0, 2.0, 1H), 7.23 (dd, J=8.4, 1.6, 1H), 7.11 (dd, J=11.2, 8.0, 1H), 6.83 to 6.78 (m, 1H), 6.73 (s, 1H), 4.02 (s, 2H), 3.12 to 3.09 (m, 4H), 2.96 to 2.93 (m, 4H), 2.26 (s, 3H); MS $[M+H]^+$=542.2; LCMS RT=2.72.

Example 142

Preparation of N-(4-{4-amino-7-[(1,1-dioxidothiomorpholin-4-yl)methyl]pyrrolo[2,1-f][1,2,4]triazin-5-yl}-2-fluorophenyl)-N'-(3,4-dichlorophenyl)urea

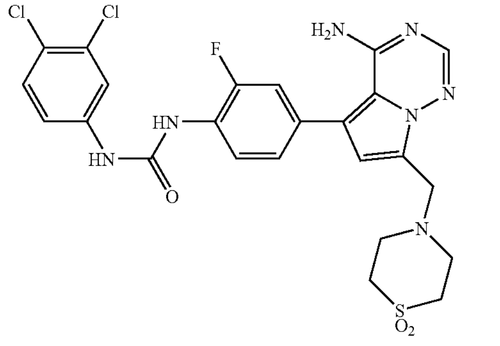

The title compound was prepared in a manner similar to the procedure described for the preparation of Example 137, using 1,2-dichloro-4-isocyanatobenzene in place of 1-chloro-3-isocyanatobenzene. 8 mg (8%) of the desired product was isolated. $^1$H-NMR (DMSO-$d_6$) δ 11.01 (s, 1H), 10.05 (s, 1H), 8.03 (t, J=9.2, 1H), 7.94 (d, J=2.4, 11-1), 7.91 (s, 1H), 7.49 (d, J=8.4, 1H), 7.41 (dd, J=8.8, 2.0, 1H), 7.29 (dd, J=12.0, 1.6, 1H), 7.21 (dd, J=6.4, 2.0, 1H), 6.74 (s, 1H), 4.02 (s, 2H), 3.11 to 3.09 (m, 4H), 2.96 to 2.93 (m, 4H); MS $[M+H]^+$=580.9; LCMS RT=2.81.

Example 143

Preparation of N-4-[4-amino-7-(morpholin-4-ylmethyl)pyrrolo[2,1-f][1,2,4]triazin-5-yl]-2,5-difluorophenyl}-M-(3-chlorophenyl)urea

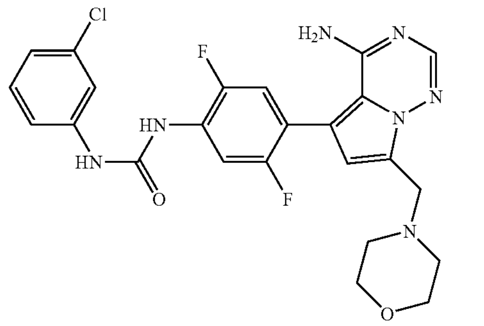

The title compound was prepared using the procedure to make Example 7 by substituting 1-(3-chlorophenyl)-3-[2,5-difluoro-4-(4,4,5,5-tetramethyl-1,3,2-dioxaborolan-2-yl) phenyl]urea for Intermediate R. The boronate was made using the procedure used to make Intermediate R. $^1$H-NMR (MeOD-$d_4$) δ 8.29-8.27 (m, 1H), 8.04 (s, 1H), 7.70-7.69 (m, 1H), 7.30-7.26 (m, 3H), 7.06-7.04 (m, 1H), 7.03 (s, 1H), 4.82 (s, 2H), 4.11-3.95 (m, 2H), 3.85-3.71 (m, 2H), 3.48-3.30 (m, 4H); MS $[M+H]^+$=514.0; LCMS RT=2.46 min Example 144

Preparation of N-{4-[4-amino-7-(morpholin-4-ylmethyl)pyrrolo[2,1-f][1,2,4]triazin-5-yl]-2,5-difluorophenyl}-N'-[2-chloro-5-(trifluoromethyl)phenyl] urea

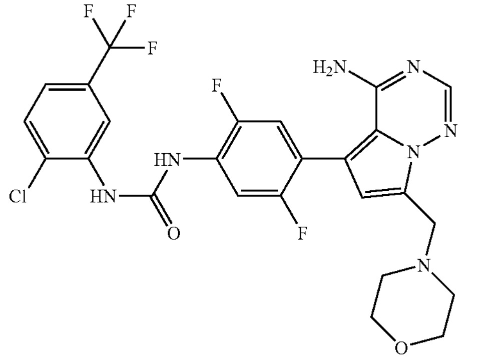

The title compound was prepared using the procedure to make Example 7 by substituting boronate, Intermediate AZ for Intermediate R. $^1$H-NMR (DMSO-$d_6$) δ 9.93 (s, 1H), 9.34 (s, 1H), 8.64 (d, J=2.0 Hz, 1H), 8.18 (dd, J=12, 7.2 Hz 1H), 7.95 (s, 1H), 7.77 (d, J=8.4 Hz, 1H), 7.45 (dd, J=8.4, 2.0 Hz, 1H), 7.36 (dd, J=11.6, 6.8 Hz 1H), 6.68 (s, 1H), 3.85 (s, 2H), 3.40-3.37 (m, 4H), 2.48-2.46 (m, 4H); MS $[M+H]^+$=582.2; LCMS RT=2.78 min.

Example 145

Preparation of N-{4-[4-amino-7-(morpholin-4-ylmethyl)pyrrolo[2,1-f][1,2,4]triazin-5-yl]-2,5-difluorophenyl}-N'-(2-fluoro-5-methylphenyl)urea

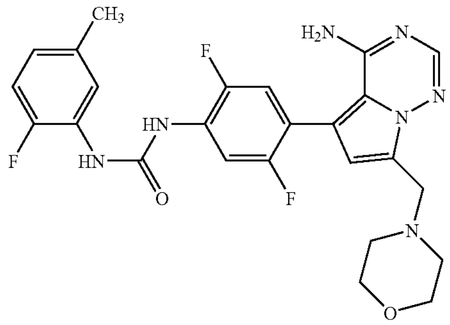

The title compound was prepared using the procedure to make Example 7 by substituting boronate, 1-[2,5-difluoro-4-(4,4,5,5-tetramethyl-1,3,2-dioxaborolan-2-yl)phenyl]-3-(2-fluoro-5-methylphenyl)urea for Intermediate R. The boronate was made using the procedure used to make Intermediate R. $^1$H-NMR (MeOD-$d_4$) δ 8.25-8.19 (m, 1H), 8.04 (s, 1H), 7.98-7.95 (m, 1H), 7.30-7.23 (m, 1H), 7.05-6.97 (m, 2H), 7.88-6.83 (m, 1H), 4.82 (s, 2H), 4.13-3.95 (m, 2H), 3.72-3.60 (m, 2H), 3.48-3.32 (m, 4H), 2.32 (s, 3H); MS $[M+H]^+$=512.1; LCMS RT=2.93 min.

Example 146

Preparation of N-{4-[4-amino-7-(morpholin-4-ylmethyl)pyrrolo[2,1-f][1,2,4]triazin-5-yl]-2-fluoro-5-methylphenyl}-N'-(2-fluoro-5-methylphenyl)urea

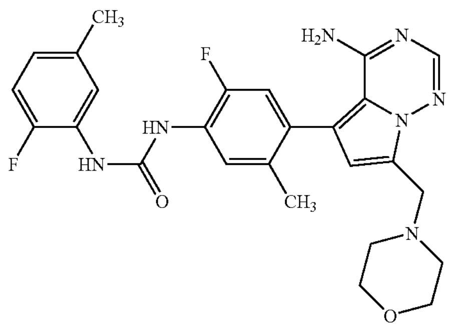

The title compound was prepared using the procedure to make Example 7 by substituting boronate, 1-(2-fluoro-5-methylphenyl)-3-[2-fluoro-5-methyl-4-(4,4,5,5-tetramethyl-1,3,2-dioxaborolan-2-yl)phenyl]urea for Intermediate R. The boronate was made using the procedure used to make Intermediate R. $^1$H-NMR (DMSO-$d_6$) δ 9.12 (d, J=2.4 Hz, 1H), 9.06 (d, J=2.4 Hz, 1E1), 8.18 (d, J=8.4 Hz, 1H), 8.02 (dd, J=8.0, 2.4 Hz 1H), 7.88 (s, 1H), 7.13-7.07 (m, 2H), 6.80-7.91

(m, 1H), 6.53 (s, 1H), 3.81 (s, 2H), 3.54 (t, J=4.4 Hz, 4H), 2.43 ((t, J=4.4 Hz, 4H), 2.26 (s, 3H), 2.10 (s, 3H); MS $[M+H]^+$=508.2; LCMS RT=2.83 min.

Example 147

Preparation of N-{4-[4-amino-7-(morpholin-4-ylmethyl)pyrrolo[2,1-f][1,2,4]triazin-5-yl]-2-fluoro-5-methylphenyl}-N'-[2-chloro-5-(trifluoromethyl)phenyl]urea

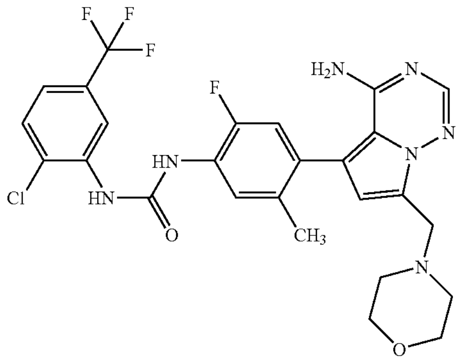

The title compound was prepared using the procedure to make Example 7 by substituting boronate, 1-[2-chloro-5-(trifluoromethyl)phenyl]-3-[2-fluoro-5-methyl-4-(4,4,5,5-tetramethyl-1,3,2-dioxaborolan-2-yl)phenyl]urea for Intermediate R. The boronate was made using the procedure used to make Intermediate R. $^1$H-NMR (DMSO-$d_6$) δ 9.68 (s, 1H), 9.23 (s, 1H), 8.62 (d, J=2.0 Hz, 1H), 8.15 (d, J=8.4 Hz, 1H), 7.88 (s, 1H), 7.71 (d, J=8.4 Hz, 1H), 7.38 (dd, J=8.4, 2.4 Hz, 1H), 7.14 (d, J=11.6 Hz, 1H), 6.53 (s, 1H), 3.81 (s, 2H), 3.54 (t, J=4.4 Hz, 4H), 2.43 ((t, J=4.4 Hz, 4H), 2.11 (s, 314); MS $[M+H]^+$=578.1; LCMS RT=3.06 min.

Example 148

Preparation of N-{4-[4-amino-7-(morpholin-4-ylmethyl)pyrrolo[2,1-f][1,2,4]triazin-5-yl]-2-fluoro-5-methylphenyl}-N'-(3-methylphenyl)urea

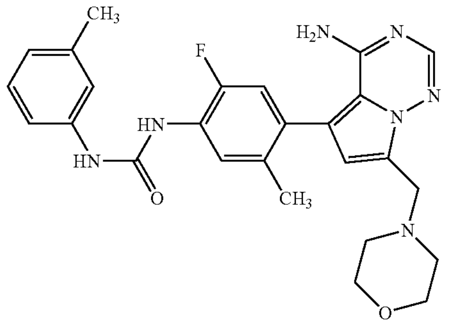

The title compound was prepared using the procedure to make Example 7 by substituting boronate, 1-[2-fluoro-5-methyl-4-(4,4,5,5-tetramethyl-1,3,2-dioxaborolan-2-yl)phenyl]-3-(3-methylphenyl)urea for Intermediate R. The boronate was made using the procedure used to make Intermediate R. $^1$H-NMR (MeOD-$d_4$) δ 8.12-8.10 (m, 2H), 7.30-7.28 (m, 2H), 7.18-7.12 (m, 2H), 7.00 (s, 1H), 6.87 (d, J=8.0 Hz, 1H), 4.81 (d, J=4.4 Hz, 2H), 4.09-3.75 (m, 4H), 3.48-3.33 (m, 4H), 2.33 (s, 3H), 2.20 (s, 3H); MS $[M+H]^+$=490.2; LCMS RT=2.28 min.

Example 149

Preparation of N-{4-[4-amino-7-(morpholin-4-ylmethyl)pyrrolo[2,1-f][1,2,4]triazin-5-yl]-2-fluorophenyl}-N'-(2-fluoro-5-methylphenyl)urea

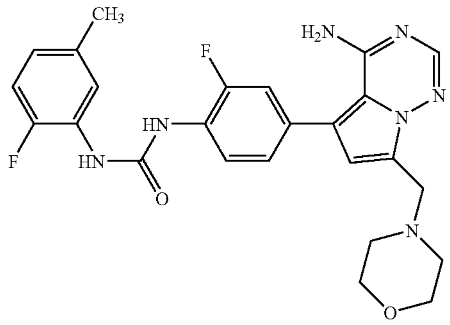

The procedure used for the preparation of Example 4 was used to prepare the title compound by substituting Intermediate F for Intermediate E and by substituting 2-fluoro-5-methylphenyl isocyanate for 2-fluoro-5-trifluoromethylphenyl isocyanate. $^1$H-NMR (DMSO-$d_6$) δ 9.19 (d, J=2.4 Hz, 1H), 9.05 (d, J=2.4 Hz, 1H), 8.33 (t, J=8.8 Hz, 1H), 8.10 (s, 1H), 8.02 (dd, J=7.6, 1.6 Hz, 1H), 7.35 (dd, J=12, 2.0 Hz, 1H), 7.25 (dd, J=8.0, 1.6 Hz, 1H), 7.13 (dd, J=11.2, 8.0 Hz, 1H), 6.98 (s, 1H), 6.84-6.81 (m, 1H), 4.73 (s, 2H), 4.0-3.92 (m, 2H), 3.69-3.58 (m, 2H), 3.43-3.35 (m, 2H), 3.26-3.17 (m, 2H), 2.28 (s, 3H); MS $[M+H]^+$=494.2; LCMS RT=2.54.

Example 150

Preparation of N-{4-[4-amino-7-(morpholin-4-ylmethyl)pyrrolo[2,1-f][1,2,4]triazin-5-yl]-2-fluorophenyl}-N'-[4-chloro-3-(trifluoromethyl)phenyl]urea

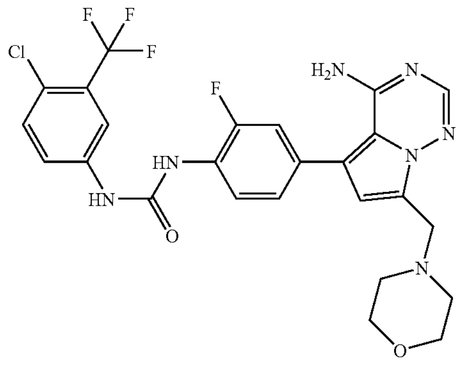

The procedure used for the preparation of Example 4 was used to prepare the title compound by substituting Intermediate F for Intermediate E and by substituting 4-chloro-3-(trifluoromethyl)phenyl isocyanate for 2-fluoro-5-trifluoromethylphenyl isocyanate. $^1$H-NMR (MeOD-$d_4$) δ 8.25 (t, J=8.0 Hz, 1H), 8.08 (s, 1H), 8.06 (d, J=2.8 Hz, 1H), 7.62 (dd, J=8.8, 2.8 Hz, 1H), 7.53 (d, J=8.8 Hz, 1H), 7.36 (dd, J=11.6, 1.6 Hz, 1H), 7.32-7.30 (m, 1H), 7.06 (s, 1H), 4.82 (s, 2H), 4.15-3.95 (m, 2H), 3.89-3.70 (m, 2H), 3.49-3.32 (m, 4H); MS $[M+H]^+$=564.0; LCMS RT=2.74.

Example 151

Preparation of N-{4-[4-amino-7-(morpholin-4-ylmethyl)pyrrolo[2,1-f][1,2,4]triazin-5-yl]-2-fluorophenyl}-N'-(4-tert-butylpyridin-2-yl)urea

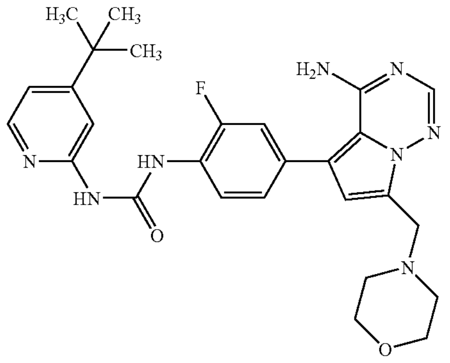

The procedure used for the preparation of Example 4 was used to prepare the title compound by substituting Intermediate F for Intermediate E and by substituting phenyl (4-tert-butylpyridin-2-yl)carbamate for 2-fluoro-5-trifluoromethylphenyl isocyanate. $^1$H-NMR ($CD_3OD$) δ 8.29 (t, J=8.4 Hz, 1H), 8.21 (d, J=6.4 Hz, 1H), 8.07 (s, 1H), 7.42-7.33 (m, 3H), 7.28 (s, 1H), 7.06 (s, 1H), 4.82 (s, 2H), 4.11-3.62 (m, 4H), 3.49-3.33 (m, 4H), 1.30 (s, 9H); MS $[M+H]^+$=518.8; LCMS RT=2.26.

Example 152

Preparation of N-{4-[4-amino-7-(morpholin-4-ylmethyl)pyrrolo[2,1-f][1,2,4]triazin-5-yl]-2-fluorophenyl}-N'-(4-tert-butylpyridin-2-yl)urea

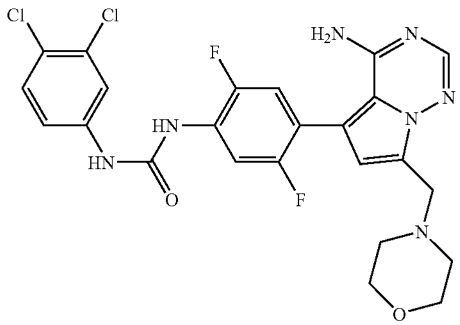

The title compound was prepared using the procedure to make Example 7 by substituting boronate, Intermediate BA for Intermediate R. $^1$H-NMR (DMSO-$d_6$) δ 9.71 (s, 1H), 9.18 (s, 1H), 8.09 (dd, J=12, 6.8 Hz, 1H), 7.92 (s, 2H), 7.55 (d, J=8.8 Hz, 1H), 7.35-7.30 (m, 2H), 6.64 (s, 1H), 3.82 (s, 2H), 3.56 (t, J=4.4 Hz, 4H), 2.45 (t, J=4.4 Hz, 4H); MS [M+H]-1-=548.1; LCMS RT=3.00 min.

Example 153

Preparation of N-{4-[4-amino-7-(morpholin-4-ylmethyl)pyrrolo[2,1-f][1,2,4]triazin-5-yl]-2,5-difluorophenyl}-N'-(4-tert-butylpyridin-2-yl)urea

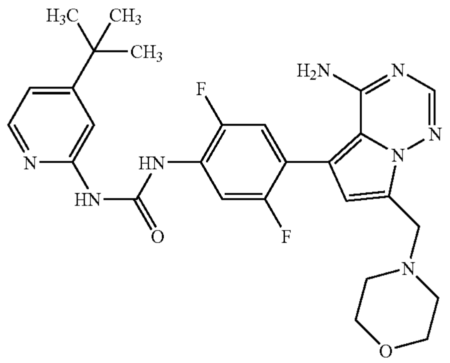

The title compound was prepared using the procedure to make Example 7 by substituting boronate, Intermediate BB for Intermediate R. $^1$H-NMR ($CD_3OD$) δ 9.92 (a, 1H), 8.26-8.20 (m, 2H), 8.07 (s, 1H), 7.37-7.32 (m, 1H), 7.26 (s, 1H), 7.07 (s, 1H), 4.82 (s, 2H), 4.11-3.62 (m, 4H), 3.49-3.33 (m, 4H), 1.37 (s, 9H); MS $[M+H]^+$=537.0 LCMS RT=2.81 min.

Example 154

Preparation of N-{4-[4-amino-7-(morpholin-4-ylmethyl)pyrrolo[2,1-f][1,2,4]triazin-5-yl]-2,5-difluorophenyl}-N-(3-tert-butylphenyl)urea

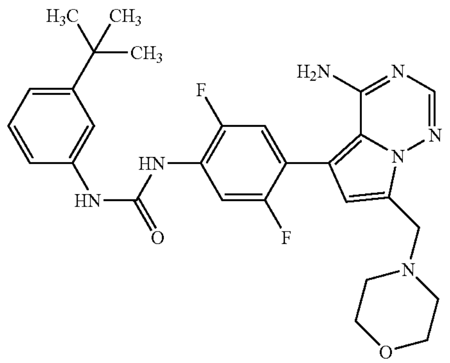

The title compound was prepared using the procedure to make Example 7 by substituting boronate, Intermediate AW for Intermediate R. $^1$H-NMR ($CD_3OD$) δ 8.20 (dd, J=12, 6.8 Hz, 1H), 8.07 (s, 1H), 7.53-7.50 (m, 1H), 7.31-7.21 (m, 3H), 7.32-7.11 (m, 1H), 7.06 (s, 1H), 4.82 (s, 2H), 4.11-3.60 (m, 4H), 3.51-3.33 (m, 4H), 1.33 (s, 9H); MS $[M+H]^+$=536.2; LCMS RT=2.85 min Example 155

Preparation of N-{4-[4-amino-7-(morpholin-4-ylmethyl)pyrrolo[2,1-f][1,2,4]triazin-5-yl]-2,5-difluorophenyl}-N'-(3-ethylphenyl)urea

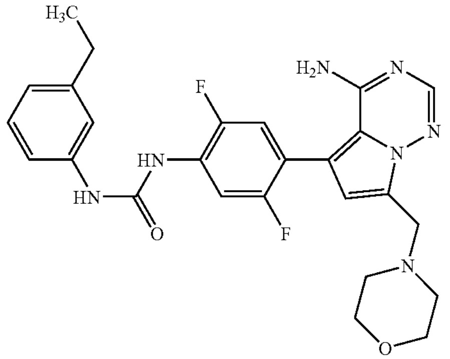

The title compound was prepared using the procedure to make Example 7 by substituting boronate, 1-[2,5-difluoro-4-(4,4,5,5-tetramethyl-1,3,2-dioxaborolan-2-yl)phenyl]-3-(3-ethylphenyl)urea for Intermediate R. The boronate was made using the procedure used to make Intermediate R. $^1$H-NMR ($CD_3OD$) δ 8.40 (s, 1H), 7.40-7.36 (m, 2H), 7.25 (t, J=7.6 Hz, 1H), 7.16 (dd, J=11.2, 6.8 Hz, 1H), 7.11 (s, 1H), 6.99 (d, J=7.6 Hz, 1H), 6.75 (dd, J=11.6, 7.6 Hz, 1H), 4.86 (s, 2H), 4.11-3.60 (m, 4H), 3.51-3.30 (m, 4H), 2.64 (q, J=7.6 Hz, 2H), 1.24 (t, J=7.6 Hz, 3H); MS $[M+H]^+$=508.3; LCMS RT=3.10 min.

Example 156

Preparation of N-{4-[4-amino-7-(morpholin-4-ylmethyl)pyrrolo[2,1-f][1,2,4]triazin-5-yl]-2-fluorophenyl}-N'-(3-ethylphenyl)urea

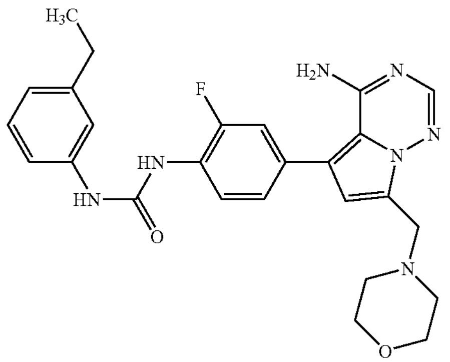

The procedure used for the preparation of Example 4 was used to prepare the title compound by substituting Intermediate F for Intermediate E and by substituting 3-ethyl-phenyl isocyanate for 2-fluoro-5-trifluoromethylphenyl isocyanate. $^1$H-NMR ($CD_3OD$) 8.25 (d, J=8.4 Hz, 1H), 8.08 (s, 1H), 7.36-7.15 (m, 5H), 7.06 (s, 1H), 6.90 (d, J=7.6 Hz, 1H), 4.82

(s, 2H), 4.11-3.60 (m, 4H), 3.51-3.30 (m, 4H), 2.63 (q, J=7.6 Hz, 2H), 1.24 (t, J=7.6 Hz, 3H); MS $[M+H]^+$=490.1; LCMS RT=2.50.

Example 157

Preparation of N-{4-[4-amino-7-(morpholin-4-ylmethyl)pyrrolo[2,1-f][1,2,4]triazin-5-yl]-2,5-difluorophenyl}-N'-[4-chloro-3-(trifluoromethyl)phenyl]urea

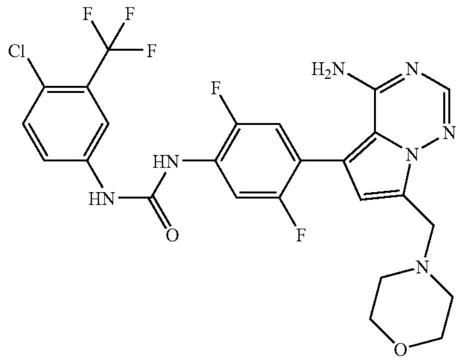

The title compound was prepared using the procedure to make Example 7 by substituting boronate, 1-[4-chloro-3-(trifluoromethyl)phenyl]-3-[2,5-difluoro-4-(4,4,5,5-tetramethyl-1,3,2-dioxaborolan-2-yl)phenyl]urea for Intermediate R. The boronate was made using the procedure used to make Intermediate R. $^1$H-NMR ($CD_3OD$) δ 8.34 (s, 1H), 8.10 (s, 1H), 7.78 (d, J=8.4 Hz, 1H), 7.55 (d, J=8.8 Hz, 1H), 7.15 (dd, J=10.8, 6.4 Hz, 1H), 7.10 (s, 1H), 6.73 (dd, J=11.2, 7.6 Hz, 1H), 4.85 (s, 2H), 4.25-3.98 (m, 2H), 3.76-3.69 (m, 2H), 3.55-3.30 (m, 4H); MS $[M+H]^+$=582.0; LCMS RT=3.17 min.

Example 158

Preparation of N-{4-[4-amino-7-(morpholin-4-ylmethyl)pyrrolo[2,1-f][1,2,4]triazin-5-yl]-2-fluorophenyl}-N'-(3,4-dichlorophenyl)urea

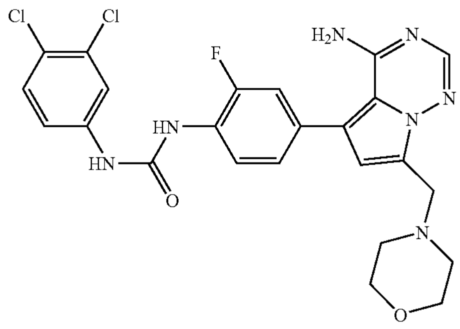

The procedure used for the preparation of Example 4 was used to prepare the title compound by substituting Intermediate F for Intermediate E and by substituting 3,4-dichlorophenyl isocyanate for 2-fluoro-5-trifluoromethylphenyl isocyanate. $^1$H-NMR ($CD_3OD$) δ 8.24 (t, J=8.4 Hz, 1H), 8.06 (s, 1H), 7.85 (d, J=2.4 Hz, 1H), 7.43 (d, J=8.8 Hz, 1H), 7.34 (dd, J=11.6, 2.0 Hz, 1H), 7.29 (dd, J=8.4, 2.4 Hz, 2H), 7.04 (s, 1H), 4.81 (s, 2H), 4.25-3.98 (m, 2H), 3.76-3.69 (m, 2H), 3.55-3.30 (m, 4H); MS $[M+H]^+$=529.8; LCMS RT=2.55.

Example 159

Preparation of N-{4-[4-amino-7-(morpholin-4-ylmethyl)pyrrolo[2,1-f][1,2,4]triazin-5-yl]-2-fluorophenyl}-N'-(3,5-dimethylphenyl)urea

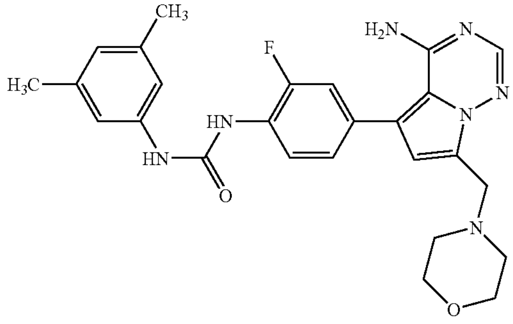

The procedure used for the preparation of Example 4 was used to prepare the title compound by substituting Intermediate F for Intermediate E and by substituting 3,5-dimethylphenyl isocyanate for 2-fluoro-5-trifluoromethylphenyl isocyanate. $^1$H-NMR ($CD_3OD$) δ 8.24 (t, J=8.4 Hz, 1H), 8.06 (s, 1H), 7.35-7.27 (m, 2H), 7.08 (s, 2H), 7.03 (s, 1H), 6.71 (s, 1H), 4.81 (s, 2H), 4.11-3.75 (m, 4H), 3.48-3.24 (m, 4H), 2.20 (s, 6H); MS $[M+H]^+$=490.1; LCMS RT=2.50.

Example 160

Preparation of N-{4-[4-amino-7-(morpholin-4-ylmethyl)pyrrolo[2,1-f][1,2,4]triazin-5-yl]-2-fluorophenyl}-N'-[3-fluoro-5-(trifluoromethyl)phenyl]urea

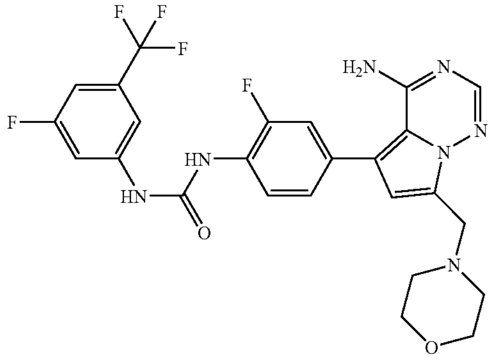

The procedure used for the preparation of Example 4 was used to prepare the title compound by substituting Intermediate F for Intermediate E and by substituting 3-fluoro-5-(trifluoromethyl)phenyl isocyanate for 2-fluoro-5-trifluoromethylphenyl isocyanate. $^1$H-NMR ($CD_3OD$) δ 8.25 (t, J=8.4 Hz, 1H), 8.07 (s, 1H), 7.85 (dt, J=11.2, 1.6 Hz, 1H), 7.60 (s, 1H), 7.36 (dd, J=11.6, 2.0 Hz, 1H), 7.33-7.30 (m, 1H), 7.08 (dt, J=8.4, 1.6 Hz, 1H), 7.05 (s, 1H), 4.81 (s, 2H), 4.25-3.98 (m, 2H), 3.76-3.69 (m, 2H), 3.55-3.30 (m, 4H); MS $[M+H]^+$=548.0; LCMS RT=2.69.

Example 161

N-(4-{4-amino-7-[(4-methylpiperazin-1-yl)carbonyl]pyrrolo[2,1-f][1,2,4]triazin-5-yl}-2-fluorophenyl)-N'-[2-fluoro-5-(trifluoromethyl)phenyl]area

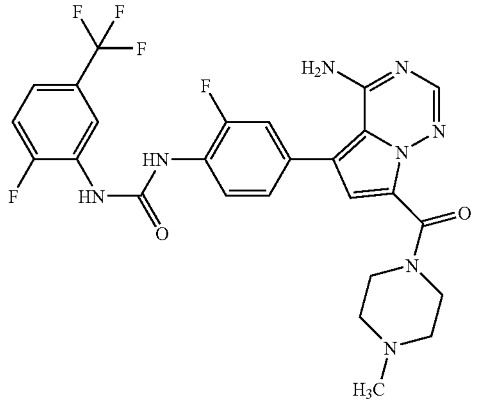

The procedure used for the preparation of Example 282 was used to prepare the title compound by substituting 1-methylpiperazine for tert-butyl 2-(aminomethyl)morpholine-4-carboxylate in step 2. $^1$H-NMR ($CD_3OD$) δ 8.65 (d, J=7.8 Hz, 1H), 8.30 (d, J=8.4 Hz, 1 H), 7.92 (s, 1H), 7.36-7.29 (m, 4H), 6.90 (s, 1H), 3.90-3.79 (m, 2H), 3.50-3.39 (m, 2H), 2.62-2.43 (m, 4H), 2.35 (s, 3H); MS $[M+H]^+$=575.1; LCMS RT=2.63 min.

Example 162

Preparation of N-(4-{4-amino-7-[(3-oxopiperazin-1-yl)methyl]-pyrrolo[2,1-f][1,2,4]triazin-5-yl}-2-fluorophenyl)-N'-[3-(trifluoromethyl)phenyl]urea

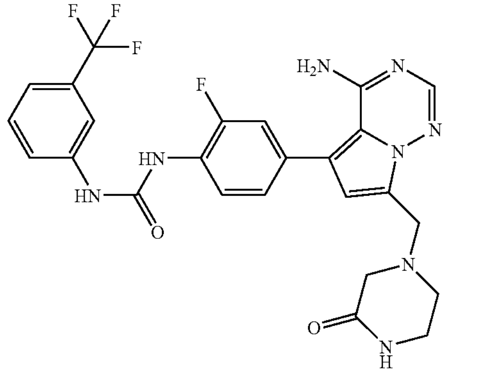

Intermediate D (70 mg, 0.215 mmol) and Intermediate Q (127 mg, 0.301 mmol) were added to a vial, dioxane (2 mL) was added followed by aq 1N sodium carbonate (646 uL, 646 mmol). The reaction was then placed under $N_2$. The reaction was taken through 3 purge-fill cycles with $N_2$ and vacuum. Tetrakistriphenylphosphinepalladuium, (25 mg, 0.022 mmol) was then added. The reaction was degassed and then heated in an oil bath at 80° C. for 16 h. The reaction mixture was partitioned between EtOAc (50 mL) and $H_2O$ (20 mL). There were solids between the layers. The solids were collected by filtration then washed with EtOAc followed by $H_2O$. The material was triturated with 25% $CH_2Cl_2$/MeOH to yield 19 mg (16%) clean product. $^1$H-NMR (DMSO-$d_6$) δ 9.43 (s, 1H), 8.74 (s, 1H), 8.21 (t, J=5.7 Hz, 1H), 8.04 (s, 1H), 7.91 (s, 1H), 7.72 (s, 1H), 7.53 (m, 3H), 7.37 to 7.23 (m, 2H), 6.70 (s, 1H), 3.87 (s, 2H), 3.30 (m, 2H), 2.60 (m, 2H); MS $[M+H]^+$=543.0; LCMS RT 2.58 min Example 163

Preparation of N-(4-{4-amino-7-[(3-oxopiperazin-1-yl)methyl]-pyrrolo[2,1f][1,2,4]triazin-5-yl}-2-fluorophenyl)-N'-[4-(trifluoromethyl)-pyridin-2-yl]urea

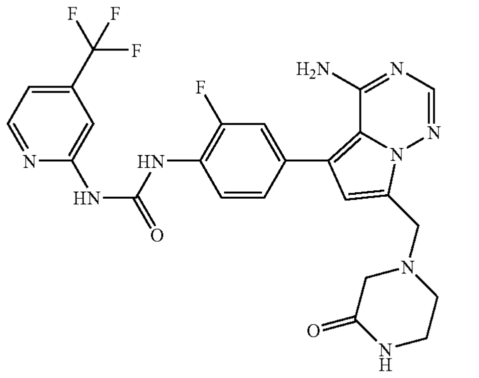

Intermediate D (70 mg, 0.215 mmol) and Intermediate AE (127 mg, 0.300 mmol) were allowed to react using the procedure to make Example 162. The solid between the two layers was isolated and triturated in the manner described previously to yield 23 mg (20%) of pure desired product. $^1$H-NMR (DMSO-$d_6$) δ 10.12 (s, 1H), 10.06 (bs, 1H), 8.40 (d, J=5.1 Hz, 1H), 8.27 (t, J=8.7 Hz, 1H), 8.00 (s, 1H), 7.92 (s, 1H), 7.71 (s, 1H), 7.38 to 7.25 (m, 3H), 6.71 (s, 1H), 3.91 (s, 2H), 3.17 (m, 2H), 2.59 (m, 2H); MS $[M+H]^+$=543.7; LCMS RT=2.38

Example 164

Preparation of N-(4-{4-amino-7-[(3-oxopiperazin-1-yl)methyl]-pyrrolo[2,1f][1,2,4]triazin-5-yl}-2,5-difluorophenyl)-N'-[2-fluoro-5-(trifluoromethyl)phenyl]urea

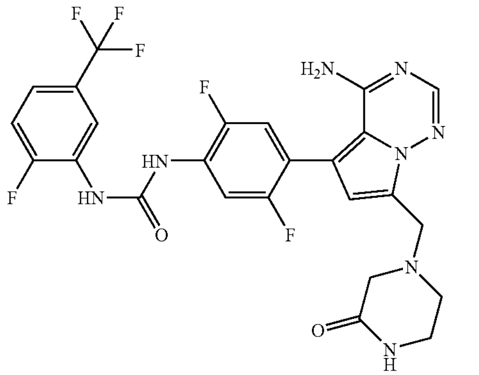

Intermediate D (70 mg, 0.215 mmol) and Intermediate AH (138 mg, 0.300 mmol) were allowed to react using the procedure to make Example 162 with substitution of DMF for dioxane. The reaction mixture was partitioned between EtOAc (100 mL) and $H_2O$ (30 mL). The organic layer was then washed (6×20 mL) with brine to remove DMF. The organic layer was dried with sodium sulfate then concentrated under vacuum. The residue is chromatographed on a MPLC 4 g Silica column. The product is eluted with a gradient of 0-6% Methanol/$CH_2Cl_2$ to yield 43 mg (35%) of clean desired product. $^1$H-NMR (DMSO-$d_6$) δ 9.48 (s, 1H), 8.44 (s, 1H), 8.63 (d, J=7.5 Hz, 1H), 8.16 (dd, J=5.7, 6.9, 1H), 7.9 (s, 1H), 7.72 (s, 1H), 7.55 to 7.31 (m, 3H), 6.67 (s, 1H), 3.91 (s, 2H), 2.62 (m, 2H); MS $[M+H]^+$=578.9; LCMS RT=2.71

Example 165

Preparation of N-(4-{4-amino-7-[(3-oxopiperazin-1-yl)methyl]-pyrrolo[2,1-f][1,2,4]triazin-5-yl}-2-methylphenyl)-N'-[2-fluoro-5-(trifluoromethyl)-phenyl] urea

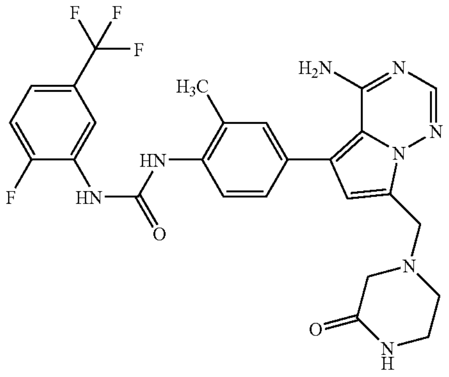

Intermediate D (70 mg, 0.215 mmol) and Intermediate AF (132 mg, 0.301 mmol) were allowed to react using the procedure to make Example 164. The residue was chromatographed on a MPLC 4 g Silica column. The product was eluted with a gradient of 0-6% Methanol/$CH_2Cl_2$ to yield 64 mg (53%) of clean desired product. $^1$H-NMR (DMSO-$d_6$) δ9.41 (s, 1H), 8.67 (d, J=7.5 Hz, 1H), 8.58 (bs, 1H), 8.00 (d, J=8.4 Hz, 1H), 7.9 1 (s, 1H), 7.72 (bs, 1H), 7.54 to 7.25 (m, 3H), 6.66 (s, 1H), 3.91 (s, 2H), 3.11 (m, 2H), 2.63 (m, 2H), 2.31 (s, 3H); MS $[M+H]^+$=556.8; LCMS RT=2.44

Example 166

Preparation of N-(4-{4-amino-7-[(3-oxopiperazin-1-yl)methyl]-pyrrolo[2,1-f][1,2,4]triazin-5-yl}-2-fluorophenyl)-N'-(2-fluoro-5-methylphenyl)urea

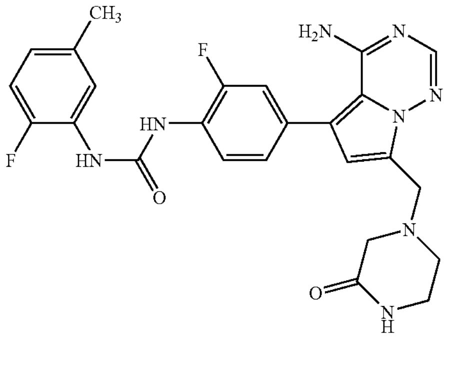

Intermediate D (75 mg, 0.232 mmol) and Intermediate AI (125 mg, 0.323 mmol) were allowed to react using the procedure to make Example 164. The residue was chromatographed on a MPLC 4 g Silica column. The product was eluted with a gradient of 0-6% Methanol/$CH_2Cl_2$ to yield 69 mg (59%) of clean desired product. $^1$H-NMR (DMSO-$d_6$) δ9.12 (s, 1H), 9.01 (s, 1H), 8.27 (t, J=8.7 Hz, 1H), 8.02 (d, J=4.8 Hz, 1H), 7.92 (s, 1H), 7.36-7.08 (m, 3H), 6.83 (m, 1H), 6.71 (s, 1H), 3.91 (s, 2H), 3.13 (m, 2H), 2.63 (m, 2H), 2.27 (s, 3H); MS $[M+H]^+$=506.8; LCMS RT=2.30.

Example 167

Preparation of N-{4-[4-amino-7-(1,4-oxazepan-4-ylmethyl)pyrrolo[2,1-f][1,2,4]triazin-5-yl]phenyl}-N'-[2-fluoro-5-(trifluoromethyl)phenyl]urea

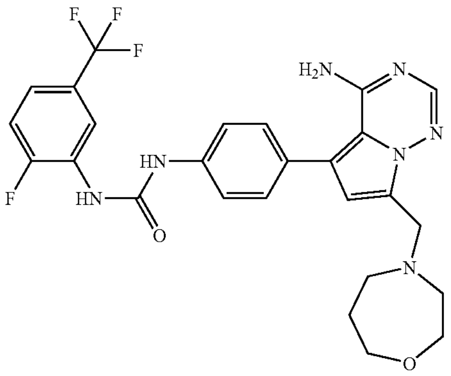

Intermediate Z (75 mg, 0.231 mmol) and Intermediate M (132 mg, 0.301 mmol) were allowed to react using the procedure to make Example 164. The residue was chromatographed on a MPLC 4 g Silica column. The product was eluted with a gradient of 0-6% Methanol/$CH_2Cl_2$ to yield 64 mg (53%) of clean desired product. $^1$H-NMR (DMSO-$d_6$) δ9.31 (s, 1H), 8.94 (s, 1H), 8.63 (dd, J=7.2 Hz, J=2.1 Hz, 1H), 7.90 (s, 1H), 7.62 to 7.39 (m, 6H), 6.63 (s, 1H), 3.99 (s, 2H), 3.69 to 3.41 (m, 4H), 2.71 (m, 2H), 1.80 (t, J=5.1, 2H); MS $[M+H]^+$=544.1; LCMS RT=2.49.

Example 168

Preparation of N-{4-[4-amino-7-(1,4-oxazepan-4-ylmethyl)pyrrolo[2,1-f][1,2,4]triazin-5-yl]-2,5-difluorophenyl}-N'-[2-fluoro-5-(trifluoromethyl)phenyl]urea

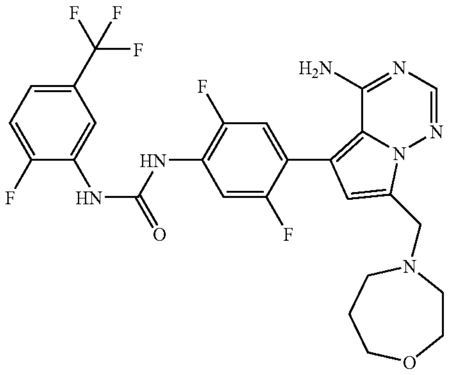

Intermediate Z (150 mg, 0.345 mmol) and Intermediate AH (206 mg, 0.448 mmol) were allowed to react using the procedure to make Example 162. The aqueous layer was back extracted with EtOAc (25 mL). The combined organic layer was washed with brine then dried with $Na_2SO_4$. The residue was chromatographed using a 4 g MPLC column. The product was eluted with a gradient of 0-10% $MeOH/CH_2Cl_2$ to yield 87 mg (44%) clean product. $^1H$-NMR (DMSO-$d_6$) δ9.48 (s, 1H), 9.44 (s, 1H), 8.63 (dd, J=4.5 Hz, J=2.4 Hz, 1H), 7.91 (s, 1H), 7.652 to 7.30 (m, 3H), 6.64 (s, 1H), 3.98 (s, 2H), 3.68 to 3.58 (m, 4H), 2.70 (m, 4H), 1.79 (m, 2H); MS $[M+H]^+$=580.1; LCMS RT=2.61.

Example 169

Preparation of N-{4-[4-amino-7-(1,4-oxazepan-4-ylmethyl)pyrrolo[2,1-[1,2,4]triazin-5-yl]-2-fluorophenyl}-N'-(4-tert-butylpyridin-2-yl)urea

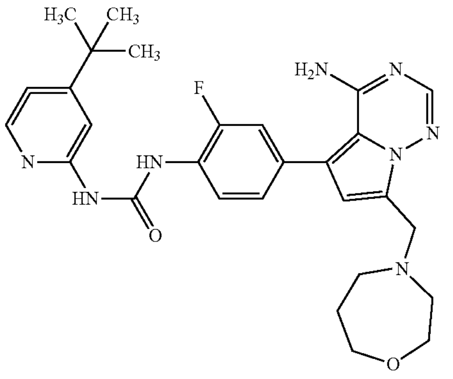

Intermediate Z and Intermediate AM (206 mg, 0.448 mmol) were allowed to react using the procedure to make Example 164. The residue was chromatographed using a 4 g MPLC column. The product was eluted with a gradient of 0-10% $MeOH/CH_2Cl_2$ to yield 3 mg (1.8%) clean product $^1H$-NMR (Methanol-$d_4$) δ8.31 (t, J=8.1 Hz, 1H), 8.17 (d, J=2.4 Hz, 1H), 7.84 (s, 1H), 7.28 (m, 2H), 7.11 (s, 1H), 7.03 (m, 1H), 6.71 (s, 1H), 4.06 (s, 2H), 3.80 to 3.72 (m, 4H), 2.85 to 2.76 (m, 4H), 1.97 to 1.89 (m, 2H), 1.39 (s, 9H); MS $[M+H]^+$=533.0; LCMS RT=2.30.

Example 170

Preparation of N-{4-[4-amino-7-(1,4-oxazepan-4-ylmethyl)pyrrolo[2,1-f][1,2,4]triazin-5-yl]-2,5-difluorophenyl}-N'-(4-tert-butylpyridin-2-yl)urea

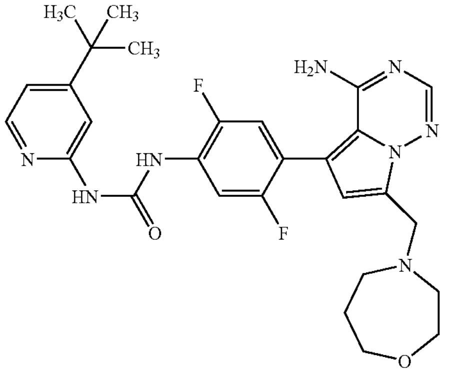

Intermediate Z and Intermediate BB (172 mg, 0.399 mmol) were allowed to react using the procedure to make Example 164. The residue was chromatographed using a 4 g MPLC column. The product was eluted with a gradient of 0-10% (2N $NH_3$ in MeOH)/$CH_2Cl_2$ to yield 9 mg (5%) clean product $^1H$-NMR (DMSO-$d_6$) δ9.90 (s, 1H), 8.24 to 8.17 (m, 3H), 7.91 (s, 1H), 7.39 to 7.30 (m, 2H), 7.10 (dd, J=4.8 Hz, J=1.8 Hz 1H), 6.65 (s, 1H), 3.98 (s, 2H), 3.68 to 3.58 (m, 4H), 2.72 to 2.67 (m, 4H), 1.81 to 1.78 (m, 2H), 1.24 (m, 9H); MS [M+H]=$^+$=551.0; LCMS RT=2.44.

Example 171

Preparation of N-{4-[4-amino-7-(1,4-oxazepan-4-ylmethyl)pyrrolo[2,1-f][1,2,4]triazin-5-yl]-2-fluorophenyl}-N'-[2-chloro-5-(trifluoromethyl)phenyl]urea

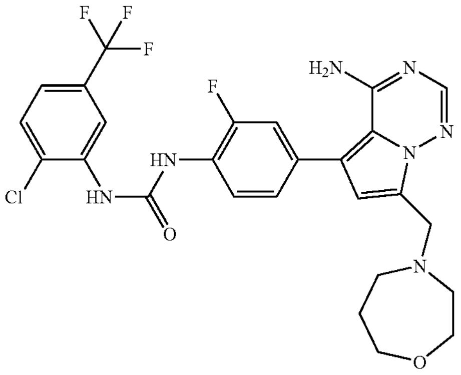

Intermediate Z and Intermediate AJ (155 mg, 0.339 mmol) were allowed to react using the procedure to make Example 164. The residue was chromatographed using a 4 g MPLC column. The product was eluted with a gradient of 0-6% $MeOH/CH_2Cl_2$ to yield 34 mg (23%) of clean product. $^1H$-NMR (DMSO-$d_6$) δ9.62 (s, 1H), 9.13 (s, 1H), 8.65 (s, 1H), 8.25 (t, J=8.7 Hz, 1H), 7.91 (s, 1H), 7.73 (d, J=8.4 Hz, 1H), 7.41 to 7.23 (m, 3H), 6.68 (s, 1H), 3.98 (s, 2H), 3.68 to 3.58 (m, 4H), 2.72 to 2.67 (m, 4H), 1.81 to 1.78 (m, 2H); MS $[M+H]^+$=578.0; LCMS RT=2.99.

Example 172

Preparation of N-{4-[4-amino-7-(1,4-oxazepan-4-ylmethyl)pyrrolo[2,1-f][1,2,4]triazin-5-yl]-2-chlorophenyl}-N'-[3-(trifluoromethyl)phenyl]urea

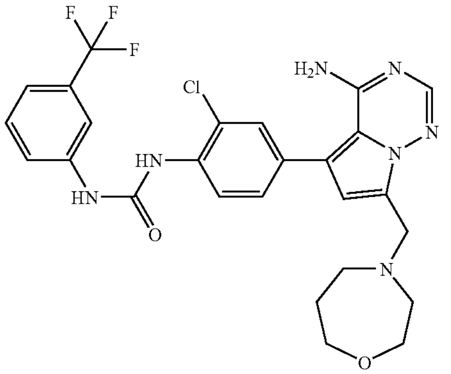

Intermediate Z (85 mg, 0.261 mmol) and Intermediate AQ (149 mg, 0.339 mmol) were allowed to react using the procedure to make Example 164. The residue was chromatographed using a 4 g MPLC column. The product was eluted with a gradient of 0-6% MeOH/$CH_2Cl_2$ to yield 31 mg (21%) of clean product. $^1$H-NMR (DMSO-$d_6$) δ 9.79 (s, 1H), 8.48 (s, 1H), 8.65 (d, J=4.8 Hz, 1H), 8.05 (s, 1H), 7.91 (s, 1H), 7.91 (s, 1H), 7.55 (m, 3H), 7.42 to 7.36 (m, 2H), 6.69 (s, 1H), 3.98 (s, 2H), 3.68 to 3.58 (m, 4H), 2.72 to 2.68 (m, 4H), 1.79 (t, J=5.4 Hz, 2H); MS $[M+H]^+$=560.0; LCMS RT=2.96.

Example 173

N-{4-[4-amino-7-(1-glycoloylpiperidin-4-yl)pyrrolo[2,1-f][1,2,4]triazin-5-yl]-2-chlorophenyl}-N'-[2-fluoro-5-(trifluoromethyl)phenyl]urea

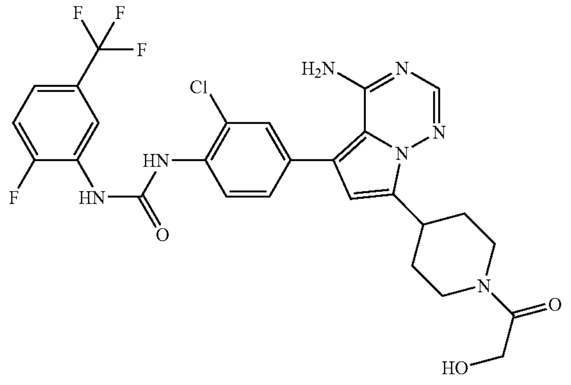

The title compound was prepared in a manner similar to the procedure described for the preparation of Example 229, using glycolic acid in place of sodium 2-hydroxypropanoate, 36 mg (65%) of the desired product was isolated. $^1$H-NMR (DMSO-$d_6$) δ 9.73 (d, J=2.4 Hz, 1H), 9.01 (s, 1H), 8.65 (dd, J=2.1, 7.2 Hz, 1H), 8.24 (d, J=8.7 Hz, 1H), 7.91 (s, 1H), 7.54-7.48 (m, 2H), 7.43-7.35 (m, 2H), 6.60 (s, 1H), 4.51 (t, J=5.4 Hz, 1H), 4.12-4.09 (m, 2H), 3.84-3.72 (m, 1H), 3.49-3.32 (m, 1H), 3.15-3.03 (m, 2H), 2.82-2.71 (m, 1H), 2.04-1.97 (m, 2H), 1.73-1.48 (m, 2H); MS $[M+H]^+$=606.3, 608.3; LCMS RT=2.91 min.

Example 174

Preparation of 1-{4-[4-amino-7-(1,4-oxazepan-4-ylmethyl)pyrrolo[2,1-f][1,2,4]triazin-5-yl]-2-fluorophenyl}-3-(4-fluoro-3-methylphenyl)urea

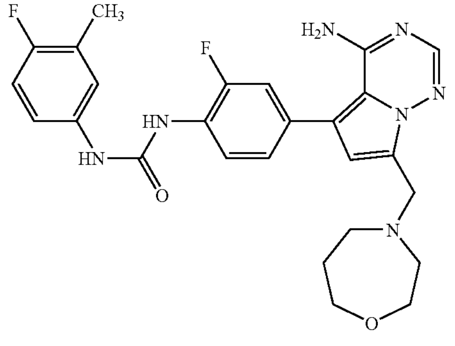

Intermediate Z (85 mg, 0.307 mmol) and Intermediate BD (132 mg, 0.5339 mmol) were allowed to react using the procedure to make Example 164. The residue was chromatographed using a 4 g MPLC column. The product was eluted with a gradient of 0-6% MeOH/$CH_2Cl_2$ to yield 3 mg (2%) of clean product. $^1$H-NMR (Methanol-$d_4$) δ 9.05 (s, 1H), 8.62 (s, 1H), 8.25 (t, J=8.7 Hz, 1H), 7.90 (s, 1H), 7.35 to 7.19 (m, 4H), 6.67 (s, 1H), 3.98 (s, 2H), 3.68 to 3.58 (m, 4H), 2.73 to 2.50 (m, 7H), 1.80 (m, 2H); MS $[M+H]^+$=508.0; LCMS RT=2.31.

Example 175

Preparation of N-{4-[4-amino-7-(1,4-oxazepan-4-ylmethyl)pyrrolo[2,1-f][1,2,4]triazin-5-yl]-2-fluorophenyl}-N-(3-ethylphenyl)urea

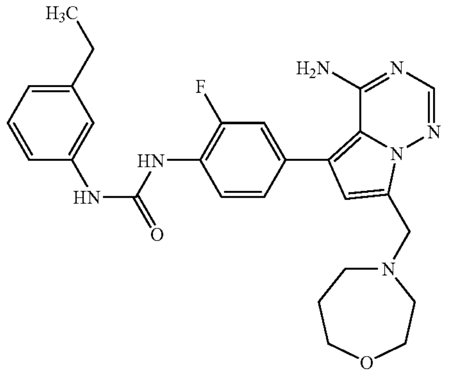

Intermediate Z (85 mg, 0.261 mmol) and Intermediate BE (130 mg, 0.339 mmol) were allowed to react using the procedure to make Example 164. The residue was chromatographed using a 4 g MPLC column. The product was eluted with a gradient of 0-6% MeOH/$CH_2Cl_2$ to yield 43 mg (33%) of clean product. MS $[M+H]^+$=504.0; LCMS RT=2.39.

Example 176

Preparation of N-{4-[4-amino-7-(1,4-oxazepan-4-ylmethyl)pyrrolo[2,1-f][1,2,4]triazin-5-yl]phenyl}-N'-[4-(trifluoromethyl)pyridin-2-yl]urea

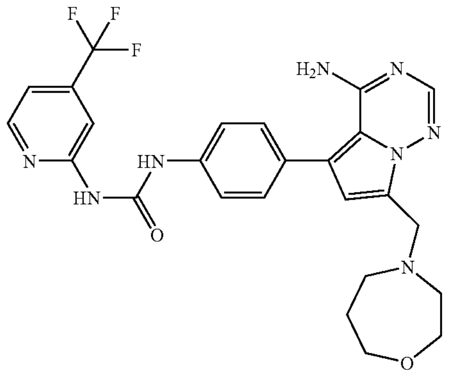

Intermediate Z (100 mg, 0.307 mmol) and Intermediate AD (174 mg, 0.429 mmol) were allowed to react using the procedure to make Example 164. The residue was chromatographed using a 4 g MPLC column. The product was eluted with a gradient of 0-20% (1:1 THF-MeOH)/$CH_2Cl_2$ to yield 30 mg (19%) of clean product. $^1$H-NMR (DMSO-$d_6$) δ9.87 (s, 1H), 9.74 (s, 1H), 8.54 (d, J=5.1 Hz, 1H), 8.06 (t, 1H), 7.90 (s, 1H), 7.62 (d, J=5.4 Hz, 2H), 7.43 to 7.36 (m, 3H), 6.64 (s, 1H), 3.99 (s, 2H), 3.68 to 3.59 (m, 4H), 2.72 to 2.69 (m, 4H), 1.81 to 1.80 (m, 2H); MS $[M+H]^+$=526.9; LCMS RT=2.46.

Example 177

Preparation of N-{4-[4-amino-7-(1,4-oxazepan-4-ylmethyl)pyrrolo[2,1-f][1,2,4]triazin-5-yl]-2-fluorophenyl}-N'-[2-fluoro-5-(trifluoromethyl)phenyl]urea

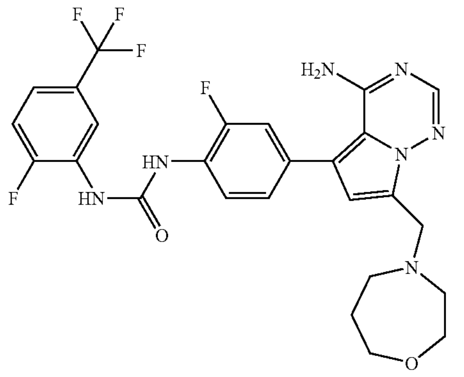

Intermediate Z (85 mg, 0.261 mmol) and Intermediate O (150 mg, 0.339 mmol) were allowed to react using the procedure to make Example 164. The residue was chromatographed using a 4 g MPLC column. The product was eluted with a gradient of 0-6% MeOH/$CH_2Cl_2$ to yield 60 mg (41%) of clean product. $^1$H-NMR (DMSO-$d_6$) δ9.87 (s, 1H), 9.74 (s, 1H), 8.54 (d, J=5.1 Hz, 1H), 8.06 (s, 1H), 7.90 (s, 1H), 7.62 (d, J=5.4 Hz, 2H), 7.43 to 7.36 (m, 3H), 6.64 (s, 1H), 3.99 (s, 2H), 3.68 to 3.59 (m, 4H), 2.72 to 2.69 (m, 4H), 1.81 to 1.80 (m, 2H); MS $[M+H]^+$=561.9; LCMS RT=2.61.

Example 178

Preparation of N-{4-[4-amino-7-(1,4-oxazepan-4-ylmethyl)pyrrolo[2,1-f][1,2,4]triazin-5-yl]-2-fluorophenyl}-N'-[3-(trifluoromethyl)phenyl]urea

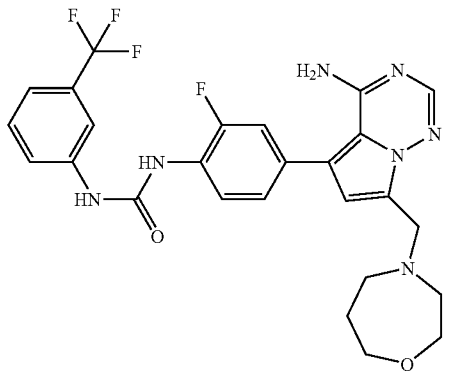

Intermediate Z (85 mg, 0.261 mmol) and Intermediate Q (144 mg, 0.339 mmol) were allowed to react using the procedure to make Example 164. The residue was chromatographed using a 4 g MPLC column. The product was eluted with a gradient of 0-6% MeOH/$CH_2Cl_2$ to yield 23 mg (16%) of clean product. $^1$H-NMR (DMSO-$d_6$) δ9.44 (s, 1H), 8.74 (s, 1H), 8.22 (t, J=8.4 Hz, 1H), 8.05 (s, 1H), 7.91 (s, 1H), 7.55 to 7.23 (m, 5H), 6.68 (s, 1H), 3.98 (s, 2H), 3.68 to 3.58 (m, 4H), 2.72 to 2.67 (m, 4H), 1.80 (m, 2H); MS $[M+H]^+$=544.0; LCMS RT=2.51.

Example 179

Preparation of N-{4-[4-amino-7-(1,4-oxazepan-4-ylmethyl)pyrrolo[2,1-f][1,2,4]triazin-5-yl]-2-fluorophenyl}-N'-[4-(trifluoromethyl)pyridin-2-yl]urea

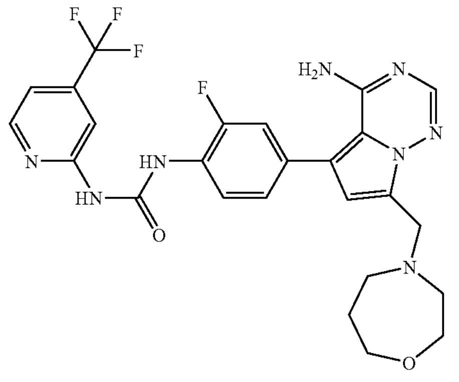

Intermediate Z (85 mg, 0.261 mmol) and Intermediate AE (144 mg, 0.339 mmol) were allowed to react using the procedure to make Example 164. The residue was chromatographed using a 4 g MPLC column. The product was eluted with a gradient of 0-6% MeOH/$CH_2Cl_2$ to yield 32 mg (23%) of clean product. $^1$H-NMR (DMSO-$d_6$) δ 10.13 (s, 11-1), 10.05 (bs, 1H), 8.55 (d, J=8.1 Hz, 1H), 8.28 (t, J=8.4 Hz, 1H), 8.01 (s, 1H), 7.91 (s, 1H), 7.39 to 7.25 (m, 3H), 6.69 (s, 1H), 3.98 (s, 2H), 3.68 to 3.58 (m, 4H), 2.72 to 2.67 (m, 4H), 1.80 (m, 2H); MS $[M+H]^+$=545.0; LCMS RT=2.42.

Example 180

Preparation of 1-{4-[4-amino-7-(1,4-oxazepan-4-ylmethyl)pyrrolo[2,1-f][1,2,4]triazin-5-yl]-2-methylphenyl}-3-[4-(trifluoromethyl)pyridin-2-yl]urea

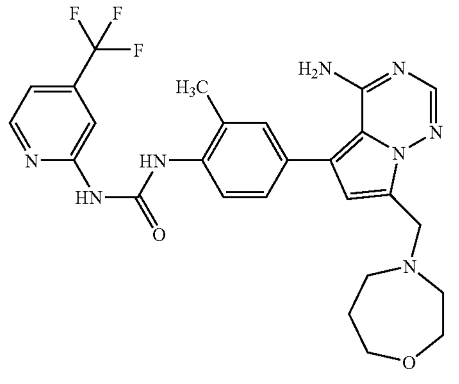

Intermediate Z (85 mg, 0.261 mmol) and Intermediate AG (144 mg, 0.339 mmol) were allowed to react using the procedure to make Example 164. The residue was chromatographed using a 4 g MPLC column. The product was eluted with a gradient of 0-6% $MeOH/CH_2Cl_2$ to yield 5.7 mg (3%) of clean product. $^1H$-NMR (DMSO-$d_6$) δ10.17 (s, 1H), 9.95 (bs, 1H), 8.55 (d, J=7.5 Hz, 1H), 8.09 (t, J=8.4 Hz, 1H), 7.89 to 7.87 (m, 2H), 7.37 to 7.26 (m, 3H), 6.63 (s, 1H), 3.96 (s, 2H), 3.68 to 3.56 (m, 4H), 2.72 to 2.60 (m, 4H), 2.32 (s, 3H), 1.79 (m, 2H); MS $[M+H]^+$=541.0; LCMS RT=2.45

Example 181

Preparation of N-{4-[4-amino-7-(1,4-oxazepan-4-ylmethyl)pyrrolo[2,1-f][1,2,4]triazin-5-yl]-2-methylphenyl}-N'-[2-fluoro-5-(trifluoromethyl)phenyl]urea

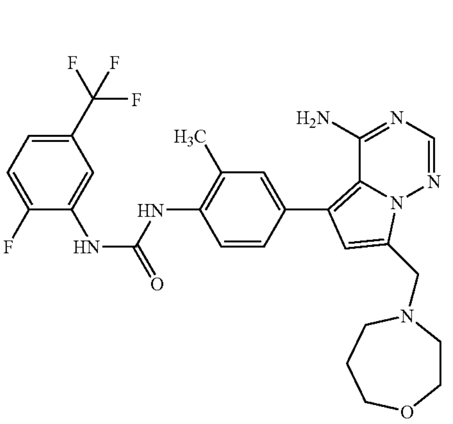

Intermediate Z (85 mg, 0.261 mmol) and Intermediate AF (148 mg, 0.339 mmol) were allowed to react using the procedure to make Example 164. The residue was chromatographed using a 4 g MPLC column. The product was eluted with a gradient of 0-6% $MeOH/CH_2Cl_2$ to yield 21 mg (14%) of clean product. $^1H$-NMR (DMSO-$d_6$) δ 9.39 (s, 1H), 8.67 (d, J=5.1 Hz, 1H), 8.57 (s, 1H), 7.99 (d, J=8.1 Hz, 1H), 7.89 (s, 1H), 7.51 to 7.25 (m, 4H), 6.63 (s, 1H), 3.99 (s, 2H), 3.68 to 3.56 (m, 4H), 2.72 to 2.67 (m, 4H), 1.78 (m, 2H); MS $[M+H]^+$=558.0; LCMS RT=2.50

Example 182

Preparation of N-{4-[4-amino-7-(1,4-oxazepan-4-ylmethyl)pyrrolo[2,1-f][1,2,4]triazin-5-yl]-2,5-difluorophenyl}-N'-(2-fluoro-5-methylphenyl)urea

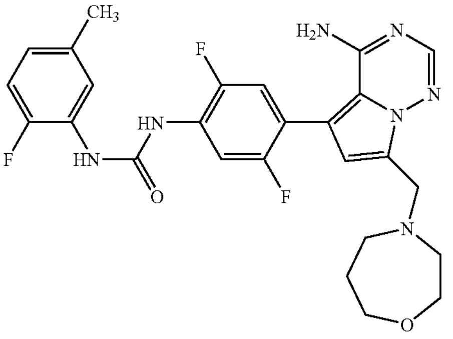

Intermediate Z (100 mg, 0.307 mmol) and Intermediate AP (162 mg, 0.399 mmol) were allowed to react using the procedure to make Example 164. The residue was chromatographed using a 4 g MPLC column. The product was eluted with a gradient of 0-6% $MeOH/CH_2Cl_2$ to yield 20 mg (12%) of clean product. $^1H$-NMR (DMSO-$d_6$) δ 9.80 (s, 1H), 9.20 (d, J=3.9 Hz, 1H), 8.61 (s, 1H), 8.14 (dd, J=7.2, J=12.0 Hz, 1H), 7.90 (s, 1H), 7.74 (d, J=8.4 Hz, 1H), 6.64 (s, 1H), 3.98 (s, 2H), 3.65 to 3.57 (m, 4H), 3.29 (s, 3H), 2.71 to 2.68 (m, 4H), 1.79 (t, J=5.7, 2H); MS $[M+H]^+$=526.2; LCMS RT=2.44.

Example 183

Preparation of N-{4-[4-amino-7-(1,4-oxazepan-4-ylmethyl)pyrrolo[2,1-f][1,2,4]triazin-5-yl]phenyl}-N'-(2-fluoro-5-methylphenyl)urea

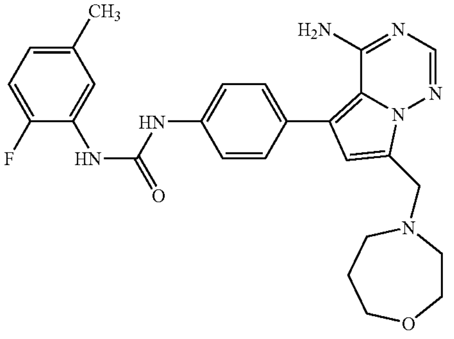

Intermediate Z (100 mg, 0.307 mmol) and Intermediate AT (148 mg, 0.399 mmol) were allowed to react using the procedure to make Example 164. The residue was chromatographed using a 4 g MPLC column. The product was eluted with a gradient of 0-6% $MeOH/CH_2Cl_2$ to yield 30 mg (20%) of clean product. $^1H$-NMR (DMSO-$d_6$) δ 9.17 (s, 1H), 8.51 (s, 1H), 7.99 (dd, J=8.1 Hz, J=2.1 Hz, 1H), 7.88 (s, 1H), 7.55 (m, 2H), 7.38 (m, 2H), 7.10 (dd, J=11.4 Hz, J=8.1 Hz, 1H), 6.72 (m, 1H), 6.62 (s, 1H), 3.97 (s, 2H), 3.67 to 3.57 (m, 4H), 3.29 (s, 3H), 2.68 (m, 4H), 2.26 (s, 3H), 1.79 (m, 2H).

Example 184

Preparation of N-[4-(4-amino-7-[3-[(2S)-2-(methoxymethyl)pyrrolidin-1-yl]propyl}pyrrolo[2,1-f][1,2,4]triazin-5-yl)-2-fluorophenyl]-N'-[2-fluoro-5-(trifluoromethyl)phenyl]urea

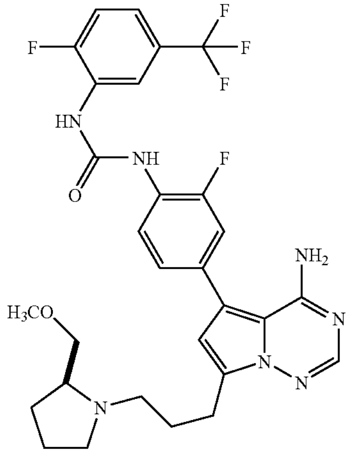

1-{4-[4-amino-7-(3-bromopropyl)pyrrolo[2,1-f][1,2,4]triazin-5-yl]-2-fluorophenyl}-3-[2-fluoro-5-(trifluoromethyl)phenyl]urea (Example 193 step 1) (50 mg, 0.088 mmol) and (2S)-2-(methoxymethyl)pyrrolidine (36 uL, 0.263 mmol) were added to a vial. DMF was added (1 mL) followed by triethylamine (15 uL, 0.109 mmol) and KI (spatula tip). The vial was capped and the reaction heated at 55° C. for two hours. Upon cooling the product precipitated out of solution. The solids were collected by filtration and rinsed with ether to yield 35 mg (65%) of clean product. $^1$H-NMR (DMSO-$d_6$) δ 9.41 (s, 1H), 9.25 (s, 1H), 8.65 (d, J=7.2 Hz, 1H), 8.26 (t, J=8.4 Hz, 1H), 7.89 (s, 1H), 7.55 to 7.21 (m, 4H), 6.57 (s, 1H), 3.32 (s, 3H), 3.18 to 2.83 (m, 7H), 2.37 to 1.45 (m, 5H); MS $[M+H]^+$=604.2; LCMS RT=2.59

Example 185

Preparation of N-{4-(4-amino-7-{3-[(2S)-2-(methoxymethyl)pyrrolidin-1-yl]propyl}pyrrolo[2,1-f][1,2,4]triazin-5-yl)-2,5-difluorophenyl}-N'-[2-fluoro-5-(trifluoromethyl)phenyl]urea

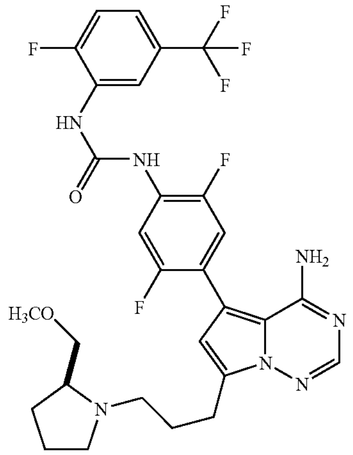

Step 1: Synthesis of 5-bromo-7-{3[(2S)-2-(methoxymethyl)pyrrolidin-1-yl]propyl}pyrrolo[2,1f][1,2,4]triazin-4-amine

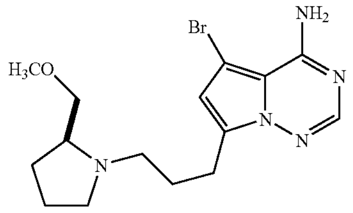

Intermediate V step 4 (947 mg, 2.8 mmol) was allowed to react with (2S)-2-(methoxymethyl)pyrrolidine (980 mg, 8.5 mmol) using the procedure to make 5-bromo-7-(3-morpholin-4-ylpropyl)pyrrolo[2,1-f][1,2,4]triazin-4-amine. The reaction was partitioned between EtOAc (100 mL) and saturated aqueous sodium bicarbonate (20 mL). The aqueous layer was extracted with EtOAc (10 mL). The combined organic layer was washed with brine (10 mL) then dried with sodium sulfate. The reaction was concentrated under vacuum to quantitatively yield crude product. $^1$H-NMR (DMSO-$d_6$) δ7.83 (s, 1H), 6.61 (s, 1H), 3.25 (m, 1H), 3.19 (s, 3H), 3.12 to 2.72 (m, 6H), 2.23 (m, 1H), 2.04 (m, 1H), 1.77 (m, 3H), 1.62 (m, 2H), 1.40 (m, 1H); MS $[M+H]^+$=622.2; LCMS RT=2.68.

Step 2: Preparation of the Title Compound

Intermediate AH (146 mg, 0.318 mmol) and 5-bromo-7-{3-[(2S)-2-(methoxymethyl)-pyrrolidin-1-yl]propyl}pyrrolo[2,1-f][1,2,4]triazin-4-amine (90 mg, 0.244 mmol) were allowed to react using the procedure to make Example 164. The product was purified by column chromatography using a 4 g MPLC column. The eluent was 0-6% (2N NH3 in MeOH)/$CH_2Cl_2$ to yield clean product (18 mg, 9%) $^1$H-NMR (DMSO-$d_6$) δ9.48 (s, 1H), 9.44 (s, 1H), 8.67 (d, J=7.5 Hz, 1H), 8.14 (m, 1H), 7.89 (s, 1H), 7.53 to 7.26 (m, 3H), 6.54 (s, 1H), 3.27 (m, 1H), 3.19 (s, 3H), 3.13 to 2.83 (m, 6H), 2.26 (m, 1H), 2.07 (m, 1H), 1.82 (m, 3H), 1.64 (m, 2H), 1.40 (m, 1H); MS $[M+H]^+$=622.2; LCMS RT=2.68.

Example 186

Preparation of N-{4-[4-amino-7-(3-pyrrolidin-1-ylpropyl)pyrrolo[2,1-f][1,2,4]triazin-5-yl]-2-fluorophenyl}-N'-[2-fluoro-5-(trifluoromethyl)phenyl]urea

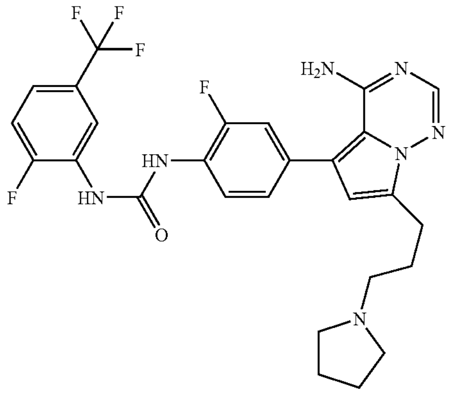

The title compound was prepared in a mannor analogous to Example 193 by substituting pyrrolidine for 1,4-oxazepane. The product was purified by column chromatography using a 4 g MPLC column. The eluent was 0-10.0% (2N $NH_3$ in MeOH)/$CH_2Cl_2$ to yield clean product (10 mg, 20%) $^1$H-NMR (Methanol-$d_4$) δ 9.41 (s, 1H), 9.25 (s, 1H), 8.67 (dd, J=7.2 Hz, J=2.4 Hz, 1H), 8.26 (t, J=8.7 Hz, 1H), 7.89 (s, 1H), 7.55 to 7.22 (m, 3H), 6.58 (s, 1H), 2.89 (t, J=7.5 Hz, 2H), 2.40 (m, 6H), 1.84 (m, 2H), 1.65 (m, 4H); MS $[M+H]^+$=560.2; LCMS RT=2.61

Example 187

Preparation of N-(4-{4-amino-7-[3-(4-methylpiperazin-1-yl)propyl]pyrrolo[2,1-f][1,2,4]triazin-5-yl}-2-fluorophenyl)-N'-[2-fluoro-5-(trifluoromethyl)phenyl]urea

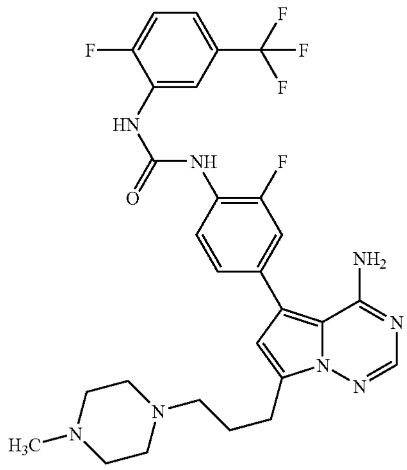

The title compound was prepared in a manor analogous to Example 193 by substituting 1-methylpiperazine for 1,4-oxazepane. The product was purified by column chromatography using a 4 g MPLC column. The eluent was 0-10.0% (2N $NH_3$ in MeOH)/$CH_2Cl_2$ to yield clean product (15 mg, 29%) $^1$H-NMR (DMSO-$d_6$) δ 9.41 (s, 1H), 9.25 (s, 1H), 8.66 (m, 1H), 8.25 (t, J=8.7 Hz, 1H), 7.89 (s, 1H), 7.52 to 7.22 (m, 4H), 6.57 (s, 1H), 2.85 (t, J=7.8 Hz, 2H), 2.42 to 2.12 (m, 11H), 1.82 (m, 2H); MS $[M+H]^+$=589.2; LCMS RT=2.44

Example 188

Preparation of N-(4-{7-[3-(4-acetylpiperazin-1-yl)propyl-4-aminopyrrolo[2,1f][1,2,4]triazin-5-yl}-2-fluorophenyl)-N'-[2-fluoro-5-(trifluoromethyl)phenyl]urea

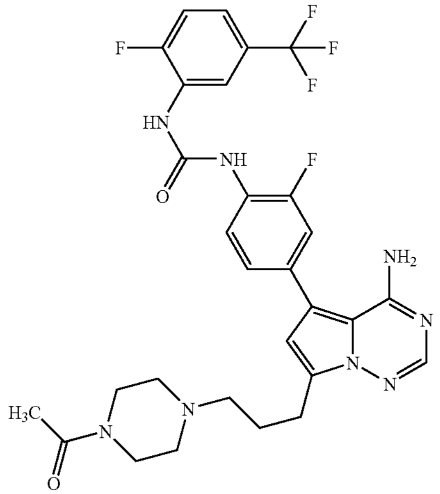

The title compound was prepared in a mannor analogous to Example 193 by substituting 1-acetylpiperazine for 1,4-oxazepane. Upon cooling the product precipitated out of solution. The solids were collected by filtration and rinsed with ether to yield (35 mg, 65%) $^1$H-NMR (DMSO-$d_6$) δ 9.41 (s, 1H), 9.25 (s, 1H), 8.66 (d, J=6.3 Hz, 1H), 8.26 (t, J=8.7 Hz, 1H), 7.89 (s, 1H), 7.52 to 7.22 (m, 4H), 6.59 (s, 1H), 3.39 (m, 4H), 2.88 (m, 2H), 2.72 to 2.27 (m, 5H), 1.97 (s, 1H), 1.85 (t, J=7.2 Hz, 2H).

Example 189

Preparation of N-(4-{4-amino-7-[3-(1,1-dioxidothiomorpholin-4-34)propyl]pyrrolo[2,1-f][1,2,4]triazin-5-yl}-2-fluorophenyl)-N'-[2-fluoro-5-(trifluoromethyl)phenyl]urea

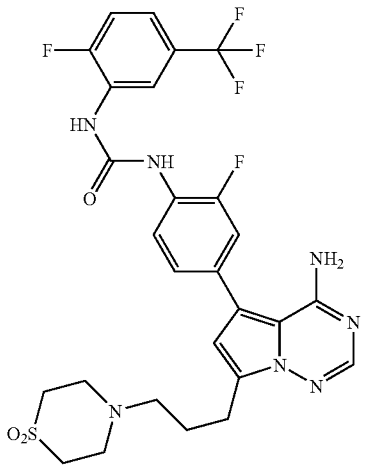

The title compound was prepared in a mannor analogous to Example 193 by substituting thiomorpholine 1,1-dioxide for 1,4-oxazepane. Upon cooling the product precipitated out of solution. The product was purified by column chromatography using a 4 g MPLC column. The eluent was 0-10.0% (2N $NH_3$ in MeOH)/$CH_2Cl_2$ to yield clean product (10 mg, 19%) $^1$H-NMR (DMSO-$d_6$) δ 9.41 (s, 1H), 9.26 (s, 1H), 8.26 (t, J=8.4 Hz, 1H), 7.89 (s, 1H), 7.35 to 7.30 (m, 4H), 6.60 (s, 1H), 3.05 (m, 4H), 2.88 (m, 4H), 2.57 (m, 2H), 1.86 (m, 4H), MS $[M+H]^+$624.1=; LCMS RT=2.72

Example 190

Preparation of N-{4-[4-amino-7-(3-morpholin-4-ylpropyl)pyrrolo[2,1-f][1,2,4]triazin-5-yl]-2,5-difluorophenyl}-N'-[2-fluoro-5-(trifluoromethyl)phenyl]urea

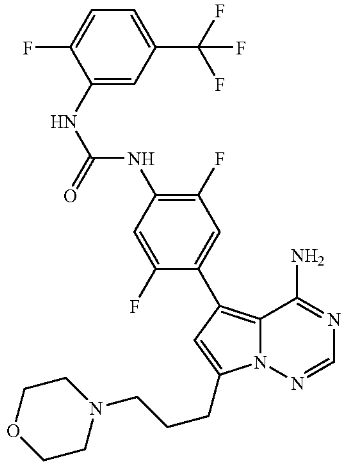

Intermediate V (70 mg, 0.206 mmol) and Intermediate AH (142 mg, 0.309 mmol) were added to a vial, Dioxane (3 mL) was added followed by Aq 1N sodium carbonate (0.620 mL, 0.620 mmol). The reaction was then placed under $N_2$. Reaction was taken through 3 purge-fill cycles with $N_2$ and Vacuum. Tetrakistriphenylphosphinepalladuium, (24 mg, 0.021 mmol) was then added and the reaction degassed using vacuum and filled with $N_2$ then heated in an oil bath at 90° C. overnight. The reaction mixture was partitioned between EtOAc (75 mL) and $H_2O$ (30 mL). The aqueous layer was back extracted with EtOAc (25 mL). The combined organic layer was washed with brine then dried with $Na_2SO_4$. After concentration, the residue was purified by preparative HPLC using a gradient elution from 10% to 70% acetonitrile to obtain 16 mg, (13%) clean product. $^1$H-NMR (DMSO-$d_6$) □19.49 (s, 1H), 9.46 (s, 1H), 8.63 (m, 1H), 8.15 (dd, J=11.7 Hz, J=6.9 Hz, 1H), 7.90 (s, 1H), 7.57 to 7.27 (m, 3H), 6.55 (s, 1H), 3.55 (m, 4H), 3.68 to 3.58 (m, 4H), 2.88 (t, J=7.5 Hz, 2H), 2.30 (m, 6H), 1.82 (m, 2H); MS $[M+H]^+$=594.2; LCMS RT=2.65.

Example 191

Preparation of N-{4-[4-amino-7-(3-morpholin-4-ylpropyl)pyrrolo[2,1-f][1,2,4]triazin-5-yl]-2-fluorophenyl}-N'-[4-(trifluoromethyl)pyridin-2-yl]urea

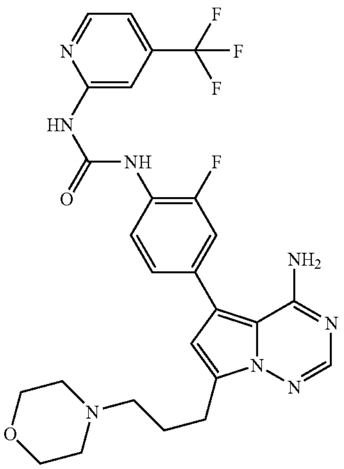

Intermediate V (70 mg, 0.206 mmol) and Intermediate AE (131 mg, 0.309 mmol) was allowed to react using the procedure to make Example 190. The material was purified by column chromatography, eluent; 0-10% MeOH/$CH_2Cl_2$, followed by preparative HPLC, eluent; 10% to 70% acetonitrile to obtain 18 mg, (16%) clean product. $^1$H-NMR (DMSO-$d_6$) δ10.13 (s, 1H), 10.05 (bs, 1H), 8.55 (d, J=5.7 Hz, 1H), 8.27 (t, J=8.4 Hz, 1H), 8.01 (s, 1H), 7.89 (s, 1H), 7.40 to 7.23 (m, 3H), 6.58 (s, 1H), 3.55 (m, 4H), 2.88 (m, 2H), 2.38 (m, 6H), 1.86 (m, 2H); MS $[M+H]^+$=558.8; LCMS RT=2.31

Example 192

Preparation of N-{4-[4-amino-7-(3-hydroxypropyl)pyrrolo[2,1-f][1,2,4]triazin-5-yl]-2-fluorophenyl}-N'-[2-fluoro-5-(trifluoromethyl)phenyl]urea

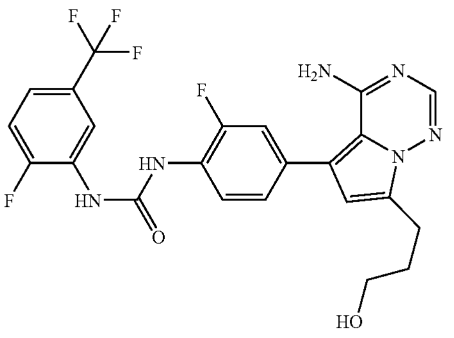

Intermediate V step 3 (800 mg, 2.95 mmol) and Intermediate O (1.44 g, 3.25 mmol) were added to a flask, Dioxane (35 mL) was added followed by Aq 1N Sodium Carbonate (8.85 mL, 8.85 mmol). The reaction was then placed under $N_2$. Reaction was taken through 3 purge-fill cycles with $N_2$ and Vacuum. Tetrakistriphenylphosphinepalladuium, (341 mg, 0.295 mmol) was then added and the reaction degassed using vacuum and filled with $N_2$ then heated in an oil bath at 80° C. overnight. The reaction mixture was partitioned between EtOAc (400 mL) and saturated sodium bicarbonate (80 mL). The aqueous layer was back extracted with EtOAc (100 mL). The combined organic layer was washed with brine then dried with $Na_2SO_4$. After concentration, the residue was purified by column chromatography using a gradient elution from 0% to 10% Methanol-$CH_2Cl_2$ to obtain 1.03 g, (69%) of clean product. MS $[M+H]^+$=507.3; LCMS RT=2.75 min Example 193

Preparation of N-(4-{4-amino-7-[3-(1,4-oxazepan-4-yl)propyl]pyrrolo[2,1f][1,2,4]triazin-5-yl}-2-fluorophenyl)-N'-[2-fluoro-5-(trifluoromethyl)phenyl]urea

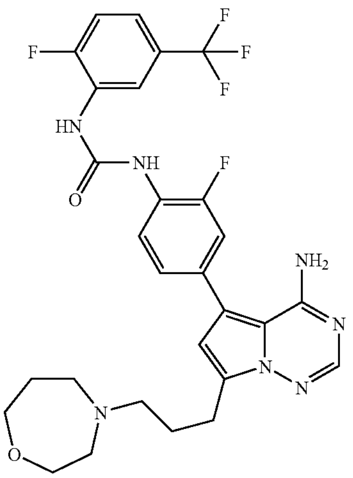

Step 1: Preparation of 1-{4-[4-amino-7-(3-bromopropyl)pyrrolo[2,1-f][1,2,4]triazin-5-yl]-2-fluorophenyl}-3-[2-fluoro-5-(trifluoromethyl)phenyl] urea

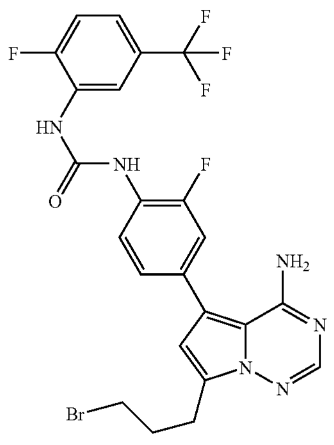

The title compound was prepared in a mannor analogous to Example 212 step 3 by substituting N-{4-[4-amino-7-(3-hydroxypropyl)pyrrolo[2,1f][1,2,4]triazin-5-yl]-2-fluoro-phenyl}-N'-[2-fluoro-5-(trifluoromethyl)phenyl]urea for 1-{4-[4-amino-7-(2-hydroxyethyl)-pyrrolo[2,1f][1,2,4]triazin-5-yl]-2-fluorophenyl}-3-[2-fluoro-5-(trifluoromethyl)-phenyl] urea. MS $[M+H]^+$=569.2; LCMS RT=3.44

Step 2: Preparation of the Title Compound

1-{4-[4-amino-7-(3-bromopropyl)pyrrolo[2,1f][1,2,4]triazin-5-yl]-2-fluorophenyl}-3-[2-fluoro-5-(trifluoromethyl) phenyl]urea (50 mg, 0.088 mmol) and 1,4-oxazepane (36 mg, 0.263 mmol) were allowed to react using the procedure to make N-[4-(4-amino-7-{3-[(2S)-2-(methoxymethyl)pyrrolidin-1-yl]propyl}pyrrolo[2,1-f][1,2,4]triazin-5-yl)-2-fluorophenyl]-N'-[2-fluoro-5-(trifluoromethyl)phenyl]urea. The product was purified by column chromatography using a 4 g MPLC column. The eluent was 0-10.0% (2N $NH_3$ in MeOH)/ $CH_2Cl_2$ to yield clean product (11 mg, 22%) $^1$H-NMR (DMSO-$d_6$) δ 9.41 (s, 1H), 9.25 (s, 1H), 8.66 (m, 1H), 8.26 (t, J=8.7 Hz, 1H), 7.89 (s, 1H), 7.52 to 7.22 (m, 4H), 6.58 (s, 1H), 3.66 to 3.56 (m, 4H), 2.90 to 2.42 (m, 8H), 2.57 (m, 2H), 1.79 (m, 4H), MS $[M+H]^+$=590.2; LCMS RT=2.61

Example 194

Preparation of N-(4-{4-amino-7-[3-(dimethylamino) propyl]pyrrolo[2,1-f][1,2,4]triazin-5-yl}-2-fluorophenyl)-N'-[2-fluoro-5-(trifluoromethyl)phenyl] urea

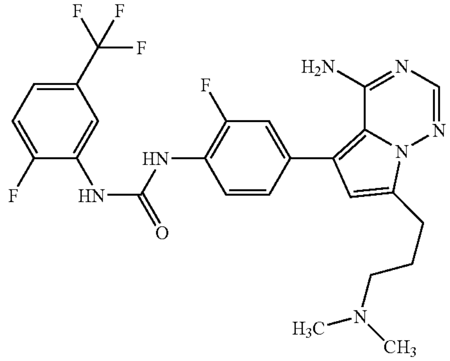

The title compound was prepared in a mannor analogous to Example 193 by substituting N-methylmethanamine (2N in THF) for 1,4-oxazepane. The product is purified by column chromatography using a 4 g MPLC column. The eluent was 0-10.0% (2N $NH_3$ in MeOH)/$CH_2Cl_2$ to yield clean product (26 mg, 56%) MS [M+H]+=534.1; LCMS RT=2.49.

Example 195

Preparation of N-(4-{4-amino-7-[3-(3-oxopiperazin-1-yl)propyl]pyrrolo[2,1-f][1,2,4]triazin-5-yl}-2-fluorophenyl)-N'-[2-fluoro-5-(trifluoromethyl)phenyl] urea

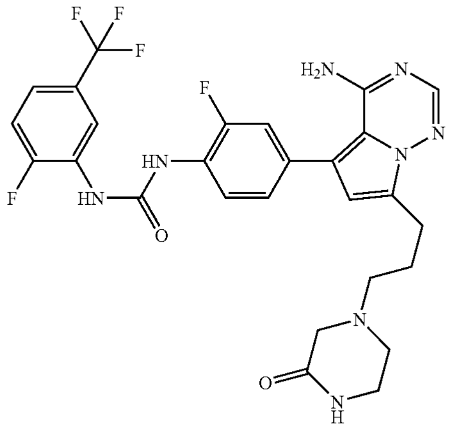

The title compound was prepared in a mannor analogous to Example 193 by substituting piperazin-2-one for 1,4-oxazepane. The product was purified by column chromatography using a 4 g MPLC column. The eluent was 0-10.0% (2N $NH_3$ in MeOH)/$CH_2Cl_2$ to yield clean product (14 mg, 27%) $^1$H-NMR (Methanol-$d_4$) δ 8.67 (m, 1H), 8.27 (m, 1H), 7.89 (s, 1H), 7.49 to 7.22 (m, 4H), 6.59 (s, 1H), 3.37 (m, 8H), 3.10 (m, 4H), 2.91 (m, 2H), 1.86 (m, 4H), MS $[M+H]^+$=589.2; LCMS RT=2.53

Example 196

Preparation of N-{4-[4-amino-7-(3-thiomorpholin-4-ylpropyl)pyrrolo[2,1f][1,2,4]triazin-5-yl]-2-fluorophenyl}-N'-[2-fluoro-5-(trifluoromethyl)phenyl] urea

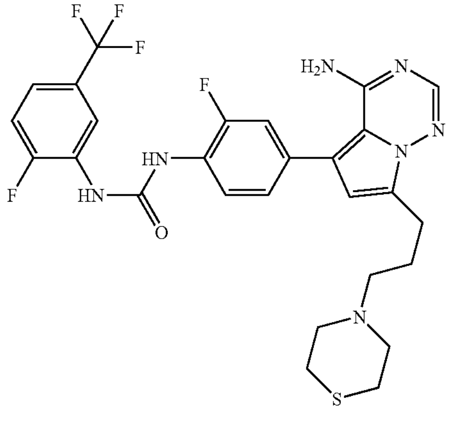

The title compound was prepared in a mannor analogous to Example 193 by substituting thiomorpholine for 1,4-oxazepane. The product was purified by column chromatography using a 4 g MPLC column. The eluent was 0-10.0% (2N $NH_3$ in MeOH)/$CH_2Cl_2$ to yield clean product (18 mg, 35%) $^1$H-NMR (DMSO-$d_6$) δ 9.41 (s, 1H), 9.25 (s, 1H), 8.65 (dd, J=7.2, Hz, J=2.1 Hz, 1H), 8.25 (t, J=8.4 Hz, 1H), 7.89 (s, 1H), 7.52 to 7.22 (m, 4H), 6.57 (s, 1H), 2.85 (t, J=8.4 Hz, 2H), 2.61 (m, 8H), 2.38 (m, 2H), 1.86 (m, 2H), MS $[M+H]^+$592.2; LCMS RT=2.49 NMR Example 197

Preparation of N-[4-(4-amino-7-{3-[ethyl(2-hydroxyethyl)amino]propyl}pyrrolo[2,1f][1,2,4]triazin-5-yl)-2-fluorophenyl]-N'-[2-fluoro-5-(trifluoromethyl)phenyl]urea

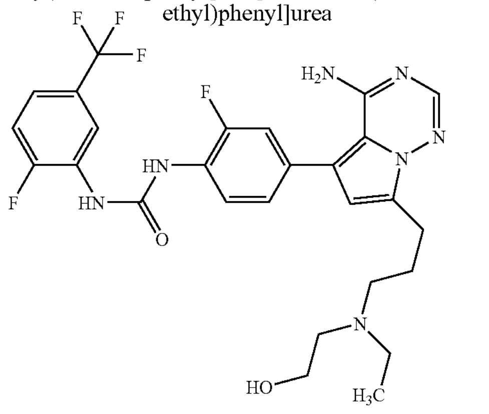

The title compound was prepared in a mannor analogous to Example 193 by substituting 2-(ethylamino)ethanol for 1,4-oxazepane. The product was purified by column chromatography using a 4 g MPLC column. The eluent was 0-10.0% (2N $NH_3$ in MeOH)/$CH_2Cl_2$ to yield clean product (15 mg, 24%) $^1$H-NMR (DMSO-$d_6$) δ 9.41 (s, 1H), 9.26 (s, 1H), 8.67 (dd, J=7.5, Hz, J=2.4 Hz, 1H), 8.26 (t, J=8.4 Hz, 1H), 7.89 (s, 1H), 7.55 to 7.22 (m, 4H), 6.58 (s, 1H), 4.29 (m, 1H), 3.43 (m, 2H), 3.38 to 3.15 (m, 6H), 1.79 (m, 2H), 0.93 (t, J=6.6 Hz, 3H), MS $[M+H]^+$=578.2; LCMS RT=2.42

Example 198

Preparation of tert-butyl 3-{4-amino-5-[3-fluoro-4-({[2-fluoro-5-(trifluoromethyl)phenyl]carbamoyl}amino)phenyl]pyrrolo[2,1f][1,2,4]triazin-7-yl}pyrrolidine-1-carboxylate

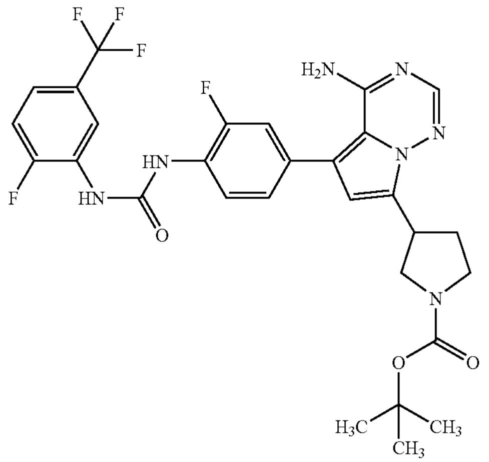

Intermediate AB (431 mg, 1.13 mmol) and Intermediate O (600 mg, 1.41 mmol) were added to a vial, DMF (2 mL) was added followed by $K_3PO_4$ (719 mg, 3.39 mmol) and water (200 uL). The reaction was then placed under $N_2$. Reaction was taken through 3 purge-fill cycles with $N_2$ and Vacuum. Tetrakistriphenylphosphine palladium, (129 mg, 0.112 mmol) was then added and the reaction degassed using vacuum and filled with $N_2$ then heated in an oil bath at 110° C. for 2 hours. The reaction mixture was partitioned between EtOAc (150 mL) and $H_2O$ (70 mL). The aqueous layer was back extracted with EtOAc (50 mL). The combined organic layer was washed with brine then dried with $Na_2SO_4$. The residue was chromatographed using a 40 g MPLC column. The product was eluted with a gradient of 0-6% MeOH/$CH_2Cl_2$ then was recrystallized from EtOAc/hexanes to yield 82 mg (12%) clean product. $^1$H-NMR (DMSO-$d_6$) δ10.12 (s, 1H), 10.05 (s, 1H), 8.53 (d, J=3.6, 1H), 8.26 (t, J=8.4 Hz, 1H), 7.91 (s, 1H), 7.38 to 7.23 (m, 2H), 6.65 (s, 1H), 3.75 (m, 2H), 3.45 to 3.24 (m, 2H), 2.27 (m, 1H), 2.08 (m, 1H), 1.38 (s, 9H); MS $[M+H]^+$=601.2; LCMS RT=3.27

Example 199

Preparation of tert-butyl 3-{4-amino-5-[4-({[2-fluoro-5-(trifluoromethyl)phenyl]carbamoyl}amino)phenyl]pyrrolo[2,1f][1,2,4]triazin-7-yl}pyrrolidine-1-carboxylate

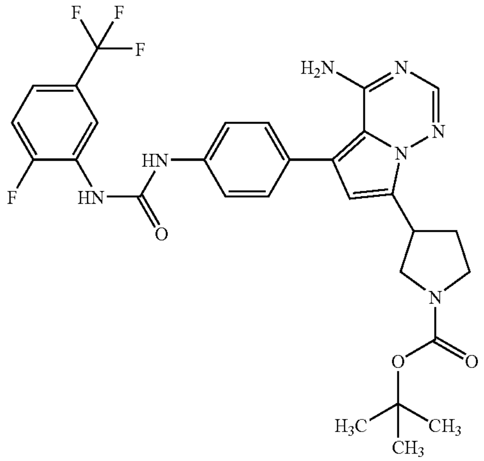

Intermediate AB (300 mg, 0.785 mmol) and Intermediate M (499 mg, 1.18 mmol) were allowed to react using the procedure to make tert-butyl 3-[4-amino-5-[3-fluoro-4-({[2-fluoro-5-(trifluoromethyl)phenyl]carbamoyl}amino)phenyl]pyrrolo[2,1-f][1,2,4]triazin-7-yl]pyrrolidine-1-carboxylate. The product was purified using flash chromatography with 0-4% MeOH/$CH_2Cl_2$ as eluent to yield 271 mg (58%) pure desired product. $^1$H-NMR (DMSO-$d_6$) δ9.30 (s, 1H), 8.94 (s, 1H), 8.63 (d, J=5.1, 1H), 7.91 (s, 1H), 7.59 to 7.37 (m, 2H), 6.60 (s, 1H), 3.75 (m, 2H), 3.45 (m, 3H), 2.40 to 2.1 (m, 1H), 2.08 (m, 1H), 0.94 (s, 9H); MS $[M+H]^+$=600.2; LCMS RT=3.27

Example 200

Preparation of N-[4-(4-amino-7-pyrrolidin-3-ylpyrrolo[2,1-f][1,2,4]triazin-5-yl)-2-fluorophenyl]-N'-[2-fluoro-5-(trifluoromethyl)phenyl]urea

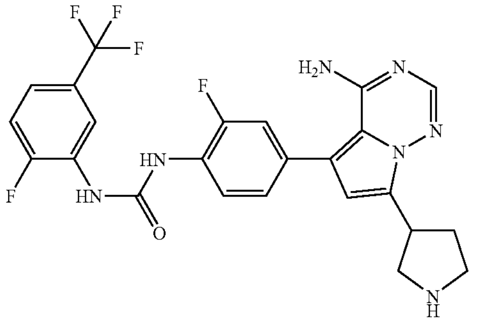

To a dry flask was added 1-[4-(4-amino-7-pyrrolidin-3-ylpyrrolo[2,1-f][1,2,4]triazin-5-yl)-2-fluorophenyl]-3-[2-fluoro-5-(trifluoromethyl)phenyl]urea (830 mg, 0.614 mmol) followed by a solution of 1:3 Trifluoroacetic acid in dichloromethane (8 mL). The mixture was stirred under N2 atmosphere for 3.5 h. The reaction was then partitioned between dichloromethane (150 mL) and 10% aqueous potassium carbonate. The aqueous layer was back extracted with dichloromethane (2×50 mL). The combined organic layer was washed with brine (50 mL) then dried with Sodium Sulfate. The solvent was evaporated under reduced pressure to yield 485 mg (70%) of the desired product. $^1$H NMR (300 MHz, DMSO-$d_6$) δ 9.41 (bs, 1H), 9.26 (bs, 1H), 8.60 (d, J=2.4 Hz, H), 8.29 (t, 8.4 Hz, 1H), 7.93 (s, 1H), 7.51-7.22 (m, 4H), 6.74 (s, 1H), 3.86 (m, 2H), 3.35-3.10 (m, 3H), 2.41 (m, 1H), 2.15 (m, 1H); MS $[M+H]^+$=518.3; HPLC RT=2.40.

Example 201

Preparation of N-(4-{4-amino-7-[1-(methylsulfonyl)pyrrolidin-3-yl]pyrrolo[2,1-f][1,2,4]triazin-5-yl}-2-fluorophenyl)-N'-[2-fluoro-5-(trifluoromethyl)phenyl]urea

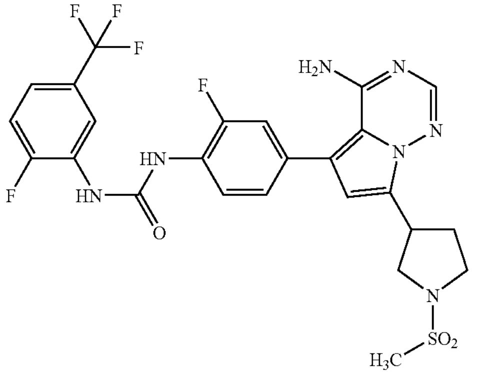

Example 200 (70 mg, 0.135 mmol) was dissolved in anhydrous THF (2 mL). Methanesulfonyl chloride (16 uL, 0.135 mmol) was added to the reaction mixture followed by triethylamine (56 uL, 0.406 mmol). The suspension was stirred at rt overnight. The product was purified using flash chromatography with 0-6% (2N $NH_3$ in MeOH/$CH_2Cl_2$ as eluent to yield 71 mg (88%) pure desired product. $^1$H NMR (300 MHz, DMSO-$d_6$) δ 9.41 (s, 1H), 9.26 (s, 1H), 8.66 (m, 1H), 8.26 (t, J=8.4 Hz, 1H), 7.93 (s, 1H), 7.54 to 7.22 (m, 4H), 6.74 (s, 1H), 3.88 to 3.74 (m, 2H), 3.88 to 3.30 (m, 3H), 2.92 (m, 3H), 2.48 (m, 1H), 2.27 (m, 1H); MS $[M+H]^+$=596.3; HPLC RT=2.98.

Example 202

Preparation of N-{4-[7-(1-acetylpyrrolidin-3-yl)-4-aminopyrrolo[2,1-f][1,2,4]triazin-5-yl]-2-fluorophenyl}-N'-[2-fluoro-5-(trifluoromethyl)phenyl]urea

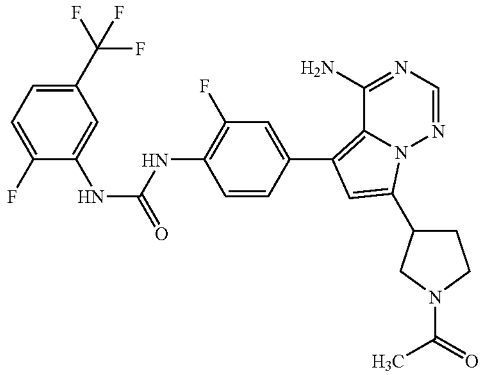

Example 200 (91 mg, 0.182 mmol) was dissolved in anhydrous THF (2 mL). Acetic anhydride (19 uL, 0.200 mmol) was added to the reaction mixture followed by triethylamine (76 uL, 0.542 mmol). The relation mixture was stirred at room temperature for 3 hours. The product was purified using ether trituration to yield 44 mg (58%) pure desired product. $^1$H NMR (300 MHz, DMSO-$d_6$) δ 9.49 (bs, 1H), 9.34 (bs, 1H), 8.64 (dd, J=7.5 Hz, J=2.1 Hz, 1H), 8.25 (t, J=8.4 Hz, 1H), 7.92 (s, 1H), 7.54 to 7.22 (m, 5H), 6.67 (d, J=15 Hz, 1H), 3.80 (m, 2H), 3.60 (m, 2H), 3.40 (m, 1H), 2.43 to 2.10 (m, 2H), 1.96 (s, 3H); MS $[M+H]^+$=560.2; HPLC RT=3.13.

Example 203

Preparation of 3-{4-amino-5-[3-fluoro-4-({[2-fluoro-5-(trifluoromethyl)phenyl]carbamoyl}amino)phenyl]pyrrolo[2,1f][1,2,4]triazin-7-yl}-N,N-dimethylpyrrolidine-1-carboxamide

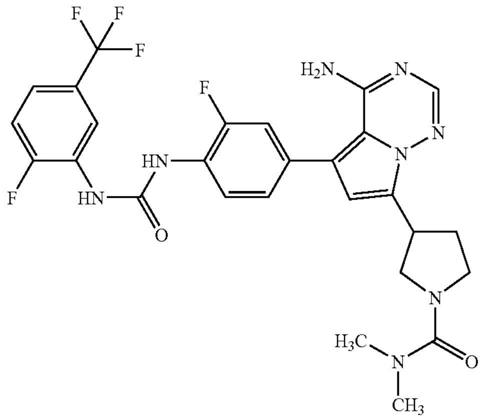

Example 200 (70 mg, 0.135 mmol) was dissolved in anhydrous THF (2 mL) and dimethylcarbamic chloride (15 uL, 0.149 mmol) was added to the reaction mixture followed by triethylamine (63 uL, 0.406 mmol). The reaction mixture was stirred at room temperature for overnight. The product was purified using flash chromatography with 0-6% (2N $NH_3$ in MeOH)/$CH_2Cl_2$ as eluent to yield 46 mg (58%) pure desired product. $^1$H NMR (300 MHz, DMSO-$d_6$) δ 9.43 (s, 1H), 9.28 (s, 1H), 8.65 (m, 1H), 8.25 (t, J=8.4 Hz, 1H), 7.91 (s, 1H), 7.51 to 7.21 (m, 4H), 6.64 (s, 1H), 3.75 (m, 2H), 3.45 to 3.29 (m, 3H), 2.73 (s, 6H), 2.25 (m, 1H), 2.00 (m, 1H); MS $[M+H]^+$=589.2; HPLC RT=3.21.

Example 204

Preparation of N-{4-[4-amino-7-(1-glycoloylpyrrolidin-3-yl)pyrrolo[2,1-f][1,2,4]triazin-5-yl]-2-fluorophenyl}-N'-[2-fluoro-5-(trifluoromethyl)phenyl] urea

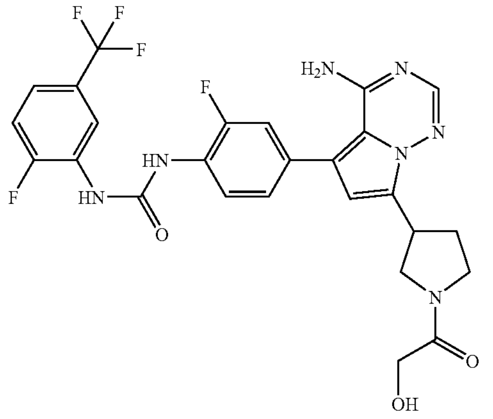

Example 200 (70 mg, 0.135 mmol) in DMF (1.5 mL) was added glycol acid (11 mg, 0.149 mmol), triethylamine (57 ul, 0.406 mmol), and (BOP) benzoltriazolyloxytris(dimethylamino) phosphonium-hexafluorophosphate (66 mg, 0.149 mmol). The reaction was stirred at room temperature overnight. The mixture was partitioned between ethyl acetate (25 mL) and H2O (25 mL). The layers were separated and the organic was washed with $H_2O$ (20 mL). The combined aqueous layers were extracted with ethyl acetate (20 mL). The combined organics were washed with water (5×20 mL) to remove DMF, dried (Na2SO4), and evaporated. The crude material was purified by trituration with ether to yield 11 mg (14%) of the desired product. MS $[M+H]^+$=576.2; HPLC RT=2.97.

Example 205

Preparation of N-{4-[7-(1-acetylpyrrolidin-3-yl)-4-aminopyrrolo[2,1-f][1,2,4]triazin-5-yl]-2-fluorophenyl}-N'-[4-(trifluoromethyl)pyridin-2-yl]urea

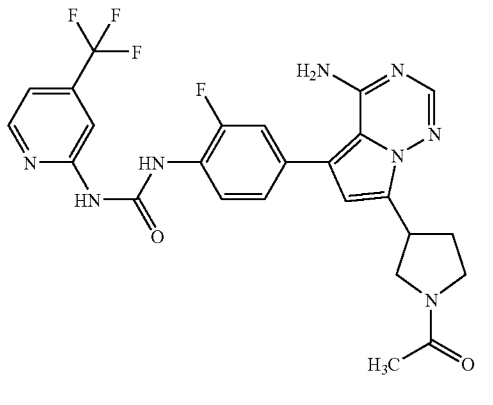

Example 208 was deprotected using the procedure described in Example 200. The crude intermediate was then treated under the procedure described in Example 202 to provide the title compound. $^1$H NMR (300 MHz, DMSO-$d_6$) δ 10.12 (s, 1H), 10.05 (bs, 1H), 8.54 (d, J=5.1 Hz, 1H), 8.26 (t, J=8.4 Hz, 1H), 8.00 (s, 1H), 7.92 (s, 1H), 7.39 to 7.23 (m, 3H), 6.65 (d, J=4.5 Hz, 1H), 3.94 to 3.29 (m, 5H), 2.94 to 2.15 (m, 2H), 1.95 (s, 3H); MS $[M+H]^+$=543.2; HPLC RT=2.66.

Example 206

Preparation of 1-[4-(4-amino-7-pyrrolidin-3-ylpyrrolo[2,1-f]1][1,2,4]triazin-5-yl)phenyl]-3-[2-fluoro-5-(trifluoromethyl)phenyl]urea

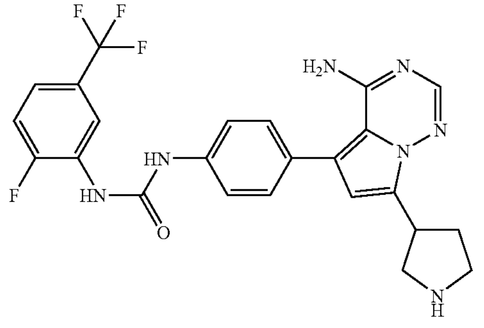

Example 199 was deprotected using the procedure described in Example 200. $^1$H NMR (300 MHz, DMSO-$d_6$) δ 8.58 (s, 1H), 8.56 (s, 1H), 7.88 (s, 1H), 7.86 (s, 1H), 7.61 to 7.35 (m, 6H), 6.56 (s, 1H), 3.64 (m, 1H), 3.59 (m, 1H), 3.22 (m, 1H), 2.93 (m, 1H,) 2.74 (m, 1H), 2.14 (m, 1H), 1.83 (m, 1H), MS $[M+H]^+$, =499.9; HPLC RT=2.33.

Example 207

Preparation of 1-{4-[7-(1-acetylpyrrolidin-3-yl)-4-aminopyrrolo[2,1-f][1,2,4]triazin-5-yl]phenyl}-3-[2-fluoro-5-(trifluoromethyl)phenyl]urea

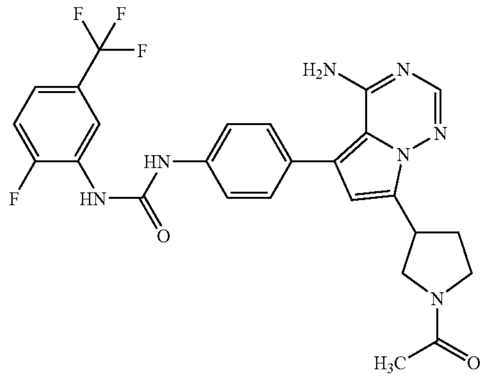

Example 206 (91 mg, 0.182 mmol) is allowed to react with acetic anhydride (20 mg, 0.200 mmol) following the procedure to make N-{4-[7-(1-acetylpyrrolidin-3-yl)-4-aminopyrrolo[2,1-f][1,2,4]triazin-5-yl]-2-fluorophenyl}-N' [2-fluoro-5-(trifluoromethyl)-phenyl]urea. The product was purified by ether trituration to yield 25 mg (25%) pure desired product.

$^1$H NMR (300 MHz, DMSO-$d_6$) δ 10.12 (s, 1H), 10.05 (bs, 1H), 8.54 (d, J=5.1 Hz, 1H), 8.26 (t, J=8.4 Hz, 1H), 8.00 (s, 1H), 7.92 (s, 1H), 7.39 to 7.23 (m, 3H), 6.65 (d, J=4.5 Hz, 1H), 3.94 to 3.29 (m, 5H), 2.94 to 2.15 (m, 2H), 1.95 (s, 3H); MS $[M+H]^+$=543.2; HPLC RT=2.66.

Example 208

Preparation of tert-butyl 3-{4-amino-5-[3-fluoro-4-({[4-(trifluoromethyl)pyridin-2-yl]carbamoyl}amino)phenyl]pyrrolo[2,1f][1,2,4]triazin-7-yl}pyrrolidine-1-carboxylate

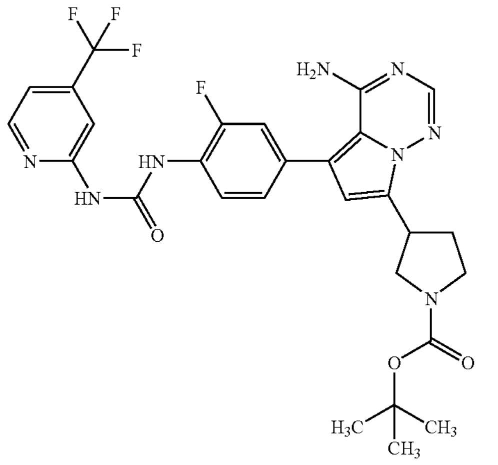

Intermediate AB (432 mg, 1.13 mmol) and 1-[2-fluoro-4-(4,4,5-trimethyl-1,3,2-dioxaborolan-2-yl)phenyl]-3-[4-(trifluoromethyl)pyridin-2-yl]urea (600 mg, 1.41 mmol) were allowed to react using the procedure to make Example 198. The product was purified using flash chromatography with 0-6% (2N $NH_3$ in MeOH/$CH_2Cl_2$ as eluent to yield 149 mg (22%) pure desired product. $^1$H-NMR (DMSO-$d_6$) δ10.12 (s, 1H), 10.05 (s, 1H), 8.54 (d, J=5.7 Hz, 1H), 8.26 (t, J=8.7 Hz, 1H), 8.00 (s, 1H), 7.92 (s, 1H), 7.39 to 7.23 (m, 3H), 6.65 (s, 1H), 3.75 (m, 2H), 3.48 to 3.30 (m, 3H), 2.27 (m, 1H), 2.08 (m, 1H), 1.39 (s, 9H); MS $[M+H]^+$=601.2; LCMS RT=3.27

Example 209

Preparation of 4-{4-amino-5-[3-fluoro-4-({[2-fluoro-5-(trifluoromethyl)phenyl]carbamoyl}amino)phenyl]pyrrolo[2,1f][1,2,4]triazin-7-yl}-N-methylpiperidine-1-carboxamide

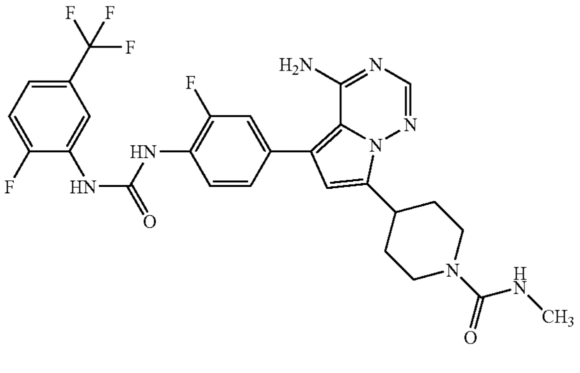

To a flask containing 3 ml of methylene chloride was added 1-[4-(4-amino-7-piperidin-4-ylpyrrolo[2,1-f][1,2,4]triazin-5-yl)-2-fluorophenyl]-3-[2-fluoro-5-(trifluoromethyl)phenyl]urea (Example 111) (75 mg, 0.141 mmol, 1.0 eq). To this suspension was added THF dropwise until complete dissolution occurs. To this solution was added methyl isocyanate (8.8 μl, 0.148 mmol, 1.05 eq.) and reaction allowed to stir at room temperature for 17 h. Reaction solution was concentrated to dryness and residue dissolved in EtOAc. Wash 2× with saturated sodium bicarbonate, 1× brine, layers separated, organics dried ($Na_2SO_4$), filtered, condensed and purified via flash chromatography (1:1 THF:hexanes). The purified fractions collected and concentrated to dryness. Residue was stirred in hexanes and filtered to obtain title compound (50 mg, 60.2% yield). $^1$H-NMR (DMSO-$d_6$) δ 9.41 (d, J=2.8 Hz, 1H), 9.25 (d, J=2.3 Hz, 1H), 8.65 (dd, J=7.5, 2.4 Hz, 1H), 8.25 (t, J=8.6 Hz, 1H), 7.90 (s, 1H), 7.51 (m, 1H), 7.41 (m, 1H), 7.32 (dd, J=12.4, 2.0 Hz, 1H), 7.23 (dd, J=8.5, 1.4 Hz, 1H), 6.57 (s, 1H) 6.44 (q, J=4.3 Hz, 1H), 4.05 (d, J=13.3 Hz, 2H), 3.28 (m, 1H), 2.80 (t, J=12.2 Hz, 2H), 2.56 (d, J=4.5 Hz, 3H), 1.95 (d, J=11.3 Hz, 2H), 1.52 (m, 2H); MS $[M+H]^+$=589; LCMS RT=3.11 min.

Example 210

Preparation of 4-{4-amino-5-[3-fluoro-4-({[2-fluoro-5-(trifluoromethyl)phenyl]carbamoyl}amino)phenyl]pyrrolo[2,1f][1,2,4]triazin-7-yl}-N,N-dimethylpiperidine-1-carboxamide

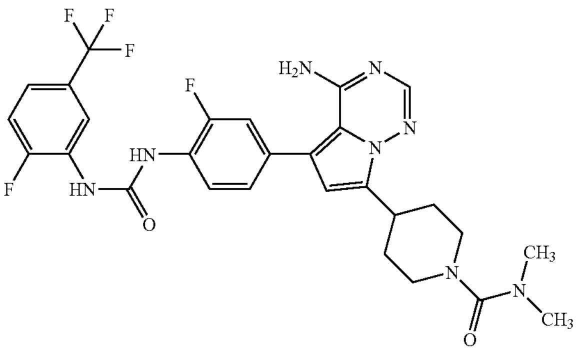

To a flask containing 3 ml of methylene chloride was added 1-[4-(4-amino-7-piperidin-4-ylpyrrolo[2,1-f][1,2,4]triazin-5-yl)-2-fluorophenyl]-3-[2-fluoro-5-(trifluoromethyl)phenyl]urea (Example 111) (75 mg, 0.141 mmol, 1.0 eq). To this suspension was added THF dropwise until complete dissolution occurs. To this solution was added dimethylcarbomoyl chloride (13.6 μl, 0.148 mmol, 1.05 eq.) and reaction allowed to stir at room temperature for 17 h. Reaction solution was concentrated to dryness and residue dissolved in EtOAc. Washed 2× with saturated sodium bicarbonate, 1× brine, layers were separated, organics dried ($Na_2SO_4$), filtered, condensed and purified via flash chromatography (1:1 THF:hex). The purified fractions collected and concentrated to dryness. Residue was stirred in hexanes and filtered to obtain title compound (26 mg, 30.6% yield). $^1$H-NMR (DMSO-$d_6$) 9.41 (d, J=2.6 Hz, 1H), 9.25 (d, J=2.6 Hz, 1H), 8.65 (dd, J=7.1, 2.5 Hz, 1H), 8.26 (t, J=8.6 Hz, 1H), 7.90 (s, 1H), 7.51 (m, 1H), 7.41 (m, 1H), 7.33 (dd, J=12.3, 2.0 Hz, 1H), 7.23 (dd, J=8.6, 1.6 Hz, 1H), 6.59 (s, 1H), 3.65 (d, J=13.2 Hz, 2H), 3.28 (m, 1H), 2.85 (t, J=12.3 Hz, 2H), 2.74 (s, 6H), 1.99 (m, 2H), 1.52 (m, 2H) MS $[M+H]^+$=603; LCMS RT=3.20 min

Example 211

N-{4-[4-amino-7-(2-morpholin-4-ylethyl)pyrrolo[2,1f][1,2,4]triazin-5-yl]-2,5-difluorophenyl}-N'-[2-fluoro-5-(trifluoromethyl)phenyl]urea

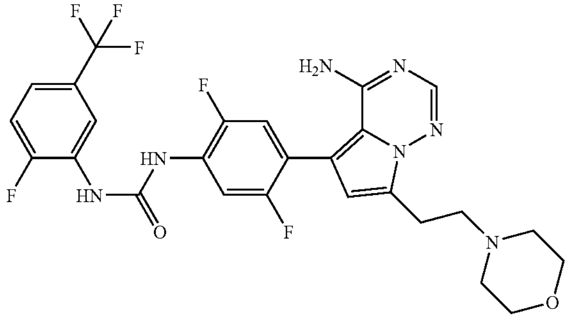

Step 1: Preparation of 2-(4-aminopyrrolo[2,1f][1,2,4]triazin-7-yl)ethanol

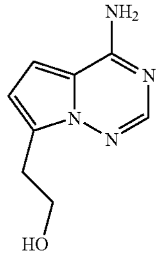

To a solution of Intermediate B (195 mg, 0.91 mmol) in THF at −78° C. under $N_2$ was added dropwise n-butyllithium (1.46 ml, 3.66 mmol). The reaction mixture was stirred for 15 min and then gaseous ethylene oxide was bubbled into the reaction mixture for 5 min. The dry-ice bath was removed and warmed up to rt. Analytical HPLC found a new peak and then the reaction was quenched with 2 ml saturated aq $NH_4Cl$ followed by addition of 10 ml EtOAc and $H_2O$ (2 ml). The organic phase was collected and washed with brine and dried over $Na_2SO_4$ and evaporated to crude as yellow oil. The crude was dissolved in 5 ml 10% $MeOH/CH_2Cl_2$ and 4 ml silica gel was added and then solvent evaporated. The crude in the silica gel was loaded on an MPLC column and was eluted with a gradient 0-10% MeOH in $CH_2Cl_2$ to give 20 mg of the desired product.; MS $[M+H]^+$=178.9; LCMS RT=1.1 min Step 2: Preparation of 7-(2-morpholin-4-ylethyl) pyrrolo[2,1f][1,2,4]triazin-4-amine

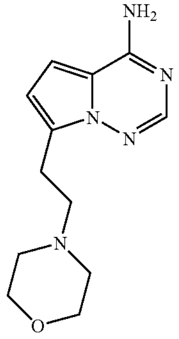

To a solution of 2-(4-aminopyrrolo[2,1-f][1,2,4]triazin-7-yl)ethanol (440 mg, 2.5 mmol) in THF (10 ml) and $CH_2Cl_2$ anhydrous (10 ml) and was added $SOCl_2$ (0.36 ml, 4.9 mmol) and stirred at rt. After 20 min all starting material was consumed. The crude reaction mixture was concentrated in vacuo to dryness and was suspended in dry $CH_2Cl_2$. The solvent was evaporated and the crude was re-suspended in $CH_2Cl_2$ and concentrated in vacuo to dryness. The resulting solid was dissolved in DMF (10 ml) and was added triethylamine (0.97 ml, 7.2 mmol), morpholine (1.0 ml, 11.7 mmol) and NaI (280 mg, 1.87 mmol) and heated at 55° C. 24 h. Cooled to rt, the reaction crude was diluted with EtOAc (30 ml) and washed with $H_2O$ (2×) and brine (2×), dried over $Na_2SO_4$ and concentrated to give yellow solid. The crude was purified by MPLC with 0-10% $MeOH/CH_2Cl_2$ to give 149 mg of the titled compound (yield 25%). MS $[M+H]^+$=248; LCMS RT=1.05 min.

Step 3: Preparation of 5-bromo-7-(2-morpholin-4-ylethyl)pyrrolo[2,1f][1,2,4]triazin-4-amine

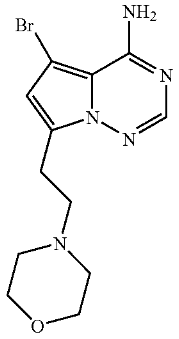

To a solution of 7-(2-morpholin-4-ylethyl)pyrrolo[2,1-f][1,2,4]triazin-4-amine (149 mg, 0.6 mmol) in DMF (3 ml) at −20 C was added 1,3-dibromo-5,5-dimethylimidazolidine-2,4-dione (69 mg, 0.24 mmol) in three portions. The reaction was stirred at −20 C for 3 h. Upon the completion, the reaction was quenched with aqueous saturated $Na_2SO_3$ and allowed to warm up to rt. The crude was extracted with ethyl acetate. The organic layer was collected and washed with brine, dried over $Na_2SO_4$ and concentrated. The resulting crude was purified via column chromatography (95:5 v/v $CH_2Cl_2$—$CH_3OH$) to afford 75 mg of the title compound as yellow solid (yield 39%). MS $[M+H]^+$=326.2; LCMS RT=1.15 min Step 4: Preparation of Title Compound The procedure used for the preparation of Example 108 was used to prepare the title compound by substituting 5-bromo-7-(2-morpholin-4-ylethyl)pyrrolo[2,1-f][1,23]triazine-4-amine for Intermediate V and Intermediate AH for (N-[2-fluoro-4-(4,4,5,5-tetramethyl-1,3,2-dioxaborolan-2-yl)phenyl]-N'-[2-fluoro-5-(trifluoromethyl)phenyl]urea. $^1$H-NMR (DMSO-$d_6$) δ 9.45 (dd, J=15, 3 Hz, 2H), 8.65-8.61 (m, 1H), 8.17-8.11 (m, 1H), 7.85 (s, 1H), 7.53-7.43 (m, 2H), 6.58 (s, 1H), 3.56 (t, J=5 Hz, 4H), 3.05 (t, J=4 Hz, 2H), 2.63 (t, J=8 Hz, 2H), 2.46-2.43 (m, 4H); MS $[M+H]^+$=580.2; LCMS RT=2.67 min.

Example 212

N-{4-[4-amino-7-(2-morpholin-4-ylethyl)pyrrolo[2,1-f][1,2,4]triazin-5-yl]-2-fluorophenyl}-N'-[2-fluoro-5-(trifluoromethyl)phenyl]urea

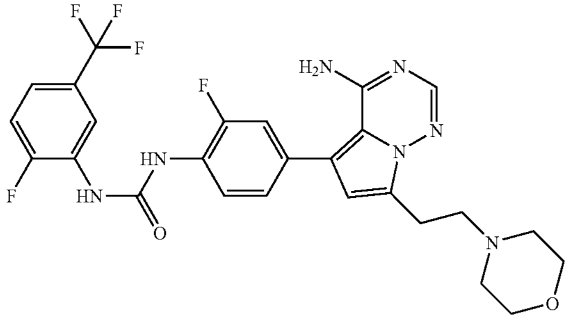

Step 1: Preparation of 2-(4-amino-5-bromopyrrolo[2,1f][1,2,4]triazin-7-yl)ethanol

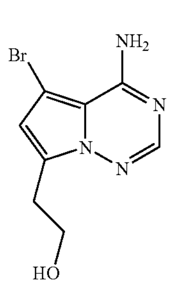

To a solution of 2-(4-aminopyrrolo[2,1-f][1,2,4]triazin-7-yl)ethanol (777 mg, 4.3 mmol.) in DMF (22 mL) at −20° C. (WA and dry ice) was added 1,3-dibromo-5,5-dimethyl-imidazolidine-2,4-dione (359 mg, 1.72 mmol)) was added in 4 portions within 20 min. The reaction was stirred at −20° C. for 30 min. Analytical HPLC indicated 22% starting material remainded, additional B (90 mg, 0.30 mmol) was added and stirred for 20 min. The reaction was quenched with satd. $Na_2SO_3$ and warmed up to rt. The crude was extracted w/EtOAc 5×. The organic was washed with 5% aq $K_2CO_3$ and brine. Dried over $Na_2SO_4$ and concentrated. The crude was purified by MPLC with 0-7% MeOH/$CH_2Cl_2$ to give 814 mg of desired product (yield, 72.6%). MS $[M+H]^+$=257.3; LCMS RT=1.14 min.

Step 2: Preparation of 1-{4-[4-amino-7-(2-hydroxyethyl)pyrrolo[2,1-f][1,2,4]triazin-5-yl]-2-fluorophenyl}-3-[2-fluoro-5-(trifluoromethyl)phenyl]urea

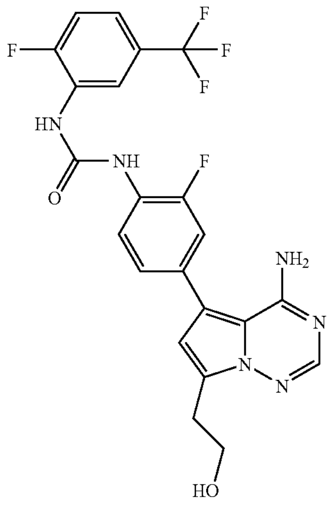

A mixture of 2-(4-amino-5-bromopyrrolo[2,1f][1,2,4]triazin-7-yl)ethanol (750 mg, 2.9 mmol) and Intermediate O (1.55 g, 3.5 mmol) and 1M $Na_2CO_3$ in 1,4-dioxane (32 ml) was degassed and added $Pd(PPh_3)_4$ then was heated at 80° C. for 16 h. Cooled to rt, diluted with EtOAc and washed with sat'd $NaHCO_3$ and dried ($Na_2SO_4$) and concentrated. The crude was purified by MPLC with 5% MeOH/$CH_2Cl_2$ to afford 1.2 g of the titled compound (yield, 89%). MS $[M+H]^+$=493.3; LCMS RT=2.84 min.

Step 3; Preparation of 1-{4-[4-amino-7-(2-bromoethyl)pyrrolo[2,1f][1,2,4]triazin-5-yl}-2-fluorophenyl]-3-[2-fluoro-5-(trifluoromethyl)phenyl]urea

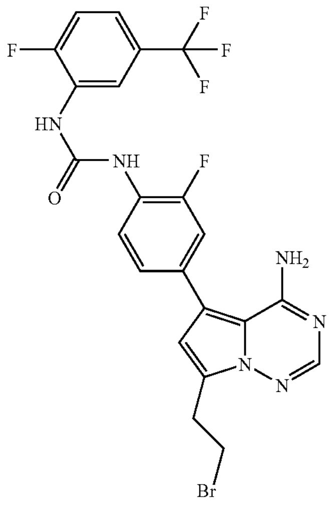

To a suspension of 1-{4-[4-amino-7-(2-hydroxyethyl)pyrrolo[2,1-f][1,2,4]triazin-5-yl]-2-fluorophenyl}-3-[2-fluoro-5-(trifluoromethyl)phenyl]urea (1.28 g, 2.60 mmol) in anhydrous THF (32 ml) at 0° C. was added $CBr_4$ (1.03 g, 3.1 mmol)) followed by $Ph_3P$ (0.75 g, 2.9 mmol) and the reaction was stirred at rt for 24 h. The reaction mixture was poured into $H_2O$ (100 ml) and extracted with 150 ml EtOAc. The organic layer was washed with satd. aq $NaHCO_3$, brine and dried over $Na_2SO_4$ and was concentrated to give a yellow oil (1.6 g), which was used without further purification. MS $[M+H]^+$=557.2; LCMS RT=3.27 min.

Step 4: Preparation of the Title Compound

A mixture of the crude 1-{4-[4-amino-7-(2-bromoethyl) pyrrolo[2,1-f][1,2,4]triazin-5-yl]-2-fluorophenyl}-3-[2-fluoro-5-(trifluoromethyl)phenyl]urea (500 mg, crude, 0.31 mmol), morpholine (0.10 ml, 1.12 mmol), triethylamine (0.08 ml, 0.60 mmol) and sodium iodide (7 mg, 0.05 mmol) in 4 ml DMF was heated at 55° C. in a closed vial for 16 h. Cooled to rt, the crude was diluted with 20 ml EtOAc and was washed with aq saturated $NaHCO_3$, brine and dried over $Na_2SO_4$. The crude was concentrated and purified via column chromatography (95:5 v/v $CH_2Cl_2$-$CH_3OH$) to afford 64 mg of the title compound (yield 47%). $^1$H-NMR (DMSO-$d_6$ and 1 drop TFA-d) δ 9.44 (d, J=3 Hz, 1H), 9.33 (d, J=3 Hz, 1H), 8.65 (dd, J=7, 2 Hz, 1H, 8.32 (t, J=8 Hz, 1H), 8.15 (s, 1H), 7.55-7.51 (m, 1H), 7.48-7.24 (m, 4H), 6.83 (s, 1H), 4.03-4.01 (m, 2H), 3.69-3.49 (m, 8H), 3.38-3.33 (m, 2H); MS $[M+H]^+$=562.3; LCMS RT=2.84 min.

Example 213

N-(4-{4-amino-7-[2-(dimethylamino)ethyl]pyrrolo [2,1f][1,2,4]triazin-5-yl}-2-fluorophenyl)-N'-[2-fluoro-5-(trifluoromethyl)phenyl]urea

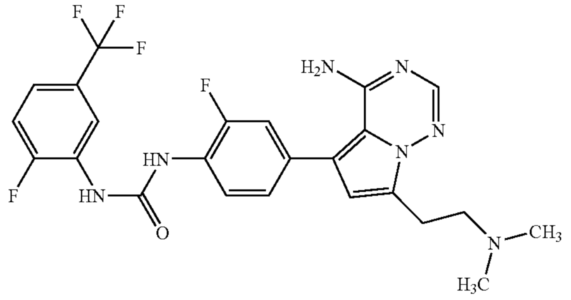

The procedure used for the preparation of Example 212 was used to prepare the title compound by substituting diethylamine for morpholine in step 4. $^1$H-NMR ($CD_3OD$) δ 8.65 (d, J=8 Hz, 1H), 8.25 (t, J=8 Hz, 1H), 7.83 (s, 1H), 7.36-7.25 (m, 4H), 6.61 (s, 1H), 3.20 (t, J=7 Hz, 2H), 2.86-2.81 (m, 2H), 2.40 (s, 6H); MS $[M+H]^+$=520.3; LCMS RT=2.42 min.

Example 214

N-(4-{4-amino-7,2-(4-methylpiperazin-1-yl)ethyl] pyrrolo[2,1-f][1,2,4]triazin-5-yl}-2-fluorophenyl)-N'-[2-fluoro-5-(trifluoromethyl)phenyl]urea

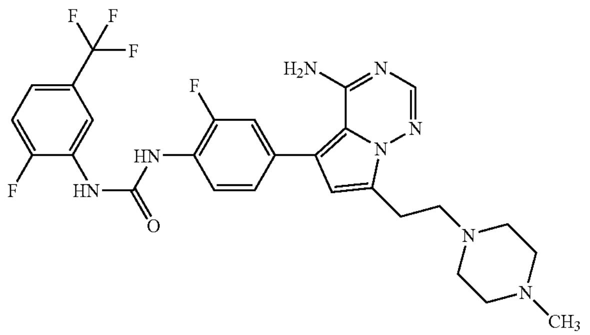

The procedure used for the preparation of Example 212 was used to prepare the title compound by substituting 1-methylpiperazine for morpholine in step 4. $^1$H-NMR (DMSO-$d_6$) δ 9.42 (d, J=2 Hz, 1H), 9.26 (d, J=2 Hz, 1H), 8.65 (dd, J=8, 2 Hz, 1H), 8.26 (t, J=9 Hz, 1H), 7.89 (s, 1H), 7.43-7.20 (m, 3H), 6.61 (s, 1H), 3.05 (m, 2H), 2.68-2.58 (m, 4H), 2.43-2.40 (m, 3H); MS $[M+H]^+$=575.2; LCMS RT=2.39 min.

Example 215

N-[4-(4-amino-7-{2-[2-(methoxymethyl)pyrrolidin-1-yl]ethyl}pyrrolo-[2,1-f][1,2,4]triazin-5-yl)-2-fluorophenyl]-N'-[2-fluoro-5-(trifluoromethyl)phenyl] urea

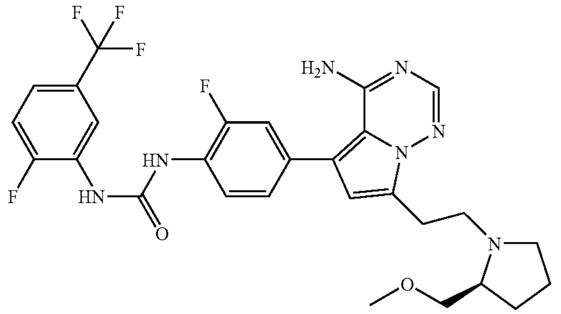

The procedure used for the preparation of Example 212 was used to prepare the title compound by substituting (2S)-2-(methoxymethyl)pyrrolidine for morpholine in step 4. $^1$H-NMR ($CD_3OD$) δ 9.64 (d, J=9 Hz, 1H), 8.24 (t, J=9 Hz, 1H), 7.82 (s, 1H), 7.35-7.24 (m, 4H), 6.58 (s, 1H), 3.63-3.43

(m, 3H), 3.19-3.16 (m, 2H), 2.83-2.73 (brd, 2H), 2.47-2.44 (m, 2H), 2.0-1.94 (m, 1H), 1.64-1.58 (m, 1H); MS $[M+H]^+$=590.3; LCMS RT=2.51 min.

Example 216

N-{4-[4-amino-7-(2-pyrrolidin-1-ylethyl)pyrrolo[2,1-f][1,2,4]triazin-5-yl]-2-fluorophenyl}-N'-[2-fluoro-5-(trifluoromethyl)phenyl]urea

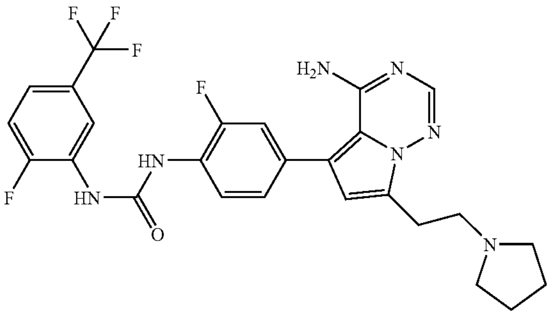

The procedure used for the preparation of Example 212 was used to prepare the title compound by substituting pyrrolidine for morpholine in step 4. $^1$H-NMR (DMSO-$d_6$) δ 9.40 (d, J=3 Hz, 1H), 9.25 (t, J=2 Hz, 1H), 8.65 (dd, J=8, 2 Hz, 1H), 8.26 (t, J=8 Hz, 1H), 7.89 (s, 1H), 7.51 (t, J=10 Hz, 1H), 7.42-7.40 (m, 1H), 7.30 (dd, J=10, 2 Hz, 1H), 7.22 (dd, J=8, 2 Hz, 1H), 6.61 (s, 1H), 3.05 (t, J=8 Hz, 2H), 2.82-2.77 (m, 2H), 2.54-2.51 (m, 4H), 1.68-1.65 (m, 4H); MS $[M+H]^+$=546.3; LCMS RT=2.47 min.

Example 217

N-{4-[4-amino-7-(3-morpholin-4-ylpropyl)pyrrolo[2,1f][1,2,4]triazin-5-yl]-2-fluorophenyl}-N'-[2-chloro-5-(trifluoromethyl)phenyl]urea

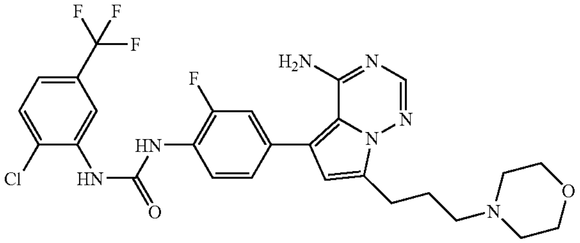

The procedure used for the preparation of Example 108 was used to prepare the title compound by substituting Intermediate AJ for intermediate M. $^1$H-NMR (DMSO-$d_6$ and 1 drop TFA-d) δ 9.69 (d, J=2 Hz, 1H), 9.19 (s, 1H), 8.62 (d, J=2 Hz, 1H), 8.27 (t, J=8 Hz, 1H), 8.00 (d, J=2 Hz, 1H), 7.74 (d, J=8 Hz, 1H), 7.41-7.23 (m, 3H), 6.73 (s, 1H), 3.97-3.41 (m, 5H), 3.25-2.95 (m, 7H), 2.48-2.25 (m, 2H); MS $[M+H]^+$=592.2; LCMS RT=2.65 min.

Example 218

N-{4-[4-amino-7-(3-morpholin-4-ylpropyl)pyrrolo[2,1f][1,2,4]triazin-5-yl}-2-fluorophenyl]-N'-(2-fluoro-5-methylphenyl)urea

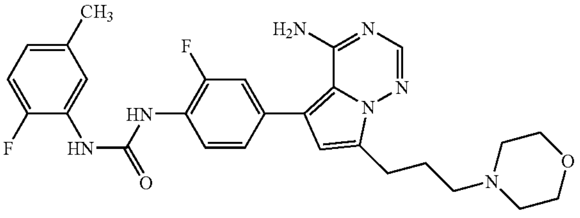

The procedure used for the preparation of Example 108 was used to prepare the title compound by substituting Intermediate AI for intermediate M. $^1$H-NMR (DMSO-$d_6$) δ 9.16 (d, J=2 Hz, 1H), 9.05 (d, J=2 Hz, 1H), 8.29 (t, J=8 Hz, 1H), 8.04 (dd, J=8, 2 Hz, 1H), 7.91 (s, 1H), 7.35-7.31 (m, 3H), 6.86-6.82 (m, 1H), 6.60 (s, 1H), 3.58 (t, J=4 Hz, 4H), 2.91 (t, J=8 Hz, 2H), 2.45-2.30 (m, 9H), 1.9-1.77 (m, 2H); MS $[M+H]^+$=576.7; LCMS RT=2.57 min.

Example 219

N-{4-[7-(1-acetylpiperidin-4-yl)-4-aminopyrrolo[2,1-f][1,2,4]triazin-5-yl]-2-chlorophenyl}-N'-[2-fluoro-5-(trifluoromethyl)phenyl]urea

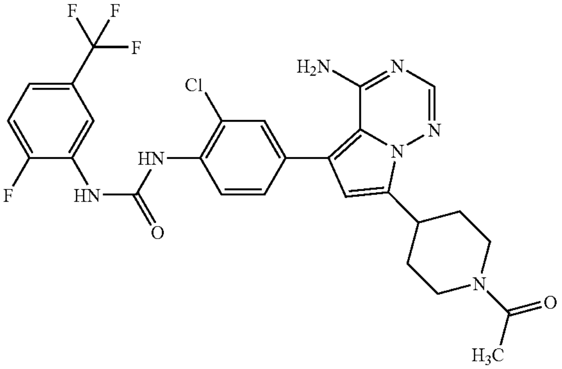

The title compound was prepared in a manner similar to the procedure described for the preparation of Example 232, using acetic anhydride in place of methanesulfonyl chloride 34 mg (63%) of the desired product was isolated. $^1$H-NMR (DMSO-$d_6$) δ 9.74 (d, J=2.7 Hz, 1H), 9.01 (s, 1H), 8.65 (dd, J=2.1, 7.2 Hz, 1H), 8.24 (d, J=8.7 Hz, 1H), 7.92 (s, 1H), 7.54-7.48 (m, 2H), 7.42-7.35 (m, 2H), 6.61 (s, 1H), 4.51-4.46

(m, 1H), 3.93-3.89 (m, 1H), 3.45-3.14 (m, 5H), 2.03 (s, 3H), 1.67-1.46 (m, 2H); MS $[M+H]^+$=590.3, 592.2; LCMS RT=2.98 min.

Example 220

N-{4-[4-amino-7-(2-hydroxyethyl)pyrrolo[2,1f][1,2,4]triazin-5-yl]-2-fluorophenyl}-N'-[2-fluoro-5-(trifluoromethyl)phenyl]urea

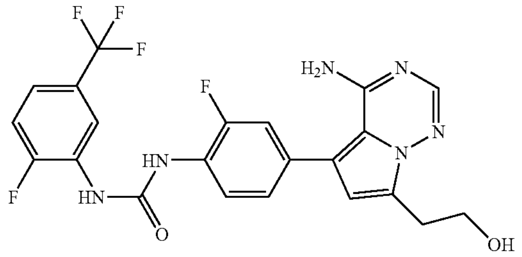

The procedure used for the preparation of Example 108 was used to prepare the title compound by substituting 2-(4-amino-5-bromopyrrolo[2,1-f][1,2,4]triazin-7-yl)ethanol for Intermediate V and substituting Intermediate O for intermediate M. $^1$H-NMR (DMSO-$d_6$) δ 9.41 (dd, J=3 Hz, 1H), 9.24 (d, J=3 Hz, 1H), 8.67-8.63 (dd, J=8, 3 Hz, 1H), 8.26 (t, J=9 Hz, 1H), 7.89 (s, 1H), 7.54-7.47 (m, 1H), 7.43-7.7.20 (m, 3H), 6.60 (s, 1H), 4.76 (t, J=5 Hz, 1H), 3.73 (t, J=5 Hz, 2H), 3.03 (t, J=7 Hz, 2H); MS $[M+H]^+$=493.2; LCMS RT=2.70 min.

Example 221

N-{4-[4-amino-7-(3-morpholin-4-ylpropyl)pyrrolo[2,1f][1,2,4]triazin-5-yl]-2-methylphenyl}-N'-[2-fluoro-5-(trifluoromethyl)phenyl]urea

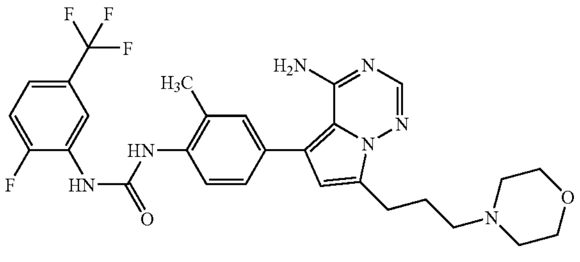

The procedure used for the preparation of Example 108 was used to prepare the title compound by substituting Intermediate AF for intermediate M. $^1$H-NMR (DMSO-$d_6$) 89.37 (d, J=2 Hz, 1H), 8.66 (dd, J=8, 2 Hz, 1H), 8.55 (d, J=2 Hz, 1H), 7.98 (d, J=2 Hz, 1H), 7.87 (s, 1H), 7.54-7.47 (m, 1H), 7.39-7.36 (m, 1H), 7.28 (d, J=2 Hz, 1H), 7.24 (dd, J=8, 2 Hz, 1H), 6.52 (s, 1H), 3.56-3.54 (m, 4H), 2.88 (t, J=5 Hz, 2H), 2.36-2.30 (m, 9H), 1.89-1.81 (m, 2H); MS $[M+H]^+$=572.2; LCMS RT=2.50 min.

Example 222

N-{4-[4-amino-7-(3-morpholin-4-ylpropyl)pyrrolo[2,1f][1,2,4]triazin-5-yl]-2-fluorophenyl}-N'-(3-methylphenyl)urea

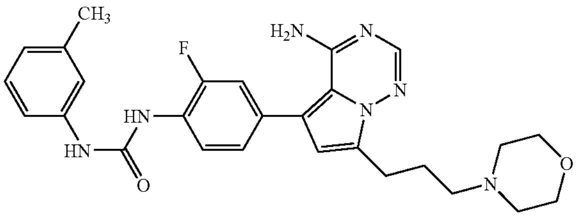

The procedure used for the preparation Example 108 was used to prepare the title compound by substituting 1-[2-fluoro-4-(4,4,5,5-tetramethyl-1,3,2-dioxaborolan-2-yl)phenyl]-3-(3-methylphenyl)urea for intermediate M. $^1$H-NMR (DMSO-$d_6$) δ 9.01 (s, 1H), 8.61 (d, J=3 Hz, 1H), 8.24 (t, J=8 Hz, 1H), 7.88 (s, 1H), 7.31-7.13 (m, 4H), 6.80 (d, J=7 Hz, 1H), 6.56 (s, 1H), 3.54 (t, J=4 Hz, 4H), 2.87 (t, J=8 Hz, 2H), 2.36-2.27 (m, 9H), 1.86-1.81 (m, 2H); MS $[M+H]^+$=504.2; LCMS RT=2.26 min.

Example 223

N-{4-[4-amino-7-(3-morpholin-4-ylpropyl)pyrrolo[2,1f][1,2,4]triazin-5-yl]-2-fluorophenyl}-N'-[3-(trifluoromethyl)phenyl]urea

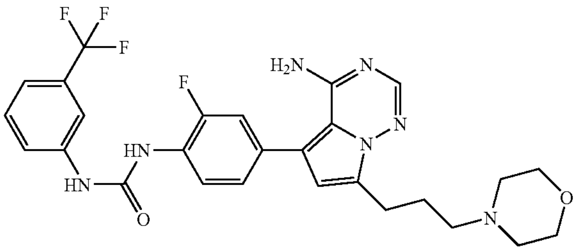

The procedure used for the preparation Example 108 was used to prepare the title compound by substituting Intermediate Q for intermediate M. $^1$H-NMR (DMSO-$d_6$) δ 9.44 (s, 1H), 8.74 (d, J=2 Hz, 1H), 8.20 (t, J=8 Hz, 1H), 8.05 (s, 1H), 7.88 (s, 1H), 7.54-7.52 (m, 2H), 7.35-7.20 (m, 3H), 6.57 (s, 1H), 3.54 (t, J=4 Hz, 3H), 3.32 (m, 5H), 2.87 (t, J=7 Hz, 2H), 2.47-2.32 (m, 4H), 1.86-1.81 (m, 2H); MS $[M+H]^+$=558.2; LCMS RT=2.39 min.

Example 224

N-{4-[4-amino-7-(4-morpholin-4-ylbutyl)pyrrolo[2,14f][1,2,4]triazin-5-yl]-2-fluorophenyl}-N'-[2-fluoro-5-(trifluoromethyl)phenyl]urea

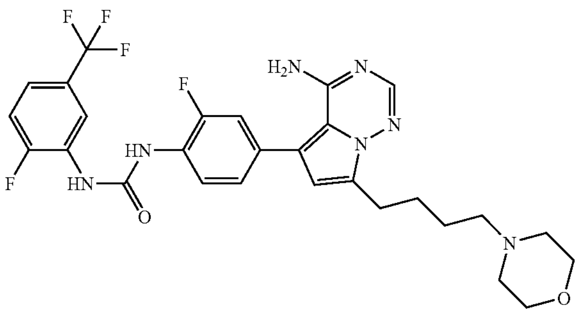

Step 1: Preparation of 7-((1E)-4-{[tert-butyl(dimethyl)silyl]oxy}but-1-en-1-yl)pyrrolo[2,1f][1,2,4]triazin-4-amine

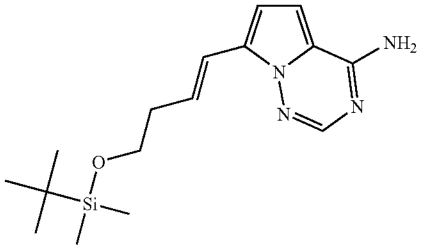

To a stirred suspension of 7-bromopyrrolo[2,1f][1,2,4]triazin-4-amine (5.0 g, 23.5 mmol), trans-1-buten-1-yl-(4-tert-butylsimethylsiloxy-4',4',5',5'-tetramethyl-(1',3',2')-dioxaborolane (14.6 g, 46.9 mmol), and [1,1'-bis (diphenylphosphino)-ferrocene]dichloro palladium(II) complex with dichloromethane (1.72 g, 2.35 mmol) in degassed DME (175 mL) was added aqueous $Na_2CO_3$ solution (2 M, 35.2 mL). The reaction was heated (80° C.) for 17 h and then cooled to rt. The mixture was partitioned between ethyl acetate (200 mL) and water (200 mL) and the layers were separated. The organic phase was further washed with water (200 mL), brine, dried ($Na_2SO_4$), and concentrated. The crude material was purified by MPLC chromatography using a gradient of 50 to 75% ethyl acetate in hexanes to afford 5.35 g (72%) of the desired product as a pale yellow solid. $^1H$ NMR (300 MHz, DMSO-$d_6$) δ 7.76 (s, 1H), 7.59 (br s, 2H), 6.81-6.78 (m, 1H), 6.76-6.67 (m, 2H), 6.38-6.29 (m, 1H), 3.65 (t, 2H), 2.35 (q, 2H), 0.82 (s, 9H) 0.00 (s, 6H); ES-MS m/z 319.3 $[M+]^+$, HPLC RT (min) 3.01.

Step 2: Preparation of 7-(4-{[tert-butyl(dimethyl)silyl]oxy}butyl)pyrrolo[2,1-f][1,2,4]triazin-4-amine

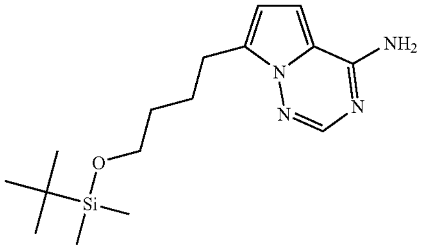

To a dry flask purged with $N_2$ was added platinum(IV) oxide (635 mg, 2.80 mmol) followed by 7-((1E)-4-{[tert-butyl(dimethyl)silyl]oxy}but-1-en-1-yl)pyrrolo[2,1-f][1,2,4]triazin-4-amine (6.35 g, 19.9 mmol) as a solution in acetic acid (100 mL). The mixture was stirred under an $H_2$ atmosphere for 16 h. The mixture was filtered through a pad of Celite® rinsing with acetic acid. The solvent was evaporated under reduced pressure and the residue was made basic with saturated aqueous $NaHCO_3$ solution. The resulting solid was collected by filtration and dried in vacuo to afford 5.6 g (88%) of the desired product. $^1H$ NMR (300 MHz, DMSO-$d_6$) δ 7.76 (s, 1H), 7.52 (br s, 2H), 6.77 (d, 1H), 6.38 (d, 2H), 3.57 (t, 2H), 2.82 (t, 2H), 1.74-1.62 (m, 2H), 1.54-1.43 (m, 2H), 0.83 (s, 9H), 0.00 (s, 6H); ES-MS m/z 321.2 $[M+H]^+$, HPLC RT (min) 3.11.

Step 3: Preparation of 5-bromo-7-(4-{[tert-butyl(dimethyl)silyl]oxy}butyl)pyrrolo[2,1-f][1,2,4]triazin-4-amine

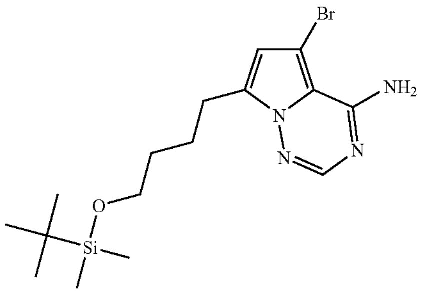

To a cooled (−20° C.) solution of 7-(4-{[tert-butyl(dimethyl)silyl]oxy}butyl)pyrrolo[2,1-f][1,2,4]triazin-4-amine (5.60 g, 17.5 mmol) in tetrahydrofuran (85 mL) was added 1,3-dibromo-5,5-dimethylhydantoin (2.50 g, 8.74 mmol) in four portions over 15 min. The mixture was allowed to stir (−20° C.) for 2 h. The reaction was quenched with the addition saturated aqueous $Na_2SO_3$ solution and was allowed to warm to rt. The mixture was extracted with ethyl acetate (3×75 mL). The combined organics were washed with brine, dried ($Na_2SO_4$) and concentrated to dryness. The crude material was purified by MPLC chromatography using a gradient of 50% to 75% ethyl acetate in hexanes to afford 6.29 g (90%) of the desired product. $^1$H NMR (300 MHz, DMSO-$d_6$) δ 7.80 (s, 1H), 6.58 (s, 1H), 3.56 (t, 2H), 2.81 (t, 2H), 1.72-1.61 (m, 2H), 1.51-1.42 (m, 2H), 0.83 (s, 9H), 0.00 (s, 6H); ES-MS m/z 399.2 $[M+H]^+$, HPLC RT (min) 3.72.

Step 4: Preparation of 1-{4-[4-amino-7-(4-{[tert-butyl(dimethyl)silyi]oxy}butyl)pyrrolo[2,1-f][1,2,4]triazin-5-yl]-2-fluorophenyl}-3-[2-fluoro-5-(trifluoromethyl)phenyl]urea

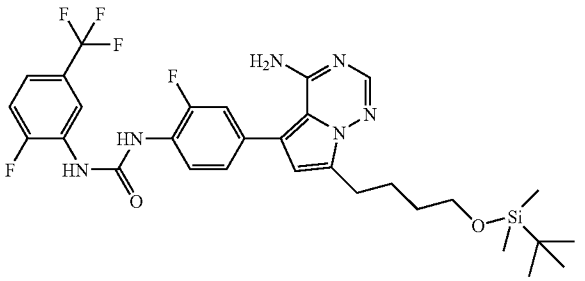

The procedure used for the preparation of Example 7 was used to prepare the title compound by substituting 5-bromo-7-(4-{[tert-butyl(dimethyl)silyl]oxy}butyl)pyrrolo[2,1-f][1,2,4]triazin-4-amine for (5-bromo-7-(morpholin-4-ylmethyl)pyrrolo[2,1-f][1,2,4]triazin-4-amine and Intermediate O for Intermediate R. MS $[M+H]^+$=635.0; LC/MS RT=4.04 min.

Step 5: 1-{4-[4-amino-7-(4-hydroxybutyl)pyrrolo[2,1-f][1,2,4]triazin-5-yl]-2-fluorophenyl}-3-[2-fluoro-5-(trifluoromethyl)phenyl]urea

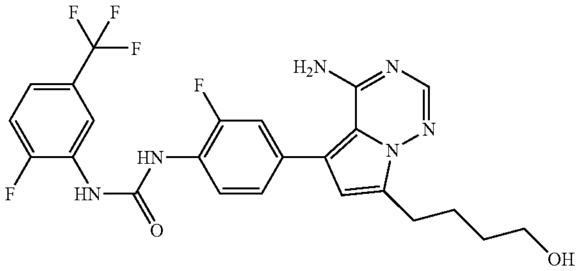

To a suspension of 1-{4-[4-amino-7-(4-{[tert-butyl(dimethyl)silyl]oxy}butyl)pyrrolo[2,1-f][1,2,4]triazin-5-yl]-2-fluorophenyl}-3-[2-fluoro-5-(trifluoromethyl)-phenyl]urea in 3 ml 95:5 EtOH/$H_2O$ was added 30 μL conc. HCl. for 30 min. The reaction mixture was quenched with 5 ml saturated $NaHCO_3$. After the solvent EtOH was evaporated, the crude was extracted with EtOAc (3×). The resulting crude organic was dried and concentrated and triturated with EtOAc and hexane to give 115 mg of pure title compound as a white solid. MS $[M+H]^+$=521.2; LC/MS RT=2.94 min.

Step 6: Preparation of 1-{4-[4-amino-7-(4-bromobutyl)pyrrolo[2,14f][1,2,4]triazin-5-yl]-2-fluorophenyl}-3-[2-fluoro-5-(trifluoromethyl)phenyl]urea

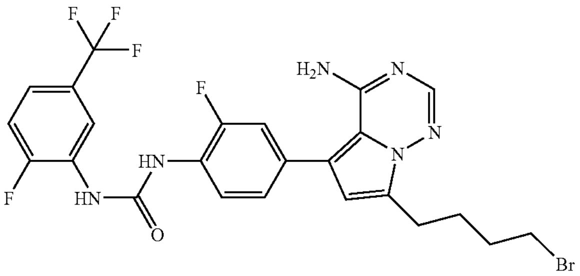

The procedure used for the preparation of Example 212 Step 3 was used to prepare the title compound by substituting 1-{4-[4-amino-7-(4-hydroxybutyl)pyrrolo[2,1-f][1,2,4]triazin-5-yl]-2-fluorophenyl}-3-[2-fluoro-5-(trifluoromethyl)phenyl]urea for 1-(4-[4-amino-7-(2-hydroxyethyl)pyrrolo[2,1-f][1,2,4]triazin-5-yl]-2-fluorophenyl}-3-[2-fluoro-5-(trifluoromethyl)phenyl]urea. MS $[M+H]^+$=583.2; LC/MS RT=3.50 min.

Step 7: Preparation of Title Compound

The procedure used for the preparation of Experiment 212 Step 4 was used to prepare the title compound by substituting 1-{4-[4-amino-7-(4-bromobutyl)pyrrolo[2,1-f][1,2,4]triazin-5-yl]-2-fluorophenyl}-3-[2-fluoro-5-(trifluoromethyl)phenyl]urea for 1-{4-[4-amino-7-(2-bromoethyl)pyrrolo[2,1-f][1,2,4]triazin-5-yl]-2-fluorophenyl}-3-[2-fluoro-5-(trifluoromethyl)phenyl]urea. $^1$H-NMR (DMSO-$d_6$) δ 9.40 (d, J=3 Hz, 1H), 9.24 (t, J=3 Hz, 1H) 6.65 (dd, J=8, 3 Hz, 1H), 8.25 (t, J=8 Hz, 1H), 7.89 (s, 1H), 7.54-7.39 (m, 2H), 7.33 (dd, J=4, 2 Hz, 1H), 7.24-7.21 (m, 1H), 6.56 (s, 1H), 3.53 (t, J=5 Hz, 4H), 2.87 (t, J=2 Hz, 2H), 2.31-2.25 (m, 6H), 1.72-1.52 (m, 4H); MS $[M+H]^+$=590.2; LCMS RT=2.46 min.

Example 225

N-(4-{4-amino-7-(3-morpholin-4-ylpropyl)pyrrolo[2,1f][1,2,4]triazin-5-yl]-2-chlorophenyl}-N'-[2-fluoro-5-(trifluoromethyl)phenyl]urea

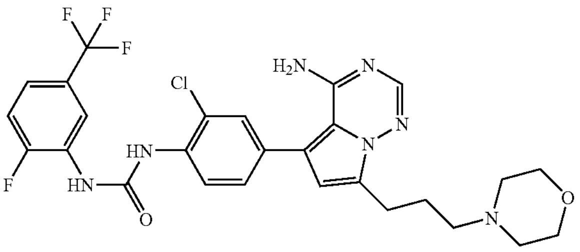

The procedure used for the preparation Example 108 was used to prepare the title compound by substituting Intermediate AV for intermediate M. $^1$H-NMR ($CD_3OD$) δ 8.64 (d, J=8 Hz, 1H), 8.24 (d, J=8 Hz, 1H), 7.82 (s, 1H), 7.55 (d, J=2

Hz, 1H), 7.43-7.33 (m, 3H), 6.58 (s, 1H), 3.69 (t, J=5 Hz, 4H), 2.52-2.47 (m, 6H), 2.02-1.97 (m, 2H), MS $[M+H]^+$=592.2; LCMS RT=2.60 min.

Example 226

N-(4-{4-amino-7-[2-(1,4-oxazepan-4-yl)ethyl]pyrrolo[2,1-f][1,2,4]triazin-5-yl}-2-fluorophenyl)-N'-[2-fluoro-5-(trifluoromethyl)phenyl]urea

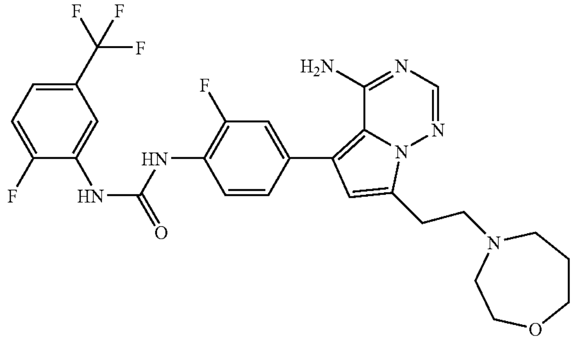

The procedure used for the preparation of Example 212 was used to prepare the title compound by substituting 1,4-oxazepane for morpholine in step 4. $^1$H-NMR (Acetone-$d_6$) δ 8.84 (t, J=2 Hz, 1H), 8.68 (brd, 1H), 8.44-8.38 (m, 1H), 7.87 (s, 1H), 7.44-7.41 (m, 2H), 7.31-7.29 (m, 2H), 6.64 (s, 1H), 3.73-3.63 (m, 4H), 3.14 (dd, J=8, 7 Hz, 2H), 2.92 (dd, J=8.7 Hz, 2H), 2.80-2.75 (m, 6H); MS $[M+H]^+$=576.2; LCMS RT=2.91 min.

Example 227

N-(4-{4-amino-7-[(3-oxopiperazin-1-yl)methyl]pyrrolo[2,1-f][1,2,4]triazin-5-yl}-2-fluorophenyl)-N'-[2-chloro-5-(trifluoromethyl)phenyl]urea

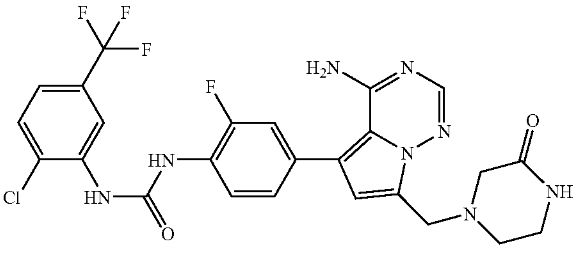

The procedure used for the preparation of Example 162 was used to prepare the title compound by substituting Intermediate AJ for Intermediate Q and by substituting 1,4-dioxane for toluene as solvent. $^1$H-NMR (DMSO-$d_6$) δ 9.62 (d, J=2 Hz, 1H), 9.13 (s, 1H), 8.64 (d, J=2 Hz, 1H), 8.25 (t, J=8 Hz, 1H), 7.92 (s, 1H), 7.72 (d, J=8 Hz, 1H), 7.41-7.23 (m, 3H), 6.71 (s, 1H), 3.91 (s, 2H), 3.16-3.11 (m, 2H), 2.99 (s, 2H), 2.61 (t, J=6 Hz, 1H); MS $[M+H]^+$=576.8; LCMS RT=2.58 min.

Example 228

N-{4-[4-amino-7-(2-morpholin-4-ylethyl)pyrrolo[2,1-f][1,2,4]triazin-5-yl]-2-fluorophenyl}-N'-(4-tert-butylpyridin-2-yl)urea

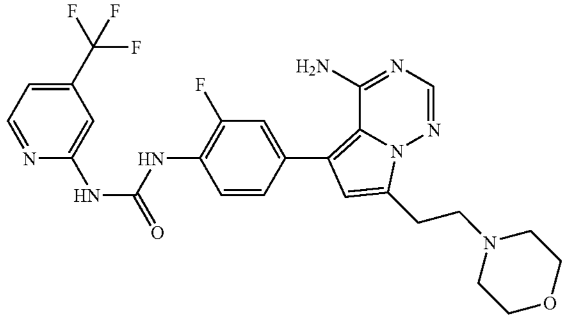

The procedure used for the preparation of Example 211 was used to prepare the title compound by substituting, in step 4, Intermediate AE for Intermediate AH and by substituting 1,4-dioxane for toluene as solvent. $^1$H-NMR (DMSO-$d_6$) δ 9.79 (s, 1H), 8.31 (t, J=8 Hz, 1H), 8.16 (dd, J=5, 1 Hz, 1H), 7.89 (s, 1H), 7.389s, 1H), 7.33-7.20 (m, 2H), 7.08 (dd, J=5, 2 Hz, 1H), 6.61 (s, 1H), 3.59 (t, J=4 Hz, 4H), 3.04 (t, J=7 Hz, 2H), 2.63 (t, J=7 Hz, 2H), 2.43 (m, 4H), 1.25 (s, 9H); MS $[M+H]^+$=533.1; LCMS RT=2.38 min.

Example 229

N-{4-[4-amino-7-(1-lactoylpiperidin-4-yl)pyrrolo[2,1-f][1,2,4]triazin-5-yl]-2-chlorophenyl}-N'-[2-fluoro-5-(trifluoromethyl)phenyl]urea

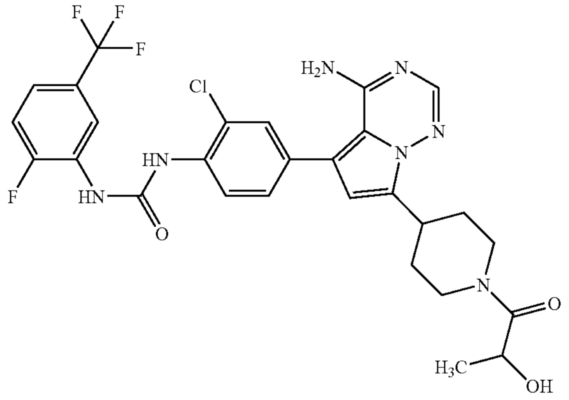

To a stirring solution of DMF (1.0 mL) and Example 267 (50 mg, 0.091 mmol), was added sodium 2-hydroxypropanoate (11 mg, 0.100 mmol), benzotriazolyloxytris(dimethylamino)phosphonium hexafluorophosphate (42 mg, 0.094 mmol), and triethylamine (32 μL, 0.228 mmol). The solution was stirred at rt for 20 min, then concentrated under reduced pressure, diluted with EtOAc (20 mL), and washed with $Na_2CO_3$ (10 mL) followed by citrate buffer (5 mL, pH 3-4) and brine (5 mL). The organic phase was dried ($Na_2SO_4$) and concentrated to dryness. Trituration with 10% EtOAc/Hex afforded 25 mg (45%) of the desired compound. $^1$H-NMR (DMSO-$d_6$) δ 9.74 (d, J=2.4 Hz, 1H), 9.01 (s, 1H), 8.65 (dd, J=2.1, 7.5 Hz, 1H), 8.25 (d, J=8.4 Hz, 1H), 7.94 (s, 1H), 7.54-7.48 (m, 2H), 7.40-7.36 (m, 2H), 6.64 (d, J=7.2 Hz, 1H), 4.48-4.44 (m, 2H), 4.07-4.00 (m, 1H), 3.45-3.37 (2H), 3.21-3.12 (m, 1H), 2.81-2.66 (m, 2H), 2.05-2.01 (m, 2H), 1.69-1.48 (m, 2H), 1.21-1.13 (m, 2H); MS $[M+H]^+$=620.3, 622.2; LCMS RT=2.96 min.

Example 230

N-(4-{4-amino-7-[1-(cyclopropylcarbonyl)piperidin-4-yl]pyrrolo[2,1-f][1,2,4]triazin-5-yl}-2-chlorophenyl)-N'-[2-fluoro-5-(trifluoromethyl)phenyl]urea

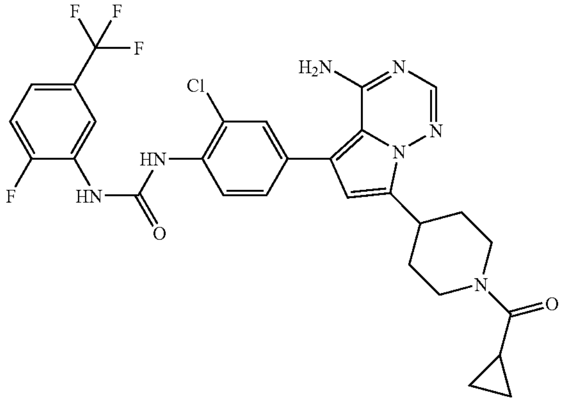

The title compound was prepared in a mariner similar to the procedure described for the preparation of Example 229, using cyclopropanecarboxylic acid in place of sodium 2-hydroxypropanoate, 33 mg (59%) of the desired product was isolated. $^1$H-NMR (DMSO-$d_6$) δ 9.73 (d, J=2.7 Hz, 1H), 9.01 (s, 1H), 8.65 (dd, J=2.4, 7.5 Hz, 1H), 8.24 (d, J=8.7 Hz, 1H), 7.91 (s, 1H), 7.54-7.48 (m, 2H), 7.43-7.36 (m, 2H), 6.62 (s, 1H), 4.52-4.35 (m, 2H), 3.49-3.36 (m, 1H), 3.26-3.22 (m, 1H), 2.87-2.55 (m, 2H), 2.10-2.00 (m, 2H), 1.67-1.42 (m, 2H), 0.86-0.65 (m, 4H); MS $[M+H]^+$=616.3, 618.2; LCMS RT=3.17 min.

Example 231

N-(4-{4-amino-7-[1-(morpholin-4-ylacetyl)piperidin-4-yl]pyrrolo[2,1-f][1,2,4]triazin-5-yl}-2-chlorophenyl)-N'-[2-fluoro-5-(trifluoromethyl)phenyl]urea

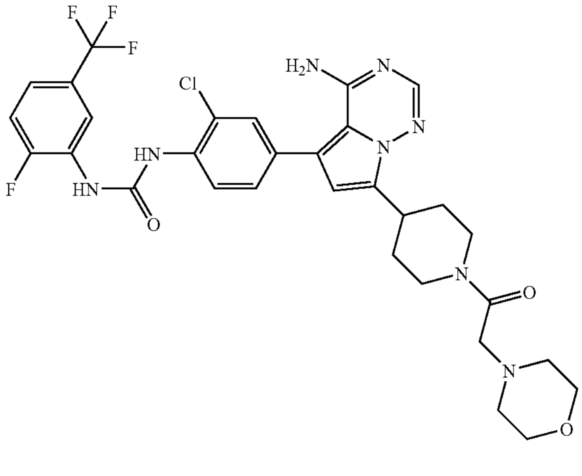

The title compound was prepared in a manner similar to the procedure described for the preparation of Example 229, using morpholin-4-ylacetic acid in place of sodium 2-hydroxypropanoate, 32 mg (52%) of the desired product was isolated. $^1$H-NMR (DMSO-$d_6$) δ 9.73 (d, J=2.7 Hz, 1H), 9.01 (s, 1H), 8.65 (dd, J=2.7, 6.9 Hz, 1H), 8.24 (d, J=8.7 Hz, 1H), 7.91 (s, 1H), 7.55-7.48 (m, 2H), 7.44-7.36 (m, 2H), 6.59 (s, 1H), 4.49-4.44 (m, 1H), 4.20-4.10 (m, 1H), 3.58-3.56 (m, 4H), 3.40-3.38 (m, 1H), 3.24-3.03 (m, 2H), 2.71-2.68 (m, 1H), 2.39-2.42 (m, 4H), 2.22-2.20 (m, 1H), 2.06-1.99 (m, 2H), 1.70-1.62 (m, 1H), 1.60-1.42 (m, 1H); MS $[M+H]^+$=675.3, 677.2; LCMS RT=2.56 min.

Example 232

N-(4-{4-amino-7-[1-(methylsulfonyl)piperidin-4-yl]pyrrolo[2,1-f][1,2,4]triazin-5-yl}-2-chlorophenyl)-N'-[2-fluoro-5-(trifluoromethyl)phenyl]urea

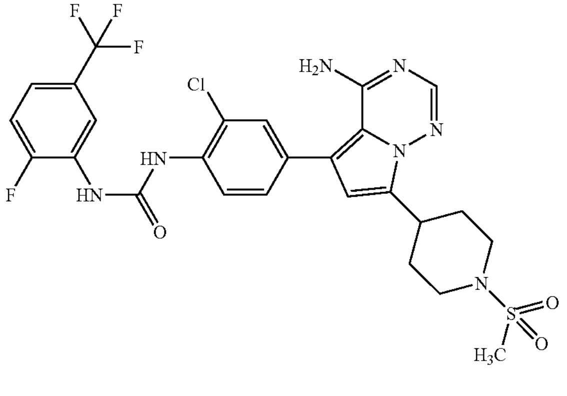

To a stirred solution of DMF (1.0 mL) and Example 267 (50 mg, 0.091 mmol) at 0° C., was added triethylamine (32 μL, 0.228 mmol) followed by methanesulfonyl chloride (11 mg, 0.092 mmol). The solution was stirred while warming to rt for 30 min, then concentrated under reduced pressure, diluted with EtOAc (20 mL), and washed with $Na_2CO_3$ (10 mL) and brine (5 mL). The organic phase was dried ($Na_2SO_4$) and concentrated to dryness. Trituration with $Et_2O$ afforded 26 mg (45%) of the desired compound. $^1$H-NMR (DMSO-$d_6$) δ 9.73 (d, J=2.7 Hz, 1H), 9.01 (s, 1H), 8.65 (dd, J=.=2.4, 7.2 Hz, 1H), 8.25 (d, J=8.4 Hz, 1H), 7.91 (s, 1H), 7.55-7.48 (m, 2H), 7.44-7.36 (m, 2H), 6.65 (s, 1H), 3.68-3.64 (m, 2H), 3.31-3.24 (m, 2H), 2.93-2.85 (m, 1H), 2.90 (s, 3H), 2.16-2.09 (m, 2H), 1.76-1.71 (m, 2H); MS $[M+H]^+$=626.3, 628.2; LCMS RT=3.30 min.

Example 233

N-{4-[4-amino-7-(1-glycoloylpiperidin-4-yl)pyrrolo[2,1f][1,2,4]triazin-5-yl]-2,5-difluorophenyl}-N'-[2-fluoro-5-(trifluoromethyl)phenyl]urea

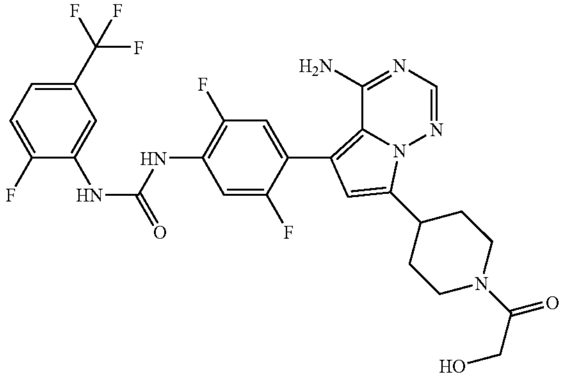

The title compound was prepared in a manner similar to the procedure described for the preparation of Example 229, using Example 275 in place of Example 267, and glycolic acid in place of sodium 2-hydroxypropanoate, 101 mg (22%) of the desired product was isolated. $^1$H-NMR (DMSO-$d_6$) δ 9.47 (s, 1H), 9.42 (s, 1H), 8.63 (dd, J=1.8, 7.2 Hz, 1H), 8.17-8.11 (m, 1H), 7.90 (s, 1H), 7.55-7.48 (m, 1H), 7.44-7.39 (m, 1H), 7.32-7.26 (s, 1H), 6.52 (s, 1H), 4.51-4.43 (m, 1H), 4.11-4.07 (m, 2H), 3.78-3.74 (m, 1H), 3.43-3.32 (m, 1H), 3.15-3.12 (m, 1H), 2.76-2.71 (m, 1H), 2.04-1.97 (m, 2H), 1.65-1.48 (m, 2H); MS [M+H]$^+$=608.3; LCMS RT=3.03 min.

Example 234

N-[4-(4-amino-7-glycoloylpyrrolo[2,1f][1,2,4]triazin-5-yl)-2-fluorophenyl]-N'-[2-fluoro-5-(trifluoromethyl)phenyl]urea

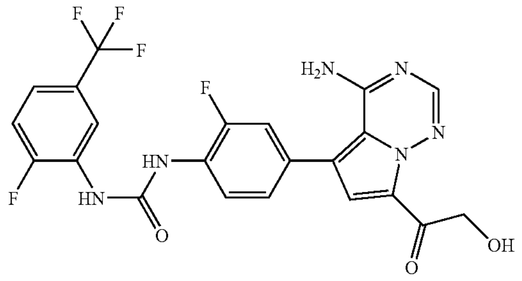

To a stirred solution of Example 256 (337 mg, 0.615 mmol), in MeOH (5 mL), was added crushed anhydrous $K_2CO_3$ (250 mg, 1.81 mmol). The slurry was allowed to stir for 20 min and partitioned between EtOAc (50 mL) and saturated aq $Na_2CO_3$ (20 mL). The organic phase was washed with brine (10 mL), dried ($Na_2SO_4$) and concentrated under reduced pressure. Trituration with $Et_2O$ afforded 18 mg (6%) of the desired product. $^1$H-NMR (DMSO-$d_6$) δ 9.60-9.39 (m, 2H), 8.65 (dd, J=2.1, 7.2 Hz, 1H), 8.24 (t, J=8.4 Hz, 1H), 7.90 (s, 1H), 7.53-7.47 (m, 1H), 7.42-7.37 (m, 1H), 7.31 (dd, J=2.1, 12 Hz, 1H), 7.21 (d, J=9.6 Hz, 1H), 6.87 (s, 1H), 2.60-2.51 (m, 2H); MS [M+H]$^+$=507.1; LCMS RT=3.28 min.

Example 235

N-{4-[4-amino-7-(1-cyclopropylpiperidin-4-yl)pyrrolo[2,1-f][1,2,4]triazin-5-yl]2-fluorophenyl}-N'-[4-(trifluoromethyl)pyridin-2-yl]urea

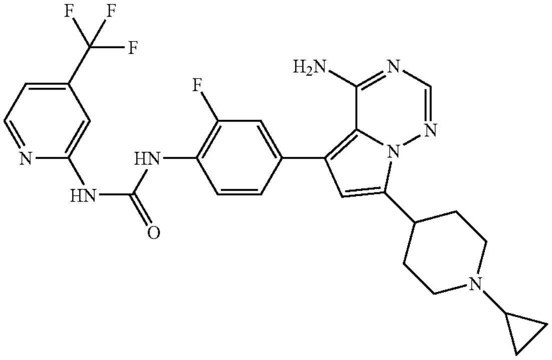

To a stirred solution of Example 271 (100 mg, 0.19 mmol) in ethanol (1 mL) with freshly activated powdered 3 Å molecular seives, was added acetic acid (195 μL, 1.94 mmol), sodium cyanoborohydride (34 mg, 0.78 mmol) and [(1-methoxycyclopropyl)oxy](trimethyl)silane (233 μL, 1.17 mmol). The reaction was heated to 60° C. and allowed to stir for 2 h. The mixture was allowed to cool and partitioned between EtOAc (40 mL) and 1N NaOH (20 mL). The organic phase was washed with brine (10 mL), dried ($Na_2SO_4$) and concentrated under reduced pressure. Trituration with $Et_2O$ afforded 22 mg (20%) of the desired product. $^1$H-NMR (DMSO-$d_6$) δ 10.07 (s, 1H), 9.99 (br s, 1H), 8.49 (d, J=5.1 Hz, 1H), 8.20 (t, J=8.7 Hz, 1H), 7.94 (s, 1H), 7.84 (s, 1H), 7.34-7.25 (m, 2H), 7.18 (d, J=8.7 Hz, 1H), 6.47 (s, 1H), 3.01-2.92 (m, 2H), 2.30-2.20 (m, 2H), 1.95-1.85 (m, 2H), 1.76-1.50 (m, 2H), 1.31-1.25 (m, 2H), 0.85-1.75 (m, 1H), 0.40-0.30 (m, 1H), 0.30-0.21 (m, 1H), 0.05-0.00 (m, 1H); MS [M+H]$^+$=555.2; LCMS RT=2.80 min.

Example 236

N-{4-[4-amino-7-(1-glycoloylpiperidin-4-yl)pyrrolo[2,1f][1,2,4]triazin-5-yl]-2-fluorophenyl}-N'-[4-(trifluoromethyl)pyridin-2-yl]urea

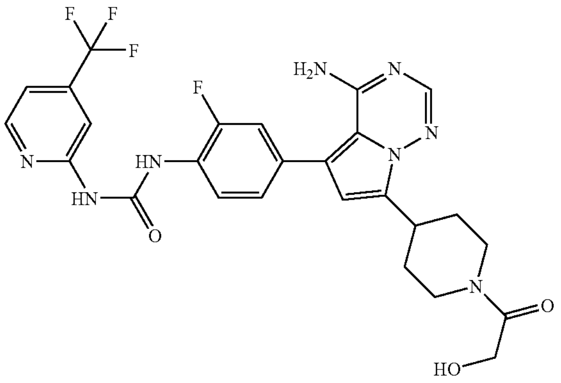

The title compound was prepared in a manner similar to the procedure described for the preparation of Example 229, using Example 271 in place of Example 267, and glycolic acid in place of sodium 2-hydroxypropanoate, 36 mg (17%) of the desired product was isolated. $^1$H-NMR (DMSO-$d_6$) δ 10.13 (s, 1H), 10.06 (br s, 1H), 8.54 (d, J=5.1 Hz, 1H), 8.27 (t, J=8.7 Hz, 1H), 8.01 (s, 1H), 7.96 (s, 1H), 7.39-7.32 (m, 2H), 7.24 (d, J=8.4 Hz, 1H), 6.60 (s, 1H), 4.48-4.36 (m, 1H), 4.11 (d, J=2.7 Hz, 2H), 3.81-3.75 (m, 1H), 3.47-3.34 (m, 1H), 3.18-3.12 (m, 1H), 2.78-2.66 (m, 1H), 2.05-1.97 (m, 2H), 1.66-1.54 (m, 2H); MS [M+H]$^+$=573.2; LCMS RT=2.98 min.

Example 237

N-{4-[7-(1-acetylpiperidin-4-yl)-4-aminopyrrolo[2,1f][1,2,4]triazin-5-yl]-2-fluorophenyl}-N'-[4-(trifluoromethyl)pyridin-2-yl]urea

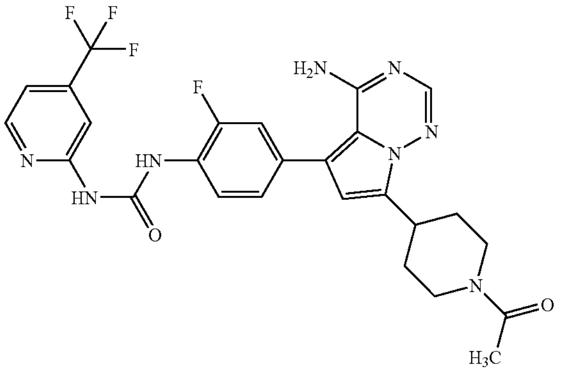

The title compound was prepared in a manner similar to the procedure described for the preparation of Example 232, using Example 271 in place of Example 267, and acetic anhydride in place of methanesulfonyl chloride, 45 mg (69%) of the desired product was isolated. $^1$H-NMR (DMSO-$d_6$) δ 10.14 (s, 1H), 10.07 (br s, 1H), 8.54 (d, J=5.4 Hz, 1H), 8.27 (t, J=8.7 Hz, 1H), 8.01 (s, 1H), 7.95 (s, 1H), 7.39-7.32 (m, 2H), 7.26 (d, J=8.4 Hz, 1H), 6.63 (s, 1H), 4.51-4.47 (m, 1H), 3.94-3.89 (m, 1H), 3.75-3.65 (m, 1H), 3.24-3.15 (m, 1H), 2.71 (s, 3H), 2.67-2.65 (m, 1H), 2.03-21.97 (m, 2H), 1.69-1.46 (m, 2H); MS [M+H]+=557.2; LCMS RT=3.08 min.

Example 238

N-(4-{4-amino-7-[1-(cyclopropylcarbonyl)piperidin-4-yl]pyrrolo[2,1-f][1,2,4]triazin-5-yl}-2-fluorophenyl)-N'-[4-(trifluoromethyl)pyridin-2-yl]urea

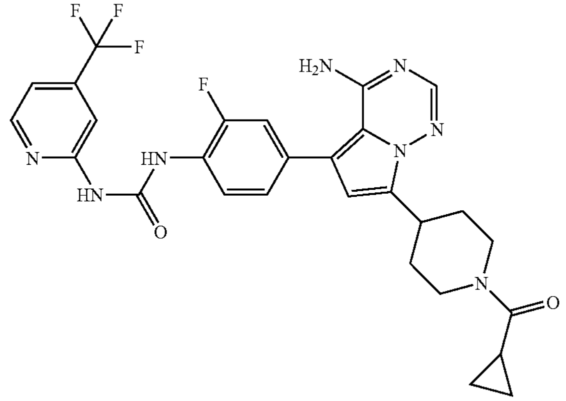

The title compound was prepared in a manner similar to the procedure described for the preparation of Example 229, using Example 271 in place of Example 267, and cyclopropanecarboxylic acid in place of sodium 2-hydroxypropanoate, 42 mg (62%) of the desired product was isolated. $^1$H-NMR (DMSO-$d_6$) δ 10.13 (s, 1H), 10.05 (br s, 1H), 8.54 (d, J=5.4 Hz, 1H), 8.26 (t, J=8.7 Hz, 1H), 8.01 (s, 1H), 7.91 (s, 1H), 7.39-7.32 (m, 2H), 7.26 (d, J=8.4 Hz, 1H), 6.61 (s, 1H), 4.51-4.32 (m, 2H), 3.49-3.35 (m, 1H), 3.10-2.90 (m, 3H), 2.07-1.97 (m, 2H), 1.70-1.40 (m, 2H), 1.12 (t, J=7.2H, 2H), 0.72-0.67 (m, 2H); MS $[M+H]^+$=583.2; LCMS RT=3.10 min.

Example 239

N-(4-{4-amino-7,1-(methylsulfonyl)piperidin-4-yl]pyrrolo[2,1-f][1,2,4]triazin-5-yl}-2-fluorophenyl)-N'-[4-(trifluoromethyl)pyridin-2-yl]urea

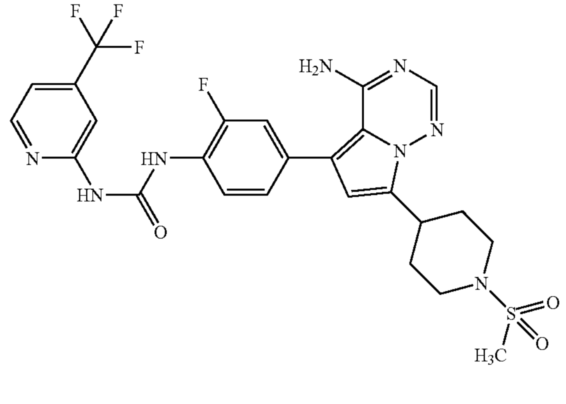

The title compound was prepared in a manner similar to the procedure described for the preparation of Example 232, using Example 271 in place of Example 267, 18 mg (26%) of the desired product was isolated. $^1$H-NMR (DMSO-$d_6$) δ 10.13 (s, 1H), 10.05 (br s, 1H), 8.54 (d, J=5.1 Hz, 1H), 8.27 (t, J=8.4 Hz, 1H), 8.01 (s, 1H), 7.91 (s, 1H), 7.39-7.32 (m, 2H), 7.25 (dd, J=1.8 Hz, 1H), 6.63 (s, 1H), 3.68-3.64 (m, 1H), 3.32-3.24 (m, 2H), 2.89 (s, 3H), 2.13-2.07 (m, 2H), 1.76-1.70 (m, 2H), 1.25-1.20 (m, 2H); MS $[M+H]^+$=593.2; LCMS RT=3.10 min.

Example 240

N-(4-{4-amino-7-[1-(N,N-dimethylglycyl)piperidin-4-yl]pyrrolo[2,1-f][1,2,4]triazin-5-yl}-2-chlorophenyl)-N'-[2-fluoro-5-(trifluoromethyl)phenyl]urea

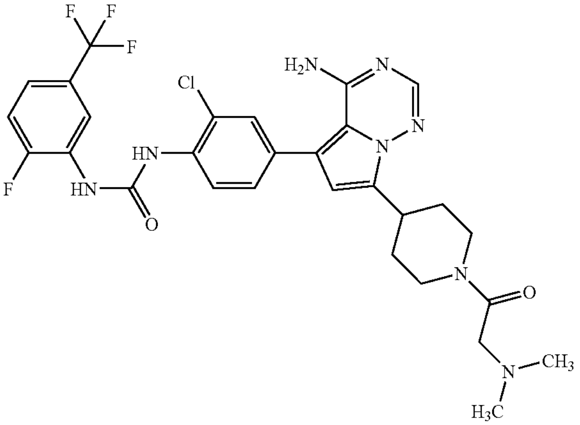

The title compound was prepared in a manner similar to the procedure described for the preparation of Example 229, using N,N-dimethylglycine hydrochloride in place of sodium 2-hydroxypropanoate, 23 mg (20%) of the desired product was isolated. $^1$H-NMR (DMSO-$d_6$) δ 9.73 (d, J=2.7 Hz, 1H), 9.01 (s, 1H), 8.65 (dd, J=1.8, 7.5 Hz, 1H), 8.24 (d, J=8.7 Hz, 1H), 7.91 (s, 1H), 7.53-7.48 (m, 2H), 7.44-7.36 (m, 2H), 6.59 (s, 1H), 4.49-4.44 (m, 1H), 4.14-4.09 (m, 1H), 3.50-3.30 (m, 1H), 3.22-3.11 (m, 3H), 2.72-2.71 (m, 1H), 2.24 (s, 6H), 2.05-2.01 (m, 2H), 1.70-1.42 (m, 2H); MS $[M+H]^+$=633.2, 635.2; LCMS RT=2.54 min.

Example 241

N-(4-{4-amino-7-[1-(2-methoxyethyl)piperidin-4-yl]pyrrolo[2,1-f][1,2,4]triazin-5-yl}-2-chlorophenyl)-N'-[2-fluoro-5-(trifluoromethyl)phenyl]urea

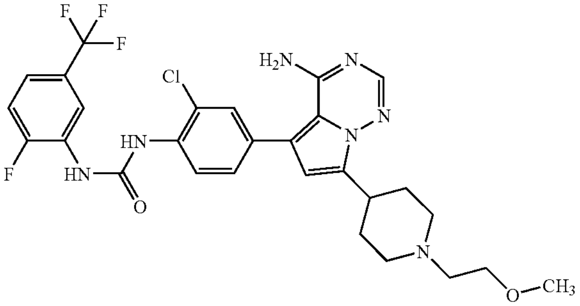

To a stirred solution of Example 267 (50 mg, 0.091 mmol) in NMP (1 mL), was added triethylamine (24 μL, 0.18 mmol) and 1-bromo-2-methoxyethane (10 μL, 0.10 mmol). The reaction was heated to 60° C. and allowed to stir for 17 hr. The mixture was allowed to cool and partitioned between EtOAc (30 mL) and saturated aq $NaHCO_3$ (15 mL). The organic phase was washed with brine (10 mL), dried ($Na_2SO_4$) and concentrated to dryness. Trituration with $Et_2O$ afforded 13 mg (24%) of the desired product. $^1$H-NMR (DMSO-$d_6$) δ 9.73 (d, J=2.4 Hz, 1H), 9.01 (s, 1H), 8.65 (dd, J=2.1, 7.2 Hz, 1H), 8.24 (d, J=8.7 Hz, 1H), 7.91 (s, 1H), 7.55-7.49 (m, 2H), 7.44-7.36 (m, 2H), 6.60 (s, 1H), 3.38-3.26 (m, 7H), 2.67 (s, 3H), 2.19-2.14 (m, 3H), 1.93-1.83 (m, 3H); MS $[M+H]^+$=606.4, 608.3; LCMS RT=2.99 min.

Example 242

N-[4-(4-amino-7-piperidin-4-ylpyrrolo[2,1-f][1,2,4]triazin-5-yl)phenyl]-N'-[2-fluoro-5-(trifluoromethyl)phenyl]urea

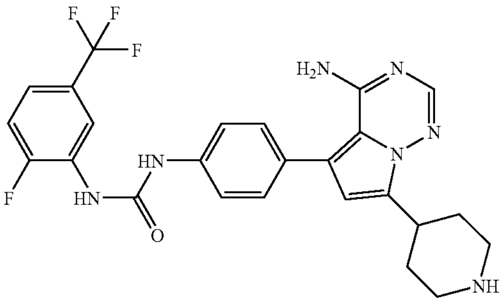

The title compound was prepared in a manner similar to the procedure described for the preparation of Example 111, using Example 272 in place of Example 110, 400 mg (96%) of the desired product was isolated. $^1$H-NMR (DMSO-$d_6$) δ 9.47-9.40 (m, 1H), 9.02-8.99 (m, 1H), 8.62 (dd, J=2.1, 6.9 Hz, 1H), 7.89 (s, 1H), 7.59-7.46 (m, 3H), 7.40-7.36 (m, 3H), 6.51 (s, 1H), 3.32-3.29 (m, 1H), 3.27-3.17 (m, 2H), 2.89-2.81 (m, 2H), 2.07-2.03 (m, 2H), 1.75-1.66 (m, 2H); MS $[M+H]^+$=514; LCMS RT=2.74 min.

Example 243

N-(4-{4-amino-7-[1-(2-ethoxyethyl)piperidin-4-yl]pyrrolo[2,1-f][1,2,4]triazin-5-yl}-2-chlorophenyl)-N'-[2-fluoro-5-(trifluoromethyl)phenyl]urea

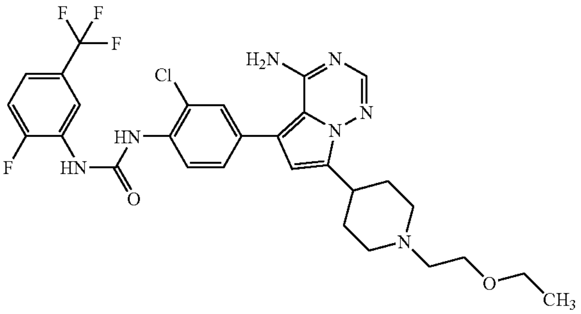

The title compound was prepared in a manner similar to the procedure described for the preparation of Example 241, using 1-bromo-2-ethoxyethane in place of 1-bromo-2-methoxyethane, 29 mg (51%) of the desired product was isolated. $^1$H-NMR (DMSO-$d_6$) δ 9.73 (d, J=2.7 Hz, 1H), 9.00 (s, 1H), 8.65 (dd, J=2.1, 7.5 Hz, 1H), 8.24 (d, J=8.4 Hz, 1H), 7.89 (s, 1H), 7.55-7.49 (m, 2H), 7.44-7.36 (m, 2H), 6.59 (s, 1H), 3.47 (t, J=6.3 Hz, 2H), 3.28 (t, J=6.9 Hz, 3H), 3.10-2.95 (m, 3H), 2.19-2.09 (m, 4H), 1.93-1.83 (m, 4H), 1.75-1.60 (m, 2H); MS $[M+H]^+$=620.4, 622.3; LCMS RT=2.97 min.

Example 244

N-(4-{4-amino-7-[1-(2-ethoxyethyl)piperidin-4-yl]pyrrolo[2,1-f][1,2,4]triazin-5-yl}phenyl)-N'-[2-fluoro-5-(trifluoromethyl)phenyl]urea

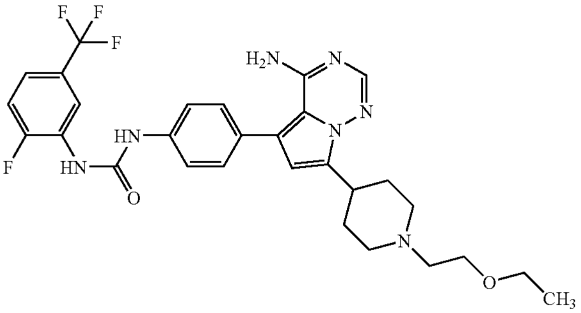

The title compound was prepared in a manner similar to the procedure described for the preparation of Example 241, using Example 242 in place of Example 267 and 1-bromo-2-ethoxyethane in place of 1-bromo-2-methoxyethane, 20 mg (35%) of the desired product was isolated. $^1$H-NMR (DMSO-$d_6$) δ 9.29 (s, 1H), 8.94 (d, 7=2.7 Hz, 1H), 8.63 (dd, J=2.4, 7.2 Hz, 1H), 7.87 (s, 1H), 7.58-7.46 (m, 3H), 7.40-7.36 (m, 3H), 6.52 (s, 1H), 3.47 (t, J=6.3 Hz, 2H), 3.41 (q, J=6.9 Hz, 2H), 3.06-2.95 (m, 3H), 2.48-2.46 (m, 2H), 2.13-2.06 (m, 2H), 1.97-1.93 (m, 2H), 1.70-1.65 (m, 2H), 1.09 (t, J=6.9 Hz, 3H); MS $[M+H]^+$=586.3; LCMS RT=2.54 min.

Example 245

N-(4-{4-amino-7,1-(2,2-difluoroethyl)piperidin-4-yl]pyrrolo[2,1-f][1,2,4]triazin-5-yl}phenyl)-N'-[2-fluoro-5-(trifluoromethyl)phenyl]urea

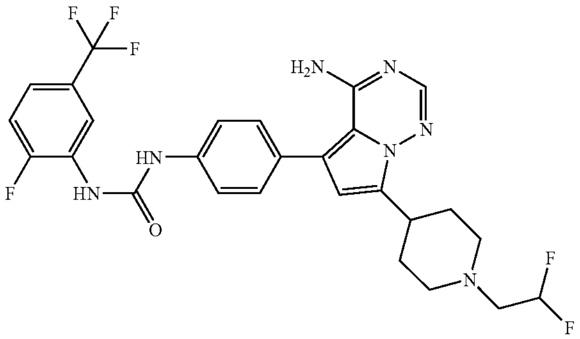

The title compound was prepared in a manner similar to the procedure described for the preparation of Example 241, using Example 242 in place of Example 267 and 2-bromo-1,1-difluoroethane in place of 1-bromo-2-methoxyethane, 23 mg (40%) of the desired product was isolated. $^1$H-NMR (DMSO-$d_6$) δ 9.30 (s, 1H), 8.94 (d, J=2.1 Hz, 1H), 8.63 (dd, J=2.4, 7.2 Hz, 1H), 7.87 (s, 1H), 7.58-7.46 (m, 3H), 7.413-7.35 (m, 3H), 6.48 (s, 1H), 6.15 (tt, J=4.5, 55.8 Hz, 1H), 3.01-2.98 (m, 2H), 2.79-2.70 (m, 2H), 2.30-2.26 (m, 2H), 2.19-2.13 (m, 2H), 1.73-1.69 (m, 2H); MS $[M+H]^+$=578.3; LCMS RT=2.50 min.

Example 246

N-{4-[4-amino-7-(1-glycoloylpiperidin-4-yl)pyrrolo[2,1-f][1,2,4]triazin-5-yl]phenyl}-N'-[2-fluoro-5-(trifluoromethyl)phenyl]urea

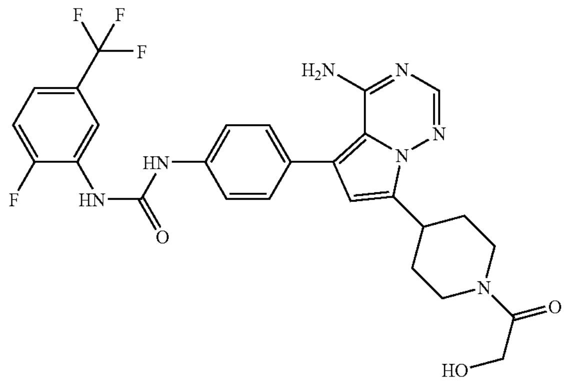

The title compound was prepared in a manner similar to the procedure described for the preparation of Example 229, using Example 242 in place of Example 267, and glycolic acid in place of sodium 2-hydroxypropanoate, 11 mg (20%) of the desired product was isolated. $^1$H-NMR (DMSO-$d_6$) δ 9.29 (s, 1H), 8.94 (d, J=3.0 Hz, 1H), 8.63 (dd, J=2.1, 7.5 Hz, 1H), 7.89 (s, 1H), 7.57-7.46 (m, 3H), 7.39-7.36 (m, 3H), 6.52 (s, 1H), 4.50 (t, J=5.4 Hz, 1H), 4.12-4.09 (m, 2H), 3.79-3.75 (m, 1H), 3.44-3.35 (m, 1H), 3.18-3.09 (m, 1H), 2.87-2.72 (m, 1H), 2.07-2.00 (m, 2H), 1.67-1.50 (m, 2H); MS $[M+H]^+$=572.5; LCMS RT=3.04 min.

Example 247

4-(4-amino-5-{4-[({[2-fluoro-5-(trifluoromethyl)-phenyl]amino}-carbonyl)amino]phenyl}pyrrolo[2,1f][1,2,4]triazin-7-yl)-N,N-dimethylpiperidine-1-carboxamide

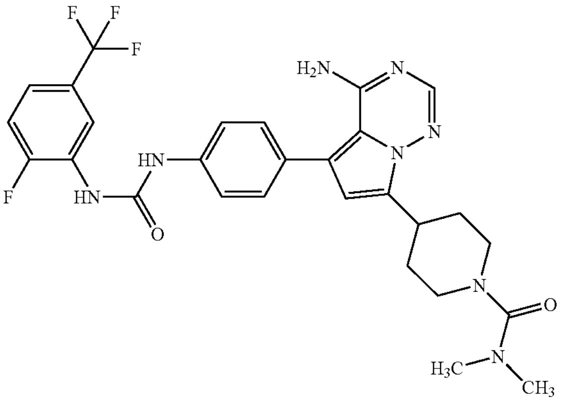

The title compound was prepared in a manner similar to the procedure described for the preparation of Example 232, using Example 242 in place of Example 267, and dimethylcarbamic chloride in place of methanesulfonyl chloride 18 mg (26%) of the desired product was isolated. $^1$H-NMR (DMSO-$d_6$) δ 9.29 (s, 1H), 8.94 (d, J=2.7 Hz, 1H), 8.63 (dd, J=2.4, 6.9 Hz, 1H), 7.89 (s, 1H), 7.58-7.47 (m, 3H), 7.40-7.37 (m, 3H), 6.54 (s, 1H), 3.67-3.62 (m, 2H), 2.87-2.80 (m, 3H), 2.73 (s, 6H), 2.01-1.97 (m, 2H), 1.66-1.62 (m, 2H); MS $[M+H]^+$=585.3; LCMS RT=3.15 min.

Example 248

N-{4-[4-amino-7-(1-cyclopropylpiperidin-4-yl)pyrrolo[2,1-f][1,2,4]triazin-5-yl]phenyl}-N'-[2-fluoro-5-(trifluoromethyl)phenyl]urea

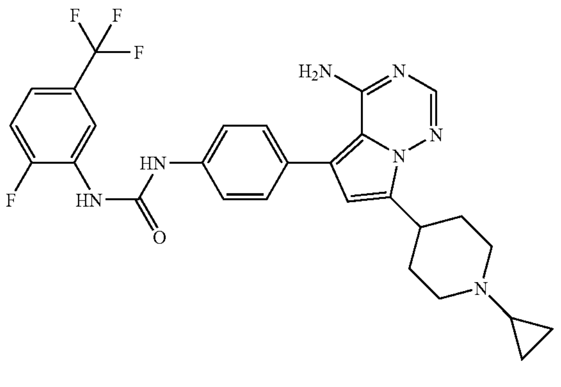

The title compound was prepared in a manner similar to the procedure described for the preparation of Example 235, using Example 242 in place of Example 271, 19 mg (24%) of the desired product was isolated. $^1$H-NMR (DMSO-$d_6$) δ 9.29 (s, 1H), 8.95 (s, 1H), 8.63 (dd, J=1.8, 7.2 Hz, 1H), 7.88 (s, 1H), 7.58-7.43 (m, 3H), 7.39-7.36 (m, 3H), 6.50 (s, 1H), 3.11-3.01 (m, 3H), 2.33-2.26 (m, 2H), 2.02-1.89 (m, 2H), 1.67-1.59 (m, 3H), 1.17-1.07 (m, 1H), 0.43-0.29 (m, 3H); MS $[M+H]^+$=554.3; LCMS RT=2.42 min.

Example 249

1-{4-[4-amino-7-(2-morpholin-4-ylethyl)pyrrolo[2,1f][1,2,4]triazin-5-yl]phenyl}-3-[2-fluoro-5-(trifluoromethyl)phenyl]urea

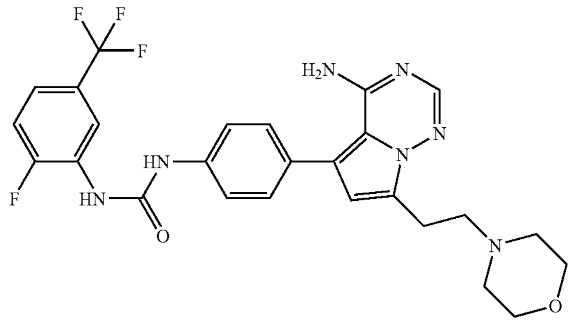

The title compound was prepared in a manner similar to the procedure described for the preparation of Example 108, using 5-bromo-7-(2-morpholin-4-ylethyl)pyrrolo[2,1-f][1,2,4]triazin-4-amine in place of Intermediate V to provide 53 mg (17%) of the desired product was isolated. $^1$H-NMR (DMSO-$d_6$) δ 9.31 (s, 1H), 8.94 (s, 1H), 8.62 (dd, J=1.8, 7.5 Hz, 1H), 7.87 (s, 1H), 7.57-7.46 (m, 3H), 7.41-7.35 (m, 3H), 6.56 (s, 1H), 3.58-3.54 (m, 4H), 3.04 (t, J=7.2 Hz, 2H), 2.63 (t, J=7.2 Hz, 2H), 2.46-2.41 (m, 4H); MS $[M+H]^+$=544.2; LCMS RT=2.82 min.

Example 250

1-{4-[4-amino-7-(2-morpholin-4-ylethyl)pyrrolo[2,1f][1,2,4]triazin-5-yl]-2-fluorophenyl}-3-[4-(trifluoromethyl)pyridin-2-yl]urea

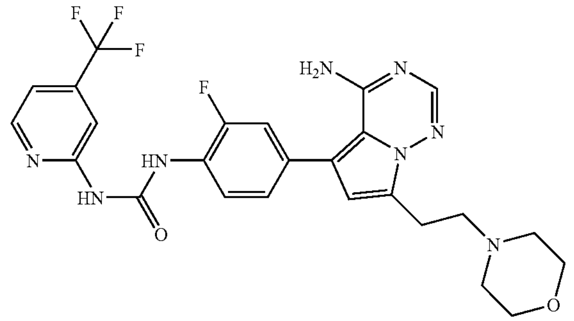

The title compound was prepared in a manner similar to the procedure described for the preparation of Example 108, using 5-bromo-7-(2-morpholin-4-ylethyl)pyrrolo[2,1-f][1,2,4]triazin-4-amine in place of Intermediate V and Intermediate AE in place of Intermediate M (N-[2-fluoro-5 (trifluoromethyl)phenyl]-N'-[4-(4,4,5,5-tetramethyl-1,3,2-dioxaborolan-2-yl)phenyl]urea), 45 mg (13%) of the desired product was isolated. $^1$H-NMR (DMSO-$d_6$) δ 10.13-10.0 (m, 2H), 8.54 (d, J=5.1 Hz, 1H), 8.26 (t, J=8.4 Hz, 1H), 8.01 (s, 1H), 7.90 (s, 1H), 7.38-7.21 (m, 3H), 6.62 (s, 1H), 3.60-3.54 (m, 4H), 3.04 (t, J=7.2 Hz, 2H), 2.63 (t, J=8.1 Hz, 2H), 2.45-2.39 (m, 4H); MS $[M+H]^+$=545.1; LCMS RT=2.43 min.

Example 251

N-{4-[4-amino-7-(1-hydroxyprop-2-en-1-yl)pyrrolo[2,1f][1,2,4]triazin-5-yl]-2-fluorophenyl}-N'-[2-fluoro-5-(trifluoromethyl)phenyl]urea

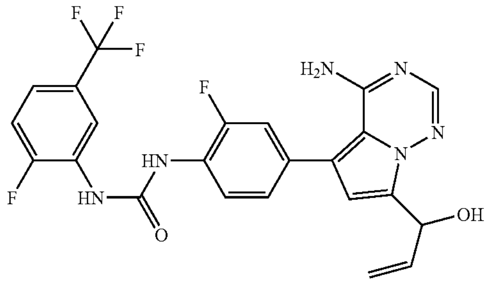

Step 1: Preparation of 1-[4-(4-amino-7-formylpyrrolo[2,1-f][1,2,4]triazin-5-yl)-2-fluorophenyl]-3-[2-fluoro-5-(trifluoromethyl)phenyl]urea

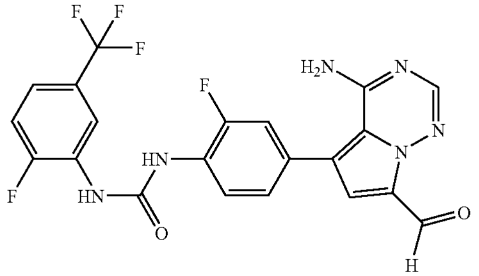

In a manner similar to the procedure described for the preparation of Example 268, using Intermediate O in place Intermediate AE, 727 mg (74%) of the desired product was isolated. MS $[M+H]^+$=477.1; LCMS RT=3.47 min.

Step 2: Preparation of the Title Compound

To a stirred solution of 1-[4-(4-amino-7-formylpyrrolo[2,1-f][1,2,4]triazin-5-yl)-2-fluorophenyl]-3-[2-fluoro-5-(trifluoromethyl)phenyl]urea (450 mg, 0.95 mmol) dissolved in THF (10 mL), was added vinyl magnesium bromide (9.45 mL, 9.45 mmol, 1.0 M in THF) at rt. The reaction was allowed to stir for 1 hr and then quenched with MeOH (1 mL). The mixture was partitioned between EtOAc (250 mL) and saturated aq. $Na_2CO_3$ (100 mL). The organic phase was washed with brine (100 mL), dried ($Na_2SO_4$), and concentrated to dryness. Trituration with $Et_2O$ afforded 300 mg (63%) of the desired product. $^1$H-NMR (DMSO-$d_6$) δ 8.65 (d, J=7.8 Hz, 1H), 8.27 (t, J=8.4 Hz, 1H), 7.85 (s, 1H), 7.36-7.27 (m, 5H), 7.13-7.07 (m, 1H), 6.90 (s, 1H), 6.70-6.60 (m, 1H), 4.29 (dd, J=1.5, 5.7 Hz, 1H); MS $[M+H]^+$=505.2; LCMS RT=2.85 min.

Example 252

N-{4-[4-amino-7-(1-hydroxyethyl)pyrrolo[2,1-f][1,2,4]triazin-5-yl]-2-fluorophenyl}-N'-[2-fluoro-5-(trifluoromethyl)phenyl]urea

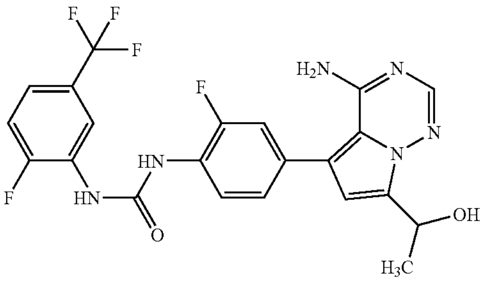

The title compound was prepared in a manner similar to the procedure described for the preparation of Example 101, using Example 253 in place of Example 98, 5 mg (3%) of the desired product was isolated. $^1$H-NMR ($CD_3OD$) δ 8.64 (d, J=8.1 Hz, 1H), 8.26 (t, J=8.7 Hz, 1H), 7.84 (s, 1H), 7.36-7.25 (m, 4H), 6.71 (s, 1H), 5.40 (q, J=6.6 Hz, 1H), 1.61 (d, J=6.6 Hz, 3H); MS $[M+H]^+$=493.2; LCMS RT=2.84 min.

Example 253

N-[4-(7-acetyl-4-aminopyrrolo[2,1f][1,2,4]triazin-5-yl)-2-fluorophenyl]-N'-[2-fluoro-5-(trifluoromethyl)phenyl]urea

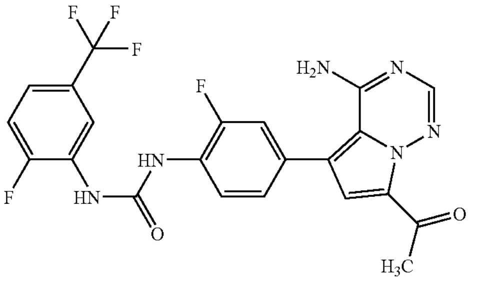

The title compound was prepared in a manner similar to the procedure described for the preparation of Example 103 Step 1, using Intermediate O in place of Intermediate M, 600 mg (78%) of the desired product was isolated. $^1$H-NMR (DMSO-$d_6$) δ 9.43 (br s, 1H), 9.32 (br s, 1H), 8.66 (d, J=6.6 Hz, 1H), 8.30 (t, J=8.7 Hz, 1H), 8.14 (s, 1H), 7.57-7.46 (m, 1H), 7.41-7.35 (m, 3H), 7.27 (d, J=8.4 Hz, 1H), 2.68 (s, 3H); MS $[M+H]^+$=491.2; LCMS RT=3.46 min.

Example 254

N-{4-[4-amino-7-(1,2-dihydroxyethyl)pyrrolo[2,1-f][1,2,4]triazin-5-yl]-2-fluorophenyl}-N'-[2-fluoro-5-(trifluoromethyl)phenyl]urea

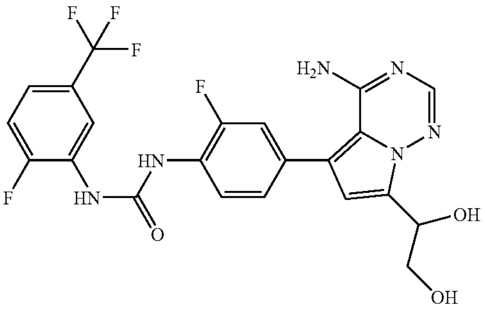

To a stirred solution of Example 234 (150 mg, 0.30 mmol) in THF (2 mL) at 0° C., was added DIBAL-H (2.96 mL, 2.96 mmol, 1.0 M in THF). The reaction was allowed to stir for 30 min while warming to rt. The mixture was quenched with MeOH (1 mL) and diluted with EtOAc (300 mL) and saturated aq sodium potassium tartrate (200 mL). This solution was stirred at 50° C. for 17 hr. The mixture was allowed to cool and the organic phase was washed with brine (50 mL), dried ($Na_2SO_4$) and concentrated to dryness. The residue was purified by preparative HPLC using a gradient elution from 10% to 70% acetonitrile to obtain 31 mg (20%) of the desired product. $^1$H-NMR (DMSO-$d_6$) δ 9.51 (br s, 1H), 9.35 (br s, 1H), 8.73 (d, J=6.0 Hz, 1H), 8.35 (t, J=8.7 Hz, 1H), 7.98 (s, 1H), 7.62-7.55 (m, 1H), 7.49-7.47 (m, 1H), 7.41-7.27 (m, 2H), 6.76 (s, 1H), 5.27 (t, J=5.7 Hz, 1H), 4.59-4.58 (m, 1H), 4.11 (s, 1H), 3.39 (d, J=6.9 Hz, 2H); MS $[M+H]^+$=509.2; LCMS RT=2.98 min.

Example 255

N-{4-[4-amino-7-(1,2,3-trihydroxypropyl)pyrrolo[2,1f][1,2,4]triazin-5-yl]-2-fluorophenyl}-N'-[2-fluoro-5-(trifluoromethyl)phenyl]urea

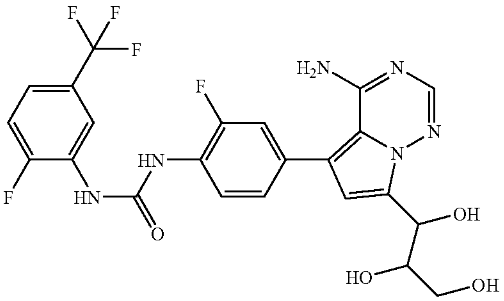

The title compound was prepared in a manner similar to the procedure described for the preparation of Example 121, using Example 251 in place of Example 117, 17 mg (16%) of the desired product was isolated. $^1$H-NMR ($CD_3OD$) δ 8.64

(d, J=7.2, 1H), 8.25 (t, J=8.1 Hz, 1H), 7.83 (s, 1H), 7.67-7.54 (m, 1H), 7.35-7.23 (m, 3H), 6.79 (s, 1H), 5.33 (d, J=6.6 Hz, 1H), 4.14-4.11 (m, 1H), 3.74-3.63 (m, 2H); MS $[M+H]^+$=539.3; LCMS RT=2.59 min.

Example 256

2-(4-amino-5-{3-fluoro-4-[({[2-fluoro-5-(trifluoromethyl)-phenyl]amino}carbonyl)amino]phenyl}pyrrolo[2,1-f][1,2,4]triazin-7-yl)-2-oxoethyl acetate

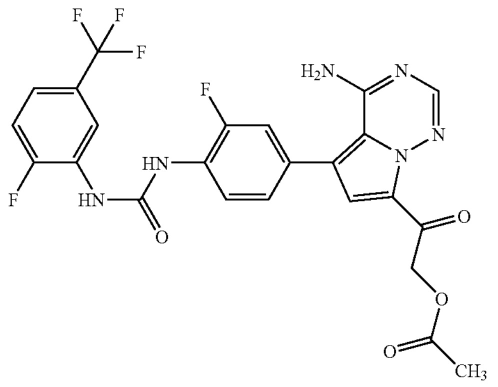

To a stirred solution of Example 257 (350 mg, 0.62 mmol) in DMSO (3 mL), was added potassium acetate (302 mg, 3.07 mmol) at rt. The reaction was allowed to stir for 15 min. The mixture was partitioned between EtOAc (100 mL) and saturated aq $Na_2CO_3$ (50 mL) The organic phase was dried ($Na_2SO_4$) and concentrated under reduced pressure. Trituration with $Et_2O$ afforded 150 mg (44%) of the desired product. $^1$H-NMR (DMSO-$d_6$) δ 9.43 (d, J=2.7 Hz, 1H), 9.30 (d, J=2.1 Hz, 1H), 8.65 (dd, J=2.1, 7.5 Hz, 1H), 8.30 (t, J=8.7 Hz, 1H), 8.18 (s, 1H), 7.55-7.51 (m, 1H), 7.43-7.38 (m, 2H), 7.37 (s, 1H), 7.27 (dd, J=1.8, 8.4 Hz, 1H), 5.44 (s, 2H), 2.14 (s, 3H); MS $[M+H]^+$=549.2; LCMS RT=3.60 min.

Example 257

N-{4-[4-amino-7-(bromoacetyl)pyrrolo[2,1-f]{1,2,4]triazin-5-yl]-2-fluorophenyl}-N'-[2-fluoro-5-(trifluoromethyl)phenyl]urea

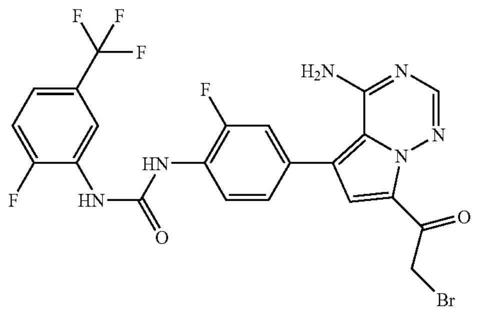

The title compound was prepared in a manner similar to the procedure described for the preparation of Example 103 Step 2, using Example 253 in place of Example 100, 340 mg (59%) of the desired product was isolated. $^1$H-NMR (DMSO-$d_6$) δ 9.13 (d, J=3.0 Hz, 1H), 9.00 (d, J=2.4 Hz, 1H), 8.35 (dd, J=2.1, 7.8 Hz, 1H), 8.01 (t, J=8.7 Hz, 1H), 7.89 (s, 1H), 7.24-7.18 (m, 1H), 7.18 (s, 1H), 7.13-7.09 (m, 2H), 6.98 (dd, J=1.8, 8.4 Hz, 1H), 4.63 (s, 2H); MS $[M+H]^+$=569.4, 571.3; LCMS RT=3.81 min.

Example 258

N-(4-{4-amino-7-[(3-morpholin-4-ylpropoxy)acetyl]pyrrolo[2,1-f][1,2,4]triazin-5-yl}-2-fluorophenyl)-N'-[2-fluoro-5-(trifluoromethyl)phenyl]urea

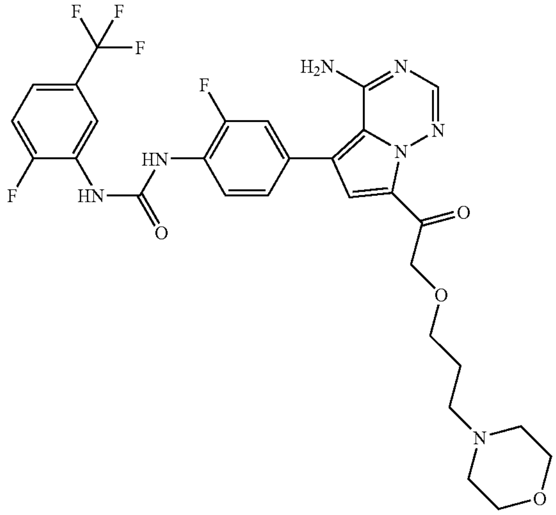

To a stirred solution of Example 257 (200 mg, 0.351 mmol) in DMSO (1 mL), was added diisopropylethylamine (435 µL, 2.64 mmol) and 3-morpholin-4-ylpropan-1-ol (364 uL, 2.64 mmol) at rt. The reaction was allowed to stir at 40° C. for 17 hr. The mixture was allowed to cool and purified by preparative HPLC using a gradient elution from 10% to 70% acetonitrile to obtain 37 mg (17%) of the desired product. $^1$H-NMR (DMSO-$d_6$) δ 9.62 (br s, 1H), 9.47 (br s, 1H), 8.65 (dd, J=-2.4, 7.2 Hz, 1H), 8.23 (t, J=8.4 Hz, 1H), 7.92 (s, 1H), 7.54-7.47 (m, 1H), 7.42-7.38 (m, 1H), 7.31 (dd, J=2.1, 12.3 Hz, 1H), 7.22 (d, J=8.1 Hz, 1H), 6.88 (s, 1H), 4.24 (d, J=11.7 Hz, 2H), 4.05-3.96 (m, 4H), 3.86-3.77 (m, 4H), 3.43 (t, J=5.7 Hz, 2H), 3.24-3.20 (m, 2H), 1.91-1.85 (m, 2H); MS $[M+H]^+$=634.2; LCMS RT=2.75 min.

Example 259

N-[4-(7-acetyl-4-aminopyrrolo[2,1-f][1,2,4]triazin-5-yl)-2-fluorophenyl]-N'-[4-(trifluoromethyl)pyridin-2-yl]urea

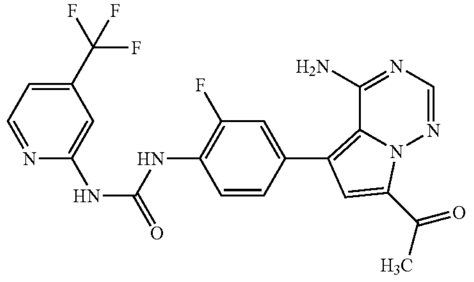

The title compound was prepared in a manner similar to the procedure described for the preparation of Example 100 using Intermediate AE in place of Intermediate M, 540 mg (58%) of the desired product was isolated. $^1$H-NMR (DMSO-$d_6$) δ 8.54 (d, J=5.1 Hz, 1H), 8.30 (t, J=8.1 Hz, 1H), 8.13 (s, 1H), 8.02 (s, 1H), 7.43-7.35 (m, 3E1), 7.28 (dd, J=1.8, 8.4 Hz, 1H), 2.68 (s, 3H); MS [M+H]$^+$=474.0; LCMS RT=3.29 min.

Example 260

N-(4-{4-amino-7-[(2-morpholin-4-ylethoxy)acetyl]pyrrolo[2,1-f][1,2,4]triazin-5-yl}-2-fluorophenyl)-N'-[2-fluoro-5-(trifluoromethyl)phenyl]urea

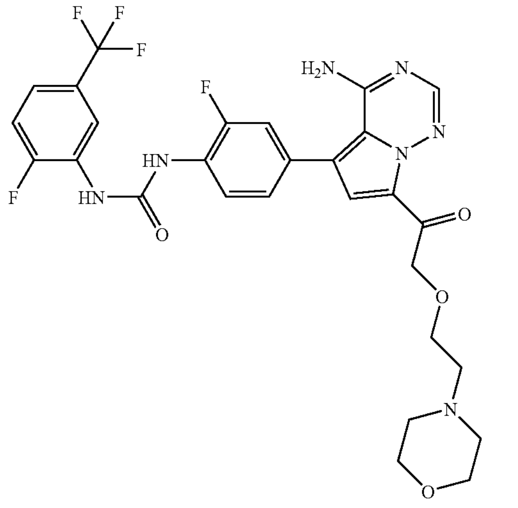

The title compound was prepared in a manner similar to the procedure described for the preparation of Example 258, using 2-morpholin-4-ylethanol in place of 3-morpholin-4-ylpropan-1-ol, 20 mg (12%) of the desired product was isolated. $^1$H-NMR (DMSO-$d_6$) δ 8.64 (d, J=7.2 Hz, 1H), 8.27 (t, J=8.1 Hz, 1H), 7.98 (s, 1H), 7.52-7.48 (m, 1H), 7.41-7.38 (m, 1H), 7.33-7.19 (m, 2H), 6.82 (s, 1H), 4.52-4.47 (m, 2H), 4.31-4.26 (m, 2H), 4.13-3.73 (m, 8H), 3.57-3.51 (m, 2H); MS [m+H]$^+$=620.2; LCMS RT=2.74 min.

Example 261

2-(4-[4-amino-5-[3-chloro-4-({[2-fluoro-5-(trifluoromethyl)phenyl]carbamoyl}amino)phenyl]pyrrolo[2,1-f][1,2,4]triazin-7-yl}piperidin-1-yl)-N,N,N-trimethyl-2-oxoethanaminium chloride

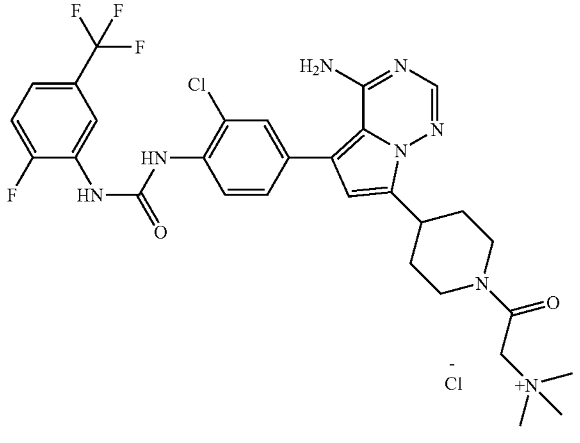

The title compound was prepared in a manner similar to the procedure described for the preparation of Example 229, using carboxy-N,N,N-trimethylmethanaminium chloride in place of sodium 2-hydroxypropanoate, 37 mg (59%) of the desired product was isolated. $^1$H-NMR (DMSO-$d_6$) δ 9.73 (d, J=2.7 Hz, 1H), 9.01 (s, 1H), 8.65 (dd, J=2.1, 7.5 Hz, 1H), 8.25 (d, J=8.7 Hz, 1H), 7.92 (s, 1H), 7.52-7.49 (m, 2H), 7.42-7.35 (m, 2H), 6.58 (s, 1H), 3.85-3.75 (m, 2H), 3.50-3.39 (m, 2H), 3.24 (m, 9H), 2.85-2.55 (m, 1H), 2.15-2.02 (m, 2H), 1.96 (s, 1.73-1.54 (m, 2H); MS [M]$^{30}$ =647.4; LCMS RT=2.60 min.

Example 262

N-(4-{4-amino-7-[1-(2,2-difluoroethyl)piperidin-4-yl]pyrrolo[2,1-f][1,2,4]triazin-5-yl}-2,5-difluorophenyl)-N'-[2-fluoro-5-(trifluoromethyl)phenyl]urea

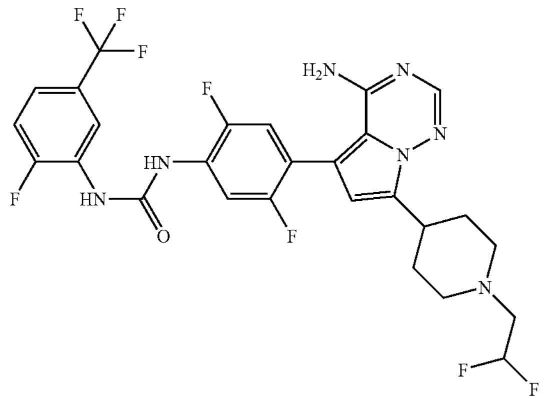

A solution of Example 275 (75 mg, 0.136 mmol), 2-bromo-1,1-difluoroethane (40 mg, 0.27 mmol) and TEA (14 mg, 0.14 mmol) in 1 mL NMP were stirred at rt for 1 h and at 60° C. for 36 h. The reaction was diluted with EtOAc and washed with aq. sodium carbonate. The volatiles were removed in vacuo to provide the title compound (52 mg, 62%) as a yellow solid. $^1$H NMR (300 MHz, DMSO-$d_6$) δ 9.56 (s, 1H), 9.55 (s, 1H), 8.71 (dd, 1H), 8.22 (dd, 1H), 7.97 (s, 1H), 7.55-7.66 (m, 1H), 7.47-7.54 (m, 1H), 7.38 (dd, 1H), 6.62 (s, 1H), 6.23 (tt, J=56, 5 Hz, 1H), 3.34-3.39 (m, 1H), 3.09-3.21 (m, 2H), 2.82 (td, J=16, 5 Hz, 2H), 2.32-2.44 (m, 2H), 1.92-2.03 (m, 2H), 1.71-1.84 (m, 2H); ES-MS m/z 614.3 [M+H]$^+$, HPLC RT (min) 2.65.

Example 263

N-{4-[4-amino-7-(1-cyclopropylpiperidin-4-yl)pyrrolo[2,1-f][1,2,4]triazin-5-yl]-2,5-difluorophenyl}-N'-[2-fluoro-5-(trifluoromethyl)phenyl]urea

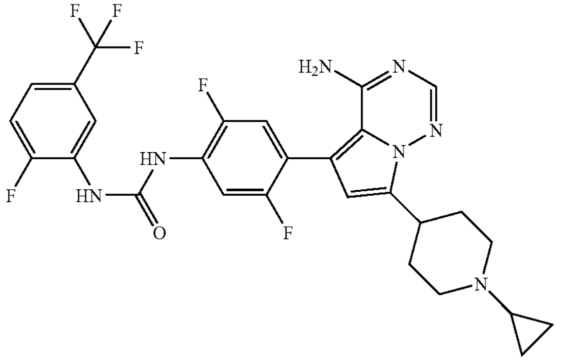

A solution of Example 275 (122.8 mg, 0.223 mmol) in MeOH (2 mL) was treated with acetic acid (134 mg, 2.24 mmol), [(1-methoxycyclopropyl)oxy](trimethyl)silane (234 mg, 1.34 mmol), sodium cyanoborohydride (56 mg, 0.89 mmol) and 3 A Molecular sieves was heated at 60° C. overnight. The reaction was cooled to rt, diluted with EtOAc and washed with sodium carbonate solution. The organic layer was dried with sodium sulfate and filtered thru a silica plug. The filtrate was concentrated and the residue purified by flash column (100% $CH_2Cl_2$ to 5% 2N $NH_3$ in MeOH) to provide the title compound (23 mg, 21%) as a white solid. $^1$H NMR (300 MHz, DMSO-$d_6$) δ 9.55 (s, 1H), 9.51 (s, 1H), 8.71 (dd, 1H), 8.22 (dd, 1H), 7.55 to 7.64 (m, 1H), 7.49 to 7.54 (m, 1H), 7.37 (dd, 1H), 6.58 (s, 1H), 3.05 to 3.19 (m, 3H), 2.30 to 2.41 (m, 1H) 2.0-2.08 (m, 2H), 1.60 to 1.76 (m, 4 H), 0.46 to 0.52 (m, 2H), 0.33 to 0.40 (m, 2H); ES-MS m/z 590.3 [M+H]$^+$, HPLC RT (min) 2.53.

Example 264

N-(4-{4-amino-7-[1-(2,2-difluoroethyl)piperidin-4-yl]pyrrolo[2,1-f][1,2,4]triazin-5-yl}-2-chlorophenyl)-N'-[2-fluoro-5-(trifluoromethyl)phenyl]urea

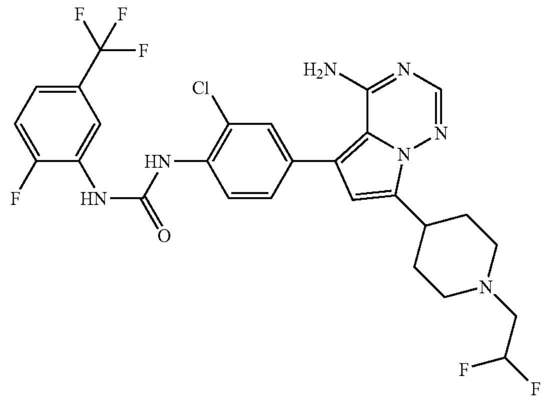

Prepared by the same method as Example 262 by substituting Example 267 for Example 275. $^1$H NMR (300 MHz, DMSO-$d_6$) δ 9.01 (s, 1H), 8.65 (dd, 1H), 8.24 (d, 1H), 7.90 s, 1H), 7.36-7.58 (m, 5H), 6.60 (s, 1H), 6.15 (tt, J=56, 4 Hz, 1H), 2.95-3.14 (m, 2H), 3.29-3.31 (m, 1H), 2.95-3.14 (m, 2H), 2.75 (td, J=16, 4 Hz; 2H), 2.12-2.21 (m, 2H), 1.83-2.01 (m, 2H), 1.62-1.79 (m, 2H). ES-MS m/z 612.3 [M+H]$^+$, HPLC RT (min) 2.51.

Example 265

N-{4-[4-amino-7-(1-cyclopropylpiperidin-4-yl)pyrrolo[2,1-f][1,2,4]triazin-5-yl]-2-chlorophenyl}-N'-[2-fluoro-5-(trifluoromethyl)phenyl]urea

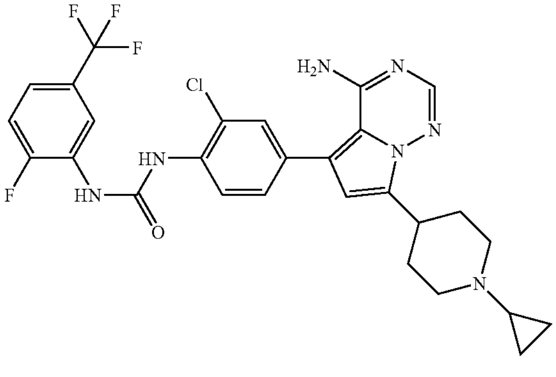

Prepared by the same method as Example 263 by substituting Example 267 for Example 275. $^1$H NMR (300 MHz, DMSO-$d_6$) δ 9.51 (bs, 1H), 8.78 (bs, 1H), 8.35 (dd, 1H), 7.93 (d, 1H), 7.13-7.30 (m, 2H), 7.05-7.10 (m, 2H), 6.27 (s, 1H), 2.68-2.88 (m, 3H), 1.94-2.06 (m, 1H), 1.94-2.06 (m, 2H), 1.61-1.68 (m, 1H), 1.28-1.41 (m, 3H), 0.08-0.17 (m, 2H), −0.03-0.04 (m, 2H); ES-MS m/z 588.3 [M+H]$^+$, HPLC RT (min) 2.48.

Example 266 tert-butyl 4-(4-amino-5-{3-chloro-4-[({[2-fluoro-5-(trifluoromethyl)phenyl]amino}carbonyl)amino]phenyl}pyrrolo[2,1-f][1,2,4]triazin-7-yl)piperidine-1-carboxylate

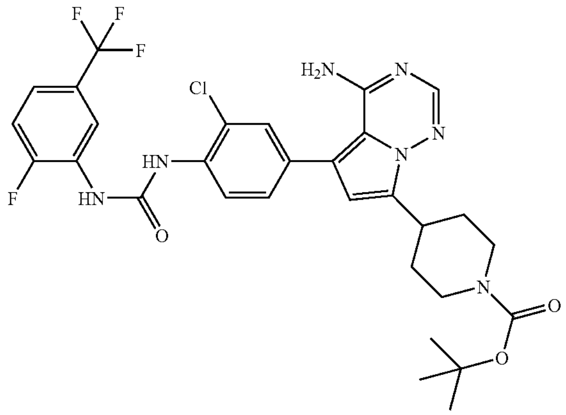

To a flask charged with $N_2$ was added Intermediate AC (1.00 g, 3.79 mmol) and Intermediate AV (1.91 g, 4.16 mmol) followed by DMF (10 mL). $N_2$ was bubbled through the solution for 15 min and then palladium acetate (85 mg mg, 0.38 mmol) and triphenylphosphine (397 mg, 1.5 mmol) was added followed by aq 2M $Na_2CO_3$ (2.5 mL, 5.0 mmol). $N_2$ was bubbled through the solution for an additional 15 min and the reaction was then heated to 80° C. for 17 h. The reaction material was allowed to cool to rt and was diluted with $CH_2Cl_2$. This suspension was filtered thru celite and the volatiles removed in vacuo. The residue was taken up in $CH_2Cl_2$ and purified with a short silica column (eluting with 1-5% MeOH in $CH_2Cl_2$). All fractions containing the product were combined and filtered thru silica (removing most of the color) and the filtrate concentrated. Trituration in boiling ether gave the title compound (1.65 g, 67% yield) as a white solid. This material contained about 10% dehalogenated starting material. $^1$H-NMR (DMSO-$d_6$) δ 9.73 (s, 1H), 9.00 (s, 1H), 8.65 (dd, 1H), 8.24 (dd, J=8.5 Hz, 1H), 7.90 (s, 1H), 7.46-7.55 (m, 2H), 7.40-7.45 (m, 1H), 7.38 (dd, 1H), 6.62 (s, 1H), 4.01-4.12 (m, 2H), 3.28-3.35 (m, 1H), 2.75-2.98 (m, 2H), 1.91-2.02 (m, 2H), 1.55 (ddd, 2H), 1.42 (s, 9H); MS [M+H]$^+$=648.2; LCMS RT=3.43 min.

Example 267

N-[4-(4-amino-7-piperidin-4-ylpyrrolo[2,1-f][1,2,4]triazin-5-yl)-2-chlorophenyl]-N'-[2-fluoro-5-(trifluoromethyl)phenyl]urea

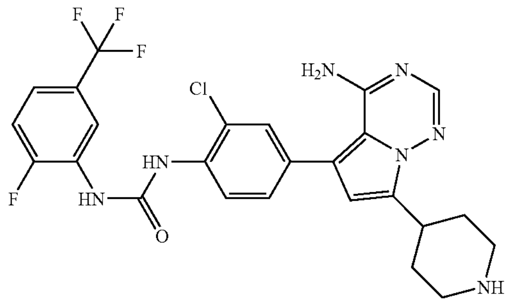

A suspension of Example 266 (1.64 g, 2.53 mmol) in 50 mL 1,2-dichloroethane was treated with 10 mL TFA at rt. The reaction quickly became homogeneous and at 10 min no starting material remained by RP-HPLC. The reaction mixture was concentrated in vacuo, and the residue taken up again in fresh 1,2-dichloroethane and concentrated again; this was repeated 2 times. The residue was taken up in THF (15 mL) and EtOAc (85 mL) and washed with aq. sodium carbonate. The organic layer was dried with sodium sulfate and concentrated in vacuo to provide a tan solid. Trituration with ethyl acetate provided the title compound (1.2 g, 87%) as a tan solid. $^1$H-NMR (DMSO-$d_6$) δ 8.64 (dd, 1H), 8.23 (d, 1H), 7.88 (s, 1H), 7.46-7.54 (m, 2H), 7.34-7.43 (m, 2H), 6.55 (s, 1H), 3.17 (tt, 2H), 2.96-3.05 (m, 2H), 2.60 (dd, 2H), 1.60-1.85-1.95 (m, 2H), 1.56 (ddd, 2H); MS [M+H]$^+$=548.3; LCMS RT=2.94 min.

Example 268

N-[4-(4-amino-7-formylpyrrolo[2,1f][1,2,4]triazin-5-yl)-2-fluorophenyl]-N'-[4-(trifluoromethyl)pyridin-2-yl]urea

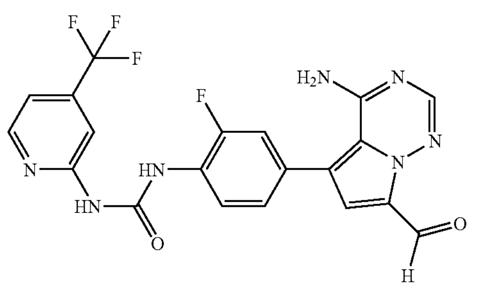

Step 1: Preparation of 4-aminopyrrolo[2,1-f][1,2,4]triazine-7-carbaldehyde

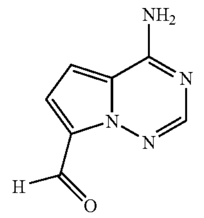

A solution of Intermediate B (4.25 g, 19.9 mmol) was suspended in 100 mL THF and treated with 60% sodium hydride (798 mg, 19.9 mmol) and allowed to stir at rt for 30 min. The reaction mixture was then cooled to −78° C. and tert-butyllithium was added dropwise and the reaction allowed to stir for an additional 10 min. A solution of with DMF (15 mL) in THF (15 mL) was added and the reaction stirred for an additional 10 min. The reaction was then removed from the ice bath and allowed to warm up for an additional 30 min. The reaction was quenched with methanol (2 mL) and diluted with ethyl acetate (200 mL) and pH 7 phosphate buffer (150 mL). The organic layer was washed with water (2 times), brine, dried with sodium sulfate and filtered thru a silica plug. Concentration of the filtrate in vacuo provided a brown solid which H-NMR revealed to be a 4:1 mixture of the desired product and Intermediate A. Suspension of this solid in a minimum of boiling MeOH and filtration of the solid provided the title compound (1.78 g, 55%) as an off white solid. $^1$H-NMR (DMSO-$d_6$) δ 10.25 (d, J=1 Hz, 1H), 8.21 (bs, 1H), 8.07 (s, 1H), 7.25 (d, J=5 Hz, 1H), 7.00 (dd, J=5, 1 Hz, 1H); MS [M+H]$^+$=163.3; LCMS RT=1.14 min.

Step 2: Preparation of the Title Compound

A solution of 4-aminopyrrolo[2,1-f][1,2,4]triazine-7-carbaldehyde (1.781 g, 10.98 mmol) in 25 mL DMF was cooled to −15° C. and treated with 1,3-N,N-dibromo-4,4-dimethylhydantoin (3.30 g, 11.5 mmol). Reaction stirred for 30 min, the volatiles were removed in vacuo and the residue triturated with hot methanol to provide the intermediate bromide as a yellow solid. This bromide was taken up in dioxane (70 mL) and DMF (10 mL) and Intermediate AE (3.43 g, 8.80 mmol) was added as a solid. The solution was degassed for 15 min with $N_2$ before the addition of tetrakis(triphenylphosphine) palladium(0) (851 mg, 0.74 mmol) and 2M sodium carbonate (7.34 mL, 14.7 mmol). The solution was again degassed with $N_2$ for 15 min before heating to 80° C. overnight. After cooling to rt, the reaction mixture was diluted with EtOAc (300 ml) and washed 2× with 1 N phosphate buffer (pH 7.0), 1× brine, dried over sodium sulfate, filtered and concentrated to dryness. Trituration of the residue with boiling ether provided the title compound (1.83 g, 36% 2 steps) as a yellow solid. $^1$H-NMR (DMSO-$d_6$) δ 10.34 (s, 1H), 10.15 (bs, 1H), 10.10 (bs, 1H), 8.56 (d, 1H), 8.31 (t, 1H), 8.16 (s, 1H), 8.01 (s, 1H), 7.36-7.41 (m, 2H), 7.43 (dd, 1H), 7.31 (s, 1H); MS [M+H]$^+$=460.0; LCMS RT=3.39 min.

Example 269

N-[4-[4-amino-7-(morpholin-4-ylmethyl)pyrrolo[2,1f][1,2,4]triazin-5-yl]-2-(trifluoromethyl)phenyl]-N'-[3-(trifluoromethyl)phenyl]urea

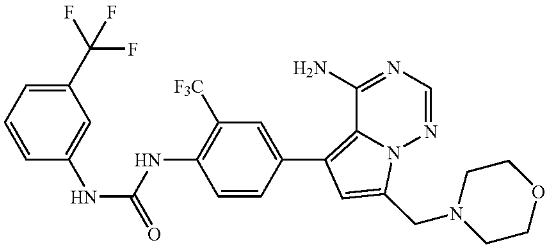

Example 277 was prepared using the same procedure used for Example 1, by substituting Intermediate AU for Intermediate O. $^1$H-NMR (DMSO-$d_6$) δ 9.74 (s, 1H), 8.23 (s, 1H), 8.01-8.06 (m, 2H), 7.94 (s, 1H), 7.70-7.74 (m, 1H), 7.70 (s, 1H), 7.50-7.58 (m, 1H), 7.56 (s, 1H), 7.41-7.46 (m, 1H), 6.75 (s, 1H), 3.82 (s, 2H), 3.52-3.59 (m, 4H), 2.40-2.50 (m, 4H); MS $[M+H]^+$=580.2; LCMS RT=2.66 min.

Example 270 tert-butyl 4-(4-amino-5-{3-fluoro-4-[({[4-(trifluoromethyl)pyridin-2-yl]amino}carbonyl)amino]phenyl}pyrrolo[2,1f][1,2,4]triazin-7-yl)piperidine-1-carboxylate

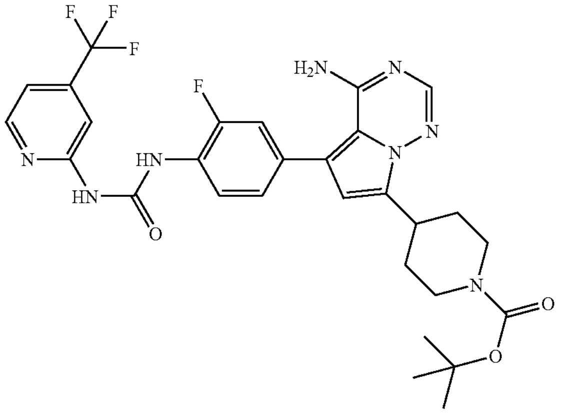

To a flask charged with $N_2$ was added Intermediate AC (850 mg, 2.15 mmol) and Intermediate AE (1.37 g, 3.22 mmol) followed by dioxane (20 mL). $N_2$ was bubbled through the solution for 15 min and then tetrakis(triphenylphosphine) palladium (248 mg, 0.21 mmol) was added followed by aq 2M $Na_2CO_3$ (3.2 mL, 6.4 mmol). $N_2$ was bubbled through the solution for an additional 15 min and, then the reaction was heated to 80° C. for 17 h. The reaction material was allowed to cool to rt and was diluted with $CH_2Cl_2$. This suspension was filtered thru celite and the volatiles removed in vacuo. The residue was taken up in $CH_2Cl_2$ and purified with a short silica column (eluting with 1-5% MeOH in $CH_2Cl_2$). All fractions containing the product were combined and filtered thru silica (removing most of the color) and the filtrate concentrated. Trituration in boiling ether gave the title compound (934 mg, 71% yield) as a white solid. $^1$H-NMR (DMSO-$d_6$) δ 8.53 (d, 1H), 8.26 (t, 1H), 8.01 (s, 1H), 7.90 (s, 1H), 7.20-7.40 (m, 3H), 6.61 (s, 1H), 4.00-4.11 (m, 2H), 3.25-3.39 (m, 1H), 2.77-3.00 (m, 2H), 1.91-2.02 (m, 2H), 1.54 (ddd, 2H), 1.40 (s, 9H); MS $[M+H]^+$=614.6; LCMS RT=3.29.

Example 271

N-[4-(4-amino-7-piperidin-4-ylpyrrolo[2,1-f][1,2,4]triazin-5-yl)-2-fluorophenyl]-N'-[4-(trifluoromethyl)pyridin-2-yl]urea

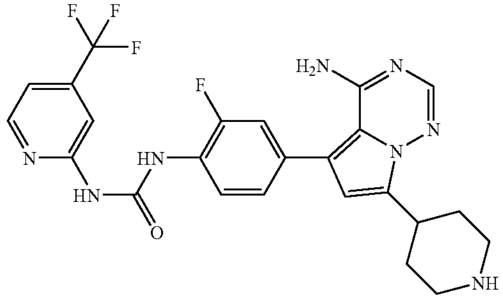

A suspension of Example 270 (930 mg, 1.5 mmol) in 60 mL 1,2-dichloroethane was treated with 15 mL TFA at rt. The reaction quickly became homogeneous and at 10 min no starting material remained by RP-HPLC. The reaction mixture was concentrated in vacuo, and the residue taken up again in fresh 1,2-dichloroethane and concentrated again; this was repeated 2 times. The residue was taken up in THF (15 mL) and EtOAc (85 mL) and washed with aq. sodium carbonate. The organic layer was dried with sodium sulfate and concentrated in vacuo to provide a tan solid. Trituration with ethyl acetate provided the title compound (705 mg, 91%) as a tan solid. $^1$H-NMR (DMSO-$d_6$) δ 10.14 (bs, 1H), 10.06 (bs, 1H), 8.54 (d, 1H), 8.26 (t, 1H), 8.01 (s, 1H), 7.88 (s, 1H), 7.31-7.40 (m, 2H), 7.24 (dd, 1H), 6.65 (s, 1H), 3.18 (tt, 1H), 3.01 (broad d, 2H), 2.61 (td, 2H), 1.92 (broad d, 2H), 1.54 (ddd, 2H); MS $[M+H]^+$=515.2; LCMS RT=2.34.

Example 272 tert-butyl 4-(4-amino-5-{4-[({[2-fluoro-5-(trifluoromethyl)phenyl]amino}carbonyl)amino]phenyl}pyrrolo[2,1-f][1,2,4]triazin-7-yl)piperidine-1-carboxylate

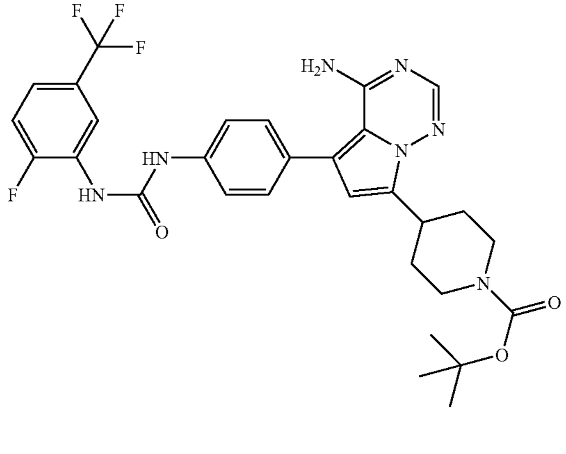

A solution of Intermediate AC (700 mg, 1.77 mmol) and Intermediate M (974 mg, 2.30 mmol) in 10 mL dioxane was treated with 5 mL DMF and degassed well with $N_2$ gas. Tetrakis(triphenylphosphine)palladium (248 mg, 0.21 mmol) was added followed by aq 2M $Na_2CO_3$ (3.2 mL, 6.4 mmol) and $N_2$ was bubbled through the solution for an additional 15 min. The reaction was heated to 80° C. for 16 h. The reaction material was allowed to cool to rt and was diluted with $CH_2Cl_2$. This suspension was filtered thru celite and the volatiles removed in vacuo. The residue was taken up in $CH_2Cl_2$ and purified with a short silica column (eluting with 1-5% MeOH in $CH_2Cl_2$). All fractions containing the product were combined and filtered thru silica (removing most of the color) and the filtrate concentrated. Trituration in boiling ether gave the title compound (437 mg, 40% yield) as a white solid. $^1$H-NMR (DMSO-$d_6$) δ 9.29 (s, 1H), 8.94 (d, 1H), 8.62 (dd, 1H), 7.88 (s, 1H), 7.56 (d, 2H), 7.45-7.55 (m, 1H), 7.38-7.43 (m, 2H), 1.55 (ddd, 2H), 1.40 (s, 9H); MS $[M+H]^+$=614.0; LCMS RT=3.40 min.

Example 273

N-{4-[4-amino-7-(1,3-oxazol-5-yl)pyrrolo[2,1-f][1,2,4]triazin-5-yl]-2-fluorophenyl}-N'-[4-(trifluoromethyl)pyridin-2-yl]urea

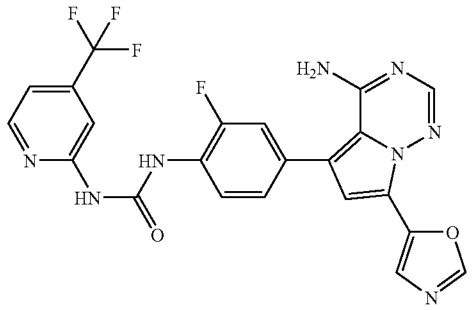

A solution of sodium methoxide in MeOH (25% by wt, 211 mg, 0.98 mmol) was taken up in MeOH (2 mL) and THF (8 mL) and the solution cooled to 0° C. Toluenesulfonylmethylisocyanide (96.6 mg, 0.49 mmol) and N-[4-(4-amino-7-formylpyrrolo[2,1-f][1,2,4]triazin-5-yl)-2-fluorophenyl]-N'-[4-(trifluoromethyl)pyridin-2-yl]urea (150 mg, 0.33 mmol) were added in succession to the solution. The reaction was stirred at 0° C. for 5 min, then heated at 60° C. for 1 h. The reaction was cooled to rt and diluted with EtOAc (100 mL). The organic layer was wash with water (2×) and dried with sodium sulfate. The suspension was filtered and the filtrate concentrated in vacuo. The resulting solid was triturated with ether, and subsequently with THF to provide the title compound (67 mg, 41%) as a tan solid. $^1$H-NMR (DMSO-$d_6$) δ 9.43 (s, 1H), 9.30 (s, 1H), 8.65 (dd, 1H), 8.31 (t, 1H), 8.17 (s, 1H), 7.52 (t, 1H), 7.37-7.46 (m, 2H), 7.26-7.32 (m, 1H), 7.23 (m, 1H); MS $[M+H]^+$=499.1; LCMS RT=3.00 min.

Example 274 tert-butyl 4-(4-amino-5-{2,5-difluoro-4-[({[2-fluoro-5-(trifluoromethyl)phenyl]amino}carbonyl)amino]phenyl}pyrrolo[2,1f][1,2,4]triazin-7-yl)piperidine-1-carboxylate

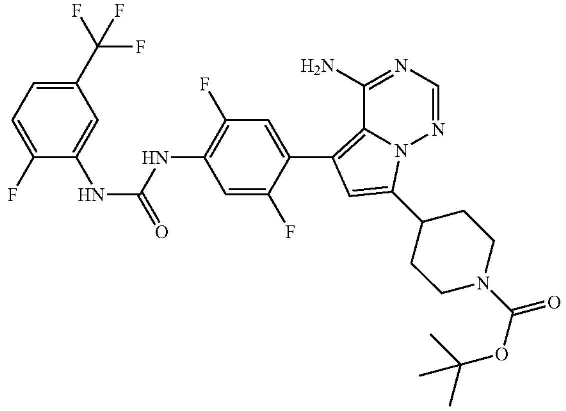

To a flask charged with $N_2$ was added Intermediate AC (1.00 g, 2.52 mmol) and Intermediate AH (1.28 g, 2.78 mmol) followed by DMF (10 mL). $N_2$ was bubbled through the solution for 15 min and then tetrakis(triphenylphosphine) palladium (292 mg, 0.252 mmol) was added followed by aq 2M $Na_2CO_3$ (2.5 mL, 5.0 mmol). $N_2$ was bubbled through the solution for an additional 15 min and, then the reaction was heated to 80° C. for 17 h. The reaction material was allowed to cool to rt and was diluted with $CH_2Cl_2$. This suspension was filtered thru celite and the volatiles removed in vacuo. The residue was taken up in $CH_2Cl_2$ and purified with a short silica column (eluting with 1-5% MeOH in $CH_2Cl_2$). All fractions containing the product were combined and filtered thru silica (removing most of the color) and the filtrate concentrated. Trituration in boiling ether gave the title compound (980 mg, 59% yield) as a white solid. $^1$H-NMR (DMSO-$d_6$) δ 9.48 (s, 1H), 9.43 (s, 1H), 8.63 (dd, 1H), 8.14 (dd, 1H), 7.90 (s, 1H), 7.39-7.54 (m, 3H), 7.30 (dd, 1H), 6.55 (s, 1H), 4.05 (bd, 2H), 3.56-3.63 (m, 1H), 2.86 (br s, 2H), 1.89-2.02 (m, 2H), 1.53 (ddd, 2H), 1.40 (s, 9H); MS $[M+H]^+$=650.2; LCMS RT=3.45 min.

Example 275

N-[4-(4-amino-7-piperidin-4-ylpyrrolo[2,14f][1,2,4]triazin-5-yl)-2,5-difluorophenyl]-N'-[2-fluoro-5-(trifluoromethyl)phenyl]urea

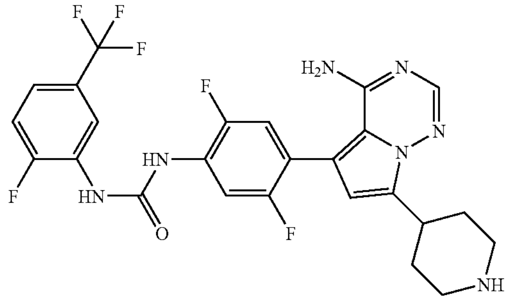

A suspension of Example 274 (498 mg, 0.77 mmol) in 10 mL 1,2-dichloroethane was treated with 3 mL TFA at rt. The reaction quickly became homogeneous and at 10 min no starting material remained by RP-HPLC. The reaction mixture was concentrated in vacuo, and the residue taken up again in fresh 1,2-dichloroethane and concentrated again; this was repeated 2 times. The residue was taken up in THF (5 mL) and EtOAc (35 mL) and washed with aq. sodium carbonate. The organic layer was dried with sodium sulfate and concentrated in vacuo to provide a tan solid. Trituration with ethyl acetate provided the title compound (178 mg, 42%) as a tan solid. Concentration of the mother liquor provided an additional the title compound (201 mg, 48 mmol) of similar purity. $^1$H-NMR (DMSO-$d_6$) δ 9.54 (bs, 2H), 8.70 (dd, 1H), 8.21 (dd, 1H), 7.96 (s, 1H), 7.60 (dd, 1H), 7.30-7.46 (m, 1H), 7.38 (dd, 1H), 6.57 (s, 1H), 3.16-3.31 (m, 1H), 3.02-3.12 (m, 2H), 2.60-2.74 (m, 2H), 1.89-2.02 (m, 2H), 1.60 (ddd, 2H), 1.42 (s, 9H); MS $[M+H]^+$=550.2; LCMS RT=2.43 min.

Example 276

N-{4-[4-amino-7-(morpholin-2-ylmethyl)pyrrolo[2,1-f][1,2,4]triazin-5-yl]-2-fluorophenyl}-N'-[2-fluoro-5-(trifluoromethyl)phenyl]urea

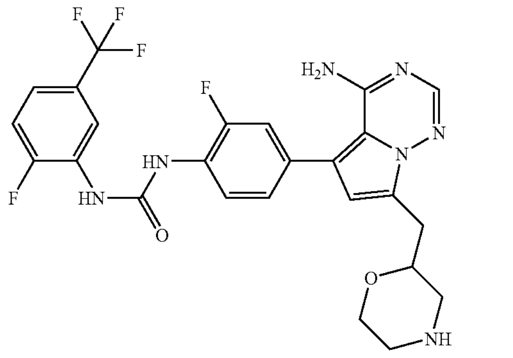

A suspension of the product formed in step 4 of Example 289 (100 mg, 0.15 mmol) in triethylsilane (1 mL) was treated with borontrifluoride diethyl etherate (50 μL, 0.39 mmol) and heated to 80° C. in a sealed tube for 1 h. The reaction was quenched with 2N NaOH (2 mL) and diluted with ether. The ether layer was separated. The aqueous was then extracted with EtOAc. The EtOAc layer was dried ($MgSO_4$) and concentrated. The crude residue was purified over silica (MPLC, 10-25% MeOH/$CH_2Cl_2$). A pale yellow solid was isolated (25 mg, 30%). $^1$H-NMR ($CD_3OD$) δ 8.64 (d, J=7.7 Hz, 1H), 8.26 (t, J=8.6 Hz, 1H), 7.84 (s, 1H), 7.36-7.26 (m, 4H), 6.64 (s, 1H), 4.10-3.98 (m, 2H), 3.73 (dd, $J_1$=12 Hz, $J_2$=3.3 Hz, 1H), 3.22-2.97 (m, 5H), 2.83 (dd, $J_1$=13 Hz, $J_2$=11 Hz, 1H); MS $[M+H]^+$=548.2; LCMS RT=2.87 min.

Example 277

N-[4-(4-amino-7-(morpholin-4-ylmethyl)pyrrolo[2,1f][1,2,4]triazin-5-yl]-2-(trifluoromethoxy)phenyl]-N'-[2-fluoro-5-(trifluoromethyl)phenyl]urea

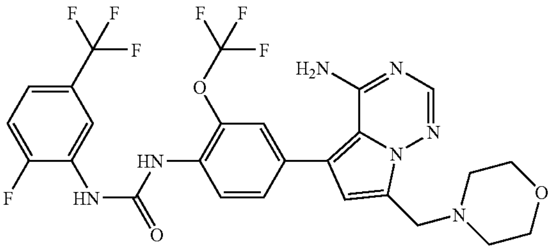

Example 277 was prepared using the same procedure used for Example 1, by substituting Intermediate AL for Intermediate O. $^1$H-NMR (DMSO-$d_6$) δ 9.61 (s, 1H), 9.12 (s, 1H), 8.61-8.67 (m, 1H), 8.36 (d, 1H, 7.92 (s, 1H), 7.37-7.56 (m, 5H), 6.70 (s, 1H), 3.82 (s, 2H), 3.50-3.85 (m, 4H), 2.40-2.48 (m, 4H); MS $[M+H]^+$=614.0; LCMS RT=3.03 min.

Example 278

N-{4-[4-amino-7-(morpholin-4-ylmethyl)pyrrolo[2,1f][1,2,4]triazin-5-yl]-2-methylphenyl}-N'-(4-tert-butylpyridin-2-yl)urea

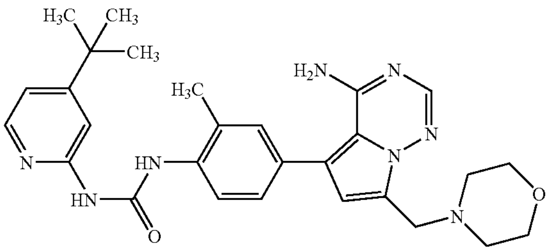

Step 1. Preparation of 5-(4-amino-3-methylphenyl)-7-(morpholin-4-ylmethyl)pyrrolo[2,1-f][1,2,4]triazin-4-amine

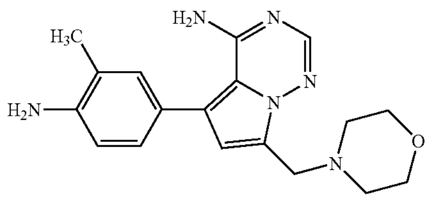

The procedure used for the preparation of Intermediate E was used to prepare the title compound by substituting Intermediate AK for 4-(4,4,5,5-tetramethyl-1,3,2-dioxaborolan-2-yl)aniline in step 4. $^1$H-NMR (DMSO-$d_6$) δ 7.84 (s, 1H), 7.03-6.96 (m, 2H), 6.68 (d, J=8.0 Hz, 1H), 6.50 (s, 1H), 5.03 (s, 2H), 3.79 (s, 2H), 3.56-3.53 (m, 4H), 2.46-2.40 (m, 4H), 2.09 (s, 3H); MS [M+H]$^+$=339.0; LCMS RT=1.02 min.

Step 2. Preparation of the Title Compound

The procedure used for the preparation of Example 2 was used to prepare the title compound by substituting phenyl (4-tert-butylpyridin-2-yl)carbamate for phenyl (3-tert-butylisoxazol-5-yl)carbamate and 5-(4-amino-3-methylphenyl)-7-(morpholin-4-ylmethyl)pyrrolo[2,1-f][1,2,4]triazin-4-amine for Intermediate E. $^1$H-NMR (DMSO-$d_6$) δ9.76 (s, 1H), 8.22-8.19 (m, 2H), 7.90 (s 1H), 7.34-7.25 (m, 3H), 7.08 (dd, $J_1$=5.6 Hz, $J_2$=1.7 Hz, 1H), 6.62 (s, 1H), 3.83 (s, 2H), 3.56 (t, J=4.1 Hz, 4H), 2.49-2.44 (m, 4H), 2.39 (s, 3H), 1.26 (s, 9H); MS [M+H]$^+$=515.1; LCMS RT=2.21 min.

Example 279

N-{4-[4-amino-7-(morpholin-4-ylmethyl)pyrrolo[2,1f][1,2,4]triazin-5-yl]-2-methylphenyl}-N'-(2-fluoro-5-methylphenyl)urea

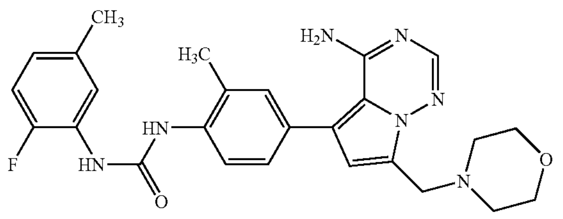

The procedure used for the preparation of Example 4 was used to prepare the title compound by substituting 1-fluoro-2-isocyanato-4-methylbenzene for 2-fluoro-5-(trifluoromethyl)phenyl isocynate and Example 278, step 1 for Intermediate E. $^1$H-NMR (DMSO-$d_6$) δ9.02 (s, 1H), 8.47 (s, 1H), 8.05-8.00 (m, 2H), 7.90 (s 1H), 7.30-7.23 (m, 2H), 7.11 (dd, $J_1$=11.5 Hz, $J_2$=7.9 Hz, 1H), 6.82-6.77 (m, 1H), 6.62 (s, 1H), 3.82 (s, 2H), 3.56 (t, J=4.7 Hz, 4H), 2.47-2.41 (m, 4H), 2.31 (s, 3H), 2.67 (s, 3H); MS [M+H]$^+$=490.3; LCMS RT=1.82 min.

Example 280

N-{4-[4-amino-7-(morpholin-4-ylmethyl)pyrrolo[2,1-f][1,2,4]triazin-5-yl]-2-methylphenyl}-N'-[2-chloro-5-(trifluoromethyl)phenyl]urea

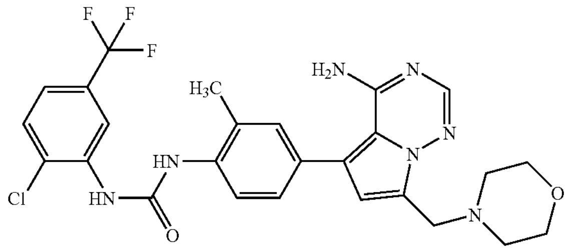

The procedure used for the preparation of Example 4 was used to prepare the title compound by substituting 1-chloro-2-isocyanato-4-(trifluoromethyebenzene for 2-fluoro-5-(trifluoromethyl)phenyl isocynate and Example 278, step 1 for Intermediate E. $^1$H-NMR (DMSO-$d_6$) δ8.63 (d, J=2.4 Hz, 1H), 7.93 (s, 1H), 7.91 (s, 1H), 7.73 (d, J=8.6 Hz, 1H), 7.38 (dd, $J_1$=8.4 Hz, $J_2$=1.6 Hz, 1H), 7.33 (d, J=2.1 Hz, 1H), 7.26 (dd, $J_1$=8.4 Hz, $J_2$=2.7 Hz, 1H), 6.63 (s, 1H), 3.83 (s, 2H), 3.56 (t, J=4.6 Hz, 4H), 2.48-2.42 (m, 4H), 2.33 (s, 3H); MS [M+H]$^+$=560.2, 562.2; LCMS RT=2.49 min.

Example 281

N-{4-[4-amino-7-(morpholin-4-ylmethyl)pyrrolo[2,1f][1,2,4]triazin-5-yl]-2-methylphenyl}-N'-[3-(trifluoromethyl)phenyl]urea

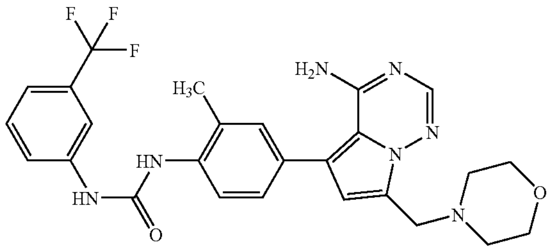

The procedure used for the preparation of Example 4 was used to prepare the title compound by substituting 1-isocyanato-3-(trifluoromethyl)benzene for 2-fluoro-5-(trifluoromethyl)phenyl isocynate and 5-(4-amino-3-methylphenyl)-7-(morpholin-4-ylmethyl)pyrrolo[2,1f][1,2,4]triazin-4-amine (Example 278, step 1) for Intermediate E. $^1$H-NMR (DMSO-$d_6$) δ8.06 (s. 1H), 7.93 (d, J=8.4 Hz, 1H), 7.91 (s, 1H), 7.59-7.49 (m, 2H), 7.32-7.29 (m, 2H), 7.25 (dd, $J_1$=8.3

Hz, $J_2$=2.3 Hz, 1H), 6.62 (s, 1H), 3.82 (s, 2H), 3.56 (t, J=4.5 Hz, 4H), 2.48-2.41 (m, 4H), 2.31 (s, 3H); MS $[M+H]^+$=526.2; LCMS RT=2.40 min Example 282 tert-butyl 2-({[(4-amino-5-[3-fluoro-4-{({[2-fluoro-5-(trifluoromethyl)phenyl]amino}carbonyl)amino]phenyl}pyrrolo[2,1f][1,2,4]triazin-7-yl)carbonyl]amino}methyl)morpholine-4-carboxylate

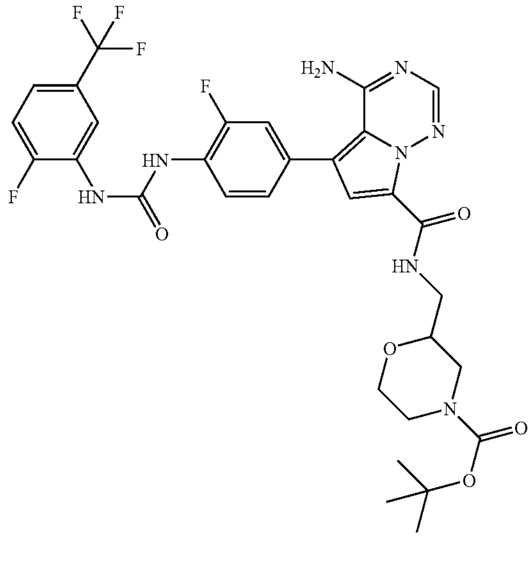

Step 1: Preparation of 4-aminopyrrolo[2,1-f][1,2,4]triazine-7-carboxylic acid

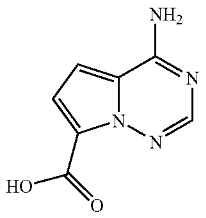

A suspension of Intermediate B (2.0 g, 9.93 mmol) in THF (100 mL) was cooled to −78° C. and slowly treated with a 1.7 N solution of nBuLi in hexanes (27.6 mL, 46.9 mmol). The suspension was stirred for 1 hr before bubbling in dry $CO_2$. The gas was bubbled in for 1 hr before the reaction was quenched with water and allowed to warm to rt. A precipitate formed in the aqueous layer. The biphasic mixture was filtered. The mother liquor was concentrated and diluted with water. The remaining solid was filtered and rinsed with water. This process was repeated three times to yield an off-white solid (1.4 g, 85%). MS=179.2; LCMS RT=1.12 min.

Step 2: Preparation of tert-Butyl 2-({[(4-aminopyrrolo[2,1f][1,2,4]triazin-7-yl)carbonyl]amino}methyl)morpholine-4-carboxylate

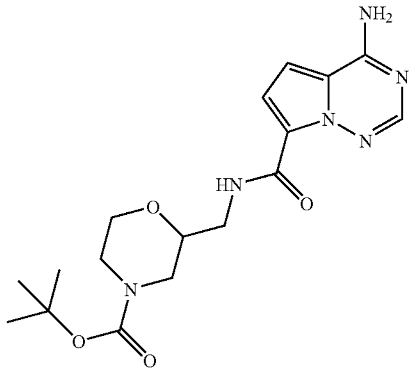

4-aminopyrrolo[2,1-f][1,2,4]triazine-7-carboxylic acid (215 mg, 1.21 mmol) was combined with 1-(3-dimethylaminopropyl)-3-ethylcarbodiimide hydrochloride (347 mg, 1.81 mmol) and 1-hydroxybenzotriazole monohydrate (245 mg, 1.81 mmol) in DMF (5 mL). The mixture was stirred at rt for 30 min. before adding tert-butyl 2-(aminomethyl)morpholine-4-carboxylate (274 mg, 1.27 mmol). After 1 hr, the reaction was poured into satd. $NaHCO_3$ solution and stirred for 1 h. The product was collected by vacuum filtration to give a tan solid (400 mg, 88%). MS $[M+H]^+$=377.0; LCMS RT=2.71 min.

Step 3: Preparation of tert-butyl 2-({[(4-amino-5-bromopyrrolo[2,1f][1,2,4]triazin-7-yl)carbonyl]amino}methyl)morpholine-4-carboxylate

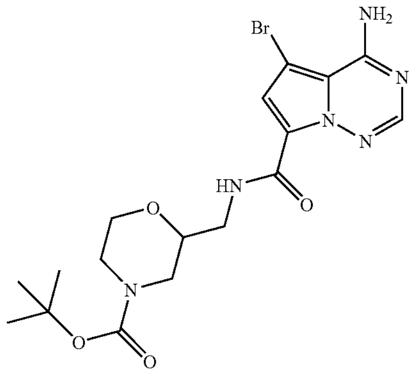

A solution of tert-butyl 2-({[(4-aminopyrrolo[2,1-f][1,2,4]triazin-7-yl)carbonyl]amino}methyl)morpholine-4-carboxylate (100 mg, 0.27 mmol) in THF (5 mL) was cooled to −50° C. and treated with 1,3-dibromo-5,5-dimethylhydantoin (37 mg, 0.13 mmol) in portions over 30 min. The reaction was then quenched with satd. $Na_2SO_3$ and warmed to rt. The product was extracted with EtOAc, dried ($MgSO_4$), and concentrated. The crude product was triturated with EtOAc and filtered. A white solid was collected (60 mg, 50%). MS $[M+H]^+$=545.96, 456.86; LCMS RT=2.90 min.

Step 4: Preparation of the Title Compound tert-Butyl-2-({[(4-amino-5-bromopyrrolo[2,1-f][1,2,4]triazin-7-yl)carbonyl]amino}methyl)morpholine-4-carboxylate (60 mg, 0.13 mmol) was dissolved in DMF (0.5 ml) and added to a solution of Intermediate O (62 mg, 0.14 mmol) in 1,4-dioxane (0.5 mL). The mixture was degassed three times then treated with $Na_2CO_3$ (2N, 127 μL, 0.26 mmol) and tetrakis(triphenylphosphine)palladium(0) (4 mg, 0.004 mmol). The mixture was degassed again and heated to 80° C. for 2 h. The reaction was cooled and pulled through a plug of silica and concentrated. The crude residue was triturated with 10% EtOAc/Hex and the desired product was collected by vacuum filtration to yield a tan solid (60 mg, 60%), $^1$H-NMR (DMSO-$d_6$) δ 9.44 (bs, 1H), 9.29 (bs, 1H), 9.19 (t, J=5.8 Hz, 1H), 8.66 (d, J=4.4 Hz, 1H), 8.30 (t, J=8.7 Hz, 1H), 8.17 (s, 1H), 7.52 (t, J=9.8 Hz, 1H), 7.44-7.38 (m, 2H), 7.27 (d, J=8.2 Hz, 1H), 7.24 (s, 1H), 3.89-3.82 (m, 2H), 3.73-3.36 (m, 4H), 2.88-2.55 (m, 2H), 2.47-2.43 (m, 1H), 1.39 (s, 9H); MS $[M+H]^+$=691.0; LCMS RT=3.66 min Example 283

4-amino-5-{3-fluoro-4-[({[2-fluoro-5-(trifluoromethyl)-phenyl]amino}carbonyl)amino]phenyl}-N-(morpholin-2-ylmethyl)pyrrolo[2,1-f][1,2,4]triazine-7-carboxamide

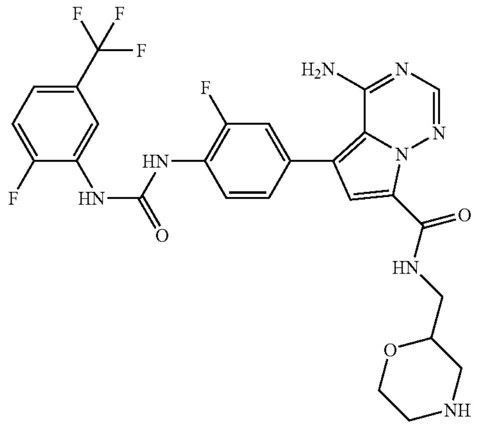

tert-Butyl-2-({[(4-amino-5-}3-fluoro-4-[({[2-fluoro-5-(trifluoromethyl)-phenyl]aminocarbonyl)amino]phenyl}pyrrolo[2,1-f][1,2,4]triazin-7-yl)-carbonyl]amino}methyl)morpholine-4-carboxylate (55 mg, 0.08 mmol) was suspended in 1,4-dioxane (1 mL) and treated with 4N HCl in dioxane (100 μL) and stirred at rt for 1 h. The suspension was concentrated then diluted with satd. $NaHCO_3$ and extracted with EtOAc. The organic layer was dried ($MgSO_4$) and concentrated. The crude sample was then triturated with EtOAc. The desired product was collected by vacuum filtration (47 mg, 99%). $^1$H-NMR (DMSO-$d_6$) δ 9.44 (bs, 1H), 9.30 (bs, 1H), 9.16 (m, 1H), 8.67 (d, J=7.0 Hz, 1H), 8.30 (t, J=8.3 Hz, 1H), 8.16 (s, 1H), 7.53 (t, J=9.6 Hz, 1H), 7.44-7.38 (m, 2 H), 7.27 (d, J=8.0 Hz, 1H), 7.23 (s, 1H), 3.77 (d, J=10.7 Hz, 1H), 3.55-3.40 (m, 4H), 2.82 (d, J=12 Hz, 1H), 2.71-255 (m, 3H), 2.47-2.38 (m, 1H); MS $[M+H]^+$=591.2; LCMS RT=2.58 min.

Example 284

N-[4-(4-amino-7-{[2-(methoxymethyl)pyrrolidin-1-yl]carbonyl}pyrrolo[2,1-f][1,2,4]triazin-5-yl)-2-fluorophenyl]-N'-[2-fluoro-5-(trifluoromethyl)phenyl]urea

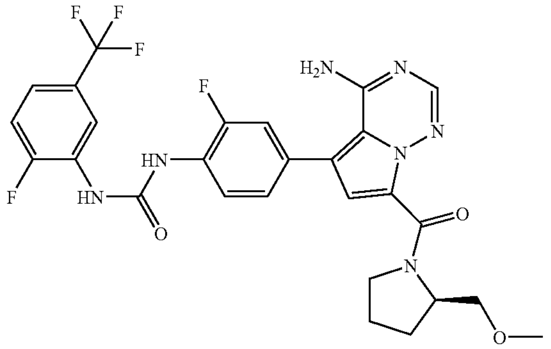

The procedure used for the preparation of Example 282 was used to prepare the title compound by substituting (2R)-2-(methoxymethyl)pyrrolidine for tert-butyl 2-(aminomethyl)morpholine-4-carboxylate in step 2. $^1$H-NMR ($CD_3OD$) δ 8.65 (d, J=8.4 Hz, 1H), 8.30 (t, J=8.4 Hz, 1H), 7.92 (s, 1H), 7.37-7.29 (m, 4H), 6.93 (s, 1H), 4.73-4.55 (m, 2H), 4.47-4.39 (m, 1H), 3.69-3.54 (m, 2H), 3.42 (s, 3H), 3.15-3.03 (m, 1H), 2.17-1.91 (m, 3H); MS $[M+H]^+$=590.8; LCMS RT=3.33 min.

Example 285

N-[4-(4-amino-7-{[2-(methoxymethyl)pyrrolidin-1-yl]carbonyl}pyrrolo[2,1-f][1,2,4]triazin-5-yl)-2-methylphenyl]-N'-[2-fluoro-5-(trifluoromethyl)phenyl]urea

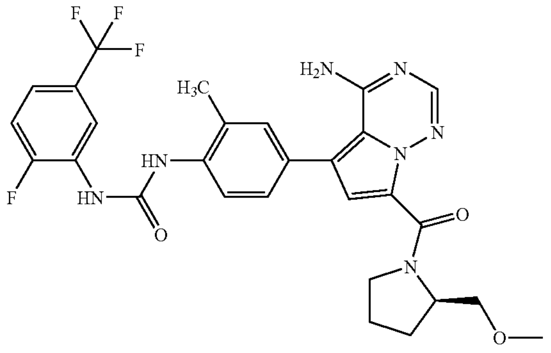

The procedure used for the preparation of Example 282 was used to prepare the title compound by substituting (2R)-2-(methoxymethyl)pyrrolidine for tert-butyl 2-(aminomethyl)morpholine-4-carboxylate in step 2 and Intermediate AF for Intermediate O in step 4. $^1$H-NMR ($CD_3OD$) δ 8.64 (d, J=8.1 Hz, 1H), 7.91 (s, 1H), 7.87 (d, J=8.2 Hz, 1H), 7.39-7.32 (m, 4H), 6.90 (s, 1H), 4.67-4.60 (m, 2H), 4.47-4.39 (m, 1H), 3.69-3.55 (m, 2H), 3.42 (s, 3H), 3.11-3.03 (m, 1H), 2.39 (s, 3H), 2.19-1.93 (m, 3. H); MS $[M-F1-1]^+$=586.7; LCMS RT=3.26 min.

Example 286

N-[4-(4-amino-7-{[2-(methoxymethyl)pyrrolidin-1-yl]carbonyl}pyrrolo[2,1f][1,2,4]triazin-5-yl)-2-fluorophenyl]-N'-[3-(trifluoromethyl)phenyl]urea

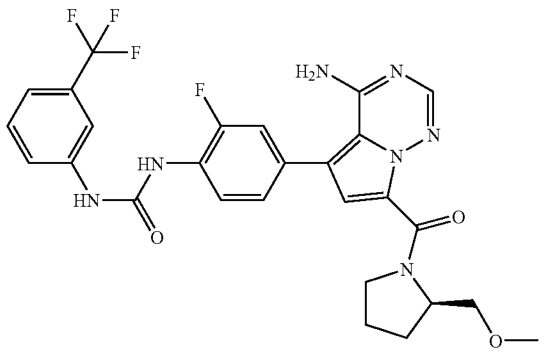

The procedure used for the preparation of Example 282 was used to prepare the title compound by substituting (2R)-2-(methoxymethyl)pyrrolidine for tert-butyl 2-(aminomethyl)morpholine-4-carboxylate in step 2 and Intermediate Q for Intermediate O in step 4. $^1$H-NMR ($CD_3OD$) δ 8.24 (t, J=8.5 Hz, 1H), 7.96 (s, 1H), 7.92 (s, 1H), 7.62 (d, J=9.2 Hz, 1H), 7.50 (t, J=7.9 Hz, 1H), 7.36-7.28 (m, 3H), 6.93 (s, 1H), 4.66-4.60 (m, 2H), 4.46-4.40 (m, 1H), 3.68-3.53 (m, 2H), 3.42 (s, 3H), 3.12-3.04 (m, 1H), 2.18-1.96 (m, 3H); MS $[M+H]^+$=572.3; LCMS RT=3.05 min.

Example 287

N-{4-[4-amino-7-(morpholin-4-ylmethyl)pyrrolo[2,1f][1,2,4]triazin-5-yl]-2-fluorophenyl}-N'-[1-oxido-4-(trifluoromethyl)pyridin-2-yl]urea

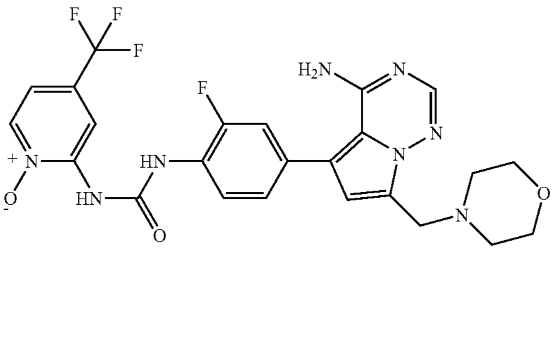

Step 1. Preparation of phenyl[1-oxido-4-(trifluoromethyl)pyridin-2-yl]carbamate

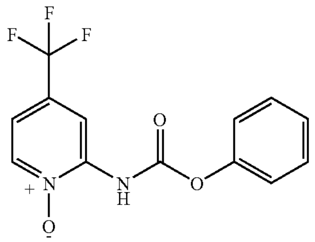

Intermediate H was (300 mg, 1.06 mmol) was suspended in $CHCl_3$ (5 mL) and treated with m-CPBA (238 mg, 1.06 mmol). The reaction was stirred at rt overnight. The reaction was quenched with satd. $NaHCO_3$ and extracted with $CHCl_3$. The organic layer was dried ($MgSO_4$) and concentrated. The crude residue was purified over silica using $CH_2Cl_2$ as the eluting solvent. (260 mg, 82%); $^1$H-NMR (DMSO-$d_5$) δ 8.53-8.49 (m, 2H), 7.49-7.41 (m, 3H), 7.33-7.25 (m, 3H); MS $[M+H]^+$=299.1; LCMS RT=2.99 min.

Step 2. Preparation of the Title Compound

The procedure used for the preparation of Example 2 was used to prepare the title compound by substituting phenyl [1-oxido-4-(trifluoromethyl)pyridin-2-yl]carbamate for phenyl (3-tert-butylisoxazol-5-yl)carbamate and 5-(4-amino-3-fluorophenyl)-7-(morpholin-4-ylmethyl)pyrrolo[2,1-f][1,2,4]triazin-4-amine for Intermediate E. $^1$H-NMR (DMSO-$d_6$) δ 10.82 (s, 1H), 10.01 (s, 1H), 8.61 (d, J=2.1 Hz, 1H), 8.57 (d, J=7.0, 1H), 8.22 (t, J=8.5, 1H), 7.92 (s, 1H), 7.44 (dd, $J_1$=7.0 Hz, $J_2$=2.8 Hz, 1H), 7.36 (dd, $J_1$=12 Hz, $J_2$=2.0 Hz, 1H), 7.27 (dd, $J_1$=8.3 Hz, $J_2$=1.7 Hz, 1H), 6.69 (s, 1H), 3.82 (s, 2H), 3.55 (t, J=4.4, 4H), 2.47-2.41 (m, 4H); MS $[M+H]^+$=547.1; LCMS RT=2.14 min.

Example 288

N-[4-O-amino-7-(morpholin-4-ylmethyl)pyrrolo[2,1-f][1,2,4]triazin-5-yl]phenyl}-N'-[1-oxido-4-(trifluoromethyl)pyridin-2-yl]urea

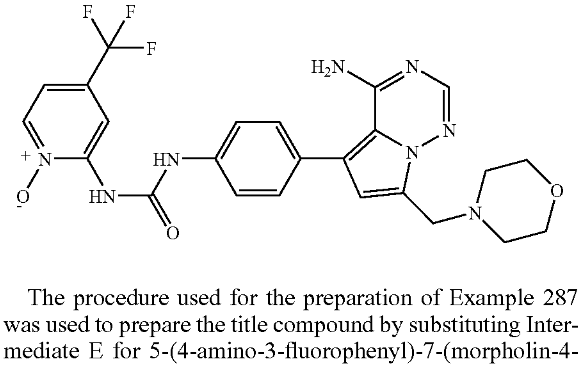

The procedure used for the preparation of Example 287 was used to prepare the title compound by substituting Intermediate E for 5-(4-amino-3-fluorophenyl)-7-(morpholin-4-ylmethyl)pyrrolo[2,1-f][1,2,4]triazin-4-amine in step 2. $^1$H-NMR (DMSO-$d_6$) δ 10.34 (s, 1H), 10.19 (s, 1H), 8.60 (d, J=2.8 Hz, 1H), 8.58 (d, J=6.8, 1H), 7.91 (s, 1H), 7.60 (d, J=8.6 Hz, 2H), 7.43 (d, J=8.4 Hz, 3H), 6.64 (s, 1H), 3.82 (s, 2H), 3.56 (t, J=4.6, 4H), 2.47-2.41 (m, 4H); MS $[M+H]^+$=529.3; LCMS RT=2.14 min.

Example 289

N-{4-[4-amino-7-(morpholin-2-ylcarbonyl)pyrrolo[2,1-f][1,2,4]triazin-5-yl]-2-fluorophenyl}-N'-[2-fluoro-5-(trifluoromethyl)phenyl]urea

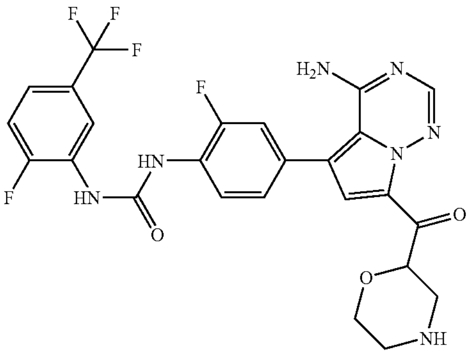

Step 1. Preparation of tert-butyl 2-[methoxy(methyl)carbamoyl]morpholine-4-carboxylate.

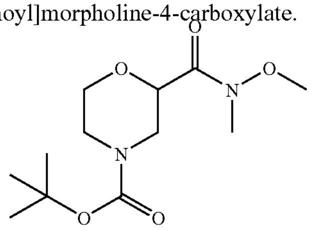

Commercially available 4-(tert-butoxycarbonyl)morpholine-2-carboxylic acid (1.95 g, 8.43 mmol), 1-(3-dimethylaminopropyl)-3-ethyl carbodiimide hydrochloride (1.94 g, 10.1 mmol) and 1-hydroxybenztriazole monohydrate (1.25 g, 9.28 mmol) were combined in DMF (10 mL) and stirred at rt for 15 min. before adding N,O-dimethylhydroxylamine (0.987 g, 10.1 mmol), The reaction was stirred at rt overnight. The reaction was then concentrated and partitioned between saturated $NaHCO_3$ and 20% isopropanol in $CHCl_3$. The organic layer was dried ($MgSO_4$) and concentrated. The crude residue was pulled through a layer of silica using $CH_2Cl_2$ and the eluting solvent. A colorless oil was isolated (0.7 g, 30%). $^1$H-NMR (DMSO-$d_6$) δ 4.31-4.18 (bs, 1H), 3.94-3.78 (m, 2H), 3.76-3.61 (m, 4H), 3.48 (dt, $J_1$=11 Hz, $J_2$=2.7 Hz, 1H), 3.19-2.80 (m, 5H), 1.39 (s, 9H).

Step 2. Preparation of tert-butyl 2-[(4-aminopyrrolo[2,1-f][1,2,4]triazin-7-yl)carbonyl]morpholine-4-carboxylate

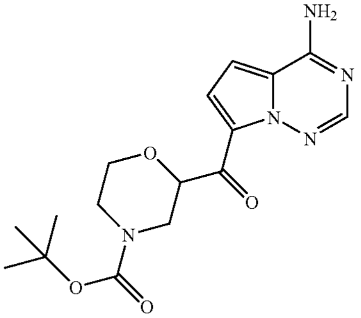

A suspension of Intermediate B (0.45 g, 2.11 mmol) in THF (5 mL) was treated with chlorotrimethylsilane (0.54 mL, 4.23 mmol) and stirred at rt overnight. The suspension was then cooled to 0° C. and slowly treated with isopropylmagnesium chloride (4.2 mL, 8.45 mmol). The suspension quickly went into solution and was stirred at rt for 2 h, checking by TLC for the disappearance of Intermediate B. The amber solution was again cooled to 0° C. then slowly treated with a solution of tert-butyl 2-[methoxy(methyl)carbamoyl]morpholine-4-carboxylate (0.7 g, 2.54 mmol) in THF (1 mL). The reaction was then stirred at rt overnight. The reaction was then poured into satd. $NH_4Cl$ solution and stirred for 15 min. The product was extracted with EtOAc, dried ($MgSO_4$) and concentrated. The residue was triturated with EtOAc and filtered. A pale yellow solid was collected (0.65 g, 88%). $^1$H-NMR (DMSO-$d_6$) δ 8.25-8.10 (m, 2H), 8.07 (s, 1H), 7.39 (d, J=5.0 Hz, 1H), 7.1 (d, J=4.7 Hz, 1H), 5.13-5.00 (m, 1H), 4.00-3.90 (m, 2H), 3.69-3.55 (m, 2H), 3.10-3.00 (m, 2H), 1.35 (bs, 9H); MS $[M+H]^+$=348.2; LCMS RT=2.66 min.

Step 3. Preparation of tert-butyl 2-[(4-amino-5-bromopyrrolo[2,1f][1,2,4]triazin-7-yl)carbonyl]morpholine-4-carboxylate

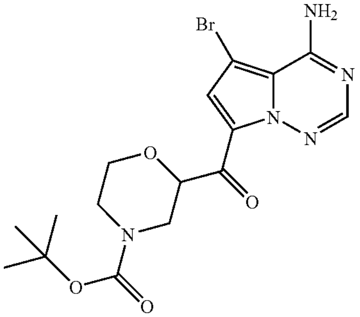

A solution of tert-butyl 2-[(4-aminopyrrolo[2,1-f][1,2,4]triazin-7-yl)carbonyl]morpholine-4-carboxylate (0.66 g, 1.90 mmol) in THF (5 mL) was cooled to −50° C. and stirred for 1 h before adding 1,3-dibromo-5,5-dimethylhydantoin (0.27 g, 0.94 mmol) in portions. The reaction was then quenched with satd. $Na_2SO_3$ solution. The product was extracted with EtOAc, dried ($MgSO_4$) and concentrated. The crude solid was triturated with EtOAc and filtered. An off-white solid was isolated (530 mg, 65%). $^1$H-NMR (DMSO-$d_5$) δ 8.10 (s, 1H), 7.54 (s, 1H), 5.05-4.95 (m, 1H), 4.00-3.89 (m, 2H), 3.69-3.55 (m, 2H), 3.10-3.00 (m, 2H), 1.33 (bs, 9H).

Step 4. Preparation of tert-butyl 2-({4-amino-5-[3-fluoro-4-({[2-fluoro-5-(trifluoromethyl)phenyl]carbamoyl}amino)phenyl]pyrrolo[2,1-f][1,2,4]triazin-7-yl}carbonyl)morpholine-4-carboxylate

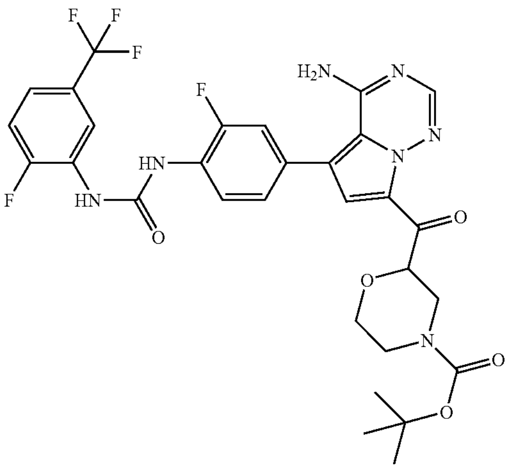

The procedure used for the preparation of Example 7 was used to prepare the title compound by substituting tert-butyl 2-[(4-amino-5-bromopyrrolo[2,1-f][1,2,4]triazin-7-yl)carbonyl]morpholine-4-carboxylate for Intermediate C and Intermediate O for Intermediate R. MS $[M+H]^+=662.1$; LCMS RT=3.50 min.

Step 5. Preparation of the Title Compound

A solution of tert-butyl 2-({4-amino-5-[3-fluoro-4-({[2-fluoro-5-(trifluoromethyl)phenyl]carbamoyl)amino)phenyl}pyrrolo[2,1f][1,2,4]triazin-7-yl}carbonyl)morpholine-4-carboxylate (50 mg, 0.076 mmol) in 1,4-dioxane (1 mL) was treated with 4N HCl (200 μL) in 1,4-dioxane and stirred at rt for 4 h. The reaction was concentrated then diluted with EtOAc and saturated $NaHCO_3$ solution. The organic layer was dried ($MgSO_4$) and concentrated. The crude residue was triturated with EtOAc and filtered. A yellow solid was isolated (24 mg, 57%). $^1H$-NMR ($CD_3OD$) δ 8.65 (d, J=8.2 Hz, 1H), 8.32 (t, J=8.5 Hz, 1H), 8.09 (s, 1H), 7.48 (s, 1H), 7.34-7.29 (m, 4H), 5.26 (dd, $J_1$=9.6 Hz, $J_2$=2.6 Hz, 1H), 4.65-4.60 (m, 1H), 4.00 (dt, $J_1$=11.6 Hz, $J_2$=2.5 Hz, 1H), 3.82-3.75 (m, 1H), 2.89-2.86 (m, 2H), 2.75 (dd, $J_1$=12.8 Hz, $J_2$=9.6 Hz, 1H); MS=562.1; LCMS RT=2.66 min.

Example 290

N-(4-{4-amino-7-[(4-methylpiperazin-1-yl)carbonyl]pyrrolo[2,1-f][1,2,4]triazin-5-yl}phenyl)-N'-[2-fluoro-5-(trifluoromethyl)phenyl]urea

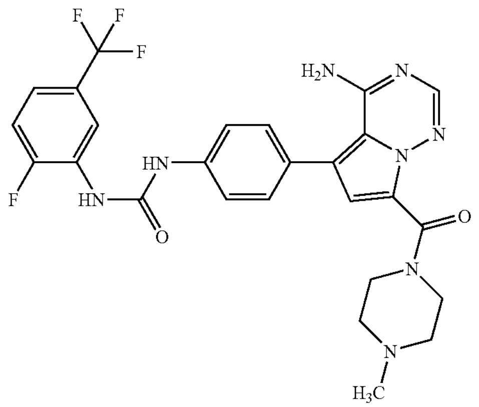

The procedure used for the preparation of Example 282 was used to prepare the title compound by substituting 1-methylpiperazine for tert-butyl 2-(aminomethyl)morpholine-4-carboxylate in step 2 and Intermediate M for Intermediate O in step 4. $^1H$-NMR ($CD_3OD$) δ 8.62 (d, J=7.6 Hz, 1H), 7.91 (s, 1H), 7.62 (d, J=8.8 Hz, 2H), 7.47 (d, J=8.7 Hz, 2H), 7.34 (d, J=8.8 Hz, 2H), 6.88 (s, 1H), 3.90-3.78 (m, 2H), 3.50-3.40 (m, 2H), 2.62-2.44 (m, 4H), 2.35 (s, 3H); MS $[M+H]^+=557.2$; LCMS RT=2.56 min.

Example 291

N-(4-{4-amino-7-[(4-methylpiperazin-1-yl)carbonyl]pyrrolo[2,1-f][1,2,4]triazin-5-yl}-2-fluorophenyl)-N'-[3-(trifluoromethyl)phenyl]urea

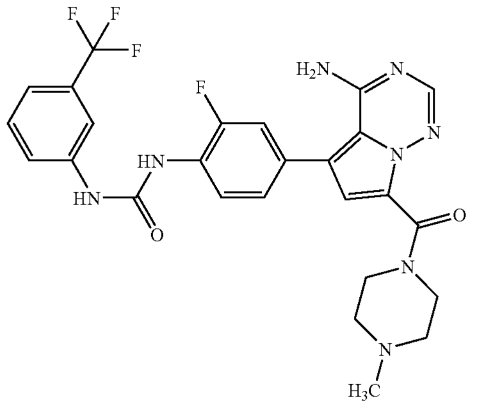

The procedure used for the preparation of Example 282 was used to prepare the title compound by substituting 1-methylpiperazine for tert-butyl 2-(aminomethyl)morpholine-4-carboxylate in step 2 and Intermediate Q for Intermediate O in step 4. $^1H$-NMR ($CD_3OD$) δ 8.23 (t, J.=8.4 Hz, 1H), 7.96 (s, 1H), 7.92 (s, 1H), 7.61 (d, J=8.4 Hz, 1H), 7.49 (t, J=7.9 Hz, 1H), 7.36-7.28 (m, 3H), 6.90 (s, 1H), 3.90-3.79 (m, 2H), 3.50-3.439 (m, 2H), 2.62-2.44 (m, 4H), 2.35 (s, 3H); MS $[M+H]^+=557.2$; LCMS RT=2.59 min.

Example 292

4-amino-5-{4-[({[2-fluoro-5-(trifluoromethyl)phenyl]-amino}carbonyl)amino]phenyl}-N-(morpholin-2-ylmethyl)pyrrolo[2,1-f][1,2,4]triazine-7-carboxamide

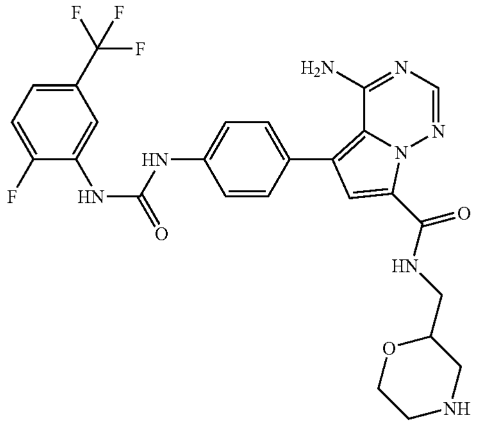

The procedure used for the preparation of Example 282 and 283 was used to prepare the title compound by substituting Intermediate M for Intermediate O in step 4 of Example 282. $^1$H-NMR (DMSO-$d_6$) δ 9.34 (s, 1H), 9.14 (t, J=5.4 Hz, 1H), 8.97 (s, 1H), 8.63 (d, J=7.1, 1H), 8.15 (s, 1H), 7.60 (d, J=8.6 Hz, 2H), 7.51 (t, J=10.0 Hz, 1H), 7.44-7.38 (m, 3 H), 7.18 (s, 1H), 3.76 (d, J=11 Hz, 1H), 3.55-3.38 (m, 4H), 2.80 (d, J=12.3 Hz, 1H), 2.69-2.57 (m, 2H), 2.45-2.37 (m, 1H); MS $[M+H]^+$=573.2; LCMS RT=2.54 min.

Example 293

4-amino-{3-fluoro-[({[3-(trifluoromethyl)phenyl]-amino}carbonyl)amino]phenyl}-N-(morpholin-2-ylmethyl)pyrrolo[2,1-f][1,2,4]-triazine-7-carboxamide

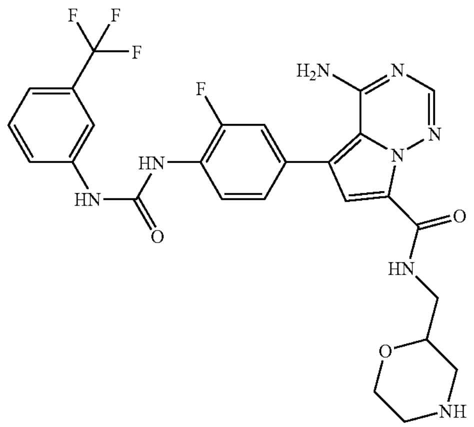

The procedure used for the preparation of Example 282 and 283 was used to prepare the title compound by substituting Intermediate Q for Intermediate O in step 4 of Example 282. $^1$H-NMR (DMSO-$d_6$) δ 9.49 (s, 1H), 9.15 (t, J=5.3 Hz, 1H), 8.80 (s, 1H), 8.25 (t, J=8.4, 1H), 8.16 (s, 1H), 8.05 (bs, 1H), 7.55-7.53 (m, 2H), 7.39 (dd, $J_1$=12.1 Hz, $J_2$=2.1 Hz, 1H), 7.35-7.33 (m, 1H), 7.26 (d, J=8.4 Hz, 1H), 7.22 (s, 1H), 3.76 (d, J=8.8 Hz, 1H), 3.52-3.41 (m, 4H), 2.80 (d, J=11.2 Hz, 1H), 2.69-2.57 (m, 2H), 2.45-2.37 (m, 1H); MS $[M+H]^+$=573.2; LCMS RT=2.56 min.

Example 294

4-amino-5-{4-[q[2-chloro-5-(trifluoromethyl)phenyl]amino)-carbonyl)amino]phenyl}-N-(morpholin-2-ylmethyl)pyrrolo[2,1-f][1,2,4]triazine-7-carboxamide

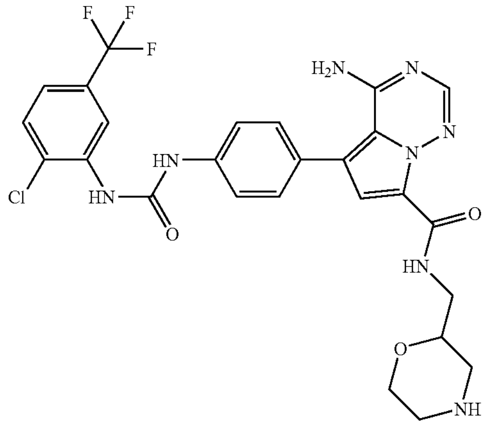

The procedure used for the preparation of Example 282 and 283 was used to prepare the title compound by substituting Intermediate N for Intermediate O in step 4 of Example 282. $^1$H-NMR (DMSO-$d_6$) δ 10.2-10.13 (bs, 1H), 9.16-9.13 (m, 2H), 8.58 (s, 1H), 8.15 (s, 1H), 7.72 (d, J=8.4 Hz, 1H), 7.63 (d, J=8.4 Hz, 2H), 7.42 (d, J=8.6 Hz, 2H), 7.38 (d, J=9.1 Hz, 1H), 7.18 (s, 1H), 3.76 (d, J=11 Hz, 0.1H), 3.55-3.38 (m, 4H), 2.79 (d, J=12 Hz, 1H), 2.67-2.59 (m, 2H), 2.46-2.38 (m, 1H); MS $[M+H]^+$=589.2, 591.1; LCMS RT=2.61 min.

Example 295

4-amino-5-{2,5-difluoro-4-[({[2-fluoro-5-(trifluoromethyl)-phenyl]amino}carbonyl)amino]phenyl}-N-(morpholin-2-ylmethyl)pyrrolo[2,1-f][1,2,4]triazine-7-carboxamide

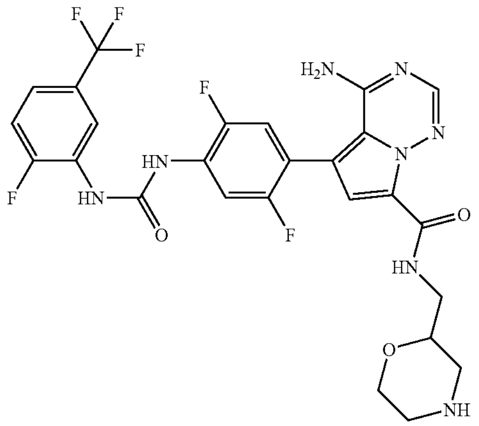

The procedure used for the preparation of Example 282 and 283 was used to prepare the title compound by substituting Intermediate AH for Intermediate O in step 4 of Example 282. $^1$H-NMR (DMSO-$d_6$) δ 9.49 (d, J=12 Hz, 2H), 9.14 (t, J=5.7 Hz, 1H), 8.63 (dd, $J_1$=7.2, $J_2$=2.0, 1H), 8.20-8.15 (m, 2H), 7.56-7.53 (m, 1H), 7.46-7.37 (m, 2H), 7.20 (s, 1H), 3.74 (d, J=11 Hz, 1H), 3.55-3.38 (m, 4H), 2.79 (d, J=11.3 Hz, 1H), 2.70-2.59 (m, 2H), 2.43-2.38 (m, 1H); MS $[M+H]^+$=609.2; LCMS RT=2.65 min.

Example 296

1-{4-[4-amino-7-(1,4-oxazepan-4-ylmethyl)pyrrolo[2,1-f][1,2,4]triazin-5-yl]-2-fluorophenyl}-3-[1-oxido-4-(trifluoromethyl)pyridin-2-yl]urea

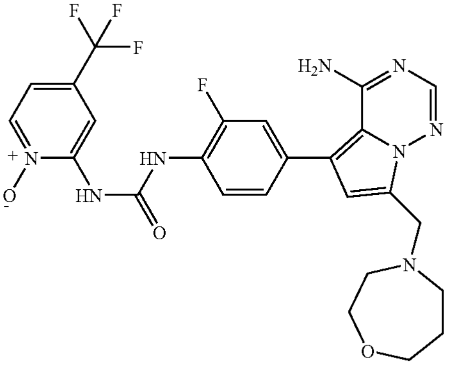

Step 1. Preparation of 4-chlorophenyl [4-(trifluoromethyl)pyridin-2-yl]carbamate

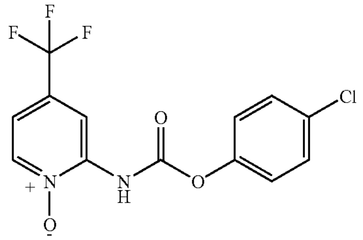

The procedure used for the preparation of Example 299 was used to prepare the title compound by substituting 4-chlorophenyl chloroformate for isopropenyl chloroformate in step 1. $^1$H-NMR (DMSO-$d_6$) δ9.66 (s, 1H), 9.22 (d, J=7.1 Hz, 1H), 8.03 (s, 1H), 7.47 (dd, =7.0 Hz, $J_2$=2.1 Hz, 1H), 7.18 (d, J=8.9 Hz, 2H), 6.75 (d, J=8.6 Hz, 2H); MS $[M+H]^+$=333.1, 335.1; LCMS RT=3.38 min.

Step 2. Preparation of the Title Compound 4-chlorophenyl [4-(trifluoromethyl)pyridin-2-yl]carbamate (35 mg, 0.098 mmol) and 5-(4-amino-3-fluorophenyl)-7-(1,4-oxazepan-4-ylmethyl)pyrrolo[2,1f][1,2,4]triazin-4-amine (36 mg, 0.11 mmol) were combined in 1,4-dioxane (1 mL) and treated with N,N-diisopropylamine (34 mL, 0.20 mmol). The reaction was heated to 80° C. overnight. The reaction was then concentrated and purified over silica (0-20%, MeOH/$CH_2Cl_2$) to yield an orange solid (13 mg, 24%). $^1$H-NMR (DMSO-$d_6$) δ10.83 (d, J=5.1 Hz, 1H), 10.09 (s, 1H), 8.61 (d, J=2.4 Hz, 1H), 8.57 (d, J=6.6 Hz, 1H), 8.22 (td, $J_1$=9.2 Hz, $J_2$=2.4 Hz, 1H), 7.92 (s, 1H), 7.44 (dd, $J_1$=6.7 Hz, $J_2$=2.9 Hz, 1H), 7.36 (dd, $J_1$=12.1 Hz, $J_2$=2.0 Hz, 1H), 7.27 (dd, $J_1$=8.3 Hz, $J_2$=1.6 Hz, 1H), 6.69 (s, 1H), 3.99 (s, 2H), 3.67 (t, J=6.0 Hz, 2H), 3.61-3.59 (m, 2H), 2.75-2.68 (m, 4H), 1.80 (q, J=5.7 Hz, 2H); MS $[M+H]^+$=561.0; LCMS RT=1.62 min.

Example 297

N-(4-{4-amino-7-[(4-methylpiperazin-1-yl)carbonyl]pyrrolo[2,1-f][1,2,4]triazin-5-yl}-2-fluorophenyl)-N'-[4-(trifluoromethyl)pyridin-2-yl]urea

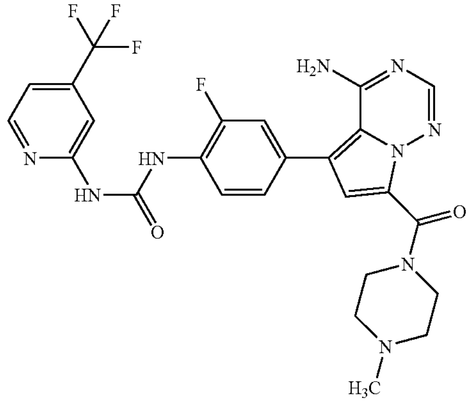

The procedure used for the preparation of Example 282 was used to prepare the title compound by substituting 1-methylpiperazine for tert-butyl 2-(aminomethyl)morpholine-4-carboxylate in step 2 and Intermediate AE for Intermediate O in step 3. $^1$H-NMR ($CD_3OD$) δ 8.51 (d, J=5.3 Hz, 1H), 8.34 (t, J=8.3 Hz, 1H), 7.93 (s, 1H), 7.67 (s, 1H), 7.38 (dd, $J_1$=11.7 Hz, $J_2$=1.9 Hz, 1H), 7.33-7.29 (m, 2H), 6.92 (s, 1H), 3.90-3.79 (m, 2H), 3.50-3.439 (m, 2H), 2.62-2.44 (m, 4H), 2.35 (s, 3H); MS $[M+H]^+$=558.1; LCMS RT=2.34 min.

Example 298

1-{4-[4-amino-7-(1,4-oxazepan-4-ylmethyl)pyrrolo[2,1f][1,2,4]triazin-5-yl]phenyl}-3-[1-oxido-4-(trifluoromethyl)pyridin-2-yl]urea

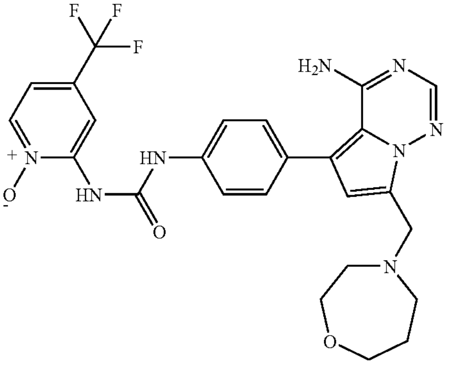

The procedure used for the preparation of Example 296 was used to prepare the title compound by substituting 5-(4-aminophenyl)-7-(1,4-oxazepan-4-ylmethyl)pyrrolo[2,1-f][1,2,4]triazin-4-amine for 5-(4-amino-3-fluorophenyl)-7-(1,4-oxazepan-4-ylmethyl)-pyrrolo[2,1-f][1,2,4]triazin-4-amine in step 2. $^1$H-NMR (DMSO-$d_6$) δ10.35 (d, J=2.0 Hz, 1H), 10.20 (d, J=3.3 Hz, 1H), 8.60 (d, J=2.4 Hz, 1H), 8.58 (d, J=6.7 Hz, 1H), 7.90 (s, 1H), 7.60 (d, J=8.8 Hz, 2H), 7.44 (d, J=8.5 Hz, 3H), 6.65 (s, 1H), 4.00 (s, 2H), 3.66 (t, J=6.1 Hz, 2H), 3.61-3.59 (m, 2H), 2.75-2.68 (m, 4H), 1.81 (q, J=5.7 Hz, 2H); MS $[M+H]^+$=543.0; LCMS RT=1.86 min.

Example 299

N-{4-[4-amino-7-(morpholin-4-ylmethyl)pyrrolo[2,1-f][1,2,4]triazin-5-yl]-2-methylphenyl}-N'-[1-oxido-4-(trifluoromethyl)pyridin-2-yl]urea

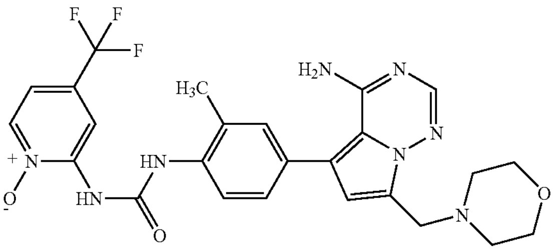

Step 1., Preparation of isopropenyl [4-(trifluoromethyl)pyridin-2-yl]carbamate

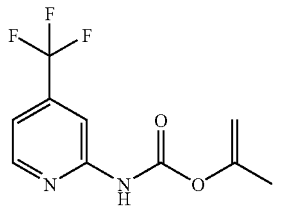

4-(trifluoromethyl)pyridin-2-amine (1.0 g, 6.17 mmol) was dissolved in THF (20 mL) and treated with pyridine (600 μL, 7.4 mmol) and isopropenyl chloroformate (596 μL, 6.17 mmol). The reaction was stirred at rt for 6 h. The reaction was then concentrated and triturated with EtOAc. The crude residue was purified by MPLC (100% $CH_2Cl_2$) to yield a pale yellow solid (1.2 g, 79%); $^1$H-NMR (DMSO-$d_6$) δ 11.0 (s, 1H), 8.57 (d, J=5.1 Hz, 1H), 8.10 (s, 1H), 7.45 (d, J=5.5 Hz, 1H), 4.81 (t, J=1.1 Hz, 1H), 4.76 (s, 1H), 1.94 (s, 3H).

Step 2. Preparation of isopropenyl [1-oxido-4-(trifluoromethyl)pyridin-2-yl]carbamate

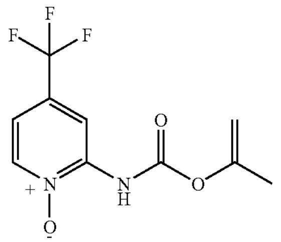

Isopropenyl [4-(trifluoromethyl)pyridin-2-yl]carbamate (1.2 g, 5.0 mmol) was suspended in $CHCl_3$ (20 mL) and treated with m-CPBA (841 mg, 5.0 mmol). The reaction was stirred at rt overnight. The reaction was quenched with satd. $NaHCO_3$ and extracted with $CHCl_3$. The organic layer was dried ($MgSO_4$) and concentrated. The crude residue was purified over silica using $CH_2Cl_2$ as the eluting solvent. An amber oil was collected (620 mg, 47%); $^1$H-NMR (DMSO-$d_6$) δ 10.2 (s, 1H), 8.56 (d, J=6.9 Hz, 1H), 8.25 (d, J=2.6 Hz, 1H), 7.52 (ddd, dd, $J_1$=6.8 Hz, $J_2$=2.5 Hz, $J_3$=0.6 Hz, 1H), 4.85 (q, J=1.2 Hz, 1H), 4.80 (d, J=1.2 Hz, 1H), 1.94 (d, J=0.4 Hz, 3H).

Step 3. Preparation of the Title Compound

The procedure used for the preparation of Example 2 was used to prepare the title compound by substituting isopropenyl [1-oxido-4-(trifluoromethyl)pyridin-2-yl]carbamate for phenyl(3-tert-butylisoxazol-5-yl)carbamate and 5-(4-amino-3-methylphenyl)-7-(morpholin-4-ylmethyl)pyrrolo[2,1-f][1,2,4]triazin-4-amine for Intermediate E. $^1$H-NMR (DMSO-$d_6$) δ10.75 (s, 1H), 9.39 (s, 1H), 8.63 (d, J=2.6 Hz, 1H), 8.57 (d, J=7.0 Hz, 1H), 7.92-7.90 (m, 2H), 7.42 (dd, $J_1$=6.0 Hz, $J_2$=2.3 Hz, 1H), 7.33 (d, J=1.8 Hz, 1H), 7.28 (dd, $J_1$=8.2 Hz, $J_2$=1.7 Hz, 1H), 6.34 (s, 1H), 3.82 (s, 2H), 3.56 (t, J=4.6 Hz, 4H), 2.47-2.41 (m, 4H), 1.98 (s, 3H); MS $[M+H]^+$=515.1; LCMS RT=2.21 min.

Example 300

N-{4-[4-amino-7-(morpholin-2-ylcarbonyl)pyrrolo[2,1-f][1,2,4]triazin-5-yl]-2-fluorophenyl}-N'-[3-(trifluoromethyl)phenyl]urea

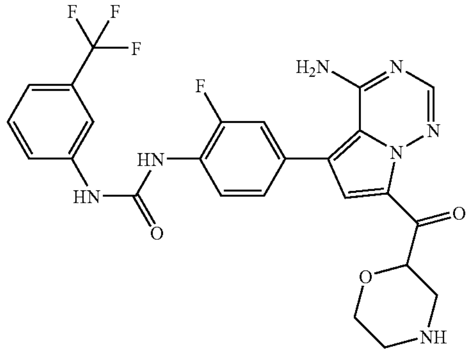

The procedure used for the preparation of Example 289 was used to prepare the title compound by substituting Intermediate Q for Intermediate O in step 4. $^1$H-NMR ($CD_3OD$) 8.25 (t, J=8.3 Hz, 1H), 8.09 (s, 1H), 7.97-7.95 (m, 1H), 7.62 (d, J=7.5 Hz, 1H), 7.52-7.47 (m, 2H), 7.37-7.28 (m, 3H), 5.26 (dd, $J_1$=9.8 Hz, $J_1$=2.6 Hz, 1H), 4.70-4.55 (bs, 1H), 3.99 (dd, $J_1$=11 Hz, $J_1$=2.7 Hz, 1H), 3.83-3.75 (m, 1H), 2.90-2.85 (m, 2H), 2.75 (dd, 13 Hz, $J_1$=9.8 Hz, 1H); MS $[M+H]^+$=575.1; LCMS RT=2.63 min.

Example 301

N-{4-[4-amino-7-(morpholin-2-ylmethyl)pyrrolo[2,1-f][1,2,4]triazin-5-yl]-2-fluorophenyl}-N'-[3-(trifluoromethyl)phenyl]urea

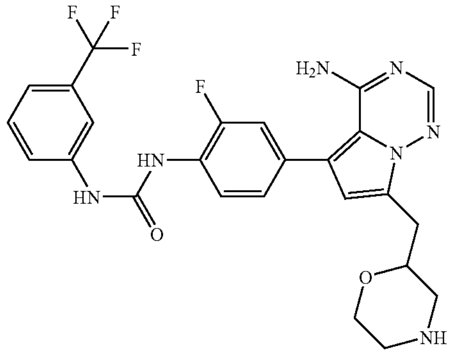

The procedure used for the preparation of Example 289 and 276 was used to prepare the title compound by substituting Intermediate Q for Intermediate O in step 4 of Example 289. $^1$H-NMR ($CD_3OD$) δ 8.19 (t, J=8.6 Hz, 1H), 7.96 (bs, 1H), 7.83 (s, 1H), 7.61 (d, J=8.3 Hz, 1H), 7.49 (t, J=7.8 Hz, 1H), 7.33-7.24 (m, 3H), 6.62 (s, 1H), 4.10-3.88 (m, 2H), 3.70-3.61 (m, 1H), 3.20-3.08 (m 2H), 2.99 (dd, $J_1$=13 Hz, $J_2$=2.1 Hz, 1H), 2.93-2.86 (m, 2H), 2.69 (dd, $J_1$=13 Hz, $J_2$=11 Hz, 1H); MS $[M+H]^+$=530.2; LCMS RT=2.80 min.

Biological Evaluation

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) were demonstrated with the use of in vitro tumor proliferation assays.

Demonstration of the activity of the compounds of the present invention may be accomplished through in vitro, ex vivo, and in vivo assays that are well known in the art. For example, to demonstrate the activity of the compounds of the present invention, the following assays may be used.

FGFR-1 TR-FRET Biochemical Assay

The FGFR-1 Assay was performed on half well 96-well opaque plates (Costar 3915) in a LANCE format. LANCE is a homogenous time resolved fluormetry based application available through Perkin Elmer. For this assay, 50 uL reactions were set up using: 0.6 uM ATP (Sigma), 25 nM poly GT-biotin (CIS BIO International), 2 nM Eu-labelled phospho-Tyr Ab (PY20 PerkinElmer), 10 nM Streptavidin-APC (Perkin Elmer), 5 nM FGFR1-GST (generated by DRT, Bayer Healthcare), 1% DMSO, 50 mM HEPES pH 7.5, 10 mM $MgCl_2$, 0.1 mM EDTA, 0.015% Brij, 0.1 mg/ml BSA, 0.1% B-mercaptoethanol. All reactions were initiated with the addition of enzyme and were left to incubate for one hour at room temperature. Time-resolved fluorescence was then read on a Perkin Elmer VictorV Multilabel counter. The reading protocol uses an excitation wavelength at 340 nm and emission reads at both 615 and 665 nm. Signal was calculated as a ratio: (Flourescence at 665 nm/Flourescence at 615 nM)*10000 for each well. The background control used for this assay is the signal produced with all assay components excluding ATP. For $IC_{so}$ generation, compounds were added prior to the enzyme initiation. A 50-fold stock plate was made with compounds serially diluted 1:5 in a 50% DMSO/50% dH2O solution. A 1 μl, addition of the stock to the assay wells gave final compound concentrations ranging from 10 μM-0.128 nM in 1% DMSO. The data were expressed as percent inhibition: % inhibition=100−((Signal with inhibitor-background)/(Signal without inhibitor−background))*100.

Tumor Cell Proliferation

Human tumor cells (e.g., HCT116 or MDA-MB-231 cells), were seeded in a Costar 96-well plate at $3.0\times10^3$ cells/well and grown in 150 μl of RPMI complete media (Invitrogen Corporation, Grand Island, N.Y.) containing 10% fetal bovine serum (Hyclone, Logan, Utah) at 37° C. for 16 h in an incubator with 5% $CO_2$. To each well, 50 μl of additional growth media containing 40 μM to 18 nM concentrations of compound with 0.4% DMSO was added. Cells were grown for another 72 h at 37° C. with 5% $CO_2$. 20 μl of Alamar Blue (Trek Diagnostic Systems, Inc., Cleveland, Ohio) reagent was added to each well and incubated for 3 h at 37° C. Plates were read in a SpectraMax Gemini (Molecular Devices, CA) with 544 nm excitation and 590 nm emission wavelength. $IC_{50}$ values were determined by linear regression analysis of log drug concentration versus percent inhibition.

p-Histone3

Compounds were assayed for the inhibition of histone 3 phosphorylation in colon carcinoma (HCT116). Briefly, 20,000 cells/well were seeded in a 96-well black-walled, poly-d-lysine plates in RPMI+10% FBS and incubated at 37° C. in 5% $CO_2$ overnight. The following day, the cells were treated with compounds for 24 hours at 37° C. Following compound treatment; plates were centrifuged at 1000 rpm for 2 minutes and washed twice with 100 μl of cold sterile TBS. Cells were then fixed with cold 3.7% formaldehyde in TBS (4° C. for 1 hour) and then permeabolized with 0.1% Triton-X-100 in TBS (room temperature for 30 minutes). Plates were then washed with of 0.25% BSA-TBS and blocked with BSA solution for 1 hour at room temperature while shaking. The supernatant was removed and replaced with diluted primary antibody (anti-phospho-histone 3, serine 10, Cell Signaling) at 1:250 in 0.25% BSA-TBS and incubated overnight at 4° C. The plates were washed and treated with diluted secondary antibody (anti-rabbit Eu-labeled) at 1:10000 in 0.25% BSA-TBS (room temperature for 1 hour). The antibody solution was removed from each well and washed eight times. The wash buffer was replaced with 50 μl pre-warmed enhancement solution and mixed on the orbital shaker for 10 minutes. Fluorescence was detected with a Victor V Fluorescence Detector. The data are expressed as percent inhibition: % inhibition=100−((Signal with inhibitor-background)/(Signal without inhibitor-background))×100.

In Vivo Efficacy Studies: Staged Human Xenograft Models

Staged human xenograft models grown in mice or rats were used to evaluate compound efficacy. To generate tumors, cells harvested from mid-log phase cultures or tumor fragments from in vivo passage were injected s.c. in the flank of athymic mice or rats. Treatment administered p.o. or i.v. was initiated when all mice in each experiment had established tumors. The general health of animals was monitored and mortality was recorded daily. Tumor dimensions and body weights were recorded two to three times a week starting with the first day of treatment. Tumor weights were calculated using the equation (l×w2)/2, where l and w refer to the larger and smaller dimensions collected at each measurement. Anti-tumor efficacy was measured as tumor growth inhibition (TGI). TGI is calculated by the equation [1−(T/C)*100], where T and C represent the mean tumor size of the treated (T) and untreated or vehicle control (C) groups, respectively, at the end of treatment.

In Vitro Soft Agar Assays Measuring Anchorage-Independent Growth:

One of the hallmarks of an oncogenically-transformed cell is its ability to survive and proliferate in an anchorage-independent manner. To measure this anchorage-independent growth, soft agar assays are performed. A mixture of 1000 cells in 100 μl of growth medium containing 0.36% agarose (supplemented with 10% (v/v) FBS) is plated onto 50 of solidified growth medium containing 0.6% (w/v) agarose in 96 well plates. Once the cell/medium/agarose mixture have solidified, 50 μl of growth medium is added to cover the wells and plates are incubated overnight at 37° C. in a 5% $CO_2$ incubator. The following day, compounds diluted in growth media with a final concentration of DMSO not to exceed 0.1% (v/v) are added to each well. Cells are further incubated for 5 days at 37° C. in a humidified incubator containing 5% $CO_2$. On day 5, 40 μl of MTS reagent (CellTiter 96 Aqueous One Solution, Promega, Madison, Wis.) is added to each well and the plates are incubated for an additional 2 hours at 37° C. Plates are then read at 490 nm on a SpectraMax 250 plate reader (Molecular Devices, Sunnyvale, Calif.).

Percent inhibition is calculated using the following equation:

$$\% \text{ inhibition}=1-(T_{5test}-T_0)/(T_{5control}-T_0)\times100.$$

$T_{5test}$=O.D. at 490 nm in the presence of test compound at day 5

$T_{5control}$=O.D. at 490 nm in the DMSO treated control cells at day 5

$T_0$=O.D. at 490 nm in the presence of compound at day 0

Apoptosis Assays: Cell Death Detection Assay to Measure DNA Fragmentation

The Cell Death Detection ELISAPlus kit (Roche, Mannheim, Germany) is used to measure DNA fragmentation as a marker for apoptosis. Cells are seeded in 96-well plates at 10,000 cells/well and after 24 hr, are dosed and grown for an additional 48 hr in media containing 10% FBS in 5% $CO_2$ at 37° C. Supernatants from control and treated cells are transferred into streptavidin-coated 96-well plates and incubated with biotinylated mouse anti-histone antibody and peroxidase-conjugated mouse anti-DNA antibody at room temperature for 2 hr. After the removal of unbound antibodies by washing, the amount of apoptosis-generated nucleosomes is quantified as the peroxidase retained in the immuno-complex using ABTS (2,2'-azino-di[3-ethylbenzthiazolin-sulfonate]) as the substrate. Absorbance is determined at 405-490 nm using a SpectraMax microplate reader (Molecular Devices, Sunnyvale, Calif.).

Apoptosis Assays: Caspase 3/7 Activation

Execution of cell death is dependent on caspase activity. Caspases 3/7 are central executioners for apoptosis. Cells ($10^4$ cells/well) are plated in 96-well microtiter plates and incubated in media containing 10% FBS at 37° C. overnight in a humidified incubator containing 5% $CO_2$. On the following day, compounds are added to wells and cultures are incubated for an additional 24 hrs. Caspase 3/7 activity is measured by adding the profluorescent substrate, Z-DEVD-AFC (7-Amino-4-Trifluorocoumarin; 75 μM; Calbiochemicals, San Diego, Calif.), freezing the plate, and then thawing the cells for 3 hours at room temperature. Plates are read at 400 nm (excitation wavelength) and 505 nm (emission wavelength) on a SpectraMax Gemini microplate reader (Molecular Devices, Sunnyvale, Calif.).

Compounds of the invention were tested for activity using the FGFR1 biochemical, tumor cell proliferation and p-Histone3.

Compounds of examples 1, 2, 3, 4, 6, 8, 9, 11, 10, 12, 15, 16, 18, 19, 20, 22, 25, 26, 27, 28, 29, 39, 40 41, 50, 52, 53, 65, 67, 75, 77, 78, 79, 81, 89, 107, 108, 109, 111, 113, 114, 116, 119, 120, 121, 128, 129, 149, 161, 163, 164, 165, 167, 168, 173, 176, 177, 179, 180, 181, 184, 186, 187, 188, 189, 190, 191, 193, 194, 195, 201, 202, 203, 204, 205, 206, 214, 219, 220, 221, 224, 226, 228, 236, 237, 240, 241, 242, 253, 259, 269 and 287 demonstrate an $IC_{50}$ of less than 10 nM in the FGFR-1 biochemical assay. Compounds of examples 21, 30, 31, 32, 33, 35, 36, 37, 38, 42, 44, 58, 59, 66, 82, 83, 84, 85, 86, 100, 103, 104, 115, 124, 133, 136, 145, 196, 200, 208, 209, 211, 212, 215, 216, 217, 230, 231, 234, 235, 243, 250, 252, 255, 273, 276, 283, 284, 289, 293 and 301 demonstrate an $IC_{50}$ greater than 10 nM but less than 100 nM in the FGFR-1 biochemical assay. Compounds of examples 7, 14, 49, 55, 57, 63, 80, 112, 147, 198, 254 and 260 demonstrate an $IC_{50}$ greater than 100 nM but less than 1 μM in FGFR-1 biochemical assay.

Compounds of examples 1, 3, 5, 6 and 8 demonstrate an $IC_{50}$ greater than 500 nM but less than 4 μM in the H460 proliferation assay.

Compounds of examples 3, 4, 5 and 6 demonstrate an $IC_{50}$ greater than 500 nM but less than 4 μM in the HCT116 proliferation assay.

Compounds of examples 3, 4, 5 and 6 demonstrate an $IC_{50}$ greater than 500 nM but less than 3 μM in the MDA-MB-231 proliferation assay.

Compound of examples 4, 10, 15, 16, 25, 83, 87, 91, 93, 94, and 105 demonstrate an $IC_{50}$ greater than 500 nM but less than 5 μM in the p-histone3 assay. Compounds of examples, 44, 46, 56, 72, 73, and 74 demonstrate an $IC_{50}$ greater than 5 μM but less than 10 μM in the p-histone3 assay.

The invention claimed is:

1. A method of treating breast cancer with a compound of formula (I)

(I)

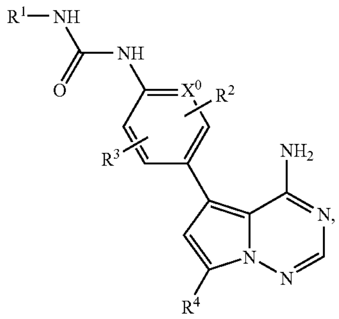

wherein $X^0$ represents C or N;

$R^1$ represents 1.1) phenyl or a bicyclic carbocycle of 9-10 ring members, in which at least one ring is aromatic, $R^1$ optionally bearing up to 4 substituents independently selected from the group consisting of 1.1.a) $(C_1-C_4)$alkyl, which may optionally bear up to 3 substituents independently selected from 1.1.a1) halogen;

1.1.a2) $OR^5$ wherein $R^5$ represents H or $(C_1-C_3)$alkyl which may optionally bear halogen or —$(C_1-C_3)$mono- or di-alkylamino;

1.1.a3) —$NR^6R^7$ in which $R^6$ and $R^7$ are independently H or —$(C_1-C_3)$alkyl which may optionally bear halogen or $OR^{7a}$ wherein $R^{7a}$ represents H or $(C_1-C_3)$alkyl, or $R^6$ and $R^7$ may be joined and taken together with the N atom to which they are attached form a 5-6 membered ring which may optionally contain a ring member selected from O, S, and $NR^8$ wherein $R^8$ represents H or $(C_1-C_3)$alkyl; and 1.1.a4) a 5-6 membered heteroaromatic containing up to two heteroatoms selected from O, S, and N;

1.1.b) —$(C_3-C_6)$cycloalkyl which may optionally bear up to 2 substituents independently selected from 1.1.b1) halogen; and 1.1.b2) $OR^9$ wherein $R^9$ represents H or $(C_1-C_3)$alkyl which may optionally bear halogen or $(C_1-C_3)$mono- or di-alkylamino;

1.1.c) $OR^{10}$ wherein $R^{10}$ represents H; phenyl; benzyl; $(C_3-C_6)$cycloalkyl; or $(C_1-C_4)$alkyl which may optionally bear up to 3 substituents independently selected from 1.1.c1) halogen;

1.1.c2) $OR^{11}$ wherein $R^{11}$ represents H or $(C_1-C_3)$alkyl which may optionally bear $(C_1-C_3)$mono- or di-alkylamino; and 1.1.c3) $NR^{12}R^{13}$ in which $R^{12}$ and $R^{13}$ are independently H or —($C_1$-$C_3$)alkyl which may optionally bear halogen, or $R^{12}$ and $R^{13}$ may be joined and taken together with the N atom to which they are attached form a 5-6 membered ring which may optionally contain a ring member selected from O, S, and $NR^{14}$ wherein $R^{14}$ represents H or ($C_1$-$C_3$)alkyl;

1.1.d) —C(O)—$OR^{15}$ wherein $R^{15}$ represents H or —($C_1$-$C_4$)alkyl which may optionally bear up to 3 halogens;

1.1.e) —C(O)—$NR^{16}R^{17}$ wherein $R^{16}$ represents H or ($C_1$-$C_3$)alkyl which may optionally bear halogen; and $R^{17}$ represents H or —($C_1$-$C_4$)alkyl which is optionally substituted with 1.1.e1) halogen;

1.1.e2) a 5-6 membered heteroaromatic containing up to two heteroatoms selected from O, S, and N;

1.1.e3) phenyl;

1.1.e4) —$SO_2CH_3$;

1.1.e5) —$OR^{18}$ wherein $R^{18}$ represents H or ($C_1$-$C_3$)alkyl which may optionally bear halogen; or 1.1.e6) —$NR^{19}R^{20}$ in which $R^{19}$ and $R^{20}$ are independently H or —($C_1$-$C_3$)alkyl which may optionally bear halogen, or $R^{19}$ and $R^{20}$ may be joined and taken together with the N atom to which they are attached form a 5-6 membered ring which may optionally contain a ring member selected from O, S, and $NR^{21}$ wherein $R^{21}$ represents H or ($C_1$-$C_3$)alkyl;

1.1.f) —N($R^{22}$)—C(O)—$R^{23}$ wherein $R^{22}$ represents H or ($C_1$-$C_3$)alkyl; and $R^{23}$ represents optionally substituted phenyl, or ($C_1$-$C_4$)alkyl which is optionally substituted with 1.1.f1) optionally substituted phenyl, 1.1.f2) $OR^{24}$ wherein $R^{24}$ represents H or ($C_1$-$C_3$) alkyl, or 1.1.f3) $NR^{25}R^{26}$ wherein $R^{25}$ and $R^{26}$ are independently H or —($C_1$-$C_3$)alkyl which may optionally bear halogen, or $R^{25}$ and $R^{26}$ may be joined and taken together with the N atom to which they are attached form a 5-6 membered ring which may optionally contain a ring member selected from O, S, and $NR^{27}$ wherein $R^{27}$ represents H or ($C_1$-$C_3$)alkyl;

1.1.g) —$SO_2NR^{28}R^{29}$ wherein $R^{28}$ represents H or ($C_1$-$C_3$)alkyl which may optionally bear halogen; and $R^{29}$ represents H or —($C_1$-$C_4$)alkyl which is optionally substituted with:

1.1.g1) halogen;

1.1.g2) a 5-6 membered heteroaromatic containing up to two heteroatoms selected from O, S, and N;

1.1.g3) phenyl;

1.1.g4) —$SO_2CH_3$;

1.1.g5) —$OR^{30}$ wherein $R^{30}$ represents H or ($C_1$-$C_3$)alkyl which may optionally bear halogen; or 1.1.g6) —$NR^{31}R^{32}$ in which $R^{31}$ and $R^{32}$ are independently H or —($C_1$-$C_3$)alkyl which may optionally bear halogen, or $R^{31}$ and $R^{32}$ may be joined and taken together with the N atom to which they are attached form a 5-6 membered ring which may optionally contain a ring member selected from O, S, and $NR^{33}$ wherein $R^{33}$ represents H or ($C_1$-$C_3$)alkyl;

1.1.h) —N($R^{34}$)—$SO_2$—$R^{35}$ wherein $R^{34}$ represents H or ($C_1$-$C_3$)alkyl, and $R^{35}$ represents optionally substituted phenyl, or ($C_1$-$C_4$)alkyl which is optionally substituted with 1.1.h1) halogen;

1.1.h2) optionally substituted phenyl, 1.1.h3) $OR^{36}$ wherein $R^{36}$ represents H or ($C_1$-$C_3$) alkyl, or 1.1.h4) $NR^{37}R^{38}$ wherein $R^{37}$ and $R^{38}$ are independently H or —($C_1$-$C_3$)alkyl which may optionally bear halogen, or $R^{37}$ and $R^{38}$ may be joined and taken together with the N atom to which they are attached form a 5-6 membered ring which may optionally contain a ring member selected from O, S, and $NR^{39}$ wherein $R^{39}$ represents H or ($C_1$-$C_3$)alkyl;

1.1.i) —$NR^{40}R^{41}$ in which $R^{40}$ and $R^{41}$ are independently H or —($C_1$-$C_3$)alkyl which may optionally bear halogen or $OR^{42}$ in which $R^{42}$ represents H or ($C_1$-$C_3$)alkyl, or $R^{40}$ and $R^{41}$ may be joined and taken together with the N atom to which they are attached form a 5-6 membered ring which may optionally contain a ring member selected from O, S, and $NR^{43}$ wherein $R^{43}$ represents H or ($C_1$-$C_3$) alkyl;

1.1.j) halogen;

1.1.k) optionally substituted phenyl;

1.1.l) $NO_2$;

1.1.m) CN; and 1.1.n) a 5-6 membered heteroaromatic containing up to two heteroatoms selected from O, S, and N;

1.1.o) —C(O)—$R^{209}$ wherein $R^{209}$ represents H or —($C_1$-$C_4$)alkyl which may optionally bear up to 3 halogens;

or $R^1$ represents 1.2) a 5-6 membered aromatic heterocycle containing up to 3 heteroatoms independently selected from the group consisting of N, O, and S; or a bicyclic heterocycle of 8-10 ring members in which at least one ring is aromatic and contains up to 3 moieties independently selected from the group consisting of N, N→O, O, and S, and any non-aromatic ring of said bicyclic heterocycle optionally contains up to three moieties independently selected from the group consisting of O, S, S(O), $S(O)_2$, and $NR^{44}$ wherein $R^{44}$ represents H or —($C_1$-$C_3$)alkyl; said $R^1$ heterocycle optionally bearing up to 4 substituents independently selected from the group consisting of 1.2.a) ($C_1$-$C_4$)alkyl, which may optionally bear up to 3 substituents independently selected from 1.2.a1) halogen;

1.2.a2) $OR^{45}$ wherein $R^{45}$ represents H or ($C_1$-$C_3$) alkyl which may optionally bear halogen or —($C_1$-$C_3$)mono- or di-alkylamino;

1.2.a3) —$NR^{46}R^{47}$ in which $R^{46}$ and $R^{47}$ are independently H or —($C_1$-$C_3$)alkyl which may optionally bear halogen or $OR^{47a}$ wherein $R^{47a}$ represents H or ($C_1$-$C_3$)alkyl, or $R^{46}$ and $R^{47}$ may be joined and taken together with the N atom to which they are attached form a 5-6 membered ring which may optionally contain a ring member selected from O, S, and $NR^{48}$ wherein $R^{48}$ represents H or ($C_1$-$C_3$)alkyl; and 1.2.a4) a 5-6 membered heteroaromatic containing up to two heteroatoms selected from O, S, and N;

1.2.b) —$(C_3-C_6)$cycloalkyl which may optionally bear up to 2 substituents independently selected from 1.2.b1) halogen; and 1.2.b2) $OR^{49}$ wherein $R^{49}$ represents H or $(C_1-C_3)$ alkyl which may optionally bear halogen or —$(C_1-C_3)$mono- or di-alkylamino;

1.2.c) $OR^{50}$ wherein $R^{50}$ represents H; phenyl; benzyl; —$(C_3-C_6)$cycloalkyl; or —$(C_1-C_4)$alkyl which may optionally bear up to 3 substituents independently selected from 1.2.c1) halogen;

1.2.c2) $OR^{51}$ wherein $R^{51}$ represents H or $(C_1-C_3)$ alkyl which may optionally bear —$(C_1-C_3)$ mono- or di-alkylamino; and 1.2.c3) —$NR^{52}R^{53}$ in which $R^{52}$ and $R^{53}$ are independently H or —$(C_1-C_3)$alkyl which may optionally bear halogen, or $R^{52}$ and $R^{53}$ may be joined and taken together with the N atom to which they are attached form a 5-6 membered ring which may optionally contain a ring member selected from O, S, and $NR^{54}$ wherein $R^{54}$ represents H or $(C_1-C_3)$alkyl;

1.2.d) —C(O)—$OR^{55}$ wherein $R^{55}$ represents H or —$(C_1-C_4)$alkyl which may optionally bear up to 3 halogens;

1.2.e) —C(O)—$NR^{56}R^{57}$ wherein $R^{56}$ represents H or $(C_1-C_3)$alkyl which may optionally bear halogen; and $R^{57}$ represents H or —$(C_1-C_4)$alkyl which is optionally substituted with 1.2.e1) halogen;

1.2.e2) a 5-6 membered heteroaromatic containing up to two heteroatoms selected from 0, S, and N;

1.2.e3) phenyl;

1.2.e4)—$SO_2CH_3$;

1.2.e5) —$OR^{58}$ wherein $R^{58}$ represents H or $(C_1-C_3)$alkyl which may optionally bear halogen; or 1.2.e6) —$NR^{59}R^{60}$ in which $R^{59}$ and $R^{60}$ are independently H or —$(C_1-C_3)$alkyl which may optionally bear halogen, or $R^{59}$ and $R^{60}$ may be joined and taken together with the N atom to which they are attached form a 5-6 membered ring which may optionally contain a ring member selected from O, S, and $NR^{61}$ wherein $R^{61}$ represents H or $(C_1-C_3)$alkyl;

1.2.f) —$N(R^{62})$—C(O)—$R^{63}$ wherein $R^{62}$ represents H or $(C_1-C_3)$alkyl; and $R^{63}$ represents optionally substituted phenyl, or $(C_1-C_4)$alkyl which is optionally substituted with 1.2.f1) optionally substituted phenyl, 1.2.f2) $OR^{64}$ wherein $R^{64}$ represents H or $(C_1-C_3)$ alkyl, or 1.2.f3) $NR^{65}R^{66}$ wherein $R^{65}$ and $R^{66}$ are independently H or —$(C_1-C_3)$alkyl which may optionally bear halogen, or $R^{65}$ and $R^{66}$ may be joined and taken together with the N atom to which they are attached form a 5-6 membered ring which may optionally contain a ring member selected from O, S, and $NR^{67}$ wherein $R^{67}$ represents H or $(C_1-C_3)$alkyl;

1.2.g) —$SO_2NR^{68}R^{69}$ wherein $R^{68}$ represents H or $(C_1-C_3)$alkyl which may optionally bear halogen; and $R^{69}$ represents H or —$(C_1-C_4)$alkyl which is optionally substituted with 1.2.g1) halogen;

1.2.g2) a 5-6 membered heteroaromatic containing up to two heteroatoms selected from 0, S, and N;

1.2.g3) phenyl;

1.2.g4) —$SO_2CH_3$;

1.2.g5) —$OR^{70}$ wherein $R^{70}$ represents H or $(C_1-C_3)$alkyl which may optionally bear halogen; or 1.2.g6 —$NR^{71}R^{72}$ in which $R^{71}$ and $R^{72}$ are independently H or —$(C_1-C_3)$alkyl which may optionally bear halogen, or $R^{71}$ and $R^{72}$ may be joined and taken together with the N atom to which they are attached form a 5-6 membered ring which may optionally contain a ring member selected from O, S, and $NR^{73}$ wherein $R^{73}$ represents H or $(C_1-C_3)$alkyl;

1.2.h) —$N(R^{74})$—$SO_2$—$R^{75}$ wherein $R^{74}$ represents H or $(C_1-C_3)$alkyl, and $R^{75}$ represents optionally substituted phenyl, or $(C_1-C_4)$alkyl which is optionally substituted with 1.2.h1) halogen;

1.2.h2) optionally substituted phenyl, 1.2.h3) $OR^{76}$ wherein $R^{76}$ represents H or $(C_1-C_3)$ alkyl, or 1.2.h4) $NR^{77}R^{78}$ wherein $R^{77}$ and $R^{78}$ are independently H or —$(C_1-C_3)$alkyl which may optionally bear halogen, or $R^{77}$ and $R^{78}$ may be joined and taken together with the N atom to which they are attached form a 5-6 membered ring which may optionally contain a ring member selected from O, S, and $NR^{79}$ wherein $R^{79}$ represents H or $(C_1-C_3)$alkyl;

1.2.i) —$NR^{80}R^{81}$ in which $R^{80}$ and $R^{81}$ are independently H or —$(C_1-C_3)$alkyl which may optionally bear halogen or $OR^{81a}$ wherein $R^{81a}$ represents H or $(C_1-C_3)$alkyl, or $R^{80}$ and $R^{81}$ may be joined and taken together with the N atom to which they are attached form a 5-6 membered ring which may optionally contain a ring member selected from O, S, and $NR^{82}$ wherein $R^{82}$ represents H or $(C_1-C_3)$ alkyl;

1.2.j) halogen;

1.2.k) optionally substituted phenyl;

1.2.l) $NO_2$;

1.2.m) CN; and 1.2.n) a 5-6 membered heteroaromatic containing up to two heteroatoms selected from O, S, and N;

1.2.o) —C(O)—$R^{210}$ wherein $R^{210}$ represents H or —$(C_1-C_4)$alkyl which may optionally bear up to 3 halogens;

$R^2$ represents hydrogen; halogen; —$(C_1-C_5)$alkyl which may optionally bear halogen; or —$O(C_1-C_3)$alkyl which may optionally bear halogen;

$R^3$ represents hydrogen; halogen; —$(C_1-C_5)$alkyl which may optionally bear halogen; or —$O(C_1-C_3)$alkyl which may optionally bear halogen;

$R^4$ represents 4.1) —$(C_1-C_5)$alkyl which is optionally substituted with 4.1.a) —$(C_3-C_5)$cycloalkyl which may optionally bear halogen or $OR^{109}$ wherein $R^{109}$ represents H or $(C_1-C_3)$alkyl;

4.1.b)-halogen;

4.1.c) —$OR^{110}$ wherein $R^{110}$ represents H or —$(C_1-C_3)$alkyl which may optionally bear up to 3 substituents independently selected from 4.1.c1) halogen;

4.1.c2) phenyl;

4.1.c3) —$S(O)_2CH_3$;

4.1.c4) $OR^{111}$ wherein $R^{111}$ represents H or ($C_1$-$C_3$)alkyl which may optionally bear halogen; and 4.1.c5) —$NR^{112}R^{113}$ in which $R^{112}$ and $R^{113}$ are independently H or —($C_1$-$C_3$)alkyl which may optionally bear halogen, or $R^{112}$ and $R^{113}$ may be joined and taken together with the N atom to which they are attached form a 5-6 membered ring which may optionally contain a ring member selected from 0, S, and $NR^{114}$ wherein $R^{114}$ represents H or ($C_1$-$C_3$)alkyl;

4.1.d) —$NR^{115}R^{116}$ wherein $R^{115}$ represents H or —($C_1$-$C_3$)alkyl which may optionally bear halogen and $R^{116}$ represents H, optionally substituted phenyl, or —($C_1$-$C_5$)alkyl which may optionally bear up to 3 substituents independently selected from 4.1.d1) halogen;

4.1.d2) —$S(O)_2CH_3$;

4.1.d3) $OR^{117}$ wherein $R^{117}$ represents H or ($C_1$-$C_3$)alkyl which may optionally bear halogen; and 4.1.d4) —$NR^{118}R^{119}$ in which $R^{118}$ and $R^{119}$ are independently H or —($C_1$-$C_3$)alkyl which may optionally bear halogen, or $R^{118}$ and $R^{119}$ may be joined and taken together with the N atom to which they are attached form a 5-6 membered ring which may optionally contain a ring member selected from O, S, and $NR^{120}$ wherein $R^{120}$ represents H or ($C_1$-$C_3$)alkyl;

4.1.e) optionally substituted phenyl; or 4.1.f) a 5-6 membered aromatic heterocycle containing up to two heteroatoms selected from O, S, and N;

4.2)

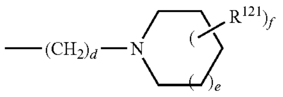

wherein $R^{121}$ represents —($C_1$-$C_3$)alkyl which may optionally bear halogen or —$OR^{122}$ in which $R^{122}$ represents H or —($C_1$-$C_3$)alkyl;

d represents 1, 2, or 3;

e represents 0 or 1;

f represents 0, 1, or 2;

4.3)

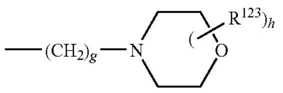

wherein $R^{123}$ represents —($C_1$-$C_3$)alkyl which may optionally bear halogen or —$OR^{124}$ in which $R^{124}$ represents H or —($C_1$-$C_3$)alkyl;

g represents 1, 2, or 3;

h represents 0, 1, or 2;

4.4)

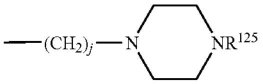

wherein $R^{125}$ represents 4.4.a) H;

4.4.b) —($C_1$-$C_3$)alkyl which may optionally bear halogen or —$OR^{126}$ in which $R^{126}$ represents H or —($C_1$-$C_3$)alkyl which in turn is optionally substituted with halogen;

4.4.c) —$SO_2R^{127}$ wherein $R^{127}$ represents optionally substituted phenyl, or —($C_1$-$C_3$)alkyl which may optionally bear halogen or $OR^{128}$ wherein $R^{128}$ represents H or ($C_1$-$C_3$)alkyl;

4.4.d) —$C(O)R^{129}$ wherein $R^{129}$ represents 4.4.d1) optionally substituted phenyl, 4.4.d2) —($C_1$-$C_3$)alkyl which may optionally bear up to 3 substituents independently selected from 4.4.d2.1) halogen;

4.4.d2.2) optionally substituted phenyl;

4.4.d2.3) —$S(O)_2$—($C_1$-$C_4$)alkyl which may optionally bear halogen;

4.4.d2.4) —$OR^{130}$ wherein $R^{130}$ represents H or ($C_1$-$C_4$)alkyl which may optionally bear halogen; and 4.4.d2.5) —$NR^{131}R^{132}$ in which $R^{131}$ and $R^{132}$ are independently H or —($C_1$-$C_3$)alkyl which may optionally bear halogen, or $R^{131}$ and $R^{132}$ may be joined and taken together with the N atom to which they are attached form a 5-6 membered ring which may optionally contain a ring member selected from O, S, and $NR^{133}$ wherein $R^{133}$ represents H or ($C_1$-$C_3$)alkyl;

4.4.d3) —$OR^{134}$ wherein $R^{134}$ represents H or ($C_1$-$C_3$)alkyl which may optionally bear halogen; or 4.4.d4) $NR^{135}R^{136}$ wherein $R^{135}$ and $R^{136}$ are independently H or —($C_1$-$C_3$)alkyl which may optionally bear halogen, or $R^{135}$ and $R^{136}$ may be joined and taken together with the N atom to which they are attached form a 5-6 membered ring which may optionally contain a ring member selected from O, S, and $NR^{137}$ wherein $R^{137}$ represents H or ($C_1$-$C_3$)alkyl; and j represents 1, 2, or 3;

4.5)

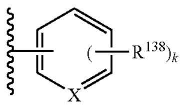

wherein

X represents C or N;

$R^{138}$ represents 4.5.a) ($C_1$-$C_4$)alkyl, which may optionally bear up to 3 substituents independently selected from 4.5.a1) halogen;

4.5.a2) $OR^{139}$ wherein $R^{139}$ represents H or ($C_1$-$C_3$)alkyl which may optionally bear halogen or —($C_1$-$C_3$)mono- or di-alkylamino;

4.5.a3) —$NR^{140}R^{141}$ in which $R^{140}$ and $R^{141}$ are independently H or —($C_1$-$C_3$)alkyl which may optionally bear halogen or $OR^{141a}$ wherein $R^{141a}$ represents H or ($C_1$-$C_3$)alkyl, or $R^{140}$ and $R^{141}$ may be joined and taken together with the N atom to which they are attached form a 5-6 membered ring which may optionally contain a ring member selected from O, S, and $NR^{142}$ wherein $R^{142}$ represents H or ($C_1$-$C_3$)alkyl; and 4.5.a4) a 5-6 membered heteroaromatic containing up to two heteroatoms selected from O, S, and N;

4.5.b) —($C_3$-$C_6$)cycloalkyl which may optionally bear up to 2 substituents independently selected from 4.5.b1) halogen; and 4.5.b2) $OR^{143}$ wherein $R^{143}$ represents H or ($C_1$-$C_3$)alkyl which may optionally bear halogen;

4.5.c) $OR^{144}$ wherein $R^{144}$ represents H; phenyl; benzyl; ($C_3$-$C_6$)cycloalkyl; or ($C_1$-$C_4$)alkyl which may optionally bear up to 3 substituents independently selected from 4.5.c1) halogen;

4.5.c2) $OR^{145}$ wherein $R^{145}$ represents H or ($C_1$-$C_3$)alkyl which may optionally bear ($C_1$-$C_3$) mono- or di-alkylamino; and 4.5.c3) $NR^{146}R^{147}$ in which $R^{146}$ and $R^{1473}$ are independently H or —($C_1$-$C_3$)alkyl which may optionally bear halogen, or $R^{146}$ and $R^{147}$ may be joined and taken together with the N atom to which they are attached form a 5-6 membered ring which may optionally contain a ring member selected from O, S, and $NR^{148}$ wherein $R^{148}$ represents H or ($C_1$-$C_3$)alkyl;

4.5.d) —C(O)—$OR^{149}$ wherein $R^{149}$ represents H or —($C_1$-$C_4$)alkyl which may optionally bear up to 3 halogens;

4.5.e) —C(O)—$NR^{150}R^{151}$ wherein $R^{150}$ represents H or ($C_1$-$C_3$)alkyl which may optionally bear halogen; and $R^{151}$ represents H or —($C_1$-$C_4$)alkyl which is optionally substituted with 4.5.e1) halogen;

4.5.e2) a 5-6 membered heteroaromatic containing up to two heteroatoms selected from O, S, and N;

4.5.e3) phenyl;

4.5.e4) —$SO_2CH_3$;

4.5.e5) —$OR^{152}$ wherein $R^{152}$ represents H or ($C_1$-$C_3$)alkyl which may optionally bear halogen; or 4.5.e6) —$NR^{153}R^{154}$ in which $R^{153}$ and $R^{154}$ are independently H or —($C_1$-$C_3$)alkyl which may optionally bear halogen, or $R^{153}$ and $R^{154}$ may be joined and taken together with the N atom to which they are attached form a 5-6 membered ring which may optionally contain a ring member selected from O, S, and $NR^{155}$ wherein $R^{155}$ represents H or ($C_1$-$C_3$)alkyl;

4.5.f) —N($R^{156}$)—C(O)—$R^{157}$ wherein $R^{156}$ represents H or ($C_1$-$C_3$)alkyl; and $R^{157}$ represents H, optionally substituted phenyl, or ($C_1$-$C_4$)alkyl which is optionally substituted with 4.5.f1) optionally substituted phenyl, 4.5.f2) $OR^{158}$ wherein $R^{158}$ represents H or ($C_1$-$C_3$)alkyl, or 4.5.f3) $NR^{159}R^{160}$ wherein $R^{159}$ and $R^{160}$ are independently H or —($C_1$-$C_3$)alkyl which may optionally bear halogen, or $R^{159}$ and $R^{160}$ may be joined and taken together with the N atom to which they are attached form a 5-6 membered ring which may optionally contain a ring member selected from O, S, and $NR^{161}$ wherein $R^{161}$ represents H or ($C_r$ $C_3$)alkyl;

4.5.g) —$SO_2NR^{162}R^{163}$ wherein $R^{162}$ represents H or ($C_1$-$C_3$)alkyl which may optionally bear halogen; and $R^{163}$ represents H or —($C_1$-$C_4$)alkyl which is optionally substituted with 4.5.g1) halogen;

4.5.g2) a 5-6 membered heteroaromatic containing up to two heteroatoms selected from O, S, and N;

4.5.g3) phenyl;

4.5.g4) —$SO_2CH_3$;

4.5.g5) —$OR^{164}$ wherein $R^{164}$ represents H or ($C_1$-$C_3$)alkyl which may optionally bear halogen; or 4.5.g6) —$NR^{165}R^{166}$ in which $R^{165}$ and $R^{166}$ are independently H or —($C_1$-$C_3$)alkyl which may optionally bear halogen, or $R^{165}$ and $R^{166}$ may be joined and taken together with the N atom to which they are attached form a 5-6 membered ring which may optionally contain a ring member selected from O, S, and $NR^{167}$ wherein $R^{167}$ represents H or ($C_1$-$C_3$)alkyl;

4.5.h) —N($R^{168}$)—$SO_2$—$R^{169}$ wherein $R^{168}$ represents represents H or ($C_1$-$C_3$)alkyl, and $R^{169}$ represents H, optionally substituted phenyl, or ($C_1$-$C_4$)alkyl which is optionally substituted with 4.5.h1) halogen, 4.5.h2) optionally substituted phenyl, 4.5.h3) $OR^{170}$ wherein $R^{170}$ represents H or ($C_1$-$C_3$)alkyl which may optionally bear halogen, or 4.5.h4) $NR^{171}R^{172}$ wherein $R^{171}$ and $R^{172}$ are independently H or —($C_1$-$C_3$)alkyl which may optionally bear halogen, or $R^{171}$ and $R^{172}$ may be joined and taken together with the N atom to which they are attached form a 5-6 membered ring which may optionally contain a ring member selected from O, S, and $NR^{173}$ wherein $R^{173}$ represents H or ($C_1$-$C_3$)alkyl;

4.5.i) —$NR^{174}R^{175}$ in which $R^{174}$ and $R^{175}$ are independently H or —($C_1$-$C_3$)alkyl which may optionally bear halogen or $OR^{175a}$ wherein $R^{175a}$ represents H or ($C_1$-$C_3$)alkyl, or $R^{174}$ and $R^{175}$ may be joined and taken together with the N atom to which they are attached form a 5-6 membered ring which may optionally contain a ring member selected from O, S, and $NR^{176}$ wherein $R^{176}$ represents H or ($C_1$-$C_3$)alkyl;

4.5.j) halogen;

4.5.k) optionally substituted phenyl;

4.5.l) $NO_2$;

4.5.m) CN; or 4.5.n) a 5-6 membered heteroaromatic containing up to two heteroatoms selected from 0, S, and N; and k represents 0, 1, or 2;

4.6)

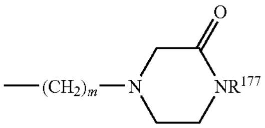

wherein $R^{177}$ represents H or —$(C_1\text{-}C_3)$alkyl; and m represents 1, 2, or 3;

4.7)

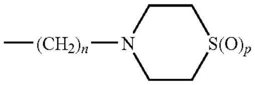

wherein n represents 1, 2, or 3; and p represents 0, 1, or 2;

4.8)

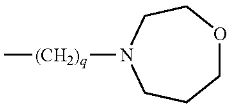

wherein q represents 1, 2, or 3;

4.9)

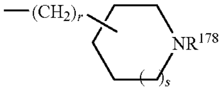

wherein $R^{178}$ represents 4.9.a) H;

4.9.b) —$(C_1\text{-}C_3)$alkyl which may optionally bear halogen or —$OR^{179}$ in which $R^{179}$ represents H or $(C_1\text{-}C_3)$alkyl optionally substituted with halogen;

4.9.c) —$(C_3\text{-}C_7)$cycloalkyl which may optionally bear halogen;

4.9.d) —$(C_2\text{-}C_5)$alkenyl which may optionally bear halogen;

4.9.e) —$SO_2R^{180}$ wherein $R^{180}$ represents optionally substitutued phenyl or —$(C_1\text{-}C_3)$alkyl, which may be substituted with halogen or —$OR^{181}$ wherein $R^{181}$ represents H or $(C_1\text{-}C_3)$ alkyl which may optionally bear halogen;

4.9.f) —$C(O)R^{182}$ wherein $R^{182}$ represents optionally substituted phenyl or —$(C_1\text{-}C_3)$alkyl which may optionally bear up to 3 substituents independently selected from 4.9.f1) halogen;

4.9.f2) optionally substituted phenyl;

4.9.f3) —$S(O)_2CH_3$;

4.9.f4) $OR^{183}$ wherein $R^{183}$ represents H or $(C_1\text{-}C_3)$alkyl which may optionally bear halogen; and 4.9.f5) —$NR^{184}R^{185}$ in which $R^{184}$ and $R^{185}$ are independently H or —$(C_1\text{-}C_3)$alkyl which may optionally bear halogen or $OR^{185a}$ wherein $R^{185a}$ represents H or $(C_1\text{-}C_3)$alkyl, or $R^{184}$ and $R^{185}$ may be joined and taken together with the N atom to which they are attached form a 5-6 membered ring which may optionally contain a ring member selected from O, S, and $NR^{186}$ wherein $R^{186}$ represents H or $(C_1\text{-}C_3)$alkyl;

4.9g) —$C(O)OR^{187}$ wherein $R^{187}$ represents $(C_1\text{-}C_4)$alkyl; or 4.9.h) —C(O)—$NR^{188}R^{189}$ wherein $R^{188}$ and $R^{189}$ each independently represents H or —$(C_1\text{-}C_4)$ alkyl which may optionally bear halogen, or $R^{188}$ and $R^{189}$ may be joined and taken together with the N atom to which they are attached form a 5-6 membered ring which may optionally contain a ring member selected from O, S, and $NR^{190}$ wherein $R^{190}$ represents H or $(C_1\text{-}C_3)$ alkyl;

r represents 0, 1, or 2; and s represents 0 or 1;

4.10)

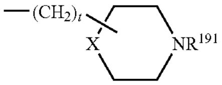

wherein $R^{191}$ represents 4.10.a) H;

4.10.b) —$(C_1\text{-}C_3)$alkyl which may optionally bear halogen or —$OR^{192}$ in which $R^{192}$ represents H or $(C_1\text{-}C_3)$alkyl;

4.10c) —$SO_2R^{193}$ wherein $R^{193}$ represents phenyl or —$(C_1\text{-}C_3)$alkyl, both of which may be substituted with halogen or —$(C_1\text{-}C_3)$alkyl;

4.10.d) —$C(O)R^{194}$ wherein $R^{194}$ represents $(C_1\text{-}C_3)$alkyl which may optionally bear up to 3 substituents independently selected from 4.10.d1) halogen;

4.10.d2) phenyl;

4.10.d3) —$S(O)_2CH_3$;

4.10.d4) $OR^{195}$ wherein $R^{195}$ represents H or $(C_1\text{-}C_3)$alkyl which may optionally bear halogen; and 4.10.d5) —$NR^{196}R^{197}$ in which $R^{196}$ and $R^{197}$ are independently H or —$(C_1\text{-}C_3)$alkyl which may optionally bear halogen or $OR^{197a}$ wherein $R^{197a}$ represents H or $(C_1\text{-}C_3)$alkyl, or $R^{196}$ and $R^{197}$ may be joined and taken together with the N atom to which they are attached form a 5-6 membered ring which may optionally contain a ring member selected from O, S, and $NR^{198}$ wherein $R^{198}$ represents H or $(C_1\text{-}C_3)$alkyl;

4.10.e) —$C(O)OR^{199}$ wherein $R^{199}$ represents $(C_1\text{-}C_3)$alkyl; or 4.10.f) —C(O)—$NR^{200}R^{201}$ wherein $R^{200}$ and $R^{201}$ each independently represents H or —$(C_1\text{-}C_3)$alkyl which may optionally bear halogen, or $R^{200}$ and $R^{201}$ may be joined and taken together with the N atom to which they are attached form a 5-6 membered ring which may optionally contain a ring member selected from O, S, and $NR^{202}$ wherein $R^{202}$ represents H or $(C_1-C_3)$ alkyl; and X represents O, S, S(O), $S(O)_2$, or $NR^{203}$ wherein $R^{203}$ represents H or —$(C_1-C_3)$alkyl; and t represents 0, 1, or 2;

4.11) —$C(O)R^{204}$ wherein $R^{204}$ represents optionally substituted phenyl or —$(C_1-C_3)$alkyl which may optionally bear up to 3 substituents independently selected from 4.11.a) halogen;

4.11.b) optionally substituted phenyl;

4.11.c) $OR^{205}$ wherein $R^{205}$ represents H or —$(C_1-C_3)$alkyl which may optionally bear halogen; and 4.11.d)

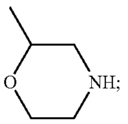

4.12) —C(O)—$NR^{206}R^{207}$ wherein $R^{206}$ and $R^{207}$ each independently represents H or $(C_1-C_3)$alkyl, or $R^{206}$ and $R^{207}$ may be joined and taken together with the N atom to which they are attached form a 5-6 membered ring which may optionally contain a ring member selected from O and S, said alkyl or ring optionally bearing up to 3 substituents independently selected from 4.12.a) halogen;

4.12.b) optionally substituted phenyl;

4.12.c) $OR^{208}$ wherein $R^{208}$ represents H or —$(C_1-C_3)$alkyl which may optionally bear halogen; and 4.12.d)

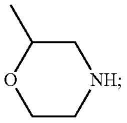

4.13) halogen; or 4.14) CN;

or a pharmaceutically acceptable salt thereof.

2. The method of claim 1 wherein said mammal is a human.

* * * * *